(12) United States Patent
Adams et al.

(10) Patent No.: US 9,056,874 B2
(45) Date of Patent: Jun. 16, 2015

(54) COMPLEMENT PATHWAY MODULATORS AND USES THEREOF

(71) Applicants: Christopher Michael Adams, Somerville, MA (US); Charles Babu, Arlington, TX (US); Michael Paul Capparelli, Cambridge, MA (US); Jian Ding, Bedford, MA (US); Takeru Ehara, Arlington, MA (US); Keith Jendza, Boston, MA (US); Nan Ji, Arlington, MA (US); Rajeshri Ganesh Karki, Somerville, MA (US); Toshio Kawanami, Boston, MA (US); Liang Xue, Arlington, TX (US); Nello Mainolfi, Boston, MA (US); James J. Powers, Waltham, MA (US); Michael H. Serrano-Wu, Belmont, MA (US); Chun Zhang, Waltham, MA (US)

(72) Inventors: Christopher Michael Adams, Somerville, MA (US); Charles Babu, Arlington, TX (US); Michael Paul Capparelli, Cambridge, MA (US); Jian Ding, Bedford, MA (US); Takeru Ehara, Arlington, MA (US); Keith Jendza, Boston, MA (US); Nan Ji, Arlington, MA (US); Rajeshri Ganesh Karki, Somerville, MA (US); Toshio Kawanami, Boston, MA (US); Liang Xue, Arlington, TX (US); Nello Mainolfi, Boston, MA (US); James J. Powers, Waltham, MA (US); Michael H. Serrano-Wu, Belmont, MA (US); Chun Zhang, Waltham, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 13/826,725

(22) Filed: Mar. 14, 2013

(65) Prior Publication Data
US 2013/0296377 A1  Nov. 7, 2013

Related U.S. Application Data

(60) Provisional application No. 61/642,798, filed on May 4, 2012.

(51) Int. Cl.
| | | |
|---|---|---|
| *C07D 403/06* | (2006.01) | |
| *C07D 403/04* | (2006.01) | |
| *C07D 403/08* | (2006.01) | |
| *C07D 403/14* | (2006.01) | |
| *C07D 401/14* | (2006.01) | |
| *C07D 413/14* | (2006.01) | |
| *C07D 487/04* | (2006.01) | |
| *C07D 491/048* | (2006.01) | |
| *A61K 31/4184* | (2006.01) | |
| *C07D 413/06* | (2006.01) | |
| *A61K 31/423* | (2006.01) | |
| *A61K 31/4439* | (2006.01) | |
| *A61K 45/06* | (2006.01) | |

(52) U.S. Cl.
CPC .......... *C07D 491/048* (2013.01); *C07D 403/06* (2013.01); *A61K 31/4184* (2013.01); *C07D 413/06* (2013.01); *A61K 31/423* (2013.01); *C07D 403/14* (2013.01); *C07D 401/14* (2013.01); *A61K 31/4439* (2013.01); *A61K 45/06* (2013.01); *C07D 403/08* (2013.01); *C07D 403/04* (2013.01); *C07D 413/14* (2013.01); *C07D 487/04* (2013.01)

(58) Field of Classification Search
USPC ....................................................... 548/305.1
See application file for complete search history.

(56) References Cited

U.S. PATENT DOCUMENTS

| | | | |
|---|---|---|---|
| 4,859,684 A | 8/1989 | Raeymaekers et al. | |
| 5,342,957 A | 8/1994 | Van Wauwe et al. | |

(Continued)

FOREIGN PATENT DOCUMENTS

| | | |
|---|---|---|
| CN | 1285557 | 11/2006 |
| EP | 0426225 A2 | 5/1991 |

(Continued)

OTHER PUBLICATIONS

Barnes et al., European Respiratory Journal (2005), 25(6), pp. 1084-1106.*

(Continued)

*Primary Examiner* — Laura L. Stockton
(74) *Attorney, Agent, or Firm* — John B. Alexander

(57) ABSTRACT

The present invention provides a compound of formula I:

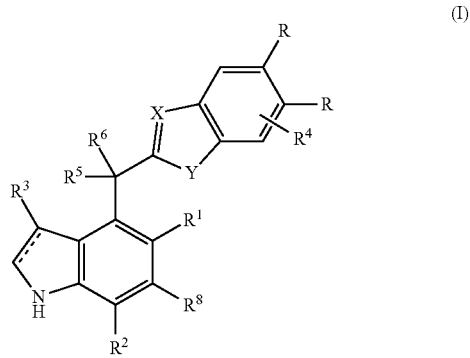

a method for manufacturing the compounds of the invention, and its therapeutic uses. The present invention further provides a combination of pharmacologically active agents and a pharmaceutical composition.

29 Claims, No Drawings

(56) References Cited

U.S. PATENT DOCUMENTS

| | | |
|---|---|---|
| 5,409,929 A | 4/1995 | Ciganek |
| 5,763,688 A | 6/1998 | Ikariya et al. |
| 8,012,682 B2 | 9/2011 | Lukyanov et al. |
| 2007/0259936 A1 | 11/2007 | Player et al. |
| 2008/0146501 A1 | 6/2008 | Hageman et al. |
| 2008/0255000 A1 | 10/2008 | Dogulu et al. |
| 2008/0280825 A1 | 11/2008 | Hageman et al. |
| 2009/0111708 A1 | 4/2009 | Seddon et al. |
| 2009/0214538 A1 | 8/2009 | Fung et al. |
| 2009/0221665 A1 | 9/2009 | Earnest |
| 2010/0069468 A1 | 3/2010 | Hess et al. |
| 2010/0120665 A1 | 5/2010 | Kaleko et al. |
| 2010/0166862 A1 | 7/2010 | Francois et al. |
| 2010/0273720 A1 | 10/2010 | Hageman et al. |
| 2011/0114888 A1 | 5/2011 | Akino |
| 2011/0117557 A1 | 5/2011 | Canter et al. |
| 2011/0229439 A1 | 9/2011 | Humphnes et al. |
| 2012/0071356 A1 | 3/2012 | Allikmets et al. |

FOREIGN PATENT DOCUMENTS

| | | |
|---|---|---|
| JP | 2010037511 | 4/2010 |
| WO | 95/04052 | 2/1995 |
| WO | 9504052 A1 | 2/1995 |
| WO | 97/07097 | 2/1997 |
| WO | 9707097 A1 | 2/1997 |
| WO | 99/40072 | 8/1999 |
| WO | 9940072 A1 | 8/1999 |
| WO | 2006041872 A2 | 4/2006 |
| WO | 2006/084338 | 8/2006 |
| WO | 2006084338 A1 | 8/2006 |
| WO | 2006/099379 | 9/2006 |
| WO | 2006099379 A2 | 9/2006 |
| WO | 2006/125324 | 11/2006 |
| WO | 2006125324 A1 | 11/2006 |
| WO | 2007/056111 | 5/2007 |
| WO | 2007/095185 | 8/2007 |
| WO | 2007095287 | 8/2007 |
| WO | 2008003703 A1 | 1/2008 |
| WO | 2008/106644 | 9/2008 |
| WO | 2008/140793 | 11/2008 |
| WO | 2009/073564 | 6/2009 |
| WO | 2009073564 A1 | 6/2009 |
| WO | 2009/105757 | 8/2009 |
| WO | 2009/157429 | 12/2009 |
| WO | 2009157429 A1 | 12/2009 |
| WO | 2010/029162 | 3/2010 |
| WO | 2010066684 A2 | 6/2010 |
| WO | 2010/085542 | 7/2010 |
| WO | 2010/127152 | 11/2010 |
| WO | 2010127152 A2 | 11/2010 |
| WO | 2011/017229 | 2/2011 |
| WO | 2013016197 A1 | 1/2013 |

OTHER PUBLICATIONS

Doan et al., The Journal of Clinical Pharmacology, 2005, 45, pp. 751-762.*
Li Qian et al., Journal of Neural Transmission, (Aug. 2010), vol. 117, Issue 8, pp. 971-979.*
Guttman et al., Canadian Medical Association Journal, Feb. 4, 2003, 168(3), pp. 293-301.*
Knaryan et al., Journal of Neurochemistry, 2011, vol. 118, pp. 326-338.*
Adams et al., PCT Application No. PCT/US2014/026875, Filed on Mar. 13, 2014.

* cited by examiner

COMPLEMENT PATHWAY MODULATORS AND USES THEREOF

FIELD OF THE INVENTION

The invention relates to the inhibition of the complement alternative pathway and particularly to inhibition of Factor B, in patients suffering from conditions and diseases associated with complement alternative pathway activation such as age-related macular degeneration, diabetic retinopathy and related ophthalmic diseases.

BACKGROUND OF THE INVENTION

The complement system is a crucial component of the innate immunity system and comprises a group of proteins that are normally present in an inactive state. These proteins are organized in three activation pathways: the classical, the lectin, and the alternative pathways (V. M. Holers, In Clinical Immunology: Principles and Practice, ed. R. R. Rich, Mosby Press; 1996, 363-391). Molecules from microorganisms, antibodies or cellular components can activate these pathways resulting in the formation of protease complexes known as the C3-convertase and the C5-convertase. The classical pathway is a calcium/magnesium-dependent cascade, which is normally activated by the formation of antigen-antibody complexes. It can also be activated in an antibody-independent manner by the binding of C-reactive protein complexed to ligand and by many pathogens including gram-negative bacteria. The alternative pathway is a magnesium-dependent cascade which is activated by deposition and activation of C3 on certain susceptible surfaces (e.g., cell wall polysaccharides of yeast and bacteria, and certain biopolymer materials).

Factor B may be a suitable target for the inhibition of this amplification of the complement pathways because its plasma concentration in humans is typically about 200 μg/mL (or about 2 μM), and it has been shown to be a critical enzyme for activation of the alternative complement pathway (P. H. Lesavre and H. J. Müller-Eberhard. J. Exp. Med., 1978; 148: 1498-1510; J. E. Volanakis et al., New Eng. J. Med., 1985; 312:395-401).

Macular degeneration is a clinical term that is used to describe a family of diseases that are characterized by a progressive loss of central vision associated with abnormalities of Bruch's membrane, the choroid, the neural retina and/or the retinal pigment epithelium. In the center of the retina is the macula lutea, which is about ⅓ to ½ cm in diameter. The macula provides detailed vision, particularly in the center (the fovea), because the cones are higher in density and because of the high ratio of ganglion cells to photoreceptor cells. Blood vessels, ganglion cells, inner nuclear layer and cells, and the plexiform layers are all displaced to the side (rather than resting above the photoreceptor cells), thereby allowing light a more direct path to the cones. Under the retina is the choroid, a part of the uveal tract, and the retinal pigmented epithelium (RPE), which is between the neural retina and the choroid. The choroidal blood vessels provide nutrition to the retina and its visual cells.

Age-related macular degeneration (AMD), the most prevalent form of macular degeneration, is associated with progressive loss of visual acuity in the central portion of the visual field, changes in color vision, and abnormal dark adaptation and sensitivity. Two principal clinical manifestations of AMD have been described as the dry, or atrophic, form and the neovascular, or exudative, form. The dry form is associated with atrophic cell death of the central retina or macula, which is required for fine vision used for activities such as reading, driving or recognizing faces. About 10-20% of these AMD patients progress to the second form of AMD, known as neovascular AMD (also referred to as wet AMD).

Neovascular AMD is characterized by the abnormal growth of blood vessels under the macula and vascular leakage, resulting in displacement of the retina, hemorrhage and scarring. This results in a deterioration of sight over a period of weeks to years. Neovascular AMD cases originate from intermediate or advanced dry AMD. The neovascular form accounts for 85% of legal blindness due to AMD. In neovascular AMD, as the abnormal blood vessels leak fluid and blood, scar tissue is formed that destroys the central retina.

The new blood vessels in neovascular AMD are usually derived from the choroid and are referred to as choroidal neovascularizaton (CNV). The pathogenesis of new choroidal vessels is poorly understood, but such factors as inflammation, ischemia, and local production of angiogenic factors are thought to be important. A published study suggests that CNV is caused by complement activation in a mouse laser model (Bora P. S., J. Immunol. 2005; 174; 491-497).

Human genetic evidence implicates the involvement of the complement system, particularly the alternative pathway, in the pathogenesis of Age-related Macular Degeneration (AMD). Significant associations have been found between AMD and polymorphisms in complement factor H(CFH) (Edwards A O, et al. Complement factor H polymorphism and age-related macular degeneration. Science. 2005 Apr. 15; 308(5720):421-4; Hageman G S, et al A common haplotype in the complement regulatory gene factor H(HF1/CFH) predisposes individuals to age-related macular degeneration. Proc Natl Acad Sci USA. 2005 May 17; 102(20):7227-32; Haines J L, et al. Complement factor H variant increases the risk of age-related macular degeneration. Science. 2005 Apr. 15; 308(5720):419-21; Klein R J, et al Complement factor H polymorphism in age-related macular degeneration. Science. 2005 Apr. 15; 308(5720):385-9; Lau L I, et al. Association of the Y402H polymorphism in complement factor H gene and neovascular age-related macular degeneration in Chinese patients. Invest Ophthalmol V is Sci. 2006 August; 47(8): 3242-6; Simonelli F, et al. Polymorphism p. 402Y>H in the complement factor H protein is a risk factor for age related macular degeneration in an Italian population. Br J. Ophthalmol. 2006 September; 90(9):1142-5; and Zareparsi S, et al Strong association of the Y402H variant in complement factor H at 1q32 with susceptibility to age-related macular degeneration. Am J Hum Genet. 2005 July; 77(1):149-53.), complement factor B (CFB) and complement $C_2$ (Gold B, et al. Variation in factor B (BF) and complement component 2 (C2) genes is associated with age-related macular degeneration. Nat. Genet. 2006 April; 38(4):458-62 and Jakobsdottir J, et al. C2 and CFB genes in age-related maculopathy and joint action with CFH and LOC387715 genes. PLoS One. 2008 May 21; 3(5):e2199), and most recently in complement C3 (Despriet D D, et al Complement component C3 and risk of age-related macular degeneration. Ophthalmology. 2009 March; 116(3):474-480.e2; Mailer J B, et al Variation in complement factor 3 is associated with risk of age-related macular degeneration. Nat. Genet. 2007 October; 39(10): 1200-1 and Park K H, et al Complement component 3 (C3) haplotypes and risk of advanced age-related macular degeneration. Invest Ophthalmol V is Sci. 2009 July; 50(7):3386-93. Epub 2009 Feb. 21.). Taken together, the genetic variations in the alternative pathway components CFH, CFB, and C3 can predict clinical outcome in nearly 80% of cases.

Currently there is no proven medical therapy for dry AMD and many patients with neovascular AMD become legally blind despite current therapy with anti-VEGF agents such as Lucentis. Thus, it would be desirable to provide therapeutic agents for the treatment or prevention of complement mediated diseases and particularly for the treatment of AMD.

SUMMARY OF THE INVENTION

The present invention provides compounds that modulate, and preferably inhibit, activation of the alternative complement pathway. In certain embodiments, the present invention provides compounds that modulate, and preferably inhibit, Factor B activity and/or Factor B mediated complement pathway activation. Such Factor B modulators are preferably high affinity Factor B inhibitors that inhibit the catalytic activity of complement Factor B, such as primate Factor B and particularly human Factor B.

The compounds of the present invention inhibit or suppress the amplification of the complement system caused by C3 activation irrespective of the initial mechanism of activation (including for example activation of the classical, lectin or alternative pathways).

Various embodiments of the invention are described herein. It will be recognized that features specified in each embodiment may be combined with other specified features to provide further embodiments.

Within certain aspects, Factor B modulators provided herein are compounds of Formula I and salts and tautomers thereof:

In another embodiment, the invention provides a pharmaceutical composition comprising a therapeutically effective amount of a compound according to the definition of formula (I) or subformulae thereof and one or more pharmaceutically acceptable carriers.

In another embodiment, the invention provides a combination, in particular a pharmaceutical combination, comprising a therapeutically effective amount of the compound according to the definition of formula (I) or subformulae thereof and one or more additional therapeutically active agents.

The invention further provides methods of treating or preventing complement mediated diseases, the method comprising the steps of identifying a patient in need of complement modulation therapy and administering a compound of Formula (I) or a subformulae thereof.

Complement mediated diseases include ophthalmic diseases (including early or neovascular age-related macular degeneration and geographic atrophy), autoimmune diseases (including arthritis, rheumatoid arthritis), respiratory diseases, cardiovascular diseases.

Other aspects of the invention are discussed infra.

DETAILED DESCRIPTION OF THE INVENTION

As noted above, the present invention provides compounds that modulate Factor B activation and/or Factor B-mediated signal transduction of the complement system. Such compounds may be used in vitro or in vivo to modulate (preferably inhibit) Factor B activity in a variety of contexts.

In a first embodiment, the invention provides compounds of Formula I and salts and tautomers thereof, which modulate the alternative pathway of the complement system.

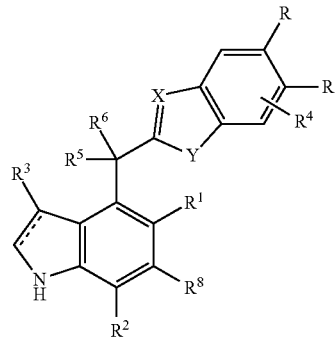

Wherein
⫽ is a single or double bond;
X is N or CH;
Y is N(H), O or S;
one occurrence of R is cyano and the other occurrence of R is hydrogen or $R^4$;
$R^1$ is halogen, hydroxyl, $C_1$-$C_6$alkyl, $C_2$-$C_6$alkenyl, $C_3$-$C_6$cycloalkyl, $C_1$-$C_6$alkoxy, halo$C_1$-$C_6$alkyl, hydroxy$C_1$-$C_6$alkyl, amino$C_1$-$C_6$alkyl, $C_1$-$C_6$alkoxy$C_1$-$C_6$alkyl, $C_1$-$C_6$alkoxy$C_1$-$C_6$alkoxy, $C_3$-$C_6$cycloalkyl$C_1$-$C_6$alkoxy, halo$C_1$-$C_6$alkoxy, $S(O)_p C_1$-$C_6$alkyl, $CH_2NHC(O)C_1$-$C_4$alkyl or $OCH_2C(O)R^7$,
p is 0, 1, or 2;
$R^2$ is $C_1$-$C_6$alkyl, $C_1$-$C_6$alkoxy, hydroxy$C_1$-$C_6$alkyl or halogen;
$R^3$ is hydrogen, halogen, cyano, $C_1$-$C_4$alkyl, halo$C_1$-$C_4$alkyl, $CH_2C(O)R^7$, phenyl or 5 or 6 member heteroaryl having 1, 2 or 3 ring heteroatoms independently selected from N, O or S, wherein the phenyl or heteroaryl is optionally substituted with 0, 1, or 2 $C_1$-$C_4$alkyl groups, and wherein alkyl and haloalkyl optionally substituted with 0 or 1 hydroxy;
$R^4$ is 0, 1, or 2 substitutents independently selected at each occurrence from halogen and $C_1$-$C_6$alkyl;
$R^5$ is hydrogen, $C_1$-$C_6$alkyl, halo$C_1$-$C_6$alkyl, $C_3$-$C_6$cycloalkyl, phenyl or 5 or 6 member heteroaryl having 1, 2 or 3 ring heteroatoms independently selected from N, O or S;
or $R^3$ and $R^5$ taken in combination form a divalent —$CH_2$—$CH_2$— or —$CH_2$—N(H)— group;
$R^6$ is hydrogen, hydroxy, amino, $C_1$-$C_6$alkyl, $C_1$-$C_6$alkoxy, $C_1$-$C_6$alkoxy$C_1$-$C_6$alkoxy, mono- and di-$C_1$-$C_4$alkylamino, amino $C_1$-$C_6$alkylamino, $[CR^A{}_2]_n R^7$, $[CR^A{}_2]_n C(O)R^7$, $O[CR^A{}_2]_n R^7$, $NHC(O)C_1$-$C_6$alkyl, $NHS(O_2)C_1$-$C_6$alkyl, $(CH_2)_n R^9$, $O(CH_2)_n R^9$, $C(O)R^7$, $N(H)[CR^A{}_2]_n R^7$, $O[CR^A{}_2]_n C(O)R^7$, $N(H)[CR^A{}_2]_n C(O)R^7$ or tetrazolyl;
or $CR^5 R^6$, taken in combination, form a divalent carbonyl group, a divalent =$CH_2$ group or cyclopropyl which cyclopropyl is optionally substituted by $CO_2H$ or $CH_2OH$;
n is 1, 2, 3 or 4;
$R^A$ is independently selected at each occurrence from hydrogen, halogen or $C_1$-$C_4$alkyl;
$R^7$ is hydroxy, $C_1$-$C_4$alkoxy, amino or mono- and di-$C_1$-$C_4$alkylamino
$R^8$ is hydrogen or halogen; and
$R^9$ is a 5 member heteroaryl having 1 to 4 ring heteroatoms selected from N, O or S and optionally substituted with 0, 1, or 2 $C_1$-$C_4$alkyl groups.

In a second embodiment, the invention provides compounds of Formula I and salts and tautomers thereof, which modulate the alternative pathway of the complement system.

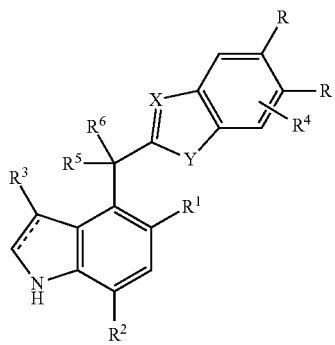

(I)

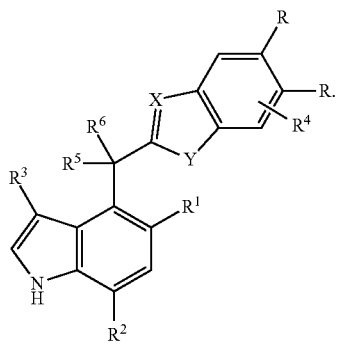

(Ia)

Wherein

⫽ is a single or double bond;

X is N or CH;

Y is N(H), O or S;

one occurrence of R is cyano and the other occurrence of R is hydrogen or $R^4$;

$R^1$ is halogen, $C_1$-$C_6$alkyl, $C_2$-$C_6$alkenyl, $C_3$-$C_6$cycloalkyl, $C_1$-$C_6$alkoxy, halo$C_1$-$C_6$alkyl, hydroxy$C_1$-$C_6$alkyl, amino$C_1$-$C_6$alkyl, $C_1$-$C_6$alkoxy$C_1$-$C_6$alkyl, $C_1$-$C_6$alkoxy$C_1$-$C_6$alkoxy, $C_3$-$C_6$cycloalkyl$C_1$-$C_6$alkoxy, halo$C_1$-$C_6$alkoxy, $S(O)_p C_1$-$C_6$alkyl, $CH_2NHC(O)C_1$-$C_4$alkyl or $OCH_2C(O)R^7$, p is 0, 1, or 2;

$R^2$ is $C_1$-$C_6$alkyl, $C_1$-$C_6$alkoxy, hydroxy$C_1$-$C_6$alkyl or halogen;

$R^3$ is hydrogen, halogen, cyano, $C_1$-$C_4$alkyl, halo$C_1$-$C_4$alkyl, $CH_2C(O)R^7$, phenyl or 5 or 6 member heteroaryl having 1, 2 or 3 ring heteroatoms independently selected from N, O or S, wherein the phenyl or heteroaryl is optionally substituted with 0, 1, or 2 $C_1$-$C_4$alkyl groups, and wherein alkyl and haloalkyl optionally substituted with 0 or 1 hydroxy;

$R^4$ is 0, 1, or 2 substitutents independently selected at each occurrence from halogen and $C_1$-$C_6$alkyl;

$R^5$ is hydrogen, $C_1$-$C_6$alkyl, halo$C_1$-$C_6$alkyl, $C_3$-$C_6$cycloalkyl, phenyl or 5 or 6 member heteroaryl having 1, 2 or 3 ring heteroatoms independently selected from N, O or S;

or $R^3$ and $R^5$ taken in combination form a divalent $CH_2$—$CH_2$— group;

$R^6$ is hydrogen, hydroxy, amino, $C_1$-$C_6$alkyl, $C_1$-$C_6$alkoxy, $C_1$-$C_6$alkoxy$C_1$-$C_6$alkoxy, mono- and di-$C_1$-$C_4$alkylamino, amino $C_1$-$C_6$alkylamino, $CH_2R^7$, $NHC(O)C_1$-$C_6$alkyl, NHS$(O_2)C_1$-$C_6$alkyl, $C(O)NH_2$, $CO_2H$, $OCR^A_2C(O)R^7$ or $N(H)CR^A_2C(O)R^7$;

or $CR^5R^6$, taken in combination, form a divalent carbonyl group or a divalent =$CH_2$ group;

$R^A$ is independently selected at each occurrence from hydrogen or $C_1$-$C_4$alkyl; and $R^7$ is hydroxy, $C_1$-$C_4$alkoxy, amino or mono- and di-$C_1$-$C_4$alkylamino.

In a third embodiment, the invention provides compounds, salts thereof and tautomers thereof of the first or second embodiment, according to Formula (Ia):

In a fourth embodiment, the invention provides compounds, salts thereof and tautomers thereof of any one of embodiments 1 to 3, in which $R^4$ is absent.

In a fifth embodiment, the invention provides compounds, salts thereof and tautomers thereof of any one of embodiments 1 to 4, in which $R^3$ is hydrogen, chloro or phenyl.

In a sixth embodiment, the invention provides compounds, salts thereof and tautomers thereof of any one of embodiments 1 to 5, in which $R^3$ is hydrogen.

In a seventh embodiment, the invention provides compounds, salts thereof and tautomers thereof of any one of embodiments 1 to 6, in which $R^2$ is methyl.

In a eighth embodiment, the invention provides compounds, salts thereof and tautomers thereof of any one of embodiments 1 to 7, in which $R^1$ is halogen, $C_1$-$C_4$alkyl, vinyl, cyclopropyl, $C_1$-$C_4$alkoxy, hydroxy$C_1$-$C_4$alkyl, $C_1$-$C_4$alkoxy$C_1$-$C_4$alkyl, $C_1$-$C_4$alkoxy$C_1$-$C_4$alkoxy, cyclopropyl$C_1$-$C_4$alkoxy, halo$C_1$-$C_4$alkoxy or $S(O)_2 C_1$-$C_4$alkyl.

In a ninth embodiment, the invention provides compounds, salts thereof and tautomers thereof of any one of embodiments 1 to 8, in which $R^1$ is $C_1$-$C_4$alkyl, $C_1$-$C_4$alkoxy, cyclopropyl, bromo or difluoromethoxy.

In a tenth embodiment, the invention provides compounds, salts thereof and tautomers thereof of any one of embodiments 1 to 9, in which $R^5$ is hydrogen, methyl, ethyl, cyclopropyl or trifluoromethyl.

In a eleventh embodiment, the invention provides compounds, salts thereof and tautomers thereof of any one of embodiments 1 to 10, in which wherein $R^6$ is hydrogen, hydroxy, methoxy, amino, mono- and di-methylamino or $CH_2R^7$; and $R^7$ is hydroxy, amino, $N(H)CH_3$ or $N(CH_3)_2$.

In a twelfth embodiment, the invention provides compounds, salts thereof and tautomers thereof of any one of embodiments 1 to 11, in which $R^5$ is methyl or trifluoromethyl; $R^6$ is hydroxy, methoxy, amino, methylamino or $CH_2R^7$; and $R^7$ is hydroxy, amino, $N(H)CH_3$ or $N(CH_3)_2$. Certain preferred compounds of the twelfth embodiment include those compounds in which $R^6$ is hydroxy, methoxy, amino or methylamino.

In a thirteenth embodiment, the invention provides compounds, salts thereof and tautomers thereof of any one of embodiments 1 to 12, in which X is N; and Y is N(H). Said compounds of the twelfth embodiment are also referred to herein as compounds of Formula II.

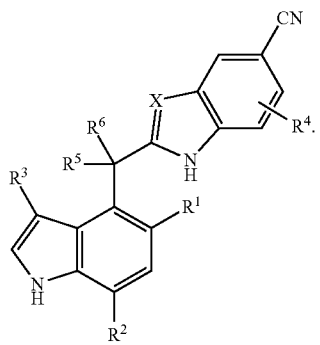
(II)

Compounds of Formula (II) exist as a mixture of tautomers in which the hydrogen of the imidazole ring may tautomerize between the two nitrogen atoms of the imidazole ring, as follows:

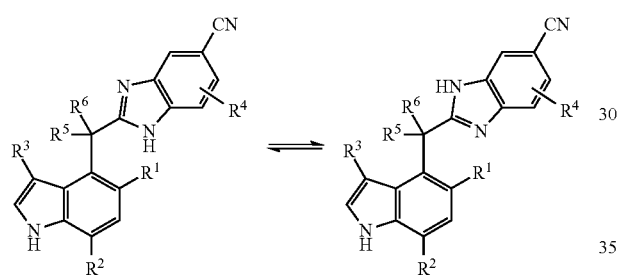

When a cyanobenzimidazole of Formula II is recited herein, it will be understood, that the recitation of a single tautomeric form will include the other tautomeric form and mixtures thereof.

In a fourteenth embodiment, the invention provides compounds, salts thereof and tautomers thereof of any one of embodiments 1 to 12, in which X is N; and Y is O. Said compounds of the thirteenth embodiment are also referred to herein as compounds of Formula IIIa and IIIb.

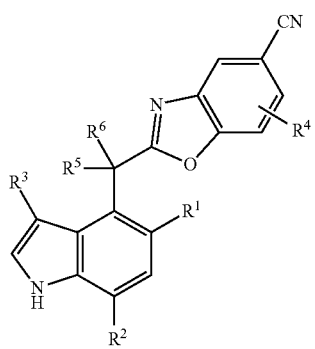
(IIIa)

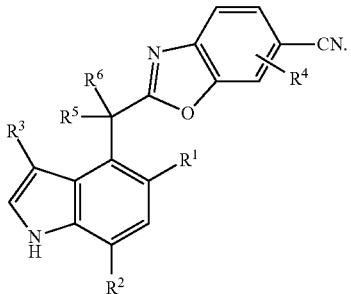
(IIIb)

In a fifteenth embodiment, the invention provides compounds, salts thereof and tautomers thereof of any one of embodiments 1 to 12, in which X is N; and Y is S. Said compounds of the fourteenth embodiment are also referred to herein as compounds of Formula IVa and IVb.

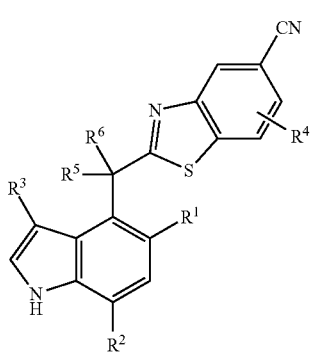
(IVa)

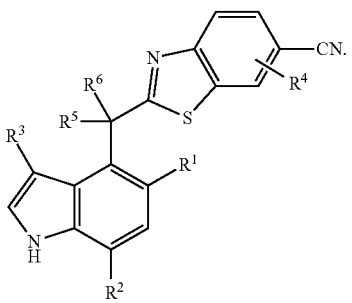
(IVb)

In a sixteenth embodiment, the invention provides compounds, salts thereof and tautomers thereof of any one of embodiments 1 to 12, in which X is CH; and Y is N(H), O or S. Said compounds of the fifteenth embodiment are also referred to herein as compounds of Formula Va and Vb.

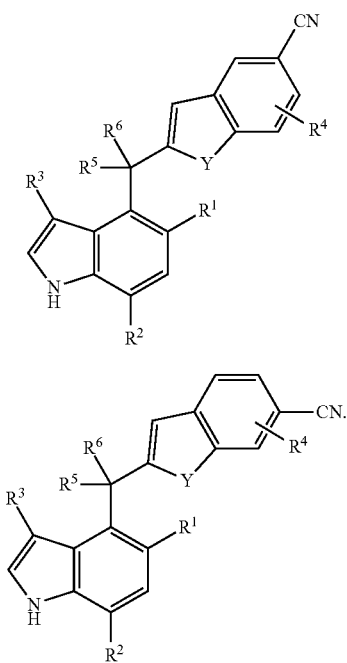

(Va)

(Vb)

In a seventeenth embodiment, the invention provides compounds, salts thereof and tautomers thereof of embodiment one, wherein $R^8$ is hydrogen.

In a eighteenth embodiment, the invention provides compounds, salts thereof and tautomers thereof of embodiment one, wherein $R^8$ is fluorine.

In a nineteenth embodiment, the invention provides compounds, salts thereof and tautomers thereof of embodiment one in which one occurrence of R is cyano and the other occurrence of R is hydrogen;
$R^1$ is methyl, hydroxyl or methoxy;
$R^2$ is methyl;
$R^3$ is hydrogen, chloro or phenyl;
$R^4$ is absent;
$R^5$ is hydrogen, methyl, ethyl or trifluoromethyl;
$R^6$ is amino, $CO_2H$, $(CH_2)_nC(O)R^7$ or $(CH_2)_n$-tetrazolyl;
n is 1, 2, or 3;
X is N and Y is NH or O.

In certain compounds of the nineteenth embodiment, $R^6$ is amino, $CO_2H$, $(CH_2)_nCO_2H$ or $CH_2$-tetrazolyl and n is 1, 2 or 3.

In a twentieth embodiment, individual compounds according to the invention are those listed in the Examples section below. In certain aspects the compound is selected from the group consisting of: (±)-2-(((2-aminoethyl)amino)(5-(difluoromethoxy)-7-methyl-1H-indol-4-yl)methyl)-1H-benzo[d]imidazole-5-carbonitrile;
(+)-2-((5-(difluoromethoxy)-7-methyl-1H-indol-4-yl)(hydroxy)methyl)-1H-benzo[d]imidazole-5-carbonitrile;
(−)-2-((5-(difluoromethoxy)-7-methyl-1H-indol-4-yl)(hydroxy)methyl)-1H-benzo[d]imidazole-5-carbonitrile;
(±)-2-((5-(difluoromethoxy)-7-methyl-1H-indol-4-yl)(methylamino)methyl)-1H-benzo[d]imidazole-5-carbonitrile;
(+)-2-(1-amino-1-(5-(difluoromethoxy)-7-methyl-1H-indol-4-yl)ethyl)-1H-benzo[d]imidazole-5-carbonitrile;
(−)-2-(1-amino-1-(5-(difluoromethoxy)-7-methyl-1H-indol-4-yl)ethyl)-1H-benzo[d]imidazole-5-carbonitrile;
(+)-2-(1-(5-(difluoromethoxy)-7-methyl-1H-indol-4-yl)-1-hydroxyethyl)-1H-benzo[d]imidazole-5-carbonitrile;
(+) and (−)-2-(1-(5-(difluoromethoxy)-7-methyl-1H-indol-4-yl)-1-hydroxyethyl)-1H-benzo[d]imidazole-5-carbonitrile;
(+) or (−)-2-(1-(3-chloro-5-(difluoromethoxy)-7-methyl-1H-indol-4-yl)-1-hydroxyethyl)-1H-benzo[d]imidazole-5-carbonitrile;
(+)-2-(1-(5-(difluoromethoxy)-7-methyl-1H-indol-4-yl)-1-methoxyethyl)-1H-benzo[d]imidazole-5-carbonitrile;
(−)-2-(1-(5-(difluoromethoxy)-7-methyl-1H-indol-4-yl)-1-methoxyethyl)-1H-benzo[d]imidazole-5-carbonitrile;
(±)-2-(hydroxy(7-methyl-5-(methylsulfonyl)-1H-indol-4-yl)methyl)-1H-benzo[d]imidazole-5-carbonitrile;
(+)-2-(1-hydroxy-1-(7-methyl-5-(methylsulfonyl)-1H-indol-4-yl)ethyl)-1H-benzo[d]imidazole-5-carbonitrile;
(−)-2-(1-hydroxy-1-(7-methyl-5-(methylsulfonyl)-1H-indol-4-yl)ethyl)-1H-benzo[d]imidazole-5-carbonitrile;
(+)-2-(1-methoxy-1-(7-methyl-5-(methylsulfonyl)-1H-indol-4-yl)ethyl)-1H-benzo[d]imidazole-5-carbonitrile;
(−)-2-(1-methoxy-1-(7-methyl-5-(methylsulfonyl)-1H-indol-4-yl)ethyl)-1H-benzo[d]imidazole-5-carbonitrile;
(+)-2-(1-amino-1-(7-methyl-5-(methylsulfonyl)-1H-indol-4-yl)ethyl)-1H-benzo[d]imidazole-5-carbonitrile;
(−)-2-(1-amino-1-(7-methyl-5-(methylsulfonyl)-1H-indol-4-yl)ethyl)-1H-benzo[d]imidazole-5-carbonitrile;
(+)-2-(2,2,2-trifluoro-1-hydroxy-1-(7-methyl-5-(methylsulfonyl)-1H-indol-4-yl)ethyl)-1H-benzo[d]imidazole-5-carbonitrile;
(−)-2-(2,2,2-trifluoro-1-hydroxy-1-(7-methyl-5-(methylsulfonyl)-1H-indol-4-yl)ethyl)-1H-benzo[d]imidazole-5-carbonitrile;
(+)-2-(2,2,2-trifluoro-1-methoxy-1-(7-methyl-5-(methylsulfonyl)-1H-indol-4-yl)ethyl)-1H-benzo[d]imidazole-5-carbonitrile;
(−)-2-(2,2,2-trifluoro-1-methoxy-1-(7-methyl-5-(methylsulfonyl)-1H-indol-4-yl)ethyl)-1H-benzo[d]imidazole-5-carbonitrile;
(+)-2-(2,2,2-trifluoro-1-(7-methyl-5-(methylsulfonyl)-1H-indol-4-yl)-1-(methylamino)ethyl)-1H-benzo[d]imidazole-5-carbonitrile;
(−)-2-(2,2,2-trifluoro-1-(7-methyl-5-(methylsulfonyl)-1H-indol-4-yl)-1-(methylamino)ethyl)-1H-benzo[d]imidazole-5-carbonitrile;
(+)-2-(1-amino-2,2,2-trifluoro-1-(7-methyl-5-(methylsulfonyl)-1H-indol-4-yl)ethyl)-1H-benzo[d]imidazole-5-carbonitrile;
(−)-2-(1-amino-2,2,2-trifluoro-1-(7-methyl-5-(methylsulfonyl)-1H-indol-4-yl)ethyl)-1H-benzo[d]imidazole-5-carbonitrile;
(+)-2-(amino(7-methyl-5-(methylsulfonyl)-1H-indol-4-yl)methyl)-1H-benzo[d]imidazole-5-carbonitrile;
(−)-2-(amino(7-methyl-5-(methylsulfonyl)-1H-indol-4-yl)methyl)-1H-benzo[d]imidazole-5-carbonitrile;
2-((5-methoxy-7-methyl-1H-indol-4-yl)methyl)-1H-benzo[d]imidazole-5-carbonitrile;
2-((5-($^2H_3$) methoxy-7-methyl-1H indol-4-yl)methyl)-1H-benzo[d]imidazole-5-carbonitrile;
2-((5-isopropoxy-7-methyl-1H-indol-4-yl)methyl)-1H-benzo[d]imidazole-5-carbonitrile;
2-((5-(2-methoxyethoxy)-7-methyl-1H-indol-4-yl)methyl)-1H-benzo[d]imidazole-5-carbonitrile;
2-((5-methoxy-7-methyl-1H-indol-4-yl)methyl)benzo[d]oxazole-5-carbonitrile;
2-((5-methoxy-7-methyl-1H-indol-4-yl)methyl)benzo[d]oxazole-6-carbonitrile;
2-((7-fluoro-5-methoxy-1H-indol-4-yl)methyl)-1H-benzo[d]imidazole-5-carbonitrile;

2-((7-chloro-5-($^2H_3$)methoxy-1H-indol-4-yl)methyl)-1H-benzo[d]imidazole-5-carbonitrile; and (±)-2-((5-((1-methoxypropan-2-yl)oxy)-7-methyl-1H-indol-4-yl)methyl)-1H-benzo[d]imidazole-5-carbonitrile.

(+)-2-(hydroxy(5-methoxy-7-methyl-1H-indol-4-yl)methyl)-1H-benzo[d]imidazole-5-carbonitrile;

(−)-2-(hydroxy(5-methoxy-7-methyl-1H-indol-4-yl)methyl)-1H-benzo[d]imidazole-5-carbonitrile;

(+)-2-((5-ethoxy-7-methyl-1H-indol-4-yl)(hydroxy)methyl)-1H-benzo[d]imidazole-5-carbonitrile;

(−)-2-((5-ethoxy-7-methyl-1H-indol-4-yl)(hydroxy)methyl)-1H-benzo[d]imidazole-5-carbonitrile;

(+)-2-(hydroxy(5-isopropoxy-7-methyl-1H-indol-4-yl)methyl)-1H-benzo[d]imidazole-5-carbonitrile;

(−)-2-(hydroxy(5-isopropoxy-7-methyl-1H-indol-4-yl)methyl)-1H-benzo[d]imidazole-5-carbonitrile;

(±)-2-((7-chloro-5-($^2H_3$)methoxy-1H-indol-4-yl)(hydroxy)methyl)benzo[d]imidazole-5-carbonitrile;

2-(5-methoxy-7-methyl-1H-indole-4-carbonyl)-1H-benzo[d]imidazole-5-carbonitrile;

(+)-2-(1-hydroxy-1-(5-methoxy-7-methyl-1H-indol-4-yl)ethyl)-1H-benzo[d]imidazole-5-carbonitrile;

(−)-2-(1-hydroxy-1-(5-methoxy-7-methyl-1H-indol-4-yl)ethyl)-1H-benzo[d]imidazole-5-carbonitrile;

(+)-2-(1-(5-ethoxy-7-methyl-1H-indol-4-yl)-1-hydroxyethyl)-1H-benzo[d]imidazole-5-carbonitrile;

(−)-2-(1-(5-ethoxy-7-methyl-1H-indol-4-yl)-1-hydroxyethyl)-1H-benzo[d]imidazole-5-carbonitrile;

(+)-2-(1-hydroxy-1-(5-isopropoxy-7-methyl-1H-indol-4-yl)ethyl)-1H-benzo[d]imidazole-5-carbonitrile;

(−)-2-(1-hydroxy-1-(5-isopropoxy-7-methyl-1H-indol-4-yl)ethyl)-1H-benzo[d]imidazole-5-carbonitrile;

(+)-2-(1-hydroxy-1-(5-isopropoxy-7-methyl-1H-indol-4-yl)propyl)-1H-benzo[d]imidazole-5-carbonitrile;

(−)-2-(1-hydroxy-1-(5-isopropoxy-7-methyl-1H-indol-4-yl)propyl)-1H-benzo[d]imidazole-5-carbonitrile;

(+)-2-(1-(5-(cyclopropylmethoxy)-7-methyl-1H-indol-4-yl)-1-hydroxyethyl)-1H-benzo[d]imidazole-5-carbonitrile;

(−)-2-(1-(5-(cyclopropylmethoxy)-7-methyl-1H-indol-4-yl)-1-hydroxyethyl)-1H-benzo[d]imidazole-5-carbonitrile;

(+)-2-(1-methoxy-1-(5-methoxy-7-methyl-1H-indol-4-yl)ethyl)-1H-benzo[d]imidazole-5-carbonitrile;

(−)-2-(1-methoxy-1-(5-methoxy-7-methyl-1H-indol-4-yl)ethyl)-1H-benzo[d]imidazole-5-carbonitrile;

(±)-2-(1-(5-isopropoxy-7-methyl-1H-indol-4-yl)-1-methoxyethyl)-1H-benzo[d]imidazole-5-carbonitrile;

(+)-2-(cyclopropyl(methoxy)(5-methoxy-7-methyl-1H-indol-4-yl)methyl)-1H-benzo[d]imidazole-5-carbonitrile;

(−)-2-(cyclopropyl(methoxy)(5-methoxy-7-methyl-1H-indol-4-yl)methyl)-1H-benzo[d]imidazole-5-carbonitrile;

(+)-2-(($^2H_3$)methyl(methoxy)(5-methoxy-7-methyl-1H-indol-4-yl)methyl)-1H-benzo[d]imidazole-5-carbonitrile;

(−)-2-(($^2H_3$)methyl(methoxy)(5-methoxy-7-methyl-1H-indol-4-yl)methyl)-1H-benzo[d]imidazole-5-carbonitrile;

(+)-2-(1-($^2H_3$)methoxy-1-(5-methoxy-7-methyl-1H-indol-4-yl)ethyl)-1H-benzo[d]imidazole-5-carbonitrile;

(−)-2-(1-($^2H_3$)methoxy-1-(5-methoxy-7-methyl-1H-indol-4-yl)ethyl)-1H-benzo[d]imidazole-5-carbonitrile;

(+)-2-((3-chloro-5-methoxy-7-methyl-1H-indol-4-yl)(hydroxy)methyl)-1H-benzo[d]imidazole-6-carbonitrile;

(−)-2-((3-chloro-5-methoxy-7-methyl-1H-indol-4-yl)(hydroxy)methyl)-1H-benzo[d]imidazole-6-carbonitrile;

(−)-2-(1-(3-Chloro-5-methoxy-7-methyl-1H-indol-4-yl)-1-hydroxyethyl)-1H-benzo[d]imidazole-5-carbonitrile;

(+)-2-(1-(3-chloro-5-methoxy-7-methyl-1H-indol-4-yl)-1-hydroxyethyl)-1H-benzo[d]imidazole-5-carbonitrile;

(+)-2-(methoxy(5-methoxy-7-methyl-1H-indol-4-yl)methyl)-1H-benzo[d]imidazole-5-carbonitrile;

(−)-2-(methoxy(5-methoxy-7-methyl-1H-indol-4-yl)methyl)-1H-benzo[d]imidazole-5-carbonitrile;

(±)-2-((4-(1-(5-cyano-1H-benzo[d]imidazol-2-yl)-1-hydroxyethyl)-7-methyl-1H-indol-5-yl)oxy)acetamide;

(±)-2-((4-(1-(5-cyano-1H-benzo[d]imidazol-2-yl)-1-hydroxyethyl)-7-methyl-1H-indol-5-yl)oxy)acetic acid;

(+)-2-(2,2,2-trifluoro-1-hydroxy-1-(5-methoxy-7-methyl-1H-indol-4-yl)ethyl)-1H-benzo[d]imidazole-5-carbonitrile;

(−)-2-(2,2,2-trifluoro-1-hydroxy-1-(5-methoxy-7-methyl-1H-indol-4-yl)ethyl)-1H-benzo[d]imidazole-5-carbonitrile;

(+)-2-(1-(5-ethoxy-7-methyl-1H-indol-4-yl)-2,2,2-trifluoro-1-hydroxyethyl)-1H-benzo[d]imidazole-5-carbonitrile;

(−)-2-(1-(5-ethoxy-7-methyl-1H-indol-4-yl)-2,2,2-trifluoro-1-hydroxyethyl)-1H-benzo[d]imidazole-5-carbonitrile;

(±)-2-(2,2,2-trifluoro-1-hydroxy-1-(5-isopropoxy-7-methyl-1H-indol-4-yl)ethyl)-benzo[d]imidazole-5-carbonitrile;

(+)-2-(2,2,2-trifluoro-1-methoxy-1-(5-methoxy-7-methyl-1H-indol-4-yl)ethyl)-1H-benzo[d]imidazole-5-carbonitrile;

(−)-2-(2,2,2-trifluoro-1-methoxy-1-(5-methoxy-7-methyl-1H-indol-4-yl)ethyl)-1H-benzo[d]imidazole-5-carbonitrile;

(±)-Methyl 2-(1-(5-cyano-1H-benzo[d]imidazol-2-yl)-2,2,2-trifluoro-1-(5-methoxy-7-methyl-1H-indol-4-yl)ethoxy)acetate;

(+)-2-(1-(5-cyano-1H-benzo[d]imidazol-2-yl)-2,2,2-trifluoro-1-(5-methoxy-7-methyl-1H-indol-4-yl)ethoxy)acetic acid;

(−)-2-(1-(5-cyano-1H-benzo[d]imidazol-2-yl)-2,2,2-trifluoro-1-(5-methoxy-7-methyl-1H-indol-4-yl)ethoxy)acetic acid;

(+)-2-(1-amino-2,2,2-trifluoro-1-(5-methoxy-7-methyl-1H-indol-4-yl)ethyl)-1H-benzo[d]imidazole-5-carbonitrile;

(−)-2-(1-amino-2,2,2-trifluoro-1-(5-methoxy-7-methyl-1H-indol-4-yl)ethyl)-1H-benzo[d]imidazole-5-carbonitrile;

(±)-2-(1-amino-2,2,2-trifluoro-1-(5-isopropoxy-7-methyl-1H-indol-4-yl)ethyl)-1H-benzo[d]imidazole-5-carbonitrile;

(+)-2-(2,2,2-trifluoro-1-(5-methoxy-7-methyl-1H-indol-4-yl)-1-(methylamino)ethyl)-1H-benzo[d]imidazole-5-carbonitrile;

(−)-2-(2,2,2-trifluoro-1-(5-methoxy-7-methyl-1H-indol-4-yl)-1-(methylamino)ethyl)-1H-benzo[d]imidazole-5-carbonitrile;

(±)-2-(1-(dimethylamino)-2,2,2-trifluoro-1-(5-methoxy-7-methyl-1H-indol-4-yl)ethyl)-1H-benzo[d]imidazole-5-carbonitrile;

(+)-2-(amino(5-methoxy-7-methyl-1H-indol-4-yl)methyl)-1H-benzo[d]imidazole-5-carbonitrile;

(−)-2-(amino(5-methoxy-7-methyl-1H-indol-4-yl)methyl)-1H-benzo[d]imidazole-5-carbonitrile;

(±)-2-(amino(5-isopropoxy-7-methyl-1H-indol-4-yl)methyl)-1H-benzo[d]imidazole-5-carbonitrile;

(−)-2-(1-amino-1-(5-methoxy-7-methyl-1H-indol-4-yl)ethyl)-1H-benzo[d]imidazole-5-carbonitrile;

(+)-2-(1-amino-1-(5-methoxy-7-methyl-1H-indol-4-yl)ethyl)-1H-benzo[d]imidazole-5-carbonitrile;

(+)-2-(1-(5-methoxy-7-methyl-1H-indol-4-yl)-1-(methylamino)ethyl)-1H-benzo[d]imidazole-5-carbonitrile;

(−)-2-(1-(5-methoxy-7-methyl-1H-indol-4-yl)-1-(methylamino)ethyl)-1H-benzo[d]imidazole-5-carbonitrile;

(±)-2-((dimethylamino)(5-methoxy-7-methyl-1H-indol-4-yl)methyl)-1H-benzo[d]imidazole-5-carbonitrile;
(±)-2-(2-amino-1-(5-ethoxy-7-methyl-1H-indol-4-yl)ethyl)-1H-benzo[d]imidazole-5-carbonitrile;
(±)-2-(1-(5-ethoxy-7-methyl-1H-indol-4-yl)-2-(methylamino)ethyl)-1H-benzo[d]imidazole-5-carbonitrile;
2-((5,7-dimethyl-1H-indol-4-yl)methyl)-1H-benzo[d]imidazole-5-carbonitrile;
2-((5-(hydroxymethyl)-7-methyl-1H-indol-4-yl)methyl)-1H-benzo[d]imidazole-5-carbonitrile;
2-((5-(aminomethyl)-7-methyl-1H-indol-4-yl)methyl)-1H-benzo[d]imidazole-5-carbonitrile;
N-((4-((5-cyano-1H-benzo[d]imidazol-2-yl)methyl)-7-methyl-1H-indol-5-yl)methyl)acetamide;
2-((5,7-dimethyl-1H-indol-4-yl)methyl)-7-fluoro-1H-benzo[d]imidazole-5-carbonitrile;
2-((5-ethyl-7-methyl-1H-indol-4-yl)methyl)-1H-benzo[d]imidazole-5-carbonitrile;
2-((5-chloro-7-methyl-1H-indol-4-yl)methyl)-1H-benzo[d]imidazole-5-carbonitrile;
2-((5-vinyl-7-methyl-1H-indol-4-yl)methyl)-1H-benzo[d]imidazole-5-carbonitrile;
2-((5-methoxymethyl-7-methyl-1H-indol-4-yl)methyl)-1H-benzo[d]imidazole-5-carbonitrile;
2-((5,7-dimethyl-1H-indol-4-yl)methyl)-4-methyl-1H-benzo[d]imidazole-5-carbonitrile;
2-((5,7-dimethyl-1H-indol-4-yl)methyl)-6-fluoro-1H-benzo[d]imidazole-5-carbonitrile;
2-((5-ethyl-7-methyl-1H-indol-4-yl)methyl)-6-fluoro-1H-benzo[d]imidazole-5-carbonitrile;
6-chloro-2-((5,7-dimethyl-1H-indol-4-yl)methyl)-1H-benzo[d]imidazole-5-carbonitrile;
2-((5,7-dimethyl-1H-indol-4-yl)methyl)-6-methoxy-1H-benzo[d]imidazole-5-carbonitrile;
(+)-2-((5,7-dimethyl-1H-indol-4-yl)(hydroxy)methyl)benzo[d]imidazole-5-carbonitrile;
(−)-2-((5,7-dimethyl-1H-indol-4-yl)(hydroxy)methyl)benzo[d]imidazole-5-carbonitrile;
(+)-2-(hydroxy(5-(hydroxymethyl)-7-methyl-1H-indol-4-yl)methyl)-1H-benzo[d]imidazole-5-carbonitrile;
(−)-2-(hydroxy(5-(hydroxymethyl)-7-methyl-1H-indol-4-yl)methyl)-1H-benzo[d]imidazole-5-carbonitrile;
(+)-2-((5-(ethoxymethyl)-7-methyl-1H-indol-4-yl)(hydroxy)methyl)-1H-benzo[d]imidazole-5-carbonitrile;
(−)-2-((5-(ethoxymethyl)-7-methyl-1H-indol-4-yl)(hydroxy)methyl)-1H-benzo[d]imidazole-5-carbonitrile;
(+)-2-((5-ethyl-7-methyl-1H-indol-4-yl)(hydroxy)methyl)-1H-benzo[d]imidazole-5-carbonitrile;
(−)-2-((5-ethyl-7-methyl-1H-indol-4-yl)(hydroxy)methyl)-1H-benzo[d]imidazole-5-carbonitrile;
(±)-2-((5-cyclopropyl-7-methyl-1H-indol-4-yl)(hydroxy)methyl)-1H-benzo[d]imidazole-5-carbonitrile;
(+)-2-(hydroxy(5-(isobutyl)-7-methyl-1H-indol-4-yl)methyl)-1H-benzo[d]imidazole-5-carbonitrile;
(−)-2-(hydroxy(5-(isobutyl)-7-methyl-1H-indol-4-yl)methyl)-1H-benzo[d]imidazole-5-carbonitrile;
(+)-2-(hydroxy(5-isopropyl-7-methyl-1H-indol-4-yl)methyl)-1H-benzo[d]imidazole-5-carbonitrile;
(−)-2-(hydroxy(5-isopropyl-7-methyl-1H-indol-4-yl)methyl)-1H-benzo[d]imidazole-5-carbonitrile;
(+)-2-((5-chloro-7-methyl-1H-indol-4-yl)(hydroxy)methyl)-1H-benzo[d]imidazole-5-carbonitrile;
(−)-2-((5-chloro-7-methyl-1H-indol-4-yl)(hydroxy)methyl)-1H-benzo[d]imidazole-5-carbonitrile;
(±)-2-((5-bromo-7-methyl-1H-indol-4-yl)(hydroxy)methyl)-1H-benzo[d]imidazole-5-carbonitrile;
(+)-2-((5,7-dimethyl-1H-indol-4-yl)(hydroxy)methyl)-4-methyl-1H-benzo[d]imidazole-5-carbonitrile;
(−)-2-((5,7-dimethyl-1H-indol-4-yl)(hydroxy)methyl)-4-methyl-1H-benzo[d]imidazole-5-carbonitrile;
(±)-2-((5-cyclopropyl-7-methyl-1H-indol-4-yl)(hydroxy)methyl)-6-fluoro-1H-benzo[d]imidazole-5-carbonitrile;
(±)-2-((5,7-dimethyl-1H-indol-4-yl)(methoxy)methyl)-1H-benzo[d]imidazole-5-carbonitrile;
(±)-2-((5-cyano-1H-benzo[d]imidazol-2-yl)(5,7-dimethyl-1H-indol-4-yl)methoxy)acetic acid;
(+)-2-((5-ethyl-7-methyl-1H-indol-4-yl)(methoxy)methyl)-1H-benzo[d]imidazole-5-carbonitrile;
(−)-2-((5-ethyl-7-methyl-1H-indol-4-yl)(methoxy)methyl)-1H-benzo[d]imidazole-5-carbonitrile;
(+)-2-((5-isobutyl-7-methyl-1H-indol-4-yl)(methoxy)methyl)-1H-benzo[d]imidazole-5-carbonitrile;
(−)-2-((5-isobutyl-7-methyl-1H-indol-4-yl)(methoxy)methyl)-1H-benzo[d]imidazole-5-carbonitrile;
(±)-2-((5,7-dimethyl-1H-indol-4-yl)(ethoxy)methyl)-1H-benzo[d]imidazole-5-carbonitrile;
(±)-2-((5,7-dimethyl-1H-indol-4-yl)(2-methoxyethoxy)methyl)benzo[d]imidazole-5-carbonitrile;
(±)-2-(1-(5,7-dimethyl-1H-indol-4-yl)ethyl)-1H-benzo[d]imidazole-5-carbonitrile;
(+)-2-(1-(5,7-dimethyl-1H-indol-4-yl)-1-hydroxyethyl)-1H-benzo[d]imidazole-5-carbonitrile;
(−)-2-(1-(5,7-dimethyl-1H-indol-4-yl)-1-hydroxyethyl)-1H-benzo[d]imidazole-5-carbonitrile;
(+)-2-(1-(5-ethyl-7-methyl-1H-indol-4-yl)-1-hydroxyethyl)-1H-benzo[d]imidazole-5-carbonitrile;
(−)-2-(1-(5-ethyl-7-methyl-1H-indol-4-yl)-1-hydroxyethyl)-1H-benzo[d]imidazole-5-carbonitrile;
2-(5-ethyl-7-methyl-1H-indole-4-carbonyl)-1H-benzo[d]imidazole-5-carbonitrile;
(±)-2-(1-hydroxy-1-(7-methyl-5-propyl-1H-indol-4-yl)ethyl)-1H-benzo[d]imidazole-5-carbonitrile;
(+)-2-(1-hydroxy-1-(5-isopropyl-7-methyl-1H-indol-4-yl)ethyl)-1H-benzo[d]imidazole-5-carbonitrile;
(−)-2-(1-hydroxy-1-(5-isopropyl-7-methyl-1H-indol-4-yl)ethyl)-1H-benzo[d]imidazole-5-carbonitrile;
(+)-2-(1-(5-cyclopropyl-7-methyl-1H-indol-4-yl)-1-hydroxyethyl)-1H-benzo[d]imidazole-5-carbonitrile;
(−)-2-(1-(5-cyclopropyl-7-methyl-1H-indol-4-yl)-1-hydroxyethyl)-1H-benzo[d]imidazole-5-carbonitrile;
(+)-2-(1-hydroxy-1-(5-isobutyl-7-methyl-1H-indol-4-yl)ethyl)-1H-benzo[d]imidazole-5-carbonitrile;
(−)-2-(1-hydroxy-1-(5-isobutyl-7-methyl-1H-indol-4-yl)ethyl)-1H-benzo[d]imidazole-5-carbonitrile;
(+)-2-(1-(5-chloro-7-methyl-1H-indol-4-yl)-1-hydroxyethyl)-1H-benzo[d]imidazole-5-carbonitrile;
(−)-2-(1-(5-chloro-7-methyl-1H-indol-4-yl)-1-hydroxyethyl)-1H-benzo[d]imidazole-5-carbonitrile;
(+)-2-(1-(5-bromo-7-methyl-1H-indol-4-yl)-1-hydroxyethyl)-1H-benzo[d]imidazole-5-carbonitrile;
(−)-2-(1-(5-bromo-7-methyl-1H-indol-4-yl)-1-hydroxyethyl)-1H-benzo[d]imidazole-5-carbonitrile;
(±)-2-(1-(5,7-dimethyl-1H-indol-4-yl)-1-hydroxypropyl)-1H-benzo[d]imidazole-5-carbonitrile;
(±)-2-(cyclopropyl(5,7-dimethyl-1H-indol-4-yl)(hydroxy)methyl)-1H-benzo[d]imidazole-5-carbonitrile;
(±)-2-((5,7-dimethyl-1H-indol-4-yl)(hydroxy)(phenyl)methyl)-1H-benzo[d]imidazole-5-carbonitrile;
(+)-2-(1-(5-ethyl-7-methyl-1H-indol-4-yl)-2,2,2-trifluoro-1-hydroxyethyl)-1H-benzo[d]imidazole-5-carbonitrile;
(−)-2-(1-(5-ethyl-7-methyl-1H-indol-4-yl)-2,2,2-trifluoro-1-hydroxyethyl)-1H-benzo[d]imidazole-5-carbonitrile;

(+)-2-(1-(5-ethyl-7-methyl-1H-indol-4-yl)-1-methoxyethyl)-1H-benzo[d]imidazole-5-carbonitrile;
(−)-2-(1-(5-ethyl-7-methyl-1H-indol-4-yl)-1-methoxyethyl)-1H-benzo[d]imidazole-5-carbonitrile;
(+)-2-(1-(5-cyclopropyl-7-methyl-1H-indol-4-yl)-2,2,2-trifluoro-1-hydroxyethyl)-1H-benzo[d]imidazole-5-carbonitrile;
(−)-2-(1-(5-cyclopropyl-7-methyl-1H-indol-4-yl)-2,2,2-trifluoro-1-hydroxyethyl)-1H-benzo[d]imidazole-5-carbonitrile;
(+)-2-(2,2,2-trifluoro-1-hydroxy-1-(5-isopropyl-7-methyl-1H-indol-4-yl)ethyl)-1H-benzo[d]imidazole-5-carbonitrile;
(−)-2-(2,2,2-trifluoro-1-hydroxy-1-(5-isopropyl-7-methyl-1H-indol-4-yl)ethyl)-1H-benzo[d]imidazole-5-carbonitrile;
(±)-2-(2,2,2-trifluoro-1-hydroxy-1-(5-(hydroxymethyl)-7-methyl-1H-indol-4-yl)ethyl)-1H-benzo[d]imidazole-5-carbonitrile;
(±)-4-(1-(5-cyano-1H-benzo[d]imidazol-2-yl)-2,2,2-trifluoro-1-hydroxyethyl)-N,7-dimethyl-1H-indole-5-carboxamide;
(±)-2-(1-hydroxy-1-(7-methyl-5-(trifluoromethyl)-1H-indol-4-yl)ethyl)-1H-benzo[d]imidazole-5-carbonitrile;
(+)-2-(1-(5,7-dimethyl-1H-indol-4-yl)-1-methoxyethyl)-1H-benzo[d]imidazole-5-carbonitrile;
(−)-2-(1-(5,7-dimethyl-1H-indol-4-yl)-1-methoxyethyl)-1H-benzo[d]imidazole-5-carbonitrile;
(+)-2-(1-(5-ethyl-7-methyl-1H-indol-4-yl)-1-methoxyethyl)-1H-benzo[d]imidazole-5-carbonitrile;
(−)-2-(1-(5-ethyl-7-methyl-1H-indol-4-yl)-1-methoxyethyl)-1H-benzo[d]imidazole-5-carbonitrile;
(+)-2-(1-(5-ethyl-7-methyl-1H-indol-4-yl)-2,2,2-trifluoro-1-methoxyethyl)-1H-benzo[d]imidazole-5-carbonitrile;
(−)-2-(1-(5-ethyl-7-methyl-1H-indol-4-yl)-2,2,2-trifluoro-1-methoxyethyl)-1H-benzo[d]imidazole-5-carbonitrile;
(+)-2-(1-(5-isobutyl-7-methyl-1H-indol-4-yl)-1-methoxyethyl)-1H-benzo[d]imidazole-5-carbonitrile;
(−)-2-(1-(5-isobutyl-7-methyl-1H-indol-4-yl)-1-methoxyethyl)-1H-benzo[d]imidazole-5-carbonitrile;
2-((3-bromo-5,7-dimethyl-1H-indol-4-yl)methyl)-1H-benzo[d]imidazole-5-carbonitrile;
2-((3-chloro-5,7-dimethyl-1H-indol-4-yl)methyl)-1H-benzo[d]imidazole-5-carbonitrile;
(±)-2-((3-chloro-5-ethyl-7-methyl-1H-indol-4-yl)(hydroxy)methyl)-1H-benzo[d]imidazole-5-carbonitrile;
(+)-2-(1-(5-ethyl-7-methyl-3-(trifluoromethyl)-1H-indol-4-yl)-1-hydroxyethyl)-1H-benzo[d]imidazole-5-carbonitrile;
(±)-2-(hydroxy(3,5,7-trimethyl-1H-indol-4-yl)methyl)-1H-benzo[d]imidazole-5-carbonitrile;
2-((3-cyano-5-ethyl-7-methyl-1H-indol-4-yl)methyl)-1H-benzo[d]imidazole-5-carbonitrile;
(−)-2-((3-cyano-5-ethyl-7-methyl-1H-indol-4-yl)(methoxy)methyl)-1H-benzo[d]imidazole-5-carbonitrile;
(±)-2-((5-ethyl-7-methyl-3-(2,2,2-trifluoro-1-hydroxyethyl)-1H-indol-4-yl)methyl)-1H-benzo[d]imidazole-5-carbonitrile;
(+)-2-(5-hydroxy-6,8-dimethyl-1,3,4,5-tetrahydrobenzo[cd]indol-5-yl)-1H-benzo[d]imidazole-5-carbonitrile;
(−)-2-(5-hydroxy-6,8-dimethyl-1,3,4,5-tetrahydrobenzo[cd]indol-5-yl)-1H-benzo[d]imidazole-5-carbonitrile;
(+)-2-(6-ethyl-5-hydroxy-8-methyl-1,3,4,5-tetrahydrobenzo[cd]indol-5-yl)-1H-benzo[d]imidazole-5-carbonitrile;
(−)-2-(6-ethyl-5-hydroxy-8-methyl-1,3,4,5-tetrahydrobenzo[cd]indol-5-yl)-1H-benzo[d]imidazole-5-carbonitrile;
(+)-2-(amino(5,7-dimethyl-1H-indol-4-yl)methyl)-1H-benzo[d]imidazole-5-carbonitrile;
(−)-2-(amino(5,7-dimethyl-1H-indol-4-yl)methyl)-1H-benzo[d]imidazole-5-carbonitrile;
(+)-2-(amino(5-ethyl-7-methyl-1H-indol-4-yl)methyl)-1H-benzo[d]imidazole-5-carbonitrile;
(−)-2-(amino(5-ethyl-7-methyl-1H-indol-4-yl)methyl)-1H-benzo[d]imidazole-5-carbonitrile;
(+)-2-(amino(5-isopropyl-7-methyl-1H-indol-4-yl)methyl)-1H-benzo[d]imidazole-5-carbonitrile;
(−)-2-(amino(5-isopropyl-7-methyl-1H-indol-4-yl)methyl)-1H-benzo[d]imidazole-5-carbonitrile;
(±)-2-((5,7-dimethyl-1H-indol-4-yl)(methylamino)methyl)-1H-benzo[d]imidazole-5-carbonitrile;
(±)-N-((5-cyano-1H-benzo[d]imidazol-2-yl)(5,7-dimethyl-1H-indol-4-yl)methyl)methanesulfonamide;
(±)-N-((5-cyano-1H-benzo[d]imidazol-2-yl)(5,7-dimethyl-1H-indol-4-yl)methyl)acetamide;
(+)-2-(1-amino-1-(5,7-dimethyl-1H-indol-4-yl)ethyl)-1H-benzo[d]imidazole-5-carbonitrile;
(−)-2-(1-amino-1-(5,7-dimethyl-1H-indol-4-yl)ethyl)-1H-benzo[d]imidazole-5-carbonitrile;
(+)-2-(1-amino-1-(5-ethyl-7-methyl-1H-indol-4-yl)ethyl)-1H-benzo[d]imidazole-5-carbonitrile;
(−)-2-(1-amino-1-(5-ethyl-7-methyl-1H-indol-4-yl)ethyl)-1H-benzo[d]imidazole-5-carbonitrile;
(+)-2-(1-amino-1-(5-cyclopropyl-7-methyl-1H-indol-4-yl)ethyl)-1H-benzo[d]imidazole-5-carbonitrile;
(−)-2-(1-amino-1-(5-cyclopropyl-7-methyl-1H-indol-4-yl)ethyl)-1H-benzo[d]imidazole-5-carbonitrile;
(+)-2-(1-amino-1-(5-isopropyl-7-methyl-1H-indol-4-yl)ethyl)-1H-benzo[d]imidazole-5-carbonitrile;
(−)-2-(1-amino-1-(5-isopropyl-7-methyl-1H-indol-4-yl)ethyl)-1H-benzo[d]imidazole-5-carbonitrile;
(±)-2-(1-(5,7-dimethyl-1H-indol-4-yl)-1-(methylamino)ethyl)-1H-benzo[d]imidazole-6-carbonitrile;
(±)-2-(1-(5,7-dimethyl-1H-indol-4-yl)-1-(dimethylamino)ethyl)-1H-benzo[d]imidazole-5-carbonitrile;
(+)-2-(1-amino-1-(5-bromo-7-methyl-1H-indol-4-yl)-2,2,2-trifluoroethyl)-1H-benzo[d]imidazole-5-carbonitrile;
(−)-2-(1-amino-1-(5-bromo-7-methyl-1H-indol-4-yl)-2,2,2-trifluoroethyl)-1H-benzo[d]imidazole-5-carbonitrile;
(+)-2-(1-(5-bromo-7-methyl-1H-indol-4-yl)-2,2,2-trifluoro-1-(methylamino)ethyl)-1H-benzo[d]imidazole-5-carbonitrile;
(−)-2-(1-(5-bromo-7-methyl-1H-indol-4-yl)-2,2,2-trifluoro-1-(methylamino)ethyl)-1H-benzo[d]imidazole-5-carbonitrile;
(+)-2-(1-(5-ethyl-7-methyl-1H-indol-4-yl)-2,2,2-trifluoro-1-(methylamino)ethyl)-1H-benzo[d]imidazole-5-carbonitrile;
(−)-2-(1-(5-ethyl-7-methyl-1H-indol-4-yl)-2,2,2-trifluoro-1-(methylamino)ethyl)-1H-benzo[d]imidazole-5-carbonitrile;
(+)-2-(1-amino-1-(5-ethyl-7-methyl-1H-indol-4-yl)-2,2,2-trifluoroethyl)-1H-benzo[d]imidazole-5-carbonitrile;
(−)-2-(1-amino-1-(5-ethyl-7-methyl-1H-indol-4-yl)-2,2,2-trifluoroethyl)-1H-benzo[d]imidazole-5-carbonitrile;
(+)-2-(1-amino-1-(5-cyclopropyl-7-methyl-1H-indol-4-yl)-2,2,2-trifluoroethyl)-1H-benzo[d]imidazole-5-carbonitrile;
(−)-2-(1-amino-1-(5-cyclopropyl-7-methyl-1H-indol-4-yl)-2,2,2-trifluoroethyl)-1H-benzo[d]imidazole-5-carbonitrile;
(+)-2-(1-(5-cyclopropyl-7-methyl-1H-indol-4-yl)-2,2,2-trifluoro-1-(methylamino)ethyl)-1H-benzo[d]imidazole-5-carbonitrile;

(−)-2-(1-(5-cyclopropyl-7-methyl-1H-indol-4-yl)-2,2,2-trifluoro-1-(methylamino)ethyl)-1H-benzo[d]imidazole-5-carbonitrile;
(±)-2-(1-(5,7-dimethyl-1H-indol-4-yl)-2-hydroxyethyl)-1H-benzo[d]imidazole-5-carbonitrile;
(±)-2-(1-(5-cyano-1H-benzo[d]imidazol-2-yl)-1-(5-ethyl-7-methyl-1H-indol-4-yl)-2,2,2-trifluoroethoxy)acetic acid;
2-((7-chloro-5-methyl-1H-indol-4-yl)methyl)-1H-benzo[d]imidazole-5-carbonitrile;
2-((7-ethyl-5-methyl-1H-indol-4-yl)methyl)-1H-benzo[d]imidazole-5-carbonitrile;
2-((7-bromo-5-methyl-1H-indol-4-yl)methyl)-1H-benzo[d]imidazole-5-carbonitrile;
2-((7-(hydroxymethyl)-5-methyl-1H-indol-4-yl)methyl)-1H-benzo[d]imidazole-5-carbonitrile;
2-(1-(5-ethyl-7-methyl-1H-indol-4-yl)vinyl)-1H-benzo[d]imidazole-5-carbonitrile;
2-(1-(5-methoxy-7-methyl-1H-indol-4-yl)vinyl)-1H-benzo[d]imidazole-5-carbonitrile;
2-((5-ethyl-7-methyl-3-(1H-pyrazol-5-yl)-1H-indol-4-yl)methyl)-1H-benzo[d]imidazole-5-carbonitrile;
(±)-2-((5-ethyl-7-methyl-3-phenyl-1H-indol-4-yl)(hydroxy)methyl)-1H-benzo[d]imidazole-5-carbonitrile;
(+)-2-((5,7-dimethyl-3-phenyl-1H-indol-4-yl)(hydroxy)methyl)-1H-benzo[d]imidazole-5-carbonitrile;
(−)-2-((5,7-dimethyl-3-phenyl-1H-indol-4-yl)(hydroxy)methyl)-1H-benzo[d]imidazole-5-carbonitrile;
(+)-2-((5,7-dimethyl-3-(1-methyl-1H-pyrazol-4-yl)-1H-indol-4-yl)(hydroxy)methyl)-1H-benzo[d]imidazole-5-carbonitrile;
(−)-2-((5,7-dimethyl-3-(1-methyl-1H-pyrazol-4-yl)-1H-indol-4-yl)(hydroxy)methyl)-1H-benzo[d]imidazole-5-carbonitrile;
(+)-2-((5,7-dimethyl-3-(pyridin-3-yl)-1H-indol-4-yl)(hydroxy)methyl)-1H-benzo[d]imidazole-5-carbonitrile;
(−)-2-((5,7-dimethyl-3-(pyridin-3-yl)-1H-indol-4-yl)(hydroxy)methyl)-1H-benzo[d]imidazole-5-carbonitrile;
(±)-2-((5,7-dimethyl-3-(1H-pyrazol-5-yl)-1H-indol-4-yl)(hydroxy)methyl)-1H-benzo[d]imidazole-5-carbonitrile;
2-(2-(5-methoxy-7-methyl-1H-indol-4-yl)propan-2-yl)-1H-benzo[d]imidazole-5-carbonitrile;
2-((5,7-dimethylindolin-4-yl)methyl)-1H-benzo[d]imidazole-5-carbonitrile;
(+)-2-(1-methoxy-1-(5-methoxy-7-methylindolin-4-yl)ethyl)-1H-benzo[d]imidazole-5-carbonitrile;
(−)-2-(1-methoxy-1-(5-methoxy-7-methylindolin-4-yl)ethyl)-1H-benzo[d]imidazole-5-carbonitrile;
(+)-2-(hydroxy(5-methoxy-7-methyl-1H-indol-4-yl)methyl)benzo[d]oxazole-5-carbonitrile;
(−)-2-(hydroxy(5-methoxy-7-methyl-1H-indol-4-yl)methyl)benzo[d]oxazole-5-carbonitrile;
(+)-2-(1-hydroxy-1-(5-methoxy-7-methyl-1H-indol-4-yl)ethyl)benzo[d]oxazole-5-carbonitrile;
(−)-2-(1-hydroxy-1-(5-methoxy-7-methyl-1H-indol-4-yl)ethyl)benzo[d]oxazole-5-carbonitrile;
(+)-2-(1-methoxy-1-(5-methoxy-7-methyl-1H-indol-4-yl)ethyl)benzo[d]oxazole-5-carbonitrile;
(−)-2-(1-methoxy-1-(5-methoxy-7-methyl-1H-indol-4-yl)ethyl)benzo[d]oxazole-5-carbonitrile;
(+)-2-(2,2,2-trifluoro-1-hydroxy-1-(5-methoxy-7-methyl-1H-indol-4-yl)ethyl)benzo[d]oxazole-5-carbonitrile;
(−)-2-(2,2,2-trifluoro-1-hydroxy-1-(5-methoxy-7-methyl-1H-indol-4-yl)ethyl)benzo[d]oxazole-5-carbonitrile;
(±)-2-(1-(5-cyanobenzo[d]oxazol-2-yl)-2,2,2-trifluoro-1-(5-methoxy-7-methyl-1H-indol-4-yl)ethoxy)acetic acid;
(±)-2-(1-amino-2,2,2-trifluoro-1-(5-methoxy-7-methyl-1H-indol-4-yl)ethyl)benzo[d]oxazole-5-carbonitrile;
(+)-2-(1-amino-1-(5-methoxy-7-methyl-1H-indol-4-yl)ethyl)benzo[d]oxazole-5-carbonitrile;
(−)-2-(1-amino-1-(5-methoxy-7-methyl-1H-indol-4-yl)ethyl)benzo[d]oxazole-5-carbonitrile;
(±)-2-(hydroxy(5-methoxy-7-methyl-1H-indol-4-yl)methyl)benzo[d]thiazole-6-carbonitrile;
(±)-2-(hydroxy(5-methoxy-7-methyl-1H-indol-4-yl)methyl)benzofuran-6-carbonitrile;
(±)-2-(hydroxy(5-methoxy-7-methyl-1H-indol-4-yl)methyl)benzofuran-5-carbonitrile;
(±)-2-(hydroxy(5-methoxy-7-methyl-1H-indol-4-yl)methyl)-1H-indole-6-carbonitrile;
(±)-2-(hydroxy(5-methoxy-7-methyl-1H-indol-4-yl)methyl)-1H-indole-5-carbonitrile;
(+)-ethyl 2-(1-(5-cyano-1H-benzo[d]imidazol-2-yl)-2,2,2-trifluoro-1-(5-methoxy-7-methyl-1H-indol-4-yl)ethoxy)acetate;
(−)-ethyl 2-(1-(5-cyano-1H-benzo[d]imidazol-2-yl)-2,2,2-trifluoro-1-(5-methoxy-7-methyl-1H-indol-4-yl)ethoxy)acetate;
(±)-2-(1-(5-cyano-1H-benzo[d]imidazol-2-yl)-2,2,2-trifluoro-1-(5-methoxy-7-methyl-1H-indol-4-yl)ethoxy)-2-fluoroacetic acid;
(±)-2-(2,2,2-trifluoro-1-(5-methoxy-7-methyl-1H-indol-4-yl)-1-((5-methyl-1,3,4-oxadiazol-2-yl)methoxy)ethyl)-1H-benzo[d]imidazole-5-carbonitrile;
(+)-2-(6-methoxy-8-methyl-5-(trifluoromethyl)-1,3,4,5-tetrahydropyrrolo[4,3,2-de]isoquinolin-5-yl)-1H-benzo[d]imidazole-5-carbonitrile;
(−)-2-(1-((2-aminoethyl)amino)-2,2,2-trifluoro-1-(5-methoxy-7-methyl-1H-indol-4-yl)ethyl)-1H-benzo[d]imidazole-5-carbonitrile;
(+)-2-(1-((2-aminoethyl)amino)-2,2,2-trifluoro-1-(5-methoxy-7-methyl-1H-indol-4-yl)ethyl)-1H-benzo[d]imidazole-5-carbonitrile;
(±)-2-(1-(5-cyano-1H-benzo[d]imidazol-2-yl)-1-(5-cyclopropyl-7-methyl-1H-indol-4-yl)-2,2,2-trifluoroethoxy)acetic acid;
(+)-2-(1-amino-1-(5-bromo-7-methyl-1H-indol-4-yl)ethyl)-1H-benzo[d]imidazole-5-carbonitrile;
(−)-2-(1-amino-1-(5-bromo-7-methyl-1H-indol-4-yl)ethyl)-1H-benzo[d]imidazole-5-carbonitrile;
(+)-2-(1-amino-2,2,2-trifluoro-1-(5-methoxy-7-methyl-1H-indol-4-yl)ethyl)benzo[d]oxazole-5-carbonitrile;
(−)-2-(1-amino-2,2,2-trifluoro-1-(5-methoxy-7-methyl-1H-indol-4-yl)ethyl)benzo[d]oxazole-5-carbonitrile;
(±)-2-(hydroxy(5-methoxy-7-methyl-1H-indol-4-yl)methyl)benzo[d]thiazole-5-carbonitrile;
(±)-2-(1-amino-1-(5-methoxy-7-methyl-1H-indol-4-yl)ethyl)benzo[d]thiazole-5-carbonitrile;
(±)-2-(amino(5-methoxy-7-methyl-1H-indol-4-yl)methyl)benzo[d]thiazole-5-carbonitrile;
(+)-2-(1-amino-1-(5-ethyl-7-methyl-1H-indol-4-yl)ethyl)benzo[d]oxazole-5-carbonitrile;
(−)-2-(1-amino-1-(5-ethyl-7-methyl-1H-indol-4-yl)ethyl)benzo[d]oxazole-5-carbonitrile;
(±)-2-(1-amino-1-(6-fluoro-5-methoxy-7-methyl-1H-indol-4-yl)ethyl)-1H-benzo[d]imidazole-5-carbonitrile;
(±)-2-(1-(6-fluoro-5-methoxy-7-methyl-1H-indol-4-yl)-1-methoxyethyl)-1H-benzo[d]imidazole-6-carbonitrile;
(−)-2-(1-($^2H_3$)methoxy-1-(5-methoxy-7-methyl-1H-indol-4-yl)ethyl)-1H-benzo[d]imidazole-5-carbonitrile;
(+)-2-(1-($^2H_3$)methoxy-1-(5-methoxy-7-methyl-1H-indol-4-yl)ethyl)-1H-benzo[d]imidazole-5-carbonitrile;
(−)-2-(2,2,2-trifluoro-1-($^2H_3$)-methoxy-1-(5-methoxy-7-methyl-1H-indol-4-yl)ethyl)-1H-benzo[d]imidazole-5-carbonitrile;

(+)-2-(2,2,2-trifluoro-1-($^2$H$_3$)-methoxy-1-(5-methoxy-7-methyl-1H-indol-4-yl)ethyl)-1H-benzo[d]imidazole-5-carbonitrile;
(+)-2-(1-methoxy-1-(5-methoxy-7-methyl-1H-indol-4-yl)ethyl)benzo[d]oxazole-5-carbonitrile;
(−)-2-(1-methoxy-1-(5-methoxy-7-methyl-1H-indol-4-yl)ethyl)benzo[d]oxazole-5-carbonitrile;
(−)-2-(1-(5-cyclopropyl-7-methyl-1H-indol-4-yl)-1-methoxyethyl)benzo[d]oxazole-5-carbonitrile;
(+)-2-(1-(5-cyclopropyl-7-methyl-1H-indol-4-yl)-1-methoxyethyl)benzo[d]oxazole-5-carbonitrile;
(+) or (−)-2-(1-(5-methoxy-7-methyl-1H-indol-4-yl)-1-(methylamino)ethyl)benzo[d]oxazole-5-carbonitrile;
(−)-2-(1-hydroxy-1-(5-methoxy-7-methyl-1H-indol-4-yl)ethyl)benzo[d]oxazole-5-carbonitrile;
(+)-2-(1-hydroxy-1-(5-methoxy-7-methyl-1H-indol-4-yl)ethyl)benzo[d]oxazole-5-carbonitrile;
(±)-2-((5,7-dimethyl-1H-indol-4-yl)(hydroxy)methyl)benzo[d]thiazole-6-carbonitrile;
(±)-2-((5,7-dimethyl-1H-indol-4-yl)(hydroxy)methyl)-1H-indole-5-carbonitrile;
(±)-2-((5,7-dimethyl-1H-indol-4-yl)(hydroxy)methyl)benzofuran-5-carbonitrile;
(±)-2-((5,7-dimethyl-1H-indol-4-yl)(hydroxy)methyl)benzo[d]thiazole-5-carbonitrile;
(±)-2-(1-hydroxy-1-(5-methoxy-7-methyl-1H-indol-4-yl)ethyl)benzo[d]thiazole-6-carbonitrile;
(±)-2-(1-hydroxy-1-(5-methoxy-7-methyl-1H-indol-4-yl)ethyl)-1H-indole-6-carbonitrile;
(±)-2-(1-hydroxy-1-(5-methoxy-7-methyl-1H-indol-4-yl)ethyl)-1H-indole-5-carbonitrile;
(±)-2-(1-hydroxy-1-(5-methoxy-7-methyl-1H-indol-4-yl)ethyl)benzofuran-5-carbonitrile;
(±)-2-(1-methoxy-1-(5-methoxy-7-methyl-1H-indol-4-yl)ethyl)benzo[d]thiazole-6-carbonitrile;
(±)-2-(1-hydroxy-1-(5-methoxy-7-methyl-1H-indol-4-yl)ethyl)benzofuran-6-carbonitrile;
(±)-2-(1-methoxy-1-(5-methoxy-7-methyl-1H-indol-4-yl)ethyl)benzofuran-6-carbonitrile;
(±)-2-(1-methoxy-1-(5-methoxy-7-methyl-1H-indol-4-yl)ethyl)benzofuran-5-carbonitrile;
(±)-3-(1-(5-cyanobenzo[d]oxazol-2-yl)-2,2,2-trifluoro-1-(5-methoxy-7-methyl-1H-indol-4-yl)ethoxy)-2,2-dimethylpropanoic acid;
(±)-2-(2,2,2-trifluoro-1-((2-hydroxyethyl)amino)-1-(5-methoxy-7-methyl-1H-indol-4-yl)ethyl)-1H-benzo[d]imidazole-5-carbonitrile;
(±)-2-((1-(5-cyano-1H-benzo[d]imidazol-2-yl)-2,2,2-trifluoro-1-(5-methoxy-7-methyl-1H-indol-4-yl)ethyl)amino)acetic acid;
(+) or (−)-2-(1-amino-2,2,2-trifluoro-1-(5-hydroxy-7-methyl-1H-indol-4-yl)ethyl)-1H-benzo[d]imidazole-6-carbonitrile;
(±)-2-(5-cyano-1H-benzo[d]imidazol-2-yl)-2-(5-methoxy-7-methyl-1H-indol-4-yl)cyclopropanecarboxylic acid;
(±)-2-(5-cyanobenzo[d]oxazol-2-yl)-2-(5-methoxy-7-methyl-1H-indol-4-yl)cyclopropanecarboxylic acid;
(±)-ethyl 2-(5-cyanobenzo[d]oxazol-2-yl)-2-(5-methoxy-7-methyl-1H-indol-4-yl)propanoate;
(±)-3-(5-cyano-1H-benzo[d]imidazol-2-yl)-3-(5-methoxy-7-methyl-1H-indol-4-yl)propanoic acid;
(±)-2-(3-hydroxy-1-(5-methoxy-7-methyl-1H-indol-4-yl)propyl)-1H-benzo[d]imidazole-5-carbonitrile;
(±)-4-(5-cyano-1H-benzo[d]imidazol-2-yl)-4-(5-methoxy-7-methyl-1H-indol-4-yl)butanoic acid;
(±)-3-(5-cyano-1H-benzo[d]imidazol-2-yl)-3-(5-methoxy-7-methyl-1H-indol-4-yl)-2-methylpropanoic acid
(±)-2-(3-hydroxy-1-(5-methoxy-7-methyl-1H-indol-4-yl)-2-methylpropyl)-1H-benzo[d]imidazole-5-carbonitrile;
(−)-3-(5-cyanobenzo[d]oxazol-2-yl)-3-(5-methoxy-7-methyl-1H-indol-4-yl)propanoic acid;
(+)-3-(5-cyanobenzo[d]oxazol-2-yl)-3-(5-methoxy-7-methyl-1H-indol-4-yl)propanoic acid;
(+)-4-(5-cyanobenzo[d]oxazol-2-yl)-4-(5-methoxy-7-methyl-1H-indol-4-yl)butanoic acid;
(−)-4-(5-cyanobenzo[d]oxazol-2-yl)-4-(5-methoxy-7-methyl-1H-indol-4-yl)butanoic acid;
(±)-4-(5-cyanobenzo[d]oxazol-2-yl)-4-(5-methoxy-7-methyl-1H-indol-4-yl)pentanoic acid;
(±)-2-(4-hydroxy-1-(5-methoxy-7-methyl-1H-indol-4-yl)-3-methylbutyl)-1H-benzo[d]imidazole-5-carbonitrile;
(±)-2-(1-(5-methoxy-7-methyl-1H-indol-4-yl)-2-(2H-tetrazol-5-yl)ethyl)-1H-benzo[d]imidazole-5-carbonitrile;
(±)-2-(1-(5-methoxy-7-methyl-1H-indol-4-yl)-2-(2H-tetrazol-5-yl)ethyl)benzo[d]oxazole-5-carbonitrile;
(±)-2-(2-(5-methoxy-7-methyl-1H-indol-4-yl)-1-(2H-tetrazol-5-yl)propan-2-yl)benzo[d]oxazole-5-carbonitrile;
(±)-4-(5-cyano-1H-benzo[d]imidazol-2-yl)-4-(5-methoxy-7-methyl-1H-indol-4-yl)pentanoic acid;
(±)-3-(5-cyano-1H-benzo[d]imidazol-2-yl)-3-(5-methoxy-7-methyl-1H-indol-4-yl)butanoic acid;
(±)-5-(5-cyano-1H-benzo[d]imidazol-2-yl)-5-(5-methoxy-7-methyl-1H-indol-4-yl)pentanoic acid;
(±)-2-(1-(6-fluoro-5-methoxy-7-methyl-1H-indol-4-yl)-1-methoxyethyl)-1H-benzo[d]imidazole-5-carbonitrile;
(±)-3-(5-cyanobenzo[d]oxazol-2-yl)-3-(5-methoxy-7-methyl-1H-indol-4-yl)-2,2-dimethylpropanoic acid; and
salts, stereoisomers, racemates and tautomers thereof.

In another embodiment, the invention provides synthetic intermediate suitable for the preparation of compounds of Formula (I), (Ia), (II), (IIIa), (IIIb), (IVa), (IVb), (Va), and (Vb). The synthetic intermediates are selected from the group consisting of,

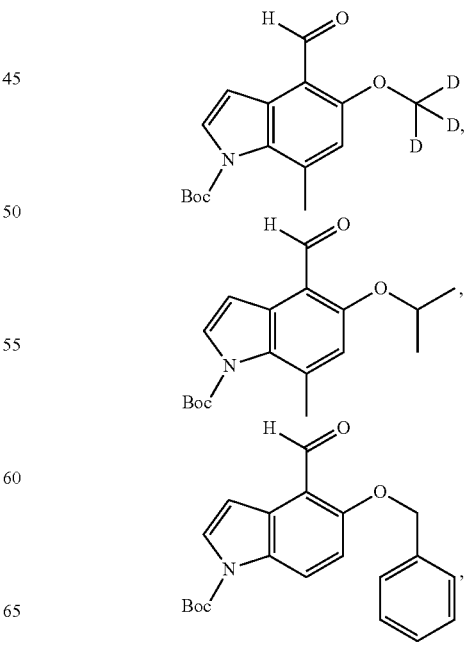

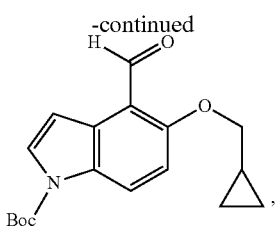
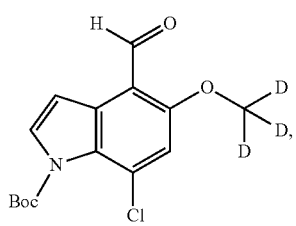
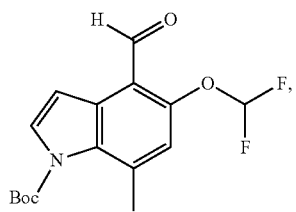
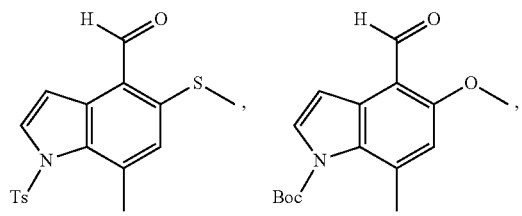
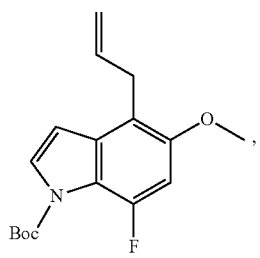
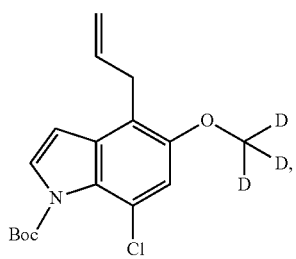
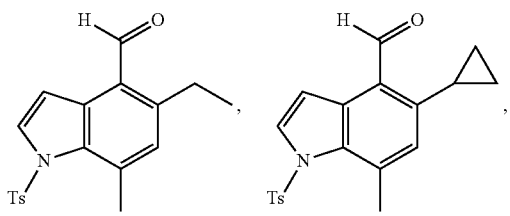

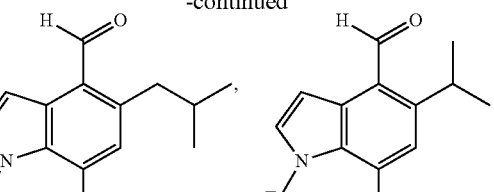
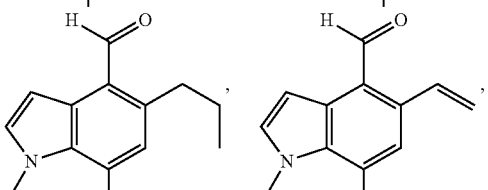
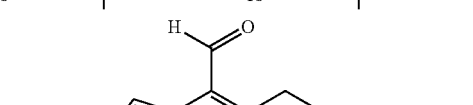
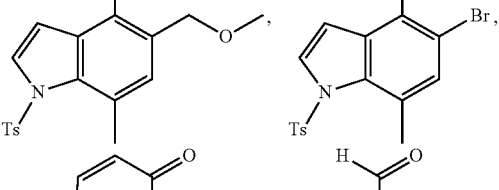
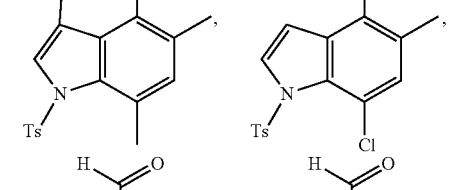
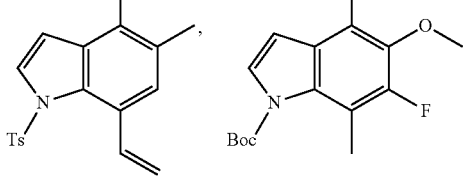

salts thereof.

In another embodiment, pharmaceutical compositions are provided which comprise one or more pharmaceutically acceptable carriers and a therapeutically effective amount of a compound of any one of formulae (I), (Ia), (II), (IIIa), (IIIb), (IVa), (IVb), (Va), and (Vb), or a subformulae thereof.

In another embodiment, combinations, in particular pharmaceutical combinations, are provided which comprise a therapeutically effective amount of the compound of any one of formulae (I), (Ia), (II), (IIIa), (IIIb), (IVa), (IVb), (Va), and (Vb), or a subformulae thereof.

In another embodiment, methods of modulating complement alternative pathway activity in a subject are provided which methods comprise administering to the subject a therapeutically effective amount of the compound of any one of formulae (I), (Ia), (II), (IIIa), (IIIb), (IVa), (IVb), (Va), and (Vb), or a subformulae thereof.

In yet other embodiments, methods of treating a disorder or a disease in a subject mediated by complement activation, in particular mediated by activation of the complement alternative pathway, are provided, which methods comprise administering to the subject a therapeutically effective amount of the compound of any one of formulae (I), (Ia), (II), (IIIa), (IIIb), (IVa), (IVb), (Va), and (Vb), or a subformulae thereof.

In another embodiment, methods of treating age related macular degeneration in a subject are provided which methods comprise administering to the subject a therapeutically effective amount of the compound of any one of formulae (I), (Ia), (II), (IIIa), (IIIb), (IVa), (IVb), (Va), and (Vb), or a subformulae thereof.

In another aspect, the invention provides for the use of compounds of any one of formulae (I), (Ia), (II), (IIIa), (IIIb), (IVa), (IVb), (Va), and (Vb), or a subformulae thereof for use in the preparation of a medicament and more particularly for use in the manufacture of a medicament for the treatment of a disorder or disease in a subject mediated by complement activation or activation of the complement alternative pathway. In certain other aspects, the invention provides for the use of a compound according to any one of formulae (I), (Ia), (II), (IIIa), (IIIb), (IVa), (IVb), (Va), and (Vb), or a subformulae thereof in the treatment of age-related macular degeneration.

In one embodiment, the invention provides a combination, in particular a pharmaceutical combination, comprising a therapeutically effective amount of the compound according to the definition of formula (I), (Ia), (II), (VII) or subformulae thereof or any one of the specifically disclosed compounds of the invention and one or more therapeutically active agents (preferably selected from those listed infra).

In another embodiment, the invention provides a compound of the formula:

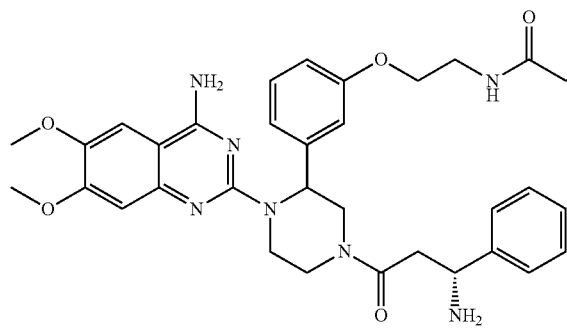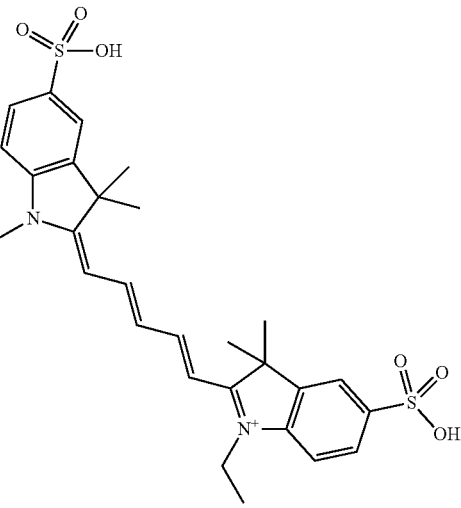

or salts, rotamers, diasteriomers or enantiomers thereof. The quinazoline compound of this embodiment is suitable for use in fluorescence based competitive binding assays to measure $IC_{50}$ values of factor B inhibitors such as compounds of any one of embodiments 1 to 20.

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety having up to 20 carbon atoms. Unless otherwise provided, alkyl refers to hydrocarbon moieties having 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "alkylene" refers to divalent alkyl group as defined herein above having 1 to 20 carbon atoms. It comprises 1 to 20 carbon atoms, Unless otherwise provided, alkylene refers to moieties having 1 to 16 carbon atoms, 1 to 10 carbon atoms, 1 to 7 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like.

As used herein, the term "haloalkyl" refers to an alkyl as defined herein, that is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

The term "aryl" refers to an aromatic hydrocarbon group having 6-20 carbon atoms in the ring portion. Typically, aryl is monocyclic, bicyclic or tricyclic aryl having 6-20 carbon atoms.

Furthermore, the term "aryl" as used herein, refers to an aromatic substituent which can be a single aromatic ring, or multiple aromatic rings that are fused together.

Non-limiting examples include phenyl, naphthyl or tetrahydronaphthyl, each of which may optionally be substituted by 1-4 substituents, such as alkyl, trifluoromethyl, cycloalkyl, halogen, hydroxy, alkoxy, acyl, alkyl-C(O)—O—, aryl-O—, heteroaryl-O—, amino, thiol, alkyl-S—, aryl-S—, nitro, cyano, carboxy, alkyl-O—C(O)—, carbamoyl, alkyl-S(O)—, sulfonyl, sulfonamido, phenyl, and heterocyclyl.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have about 1-7, more preferably about 1-4 carbons.

As used herein, the term "heterocyclyl" or "heterocyclo" refers to a saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

The term "heterocyclyl" further refers to heterocyclic groups as defined herein substituted with 1 to 5 substituents independently selected from the groups consisting of the following:
 (a) alkyl;
 (b) hydroxy (or protected hydroxy);
 (c) halo;
 (d) oxo, i.e., =O;
 (e) amino, alkylamino or dialkylamino;
 (f) alkoxy;
 (g) cycloalkyl;
 (h) carboxyl;
 (i) heterocyclooxy, wherein heterocyclooxy denotes a heterocyclic group bonded through an oxygen bridge;
 (j) alkyl-O—C(O)—;
 (k) mercapto;
 (l) nitro;
 (m) cyano;
 (n) sulfamoyl or sulfonamido;
 (o) aryl;
 (p) alkyl-C(O)—O—;
 (q) aryl-C(O)—O—;
 (r) aryl-S—;
 (s) aryloxy;
 (t) alkyl-S—;
 (u) formyl, i.e., HC(O)—;
 (v) carbamoyl;
 (w) aryl-alkyl-; and
 (x) aryl substituted with alkyl, cycloalkyl, alkoxy, hydroxy, amino, alkyl-C(O)—NH—, alkylamino, dialkylamino or halogen.

As used herein, the term "cycloalkyl" refers to saturated or unsaturated monocyclic, bicyclic or tricyclic hydrocarbon groups of 3-12 carbon atoms. Unless otherwise provided, cycloalkyl refers to cyclic hydrocarbon groups having between 3 and 9 ring carbon atoms or between 3 and 7 ring carbon atoms, each of which can be optionally substituted by one, or two, or three, or more substituents independently selected from the group consisting of alkyl, halo, oxo, hydroxy, alkoxy, alkyl-C(O)—, acylamino, carbamoyl, alkyl-NH—, (alkyl)$_2$N—, thiol, alkyl-S—, nitro, cyano, carboxy, alkyl-O—C(O)—, sulfonyl, sulfonamido, sulfamoyl, and heterocyclyl. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

As used herein, the term "aryloxy" refers to both an —O-aryl and an —O-heteroaryl group, wherein aryl and heteroaryl are defined herein.

As used herein, the term "heteroaryl" refers to a 5-14 membered monocyclic- or bicyclic- or tricyclic-aromatic ring system, having 1 to 8 heteroatoms selected from N, O or S. Typically, the heteroaryl is a 5-10 membered ring system (e.g., 5-7 membered monocycle or an 8-10 membered bicycle) or a 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4-aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

A heteroaryl group may be substituted with 1 to 5 substituents independently selected from the groups consisting of the following:
- (a) alkyl;
- (b) hydroxy (or protected hydroxy);
- (c) halo;
- (d) oxo, i.e., =O;
- (e) amino, alkylamino or dialkylamino;
- (f) alkoxy;
- (g) cycloalkyl;
- (h) carboxyl;
- (i) heterocyclooxy, wherein heterocyclooxy denotes a heterocyclic group bonded through an oxygen bridge;
- (j) alkyl-O—C(O)—;
- (k) mercapto;
- (l) nitro;
- (m) cyano;
- (n) sulfamoyl or sulfonamido;
- (o) aryl;
- (p) alkyl-C(O)—O—;
- (q) aryl-C(O)—O—;
- (r) aryl-S—;
- (s) aryloxy;
- (t) alkyl-S—;
- (u) formyl, i.e., HC(O)—;
- (v) carbamoyl;
- (w) aryl-alkyl-; and
- (x) aryl substituted with alkyl, cycloalkyl, alkoxy, hydroxy, amino, alkyl-C(O)—NH—, alkylamino, dialkylamino or halogen.

As used herein, the term "halogen" or "halo" refers to fluoro, chloro, bromo, and iodo.

As used herein, the term "optionally substituted" unless otherwise specified refers to a group that is unsubstituted or is substituted by one or more, typically 1, 2, 3 or 4, suitable non-hydrogen substituents, each of which is independently selected from the group consisting of:
- (a) alkyl;
- (b) hydroxy (or protected hydroxy);
- (c) halo;
- (d) oxo, i.e., =O;
- (e) amino, alkylamino or dialkylamino;
- (f) alkoxy;
- (g) cycloalkyl;
- (h) carboxyl;
- (i) heterocyclooxy, wherein heterocyclooxy denotes a heterocyclic group bonded through an oxygen bridge;
- (j) alkyl-O—C(O)—;
- (k) mercapto;
- (l) nitro;
- (m) cyano;
- (n) sulfamoyl or sulfonamido;
- (o) aryl;
- (p) alkyl-C(O)—O—;
- (q) aryl-C(O)—O—;
- (r) aryl-S—;
- (s) aryloxy;
- (t) alkyl-S—;
- (u) formyl, i.e., HC(O)—;
- (v) carbamoyl;
- (w) aryl-alkyl-; and
- (x) aryl substituted with alkyl, cycloalkyl, alkoxy, hydroxy, amino, alkyl-C(O)—NH—, alkylamino, dialkylamino or halogen.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. The asterisk (*) indicated in the name of a compound designate a racemic mixture. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. In certain compounds having one or more asymmetric centers, the stereoisomers are separated using chiral chromatography without absolute stereochemical identification of the (R) or (S) configuration and are uniquely identified based on the order of elution (with retention times given as $t_r$) from the chiral column (one of skill in the art could determine absolute stereochemistry using known techniques such as 2D NMR or crystallography). Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

All tautomeric forms are also intended to be included. In particular, the cyano substituted benzimidazoles of the invention may exist as a mixture of tautomeric forms, e.g., the 5-cyano-benzimidazole and 6-cyano-benzimidazole forms. Thus the N—H hydrogen may exchange between the ring nitrogens of the benzimidazole ring. These forms may interconvert at or above temperatures of about 0° C. For example, compounds of Formula (II) exist as a mixture of tautomeric forms which may readily interconvert at therapeutically relevant temperatures. For convenience, only one tautomeric form of the compounds are depicted in the instant application. However, one of ordinary skill in the art will recognize and appreciate that both tautomeric forms are contemplated to be within the scope of the invention.

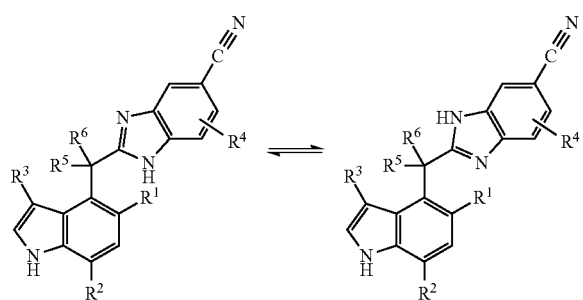

In addition, compounds of Formula (I) or subformulate thereof, in which $R^6$ is $CH_2R^9$ and $R^9$ is tetrazole are drawn in a single tautomeric form in the instant application. However, one of ordinary skill in the art will recognize and appreciate that all tautomeric forms are contemplated to be within the scope of the invention. For example, the compound of Example 152 is depicted as:

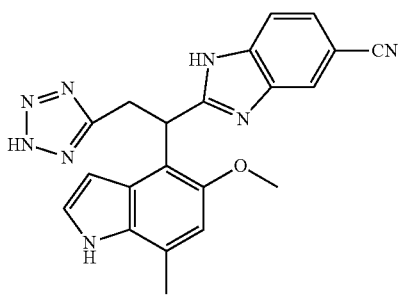 [SMILES: COc1cc(C)c2[nH]ccc2c1C(Cc1nn[nH]n1)c1nc2cc(C#N)ccc2[nH]1]

However, one of skill in the art will appreciate that this compound will exchange with tautomeric forms, i.e.,

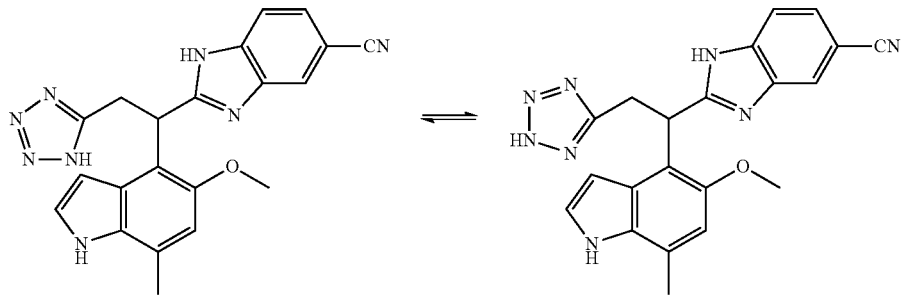 [SMILES: COc1cc(C)c2[nH]ccc2c1C(Cc1nnn[nH]1)c1nc2cc(C#N)ccc2[nH]1 ; COc1cc(C)c2[nH]ccc2c1C(Cc1nn[nH]n1)c1nc2cc(C#N)ccc2[nH]1]

As used herein, the term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts. Inorganic acids from which salts can be derived include, for example, hydrochloric acid, hydrobromic acid, sulfuric acid, nitric acid, and phosphoric acid. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of formula I in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in $C_1$-$C_4$alkyl sulfonic acid, benzenesulfonic acid or mono-, di- or tri-$C_1$-$C_4$alkyl substituted benzene sulfonic acid addition salt form.

In another aspect, the present invention provides (±)-2-(1-(6-fluoro-5-methoxy-7-methyl-1H-indol-4-yl)-1-methoxyethyl)-1H-benzo[d]imidazole-5-carbonitrile in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in $C_1$-$C_4$alkyl sulfonic acid, benzenesulfonic acid or mono-, di- or tri-$C_1$-$C_4$alkyl substituted benzene sulfonic acid addition salt form.

In another aspect, the present invention provides (−)-2-(1-(5-cyclopropyl-7-methyl-1H-indol-4-yl)-2,2,2-trifluoro-1-(methylamino)ethyl)-1H-benzo[d]imidazole-5-carbonitrile in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in $C_1$-$C_4$alkyl sulfonic acid, benzenesulfonic acid or mono-, di- or tri-$C_1$-$C_4$alkyl substituted benzene sulfonic acid addition salt form.

In another aspect, the present invention provides (±)-3-(5-cyano-1H-benzo[d]imidazol-2-yl)-3-(5-methoxy-7-methyl-1H-indol-4-yl)butanoic acid in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in $C_1$-$C_4$alkyl sulfonic acid, benzenesulfonic acid or mono-, di- or tri-$C_1$-$C_4$alkyl substituted benzene sulfonic acid addition salt form.

In another aspect, the present invention provides (±)-4-(5-cyano-1H-benzo[d]imidazol-2-yl)-4-(5-methoxy-7-methyl-1H-indol-4-yl)pentanoic acid in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in $C_1$-$C_4$alkyl sulfonic acid, benzenesulfonic acid or mono-, di- or tri-$C_1$-$C_4$alkyl substituted benzene sulfonic acid addition salt form.

In another aspect, the present invention provides (+) and (−)-2-(1-amino-2,2,2-trifluoro-1-(5-methoxy-7-methyl-1H-indol-4-yl)ethyl)benzo[d]oxazole-5-carbonitrile in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in $C_1$-$C_4$alkyl sulfonic acid, benzenesulfonic acid or mono-, di- or tri-$C_1$-$C_4$alkyl substituted benzene sulfonic acid addition salt form.

In another aspect, the present invention provides (±)-2-(1-amino-1-(6-fluoro-5-methoxy-7-methyl-1H-indol-4-yl)ethyl)-1H-benzo[d]imidazole-5-carbonitrile in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in $C_1$-$C_4$alkyl sulfonic acid, benzenesulfonic acid or mono-, di- or tri-$C_1$-$C_4$alkyl substituted benzene sulfonic acid addition salt form.

In another aspect, the present invention provides (−)-2-(1-amino-1-(5-methoxy-7-methyl-1H-indol-4-yl)ethyl)benzo[d]oxazole-5-carbonitrile in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in C₁-C₄alkyl sulfonic acid, benzenesulfonic acid or mono-, di- or tri-C₁-C₄alkyl substituted benzene sulfonic acid addition salt form.

In another aspect, the present invention provides (−)-2-(1-methoxy-1-(5-methoxy-7-methyl-1H-indol-4-yl)ethyl)-1H-benzo[d]imidazole-5-carbonitrile in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in C₁-C₄alkyl sulfonic acid, benzenesulfonic acid or mono-, di- or tri-C₁-C₄alkyl substituted benzene sulfonic acid addition salt form.

In another aspect, the present invention provides (+)-2-(1-hydroxy-1-(5-methoxy-7-methyl-1H-indol-4-yl)ethyl)-1H-benzo[d]imidazole-5-carbonitrile in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in C₁-C₄alkyl sulfonic acid, benzenesulfonic acid or mono-, di- or tri-C₁-C₄alkyl substituted benzene sulfonic acid addition salt form.

In another aspect, the present invention provides (−)-2-(1-amino-1-(5-ethyl-7-methyl-1H-indol-4-yl)ethyl)-1H-benzo[d]imidazole-5-carbonitrile in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in C₁-C₄alkyl sulfonic acid, benzenesulfonic acid or mono-, di- or tri-C₁-C₄alkyl substituted benzene sulfonic acid addition salt form.

In another aspect, the present invention provides (−)-2-(2,2,2-trifluoro-1-hydroxy-1-(5-methoxy-7-methyl-1H-indol-4-yl)ethyl)-1H-benzo[d]imidazole-5-carbonitrile in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in C₁-C₄alkyl sulfonic acid, benzenesulfonic acid or mono-, di- or tri-C₁-C₄alkyl substituted benzene sulfonic acid addition salt form.

In another aspect, the present invention provides (−)-2-(1-amino-2,2,2-trifluoro-1-(5-methoxy-7-methyl-1H-indol-4-yl)ethyl)-1H-benzo[d]imidazole-5-carbonitrile in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in C₁-C₄alkyl sulfonic acid, benzenesulfonic acid or mono-, di- or tri-C₁-C₄alkyl substituted benzene sulfonic acid addition salt form.

In another aspect, the present invention provides (−)-2-(1-amino-1-(5-methoxy-7-methyl-1H-indol-4-yl)ethyl)-1H-benzo[d]imidazole-5-carbonitrile in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds of formula I in C₁-C₄alkyl sulfonic acid, benzenesulfonic acid or mono-, di- or tri-C₁-C₄alkyl substituted benzene sulfonic acid addition salt form.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}F$, $^{32}F$, $^{35}S$, $^{36}Cl$, $^{125}I$ respectively. The invention includes various isotopically labeled compounds as defined herein, for example those into which radioactive isotopes, such as $^3H$, $^{13}C$, and $^{14}C$, are present. Such isotopically labeled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In certain embodiments, selective deuteration of compounds of Formula (I) include deuteration of $R^1$, $R^3$, $R^5$ and/or $R^6$, for example when any of $R^1$, $R^3$, $R^5$ and/or $R^6$ are methyl, methoxy, or ethoxy, the alkyl residue is preferably deuterated, e.g. $CD_3$, $OCD_3$ or $OC_2D_5$. when $R^3$ is alkanoyl, e.g., $C(O)CD_3$. Certain preferred deuterated compounds are provided in Examples 20-D, 22, 24-E, 27-E, 27-F.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

The compounds of the present invention may inherently or by design form solvates with solvents (including water). Therefore, it is intended that the invention embrace both solvated and unsolvated forms. The term "solvate" refers to a molecular complex of a compound of the present invention (including salts thereof) with one or more solvent molecules. Such solvent molecules are those commonly used in the pharmaceutical art, which are known to be innocuous to a recipient, e.g., water, ethanol, dimethylsulfoxide, acetone and other common organic solvents. The term "hydrate" refers to a molecular complex comprising a compound of the invention and water. Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder, or a disease or biological process (e.g., tissue regeneration and reproduction) (i) mediated by Factor B, or (ii) associated with Factor B activity, or (iii) characterized by activity (normal or abnormal) of the complement alternative pathway; or (2) reducing or inhibiting the activity of Factor B; or (3) reducing or inhibiting the expression of Factor B; or (4) reducing or inhibiting activation of the complement system and particularly reducing or inhibiting generation of C3a, iC3b, C5a or the membrane attack complex generated by activation of the complement alternative pathway. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of Factor B and/or the complement alternative pathway; or at least partially reducing or inhibiting the expression of Factor B and/or the complement alternative pathway. The meaning of the term "a therapeutically effective amount" as illustrated in the above embodiment for Factor B and/or the complement alternative pathway.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosauren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 250° C., including, for example, from approximately −80° C. to approximately 250° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin- 2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

The following Examples serve to illustrate the invention without limiting the scope thereof.

General Synthetic Aspects

The following Examples serve to illustrate the invention without limiting the scope thereof.

Typically, the compounds of formula (I) can be prepared according to the Schemes provided below.

Compounds such as 5, wherein PG is a protecting group (preferably Boc or Ts), $R^a$ is halo or alkyl, and $R^b$ is alkoxyl, and $F^a$ is hydrogen or fluoro can be prepared by the general method outlined in Scheme 1.

Scheme 1

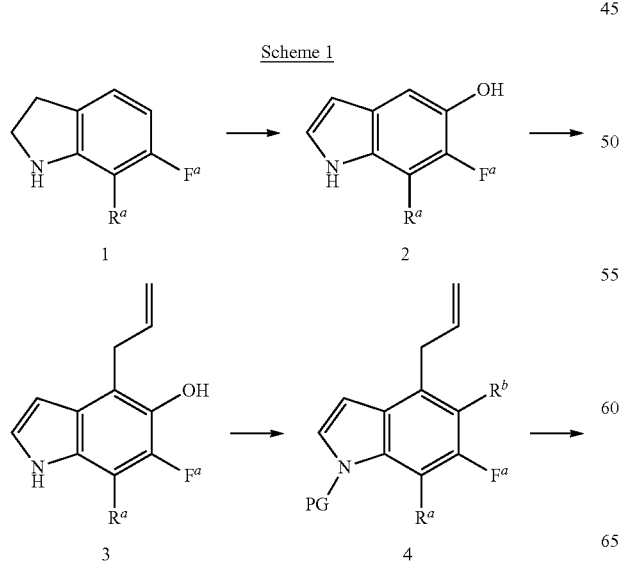

-continued

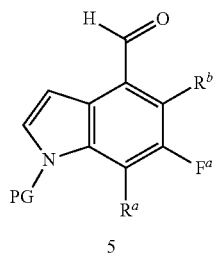

5

Transformation of indoline 1 to the corresponding 5-hydroxyindole 2 can be accomplished by treatment with potassium nitrosodisulfonate preferably in a solvent mixture of acetone/aq. buffer at pH=7 either at 0° C. or room temperature. The hydroxyl group of 2 can then be alkylated with allyl alcohol utilizing a Mitsunobu type reaction in a suitable solvent such as toluene. The product can then be converted to C-allyl derivatives such as 3 by thermally promoted sigmatropic rearrangement at temperatures between 200° C. and 250° C. without the use of solvent. Compound 3 can then be reacted with alcohols (e.g. MeOH, BnOH) utilizing Mitsunobu-type conditions permitting differentiation at $R^b$. Subsequent protection of the nitrogen of the indole employing TsCl and an appropriate base, preferably NaH, or alternatively with Boc$_2$O in the presence of a catalytic amount of DMAP can afford compounds such as 4. Isomerization of the double bond of 4 can be accomplished via treatment with Pd(OAc)$_2$ in hexafluoroisopropyl alcohol (HFIPA). Cleavage of the olefin can then be effected by reaction with osmium tetraoxide and sodium periodate to afford 5.

Compounds such as 5, wherein PG is a protecting group (preferably Boc), $R^a$ is alkyl, $R^b$ is alkoxyl, and $F^a$ is hydrogen can be also prepared by formylation of indole 5a using Vilsmeier-type reagents such as N-(chloromethylene)-N-methylbenzenaminium chloride in acetonitrile at temperatures between 0° C. and room temperature as shown in Scheme 1a.

Scheme 1a

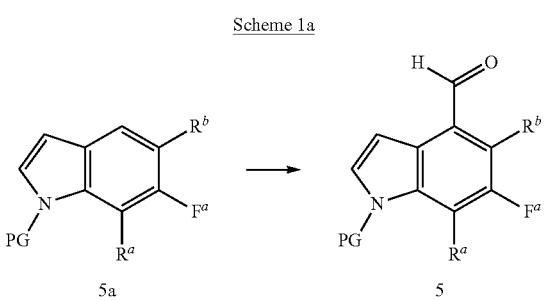

Compounds such as 10, wherein is $X^a$ is —Cl, —Br, or —SMe, can be prepared according to Scheme 2.

Scheme 2

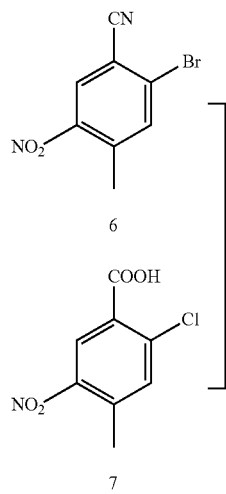

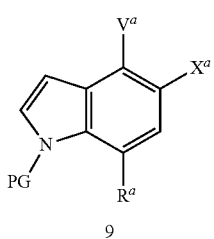 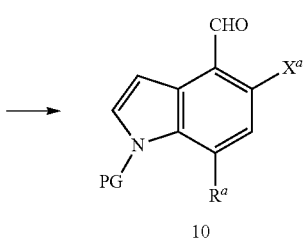

Nucleophilic aromatic substitution of 6 (CAS#1202858-65-8) can be achieved by sodium thiomethoxide in DMF at 60° C. to afford 8 ($X^a$=SMe). Alternatively, 7 (CAS#101580-96-5) can be transformed into 8 ($X^a$=Cl, $V^a$=CH$_2$OTHP) by reduction employing 1,1,1-trichloro-2-methylpropan-2-yl carbonochloridate and NaBH$_4$, followed by protection of the resulting hydroxyl with 3,4-dihydro-2H-pyran in the presence of TsOH. Transformation of 8 ($V^a$ is either —CN or —CH$_2$—OTHP) to the indole 9 can be achieved by Bartoli reaction using vinylmagnesium bromide in THF at temperatures ranging from –78° C. to room temperature, followed by protection of the indole. Protection can be effected by employing TsCl and an appropriate base preferably NaH, or alternatively protection can be accomplished with Boc$_2$O in the presence of a catalytic amount of DMAP. The aldehyde 10 can be accessed by when $V^a$=CN by reduction with DIBAL followed by acid hydrolysis preferably employing aq. HCl. Alternatively when $V^a$=CH$_2$OTHP 10 can be accessed by deprotection of the THP protecting group via acid mediated hydrolysis preferably employing TsOH in EtOH, followed by oxidation preferably using MnO$_2$ or SO$_3$-pyridine complex.

Compounds such as 14, wherein $R^c$ is alkyl and $R^d$ is —CH$_2$O-alkyl, or CH$_2$-phthaloyl, can be prepared according to Scheme 3.

Scheme 3

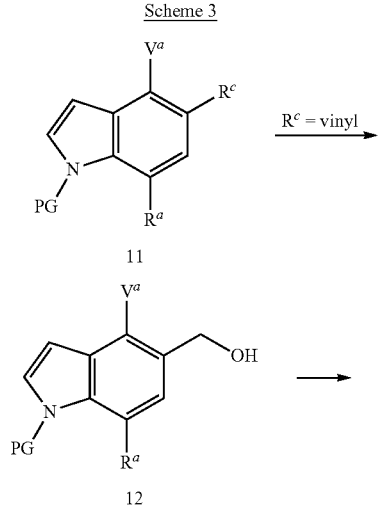

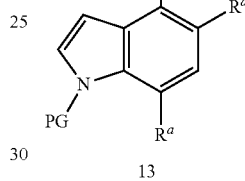 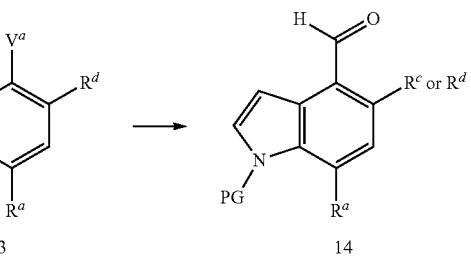

Indole 9 ($X^2$=Cl or Br, $V^a$=CN or CH$_2$OTHP) can be transformed to 11 wherein $R^c$=alkyl or vinyl utilizing a Suzuki-coupling with an appropriate boronate (such as alkyl trifluoroborates, or 2,4,6-trivinylcyclotriboroxane-pyridine complex). Alternatively a Negishi-type coupling employing an alkylzinc halide can be used in place of the Suzuki reaction. When $R^c$=vinyl 11 can be further transformed into 12 by a dihydroxylation preferably employing ADmix-α, followed by oxidative cleavage using NaIO$_4$ and reduction of the resulting aldehyde with NaBH$_4$. Alkylation of the hydroxyl group of 12 can be achieved by deprotonation with an appropriate base, preferably NaH, and reaction with an appropriate electrophile such as MeI or SEM-Cl to afford 13. Alternatively 12 can undergo Mitsunobu reaction with phthalimide. Lastly, indoles of type 13 can be converted to 14 in accordance with Scheme 2 (i.e. 9→10).

Aldehydes such as 18 or 19 can be prepared as described in Scheme 4.

Scheme 4

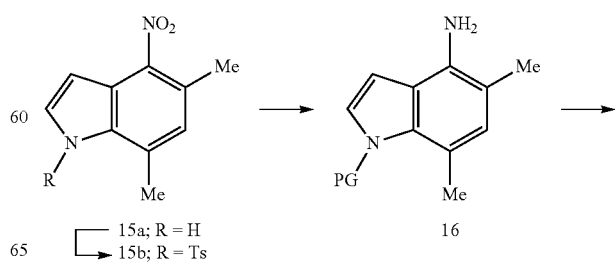

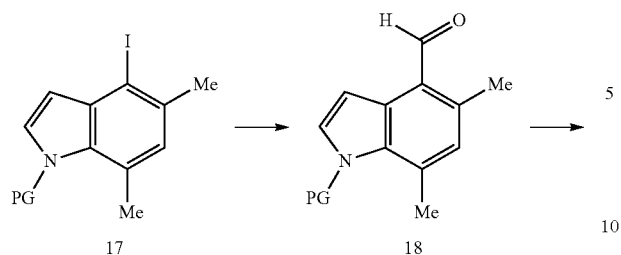
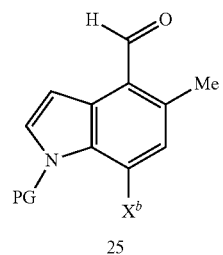

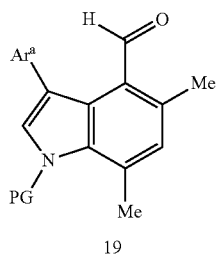

Indole 15a (CAS#1190314-35-2) can be protected by employing TsCl and an appropriate base preferably NaH to afford 15b. Reduction of the nitro functionality preferably by employing zinc metal in a solvent mixture of EtOAc/MeOH can afford aniline 16, which can be converted to iodide 17 upon treatment with NaNO$_2$, followed by I$_2$. Treatment of 17 with butyl lithium in the presence of DMF can provide the aldehyde 18. Further elaboration can be accomplished by employing NBS to effect bromination of the indole, followed by Suzuki-coupling with an appropriate aryl or heteroaryl boronate.

Compounds such 25 where $X^b$=Cl, Br can be prepared by the sequence described in Scheme 5.

Indole 20a (CAS#4769-97-5) can be protected by employing TsCl and an appropriate base preferably NaH to afford 20b. Reduction of the nitro functionality of 20b preferably employing zinc metal in a solvent mixture of EtOAc/MeOH followed by bromination preferably with NBS can afford 21. Boc protection of the aniline 21 followed by Suzuki-coupling using potassium methyltrifluoroborate can afford 22. Acid mediated deprotection of the Boc group of 22, followed by halogenation using NBS or NCS can yield halides of type 23. Transformation of the aniline 23 to aldehyde 25 can be accomplished in accordance with Scheme 4 (i.e. 17418).

Heterocycles of type 26 wherein: $W^a$ is N-SEM, O, or S; Q is N or CH, $Y^a$ and $Z^a$ can be H, halo, or nitrile, but at least either $Y^a$ or $Z^a$ is a nitrile; $R^f$ is halo or alkyl or H; can be employed to access compounds such as 28 as outlined in Scheme 6.

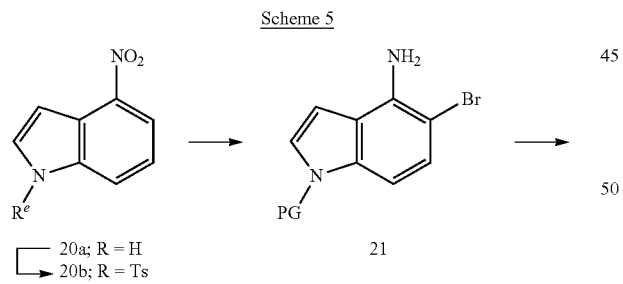

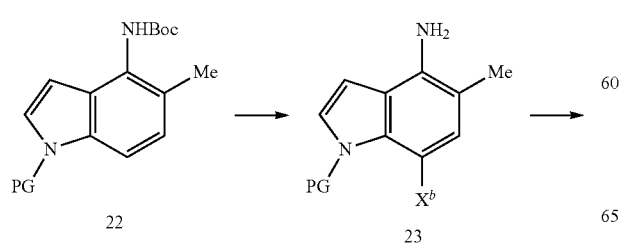

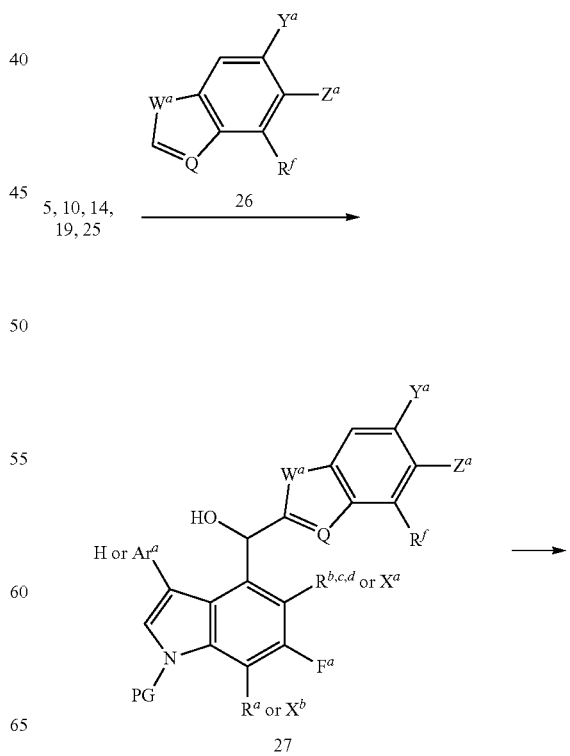

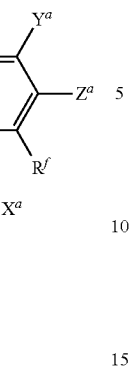

28

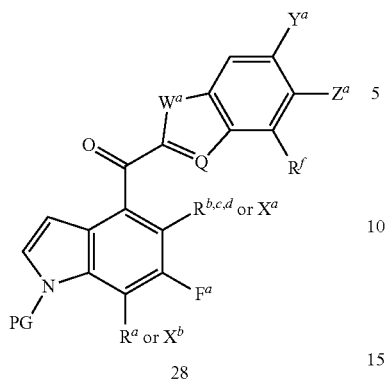

30

Nucleophilic addition of 26 into aldehydes of type 5, 10, 14, 19, 25 can be achieved with an appropriate base preferably LDA at temperatures between 0° C. and −78° C. Particularly, when 26 is a benzoxazole ($W^a$=O, Q=N) the addition can be achieved by employing TMPMgCl-LiCl complex (CAS#898838-07-8) as a base at temperatures between 0° C. and −78° C., with −78° C. being preferred, followed by warming up to the temperatures between room temperature and 70° C. Oxidation of the resulting hydroxyl group of 27 can be achieved by using an oxidant such as $MnO_2$ to afford ketones of type 28.

Compounds such as 30, wherein $R^g$ is alkyl, aryl or $CF_3$ and $R^h$ is alkyl, or substituted alkyl, can be prepared by the general method outlined in Scheme 7.

Ketones of type 28 can afford alcohols of type 29 by addition of an appropriate nucleophile, preferably a Grignard reagent. Alternatively, $CF_3$-TMS can be employed in the presence of a fluoride source such as TBAF. 29 can be further elaborated via alkylation of the hydroxyl with an appropriate electrophile such as MeI or methyl bromoacetate in the presence of strong base preferably NaH to furnish compounds of type 30.

Alkenes of type 31 can be prepared by treatment of the tertiary alcohol 29 ($R^g$=Me) with MsCl in the presence of base such as $Et_3N$ and catalytic amount of DMAP at 0° C., followed by warming to room temperature as shown in Scheme 8.

Scheme 7

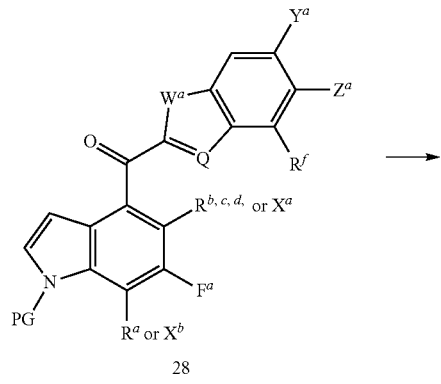

28

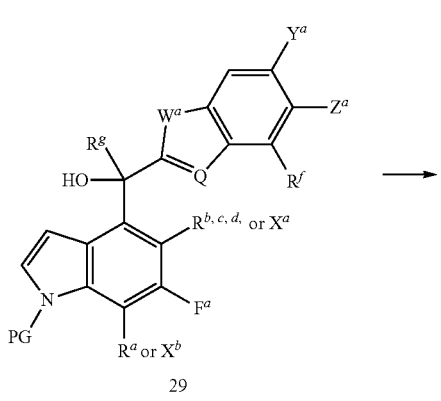

29

Scheme 8

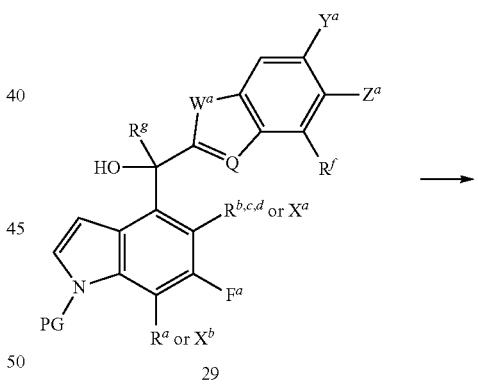

29


31

Compounds such as 32 ($R^b$=alkoxy) can be prepared by hydrogenolysis of compounds of type 29a where in $R^b$=–OBn in Scheme 7, followed by alkylation with an appropriate electrophile (e.g. MeI or BrCH$_2$COOMe) in the presence of a suitable base such as Cs$_2$CO$_3$ as shown in Scheme 9.

Scheme 9

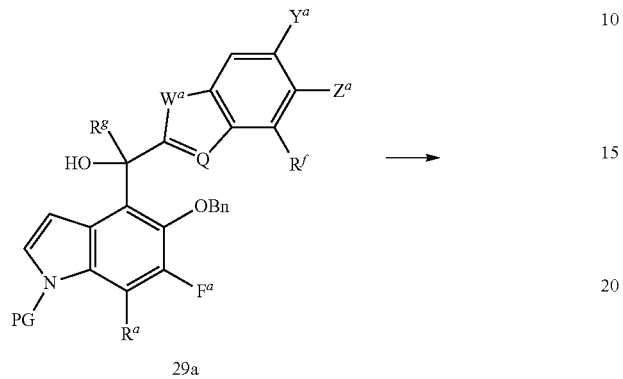

29a

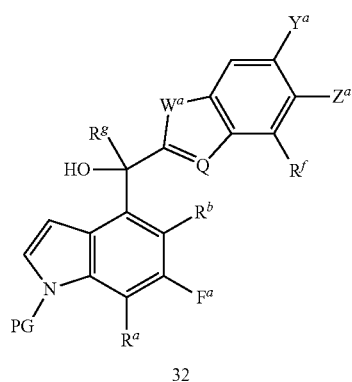

32

Compound such as 34, wherein $R^g$ is equal to H or alkyl or CF$_3$, can be prepared as described in Scheme 10.

Scheme 10

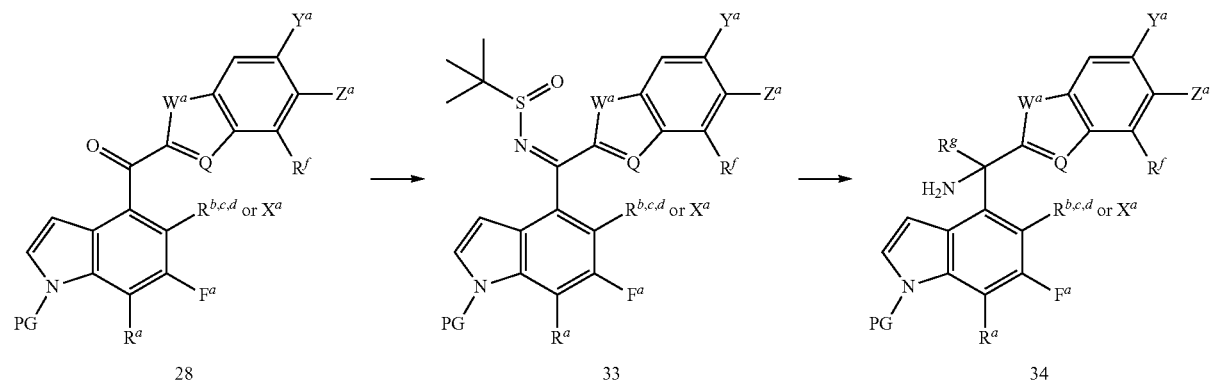

28    33    34

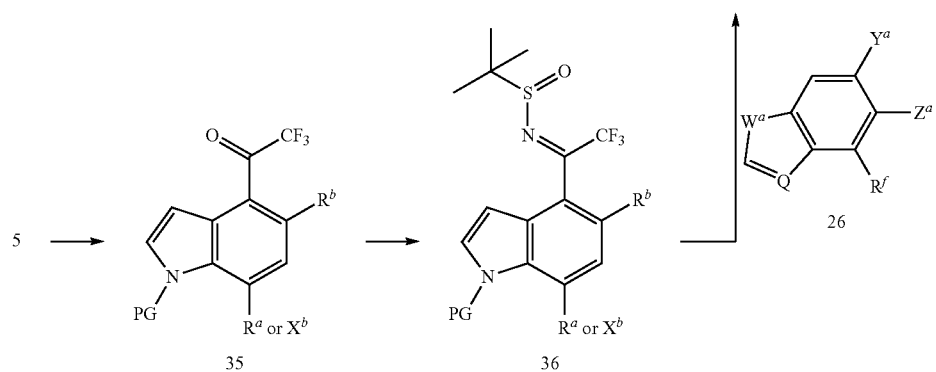

35    36

The ketone 28 wherein can be transformed into the sulfinyl imine 33 by employing a dehydrating reagent such Ti(O-i-Pr$_4$) in the presence of tert-butyl sulfinamide without the need for additional solvent. Alternatively, the dehydration can be achieved by utilizing Zr(O-t-Bu)$_4$ in a suitable solvent such as toluene. The sulfinyl imine 33 can be reacted with a suitable organometallic nucleophile such as MeMgI, followed by treatment with HCl in MeOH to furnish 34. Alternatively, 33 can be reduced with NaBH$_4$ in MeOH to afford compounds wherein R$^g$=H, and the resulted sulfinyl group can then be removed by treatment with HCl in MeOH to afford 34. Compounds such as 34 wherein R$^g$=CF$_3$, especially when W$^a$=O can be accessed by reacting 33 with trifluoromethyltriethylsilane in presence of tetramethylammonium fluoride in THF at temperatures between 0° C. and room temperature, followed by removal of the sulfinyl group by treatment with HCl in MeOH.

Compounds such 34, wherein R$^g$ is CF$_3$, can also be prepared starting from aldehydes such as 5. For example, treating 5 with trifluoromethyltrimethylsilane in presence of TBAF in THF at temperatures between 0° C. and room temperature, followed by oxidation using for example Dess-Martin Periodinane (CAS#87413-09-0) in DCM can afford ketone 35. Ketone 35 can be transformed into the sulfinyl imine 36 by employing a dehydrating reagent such Ti(O-i-Pr$_4$) in the presence of tert-butyl sulfinamide without the need for additional solvent. Alternatively, the dehydration can be achieved by utilizing Zr(O-t-Bu)$_4$ in a suitable solvent such as toluene. Nucleophilic addition of 26 into sulfinyl imine 36 can be achieved, especially when Q=N and W$^a$=N-SEM, with an appropriate base preferably LDA at temperatures between 0° C. and −78° C. Removal of sulfinyl group to provide 34 can be accomplished by treatment with HCl in MeOH. Using enantiomerically pure (R) or (S)-tert-butyl sulfinamide in the reaction with ketone 28 or ketone 35 leads to non racemic chiral sulfinyl imine 33 and 36 respectively. Addition of 26 into non racemic chiral sulfinyl imine 36 can be achieved, especially when Q=N and W$^a$=N-SEM, with an appropriate base, preferably LDA, at temperatures between 0° C. and −78° C. leading to high level of diastereoselectivity (>95:5) of the addition product. Addition of a suitable organometallic nucleophile such as MeMgI to non racemic chiral sulfinyl imine 33 at temperatures between 0° C. and −78° C., followed by treatment with HCl in MeOH furnishes high level of enantioenrichment (>95:5) of 34 especially if Q=N and W$^a$=N-SEM.

Compound such as 37 wherein R$^h$ is Me, —Ac, or Ms can be prepared according to Scheme 11.

Scheme 11

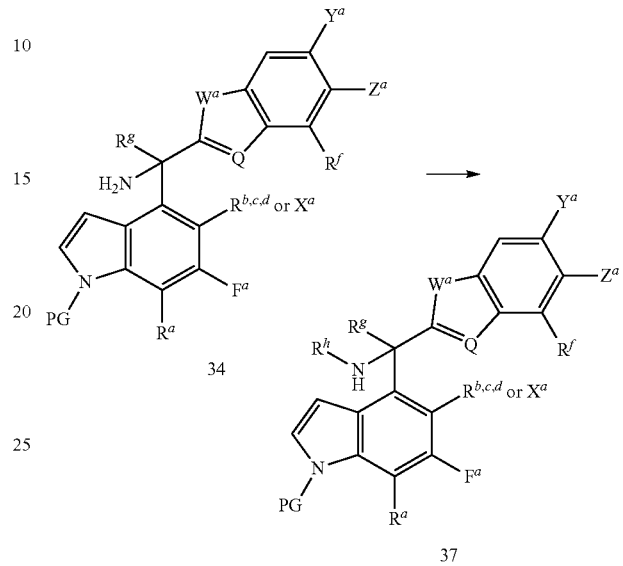

Amine 34 (when R$^g$=H) can be reacted with a variety of electrophiles such as MeI, MsCl, AcCl in the presence of an appropriate base (e.g. DIPEA) to furnish 37 wherein R$^g$=H. Alternatively, when R$^g$=Me the amine in 34 can be first protected utilizing neat Boc$_2$O at 60° C. Then alkylation can be accomplished with MeI in the presence of a strong base preferably NaH. Subsequent acid promoted Boc removal can provide 37 wherein R$^g$ and R$^h$=Me.

Compound such as 41, wherein W$^b$ is NH or O, can be prepared by the general method outlined in Scheme 12.

Scheme 12

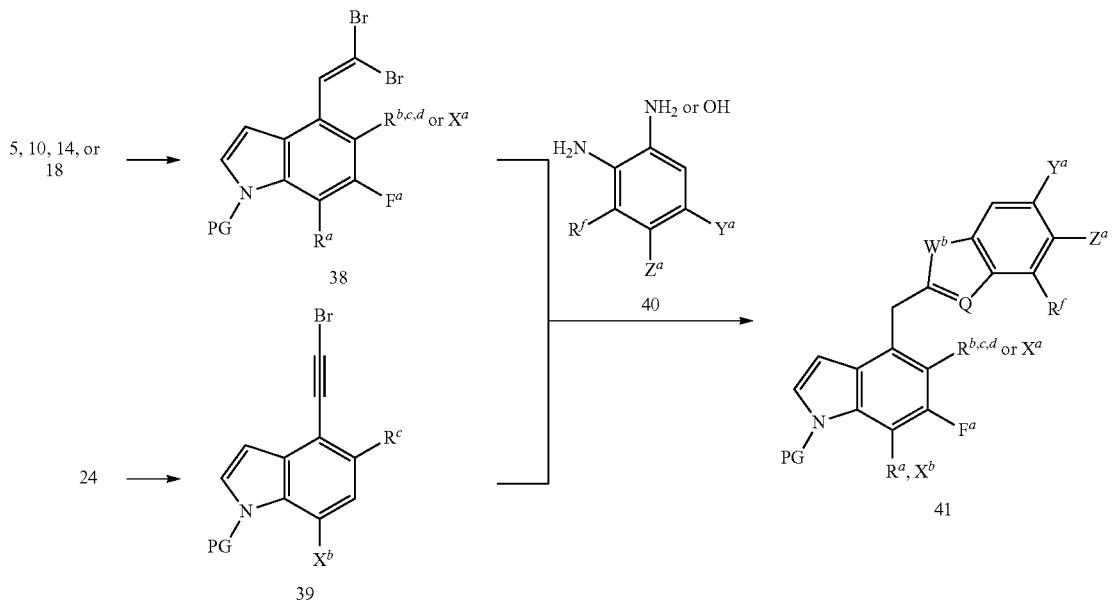

Compounds of the type 38 can be obtained by transformation of aldehydes such as 5, 10, 14 and 18 by employing PPh₃ and CBr₄. Coupling between 38 and 40 can then be accomplished utilizing DABCO as a base in a suitable solvent such as N-methylpyrrolidone at the temperature between 100° C. and 120° C. to afford 41. Alternatively, Sonogashira-type coupling with iodides of type 24 and TMS-acetylene, followed by treatment with NBS can afford bromoalkynes such as 39. Coupling between 39 and 40 can then be accomplished utilizing DABCO as a base in a suitable solvent such as N-methylpyrrolidinone at the temperature between 100° C. and 120° C. to afford 41.

Compounds such as 43, wherein R' is $NH_2$ or N-alkyl, can be prepared as described in Scheme 13.

42 with $SOCl_2$ in the presence of a catalytic amount of DMF in $CH_3Cl$ at 60° C. followed by reaction with alcoholic solutions of amines such 2M ammonia in EtOH or 33% methylamine in EtOH can furnish amines of type 43.

Compounds of type 46, wherein: $W^a$ is N-SEM, O, or S ($W^c$ is N—H, O or S); Q is N or CH, $R^j$ is equal to H or $R^g$ ($R^g$ is alkyl, aryl or $CF_3$), $R^k$ is OH, $OR^h$, $NH_2$, $NHR^h$ ($R^h$ is Me, –Ac, or –Ms); or $R^j$ and $R^k$ taken together to give $=CH_2$ or $=O$; or $R^j=R^k=H$: can be obtained by deprotections outlined in Scheme 14.

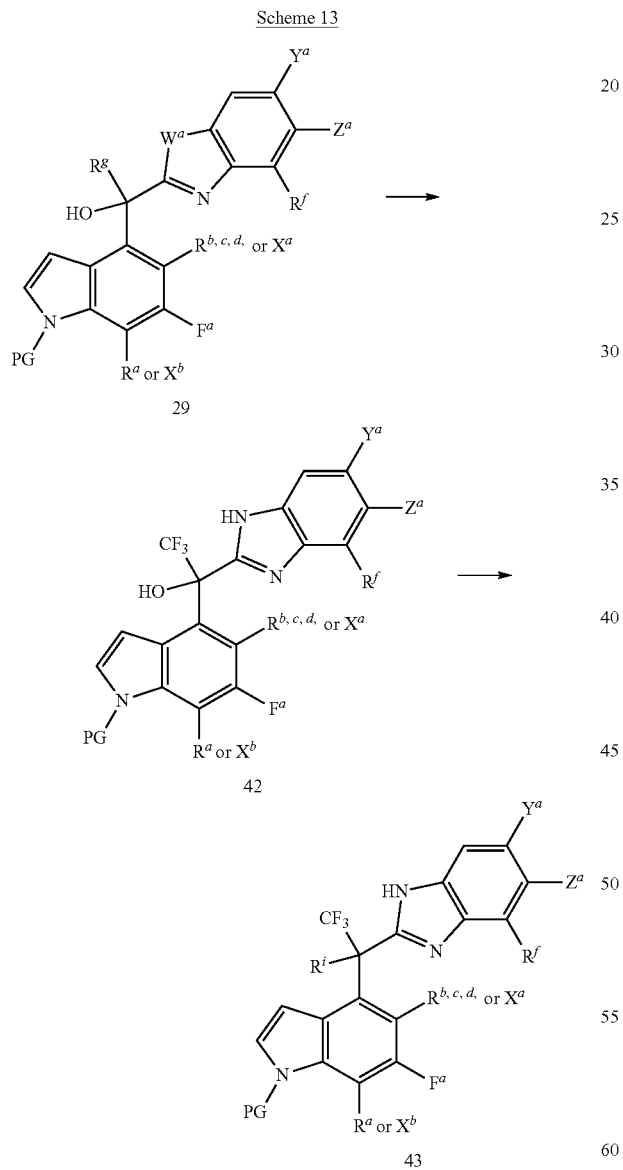

Scheme 13

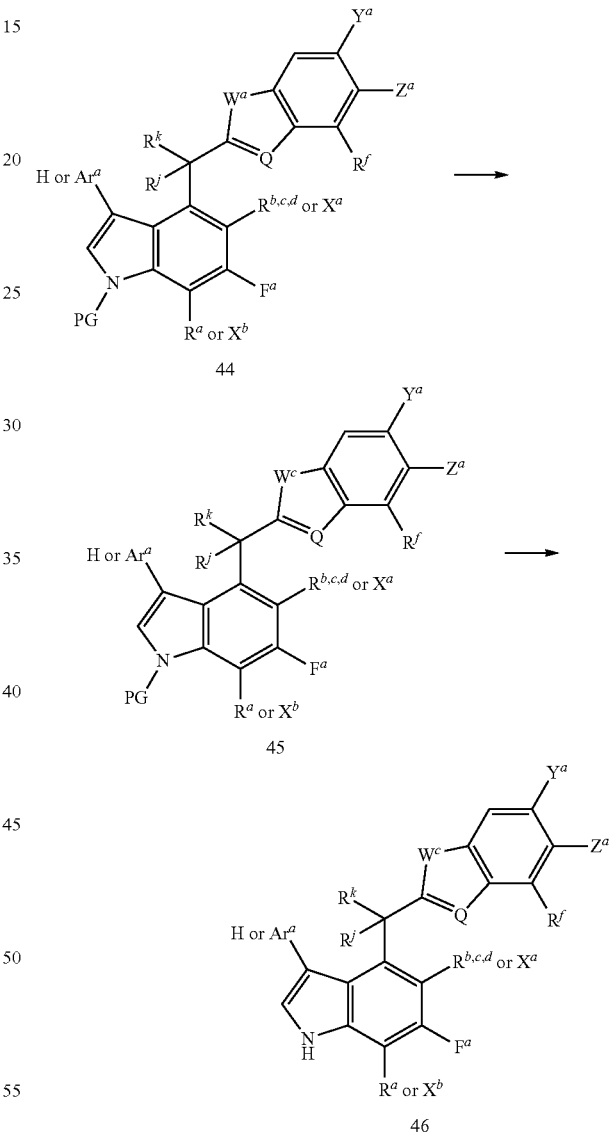

Scheme 14

Removal of the SEM group from 29 ($W^a$=N-SEM, $R^g$=$CF_3$) to provide 42 can be accomplished by treatment with HCl in MeOH at 60° C., or by employing TBAF in the presence of ethylenediamine in THF at temperatures between room temperature and 70° C. preferably 60° C. Treatment of Deprotection of compound 44 (which process is also suitable for deprotection of other compounds of the invention such as 28, 30, 31, 32, 34, 37, 41, 43 supra) is shown here. Removal of the SEM group of 44 when $W^a$=N-SEM can be achieved by employing an appropriate acid solution preferably HCl in MeOH, $BF_3$-$Et_2O$ in $CH_2Cl_2$, or $LiBF_4$ in aqueous $CH_3CN$ at the temperatures between 0° C. to 70° C. Alternatively, TBAF preferably in the presence of ethylenediamine at temperatures between 50° C. to 70° C. in THF can be used to remove the SEM group of 44. Finally, deprotection of PG (when PG=Ts) in indole 45 wherein $W^c$=NH, O, or S, can be achieved by treatment with KOH in the presence of primary amine preferably isoamylamine in alcoholic solvent such as EtOH at temperatures between 80° C. to 100° C. to afford 46. Alternatively $Cs_2CO_3$ in alcoholic solvents such as MeOH at elevated temperature preferably 60° C. can provide 46 when PG=Boc. Alternatively HCl in anhydrous solvent such as dioxane can be employed when PG=Boc to afford compounds such as 46.

Compound 49, wherein $W^c$=NH, O or S and especially when $W^a$=NSEM ($W^c$=NH) and Q=N, $R^m$ is H or Me and $R^n$ is OH, or OMe in Scheme 6 and Scheme 7, can be obtained as outlined in Scheme 15.

Scheme 15

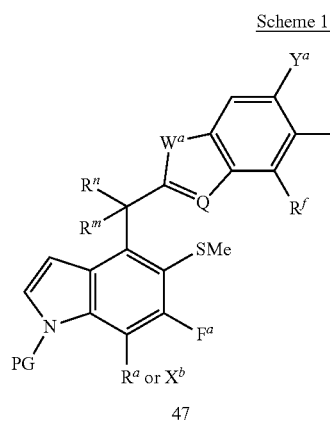

47

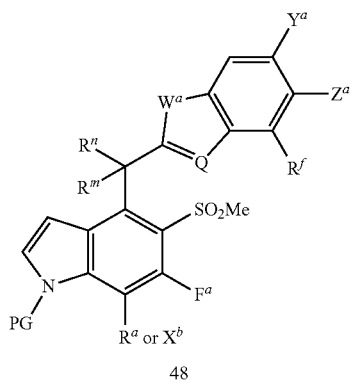

48

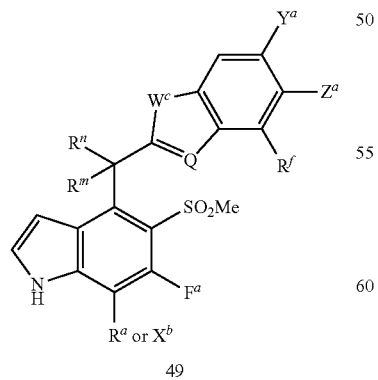

49

Sulfide 47 can be oxidized by ammonium molybdate tetrahydrate in the presence of hydrogen peroxide to provide sulfone 48. Removal of SEM group and then PG in accordance with Scheme 14 can afford compound of type 49.

Compounds such as 52, wherein: $W^c$=NH, O or S and especially when $W^a$=NSEM ($W^c$=NH) and Q=N, $R^p/R^q$ taken in combination can be H and $NH_2$, Me and $NH_2$, $CF_3$ and OH, $CF_3$ and $NH_2$, or $CF_3$ and NH-alkyl: can be obtained as outlined in Scheme 16.

Scheme 16

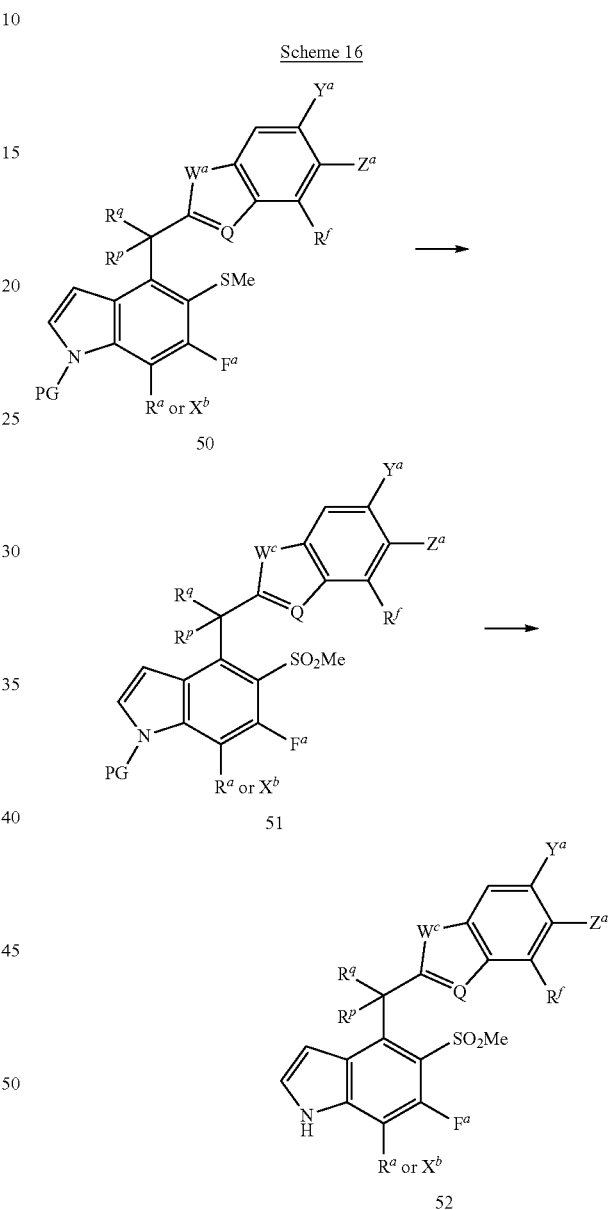

51 can be obtained by removal of the SEM group of 50 by treatment with HCl in MeOH at 60° C., followed by oxidation of the sulfide by employing ammonium molybdate tetrahydrate in the presence of hydrogen peroxide. Removal of PG can afford 52 according to Scheme 14.

Compounds such as 53, wherein $W^c$=NH, O or S and especially when $W^a$=NSEM ($W^c$=NH) and Q=N, $R^r$ is halo, —$CF_3$, —CN, methyl, 2,2,2-trifluoro-1-hydroxyethyl) can be prepared as shown in Scheme 17.

Scheme 17

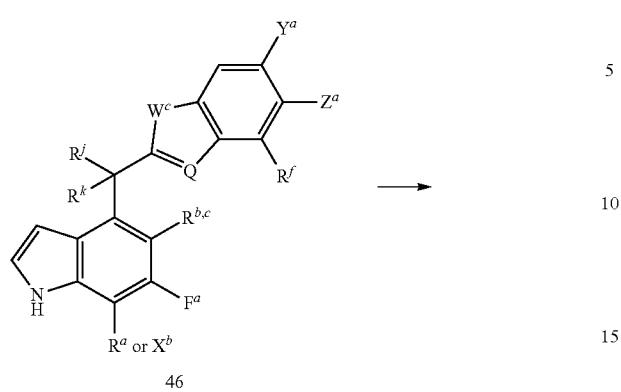

46

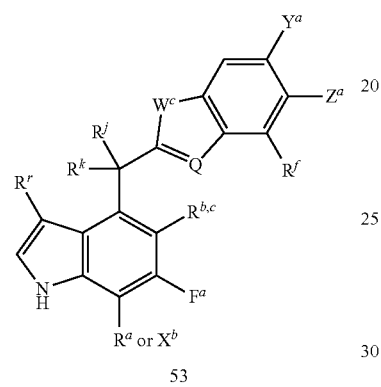

53

Indole 46 can be reacted with an appropriate electrophile such as NCS, chlorosulfonyl isocyanate, in suitable solvent such as DMF to furnish 53 (e.g. $R^r$=Cl, CN). Alternatively, 46 can be reacted with anhydrides and chloro-imminium ions followed by reductions with $LiBH_4$ in THF to afford compounds of type 53 wherein $R^r$ is equal to alkyl or hydroxy substituted alkyls.

Compound such as 58 especially when $W^a$=NSEM ($W^c$=NH) and Q=N can be prepared according to Scheme 18.

Scheme 18

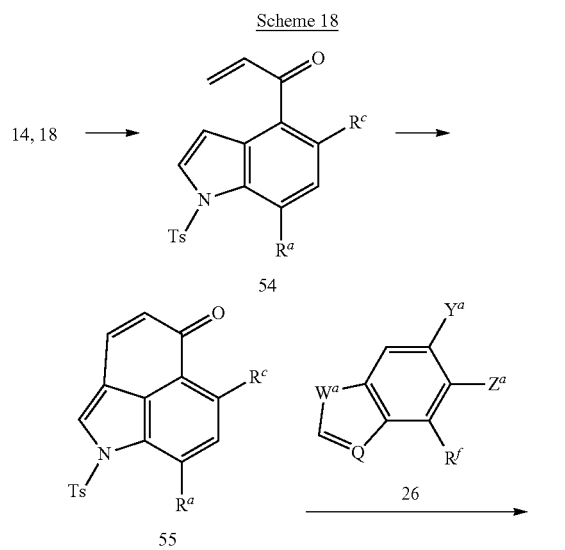

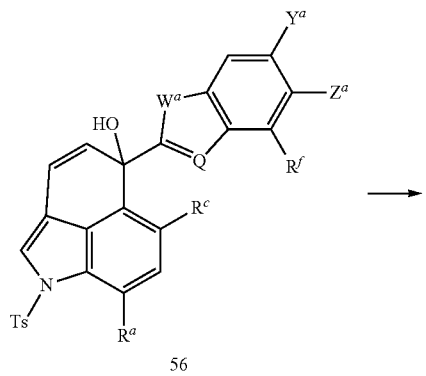

56

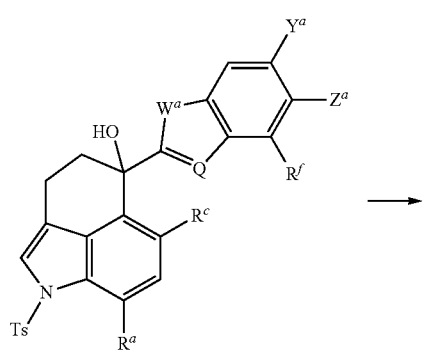

57

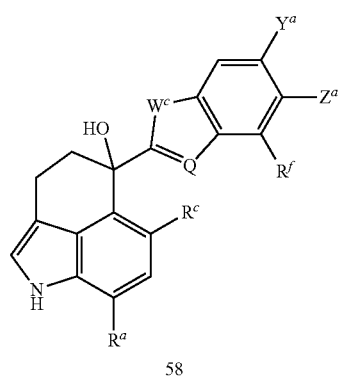

58

Ketone 54 can be obtained by nucleophilic addition of vinylmagnesium bromide to aldehydes of type 14 and 18 (PG=Ts) at temperatures between −78° C. to 0° C., in a suitable solvent such as THF, followed by treatment with an oxidant such as Dess-Martin Periodinate in an appropriate solvent such as DCM at temperatures between 0° C. and room temperature, preferably at room temperature. Intramolecular cyclization of 54 can be achieved by treatment with a stoichiometric amount of $Pd(OAc)_2$ in the presence of oxidants such as tetrachloro-1,4-benzoquinone in an appropriate solvent such as AcOH at elevated temperature preferably 100° C. to afford 55. Nucleophilic addition of 26 (especially when $W^a$=N-SEM, Q=N) can be achieved to provide 56 similarly to the examples in Scheme 6. 56 can be hydrogenated in the presence of Pd/C in a suitable solvent such as MeOH under $H_2$ atmosphere to provide 57. Deprotection of SEM and Ts groups as shown in Scheme 14 can afford 58.

Compound such as 60 where $R^r$ is alkyl, or substituted alkyl, can be prepared by the general method outlined in Scheme 19.

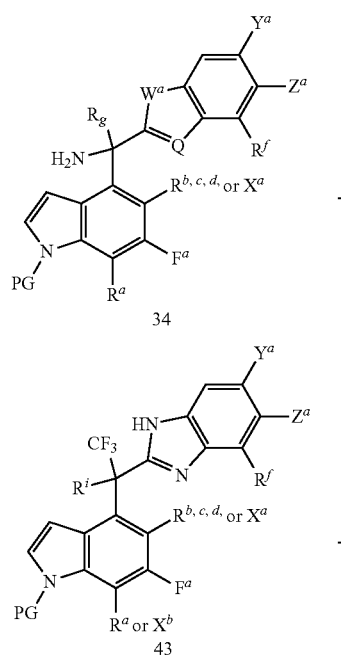

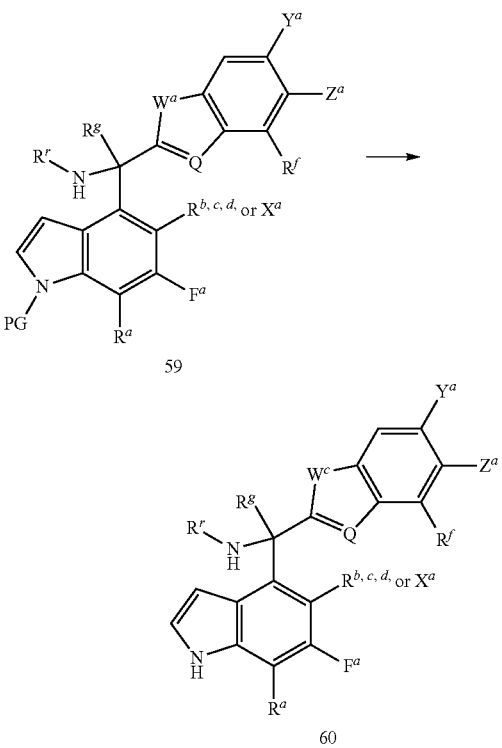

Indole 34 and 43 (where $R^i$=NH$_2$), prepared as shown in Scheme 10 and 13 can be reacted with the appropriate aldehyde (such as ethyl glyoxylate) in the presence of a mild reducing agent such as NaBH$_4$ or sodium triacetoxyborohydride, in alcoholic solvents, such as MeOH to give compound 59. Indole 60 can be obtained after deprotection of the protecting groups as shown in Scheme 14.

Compound such as 63 and 64 where $R^s$ and $R^t$ can be alkyl, substituted alkyl or carboxy, and especially when $W^a$ is N-SEM or O($W^b$ is N—H or O) and Q is N, can be accessed by the general method outlined in Scheme 20.

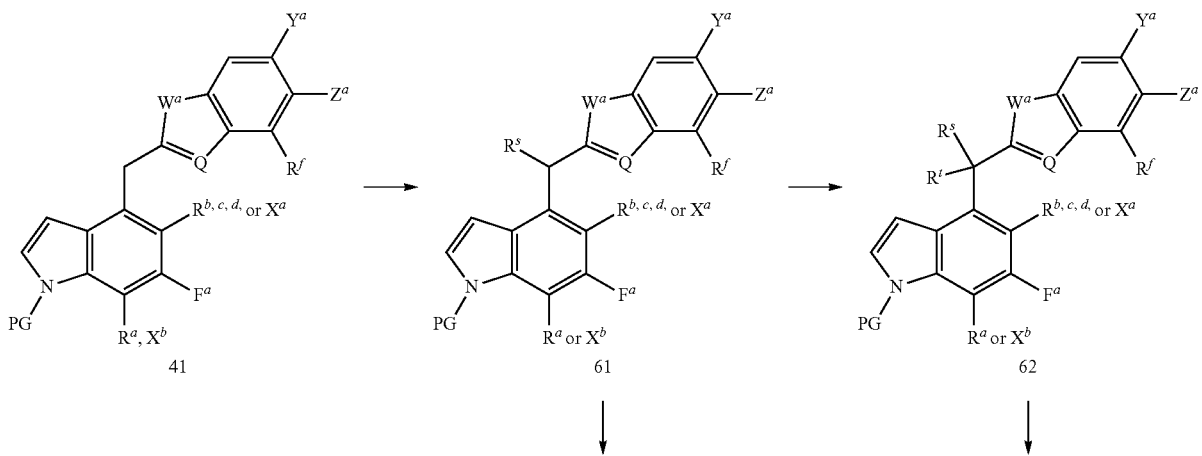

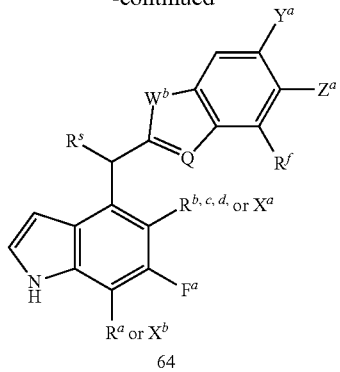

64

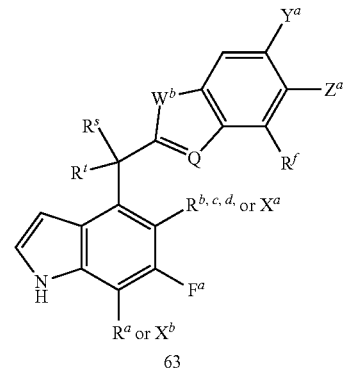

63

Indole 41 can be deprotonated with a suitable base such as NaH (especially when using MeI as the electrophile), LiHMDS or potassium tert-butoxide (with 18-crown-6) in a suitable solvent, such as THF (for LiHMDS and potassium tert-butoxide) and DMF (for NaH) and the anion quenched with the appropriate electrophiles such as: MeI, methyl bromoacetate, ethyl chloroformate, methyl acrylate to obtain compound 61. 61 can be further functionalized to introduce further benzylic substitutions ($R^r$) to give compound 62 using similar deprotonation/quench strategy as of 61. 61 and 62 can be deprotected using sequences presented in Scheme 14.

When $R^s$ and/or $R^t$ bear an ester moiety, this can be hydrolyzed to the carboxylic acid using bases such as NaOH or $Cs_2CO_3$ in protic solvents such as MeOH and/or water at temperatures that range from room temperature to 60° C. In other examples where $R^s$ and/or $R^t$ bear an ester moiety and especially when $W^b$=O, 61 or 62 can be reacted with $SnCl_4$ in dichloromethane at temperatures between 0° C. and room temperature to allow for deprotection of protecting groups.

Compound such as 70 can be accessed by the general method outlined in Scheme 21.

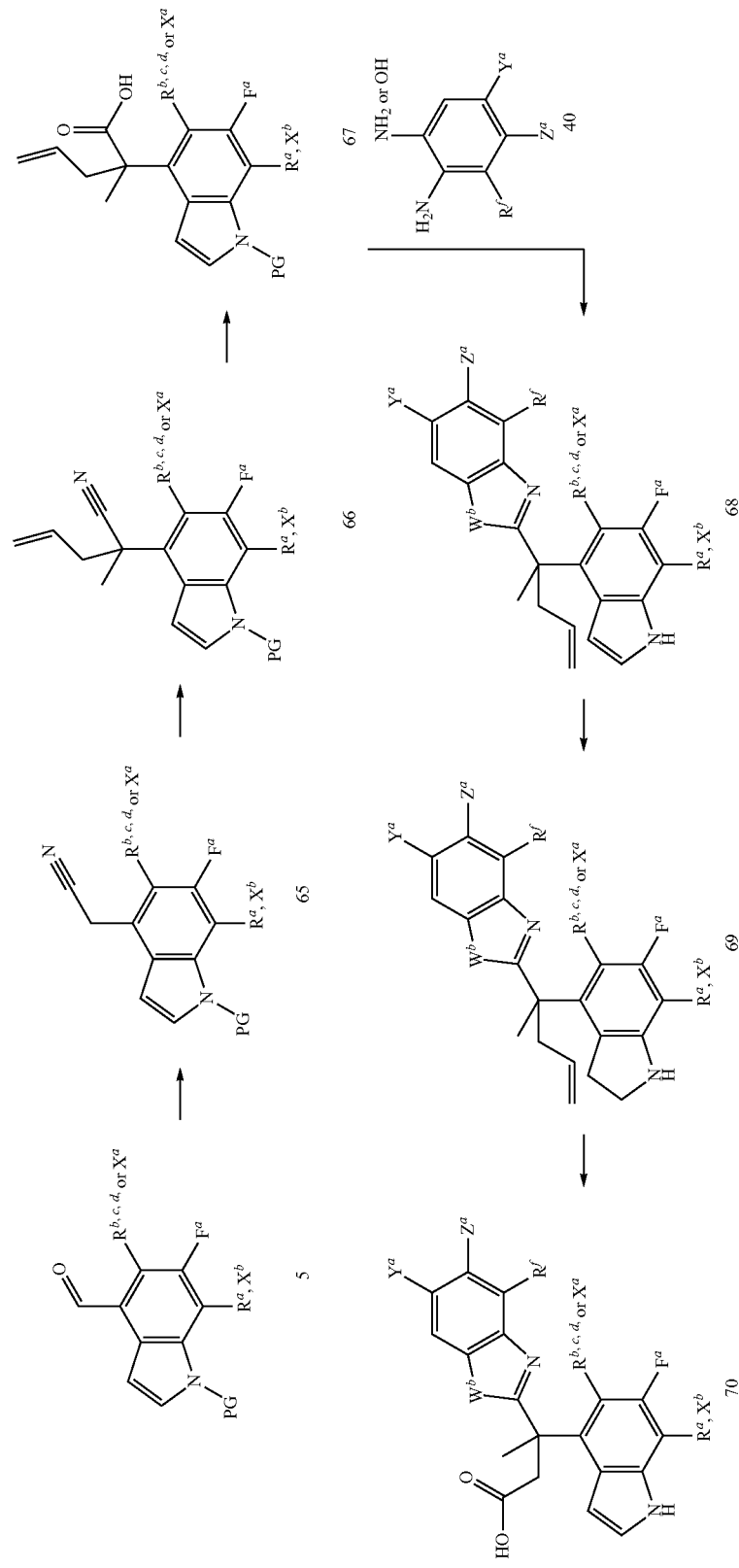

Aldehyde 5 can be reacted with TOSMIC in presence of a base such as potassium tert-butoxide in a solvent such as THF at −78° C. to give nitrile 65. The resulting nitrile 65 can be reacted in the presence of a base such as LiHMDS in THF at −78° C. with an electrophile such as MeI and then further deprotonated with the same base and reacted with allyl bromide to give compound 66. Nitrile 66 can be transformed into carboxylic acid 67 via first reduction of the nitrile with a reducing agent such as DIBAL-H in aprotic solvents such as DCM at −78° C. to the aldehyde and then its oxidation using standard oxidation conditions such as sodium chlorite in the presence of sodium dihydrogen phosphate and 2-methyl-2-butene in tert-BuOH/water at room temperature. Acid 67 can be condensed with 40 using standard coupling conditions (oxalyl chloride/DMF) followed by acid mediated cyclization (such as p-TsOH in dioxane at 135° C.) to give 68. 68 can be reduced to indoline 69 using a mild reducing agent such as sodium cyanoborohydride in acidic media (AcOH). After reaction of indoline 69 with excess Boc$_2$O to protect indoline's and benzimidazole's NH's (when W$^b$ is NH), the double bond of 69 can be oxidized to the aldehyde using osmium tetroxide, sodium periodate and 2,6-lutidine in dioxane/water mixture. Further oxidation to the wanted carboxylic acid can be attained using standard oxidation conditions such as sodium chlorite in the presence of sodium dihydrogen phosphate and 2-methyl-2-butene in tert-BuOH/water at room temperature. Submitting the oxidized intermediate to first acidic (HCl in MeOH at 50° C.) and then basic conditions (LiOH in THF/MeOH/water at rt, in which step indoline is oxidized to indole) leads to fully deprotected carboxylic acid 70.

Compound such as 76 can be accessed by the general method outlined in Scheme 22.

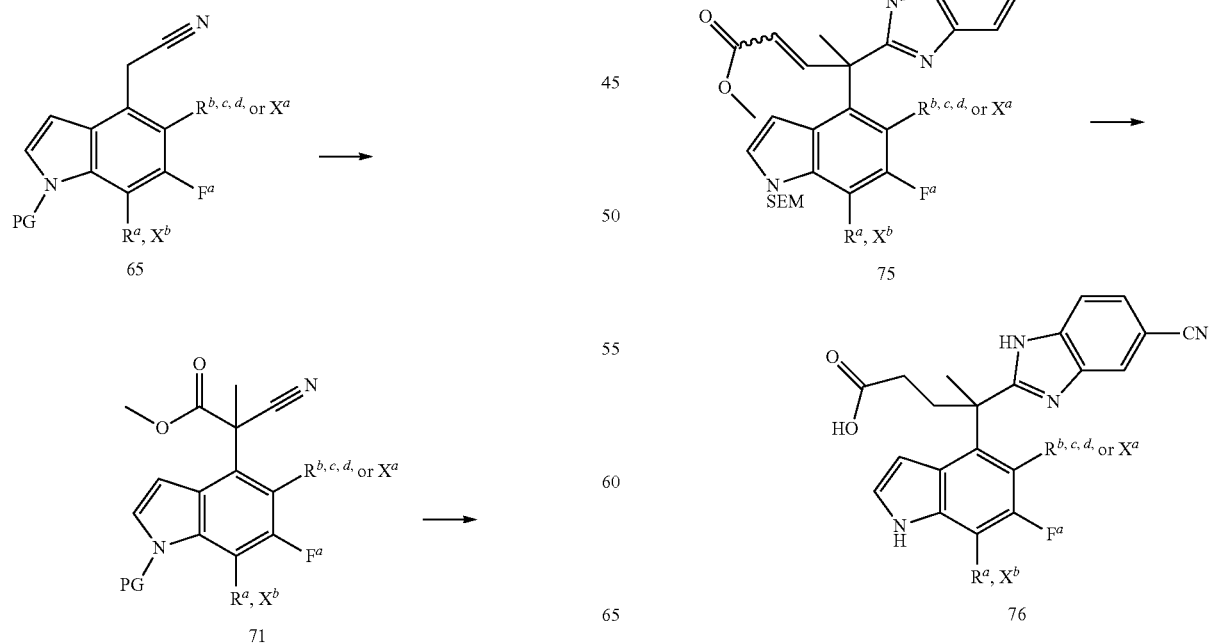

Nitrile 65 can be reacted with methyl chloroformate in the presence of a strong base such as potassium tert-butoxide (with 18-crown-6) in an appropriate solvent such as THF at temperatures between −78° C. and room temperature. The product can be further reacted with methyl iodide in the presence of a mild base such as potassium carbonate in acetone at rt leading to nitrile 71. The methyl ester of 71 can be hydrolyzed using basic conditions (KOH in EtOH) and the subsequent acid can be reacted with 4-bromobenzene-1,2-diamine in the presence of HBTU and an appropriate base such as DIPEA in DCM at temperatures between 0° C. and rt followed by acetic acid mediated cyclization to provide 72. After reaction of 72 with excess SEMCl in the presence of NaH to protect indole's and benzimidazole's NH's, the nitrile can be reduced to the aldehyde 73 using DIBAL-H in DCM at −78° C. 73 can be reacted with methyl (triphenylphosphoranylidene)acetate in toluene at 107° C. to furnish ester 74 that can be reacted with dicyanozinc in the presence of a palladium catalyst such as tetrakis(triphenylphosphine)palladium in DMF at 145° C. to produce nitrile 75. Sodium borohydride in the presence of $NiCl_2$ can reduce the double bond conjugated to the methyl ester of 75 before it is subjected to first acidic (HCl in MeOH at temperatures between 65 and 90° C.) and then basic conditions (KOH in MeOH at rt) to furnish the fully deprotected carboxylic acid 76.

Compound such as 79, where $W^b$ is NH or O can be accessed by the general method outlined in Scheme 23.

temperatures between 0° C. and room temperature to allow deprotection of Boc and SEM groups whilst lithium iodide in pyridine can hydrolyze the ester moiety to the wanted carboxylic acid of compound of type 79.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure materials.

Compounds of the invention and intermediates can also be converted into each other according to methods generally known to those skilled in the art.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and ophthalmic administration, etc. In addition, the pharmaceutical compositions of the present invention can be made up in a solid form (including without limitation capsules, tablets, pills, granules, powders or suppositories), or in a liquid form (including without limitation solutions, suspensions, emulsions, each of which may Scheme 23

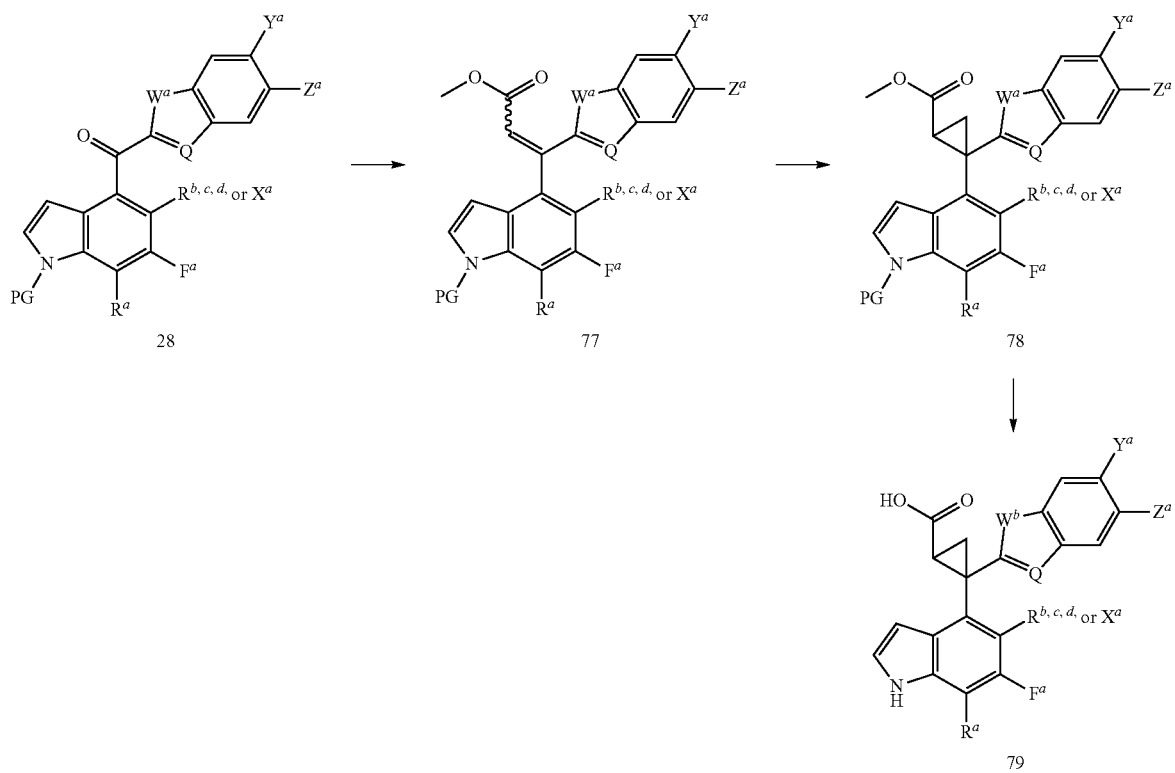

Ketone 28 can be reacted with methyl(triphenylphosphoranylidene)acetate in an appropriate solvent, such as toluene, at 110° C. to afford compound of type 77. 77 can be reacted with trimethylsulfoxonium iodide and a base such as NaH in the presence of DMSO at room temperature to afford compound 78. 78 can be reacted with $SnCl_4$ in dichloromethane at be suitable for ophthalmic administration). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for ophthalmic application, e.g., for the treatment of eye diseases e.g., for therapeutic or prophylactic use in treating age related macular degeneration and other complement mediated ophthalmic disorders. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be desirable.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (a g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Prophylactic and Therapeutic Uses

The compounds of formula I in free form or in pharmaceutically acceptable salt form, exhibit valuable pharmacological properties, e.g. Factor B modulating properties, complement pathway modulating properties and modulation of the complement alternative pathway properties, e.g. as indicated in in vitro and in vivo tests as provided in the next sections and are therefore indicated for therapy.

The present invention provides methods of treating a disease or disorder associated with increased complement activity by administering to a subject in need thereof an effective amount of the compounds of Formula (I) of the invention. In certain aspects, methods are provided for the treatment of diseases associated with increased activity of the C3 amplification loop of the complement pathway. In certain embodiments, methods of treating or preventing complement mediated diseases are provided in which the complement activation is induced by antibody-antigen interactions, by a component of an autoimmune disease, or by ischemic damage.

In a specific embodiment, the present invention provides a method of treating or preventing age-related macular degeneration (AMD) by administering to a subject in need thereof an effective amount of the compound of Formula (I) of the invention. In certain embodiments, patients who are currently asymptomatic but are at risk of developing a symptomatic macular degeneration related disorder are suitable for administration with a compound of the invention. The methods of treating or preventing AMD include, but are not limited to, methods of treating or preventing one or more symptoms or aspects of AMD selected from formation of ocular drusen, inflammation of the eye or eye tissue, loss of photoreceptor cells, loss of vision (including loss of visual acuity or visual field), neovascularization (including CNV), retinal detachment, photoreceptor degeneration, RPE degeneration, retinal degeneration, chorioretinal degeneration, cone degeneration, retinal dysfunction, retinal damage in response to light exposure, damage of the Bruch's membrane, and/or loss of RPE function.

The compound of Formula (I) of the invention can be used, inter alia, to prevent the onset of AMD, to prevent the progression of early AMD to advanced forms of AMD including neovascular AMD or geographic atrophy, to slow and/or prevent progression of geographic atrophy, to treat or prevent macular edema from AMD or other conditions (such as diabetic retinopathy, uveitis, or post surgical or non-surgical trauma), to prevent or reduce the loss of vision from AMD, and to improve vision lost due to pre-existing early or advanced AMD. It can also be used in combination with anti-VEGF therapies for the treatment of neovascular AMD patients or for the prevention of neovascular AMD. The present invention further provides methods of treating a complement related disease or disorder by administering to a subject in need thereof an effective amount of the compound(s) of the invention, wherein said disease or disorder is selected from uveitis, adult macular degeneration, diabetic retinopathy, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, and retinal vein occlusion.

In some embodiments, the present invention provides methods of treating a complement related disease or disorder by administering to a subject in need thereof an effective amount of the compounds of the invention. Examples of known complement related diseases or disorders include: neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, thermal injury including burns or frostbite, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration and neural regeneration. In addition, other known complement related disease are lung disease and disorders such as dyspnea, hemoptysis, ARDS, asthma, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), asthma, allergy, bronchoconstriction, hypersensitivity pneumonitis, parasitic diseases, Goodpasture's Syndrome, pulmonary vasculitis, Pauci-immune vasculitis, immune complex-associated inflammation, uveitis (including Behcet's disease and other sub-types of uveitis), antiphospholipid syndrome.

In a specific embodiment, the present invention provides methods of treating a complement related disease or disorder by administering to a subject in need thereof an effective amount of the compounds of the invention, wherein said disease or disorder is asthma, arthritis (e.g., rheumatoid arthritis), autoimmune heart disease, multiple sclerosis, inflammatory bowel disease, ischemia-reperfusion injuries, Barraquer-Simons Syndrome, hemodialysis, anca vasculitis, cryoglobulinemia, systemic lupus, lupus erythematosus, psoriasis, multiple sclerosis, transplantation, diseases of the central nervous system such as Alzheimer's disease and other neurodegenerative conditions, atypicaly hemolytic uremic syndrome (aHUS), glomerulonephritis (including membrane proliferative glomerulonephritis), dense deposit disease, blistering cutaneous diseases (including bullous pemphigoid, pemphigus, and epidermolysis bullosa), ocular cicatrical pemphigoid or MPGN II.

In a specific embodiment, the present invention provides methods of treating glomerulonephritis by administering to a subject in need thereof an effective amount of a composition comprising a compound of the present invention. Symptoms of glomerulonephritis include, but not limited to, proteinuria; reduced glomerular filtration rate (GFR); serum electrolyte changes including azotemia (uremia, excessive blood urea nitrogen—BUN) and salt retention, leading to water retention resulting in hypertension and edema; hematuria and abnormal urinary sediments including red cell casts; hypoalbuminemia; hyperlipidemia; and lipiduria. In a specific embodiment, the present invention provides methods of treating paroxysmal nocturnal hemoglobinuria (PNH) by administering to a subject in need thereof an effective amount of a composition comprising an compound of the present invention with or without concomitent administration of a complement C5 inhibitor or C5 convertase inhibitor such as Soliris.

In a specific embodiment, the present invention provides methods of reducing the dysfunction of the immune and/or hemostatic systems associated with extracorporeal circulation by administering to a subject in need thereof an effective amount of a composition comprising an compound of the present invention. The compounds of the present invention can be used in any procedure which involves circulating the patient's blood from a blood vessel of the patient, through a conduit, and back to a blood vessel of the patient, the conduit having a luminal surface comprising a material capable of causing at least one of complement activation, platelet activation, leukocyte activation, or platelet-leukocyte adhesion. Such procedures include, but are not limited to, all forms of ECC, as well as procedures involving the introduction of an artificial or foreign organ, tissue, or vessel into the blood circuit of a patient. More particularly, such procedures include, but are not limited to, transplantation procedures including kidney, liver, lung or heart transplant procedures and islet cell transplant procedures.

In other embodiments, the compounds of the invention are suitable for use in the treatment of diseases and disorders associated with fatty acid metabolism, including obesity and other metabolic disorders.

In another embodiment, the compounds of the invention may be used in blood ampules, diagnostic kits and other equipment used in the collection and sampling of blood. The use of the compounds of the invention in such diagnostic kits may inhibit the ex vivo activation of the complement pathway associated with blood sampling.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by alternative complement pathway. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by the complement alternative pathway, wherein the medicament is prepared for administration with another therapeutic agent. The invention also provides the use of another therapeutic agent for treating a disease or condition mediated by the complement alternative pathway, wherein the medicament is administered with a compound of formula (I).

The invention also provides a compound of formula (I) for use in a method of treating a disease or condition mediated by the complement alternative pathway, wherein the compound of formula (I) is prepared for administration with another therapeutic agent. The invention also provides another therapeutic agent for use in a method of treating a disease or condition mediated by the complement alternative pathway and/or Factor B, wherein the other therapeutic agent is prepared for administration with a compound of formula (I). The invention also provides a compound of formula (I) for use in a method of treating a disease or condition mediated by the complement alternative pathway and/or Factor B, wherein the compound of formula (I) is administered with another therapeutic agent. The invention also provides another therapeutic agent for use in a method of treating a disease or condition mediated by the complement alternative pathway and/or Factor B, wherein the other therapeutic agent is administered with a compound of formula (I).

The invention also provides the use of a compound of formula (I) for treating a disease or condition mediated by the complement alternative pathway and/or Factor B, wherein the patient has previously (e.g. within 24 hours) been treated with another therapeutic agent. The invention also provides the use of another therapeutic agent for treating a disease or condition mediated by the complement alternative pathway and/or Factor B wherein the patient has previously (e.g. within 24 hours) been treated with a compound of formula (I).

The pharmaceutical compositions can be administered alone or in combination with other molecules known to have a beneficial effect on retinal attachment or damaged retinal tissue, including molecules capable of tissue repair and regeneration and/or inhibiting inflammation. Examples of useful, cofactors include complement inhibitors (such as inhibitors of Factor D, C5a receptor and antibody or Fabs against C5, C3, properidin, factor H, and the like), anti-VEGF agents (such as an antibody or FAB against VEGF, e.g., Lucentis or Avastin), basic fibroblast growth factor (bFGF), ciliary neurotrophic factor (CNTF), axokine (a mutein of CNTF), leukemia inhibitory factor (LIF), neutrotrophin 3 (NT-3), neurotrophin-4 (NT-4), nerve growth factor (NGF), insulin-like growth factor II, prostaglandin E2, 30 kD survival factor, taurine, and vitamin A. Other useful cofactors include symptom-alleviating cofactors, including antiseptics, antibiotics, antiviral and antifungal agents and analgesics and anesthetics. Suitable agents for combination treatment with the compounds of the invention include agents known in the art that are able to modulate the activities of complement components.

A combination therapy regimen may be additive, or it may produce synergistic results (e.g., reductions in complement pathway activity more than expected for the combined use of the two agents). In some embodiments, the present invention provide a combination therapy for preventing and/or treating AMD or another complement related ocular disease as described above with a compound of the invention and an anti-angiogenic, such as anti-VEGF agent (including Lucentis and Avastin) or photodynamic therapy (such as verteporfin).

In some embodiments, the present invention provide a combination therapy for preventing and/or treating autoimmune disease as described above with a compound of the invention and a B-Cell or T-Cell modulating agent (for example cyclosporine or analogs thereof, rapamycin, RAD001 or analogs thereof, and the like). In particular, for multiple sclerosis therapy may include the combination of a compound of the invention and a second MS agent selected from fingolimod, cladribine, tysarbi, laquinimod, rebif, avonex and the like.

In one embodiment, the invention provides a method of modulating activity of the complement alternative pathway in a subject, wherein the method comprises administering to the subject a therapeutically effective amount of the compound according to the definition of formula (I). The invention further provides methods of modulating the activity of the complement alternative pathway in a subject by modulating the activity of Factor B, wherein the method comprises administering to the subject a therapeutically effective amount of the compound according to the definition of Formula (I).

In one embodiment, the invention provides a compound according to the definition of formula (I), (Ia), or any subformulae thereof, for use as a medicament.

In one embodiment, the invention provides the use of a compound according to the definition of formula (I), (Ia), or any subformulae thereof, for the treatment of a disorder or disease in a subject mediated by complement activation. In particular, the invention provides the use of a compound according to the definition of formula (I), (Ia), or any subformulae thereof, for the treatment of a disorder or disease mediated by activation of the complement alternative pathway.

In one embodiment, the invention provides the use of a compound according to the definition of formula (I), (Ia), or a subformulae thereof in the manufacture of a medicament for the treatment of a disorder or disease in a subject characterized by activation of the complement system. More particularly in the manufacture of a medicament for the treatment of a disease or disorder in a subject characterized by over activation of the complement alternative pathway.

In one embodiment, the invention provides the use of a compound according to the definition of formula (I), (Ia), or subformulae thereof for the treatment of a disorder or disease in a subject characterized by activation of the complement system. More particularly, the invention provides uses of the compounds provided herein in the treatment of a disease or disorder characterized by over activation of the complement alternative pathway or the C3 amplification loop of the alternative pathway. In certain embodiments, the use is in the treatment of a disease or disorder is selected from retinal diseases (such as age-related macular degeneration).

The present invention provides use of the compounds of the invention for treating a disease or disorder associated with increased complement activity by administering to a subject in need thereof an effective amount of the compounds of Formula (I) of the invention. In certain aspects, uses are provided for the treatment of diseases associated with increased activity of the C3 amplification loop of the complement pathway. In certain embodiments, uses of treating or preventing complement mediated diseases are provided in which the complement activation is induced by antibody-antigen interactions, by a component of an autoimmune disease, or by ischemic damage.

In a specific embodiment, the present invention provides use of the compounds of the invention for treating or preventing age-related macular degeneration (AMD). In certain embodiments, patients who are currently asymptomatic but are at risk of developing a symptomatic macular degeneration related disorder are suitable for administration with a compound of the invention. The use in treating or preventing AMD include, but are not limited to, uses in treating or preventing one or more symptoms or aspects of AMD selected from formation of ocular drusen, inflammation of the eye or eye tissue, loss of photoreceptor cells, loss of vision (including loss of visual acuity or visual field), neovascularization (including CNV), retinal detachment, photoreceptor degeneration, RPE degeneration, retinal degeneration, chorioretinal degeneration, cone degeneration, retinal dysfunction, retinal damage in response to light exposure, damage of the Bruch's membrane, and/or loss of RPE function.

The compound of Formula (I) of the invention can be used, inter alia, to prevent the onset of AMD, to prevent the progression of early AMD to advanced forms of AMD including neovascular AMD or geographic atrophy, to slow and/or prevent progression of geographic atrophy, to treat or prevent macular edema from AMD or other conditions (such as diabetic retinopathy, uveitis, or post surgical or non-surgical trauma), to prevent or reduce the loss of vision from AMD, and to improve vision lost due to pre-existing early or advanced AMD. It can also be used in combination with anti-VEGF therapies for the treatment of neovascular AMD patients or for the prevention of neovascular AMD. The present invention further provides methods of treating a complement related disease or disorder by administering to a subject in need thereof an effective amount of the compound(s) of the invention, wherein said disease or disorder is selected from uveitis, adult macular degeneration, diabetic retinopathy, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, and retinal vein occlusion.

In some embodiments, the present invention provides uses for treating a complement related disease or disorder. Examples of known complement related diseases or disorders include: neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, thermal injury including burns or frostbite, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration and neural regeneration. In addition, other known complement related disease are lung disease and disorders such as dyspnea, hemoptysis, ARDS, asthma, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), asthma, allergy, bronchoconstriction, hypersensitivity pneumonitis, parasitic diseases, Goodpasture's Syndrome, pulmonary vasculitis, Pauci-immune vasculitis, immune complex-associated inflammation, uveitis (including Behcet's disease and other sub-types of uveitis), antiphospholipid syndrome.

In a specific embodiment, the present invention provides use of the compounds of the invention for treating a complement related disease or disorder, wherein said disease or disorder is asthma, arthritis (e.g., rheumatoid arthritis), autoimmune heart disease, multiple sclerosis, inflammatory bowel disease, ischemia-reperfusion injuries, Barraquer-Simons Syndrome, hemodialysis, systemic lupus, lupus erythematosus, psoriasis, multiple sclerosis, transplantation, diseases of the central nervous system such as Alzheimer's disease and other neurodegenerative conditions, atypically hemolytic uremic syndrome (aHUS), glomerulonephritis (including membrane proliferative glomerulonephritis), blistering cutaneous diseases (including bullous pemphigoid, pemphigus, and epidermolysis bullosa), ocular cicatrical pemphigoid or MPGN II.

In a specific embodiment, the present invention provides use of the compounds of the invention for treating glomerulonephritis. Symptoms of glomerulonephritis include, but not limited to, proteinuria; reduced glomerular filtration rate (GFR); serum electrolyte changes including azotemia (uremia, excessive blood urea nitrogen—BUN) and salt retention, leading to water retention resulting in hypertension and edema; hematuria and abnormal urinary sediments including red cell casts; hypoalbuminemia; hyperlipidemia; and lipiduria. In a specific embodiment, the present invention provides methods of treating paroxysmal nocturnal hemoglobinuria (PNH) by administering to a subject in need thereof an effective amount of a composition comprising an compound of the present invention with or without concomitent administration of a complement C5 inhibitor or C5 convertase inhibitor such as Soliris.

In a specific embodiment, the present invention provides use of the compounds of the invention for reducing the dysfunction of the immune and/or hemostatic systems associated with extracorporeal circulation. The compounds of the present invention can be used in any procedure which involves circulating the patient's blood from a blood vessel of the patient, through a conduit, and back to a blood vessel of the patient, the conduit having a luminal surface comprising a material capable of causing at least one of complement activation, platelet activation, leukocyte activation, or platelet-leukocyte adhesion. Such procedures include, but are not limited to, all forms of ECC, as well as procedures involving the introduction of an artificial or foreign organ, tissue, or vessel into the blood circuit of a patient. More particularly, such procedures include, but are not limited to, transplantation procedures including kidney, liver, lung or heart transplant procedures and islet cell transplant procedures.

In one embodiment of the present invention, there is (±)-2-(1-(6-fluoro-5-methoxy-7-methyl-1H-indol-4-yl)-1-methoxyethyl)-1H-benzo[d]imidazole-5-carbonitrile for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, anca vasculitis, cryoglobulinemia, dense deposit disease, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In another embodiment of the present invention, there is (−)-2-(1-(5-cyclopropyl-7-methyl-1H-indol-4-yl)-2,2,2-trifluoro-1-(methylamino)ethyl)-1H-benzo[d]imidazole-5-carbonitrile for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, anca vasculitis, cryoglobulinemia, dense deposit disease, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In another embodiment of the present invention, there is (±)-3-(5-cyano-1H-benzo[d]imidazol-2-yl)-3-(5-methoxy-7-methyl-1H-indol-4-yl)butanoic acid for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In another embodiment of the present invention, there is (±)-4-(5-cyano-1H-benzo[d]imidazol-2-yl)-4-(5-methoxy-7-methyl-1H-indol-4-yl)pentanoic acid for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, anca vasculitis, cryoglobulinemia, dense deposit disease, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In another embodiment of the present invention, there is (+) and (−)-2-(1-amino-2,2,2-trifluoro-1-(5-methoxy-7-methyl-1H-indol-4-yl)ethyl)benzo[d]oxazole-5-carbonitrile for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, anca vasculitis, cryoglobulinemia, dense deposit disease, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In another embodiment of the present invention, there is (±)-2-(1-amino-1-(6-fluoro-5-methoxy-7-methyl-1H-indol-4-yl)ethyl)-1H-benzo[d]imidazole-5-carbonitrile for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, anca vasculitis, cryoglobulinemia, dense deposit disease, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In another embodiment of the present invention, there is (−)-2-(1-amino-1-(5-methoxy-7-methyl-1H-indol-4-yl)ethyl)benzo[d]oxazole-5-carbonitrile for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, anca vasculitis, cryoglobulinemia, dense deposit disease, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In another embodiment of the present invention, there is (−)-2-(1-methoxy-1-(5-methoxy-7-methyl-1H-indol-4-yl)ethyl)-1H-benzo[d]imidazole-5-carbonitrile for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, anca vasculitis, cryoglobulinemia, dense deposit disease, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In another embodiment of the present invention, there is (−)-2-(1-amino-2,2,2-trifluoro-1-(5-methoxy-7-methyl-1H-indol-4-yl)ethyl)-1H-benzo[d]imidazole-5-carbonitrile for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, anca vasculitis, cryoglobulinemia, dense deposit disease, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In another embodiment of the present invention, there is (−)-2-(1-amino-1-(5-methoxy-7-methyl-1H-indol-4-yl)ethyl)-1H-benzo[d]imidazole-5-carbonitrile for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, anca vasculitis, cryoglobulinemia, dense deposit disease, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In another embodiment of the present invention, there is (+)-2-(1-hydroxy-1-(5-methoxy-7-methyl-1H-indol-4-yl) ethyl)-1H-benzo[d]imidazole-5-carbonitrile for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-choriodits, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, anca vasculitis, cryoglobulinemia, dense deposit disease, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In another embodiment of the present invention, there is (−)-2-(1-amino-1-(5-ethyl-7-methyl-1H-indol-4-yl)ethyl)-1H-benzo[d]imidazole-5-carbonitrile for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-choriodits, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, anca vasculitis, cryoglobulinemia, dense deposit disease, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

In another embodiment of the present invention, there is (−)-2-(2,2,2-trifluoro-1-hydroxy-1-(5-methoxy-7-methyl-1H-indol-4-yl)ethyl)-1H-benzo[d]imidazole-5-carbonitrile for use in the treatment of a disorder or a disease in a subject mediated by complement activation, in particular mediated by activation of the complement alternative pathway. In certain embodiments, the disease or disorder mediated by complement activation is selected from age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retino-choriodits, sympathetic ophthalmia, ocular dicatricial pemphigoid, ocular pemphigus, nonartertic ischemic optic neuropathy, post-operative inflammation, retinal vein occlusion, neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, anca vasculitis, cryoglobulinemia, dense deposit disease, glomerulonephritis and obesity. In certain preferred embodiments, the disease or disorder mediated by complement activation is selected from age-related macular degeneration, geographic atrophy, diabetic retinopathy, uveitis, retinitis pigmentosa, or macular edema.

The following examples are intended to illustrate the invention and are not to be construed as being limitations thereof. Temperatures are given in degrees centigrade (° C.). If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Inter Alia the following in vitro tests may be used

Biological Example 1

Human Complement Factor B ELISA Assay

CVF-Bb complex prepared from purified cobra venom factor (1 µM), recombinant human complement factor B (expressed in *drosophila* cells and purified using standard methods) and human complement factor D (expressed in *E. Coli*, refolded and purified using standard methods). CVF-Bb complex at 3 nM concentration was incubated with test compound at various concentrations for 1 hour at room temperature in PBS pH 7.4 containing 10 mM $MgCl_2$ and 0.05% (w/v) CHAPS. Human complement C3 substrate purified from plasma was added to a final concentration of 1 µM. After 1 hour incubation at room temperature, the enzyme reaction was stopped by addition of a cocktail of concentrated pan-protease inhibitors. The product of the reaction, C3a, was quantified by means of an enzyme-linked-immunosorbent assay. $IC_{50}$ values were calculated from percentage of inhibition of CVF-Bb activity as a function of test compound concentration.

Biological Example 2

Human Complement Factor B TR-FRET Assay

Biological Example 2.1

(+) or (−)-tert-Butyl 3-(3-hydroxyphenyl)piperazine-1-carboxylate

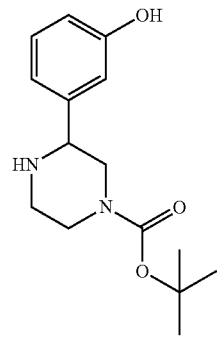 [SMILES: CC(C)(C)OC(=O)N1CCNC(c2cccc(O)c2)C1]

Resolution of the enantiomers of (±)-tert-butyl 3-(3-hydroxyphenyl)piperazine-1-carboxylate (CAS#889956-76-7) was achieved by chiral HPLC using a CHIRALPAK AD column with heptane/EtOAc/MeOH 90/5/5+0.1 diethylamine to give (+) or (−)-tert-butyl 3-(3-hydroxyphenyl)piperazine-1-carboxylate ($t_r$=9.7 min) and (−) or (+)-tert-butyl 3-(3-hydroxyphenyl)piperazine-1-carboxylate ($t_r$=15.7 min).

Biological Example 2.2

(+) or (−)-tert-Butyl 3-(3-(2-(((benzyloxy)carbonyl)amino)ethoxy)phenyl)piperazine-1-carboxylate

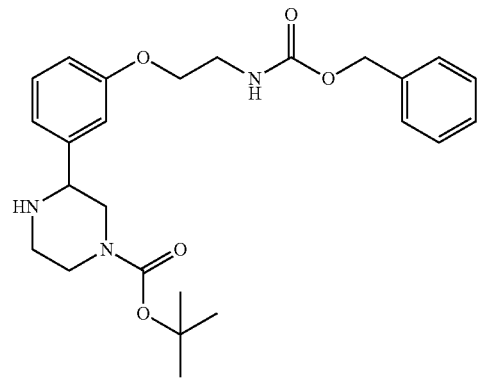 [SMILES: CC(C)(C)OC(=O)N1CCNC(c2cccc(OCCNC(=O)OCc3ccccc3)c2)C1]

(+) or (−)-tert-butyl 3-(3-hydroxyphenyl)piperazine-1-carboxylate ($t_r$=9.7 min) (Biological Example 2.1) (300 mg, 1.078 mmol) and benzyl 2-hydroxyethylcarbamate (210 mg, 1.078 mmol) were dissolved in THF (10 ml). Tributylphosphine (0.404 ml, 1.617 mmol) was added, and after cooling to 0° C., DEAD 40% in toluene (0.640 ml, 1.617 mmol) was added dropwise. The reaction was stirred for 2 h at 0° C., then overnight at rt. The reaction mixture was diluted with aqueous $NaHCO_3$. The layers were separated and the aqueous layer was extracted with AcOEt. The organic phase dried over $MgSO_4$ and concentrated in vacuum. The crude residue was purified by preparative HPLC (Macherey-Nagel Nucleosil 100-10 C18, $CH_3CN/H_2O$ (0.1% TFA)) to give the title compound. MS (ESI+) m/z 455.2 (M+H).

Biological Example 2.3

(+) or (−)-tert-Butyl 4-(4-amino-6,7-dimethoxyquinazolin-2-yl)-3-(3-(2-(((benzyloxy)carbonyl)amino)ethoxy)phenyl)piperazine-1-carboxylate

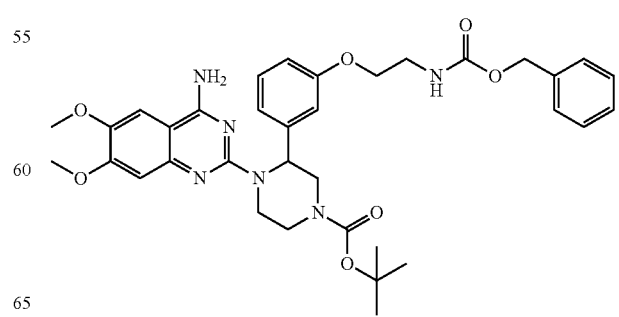

A solution of 2-chloro-6,7-dimethoxyquinazolin-4-amine (CAS#23680-84-4) (105 mg, 0.439 mmol) and (+) or (−)-tert-butyl 3-(3-(2-(((benzyloxy)carbonyl)amino)ethoxy)phenyl)piperazine-1-carboxylate (100 mg, 0.220 mmol) in isoamyl alcohol (5 ml) was stirred for 16 hr at 135° C. After evaporation, the crude was purified by preparative HPLC (Macherey-Nagel Nucleosil® 100-10 C18, $CH_3CN/H_2O$ (0.1% TFA)) to give the title compound. MS (ESI+) m/z 659.2 (M+H).

Biological Example 2.4

(+) or (−)-tert-Butyl((1R)-3-(4-(4-amino-6,7-dimethoxyquinazolin-2-yl)-3-(3-(2-(((benzyloxy)carbonyl)amino)ethoxy)phenyl)piperazin-1-yl)-3-oxo-1-phenylpropyl)carbamate

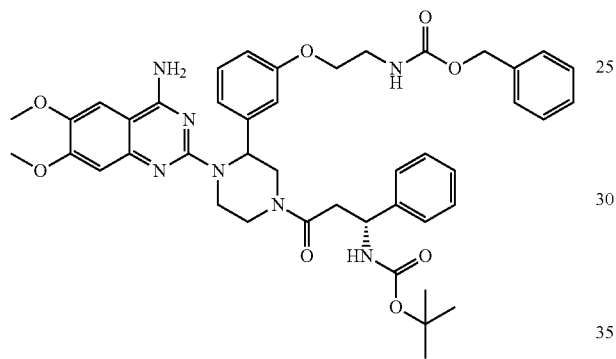

(+) or (−)-tert-Butyl 4-(4-amino-6,7-dimethoxyquinazolin-2-yl)-3-(3-(2-(((benzyloxy)carbonyl)amino)ethoxy)phenyl)piperazine-1-carboxylate (60 mg, 0.078 mmol) was dissolved in 4N HCl in dioxane (5 ml) and stirred for 1 hr at rt. The reaction mixture was evaporated. The crude residue was dissolved in DMF (3 ml), and (R)-3-((tert-butoxycarbonyl)amino)-3-phenylpropanoic acid (21.0 mg, 0.079 mmol), DIPEA (0.041 ml, 0.238 mmol) and HATU (60.2 mg, 0.158 mmol) were added. The solution was stirred for 16 hr at rt. The reaction mixture was filtrated and evaporated in vacuum. The crude residue was purified by preparative HPLC (Waters SunFire™ Prep C18 OBD, $CH_3CN/H_2O$ (0.1% TFA)) to give the title compound. MS (ESI+) m/z 806.2 (M+H).

Biological Example 2.5

(+) or (−)-2-((1E,3E,5E)-5-(1-(6-((2-(3-(1-(4-amino-6,7-dimethoxyquinazolin-2-yl)-4-((R)-3-((tert-butoxycarbonyl)amino)-3-phenylpropanoyl)piperazin-2-yl)phenoxy)ethyl)amino)-6-oxohexyl)-3,3-dimethyl-5-sulfoindolin-2-ylidene)penta-1,3-dien-1-yl)-1-ethyl-3,3-dimethyl-5-sulfo-3H-indol-1-ium

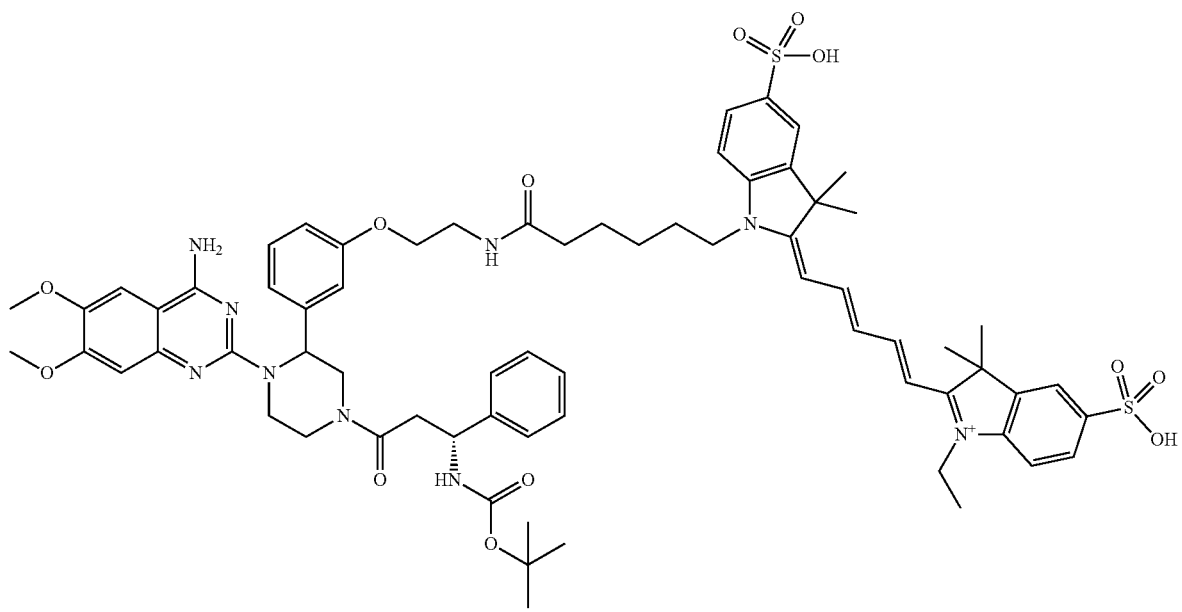 [SMILES: CC[N+]1=C(/C=C/C=C/C=C2/N(CCCCCC(=O)NCCOc3cccc(C4CN(C(=O)C[C@@H](NC(=O)OC(C)(C)C)c5ccccc5)CCN4c4nc(N)c5cc(OC)c(OC)cc5n4)c3)c3ccc(S(=O)(=O)O)cc3C2(C)C)C(C)(C)c2cc(S(=O)(=O)O)ccc21]

(+) or (−)-tert-Butyl((1R)-3-(4-(4-amino-6,7-dimethoxyquinazolin-2-yl)-3-(3-(2-(((benzyloxy)carbonyl)amino)ethoxy)phenyl)piperazin-1-yl)-3-oxo-1-phenylpropyl)carbamate (17 mg, 0.021 mmol) was dissolved in EtOH (5 ml), and added Pd/C (2.24 mg, 2.109 µmol). The reaction was stirred under $H_2$ for 16 hr at room temperature. The reaction mixture was filtered and evaporated. The resulting residue was dissolved in DMF (2 ml), and 2-((1E,3E,5E)-5-(1-(6-((2,5-dioxopyrrolidin-1-yl)oxy)-6-oxohexyl)-3,3-dimethyl-5-sulfoindolin-2-ylidene)penta-1,3-dien-1-yl)-1-ethyl-3,3-dimethyl-3H-indol-1-ium-5-sulfonate (Cy-5, CAS#146368-14-1) (13.32 mg, 0.020 mmol), DIPEA (0.018 ml, 0.101 mmol) and HATU (15.40 mg, 0.040 mmol) were added. The solution stirred for 16 hr at rt. The reaction mixture evaporated in vacuum and purified by preparative HPLC (Macherey-Nagel Nucleosil® 100-10 C18, $CH_3CN/H_2O$ (0.1% TFA)) to give the title compound. MS (ESI+) m/z 656.1 (M/2).

Biological Example 2.6

(+) or (−)-2-((1E,3E,5E)-5-(1-(6-((2-(3-(4-((R)-3-amino-3-phenylpropanoyl)-1-(4-amino-6,7-dimethoxyquinazolin-2-yl)piperazin-2-yl)phenoxy)ethyl)amino)-6-oxohexyl)-3,3-dimethyl-5-sulfoindolin-2-ylidene)penta-1,3-dien-1-yl)-1-ethyl-3,3-dimethyl-5-sulfo-3H-indol-1-ium (+) or (−)-2-((1E,3E,5E)-5-(1-(6-((2-(3-(1-(4-amino-6,7-dimethoxyquinazolin-2-yl)-4-((R)-3-((tert-butoxycarbonyl)amino)-3-phenylpropanoyl)piperazin-2-yl)phenoxy)ethyl)amino)-6-oxohexyl)-3,3-dimethyl-5-sulfoindolin-2-ylidene)penta-1,3-dien-1-yl)-1-ethyl-3,3-dimethyl-5-sulfo-3H-indol-1-ium (4 mg, 3.05 µmol) was dissolved in 4N HCl in dioxane (3 ml) and stirred for 1 hr at rt. The crude mixture was purified by preparative HPLC (Waters Sunfire™ C18 OBD, $CH_3CN/H_2O$ (0.1% TFA)) to give the title compound. Fractions were combined and evaporated to dryness. The residue was dissolved in a minimum amount of $CH_3CN$ and 1M aqueous HCl solution (3 ml, 3.00 mmol) was added. Mixture was then evaporated to give the title compound as HCl salt. $^1H$ NMR(HCl salt, 400 MHz, METHANOL-$d_4$) δ ppm 8.30 (m, 2H), 7.90 (s, 1H), 7.89 (d, J=5.4 Hz, 1H), 7.86 (d, J=5.6 Hz, 1H), 7.72 (dd, J=8.1, 37 Hz, 1H), 7.55 (d, J=7.2 Hz, 1H), 7.37-7.47 (m, 5H), 7.07-7.28 (m, 4H), 6.86-6.95 (m, 3H), 6.68 (t, J=12.5 Hz, 1H), 6.38 (dd, J=4.5, 18.4 Hz, 1H), 6.31 (d, J=13.9 Hz, 1H), 5.95 (br. s, 1H), 4.76-4.84 (m, 1H), 4.68-4.71 (m, 1H), 4.46-4.57 (m, 1H), 4.18-4.31 (m, 3H), 4.05-4.11 (m, 3H), 3.80-4.00 (m, 8H), 3.41-3.60 (m, 3H), 3.06-3.09 (m, 2H), 2.84 (dd, J=3.8, 22.5 Hz, 1H), 2.12-2.22 (m, 2H), 1.75-1.86 (m, 2H), 1.73 (s, 6H), 1.70 (s, 6H), 1.59-1.69 (m, 2H), 1.39 (t, J=7.3 Hz, 3H), 1.29-1.37 (m, 2H). UPLC-MS (ESI+) m/z 606.1 (M/2); Instrument: Waters UPLC Acquity; column: Acquity HSS T3 1.8 µm 2.1×50 mm at 50° C., eluent A: water+0.05% HCOOH+3.75 mM ammonium acetate, B: $CH_3CN$+0.04% HCOOH, Gradient: 5 to 98% B in 1.4 min, flow: 1.0 ml/min; Retention time: 0.64 min.

Biological Example 2.7

Recombinant human factor B (expressed in *drosophila* cells and purified using standard methods) labeled with biotin (10 nM), europium-labeled streptavidin (5 nM) and (+) or (−)-2-((1E,3E,5E)-5-(1-(6-((2-(3-(4-((R)-3-amino-3-phenylpropanoyl)-1-(4-amino-6,7-dimethoxyquinazolin-2-yl)piperazin-2-yl)phenoxy)ethyl)amino)-6-oxohexyl)-3,3-dimethyl-5-sulfoindolin-2-ylidene)penta-1,3-dien-1-yl)-1-ethyl-3,3-dimethyl-5-sulfo-3H-indol-1-ium (Biological Example 2.6, 240 nM activity against factor B when tested using the assay of Biological Example 1) (75 nM) were incubated with test compound at various concentrations up to 2

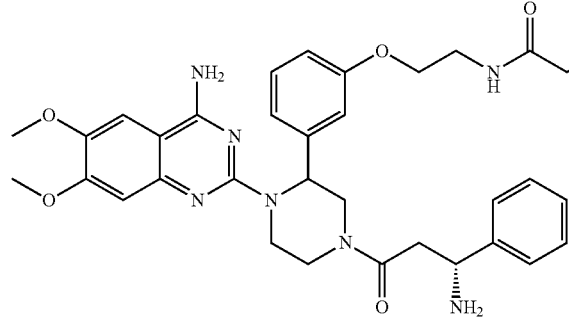
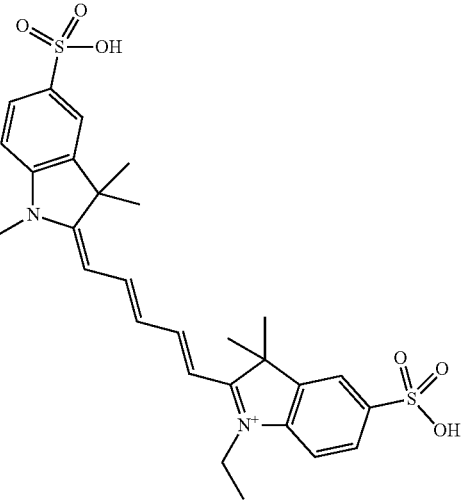

hours at room temperature in 20 mM Tris/HCl, pH 7.4, 0.005% (v/v) Tween20.

The time-gated decrease in fluorescence intensity related to the competition between labeled and unlabeled factor B ligands was recorded at both 620 nm and 665 nm, 70 µs after excitation at 337 nm using a microplate spectrofluorimeter. $IC_{50}$ values were calculated from percentage of inhibition of complement factor B-(+) or (−)-2-((1E,3E,5E)-5-(1-(6-((2-(3-(4-((R)-3-amino-3-phenylpropanoyl)-1-(4-amino-6,7-dimethoxyquinazolin-2-yl)piperazin-2-yl)phenoxy)ethyl)amino)-6-oxohexyl)-3,3-dimethyl-5-sulfoindolin-2-ylidene)penta-1,3-dien-1-yl)-1-ethyl-3,3-dimethyl-5-sulfo-3H-indol-1-ium (Biological Example 2.6, 240 nM activity against factor B when tested using the assay of Biological Example 1) displacement as a function of test compound concentration.

The following Examples, while representing preferred embodiments of the invention, serve to illustrate the invention without limiting its scope.

ABBREVIATIONS

Ac acetyl
AcOH acetic acid
app apparent
aq. aqueous
atm atmosphere
Boc tertiary butyl carboxy
br. broad
BuOH butanol
calcd. calculated
CHAPS 3-[(3-cholamidopropyl)dimethylammonio]-1-propanesulfonate
CVF Cobra Venom Factor
Cy5 2-((1E,3E,5E)-5-(1-(6-((2,5-dioxopyrrolidin-1-yl)oxy)-6-oxohexyl)-3,3-dimethyl-5-sulfoindolin-2-ylidene)penta-1,3-dien-1-yl)-1-ethyl-3,3-dimethyl-3H-indol-1-ium-5-sulfonate
d doublet
DBU 1,8-diazabicyclo[5.4.0]undec-7-ene dd doublet of doublets
DCC N,N'-Dicyclohexylcarbodiimide
DCM dichloromethane
DEA diethylamine
DIBAL-H diisobutylaluminium hydride
DIPEA N,N-diisopropylethylamine
DMAP 4,4-dimethylaminopyridine
DME 1,4-dimethoxyethane
DMF N,N-dimethylformamide
Dess-Martin Periodinane
  Dess-Martin reagent; 1,1,1-Triacetoxy-1,1-dihydro-1,2-benziodoxol-3(1H)-one
DMSO dimethylsulfoxide
ESI electrospray ionization
EtOAc, AcOEt ethyl acetate
Et ethyl
EtOH ethanol
FCC flash column chromatography
g grams
h hour(s)
HATU 2-(1H-7-azabenzotriazol-1-yl)-1,1,3,3-tetramethyl uronium hexafluorophosphate methanaminium
HC HPLC condition
HFIP 1,1,1,3,3,3-hexafluoro-2-propanol
HPLC high performance liquid chromatography
IPA 2-propanol
IR infrared spectroscopy
L liter(s)
LDA lithium diisopropyl amide
TMP 2,2',6,6'-tetramethylpiperidine, 2,2',6,6'-tetramethylpiperidyl
M molar
MHz mega Herts
m multiplet
Me methyl
MeI iodomethane
MeOH methanol
mg milligram(s)
mm millimeter(s)
min minutes
mL milliliter(s)
mmol millimoles
MP melting point
MS mass spectrometry
Ms$_2$O methanesulfonyl anhydride
m/z mass to charge ratio
N normal
NMR nuclear magnetic resonance
PBS phosphate buffered saline
Pd/C palladium on carbon
Ph phenyl
ppm parts per million
PyBOP benzotriazol-1-yloxytripyrrolidinophosphonium hexafluorophosphate
rac racemic
RP- reverse phase
rt room temperature
t$_r$ retention time
s singlet
sat. saturated
  SEM 2-(trimethylsilyl)ethoxymethyl
SFC Supercritical Fluid Chromatography
t triplet
TBAF tetra-n-butylammonium fluoride
TBSCl tert-butyldimethylsilyl chloride
TEA, Et$_3$N triethylamine
tert- tertiary
TFA trifluoroacetic acid
THF tetrahydrofuran
TIPS triethylsilyl
TOSMIC toluenesulfonylmethyl isocyanide
TMS trimethylsilyl
Ts p-toluenesulfonyl
TsOH p-toluenesulfonic acid
v/v volume per volume
w/v weight per volume
w/w weight per weight The following examples are intended to illustrate the invention and are not to be construed as being limitations thereon. Unless otherwise stated, one or more tautomeric forms of compounds of the examples described hereinafter may be prepared in situ and/or isolated. All tautomeric forms of compounds of the examples described hereafter should be considered to be disclosed. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

All reactions are carried out under nitrogen or argon unless otherwise stated. Optical rotations were measured in MeOH.

Proton NMR ($^1$H NMR) is conducted in deuterated solvent. In certain compounds disclosed herein, one or more $^1$H shifts overlap with residual proteo solvent signals; these signals have not been reported in the experimental provided hereinafter.

Multiple parent ion masses are reported for mass spectroscopy data when the compound of the invention contains one or more bromine atoms. Bromine exists as an approximately 1:1 molar ratio of $^{79}$Br:$^{81}$Br. Thus, a compound with a single bromine atom will exhibit two parent mass ions having a difference of 2 amu.

Following preparation methods were used for RP-HPLC.

HC-A:

Stationary phase: Waters SunFire™ Prep C$_{18}$ OBD™ 5 μm, 30×100 mm

Mobile phase: gradient, water with 0.1% TFA/acetonitrile

HC-B

Stationary phase: Gemini® NX 5μ C18 110 A 100×30 mm

Mobile phase: gradient, water with 0.1% (28% ammonium hydroxide)/acetonitrile

Example 1

Example 1-A

7-Methyl-1H-indol-5-ol

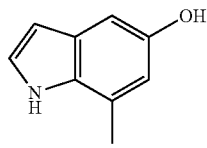

Potassium nitrosodisulfonate (46.1 g, 172 mmol) was added to a 0.1 M aqueous solution of sodium phosphate at pH=7 (1 L) at room temperature. 7-Methylindoline (CAS #: 65673-86-1) (10.4 g, 78 mmol) was dissolved in 100 mL of acetone and added to the reaction in one portion at room temperature. After 30 minutes the reaction was diluted with ethyl acetate and the organic layer was separated. The aqueous layer was then extracted with ethyl acetate. The organic layers were combined, dried over magnesium sulfate, filtered and concentrated. The resulting residue was absorbed onto silica and then purified by silica gel flash chromatography (0-50% ethyl acetate in heptanes) to provide the title compound. MS (ESI+) m/z 148.08 (M+H).

Example 1-B 5-(Allyloxy)-7-methyl-1H-indole

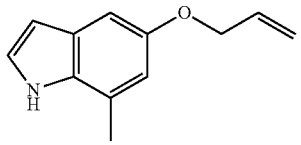

7-Methyl-1H-indol-5-ol (5.2 g, 35.3 mmol) was dissolved in toluene (221 mL) and prop-2-en-1-ol (2.42 mL, 35.3 mmol) was added followed by cyanomethylenetributylphosphorane (21.32 g, 88 mmol). The reaction was heated at 100° C. After 1 hour the reaction was cooled to room temperature, concentrated and purified by silica gel flash chromatography (0:100 EtOAc:heptanes) to provide the title compound. MS (ESI+) m/z 188.15 (M+H).

Example 1-C

4-Allyl-7-methyl-1H-indol-5-ol

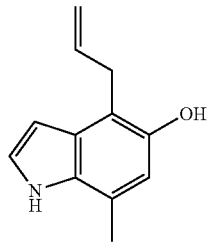

5-(Allyloxy)-7-methyl-1H-indole (2.02 g, 8.43 mmol) was heated neat at 230° C. for 6 min. The reaction was then cooled in an ice bath. The reaction was then dissolved in methanol and absorbed onto silica and then purified by silica gel flash chromatography (100% methylene chloride) to provide the title compound. MS (ESI+) m/z 188.11 (M+H).

Example 1-D tert-Butyl 4-allyl-5-hydroxy-7-methyl-1H-indole-1-carboxylate

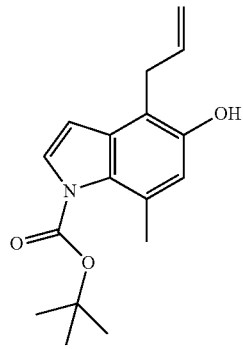 [SMILES: C=CCc1c(O)cc(C)c2c1ccn2C(=O)OC(C)(C)C]

To a solution of 4-allyl-7-methyl-1H-indol-5-ol (4.03 g, 21.52 mmol) in acetonitrile (26.9 mL) was added Boc$_2$O (15 mL, 64.6 mmol) and DMAP (0.263 g, 2.15 mmol), and the reaction was stirred at room temperature for 2 hours. The reaction was concentrated, then diluted with MeOH (75 mL) and K$_2$CO$_3$ (14.87 g, 108 mmol) was added. After 3 hours the reaction was neutralized with AcOH (6 mL). Water was then added and the layers were separated. The aqueous layer was extracted with EtOAc. The organics layer was washed with brine, dried over MgSO$_4$, filtered and concentrated. The product was purified by silica gel flash chromatography (0-50% EtOAc in heptanes) to provide the title compound. MS (ESI+) m/z 288.2 (M+H).

Example 1-E tert-Butyl 4-allyl-5-(difluoromethoxy)-7-methyl-1H-indole-1-carboxylate

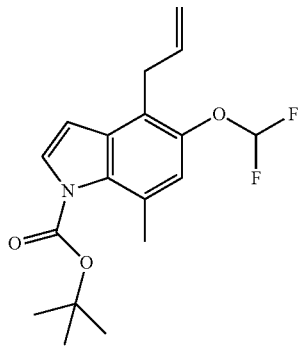 [SMILES: C=CCc1c(OC(F)F)cc(C)c2c1ccn2C(=O)OC(C)(C)C]

tert-Butyl 4-allyl-5-hydroxy-7-methyl-1H-indole-1-carboxylate (3.6 g, 12.53 mmol) was dissolved in acetonitrile (62.6 mL) and water (62.6 mL), then KOH (14.06 g, 251 mmol) was added and the solution was stirred until all the KOH went into solution. The resulting solution was then cooled to −78° C. (solution froze) and diethyl bromodifluoromethylphosphonate (4.45 mL, 25.06 mmol) was added. The reaction was removed from the dry ice bath and allowed to warm to room temperature. After 1 hour, EtOAc and water were added, and the resulting layers were separated. The aqueous layer was further extracted with EtOAc. The combined organics were washed with brine, dried over MgSO$_4$, filtered and concentrated. The resulting residue was purified by flash chromatography (0-40% EtOAc in heptanes) to provide the title compound. $^1$H NMR (400 MHz, DMSO-d$_6$) δ ppm 7.69 (d, J=3.79 Hz, 1H) 7.08 (t, J=74.7 Hz, 1H) 6.96 (s, 1H) 6.76 (d, J=3.79 Hz, 1H) 5.89 (dd, J=16.93, 10.36 Hz, 1H) 4.91-5.05 (m, 2H) 3.57 (d, J=6.32 Hz, 2H) 1.59 (s, 9H). MS (ESI+) m/z 338.1 (M+H).

Example 1-F tert-Butyl 5-(difluoromethoxy)-7-methyl-4-(prop-1-en-1-yl)-1H-indole-1-carboxylate

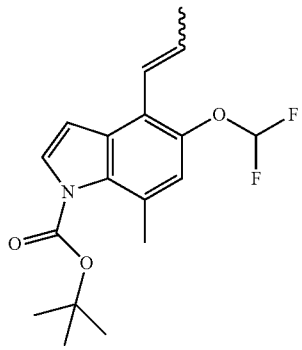

To solution of tert-butyl 4-allyl-5-(difluoromethoxy)-7-methyl-1H-indole-1-carboxylate (2.05 g, 6.08 mmol) in 1,1,1,3,3,3-hexafluoroisopropanol (7.6 mL) was added Pd(OAc)$_2$ (0.041 g, 0.182 mmol) and the reaction stirred for 45 minutes at room temperature. At this point the reaction was concentrated and purified directly by flash chromatography (0-40% EtOAc in heptanes) to provide the title compound. $^1$H NMR (400 MHz, DMSO-d$_6$) δ ppm 7.71 (d, J=4.04 Hz, 1H) 6.87-7.32 (m, 3H) 6.65 (dd, J=16.17, 1.77 Hz, 1H) 6.26-6.43 (m, 1H) 1.94 (dd, J=6.69, 1.64 Hz, 3H) 1.60 (s, 9H).

Example 1-G tert-Butyl 5-(difluoromethoxy)-4-formyl-7-methyl-1H-indole-1-carboxylate

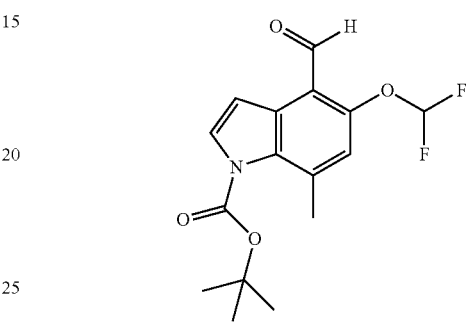

To a solution of tert-butyl 5-(difluoromethoxy)-7-methyl-4-(prop-1-en-1-yl)-1H-indole-1-carboxylate (1.83 g, 5.42 mmol) in dioxane (40 mL) and water (13.56 mL) at 0° C., 2,6-lutidine (1.26 mL, 10.85 mmol), OsO$_4$ (1.36 mL, 0.108 mmol) (2.5% in t-BuOH) and NaIO$_4$ (4.64 g, 21.70 mmol) were added and the reaction was stirred at room temperature. After 1 hour the reaction was diluted with DCM and the layers separated. The organics were washed with sat. NH$_4$Cl and water, dried over MgSO$_4$, filtered and concentrated. The resulting residue was purified by flash chromatography (0-40% EtOAc in heptanes) to provide the title compound. $^1$H NMR (400 MHz, DMSO-d$_6$) δ ppm 10.45 (s, 1H) 7.93 (d, J=3.54 Hz, 1H) 7.37 (d, J=3.54 Hz, 1H) 7.34 (t, J=73.6 Hz, 1H) 7.16 (s, 1H) 2.63 (s, 3H) 1.61 (s, 9H). MS (ESI+) m/z 326.2 (M+H).

Example 2 (Intermediate 1)

1-((2-(Trimethylsilyl)ethoxy)methyl)-1H-benzo[d]imidazole-6-carbonitrile and 1-((2-(trimethylsilyl)ethoxy)methyl)-1H-benzo[d]imidazole-5-carbonitrile

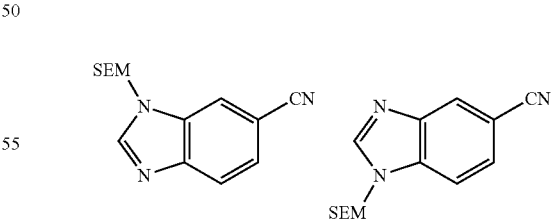

To a solution of 1H-benzo[d]imidazole-5-carbonitrile (CAS#; 6287-83-8) (1 g, 3.81 mmol) in DMF (50 mL) was added NaH (60% in mineral oil, 610 mg, 15.3 mmol), and then the mixture was stirred at room temperature for 1 hr, then cooled down to 0° C. SEMCl (0.75 mL, 4.2 mmol) was then added at 0° C., and then the mixture was stirred at 0° C. for 0.5 h. The reaction was quenched with MeOH at 0° C. and then diluted with Et$_2$O. The layers were separated and the organic layer was washed successively with H₂O and brine, it was then dried over Na₂SO₄, filtered and concentrated. The resulting residue was purified by silica gel flash chromatography (10-20% EtOAc in DCM) to give the title compounds as a mixture, which was used as is. MS (ESI+) m/z 274.3 (M+H).

Example 3

Example 3-A (±)-tert-Butyl 4-((5-cyano-1-((2-(trimethylsilyl)ethoxy)methyl)-1H-benzo[d]imidazol-2-yl)(hydroxy)methyl)-5-(difluoromethoxy)-7-methyl-1H-indole-1-carboxylate and (±)-tert-butyl 4-((6-cyano-1-((2-(trimethylsilyl)ethoxy)methyl)-1H-benzo[d]imidazol-2-yl)(hydroxy)methyl)-5-(difluoromethoxy)-7-methyl-1H-indole-1-carboxylate

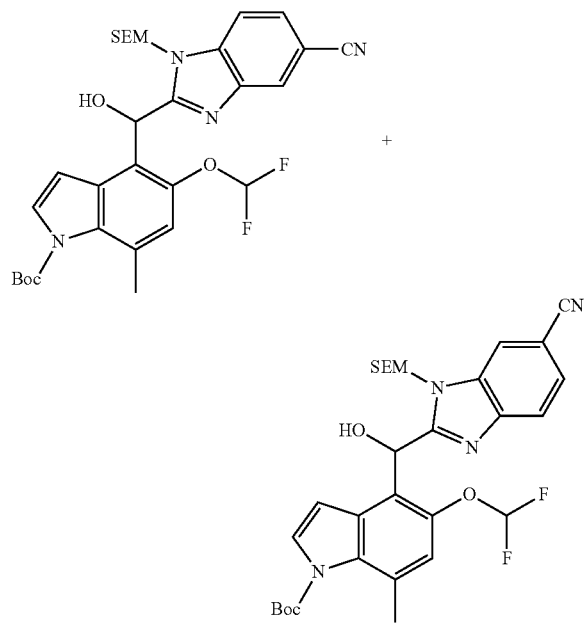

To a solution of a mixture of 1-((2-(trimethylsilyl)ethoxy)methyl)-1H-benzo[d]imidazole-5-carbonitrile and 1-((2-(trimethylsilyl)ethoxy)methyl)-1H-benzo[d]imidazole-6-carbonitrile (2.25 g, 8.24 mmol) in THF (34.0 mL), LDA (2.0M in heptane/THF/ethylbenzene, 3.71 mL, 7.41 mmol) was added at −78° C. After stirring for 30 min., a solution of tert-butyl 5-(difluoromethoxy)-4-formyl-7-methyl-1H-indole-1-carboxylate (1.34 g, 4.12 mmol) in THF (8 mL) was added to the reaction mixture. After stirring for 15 minutes, the reaction mixture was diluted with MeOH (12 mL), sat. aq. NH₄Cl (60 mL), sat. aq. brine (60 mL) and EtOAc (200 mL). The layers were separated and the aqueous layer was extracted twice with EtOAc. The organic layer was washed with brine, dried over MgSO₄, filtered, and concentrated. The resulting residue was purified by flash column chromatography (0-60% EtOAc in heptanes) to provide the mixture of title compounds. MS (ESI+) m/z 599.5 (M+H).

Example 3-B a) (±)-2-((5-(Difluoromethoxy)-7-methyl-1H-indol-4-yl)(hydroxy)methyl)-1H-benzo[d]imidazole-5-carbonitrile and (±)-2-(((2-aminoethyl)amino)(5-(difluoromethoxy)-7-methyl-1H-indol-4-yl)methyl)-1H-benzo[d]imidazole-5-carbonitrile

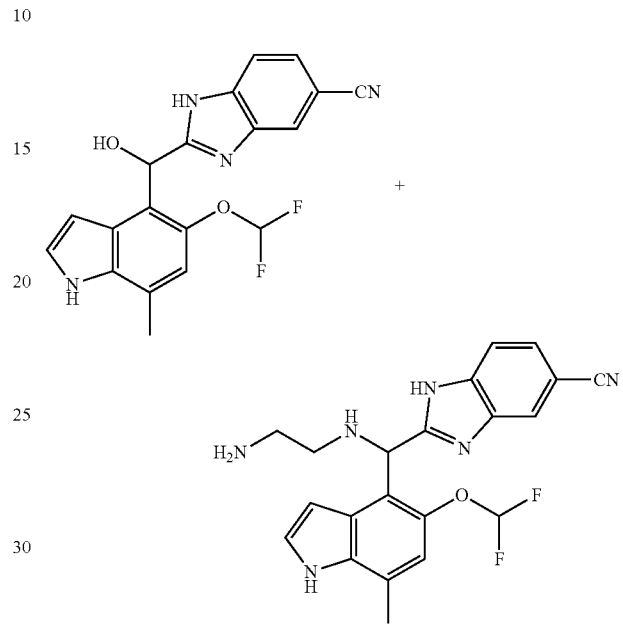

To a solution of a mixture of tert-butyl 4-((5-cyano-1-((2-(trimethylsilyl)ethoxy)methyl)-1H-benzo[d]imidazol-2-yl)(hydroxy)methyl)-5-(difluoromethoxy)-7-methyl-1H-indole-1-carboxylate and tert-butyl 4-((6-cyano-1-((2-(trimethylsilyl)ethoxy)methyl)-1H-benzo[d]imidazol-2-yl)(hydroxy)methyl)-5-(difluoromethoxy)-7-methyl-1H-indole-1-carboxylate (600 mg, 1 mmol) in THF (10.0 mL), ethylenediamine (0.67 mL, 10 mmol) was added followed by TBAF (1M in THF, 10.0 mL, 10 mmol) and the reaction was stirred overnight at 55° C. The reaction was then cooled to room temperature, quenched with sat. aq. NH₄Cl, extracted with EtOAc, and the organic extract was dried over MgSO₄, filtered and concentrated. The resulting residue was purified by flash chromatography (0-80% EtOAc in heptanes, then 0-30% (10% NH₄OH in MeOH-DCM) to provide two products in the following order.

(±)-2-((5-(difluoromethoxy)-7-methyl-1H-indol-4-yl)(hydroxy)methyl)-1H-benzo[d]imidazole-5-carbonitrile. ¹H NMR (400 MHz, DMSO-d₆) δ ppm 13.05 (br. s., 1H) 11.17 (br. s., 1H) 7.91 (s, 1H) 7.59 (br. s., 1H) 7.50 (br. s., 1H) 7.27 (t, J=2.40 Hz, 1H) 7.11 (dd, J=78.06, 73.77 Hz, 1H) 6.80 (s, 1H) 6.59 (d, J=4.04 Hz, 1H) 6.51 (d, J=4.04 Hz, 1H) 6.37-6.47 (m, 1H) 2.46 (s, 3H). HRMS calcd. for C₁₉H₁₄F₂N₄O₂ (M+H)⁺ 369.1158. found 369.1169.

(±)-2-(((2-aminoethyl)amino)(5-(difluoromethoxy)-7-methyl-1H-indol-4-yl)methyl)-1H-benzo[d]imidazole-5-carbonitrile. ¹H NMR (400 MHz, DMSO-d₆) δ ppm 11.19 (br. s., 1H) 7.84-8.02 (m, 1H) 7.59 (d, J=8.34 Hz, 1H) 7.47 (dd, J=8.34, 1.52 Hz, 1H) 7.28 (d, J=2.53 Hz, 1H) 7.06 (t, J=75.5 Hz, 1H) 6.80 (s, 1H) 6.50 (d, J=2.78 Hz, 1H) 5.66 (s, 1H) 2.53-2.73 (m, 4H) 2.46 (s, 3H). HRMS calcd. for C₂₁H₂₀F₂N₆O (M+H)⁺ 411.174. found 411.1755.

b) (+) and (−)-2-((5-(difluoromethoxy)-7-methyl-1H-indol-4-yl)(hydroxy)methyl)-1H-benzo[d]imidazole-5-carbonitrile Resolution of the enantiomers of 2-((5-(difluoromethoxy)-7-methyl-1H-indol-4-yl)(hydroxy)methyl)-1H-benzo[d]imidazole-5-carbonitrile was achieved by chiral HPLC using a CHIRALPAK® IC column with 30% IPA and 0.2% DEA in Heptanes to give (−)-2-((5-(difluoromethoxy)-7-methyl-1H-indol-4-yl)(hydroxy)methyl)-1H-benzo[d]imidazole-5-carbonitrile ($t_r$=6.87 min) and (+)-2-((5-(difluoromethoxy)-7-methyl-1H-indol-4-yl)(hydroxy)methyl)-1H-benzo[d]imidazole-5-carbonitrile ($t_r$=11.76 min).

Example 4

(±)-2-((5-(Difluoromethoxy)-7-methyl-1H-indol-4-yl)(methylamino)methyl)-1H-benzo[d]imidazole-5-carbonitrile

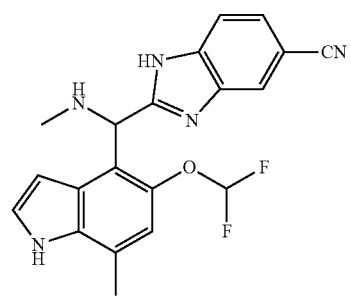 [SMILES: CNC(c1nc2cc(C#N)ccc2[nH]1)c1c(OC(F)F)cc(C)c2[nH]ccc12]

To a solution of a mixture of tert-butyl 4-((5-cyano-1-((2-(trimethylsilyl)ethoxy)methyl)-1H-benzo[d]imidazol-2-yl)(hydroxy)methyl)-5-(difluoromethoxy)-7-methyl-1H-indole-1-carboxylate and tert-butyl 4-((6-cyano-1-((2-(trimethylsilyl)ethoxy)methyl)-1H-benzo[d]imidazol-2-yl)(hydroxy)methyl)-5-(difluoromethoxy)-7-methyl-1H-indole-1-carboxylate (20 mg, 0.033 mmol) and methylamine (2.0M in THF, 0.17 mL, 0.33 mmol) in THF (0.33 mL) at room temperature, TBAF (1M in THF, 0.33 mL, 0.33 mmol) was added and the mixture was stirred at 55° C. After stirring overnight the reaction was cooled to room temperature, quenched with sat. aq. NH₄Cl, extracted with EtOAc, and the organic extract was dried over MgSO₄, filtered and concentrated. The resulting residue was purified by flash chromatography (0-100% EtOAc in heptanes) to provide the title compound. $^1$H NMR (400 MHz, DMSO-$d_6$) δ ppm 11.22 (br. s., 1H) 7.94 (br. s., 1H) 7.60 (d, J=8.34 Hz, 1H) 7.49 (dd, J=8.34, 1.52 Hz, 1H) 7.29 (t, J=2.78 Hz, 1H) 7.06 (t, J=75.5 Hz, 1H) 6.81 (s, 1H) 6.49 (dd, J=3.03, 2.02 Hz, 1H) 5.55 (s, 1H) 2.46 (d, J=0.76 Hz, 3H) 2.36 (s, 3H). HRMS calcd. for $C_{20}H_{17}F_2N_5O$ (M+H)$^+$ 382.1474. found 382.1489.

Example 5

Example 5-A tert-Butyl 4-(5-cyano-1-((2-(trimethylsilyl)ethoxy)methyl)-1H-benzo[d]imidazole-2-carbonyl)-5-(difluoromethoxy)-7-methyl-1H-indole-1-carboxylate and tert-butyl 4-(6-cyano-1-((2-(trimethylsilyl)ethoxy)methyl)-1H-benzo[d]imidazole-2-carbonyl)-5-(difluoromethoxy)-7-methyl-1H-indole-1-carboxylate

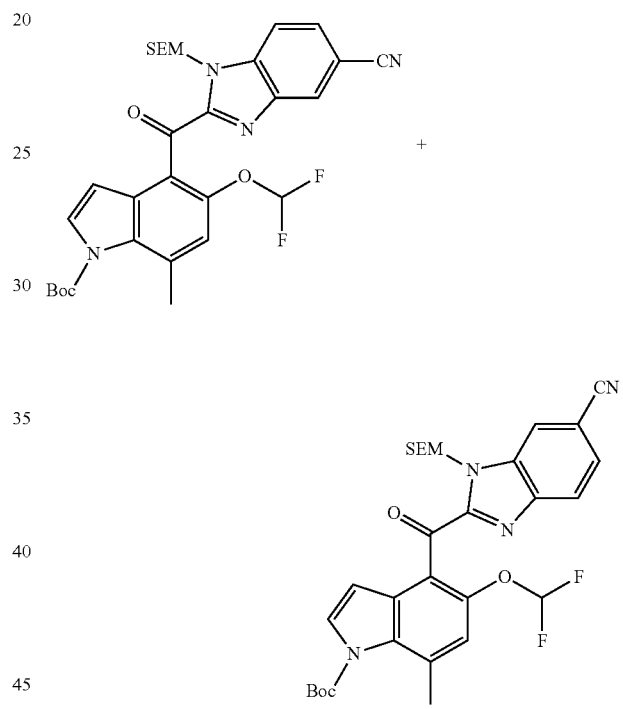

To a solution of a mixture of (±)-tert-butyl 4-((5-cyano-1-((2-(trimethylsilyl)ethoxy)methyl)-1H-benzo[d]imidazol-2-yl)(hydroxy)methyl)-5-(difluoromethoxy)-7-methyl-1H-indole-1-carboxylate and (±)-tert-butyl 4-((6-cyano-1-((2-(trimethylsilyl)ethoxy)methyl)-1H-benzo[d]imidazol-2-yl)(hydroxy)methyl)-5-(difluoromethoxy)-7-methyl-1H-indole-1-carboxylate (Example 3-A) (700 mg, 1.169 mmol) in DCM (16.7 mL), manganese dioxide (1016 mg, 11.69 mmol) was added and the reaction was stirred at room temperature. After stirring overnight additional manganese dioxide (508 mg) was added. After an additional 2 hours the solid was filtered through a pad of Celite®, washed with DCM, and the filtrate was concentrated. The resulting residue was puri1H) 2.53-2.73 (m, 4H) 2.46 (s, 3H). HRMS calcd. for $C_{21}H_{20}F_2N_6O$ (M+H)$^+$ 411.174. found 411.1755.

fied by flash chromatography (0-40% EtOAc in heptanes) to provide the mixture of title compounds. MS (ESI+) m/z 597.5 (M+H).

Example 5-B (±)-tert-Butyl 4-(((tert-butylsulfinyl)imino)(5-cyano-1-((2-(trimethylsilyl)ethoxy)methyl)-1H-benzo[d]imidazol-2-yl)methyl)-5-(difluoromethoxy)-7-methyl-1H-indole-1-carboxylate and (±)-tert-butyl 4-(((tert-butylsulfinyl)imino)(6-cyano-1-((2-(trimethylsilyl)ethoxy)methyl)-1H-benzo[d]imidazol-2-yl)methyl)-5-(difluoromethoxy)-7-methyl-1H-indole-1-carboxylate

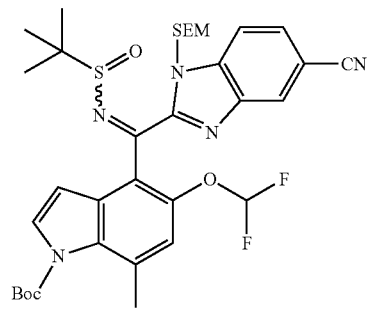

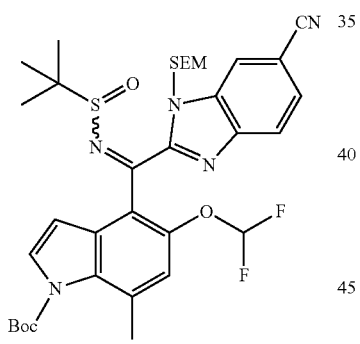

A mixture of tert-butyl 4-(5-cyano-1-((2-(trimethylsilyl)ethoxy)methyl)-1H-benzo[d]imidazole-2-carbonyl)-5-(difluoromethoxy)-7-methyl-1H-indole-1-carboxylate and tert-butyl 4-(6-cyano-1-((2-(trimethylsilyl)ethoxy)methyl)-1H-benzo[d]imidazole-2-carbonyl)-5-(difluoromethoxy)-7-methyl-1H-indole-1-carboxylate (0.41 g, 0.69 mmol), (±)-2-methylpropanesulfinamide (0.092 g, 0.76 mmol) and Ti(OiPr)$_4$ (1.4 mL, 4.81 mmol) were stirred at 90° C. After 90 minutes the reaction mixture was cooled to room temperature and diluted with EtOAc and sat. aq. brine. The resulting mixture was filtered and the organic layer of the filtrate was dried over MgSO$_4$, filtered, and concentrated. The resulting residue was purified by flash chromatography (0-50% EtOAc in heptanes) to provide a mixture of title compounds. MS (ESI+) m/z 700.6 (M+H).

Example 5-C (±)-tert-Butyl 4-(1-(5-cyano-1-((2-(trimethylsilyl)ethoxy)methyl)-1H-benzo[d]imidazol-2-yl)-1-(1,1-dimethylethylsulfinamido)ethyl)-5-(difluoromethoxy)-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-(1,1-dimethylethylsulfinamido)ethyl)-5-(difluoromethoxy)-7-methyl-1H-indole-1-carboxylate

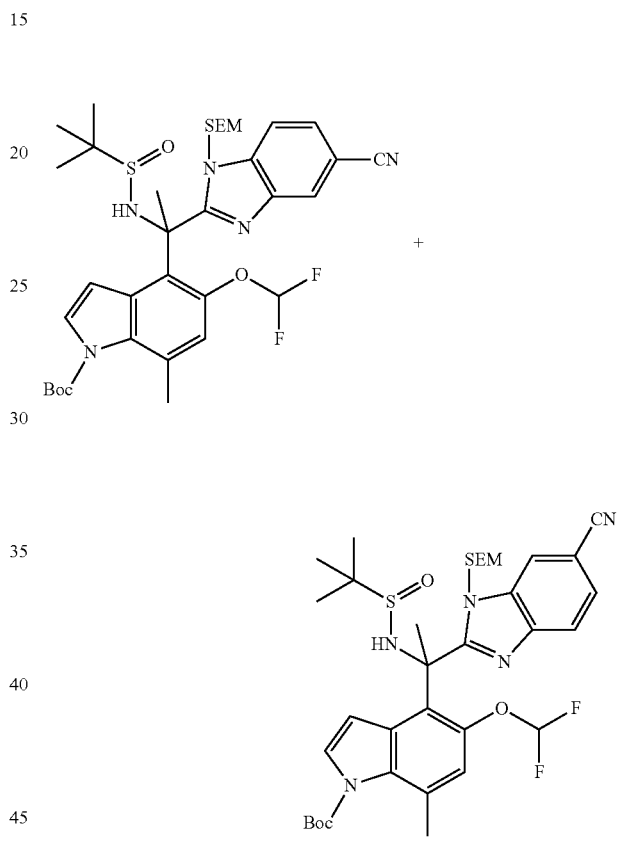

To a solution of a mixture of (±)-tert-butyl 4-(((tert-butylsulfinyl)imino)(5-cyano-1-((2-(trimethylsilyl)ethoxy)methyl)-1H-benzo[d]imidazol-2-yl)methyl)-5-(difluoromethoxy)-7-methyl-1H-indole-1-carboxylate and (±)-tert-butyl 4-(((tert-butylsulfinyl)imino)(6-cyano-1-((2-(trimethylsilyl)ethoxy)methyl)-1H-benzo[d]imidazol-2-yl)methyl)-5-(difluoromethoxy)-7-methyl-1H-indole-1-carboxylate (349 mg, 0.499 mmol) in THF (5 mL), MeMgCl (3M in THF, 0.5 mL, 1.49 mmol) was added at 0° C. After 10 minutes the mixture was diluted with sat. aq. NH$_4$Cl and EtOAc, the layers were separated and the aqueous layer was extracted with EtOAc. The combined organic layers were dried over MgSO$_4$, filtered and concentrated. The resulting residue was purified by flash chromatography (0-100% EtOAc in heptanes) to provide a mixture of the title compounds. MS (ESI+) m/z 716.5 (M+H).

Example 5-D (±)-tert-Butyl 4-(1-amino-1-(5-cyano-1H-benzo[d]imidazol-2-yl)ethyl)-5-(difluoromethoxy)-7-methyl-1H-indole-1-carboxylate

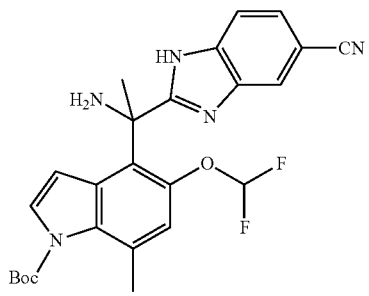 [SMILES: Cc1cc(OC(F)F)c(C(C)(N)c2nc3cc(C#N)ccc3[nH]2)c2ccn(C(=O)OC(C)(C)C)c12]

To a mixture of (±)-tert-butyl 4-(1-(5-cyano-1-((2-(trimethylsilyl)ethoxy)methyl)-1H-benzo[d]imidazol-2-yl)-1-(1,1-dimethylethylsulfinamido)ethyl)-5-(difluoromethoxy)-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-(1,1-dimethylethylsulfinamido)ethyl)-5-(difluoromethoxy)-7-methyl-1H-indole-1-carboxylate (306 mg, 0.427 mmol) was added HCl (1.25M in MeOH, 1.7 mL, 2.137 mmol) and the solution was stirred at room temperature for 90 minutes. The reaction mixture was then concentrated, diluted with sat. aq. NaHCO$_3$, the aqueous layer was extracted with EtOAc, and the organic extract was dried over MgSO$_4$, filtered and concentrated. The residue was purified by flash chromatography (0-80% EtOAc in heptanes) to provide the title compound. MS (ESI+) m/z 482.3 (M+H).

Example 5-E a) (±)-2-(1-Amino-1-(5-(difluoromethoxy)-7-methyl-1H-indol-4-yl)ethyl)-1H-benzo[d]imidazole-5-carbonitrile

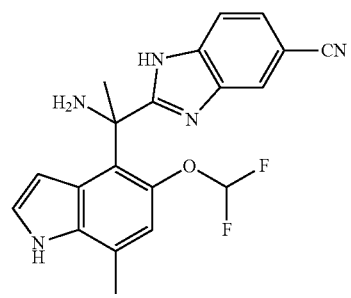 [SMILES: Cc1cc(OC(F)F)c(C(C)(N)c2nc3cc(C#N)ccc3[nH]2)c2cc[nH]c12]

To a solution of tert-butyl 4-(1-amino-1-(5-cyano-1H-benzo[d]imidazol-2-yl)ethyl)-5-(difluoromethoxy)-7-methyl-1H-indole-1-carboxylate (77 mg, 0.160 mmol) in MeOH (1.6 mL) at room temperature, Cs$_2$CO$_3$ (261 mg, 0.8 mmol) was added and the reaction was stirred at 60° C. After 1 hour the reaction mixture was loaded directly onto a silica gel column and purified by flash chromatography (0-100% EtOAc in heptanes) to provide the title compound. $^1$H NMR (400 MHz, DMSO-d$_6$) δ ppm 11.19 (br. s., 1H) 7.96 (br. s., 1H) 7.58 (br. s., 1H) 7.50 (dd, J=8.21, 1.39 Hz, 1H) 7.28 (t, J=2.91 Hz, 1H) 6.70 (s, 1H) 6.66 (t, J=75.3 Hz, 1H) 6.45 (br. s., 1H) 2.45 (d, J=0.76 Hz, 3H) 2.00 (s, 3H). HRMS calcd. for C$_{20}$H$_{17}$F$_2$N$_5$O (M+H)$^+$ 382.1474. found 382.1486.

b) (+) and (−)-2-(1-amino-1-(5-(difluoromethoxy)-7-methyl-1H-indol-4-yl)ethyl)-1H-benzo[d]imidazole-5-carbonitrile Resolution of the enantiomers of 2-(1-amino-1-(5-(difluoromethoxy)-7-methyl-1H-indol-4-yl)ethyl)-1H-benzo[c]imidazole-5-carbonitrile was achieved by chiral SFC using a CHIRALPAK®AD-H column with 25% IPA+0.2% DEA in CO$_2$ to give (+)-2-(1-amino-1-(5-(difluoromethoxy)-7-methyl-1H-indol-4-yl)ethyl)-1H-benzo[d]imidazole-5-carbonitrile (t$_r$=2.6 min) and (−)-2-(1-amino-1-(5-(difluoromethoxy)-7-methyl-1H-indol-4-yl)ethyl)-1H-benzo[d]imidazole-5-carbonitrile=3.3 min).

Example 6

Example 6-A (±)-tert-Butyl 4-(1-(5-cyano-1-((2-(trimethylsilyl)ethoxy)methyl)-1H-benzo[d]imidazol-2-yl)-1-hydroxyethyl)-5-(difluoromethoxy)-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-hydroxy ethyl)-5-(difluoromethoxy)-7-methyl-1H-indole-1-carboxylate

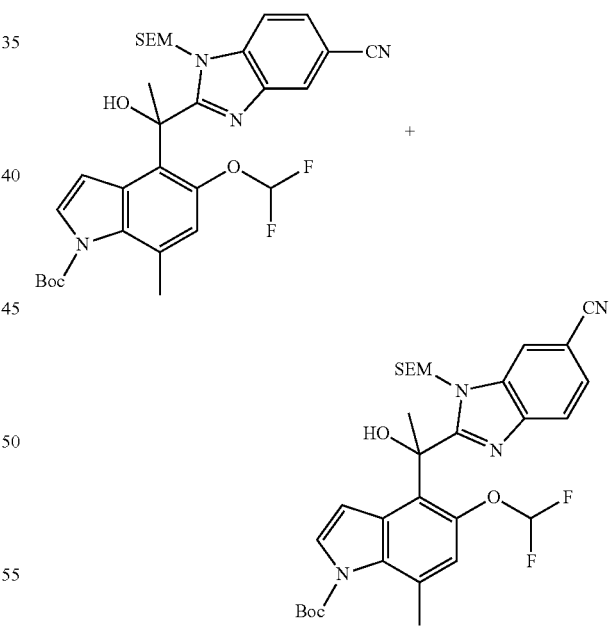

To a solution of a mixture of tert-butyl 4-(5-cyano-1-((2-(trimethylsilyl)ethoxy)methyl)-1H-benzo[d]imidazole-2-carbonyl)-5-(difluoromethoxy)-7-methyl-1H-indole-1-carboxylate and tert-butyl 4-(6-cyano-1-((2-(trimethylsilyl)ethoxy)methyl)-1H-benzo[d]imidazole-2-carbonyl)-5-(difluoromethoxy)-7-methyl-1H-indole-1-carboxylate (Example 5-A) (0.67 g, 1.12 mmol) in THF (11.23 mL) at −78° C., MeMgBr (1.0 M in butyl ether, 1.68 mL, 1.68 mmol) was added and the reaction was stirred at −78° C. After 10 minutes additional MeMgBr (1.0 M in butyl ether, 0.28 mL, 0.28 mmol) was added. After another 10 minutes the reaction was quenched with sat. aq. NH₄Cl and brine, the layers were separated and the aqueous layer was extracted with EtOAc, and the organic extract was dried over MgSO₄, filtered and concentrated. The resulting residue was purified by flash chromatography (0-70% EtOAc in heptanes) to provide a mixture of the title compounds. MS (ESI+) m/z 613.6 (M+H).

Example 6-B a) (±)-2-(1-(5-(Difluoromethoxy)-7-methyl-1H-indol-4-yl)-1-hydroxyethyl)-1H-benzo[d]imidazole-5-carbonitrile

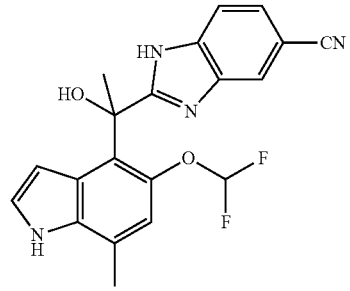 [SMILES: Cc1cc(OC(F)F)c(C(C)(O)c2nc3cc(C#N)ccc3[nH]2)c2cc[nH]c12]

To a solution of a mixture of (±)-tert-butyl 4-(1-(5-cyano-1-((2-(trimethylsilyl)ethoxy)methyl)-1H-benzo[d]imidazol-2-yl)-1-hydroxyethyl)-5-(difluoromethoxy)-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-hydroxyethyl)-5-(difluoromethoxy)-7-methyl-1H-indole-1-carboxylate (310 mg, 0.504 mmol) in THF (5 mL) at room temperature, ethylenediamine (0.34 mL, 5.04 mmol) was added followed by TBAF (1M in THF, 5.04 mL, 5.04 mmol) and the reaction was stirred at 60° C. After 2 days the reaction was cooled to room temperature, quenched with sat. aq. WWI and extracted with EtOAc. The organic layers were combined, dried over MgSO₄, filtered and concentrated. The resulting residue was purified by flash chromatography (0-100% EtOAc in heptanes) to provide the title compound. ¹H NMR (400 MHz, DMSO-d₆) δ ppm 12.51 (s, 1H) 11.12 (br. s., 1H) 8.06 (m) 7.81 (m) 7.65-7.74 (m) 7.46-7.56 (m) 7.29 (t, J=2.78 Hz, 1H) 6.72 (br. s., 1H) 6.68 (s, 1H) 6.65 (t, J=75.8 Hz, 1H) 6.22 (s, 1H) 2.45 (s, 3H) 2.09 (s, 3H). HRMS calcd. for C₂₀H₁₆F₂N₄O₂ (M+H)⁺ 383.1314. found 383.1321.

b) (+) and (−)-2-(1-(5-(difluoromethoxy)-7-methyl-1H-indol-4-yl)-1-hydroxyethyl)-1H-benzo[d]imidazole-5-carbonitrile Resolution of the enantiomers of 2-(1-(5-(difluoromethoxy)-7-methyl-1H-indol-4-yl)-1-hydroxyethyl)-1H-benzo[d]imidazole-5-carbonitrile was achieved by chiral HPLC using a CHIRALPAK® AD column with 25% EtOH (−)-0.2% DEA) in heptanes to give (−)-2-(1-(5-(difluoromethoxy)-7-methyl-1H-indol-4-yl)-1-hydroxyethyl)-1H-benzo[d]imidazole-5-carbonitrile (t$_r$=6.55 min) and (+)-2-(1-(5-(difluoromethoxy)-7-methyl-1H-indol-4-yl)-1-hydroxyethyl)-1H-benzo[d]imidazole-5-carbonitrile (t$_r$=8.52 min).

Example 7

(+) or (−)-2-(1-(3-chloro-5-(difluoromethoxy)-7-methyl-1H-indol-4-yl)-1-hydroxyethyl)-1H-benzo[d]imidazole-5-carbonitrile

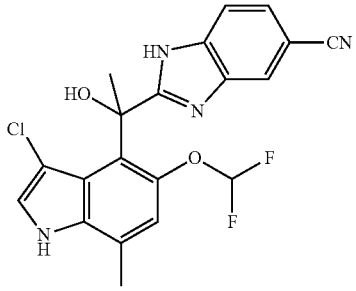 [SMILES: Cc1cc(OC(F)F)c(C(C)(O)c2nc3cc(C#N)ccc3[nH]2)c2c(Cl)c[nH]c12]

To a solution of (+)-2-(1-(5-(difluoromethoxy)-7-methyl-1H-indol-4-yl)-1-hydroxyethyl)-1H-benzo[d]imidazole-5-carbonitrile (32 mg, 0.083 mmol) in DMF (0.83 mL) was added NCS (17 mg, 0.12 mmol) at 0° C., and the reaction was warmed to room temperature. After 2 hours the reaction was quenched with sat. aq. Na₂S₂O₃ and extracted with EtOAc. The organic extract was dried over MgSO₄, filtered and concentrated. The resulting residue was purified by flash chromatography (0-100% EtOAc in heptanes) to provide the title compound. ¹H NMR (400 MHz, DMSO-d₆) δ ppm 12.51-12.66 (m, 1H) 11.56 (br. s., 1H) 8.04 (m) 7.79-7.83 (m) 7.64-7.70 (m) 7.44-7.56 (m) 6.83-6.89 (m) 6.75 (s, 1H) 6.64-6.70 (m) 6.46-6.51 (m) 6.07-6.20 (m, 1H) 2.45 (s, 3H) 2.18 (s, 3H). HRMS calcd. for C₂₀H₁₅ClF₂N₄O₂ (M+H)⁺ 417.0925. found 417.0942.

Example 8

Example 8-A (±)-tert-Butyl 4-(1-(5-cyano-1-((2-(trimethylsilyl)ethoxy)methyl)-1H-benzo[d]imidazol-2-yl)-1-methoxyethyl)-5-(difluoromethoxy)-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-methoxyethyl)-5-(difluoromethoxy)-7-methyl-1H-indole-1-carboxylate

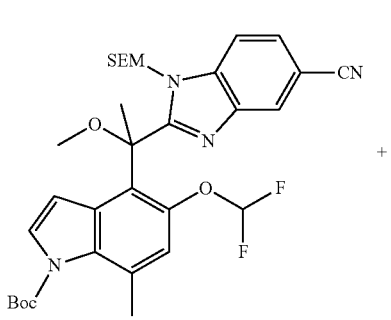

+

-continued

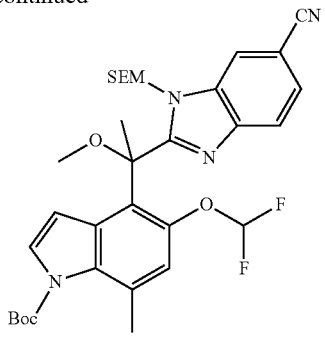

To a solution of a mixture of (±)-tert-butyl 4-(1-(5-cyano-1-((2-(trimethylsilyl)ethoxy)methyl)-1H-benzo[d]imidazol-2-yl)-1-hydroxyethyl)-5-(difluoromethoxy)-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-hydroxyethyl)-5-(difluoromethoxy)-7-methyl-1H-indole-1-carboxylate (605 mg, 0.987 mmol) in DMF (9.9 mL) at 0° C., NaH (60% in mineral oil, 59 mg, 1.5 mmol) was added followed by MeI (0.12 mL, 1.98 mmol). After stirring overnight the reaction was quenched with sat. aq. NH$_4$Cl and extracted with EtOAc. The organic extract was dried over MgSO$_4$, filtered and concentrated. The resulting residues was purified by flash chromatography (0-50% EtOAc in heptanes) to provide a mixture of the title compounds. MS (ESI+) m/z 627.6 (M+H).

Example 8-B a) (±)-2-(1-(5-(Difluoromethoxy)-7-methyl-1H-indol-4-yl)-1-methoxyethyl)-1H-benzo[d]imidazole-5-carbonitrile

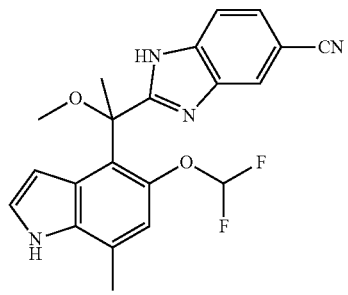 [SMILES: COC(C)(c1nc2cc(C#N)ccc2[nH]1)c1c(OC(F)F)cc(C)c2[nH]ccc12]

To a solution of a mixture of (±)-tert-butyl 4-(1-(5-cyano-1-((2-(trimethylsilyl)ethoxy)methyl)-1H-benzo[d]imidazol-2-yl)-1-methoxyethyl)-5-(difluoromethoxy)-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-methoxyethyl)-5-(difluoromethoxy)-7-methyl-1H-indole-1-carboxylate (475 mg, 0.758 mmol) in THF (7.6 mL) at room temperature, ethylenediamine (0.51 mL, 7.58 mmol) was added followed by TBAF (1M in THF, 7.6 mL, 7.6 mmol) and the reaction was stirred at 60° C. After 6 hours the reaction was cooled to room temperature, additional ethylenediamine (0.51 mL, 7.58 mmol) and TBAF (1M in THF, 7.6 mL, 7.6 mmol) were added and the reaction was stirred at 60° C. overnight. The reaction was cooled to room temperature, quenched with NH$_4$Cl and extracted with EtOAc. The organic extract was dried over MgSO$_4$, filtered and concentrated. The resulting residue was purified by flash chromatography (0-100% EtOAc in heptanes) to provide the title compound. $^1$H NMR (400 MHz, DMSO-d$_6$) δ ppm 12.68-12.85 (m, 1H) 11.19 (br. s., 1H) 8.09 (m) 7.83 (m) 7.69-7.74 (m) 7.47-7.58 (m) 7.31 (t, J=2.78 Hz, 1H) 6.89-6.96 (m) 6.70-6.77 (m) 6.46-6.58 (m) 3.01-3.17 (m, 3H) 2.46 (s, 3H) 2.07 (s, 3H). HRMS calcd. for C$_{21}$H$_{18}$F$_2$N$_4$O$_2$ (M+H)$^+$ 397.1471. found 397.1482.

b) (+) and (−)-2-(1-(5-(difluoromethoxy)-7-methyl-1H-indol-4-yl)-1-methoxyethyl)-1H-benzo[d]imidazole-5-carbonitrile Resolution of the enantiomers of 2-(1-(5-(difluoromethoxy)-7-methyl-1H-indol-4-yl)-1-methoxyethyl)-1H-benzo[d]imidazole-5-carbonitrile was achieved by chiral SFC using a CHIRALPAK® AD column with 25% MeOH in CO$_2$ to give (+)-2-(1-(5-(difluoromethoxy)-7-methyl-1H-indol-4-yl)-1-methoxyethyl)-1H-benzo[d]imidazole-5-carbonitrile (t$_r$=1.6 min) and (−)-2-(1-(5-(difluoromethoxy)-7-methyl-1H-indol-4-yl)-1-methoxyethyl)-1H-benzo[d]imidazole-5-carbonitrile (t$_r$=3.4 min).

Example 9

Example 9-A

4-Methyl-2-(methylthio)-5-nitrobenzonitrile

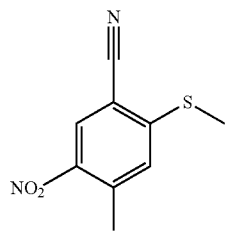

To a solution of 2-bromo-4-methyl-5-nitrobenzonitrile (3 g, 12.45 mmol) in DMF (124 mL), sodium thiomethoxide (1.31 g, 18.67 mmol) was added and the reaction heated to 60° C. for 1 h. The reaction was then cooled to room temperature, quenched with a sat. aq. solution of NaHCO$_3$ and extracted with EtOAc. The organic extract was dried over MgSO$_4$, filtered and concentrated. The resulting residue was purified using FCC eluting with heptanes:EtOAc 1:1 to give the title compound. MS (ESI−) m/z 207.3 (M−H).

Example 9-B

7-Methyl-5-(methylthio)-1H-indole-4-carbonitrile

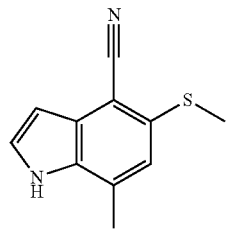

To a solution of 4-methyl-2-(methylthio)-5-nitrobenzonitrile (1.6 g, 7.68 mmol) in THF (80 mL) at −78° C. under nitrogen, was added rapidly 1M vinylmagnesium bromide in THF (30.7 mL, 30.7 mmol). After addition was complete, the reaction was stirred at −78° C. for 30 min. The reaction was then quenched with sat. aq. NH$_4$Cl and extracted with EtOAc. The organic extract was dried over MgSO$_4$, filtered and concentrated. The pure title compound was isolated using FCC (0-50% EtOAc in heptanes). MS (ESI−) m/z 201.2 (M−H).

Example 9-C

7-Methyl-5-(methylthio)-1-tosyl-1H-indole-4-carbonitrile

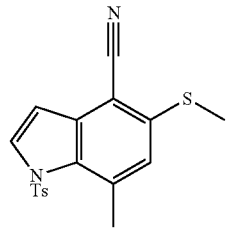 [SMILES: CSc1cc(C)c2c(ccn2S(=O)(=O)c2ccc(C)cc2)c1C#N]

To a solution of 7-methyl-5-(methylthio)-1H-indole-4-carbonitrile (500 mg, 2.47 mmol) in DMF (20 mL), was added NaH (60% in mineral oil, 148 mg, 3.71 mmol) and p-toluenenesulfonyl chloride (707 mg, 3.71 mmol). The reaction mixture was stirred at rt for 2 h, at which time additional NaH (60% in mineral oil, 148 mg, 3.71 mmol) and p-toluenenesulfonyl chloride (707 mg, 3.71 mmol) were added. After an additional 1 h of stirring the reaction mixture was then quenched with sat. aq. NH$_4$Cl and extracted with EtOAc. The organic extract was dried over MgSO$_4$, filtered and concentrated. The resulting residue was purified using FCC (0-20% EtOAc in heptanes) to afford the title compound. $^1$H NMR (400 MHz, DMSO-d$_6$) δ ppm 8.10 (d, J=3.79 Hz, 1H) 7.63-7.69 (m, 2H) 7.43 (m, 2H) 7.21 (s, 1H) 6.90 (d, J=3.79 Hz, 1H) 2.59 (s, 3H) 2.56 (d, J=0.76 Hz, 3H) 2.37 (s, 3H).

Example 9-D

7-Methyl-5-(methylthio)-1-tosyl-1H-indole-4-carbaldehyde

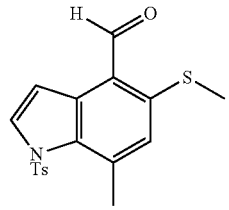 [SMILES: CSc1cc(C)c2c(ccn2S(=O)(=O)c2ccc(C)cc2)c1C=O]

To a solution of 7-methyl-5-(methylthio)-1-tosyl-1H-indole-4-carbonitrile (560 mg, 1.57 mmol) in toluene (15 mL) at −78° C., DIBAL-H (2 mL, 2 mmol) was added. After 30 minutes, a 3 N aq. HCl solution (50 mL) was added and the reaction warmed to rt and left stirring for 30 minutes. The organics were extracted with DCM, dried and concentrated. The pure title compound was isolated using FCC (0-50% EtOAc in heptanes). MS (ESI+) m/z 360.2 (M+H).

Example 10

Example 10-A (±)-2-(Hydroxy(7-methyl-5-(methylthio)-1-tosyl-1H-indol-4-yl)methyl)-1-((2-(trimethylsilyl)ethoxy)methyl)-1H-benzo[d]imidazole-6-carbonitrile and (±)-2-(hydroxy(7-methyl-5-(methylthio)-1-tosyl-1H-indol-4-yl)methyl)-1-((2-(trimethylsilyl)ethoxy)methyl)-1H-benzo[d]imidazole-5-carbonitrile

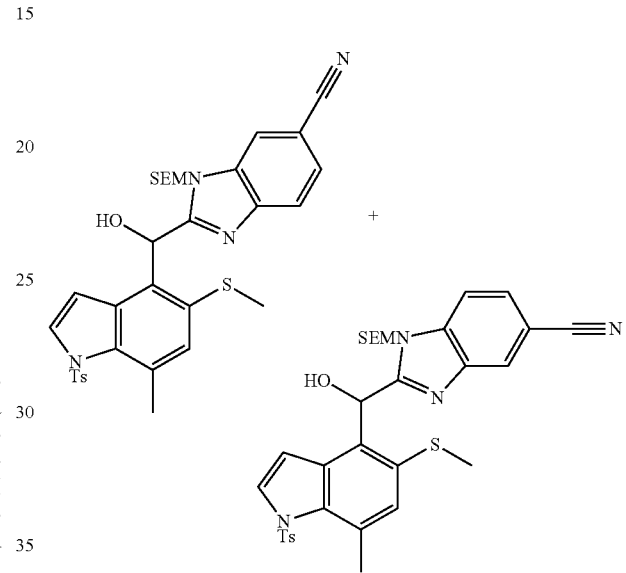

The reaction was conducted as described in Example 3-A starting from 7-methyl-5-(methylthio)-1-tosyl-1H-indole-4-carbaldehyde. MS (ESI+) m/z 633.5 (M+H).

Example 10-B (±)-2-(Hydroxy(7-methyl-5-(methylsulfonyl)-1-tosyl-1H-indol-4-yl)methyl)-1-((2-(trimethylsilyl)ethoxy)methyl)-1H-benzo[d]imidazole-6-carbonitrile and (±)-2-(hydroxy(7-methyl-5-(methylsulfonyl)-1-tosyl-1H-indol-4-yl)methyl)-1-((2-(trimethylsilyl)ethoxy)methyl)-1H-benzo[d]imidazole-5-carbonitrile

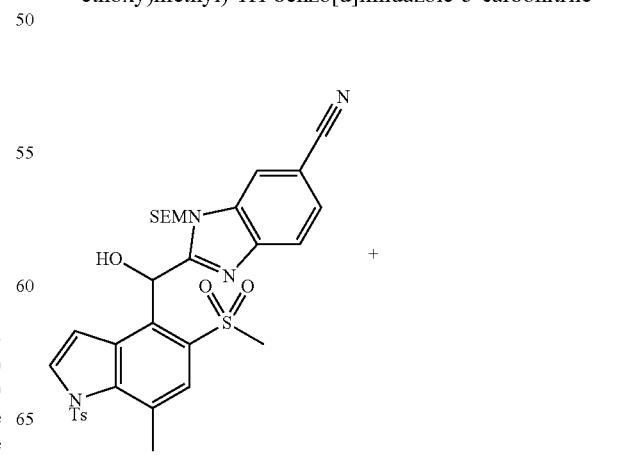

-continued

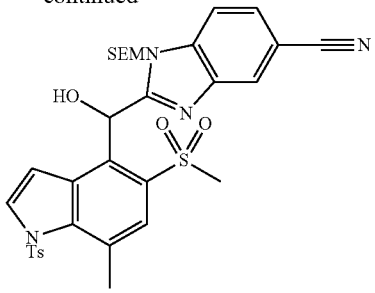

A stock solution of ammonium molibdate tetrahydrate (240 mg, 0.19 mmol) in 50% w/v aqueous peroxide (0.6 mL) was prepared at 0° C. To a solution of a mixture of (±)-2-(hydroxy(7-methyl-5-(methylthio)-1-tosyl-1H-indol-4-yl)methyl)-1-((2-(trimethylsilyl)ethoxy)methyl)-1H-benzo[d]imidazole-6-carbonitrile and (±)-2-(hydroxy(7-methyl-5-(methylthio)-1-tosyl-1H-indol-4-yl)methyl)-1-((2-(trimethylsilyl)ethoxy)methyl)-1H-benzo[d]imidazole-5-carbonitrile (100 mg, 0.158 mmol) in EtOH (2 mL), at 0° C., 0.16 mL of the above stock solution were added and the reaction allowed to reach rt. After 2 h the reaction mixture was then diluted with water (4 mL) and extracted with EtOAc. The organic extract was dried over MgSO$_4$, filtered and concentrated. The resulting residue was purified using FCC eluting with heptane:EtOAc 1:1 to give a mixture of the two title compounds. MS (ESI+) m/z 665.5 (M+H).

Example 10-C (±)-2-(Hydroxy(7-methyl-5-(methylsulfonyl)-1H-indol-4-yl)methyl)-1H-benzo[d]imidazole-5-carbonitrile

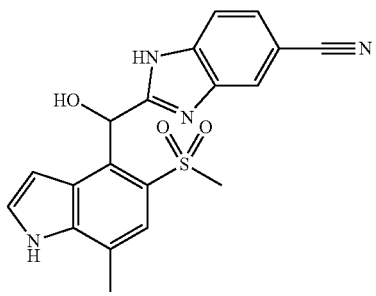 [SMILES: Cc1cc(S(C)(=O)=O)c(C(O)c2nc3cc(C#N)ccc3[nH]2)c2cc[nH]c12]

To a mixture of (±)-2-(hydroxy(7-methyl-5-(methylsulfonyl)-1-tosyl-1H-indol-4-yl)methyl)-1-((2-(trimethylsilyl)ethoxy)methyl)-1H-benzo[d]imidazole-6-carbonitrile and (±)-2-(hydroxy(7-methyl-5-(methylsulfonyl)-1-tosyl-1H-indol-4-yl)methyl)-1-((2-(trimethylsilyl)ethoxy)methyl)-1H-benzo[d]imidazole-5-carbonitrile (100 mg, 0.150 mmol) was added a 1 M solution of lithium tetrafluoroborate in MeCN (3.0 mL, 3 mmol). Water (0.3 mL) was then added and the reaction heated to 70° C. overnight. The reaction mixture was cooled to room temperature, diluted with water and extracted with EtOAc. The organic extract was dried over MgSO$_4$, filtered and concentrated. The resulting residue was dissolved in EtOH (1.3 mL) and isomylamine (0.3 mL, 2.6 mmol) and KOH (0.072 g, 1.3 mmol) were added. The mixture was then heated to 100° C. for 1 h using microwave irradiation. The mixture was then concentrated directly and purified using FCC eluting with DCM:MeOH:NH$_4$OH 100:0:0 to 80:18:2 to give the title compound. $^1$H NMR (400 MHz, DMSO-d$_6$) δ 13.17 (br. s., 1H), 11.50 (br. s., 1H), 7.83-8.00 (m, 1H), 7.61-7.67 (m, 1H), 7.49-7.58 (m, 2H), 7.41-7.49 (m, 1H), 7.35 (q, J=2.40 Hz, 1H), 6.91 (dd, J=4.67, 7.58 Hz, 1H), 6.58 (dt, J=1.89, 3.66 Hz, 1H), 3.46 (m, 3H), 2.53 (s, 3H). HRMS calcd. for C$_{19}$H$_{16}$N$_4$O$_3$S (M+H)$^+$ 381.1021. found 381.1013.

Example 11

Example 11-A 2-(7-Methyl-5-(methylthio)-1-tosyl-1H-indole-4-carbonyl)-1-((2-(trimethylsilyl)ethoxy)methyl)-1H-benzo[d]imidazole-6-carbonitrile and 2-(7-methyl-5-(methylthio)-1-tosyl-1H-indole-4-carbonyl)-1-((2-(trimethylsilyl)ethoxy)methyl)-1H-benzo[d]imidazole-5-carbonitrile

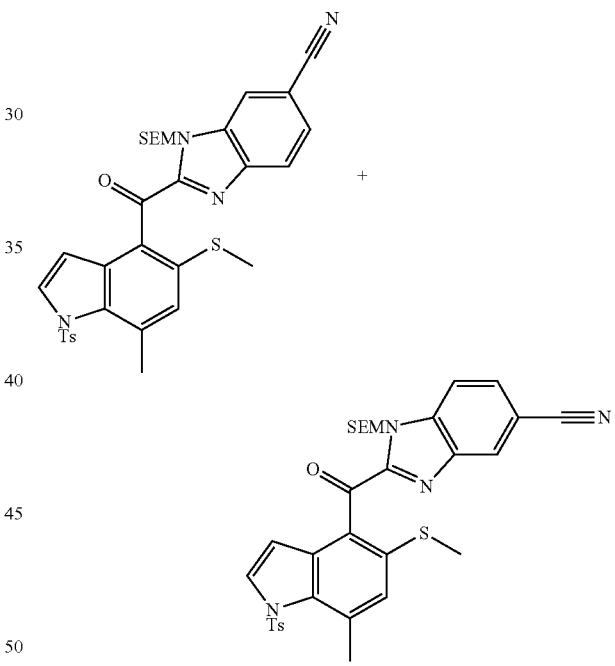

To a solution of a mixture of (±)-2-(hydroxy(7-methyl-5-(methylthio)-1-tosyl-1H-indol-4-yl)methyl)-1-((2-(trimethylsilyl)ethoxy)methyl)-1H-benzo[d]imidazole-6-carbonitrile and (±)-2-(hydroxy(7-methyl-5-(methylthio)-1-tosyl-1H-indol-4-yl)methyl)-1-((2-(trimethylsilyl)ethoxy)methyl)-1H-benzo[d]imidazole-5-carbonitrile (330 mg, 0.521 mmol) in DCM (5 mL), Dess-Martin Periodinane (332 mg, 0.782 mmol) was added. After 30 min the reaction was quenched with saturated aq. NaHCO$_3$ and 50% aq. sodium thiosulfate. The mixture was extracted with DCM and the organic extract was dried over MgSO$_4$, filtered and concentrated. The resulting residue was purified using FCC eluting with heptane:EtOAc 1:1 to give a mixture of the title compounds. MS (ESI+) m/z 631.4 (M+H).

Example 11-B (±)-2-(1-hydroxy-1-(7-methyl-5-(methylthio)-1-tosyl-1H-indol-4-yl)ethyl)-1-((2-(trimethylsilyl)ethoxy)methyl)-1H-benzo[d]imidazole-6-carbonitrile and (±)-2-(1-hydroxy-1-(7-methyl-5-(methylthio)-1-tosyl-1H-indol-4-yl)ethyl)-1-((2-(trimethylsilyl)ethoxy)methyl)-1H-benzo[d]imidazole-5-carbonitrile

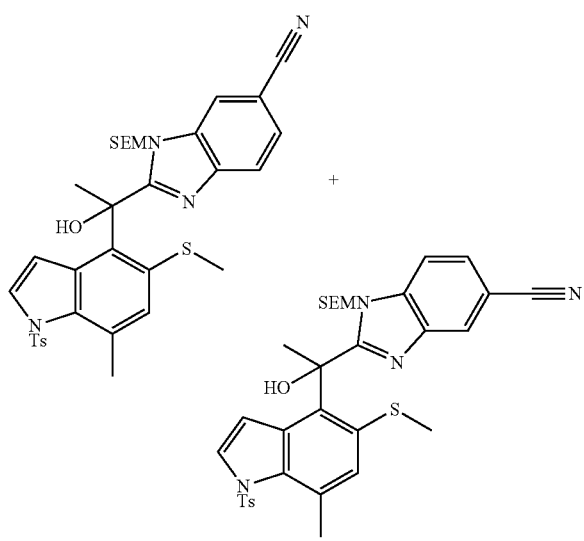

To a solution of a mixture of 2-(7-methyl-5-(methylthio)-1-tosyl-1H-indole-4-carbonyl)-1-((2-(trimethylsilyl)ethoxy)methyl)-1H-benzo[d]imidazole-6-carbonitrile and 2-(7-methyl-5-(methylthio)-1-tosyl-1H-indole-4-carbonyl)-1-((2-(trimethylsilyl)ethoxy)methyl)-1H-benzo[d]imidazole-5-carbonitrile (330 mg, 0.52 mmol) in THF (5 mL) at −78° C., was added methylmagnesium iodide (0.35 mL, 1.05 mmol). After 20 minutes of stirring the reaction was quenched with sat. aq. NH$_4$Cl and extracted with EtOAc. The organic extract was dried over MgSO$_4$, filtered and concentrated. The resulting residue was purified using FCC eluting with heptane: EtOAc 1:1 to give a mixture of the title compounds. MS (ESI+) m/z 647.5 (M+H).

Example 11-C a) (±)-2-(1-hydroxy-1-(7-methyl-5-(methylsulfonyl)-1H-indol-4-yl)ethyl)-1H-benzo[d]imidazole-5-carbonitrile

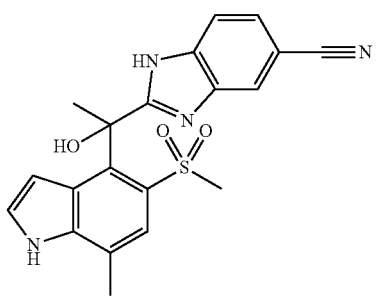

A mixture of (±)-2-(1-hydroxy-1-(7-methyl-5-(methylthio)-1-tosyl-1H-indol-4-yl)ethyl)-1-((2-(trimethylsilyl)ethoxy)methyl)-1H-benzo[d]imidazole-6-carbonitrile and (±)-2-(1-hydroxy-1-(7-methyl-5-(methylthio)-1-tosyl-1H-indol-4-yl)ethyl)-1-((2-(trimethylsilyl)ethoxy)methyl)-1H-benzo[d]imidazole-5-carbonitrile was transformed into the title compound using the same reaction conditions as described in Example 10-B and Example 10-C. $^1$H NMR (400 MHz, DMSO-d$_6$) δ 12.24-12.49 (m, 1H), 11.46 (br. s., 1H), 8.17-8.32 (m), 7.70-7.84 (m, 2H), 7.54 (m, 1H), 7.45 (m), 7.18 (t, J=2.91 Hz, 1H), 6.49-6.69 (m, 1H), 5.63 (dt, J=1.83, 3.82 Hz, 1H), 3.55 (s, 3H), 2.51 (s, 3H), 2.27 (s, 3H). HRMS calcd. for C$_{20}$H$_{18}$N$_4$O$_3$S (M+H)$^+$ 395.1173. found 395.1173.

b) (+) and (−)-2-(1-hydroxy-1-(7-methyl-5-(methylsulfonyl)-1H-indol-4-yl)ethyl)-1H-benzo[d]imidazole-5-carbonitrile Resolution of the enantiomers of 2-(1-hydroxy-1-(7-methyl-5-(methylsulfonyl)-1H-indol-4-yl)ethyl)-1H-benzo[d]imidazole-5-carbonitrile was achieved by chiral SFC using a CHIRALPAK®AD-H column with 20% MeOH in CO$_2$ to give (+) or (−)-2-(1-hydroxy-1-(7-methyl-5-(methylsulfonyl)-1H-indol-4-yl)ethyl)-1H-benzo[d]imidazole-5-carbonitrile (t$_r$=3 min) and (−) or (+)-2-(1-hydroxy-1-(7-methyl-5-(methylsulfonyl)-1H-indol-4-yl)ethyl)-1H-benzo[d]imidazole-5-carbonitrile (t$_r$=4.2 min).

Example 12

Example 12-A (±)-2-(1-Methoxy-1-(7-methyl-5-(methylsulfonyl)-1-tosyl-1H-indol-4-yl)ethyl)-1-((2-(trimethylsilyl)ethoxy)methyl)-1H-benzo[d]imidazole-6-carbonitrile and (±)-2-(1-methoxy-1-(7-methyl-5-(methylsulfonyl)-1-tosyl-1H-indol-4-yl)ethyl)-1-((2-(trimethylsilyl)ethoxy)methyl)-1H-benzo[d]imidazole-5-carbonitrile

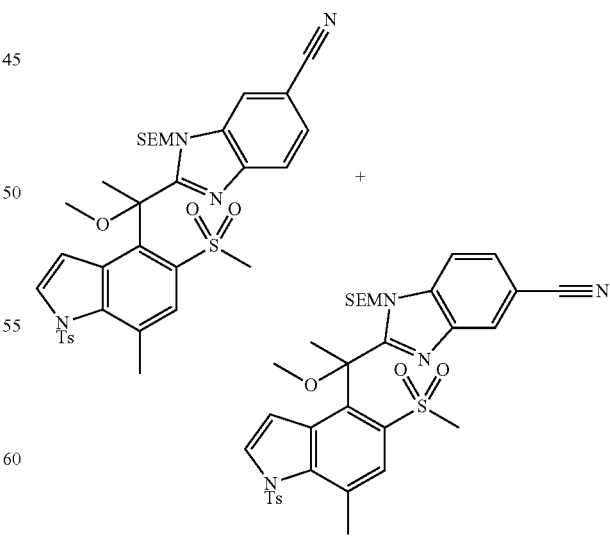

To a solution of a mixture of (±)-2-(1-hydroxy-1-(7-methyl-5-(methylthio)-1-tosyl-1H-indol-4-yl)ethyl)-1-((2-(trimethylsilyl)ethoxy)methyl)-1H-benzo[d]imidazole-6-carbonitrile and (±)-2-(1-hydroxy-1-(7-methyl-5-(methylthio)-1-tosyl-1H-indol-4-yl)ethyl)-1-((2-(trimethylsilyl)ethoxy)methyl)-1H-benzo[d]imidazole-5-carbonitrile (Example 11-B) (0.54 g, 0.835 mmol) in DMF (8.35 mL) at 0° C. was added MeI (0.08 mL, 1.25 mmol) and 60% NaH in mineral oil (0.050 g, 1.25 mmol). After stirring for 1 h the reaction was quenched with a sat. aq. solution of NH$_4$Cl and extracted with EtOAc. The organic extract was dried over MgSO$_4$, filtered and concentrated. The resulting residue was dissolved in EtOH (5 mL) and placed at 0° C. 0.6 mL of an ammonium molibdate tetradydrate stock solution [ammonium molibdate tetradydrate (240 mg, 0.19 mmol) in 50% w/v aqueous peroxide (0.6 mL) prepared at 0° C.] was added and the reaction allowed to warm to rt. It was then diluted with water and extracted with EtOAc. The organic extract was dried over MgSO$_4$, filtered and concentrated. The resulting residue was purified using FCC eluting with DCM/MeOH 95:5 to give a mixture of the title compounds. MS (ESI+) m/z 693.4 (M+H).

Example 12-B a) (±)-2-(1-Methoxy-1-(7-methyl-5-(methylsulfonyl)-1H-indol-4-yl)ethyl)-1H-benzo[d]imidazole-5-carbonitrile

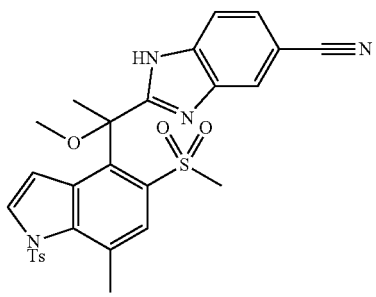 [SMILES: COC(C)(c1nc2cc(C#N)ccc2[nH]1)c1c(S(C)(=O)=O)cc(C)c2c1ccn2S(=O)(=O)c1ccc(C)cc1]

A mixture of (±)-2-(1-methoxy-1-(7-methyl-5-(methylsulfonyl)-1-tosyl-1H-indol-4-yl)ethyl)-1-((2-(trimethylsilyl)ethoxy)methyl)-1H-benzo[d]imidazole-6-carbonitrile and (±)-2-(1-methoxy-1-(7-methyl-5-(methylsulfonyl)-1-tosyl-1H-indol-4-yl)ethyl)-1-((2-(trimethylsilyl)ethoxy)methyl)-1H-benzo[d]imidazole-5-carbonitrile was transformed into the title compound using the same reaction conditions as described in Example 10-C. $^1$H NMR (400 MHz, DMSO-d$_6$) δ 12.51-12.55 (m, 1H), 11.48 (br. s., 1H), 8.32-8.33 (m), 7.80-7.98 (m, 2H), 7.56-7.61 (m), 7.42-7.44 (m), 7.18 (t, J=2.91 Hz, 1H), 5.3 (br. s., 1H), 3.41 (s, 3H), 3.05 (s, 3H), 2.18 (s, 3H). MS (ESI+) m/z 409.1 (M+H).

b) (+) and (−)-2-(1-methoxy-1-(7-methyl-5-(methylsulfonyl)-1H-indol-4-yl)ethyl)-1H-benzo[d]imidazole-5-carbonitrile Resolution of the enantiomers of 2-(1-methoxy-1-(7-methyl-5-(methylsulfonyl)-1H-indol-4-yl)ethyl)-1H-benzo[d]imidazole-5-carbonitrile was achieved by chiral SFC using a Lux® Cellulose-2 column with 25% MeOH in CO$_2$ to give (+) or (−)-2-(1-methoxy-1-(7-methyl-5-(methylsulfonyl)-1H-indol-4-yl)ethyl)-1H-benzo[d]imidazole-5-carbonitrile (t$_r$=3.5 min) and (−) or (+)-2-(1-methoxy-1-(7-methyl-5-(methylsulfonyl)-1H-indol-4-yl)ethyl)-1H-benzo[d]imidazole-5-carbonitrile (t$_r$=6.1 min).

Example 13

Example 13-A (±)-N-((6-cyano-1-((2-(trimethylsilyl)ethoxy)methyl)-1H-benzo[d]imidazol-2-yl)(7-methyl-5-(methylthio)-1-tosyl-1H-indol-4-yl)methylene)-2-methylpropane-2-sulfinamide and (±)-N-((5-cyano-1-((2-(trimethylsilyl)ethoxy)methyl)-1H-benzo[d]imidazol-2-yl)(7-methyl-5-(methylthio)-1-tosyl-1H-indol-4-yl)methylene)-2-methylpropane-2-sulfinamide

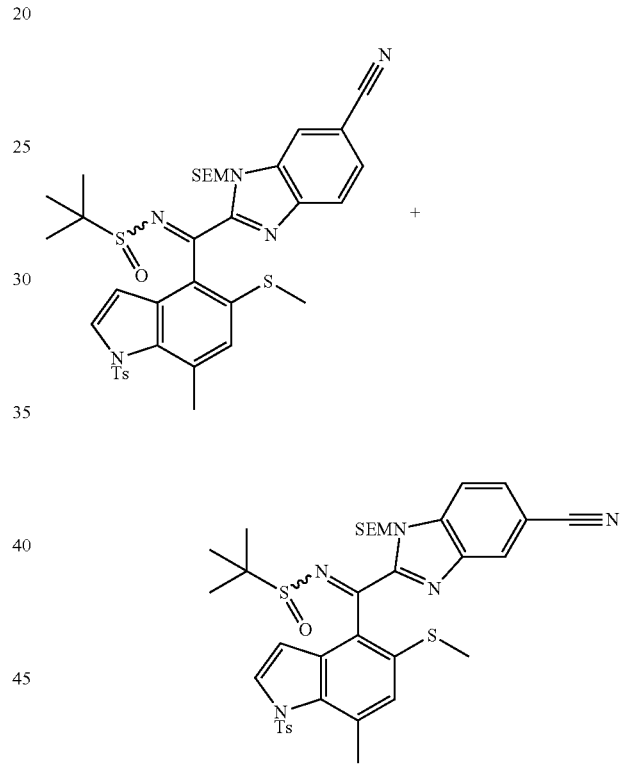

A mixture of 2-(7-methyl-5-(methylthio)-1-tosyl-1H-indole-4-carbonyl)-1-((2-(trimethylsilyl)ethoxy)methyl)-1H-benzo[d]imidazole-6-carbonitrile and 2-(7-methyl-5-(methylthio)-1-tosyl-1H-indole-4-carbonyl)-1-((2-(trimethylsilyl)ethoxy)methyl)-1H-benzo[d]imidazole-5-carbonitrile (Example 11-A) (600 mg, 0.951 mmol), 2-methylpropanesulfinamide (127 mg, 1.046 mmol) and Ti(OiPr)$_4$ (2 mL, 6.7 mmol) was stirred at 90° C. After 20 minutes the reaction mixture was cooled to room temperature and diluted with EtOAc and brine. The resulting mixture was filtered and the organic layer of the filtrate was dried over MgSO$_4$, filtered, and concentrated. The resulting residue was purified by flash chromatography (0-60% EtOAc in heptanes) to give a mixture of the title compounds. MS (ESI+) m/z 734.6 (M+).

Example 13-B (±)-N-(1-(6-cyano-1-((2-(trimethylsilyl)ethoxy)methyl)-1H-benzo[d]imidazol-2-yl)-1-(7-methyl-5-(methylthio)-1-tosyl-1H-indol-4-yl)ethyl)-2-methylpropane-2-sulfinamide and (±)-N-(1-(5-cyano-1-((2-(trimethylsilyl)ethoxy)methyl)-1H-benzo[d]imidazol-2-yl)-1-(7-methyl-5-(methylthio)-1-tosyl-1H-indol-4-yl)ethyl)-2-methylpropane-2-sulfinamide

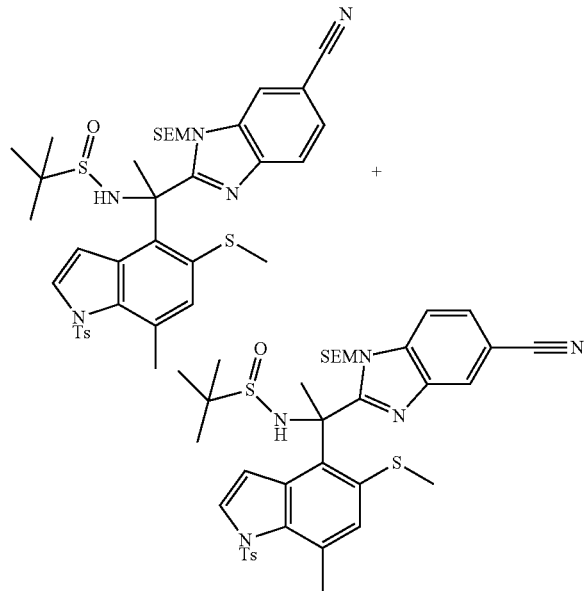

To a solution of a mixture of (±)-N-((6-cyano-1-((2-(trimethylsilyl)ethoxy)methyl)-1H-benzo[d]imidazol-2-yl)(7-methyl-5-(methylthio)-1-tosyl-1H-indol-4-yl)methylene)-2-methylpropane-2-sulfinamide and (±)-N-((5-cyano-1-((2-(trimethylsilyl)ethoxy)methyl)-1H-benzo[d]imidazol-2-yl)(7-methyl-5-(methylthio)-1-tosyl-1H-indol-4-yl)methylene)-2-methylpropane-2-sulfinamide (590 mg, 0.804 mmol) in THF (8 mL) at 0° C. was added methylmagnesium iodide (0.8 mL, 2.41 mmol). After 10 minutes the mixture was diluted with a saturated aq. solution of NH₄Cl and EtOAc. The layers were separated and the aqueous layer was extracted with EtOAc. The combined organics were dried over MgSO₄, filtered and concentrated. The resulting residue was purified by flash chromatography (0-100% EtOAc in heptanes) to give a mixture of the title compounds. MS (ESI+) m/z 750.5 (M+).

Example 13-C (±)-2-(1-Amino-1-(7-methyl-5-(methylthio)-1-tosyl-1H-indol-4-yl)ethyl)-1H-benzo[d]imidazole-5-carbonitrile

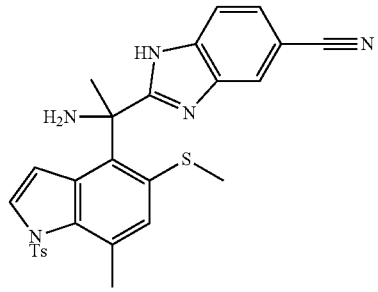 [SMILES: CSc1cc(C)c2c(ccn2S(=O)(=O)c2ccc(C)cc2)c1C(C)(N)c1nc2cc(C#N)ccc2[nH]1]

To a mixture of (±)-N-(1-(6-cyano-1-((2-(trimethylsilyl)ethoxy)methyl)-1H-benzo[d]imidazol-2-yl)-1-(7-methyl-5-(methylthio)-1-tosyl-1H-indol-4-yl)ethyl)-2-methylpropane-2-sulfinamide and (±)-N-(1-(5-cyano-1-((2-(trimethylsilyl)ethoxy)methyl)-1H-benzo[d]imidazol-2-yl)-1-(7-methyl-5-(methylthio)-1-tosyl-1H-indol-4-yl)ethyl)-2-methylpropane-2-sulfinamide (0.63 g, 0.840 mmol), was added 1.25 M HCl in MeOH (14.00 mL, 16.80 mmol) and the reaction mixture was then heated to 60° C. for 2 h. The reaction mixture was then evaporated directly, basified with ammonium hydroxide and directly loaded onto silica gel and purified by FCC and eluted with heptane/EtOAc 1:1 to give the title compound. MS (ESI−) m/z 514.2 (M−1).

Example 13-D (±)-2-(1-Amino-1-(7-methyl-5-(methylsulfonyl)-1-tosyl-1H-indol-4-yl)ethyl)-1H-benzo[d]imidazole-5-carbonitrile

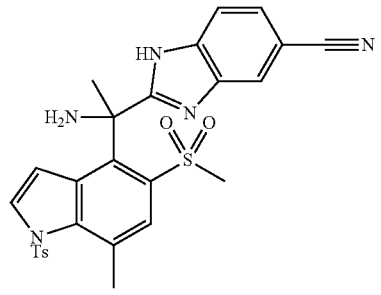 [SMILES: Cc1ccc(S(=O)(=O)n2ccc3c(C(C)(N)c4nc5cc(C#N)ccc5[nH]4)c(S(C)(=O)=O)cc(C)c32)cc1]

(±)-2-(1-Amino-1-(7-methyl-5-(methylthio)-1-tosyl-1H-indol-4-yl)ethyl)-1H-benzo[d]imidazole-5-carbonitrile was transformed into the title compound using the same reaction conditions as described in Example 10-B. MS (ESI+) m/z 548.2 (M+H).

Example 13-E a) (±)-2-(1-Amino-1-(7-methyl-5-(methylsulfonyl)-1H-indol-4-yl)ethyl)-1H-benzo[d]imidazole-5-carbonitrile

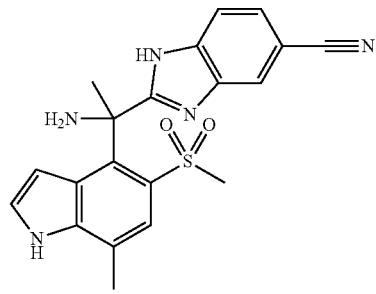

To a solution of (±)-2-(1-amino-1-(7-methyl-5-(methylsulfonyl)-1-tosyl-1H-indol-4-yl)ethyl)-1H-benzo[c]imidazole-5-carbonitrile (0.550 g, 1 mmol) in EtOH (10 mL), sodium ethoxide (22% solution in EtOH) (5.94 g, 20.09 mmol) was added and the reaction heated to 60° C. for 1 h. The mixture was then evaporated and directly purified using FCC eluting with heptane:EtOAc 100:0 to 0:100 to give the title compound. ¹H NMR (400 MHz, DMSO-$d_6$) δ 12.20 (br. s., 1H), 11.42 (br. s., 1H), 8.19 (m), 7.79-7.91 (m), 7.47-7.62 (m), 7.34-7.47 (m), 7.18 (m, 1H), 5.72 (br. s., 1H), 3.73 (s, 3H), 3.14 (s, 3H), 2.18 (s, 3H). HRMS calcd. for $C_{20}H_{19}N_5O_2S$ (M+H)⁺ 394.1332. found 394.1334.

b) (+) and (−)-2-(1-Amino-1-(7-methyl-5-(methylsulfonyl)-1H-indol-4-yl)ethyl)-1H-benzo[d]imidazole-5-carbonitrile Resolution of the enantiomers of 2-(1-amino-1-(7-methyl-5-(methylsulfonyl)-1H-indol-4-yl)ethyl)-1H-benzo[c]imidazole-5-carbonitrile was achieved by chiral SFC using CHIRALCEL® OJ-H column with 10% MeOH (−)-0.2% DEA) in $CO_2$ (due to miscibility issues of this compound a (21×50 mm) AD column in front of OJ-H was used as mixer) to give (+)-2-(1-amino-1-(7-methyl-5-(methylsulfonyl)-1-tosyl-1H-indol-4-yl)ethyl)-1H-benzo[d]imidazole-5-carbonitrile ($t_r$=8.2 min) and (−)-2-(1-amino-1-(7-methyl-5-(methylsulfonyl)-1-tosyl-1H-indol-4-yl)ethyl)-1H-benzo[d]imidazole-5-carbonitrile ($t_r$=11 min).

Example 14

Example 14-A (±)-2-(2,2,2-Trifluoro-1-hydroxy-1-(7-methyl-5-(methylthio)-1-tosyl-1H-indol-4-yl)ethyl)-1-((2-(trimethylsilyl)ethoxy)methyl)-1H-benzo[d]imidazole-5-carbonitrile and (±)-2-(2,2,2-trifluoro-1-hydroxy-1-(7-methyl-5-(methylthio)-1-tosyl-1H-indol-4-yl)ethyl)-1-((2-(trimethylsilyl)ethoxy)methyl)-1H-benzo[d]imidazole-6-carbonitrile

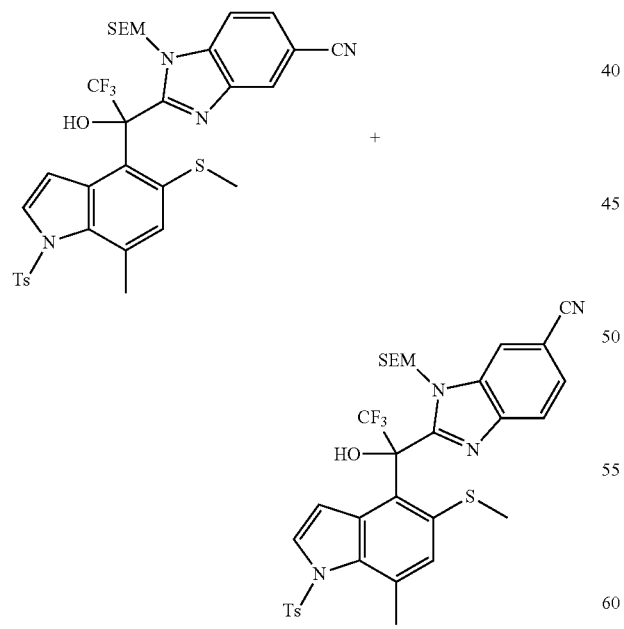

To a solution of a mixture of 2-(7-methyl-5-(methylthio)-1-tosyl-1H-indole-4-carbonyl)-1-((2-(trimethylsilyl)ethoxy)methyl)-1H-benzo[d]imidazole-5-carbonitrile and 2-(7-methyl-5-(methylthio)-1-tosyl-1H-indole-4-carbonyl)-1-((2-(trimethylsilyl)ethoxy)methyl)-1H-benzo[d]imidazole-6-carbonitrile (Example 11-A) (1.98 g, 3.14 mmol) in THF (31.4 mL) at 0° C. was added trifluoromethyltrimethylsilane (4.90 mL, 31.4 mmol), then TBAF (1M in THF, 31.4 mL, 31.4 mmol) was added and the mixture was warmed to room temperature. After 10 minutes the reaction was diluted with water, extracted with EtOAc, and the organic extract was dried over $MgSO_4$, filtered and concentrated. The resulting residue was purified by flash chromatography (0-60% EtOAc in heptanes) to afford the mixture of the title compounds. MS (ESI+) m/z 701.3 (M+H).

Example 14-B (±)-2-(2,2,2-Trifluoro-1-hydroxy-1-(7-methyl-5-(methylthio)-1-tosyl-1H-indol-4-yl)ethyl)-1H-benzo[d]imidazole-5-carbonitrile

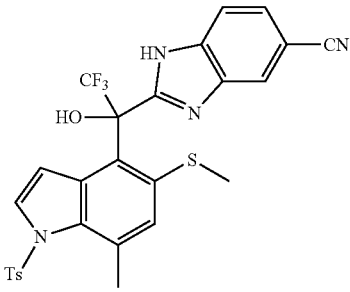 [SMILES: CSc1cc(C)c2c(ccn2S(=O)(=O)c2ccc(C)cc2)c1C(O)(c1nc2cc(C#N)ccc2[nH]1)C(F)(F)F]

To a mixture of (±)-2-(2,2,2-trifluoro-1-hydroxy-1-(7-methyl-5-(methylthio)-1-tosyl-1H-indol-4-yl)ethyl)-1-((2-(trimethylsilyl)ethoxy)methyl)-1H-benzo[d]imidazole-5-carbonitrile and (±)-2-(2,2,2-trifluoro-1-hydroxy-1-(7-methyl-5-(methylthio)-1-tosyl-1H-indol-4-yl)ethyl)-1-((2-(trimethylsilyl)ethoxy)methyl)-1H-benzo[d]imidazole-6-carbonitrile (246 mg, 0.351 mmol) was added HCl (1.25M in MeOH, 2.8 mL, 3.51 mmol) and the mixture was stirred at 60° C. After 30 minutes the reaction was cooled to room temperature, concentrated and basified with aq. $NH_4OH$. The mixture was further diluted with MeOH. The resulting residue was purified directly by flash chromatography (0-80% EtOAc in heptanes) to provide the title compound. MS (ESI+) m/z 571.1 (M+H).

Example 14-C (±)-2-(2,2,2-Trifluoro-1-hydroxy-1-(7-methyl-5-(methylsulfonyl)-1-tosyl-1H-indol-4-yl)ethyl)-1H-benzo[d]imidazole-5-carbonitrile

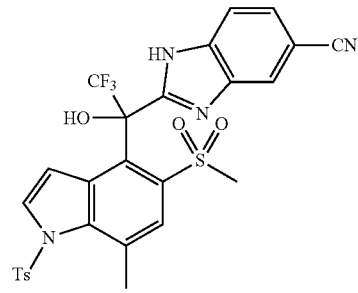 [SMILES: Cc1ccc(S(=O)(=O)n2ccc3c(C(O)(c4nc5cc(C#N)ccc5[nH]4)C(F)(F)F)c(S(C)(=O)=O)cc(C)c32)cc1]

A stock solution of ammonium molybdate tetrahydrate (240 mg, 0.19 mmol) in 50% w/v aqueous hydrogen peroxide (0.6 mL) was prepared. To a solution of (±)-2-(2,2,2-trifluoro-1-hydroxy-1-(7-methyl-5-(methylthio)-1-tosyl-1H-indol-4-yl)ethyl)-1H-benzo[d]imidazole-5-carbonitrile (191 mg, 0.335 mmol) in EtOH (2.8 mL), at 0° C., 0.6 mL of the molybdate stock solution was added and the reaction allowed to reach room temperature. After 45 minutes the reaction was diluted with water, extracted with EtOAc, and the organic extract was dried over MgSO₄, filtered and concentrated. The product was purified by flash chromatography (0-100% EtOAc in heptanes) to provide the title compound. MS (ESI+) m/z 603.0 (M+H).

Example 14-D a) (±)-2-(2,2,2-Trifluoro-1-hydroxy-1-(7-methyl-5-(methylsulfonyl)-1H-indol-4-yl)ethyl)-1H-benzo[d]imidazole-5-carbonitrile

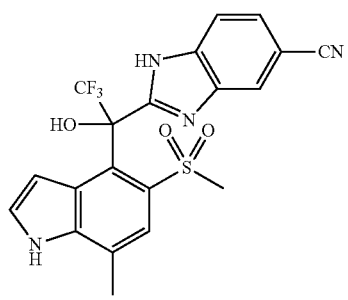 [SMILES: Cc1cc(S(C)(=O)=O)c(C(O)(c2nc3cc(C#N)ccc3[nH]2)C(F)(F)F)c2cc[nH]c12]

To a solution of 2-(2,2,2-trifluoro-1-hydroxy-1-(7-methyl-5-(methylsulfonyl)-1-tosyl-1H-indol-4-yl)ethyl)-1H-benzo[d]imidazole-5-carbonitrile (187 mg, 0.310 mmol) in EtOH (3103 µL) was added sodium ethoxide (21% in EtOH, 2.3 mL, 6.21 mmol) and the mixture was stirred at 60° C. After 2 hours the reaction was cooled to room temperature and stirred overnight. The mixture was concentrated and then purified directly by flash chromatography (0-100% EtOAc in heptanes) to provide the title compound. ¹H NMR (400 MHz, DMSO-d₆) δ ppm 12.64-12.79 (m, 1H) 11.60 (br. s., 1H) 8.38-8.49 (m) 8.05 (s, 1H) 7.97-8.03 (m) 7.89 (m) 7.58-7.66 (m, 1H) 7.48-7.55 (m) 7.18-7.32 (m, 1H) 5.61 (br. s., 1H) 3.52 (s, 3H) 2.57 (s, 3H). HRMS calcd. for $C_{20}H_{16}F_3N_4O_3S$ (M+H)⁺ 449.0895. found 449.0889.

b) (+) and (−)-2-(2,2,2-Trifluoro-1-hydroxy-1-(7-methyl-5-(methylsulfonyl)-1H-indol-4-yl)ethyl)-1H-benzo[d]imidazole-5-carbonitrile Resolution of the enantiomers of 2-(2,2,2-trifluoro-1-hydroxy-1-(7-methyl-5-(methylsulfonyl)-1H-indol-4-yl)ethyl)-1H-benzo[d]imidazole-5-carbonitrile was achieved by chiral HPLC using a Lux® Cellulose-2 column with 20% EtOH in heptanes to give (+)-2-(2,2,2-trifluoro-1-hydroxy-1-(7-methyl-5-(methylsulfonyl)-1H-indol-4-yl)ethyl)-1H-benzo[d]imidazole-5-carbonitrile ($t_r$=11.44 min) and (−)-2-(2,2,2-trifluoro-1-hydroxy-1-(7-methyl-5-(methylsulfonyl)-1H-indol-4-yl)ethyl)-1H-benzo[d]imidazole-5-carbonitrile ($t_r$=14.44 min).

Example 15

Example 15-A (±)-2-(2,2,2-Trifluoro-1-methoxy-1-(7-methyl-5-(methylthio)-1-tosyl-1H-indol-4-yl)ethyl)-1-((2-(trimethylsilyl)ethoxy)methyl)-1H-benzo[d]imidazole-5-carbonitrile and (±)-2-(2,2,2-trifluoro-1-methoxy-1-(7-methyl-5-(methylthio)-1-tosyl-1H-indol-4-yl)ethyl)-1-((2-(trimethylsilyl)ethoxy)methyl)-1H-benzo[d]imidazole-6-carbonitrile

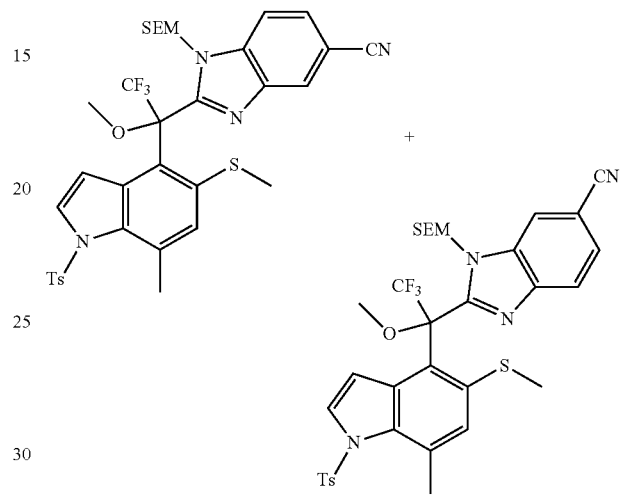

To a solution of a mixture of (±)-2-(2,2,2-trifluoro-1-hydroxy-1-(7-methyl-5-(methylthio)-1-tosyl-1H-indol-4-yl)ethyl)-1-((2-(trimethylsilyl)ethoxy)methyl)-1H-benzo[d]imidazole-5-carbonitrile and (±)-2-(2,2,2-trifluoro-1-hydroxy-1-(7-methyl-5-(methylthio)-1-tosyl-1H-indol-4-yl)ethyl)-1-((2-(trimethylsilyl)ethoxy)methyl)-1H-benzo[d]imidazole-6-carbonitrile (Example 14-A) (300 mg, 0.428 mmol) in DMF (4.3 mL) at 0° C., MeI (0.27 mL, 4.28 mmol) was added followed by NaH (60% in mineral oil, 34.2 mg, 0.856 mmol). After 5 minutes the mixture was warmed to room temperature. After 15 minutes the reaction was quenched with sat. aq. NH₄Cl, extracted with EtOAc, and the organic extract was dried over MgSO₄, filtered and concentrated. The resulting residues was purified by flash chromatography (0-50% EtOAc in heptanes) to provide a mixture of the title compounds. MS (ESI+) m/z 715.4 (M+H).

Example 15-B (±)-2-(2,2,2-Trifluoro-1-methoxy-1-(7-methyl-5-(methylthio)-1-tosyl-1H-indol-4-yl)ethyl)-1H-benzo[d]imidazole-5-carbonitrile

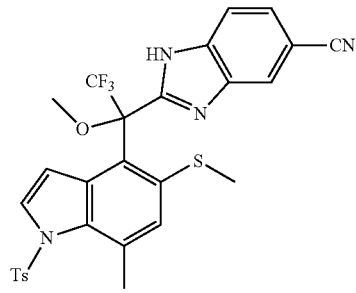 [SMILES: COC(c1nc2cc(C#N)ccc2[nH]1)(c1c(SC)cc(C)c2c1ccn2S(=O)(=O)c1ccc(C)cc1)C(F)(F)F]

To a mixture of (±)-2-(2,2,2-trifluoro-1-methoxy-1-(7-methyl-5-(methylthio)-1-tosyl-1H-indol-4-yl)ethyl)-1-((2-(trimethylsilyl)ethoxy)methyl)-1H-benzo[d]imidazole-5-carbonitrile and (±)-2-(2,2,2-trifluoro-1-methoxy-1-(7-methyl-5-(methylthio)-1-tosyl-1H-indol-4-yl)ethyl)-1-((2-(trimethylsilyl)ethoxy)methyl)-1H-benzo[d]imidazole-6-carbonitrile (265 mg, 0.371 mmol) was added HCl (1.25M in MeOH, 2.9 mL, 3.71 mmol) and the mixture was stirred at 60° C. After 20 minutes the reaction was cooled to room temperature, concentrated and basified with aq. NH$_4$OH. The mixture was further diluted with MeOH. The resulting residue was purified directly by flash chromatography (0-80% EtOAc in heptanes) to provide the title compound. MS (ESI+) m/z 585.1 (M+H).

Example 15-C (±)-2-(2,2,2-Trifluoro-1-methoxy-1-(7-methyl-5-(methylsulfonyl)-1-tosyl-1H-indol-4-yl)ethyl)-1H-benzo[d]imidazole-5-carbonitrile

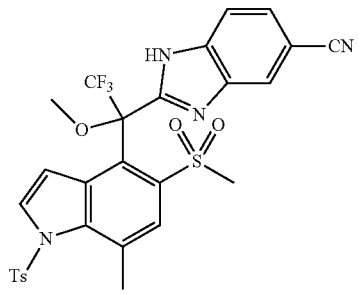 [SMILES: COC(c1nc2cc(C#N)ccc2[nH]1)(c1c(S(C)(=O)=O)cc(C)c2c1ccn2S(=O)(=O)c1ccc(C)cc1)C(F)(F)F]

A stock solution of ammonium molybdate tetrahydrate (240 mg, 0.19 mmol) in 50% w/v aqueous hydrogen peroxide (0.6 mL) was prepared. To a solution of (±)-2-(2,2,2-trifluoro-1-methoxy-1-(7-methyl-5-(methylthio)-1-tosyl-1H-indol-4-yl)ethyl)-1H-benzo[d]imidazole-5-carbonitrile (223 mg, 0.381 mmol) in EtOH (3.2 mL), at 0° C., 0.6 mL of the molybdate stock solution was added and the reaction was allowed to reach room temperature. After 70 minutes an additional aliquot of the ammonium molybdate stock solution (0.3 mL) was added. After another 65 minutes an additional aliquot of the ammonium molybdate stock solution (0.3 mL) was added. After a total of 5 hours, the reaction was diluted with water, extracted with EtOAc, and the organic extract was dried over MgSO$_4$, filtered and concentrated. The product was purified by flash chromatography (0-100% EtOAc in heptanes) to provide the title compound. MS (ESI+) m/z 617.1 (M+H).

Example 15-D a) (±)-2-(2,2,2-Trifluoro-1-methoxy-1-(7-methyl-5-(methylsulfonyl)-1H-indol-4-yl)ethyl)-1H-benzo[d]imidazole-5-carbonitrile

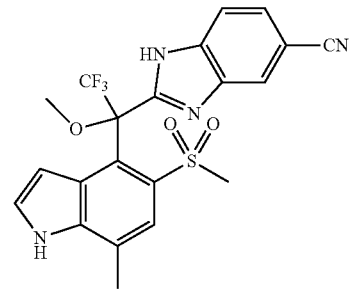 [SMILES: COC(c1nc2cc(C#N)ccc2[nH]1)(c1c(S(C)(=O)=O)cc(C)c2[nH]ccc12)C(F)(F)F]

To (±)-2-(2,2,2-trifluoro-1-methoxy-1-(7-methyl-5-(methylsulfonyl)-1-tosyl-1H-indol-4-yl)ethyl)-1H-benzo[d]imidazole-5-carbonitrile (172 mg, 0.279 mmol) in EtOH (2.8 mL) was added sodium ethoxide (21% in EtOH, 2 mL, 5.58 mmol) and the mixture was stirred at 60° C. After 45 minutes the reaction was cooled to room temperature and purified directly by flash chromatography (0-100% EtOAc in heptanes) to provide the title compound. $^1$H NMR (400 MHz, DMSO-d$_6$) δ ppm 12.84-13.00 (m, 1H) 11.59 (br. s., 1H) 8.47 (m) 8.00-8.19 (m) 7.94 (m) 7.61-7.72 (m, 1H) 7.50-7.61 (m) 7.27 (br. s., 1H) 5.45 (br. s., 1H) 3.39 (br. s., 3H) 3.21 (br. s., 3H) 2.57 (s, 3H). HRMS calcd. for C$_{21}$H$_{17}$F$_3$N$_4$O$_3$S (M+H)$^+$ 463.1052. found 463.1031.

b) (+) and (−)-2-(2,2,2-trifluoro-1-methoxy-1-(7-methyl-5-(methylsulfonyl)-1H-indol-4-yl)ethyl)-1H-benzo[d]imidazole-5-carbonitrile Resolution of the enantiomers of 2-(2,2,2-trifluoro-1-methoxy-1-(7-methyl-5-(methylsulfonyl)-1H-indol-4-yl)ethyl)-1H-benzo[d]imidazole-5-carbonitrile was achieved by chiral SFC using a Lux® Cellulose-2 column with 20-30% MeOH (5 mM NH$_3$OH) in CO$_2$ to give (+)-2-(2,2,2-trifluoro-1-methoxy-1-(7-methyl-5-(methylsulfonyl)-1H-indol-4-yl)ethyl)-1H-benzo[d]imidazole-5-carbonitrile (t$_r$=2.8 min) and (−)-2-(2,2,2-trifluoro-1-methoxy-1-(7-methyl-5-(methylsulfonyl)-1H-indol-4-yl)ethyl)-1H-benzo[d]imidazole-5-carbonitrile (t$_r$=3.5 min).

Example 16

Example 16-A (±)-2-(2,2,2-Trifluoro-1-(7-methyl-5-(methylthio)-1-tosyl-1H-indol-4-yl)-1-(methylamino)ethyl)-1H-benzo[d]imidazole-5-carbonitrile

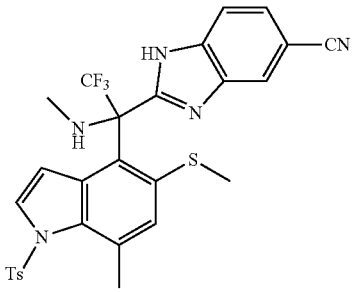 [SMILES: CNC(c1nc2cc(C#N)ccc2[nH]1)(c1c(SC)cc(C)c2c1ccn2S(=O)(=O)c1ccc(C)cc1)C(F)(F)F]

To a mixture of (±)-2-(2,2,2-trifluoro-1-hydroxy-1-(7-methyl-5-(methylthio)-1-tosyl-1H-indol-4-yl)ethyl)-1-((2-(trimethylsilyl)ethoxy)methyl)-1H-benzo[d]imidazole-5-carbonitrile and (±)-2-(2,2,2-trifluoro-1-hydroxy-1-(7-methyl-5-(methylthio)-1-tosyl-1H-indol-4-yl)ethyl)-1-((2-(trimethylsilyl)ethoxy)methyl)-1H-benzo[d]imidazole-6-carbonitrile (Example 14-A) (0.37 g, 0.528 mmol) was added HCl (1.25M in MeOH, 4.22 mL, 5.28 mmol) and the mixture was stirred at 60° C. After 40 minutes the mixture was cooled to room temperature and concentrated. The residue was dissolved in CHCl$_3$ (10.56 mL), and thionyl chloride (0.385 mL, 5.28 mmol) and a few drops of DMF were added and the mixture was heated at 70° C. After 2 hours the reaction was cooled to room temperature and concentrated. The residue was dissolved in methylamine (33% in EtOH, 6.57 mL, 52.8 mmol) and stirred at room temperature. After 5 minutes the reaction was concentrated and purified directly by flash chromatography (0-100% EtOAc in heptanes) to provide the title compound. MS (ESI+) m/z 584.2 (M+H).

Example 16-B a) (±)-2-(2,2,2-Trifluoro-1-(7-methyl-5-(methylsulfonyl)-1H-indol-4-yl)-1-(methylamino)ethyl)-1H-benzo[d]imidazole-5-carbonitrile

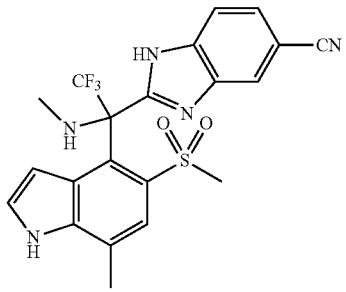 [SMILES: CNC(c1nc2cc(C#N)ccc2[nH]1)(c1c(S(C)(=O)=O)cc(C)c2[nH]ccc12)C(F)(F)F]

(±)-2-(2,2,2-Trifluoro-1-(7-methyl-5-(methylthio)-1-tosyl-1H-indol-4-yl)-1-(methylamino)ethyl)-1H-benzo[d]imidazole-5-carbonitrile was transformed into the title compound using the same procedure as described in Example 14-C and Example 14-D. $^1$H NMR (400 MHz, DMSO-$d_6$) δ ppm 12.60-12.75 (m, 1H) 11.55 (br. s., 1H) 8.42 (m) 7.98-8.09 (m) 7.84-7.92 (m) 7.57-7.66 (m, 1H) 7.46-7.54 (m) 7.22 (t, J=3.03 Hz, 1H) 5.61 (br. s., 1H) 5.04 (br. s., 1H) 3.65 (s, 3H) 2.56 (s, 3H) 2.04 (d, J=4.04 Hz, 3H). HRMS calcd. for $C_{21}H_{18}F_3N_5O_2S$ (M+H)$^+$ 462.1212. found 462.1198.

b) (+) and (−)-2-(2,2,2-trifluoro-1-(7-methyl-5-(methylsulfonyl)-1H-indol-4-yl)-1-(methylamino)ethyl)-1H-benzo[d]imidazole-5-carbonitrile Resolution of the enantiomers of 2-(2,2,2-trifluoro-1-(7-methyl-5-(methylsulfonyl)-1H-indol-4-yl)-1-(methylamino)ethyl)-1H-benzo[d]imidazole-5-carbonitrile was achieved by chiral SFC using a Lux® Cellulose-2 column with 17-27% MeOH in $CO_2$ to give (+)-2-(2,2,2-trifluoro-1-(7-methyl-5-(methylsulfonyl)-1H-indol-4-yl)-1-(methylamino)ethyl)-1H-benzo[d]imidazole-5-carbonitrile ($t_r$=3.6 min) and (−)-2-(2,2,2-trifluoro-1-(7-methyl-5-(methylsulfonyl)-1H-indol-4-yl)-1-(methylamino)ethyl)-1H-benzo[d]imidazole-5-carbonitrile ($t_r$=4.4 min).

Example 17

Example 17-A (±)-2-(1-Amino-2,2,2-trifluoro-1-(7-methyl-5-(methylthio)-1-tosyl-1H-indol-4-yl)ethyl)-1H-benzo[d]imidazole-5-carbonitrile

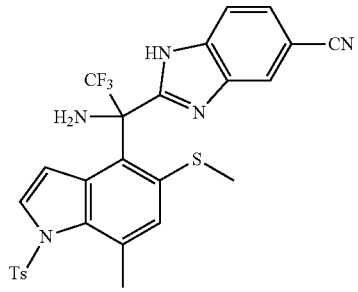 [SMILES: CSc1cc(C)c2c(ccn2S(=O)(=O)c2ccc(C)cc2)c1C(N)(c1nc2cc(C#N)ccc2[nH]1)C(F)(F)F]

To a mixture of (±)-2-(2,2,2-trifluoro-1-hydroxy-1-(7-methyl-5-(methylthio)-1-tosyl-1H-indol-4-yl)ethyl)-1-((2-(trimethylsilyl)ethoxy)methyl)-1H-benzo[d]imidazole-5-carbonitrile and (±)-2-(2,2,2-trifluoro-1-hydroxy-1-(7-methyl-5-(methylthio)-1-tosyl-1H-indol-4-yl)ethyl)-1-((2-(trimethylsilyl)ethoxy)methyl)-1H-benzo[d]imidazole-6-carbonitrile (Example 14-A) (425 mg, 0.6 mmol) was added HCl (1.25M in MeOH, 4.85 mL, 6.06 mmol) and the mixture was stirred at 60° C. After 40 minutes the mixture was cooled to room temperature and concentrated. The mixture was dissolved in $CHCl_3$ (12 mL), then was added thionyl chloride (0.44 mL, 6.06 mmol) and one drop of DMF and the mixture was heated at 70° C. After 4 hours the reaction was cooled to room temperature and stirred at room temperature overnight. The reaction was then concentrated, dissolved in ammonia in ethanol (2.0M, 30.3 mL, 60.6 mmol) and stirred at room temperature. After 15 minutes the reaction was concentrated and purified directly by flash chromatography (0-70% EtOAc in heptanes). MS (ESI+) m/z 570.3 (M+H).

Example 17-B a) (±)-2-(1-Amino-2,2,2-trifluoro-1-(7-methyl-5-(methylsulfonyl)-1H-indol-4-yl)ethyl)-1H-benzo[d]imidazole-5-carbonitrile

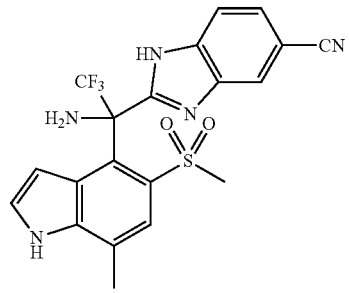 [SMILES: Cc1cc(S(C)(=O)=O)c(C(N)(c2nc3cc(C#N)ccc3[nH]2)C(F)(F)F)c2cc[nH]c12]

(±)-2-(1-Aamino-2,2,2-trifluoro-1-(7-methyl-5-(methylthio)-1-tosyl-1H-indol-4-yl)ethyl)-1H-benzo[d]imidazole-5-carbonitrile was transformed into the title compound using the same procedures as described in Example 14-C and Example 14-D. $^1$H NMR (400 MHz, DMSO-$d_6$) δ ppm 12.47-12.64 (m, 1H) 11.55 (br. s., 1H) 8.37-8.41 (m) 8.00-8.02 (m, 1H) 7.96-8.00 (m) 7.83-7.85 (m) 7.56-7.63 (m, 1H) 7.45-7.49 (m) 7.15-7.27 (m, 1H) 5.54-5.71 (m, 1H) 4.12 (s, 2H) 3.74 (s, 3H) 2.56 (s, 3H). HRMS calcd. for $C_{20}H_{16}F_3N_5O_2S$ (M+H)$^+$ 448.105. found 448.1058.

b) (+) and (−)-2-(1-amino-2,2,2-trifluoro-1-(7-methyl-5-(methylsulfonyl)-1H-indol-4-yl)ethyl)-1H-benzo[d]imidazole-5-carbonitrile Resolution of the enantiomers of 2-(1-amino-2,2,2-trifluoro-1-(7-methyl-5-(methylsulfonyl)-1H-indol-4-yl)ethyl)-1H-benzo[d]imidazole-5-carbonitrile was achieved by chiral SFC using a CHIRALPAK® AD-H column with 25% MeOH+0.2% DEA in $CO_2$ to give (−)-2-(1-amino-2,2,2-trifluoro-1-(7-methyl-5-(methylsulfonyl)-1H-indol-4-yl)ethyl)-1H-benzo[d]imidazole-5-carbonitrile ($t_r$=1.7 min) and (+)-2-(1-amino-2,2,2-trifluoro-1-(7-methyl-5-(methylsulfonyl)-1H-indol-4-yl)ethyl)-1H-benzo[d]imidazole-5-carbonitrile ($t_r$=4.0 min).

Example 18

Example 18-A (±)-N-((6-Cyano-1-((2-(trimethylsilyl)ethoxy)methyl)-1H-benzo[d]imidazol-2-yl)(7-methyl-5-(methylthio)-1-tosyl-1H-indol-4-yl)methyl)-2-methylpropane-2-sulfinamide and (±)-N-((5-cyano-1-((2-(trimethylsilyl)ethoxy)methyl)-1H-benzo[d]imidazol-2-yl)(7-methyl-5-(methylthio)-1-tosyl-1H-indol-4-yl)methyl)-2-methylpropane-2-sulfinamide

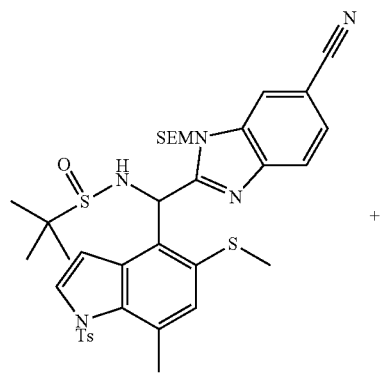

+

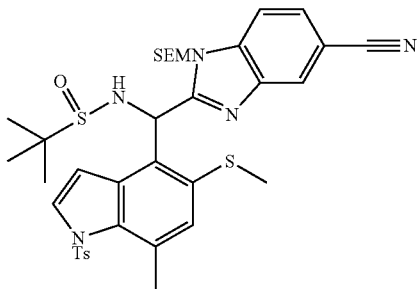

To a solution of a mixture of (±)-N-((6-cyano-1-((2-(trimethylsilyl)ethoxy)methyl)-1H-benzo[d]imidazol-2-yl)(7-methyl-5-(methylthio)-1-tosyl-1H-indol-4-yl)methylene)-2-methylpropane-2-sulfinamide and (±)-N-((5-cyano-1-((2-(trimethylsilyl)ethoxy)methyl)-1H-benzo[d]imidazol-2-yl)(7-methyl-5-(methylthio)-1-tosyl-1H-indol-4-yl)methylene)-2-methylpropane-2-sulfinamide (Example 13-A) (1.2 g, 1.63 mmol) in MeOH (15 mL), sodium borohydride (0.37 g, 9.81 mmol) was added at 0° C. After 30 minutes the reaction was complete. It was then quenched with sat. aq. NH₄Cl solution and extracted with EtOAc. The organic extract was dried over MgSO₄ filtered and concentrated. The resulting residue was purified using FCC eluting with heptanes:EtOAc 1:1 to give the mixture of title compounds. MS (ESI+) m/z 737.8 (M+H).

Example 18-B (±)-2-(amino(7-methyl-5-(methylthio)-1-tosyl-1H-indol-4-yl)methyl)-1H-benzo[d]imidazole-5-carbonitrile

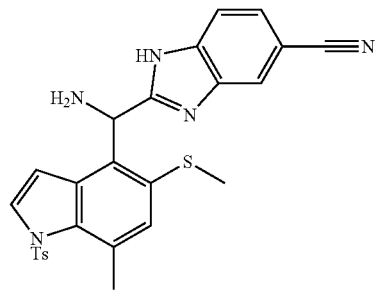

To a solution of a mixture of (±)-N-((6-cyano-1-((2-(trimethylsilyl)ethoxy)methyl)-1H-benzo[d]imidazol-2-yl)(7-methyl-5-(methylthio)-1-tosyl-1H-indol-4-yl)methyl)-2-methylpropane-2-sulfinamide and (±)-N-((5-cyano-1-((2-(trimethylsilyl)ethoxy)methyl)-1H-benzo[d]imidazol-2-yl)(7-methyl-5-(methylthio)-1-tosyl-1H-indol-4-yl)methyl)-2-methylpropane-2-sulfinamide (1 g, 1.36 mmol), HCl in methanol (1.25 M) (22 mL, 27 mmol) was added and the reaction stirred at 60° C. for 2 h. The reaction was then evaporated, basified with NH₄OH (33% NH₃ in H₂O) and extracted with EtOAc. The organic extract was dried over MgSO₄ filtered and concentrated to give the title compound without the need for further purification. MS (ESI+) m/z 502.2 (M+H).

Example 18-C (±)-2-(amino(7-methyl-5-(methylsulfonyl)-1-tosyl-1H-indol-4-yl)methyl)-1H-benzo[d]imidazole-5-carbonitrile A stock solution of ammonium molibdate tetrahydrate (480 mg, 0.19 mmol) in 50% w/v aqueous peroxide (1.2 mL) was prepared at 0° C. To a solution of (±)-2-(amino(7-methyl-5-(methylthio)-1-tosyl-1H-indol-4-yl)methyl)-1H-benzo[d]imidazole-5-carbonitrile (400 mg, 0.797 mmol) in EtOH (5 mL), at 0° C., 1.2 mL of the above stock solution was added and the reaction warmed to room temperature and stirred for 2 h. The mixture was then diluted with water, extracted with EtOAc. The organic extract was dried over MgSO₄ filtered and concentrated. The resulting residue was purified using FCC eluting with DCM/MeOH 95:5 to give the title compound. MS (ESI+) m/z 534.3 (M+H).

Example 18-D (+) and (−)-2-(amino(7-methyl-5-(methylsulfonyl)-1H-indol-4-yl)methyl)-1H-benzo[d]imidazole-5-carbonitrile

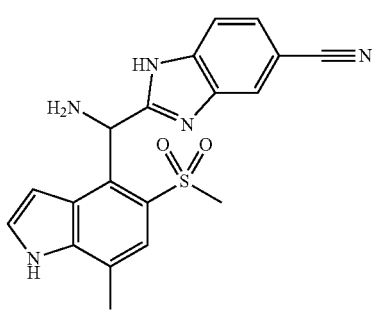 [SMILES: Cc1cc(S(C)(=O)=O)c(C(N)c2nc3cc(C#N)ccc3[nH]2)c2cc[nH]c12]

To a solution of (±)-2-(amino(7-methyl-5-(methylsulfonyl)-1-tosyl-1H-indol-4-yl)methyl)-1H-benzo[d]imidazole-5-carbonitrile (540 mg, 1.012 mmol) in EtOH (10 mL), a 21% solution of sodium ethoxide (7.6 mL, 20.24 mmol) was added and the reaction heated to 60° C. for 1 h. The reaction was cooled to room temperature and then evaporated directly. It was partially purified via FCC eluting with DCM:MeOH 95:5. The product of this purification was further purified using chiral HPLC using an AD column eluting with 45% IPA (0.2% DEA) in heptane to give (+)-2-((5,7-dimethyl-3-(pyridin-3-yl)-1H-indol-4-yl)(hydroxy)methyl)-1H-benzo[d]imidazole-5-carbonitrile ($t_r$=5.4 min) and (−)-2-((5,7-dimethyl-3-(pyridin-3-yl)-1H-indol-4-yl)(hydroxy)methyl)-1H-benzo[d]imidazole-5-carbonitrile ($t_r$=8.7 min). $^1$H NMR (HCl salt, 400 MHz, DMSO-$d_6$) δ 11.56 (br. s., 1H), 7.94 (s, 1H), 7.53-7.68 (m, 2H), 7.50 (dd, J=1.39, 8.34 Hz, 1H), 7.16-7.39 (m, 1H), 6.63 (s, 1H), 6.25 (dd, J=1.71, 3.09 Hz, 1H), 3.37 (s, 3H), 2.53 (d, J=0.76 Hz, 3H). HRMS calcd. for $C_{19}H_{17}N_5O_2S$ (M+H)$^+$, 380.1181. found 380.1184.

Example 19

Example 19-A

4-Allyl-5-methoxy-7-methyl-1H-indole

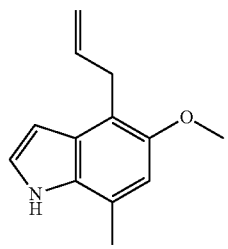

4-Allyl-7-methyl-1H-indol-5-ol (Example 1-C) (2.77 g, 14.79 mmol) was dissolved in toluene (74.0 mL) and methanol (0.599 mL, 14.79 mmol) was added followed by cyanomethylenetributylphosphorane (8.93 g, 37.0 mmol). The reaction was heated at 110° C. for 1 hour. The reaction was cooled to room temperature and then concentrated. The residue was then absorbed onto silica and purified by silica gel flash chromatography (0-50% ethyl acetate/heptanes) to provide the title compound. MS (ESI+) m/z 202.17 (M+H).

Example 19-B tert-Butyl 4-allyl-5-methoxy-7-methyl-1H-indole-1-carboxylate

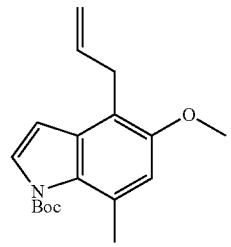 [SMILES: C=CCc1c(OC)cc(C)c2c1ccn2C(=O)OC(C)(C)C]

4-Allyl-5-methoxy-7-methyl-1H-indole (6.4 g, 31.8 mmol) was dissolved in acetonitrile (106 mL) and then Boc$_2$O (11.07 mL, 47.7 mmol) was added followed by DMAP (0.039 g, 0.318 mmol). The reaction was then stirred at room temperature overnight. The reaction was concentrated and absorbed onto silica and then purified by silica gel flash chromatography (0-50% ethyl acetate/heptanes) to provide the title compound. MS (ESI+) m/z 302.19 (M+H).

Example 19-C tert-Butyl 5-methoxy-7-methyl-4-(prop-1-en-1-yl)-1H-indole-1-carboxylate

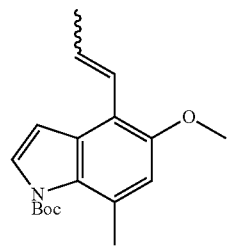

To a solution of tert-Butyl 4-allyl-5-methoxy-7-methyl-1H-indole-1-carboxylate (9.8 g, 32.5 mmol) in 1,1,1,3,3,3-hexafluoro-propanol (HFIPA) (40.6 mL) was added to palladium(II) acetate (0.073 g, 0.325 mmol) in 4 mL of HFIPA. The reaction was stirred at room temperature for 4 hours. The reaction was concentrated and absorbed onto silica and then purified by silica gel flash chromatography (0-30% ethyl acetate/heptanes) to provide the title compound. MS (ESI+) m/z 302.25 (M+H).

Example 19-D tert-Butyl 4-formyl-5-methoxy-7-methyl-1H-indole-1-carboxylate

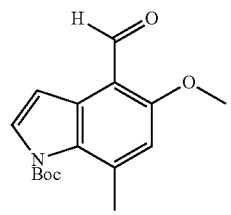 [SMILES: COc1cc(C)c2c(ccn2C(=O)OC(C)(C)C)c1C=O]

tert-Butyl 5-methoxy-7-methyl-4-(prop-1-en-1-yl)-1H-indole-1-carboxylate (0.29 g, 0.97 mmol) was dissolved in dioxane (7.27 mL) and water (2.4 mL) and 2,6-lutidine (0.23 mL, 1.94 mmol) was added followed by osmium tetroxide (0.24 mL, 0.019 mmol) and sodium periodate (0.83 g, 3.88 mmol) at 0° C. The reaction was removed from the ice bath and let stir at room temperature for 1 hour. The reaction was diluted with methylene chloride and water. The organic layer was separated, dried over sodium sulfate and then concentrated. The resulting residue was absorbed onto silica and then purified by silica gel flash chromatography (0-50% ethyl acetate/heptanes) to provide the title compound. MS (ESI+) m/z 290.1 (M+H).

The following compounds are prepared with similar methods as described in Example 19 using the appropriate alcohol in place of MeOH in Example 19-A.

| | Structure/Chemical Name | MS (ESI) m/z (M + H) |
|---|---|---|
| 19-E | tert-butyl 4-formyl-7-methyl-5-($^2H_3$)methoxy-1H-indole-1-carboxylate | 293.3 |
| 19-F | tert-butyl 5-ethoxy-4-formyl-7-methyl-1H-indole-1-carboxylate | 304.2 |
| 19-G | tert-butyl 4-formyl-5-isopropoxy-7-methyl-1H-indole-1-carboxylate | 318.3 |
| 19-H | tert-butyl 5-(benzyloxy)-4-formyl-7-methyl-1H-indole-1-carboxylate | 366.2 |
| 19-I | tert-butyl 5-(cyclopropylmethoxy)-4-formyl-7-methyl-1H-indole-1-carboxylate | 330.3 |
| 19-J | 7-Chloro-1H-indol-5-ol was used as starting material in Example 1. tert-butyl 7-chloro-4-formyl-5-($^2H_3$)methoxy-1H-indole-1-carboxylate | 313.1 |
| 19-K | tert-butyl 4-formyl-5-(2-methoxyethoxy)-7-methyl-1H-indole-1-carboxylate | 334.2 |
| 19-L | 6-fluoro-7-methyl-1H-indol-5-ol was used as starting material in Example 1. tert-butyl 6-fluoro-4-formyl-5-methoxy-7-methyl-1H-indole-1-carboxylate | 308.1 |

Example 20

Example 20-A tert-Butyl 4-(2,2-dibromovinyl)-5-methoxy-7-methyl-1H-indole-1-carboxylate

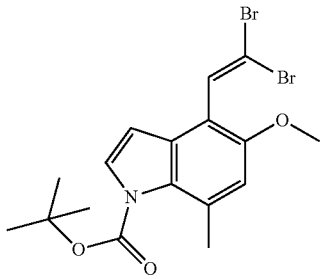 [SMILES: COc1cc(C)c2c(ccn2C(=O)OC(C)(C)C)c1C=C(Br)Br]

To a solution of tert-butyl 4-formyl-5-methoxy-7-methyl-1H-indole-1-carboxylate (902 mg, 3.12 mmol) in $CH_2Cl_2$ (30 mL), $CBr_4$ (1.55 g, 4.68 mmol) was added at 0° C. followed by $PPh_3$ (2.45 g, 9.35 mmol). The mixture was stirred at room temperature for 1.5 hours. The reaction mixture was concentrated and directly purified via FCC eluting with Heptane/DCM 100:0 to 0:100 to provide the title compound. MS (ESI+) m/z 446.0, 448.0, 444.0, 446.9 (M+H).

Example 20-B tert-Butyl 4-((5-cyano-1H-benzo[d]imidazol-2-yl)methyl)-5-methoxy-7-methyl-1H-indole-1-carboxylate

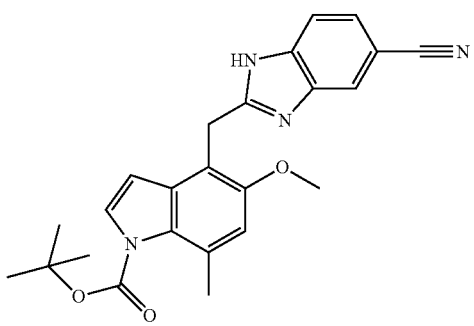 [SMILES: COc1cc(C)c2c(ccn2C(=O)OC(C)(C)C)c1Cc1nc2cc(C#N)ccc2[nH]1]

A mixture of tert-butyl 4-(2,2-dibromovinyl)-5-methoxy-7-methyl-1H-indole-1-carboxylate (1.3 g, 2.92 mmol), 3,4-diaminobenzonitrile (700 mg, 5.26 mmol) and DABCO (819 mg, 7.30 mmol) in NMP (12 mL) was stirred at 110° C. for overnight. The reaction mixture was then cooled to room temperature, diluted with EtOAc, and washed with water. The organic layer was dried over magnesium sulfate, filtered and concentrated. The residue was purified using FCC eluting with heptane/EtOAc(60-80%) to provide the title compound. MS (ESI+) m/z 417.2 (M+H).

Example 20-C 2-((5-Methoxy-7-methyl-1H-indol-4-yl)methyl)-1H-benzo[d]imidazole-5-carbonitrile

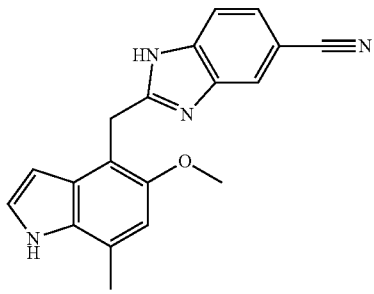 [SMILES: COc1cc(C)c2[nH]ccc2c1Cc1nc2cc(C#N)ccc2[nH]1]

To a solution of tert-butyl 4-((5-cyano-1H-benzo[d]imidazol-2-yl)methyl)-5-methoxy-7-methyl-1H-indole-1-carboxylate (878 mg, 2.108 mmol) in THF (12 mL) and MeOH (12 mL) was added $Cs_2CO_3$ (3.4 g, 10.54 mmol). The mixture was stirred at 58° C. for 1 hour. The reaction mixture was cooled to room temperature, concentrated and purified by flash chromatography (DCM:EtOAc) to provide the title compound. $^1$H NMR (400 MHz, DICHLOROMETHANE-$d_2$) δ ppm 8.24 (br. s., 1H) 7.86 (s, 1H) 7.59 (d, J=8.34 Hz, 1H) 7.46-7.54 (m, 1H) 7.30 (t, J=2.91 Hz, 1H) 6.87 (s, 1H) 6.71 (m, 1H) 4.60 (s, 2H) 4.03 (s, 3H) 2.53 (s, 3H). HRMS calcd. for $C_{13}H_{16}N_4O$ (M+H)$^+$ 317.1397. found 317.1400.

The following compounds were prepared with a similar method as described above using aldehydes in Example 19.

| | Structure/Chemical Name | $^1$H NMR | HRMS |
|---|---|---|---|
| 20-D | 2-((5-($^2H_3$)methoxy-7-methyl-1H indol-4-yl)methyl)-1H-benzo[d]imidazole-5-carbonitrile | (400 MHz, CD$_3$OD) δ ppm 7.38-7.95 (m, 3H) 7.20 (d, J = 3.03 Hz, 1H) 6.80 (s, 1H) 6.34 (d, J = 3.03 Hz, 1H) 4.49 (s, 2H) 2.51 (s, 3H). | calcd. for $C_{19}H_{13}D_3N_4O$ (M + H)$^+$ 320.1587, found 320.1603 |

| | Structure/Chemical Name | ¹H NMR | HRMS |
|---|---|---|---|
| 20-E | 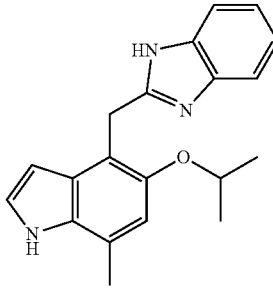<br>2-((5-isopropoxy-7-methyl-1H-indol-4-yl)methyl)-1H-benzo[d]imidazole-5-carbonitrile | (400 MHz, CD$_3$OD) δ ppm 7.91 (m), 7.68 (m), 7.46 (m) 7.19 (d, J = 3.28 Hz, 1H) 6.78 (s, 1H) 6.29 (d, J = 3.03 Hz, 1H) 4.41-4.55 (m, 4H) 2.50 (s, 3H) 1.18 (d, J = 6.06 Hz, 6H). | calcd. for C$_{21}$H$_{20}$N$_4$O (M + H)$^+$ 345.1715, found 345.1711 |
| 20-F | 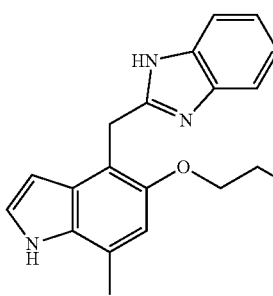<br>2-((5-(2-methoxyethoxy)-7-methyl-1H-indol-4-yl)methyl)-1H-benzo[d]imidazole-5-carbonitrile | (400 MHz, DICHLOROMETHANE-d$_2$) δ ppm 8.09 (br. s., 1H) 7.79 (br. s., 1H) 7.35-7.64 (m, 2H) 7.22 (t, J = 2.78 Hz, 1H) 6.97 (br. s., 1H) 6.63 (s, 1H) 4.56 (br. s., 2H) 4.16-4.35 (m, 2H) 3.94 (dt, J = 4.23, 2.31 Hz, 2H) 3.59 (s, 3H) 2.38 (s, 3H). | calcd. for C$_{21}$H$_{20}$N$_4$O$_2$ (M + H)$^+$ 361.1659, found 361.1662. |
| 20-G | 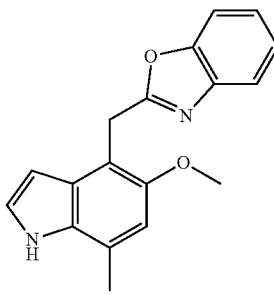<br>2-((5-methoxy-7-methyl-1H-indol-4-yl)methyl)benzo[d]oxazole-5-carbonitrile | (400 MHz, DICHLOROMETHANE-d$_2$) δ ppm 8.18 (br. s., 1H) 7.93 (d, J = 0.76 Hz, 1H) 7.49-7.60 (m, 2H) 7.25 (t, J = 2.78 Hz, 1H) 6.79 (s, 1H) 6.5 (dd, J = 3.16, 2.15 Hz, 1H) 4.54 (s, 2H) 3.84 (s, 3H) 2.51 (s, 3H) | calcd. for C$_{19}$H$_{15}$N$_3$O$_2$ (M + H)$^+$ 318.1237, found 318.1232. |
| 20-H | 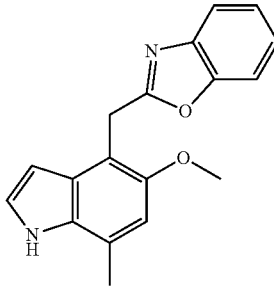<br>2-((5-methoxy-7-methyl-1H-indol-4-yl)methyl)benzo[d]oxazole-6-carbonitrile | (400 MHz, DICHLOROMETHANE-d$_2$) δ ppm 8.18 (br. s., 1H) 7.76 (dd, J = 1.52, 0.51 Hz, 1H) 7.67-7.71 (m, 1H) 7.57 (dd, J = 8.08, 1.52 Hz, 1H) 7.25 (t, J = 2.78 Hz, 1H) 6.79 (s, 1H) 6.50 (dd, J = 3.16, 2.15 Hz, 1H) 4.55 (s, 2H) 3.84 (s, 3H) 2.51 (s, 3H). | calcd. for C$_{19}$H$_{15}$N$_3$O$_2$ (M + H)$^+$ 318.1237, found 318.1231. |

Example 21

Example 21-A tert-Butyl 4-allyl-7-fluoro-5-methoxy-1H-indole-1-carboxylate

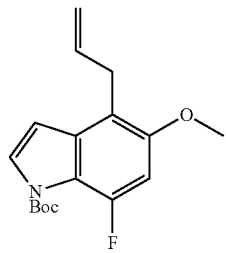 [SMILES: C=CCc1c(OC)cc(F)c2c1ccn2C(=O)OC(C)(C)C]

The title compound was synthesized from 7-fluoroindoline using the same procedure as described in Example 1-A to 1-C and 19-A to 19-B. $^1$H NMR (400 MHz, DICHLOROMETHANE-$d_2$) δ ppm 7.60 (d, J=3.79 Hz, 1H) 6.72 (d, J=14.15 Hz, 1H) 6.56 (dd, J=3.79, 2.02 Hz, 1H) 5.87-6.01 (m, 1H) 4.90-4.98 (m, 2H) 3.83 (s, 3H) 3.54 (dt, J=6.19, 1.58 Hz, 2H) 1.62 (s, 9H).

Example 21-B 2-((7-Fluoro-5-methoxy-1H-indol-4-yl)methyl)-1H-benzo[d]imidazole-5-carbonitrile

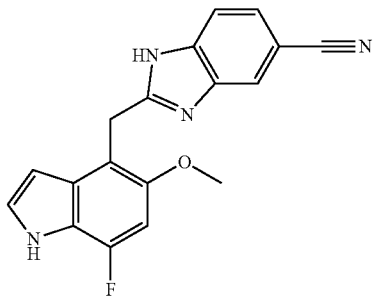 [SMILES: COc1cc(F)c2[nH]ccc2c1Cc1nc2cc(C#N)ccc2[nH]1]

A vial was charged with tert-butyl 4-allyl-7-fluoro-5-methoxy-1H-indole-1-carboxylate (60 mg, 0.196 mmol) and dioxane/water (3:1, total volume=2 mL). The mixture was charged with 2,6-lutidine (0.046 mL, 0.393 mmol) and cooled to 0° C. Osmium tetroxide (2.5 wt % solution in t-BuOH, 0.049 mmol) was added, followed by sodium periodate (168 mg, 0.786 mmol). The reaction was stirred at 0° C. for 10 min and then warmed to room temperature. The heterogeneous reaction was quenched with a 1:1 mixture of aq. saturated ammonium chloride/sodium thiosulfate. The reaction mixture was then extracted with DCM and separated via phase separation cartridge. The organic layer was evaporated to dryness. The resulting residue was dissolved in THF (2 mL), t-BuOH (0.7 mL), and water (0.3 mL). To this mixture was added 2-methyl-2-butene (1.33 mL, 2.66 mmol) as a 2M solution in THF. The reaction was then charged with NaH$_2$PO$_4$ (138 mg, 1 mmol) as a solid, cooled to 0° C., then sodium chlorite (90 mg, 1 mmol) was added as a solid. The reaction was allowed to slowly warm to room temperature and stirred overnight. The reaction mixture was diluted with a pH=7 buffer solution and extracted with EtOAc. The organic extract was dried over magnesium sulfate, filtered and evaporated. The resulting residue (69 mg, 0.213 mmol) was dissolved in DCM (3 mL). DIPEA (0.056 mL, 0.32 mmol), 3,4-diaminobenzonitrile (34 mg, 0.256 mmol) and HATU (97 mg, 0.256 mmol) were added to the mixture and the reaction was allowed to stir overnight at room temperature. The reaction was diluted with water and the layers were partitioned. The aqueous layer was extracted twice with DCM. The organic layer was separated by a phase separation cartridge (Isolute®) and concentrated to dryness. The crude material was (60 mg, 0.143 mmol) was dissolved in 2 mL 1:1 THF/MeOH and treated with solid cesium carbonate (139 mg, 0.428 mmol). The mixture was stirred for 2 h at room temperature and then purified by reverse phase preparative HPLC (HC-B) to afford the title compound. $^1$H NMR (400 MHz, CD$_3$OD) δ ppm 7.83 (s, 1H) 7.54-7.60 (m, 1H) 7.46-7.48 (m, 1H) 7.25 (d, J=3.28 Hz, 1H) 6.81 (d, J=12.63 Hz, 1H) 6.42 (t, J=3.28 Hz, 1H) 4.49 (s, 2H) 3.84 (s, 3H). HRMS calcd. for C$_{18}$H$_{13}$FN$_4$O (M+H)$^+$ 321.1152. found 321.1144.

Example 22

2-((7-Chloro-5-($^2$H$_3$)methoxy-1H-indol-4-yl)methyl)-1H-benzo[d]imidazole-5-carbonitrile

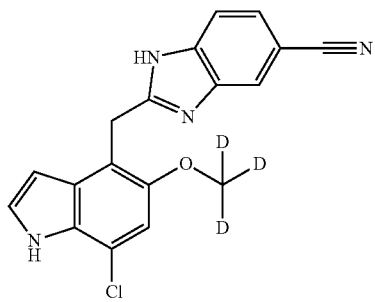 [SMILES: [2H]C([2H])([2H])Oc1cc(Cl)c2[nH]ccc2c1Cc1nc2cc(C#N)ccc2[nH]1]

The compound was synthesized using the same procedures as described in Example 19 and Example 21 starting from 7-chloroindoline and replacing MeOH with CD$_3$OD when reproducing Example 19-A. $^1$H NMR (400 MHz, DICHLOROMETHANE-$d_2$) δ ppm 9.60 (br. s., 1H) 7.81 (s, 1H) 7.48-7.56 (m, 1H) 7.37-7.46 (m, 1H) 7.22-7.31 (m, 1H) 6.99 (s, 1H) 6.57 (dd, J=3.16, 2.15 Hz, 1H) 4.50 (s, 2H). HRMS calcd. for C$_{18}$H$_{10}$ClD$_3$N$_4$O (M+H)$^+$ 340.1041. found 340.1033.

Example 23

(±)-2-((5-((1-Methoxypropan-2-yl)oxy)-7-methyl-1H-indol-4-yl)methyl)-1H-benzo[d]imidazole-5-carbonitrile

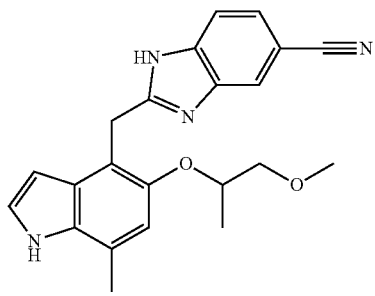 [SMILES: COCC(C)Oc1cc(C)c2[nH]ccc2c1Cc1nc2cc(C#N)ccc2[nH]1]

The compound was synthesized using the same procedures as described in Example 19 and Example 21 starting from 7-methylindoline and replacing MeOH with (±)-1-methoxy-2-propanol when reproducing Example 19-A. $^1$H NMR (400 MHz, DMSO-d$_6$) δ ppm 10.97 (br. s., 1H) 7.91 (br. s., 1H) 7.51-7.58 (m, 1H) 7.46 (dd, J=8.08, 1.52 Hz, 1H) 7.22 (t, J=2.78 Hz, 1H) 6.77 (s, 1H) 6.21 (dd, J=3.03, 2.02 Hz, 1H) 4.29-4.47 (m, 2H) 3.39-3.49 (m, 1H) 3.33-3.37 (m, 2H) 3.22 (s, 3H) 2.44 (s, 3H) 1.13 (d, J=6.32 Hz, 3H). HRMS calcd. for C$_{22}$H$_{22}$N$_4$O$_2$ (M+H)$^+$ 375.1816. found 375.1823.

Example 24

Example 24-A (±)-tert-Butyl 4-((5-cyano-1-((2-(trimethylsilyl)ethoxy)methyl)-1H-benzo[d]imidazol-2-yl)(hydroxy)methyl)-5-methoxy-7-methyl-1H-indole-1-carboxylate and (±)-tert-butyl 4-((6-cyano-1-((2-(trimethylsilyl)ethoxy)methyl)-1H-benzo[d]imidazol-2-yl)(hydroxy)methyl)-5-methoxy-7-methyl-1H-indole-1-carboxylate

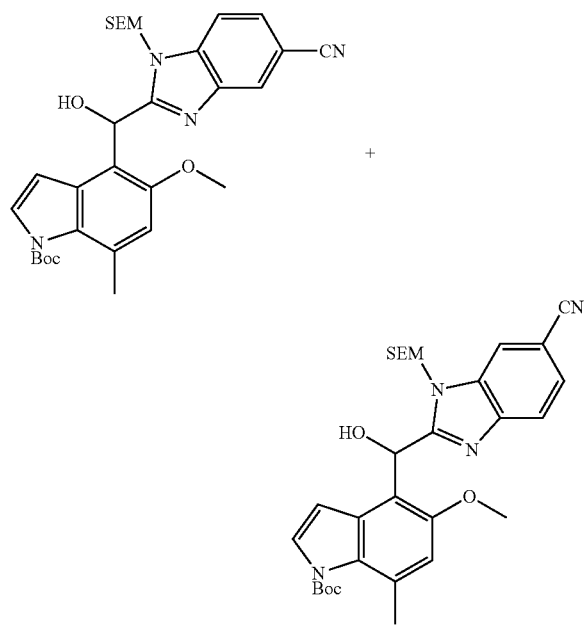

To a solution of a mixture of 1-((2-(trimethylsilyl)ethoxy)methyl)-1H-benzo[d]imidazole-5-carbonitrile and 1-((2-(trimethylsilyl)ethoxy)methyl)-1H-benzo[d]imidazole-6-carbonitrile (0.111 g, 0.409 mmol) in THF (1 mL), LDA (2 M in heptane/THF/ethylbenzene, 0.188 mL, 0.376 mmol) was added at −78° C. After stirring for 30 minutes tert-butyl 4-formyl-5-methoxy-7-methyl-1H-indole-1-carboxylate (Example 19-D) (0.103 g, 0.358 mmol) in THF (2 mL) was added at −78° C. and stirred at the same temperature for 3 hours. The reaction was quenched with MeOH (1 mL) and aq. NH$_4$Cl (15 mL) and then diluted with EtOAc (40 mL). The layers were separated and the water layer was extracted twice with EtOAc. The organic extracts were combined, dried over sodium sulfate, filtered, concentrated and purified by flash chromatography (40 g, 0-40% ethyl acetate in heptanes) to provide a mixture of the title compounds. MS (ESI+) m/z 563.36 (M+H).

Example 24-B a) (±)-2-(Hydroxy(5-methoxy-7-methyl-1H-indol-4-yl)methyl)-1H-benzo[d]imidazole-5-carbonitrile

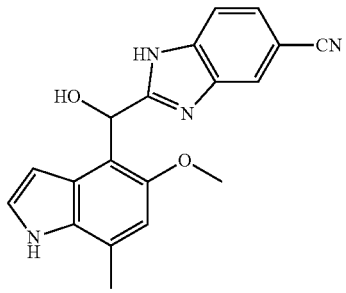 [SMILES: COc1cc(C)c2[nH]ccc2c1C(O)c1nc2cc(C#N)ccc2[nH]1]

A mixture of (±)-tert-butyl 4-((5-cyano-1-((2-(trimethylsilyl)ethoxy)methyl)-1H-benzo[d]imidazol-2-yl)(hydroxy)methyl)-5-methoxy-7-methyl-1H-indole-1-carboxylate and (±)-tert-butyl 4-((6-cyano-1-((2-(trimethylsilyl)ethoxy)methyl)-1H-benzo[d]imidazol-2-yl)(hydroxy)methyl)-5-methoxy-7-methyl-1H-indole-1-carboxylate (0.3 g, 0.533 mmol) was dissolved in THF (5.33 mL). TBAF (5.34 mL, 5.34 mmol) was added to the solution and the reaction was stirred at 50° C. for 5 hours. The reaction was diluted with ethyl acetate and then with 20 mL of a saturated aq. solution of ammonium chloride. The ethyl acetate layer was separated, washed with water, dried and concentrated. The resulting residue was dissolved in MeOH (4 mL) to which cesium carbonate (0.87 g, 2.67 mmol) was added. The reaction was heated at 50° C. for 1 hour. The reaction was then concentrated and directly purified by flash chromatography (0-10% MeOH in DCM) to provide the title compound. $^1$H NMR (400 MHz, DMSO-d$_6$) δ ppm 12.93 (d, J=3.54 Hz, 1H) 10.86 (br. s., 1H) 7.81-7.95 (m, 1H) 7.60 (m) 7.40-7.56 (m) 7.14 (t, J=2.78 Hz, 1H) 6.75 (s, 1H) 6.53-6.62 (m, 1H) 6.19-6.31 (m, 2H) 3.81 (s, 3H) 2.40-2.47 (m, 3H). HRMS calcd. for C$_{19}$H$_{16}$N$_4$O$_2$ (M+H)$^+$ 333.1346. found 333.1355.

b) (+) and (−)-2-(hydroxy(5-methoxy-7-methyl-1H-indol-4-yl)methyl)-1H-benzo[d]imidazole-5-carbonitrile Resolution of the enantiomers of 2-(hydroxy(5-methoxy-7-methyl-1H-indol-4-yl)methyl)-1H-benzo[d]imidazole-5-carbonitrile is achieved by chiral HPLC using a CHIRALPAK® AD-H column with 30% ethanol (0.2% DEA) in heptane to give (+)-2-(hydroxy(5-methoxy-7-methyl-1H-indol-4-yl)methyl)-1H-benzo[d]imidazole-5-carbonitrile (t$_r$=5.4 min) and (−)-2-(hydroxy(5-methoxy-7-methyl-1H-indol-4-yl)methyl)-1H-benzo[d]imidazole-5-carbonitrile (t$_r$=9.3 min).

The following compounds were prepared with similar method.

| Structure/Chemical Name | ¹H NMR | HRMS |
|---|---|---|
| 24-C a) <br> (±)-2-((5-ethoxy-7-methyl-1H-indol-4-yl)(hydroxy)methyl)-1H-benzo[d]imidazole-5-carbonitrile | (400 MHz, DMSO-$d_6$) δ ppm 12.88 (s, 1H) 10.84 (br. s., 1H) 7.84-7.92 (m) 7.61 (m) 7.40-7.56 (m) 7.14 (t, J = 2.78 Hz, 1H) 6.72 (s, 1H) 6.51-6.61 (m, 1H) 6.25 (d, J = 2.02 Hz, 1H) 6.18-6.23 (m, 1H) 4.09 (dd, J = 9.22, 7.20 Hz, 1H) 3.90-4.01 (m, 1H) 2.43 (s, 3H) 1.25 (t, J = 7.07 Hz, 3H). | calcd. for $C_{20}H_{18}N_4O_2$ $(M + H)^+$ 347.1503, found 347.1517 |

24-C b) (+) and (−)-2-((5-ethoxy-7-methyl-1H-indol-4-yl)(hydroxy)methyl)-1H-benzo[d]imidazole-5-carbonitrile
Resolution of the enantiomers of (2-((5-ethoxy-7-methyl-1H-indol-4-yl)(hydroxy)methyl)-1H-benzo[d]imidazole-5-carbonitrile was achieved by chiral HPLC using a CHIRALPAK ® AD-H column with 40% methanol-ethanol (0.2% DEA) in heptanes to give (+)-2-((5-ethoxy-7-methyl-1H-indol-4-yl)(hydroxy)methyl)-1H-benzo[d]imidazole-5-carbonitrile ($t_r$ = 4.11 min) and (−)-2-((5-ethoxy-7-methyl-1H-indol-4-yl)(hydroxy)methyl)-1H-benzo[d]imidazole-5-carbonitrile ($t_r$ = 6.16 min).

| Structure/Chemical Name | ¹H NMR | HRMS |
|---|---|---|
| 24-D a) <br> (±)-2-(hydroxy(5-isopropoxy-7-methyl-1H-indol-4-yl)methyl)-1H-benzo[d]imidazole-5-carbonitrile | (400 MHz, DICHLOROMETHANE-$d_2$) δ ppm 8.12 (br. s., 1H) 7.56 (br. s., 1H) 7.30-7.47 (m, 2H) 7.11 (t, J = 2.65 Hz, 1H) 6.59 (s, 1H) 6.33-6.47 (m, 2H) 4.47 (dt, J = 12.13, 6.06 Hz, 1H) 2.29 (s, 3H) 1.25 (d, J = 6.06 Hz, 3H) 0.95 (d, J = 6.06 Hz, 3H). | calcd. for $C_{21}H_{20}N_4O_2$ $(M + H)^+$ 361.1665, found 361.1667. |

24-D b) (+) and (−)-2-(hydroxy(5-isopropoxy-7-methyl-1H-indol-4-yl)methyl)-1H-benzo[d]imidazole-5-carbonitrile
Resolution of the enantiomers of 2-(hydroxy(5-isopropoxy-7-methyl-1H-indol-4-yl)methyl)-1H-benzo[d]imidazole-5-carbonitrile was achieved by chiral HPLC using a CHIRALCEL ® OD column with 30% EtOH (0.2% DEA) in heptanes to give (−)-2-(hydroxy(5-isopropoxy-7-methyl-1H-indol-4-yl)methyl)-1H-benzo[d]imidazole-5-carbonitrile ($t_r$ = 4.44 min) and (+)-2-(hydroxy(5-isopropoxy-7-methyl-1H-indol-4-yl)methyl)-1H-benzo[d]imidazole-5-carbonitrile ($t_r$ = 8.86 min).

| Structure/Chemical Name | ¹H NMR | HRMS |
|---|---|---|
| 24-E <br> (±)-2-((7-chloro-5-($^2H_3$)methoxy-1H-indol-4-yl)(hydroxy)methyl)benzo[d]imidazole-5-carbonitrile | ¹H NMR (TFA salt, 400 MHz, DMSO-$d_6$) δ ppm 11.32 (br. s, 1H) 8.01 (s, 1H) 7.62-7.69 (m, 2H) 7.30 (t, J = 2.78 Hz, 1H) 7.08 (s, 1H) 6.65 (s, 1H) 6.36-6.38 (m, 1H) | calcd. for $C_{18}H_{11}D_3ClN_4O_2$ $(M + H)^+$ 356.0990, found 356.0980. |

Example 25

Example 25-A tert-Butyl 4-(5-cyano-1-((2-(trimethylsilyl)ethoxy)methyl)-1H-benzo[d]imidazole-2-carbonyl)-5-methoxy-7-methyl-1H-indole-1-carboxylate and tert-butyl 4-(6-cyano-1-((2-(trimethylsilyl)ethoxy)methyl)-1H-benzo[d]imidazole-2-carbonyl)-5-methoxy-7-methyl-1H-indole-1-carboxylate

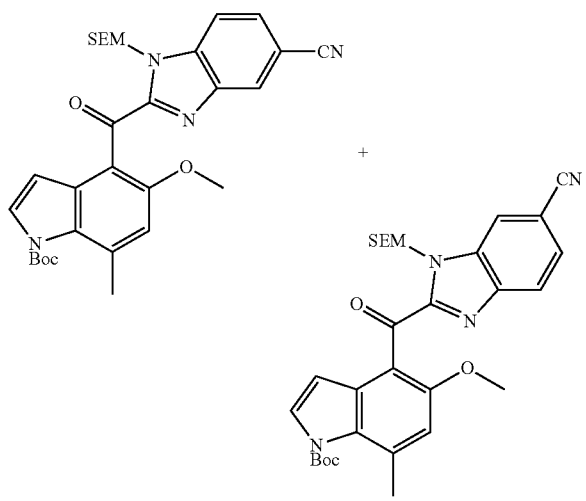

A mixture of (±)-tert-butyl 4-((5-cyano-1-((2-(trimethylsilyl)ethoxy)methyl)-1H-benzo[d]imidazol-2-yl)(hydroxy)methyl)-5-methoxy-7-methyl-1H-indole-1-carboxylate and (±)-tert-butyl 4-((6-cyano-1-((2-(trimethylsilyl)ethoxy)methyl)-1H-benzo[d]imidazol-2-yl)(hydroxy)methyl)-5-methoxy-7-methyl-1H-indole-1-carboxylate (Example 24-A) (64 mg, 0.114 mmol) was dissolved in DCM (1.2 mL). MnO$_2$ (99 mg, 1.137 mmol) was added and stirred at room temperature for 18 hours. The mixture was filtered through a pad of Celite® and concentrated to obtain the mixture of title compounds without the need of further purification. MS (ESI+) m/z 561.36 (M+H).

Example 25-B 2-(5-Methoxy-7-methyl-1H-indole-4-carbonyl)-1H-benzo[d]imidazole-5-carbonitrile

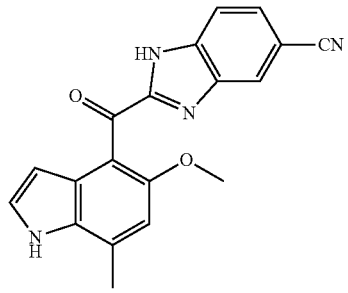 [SMILES: COc1cc(C)c2[nH]ccc2c1C(=O)c1nc2cc(C#N)ccc2[nH]1]

A mixture of tert-butyl 4-(5-cyano-1-((2-(trimethylsilyl)ethoxy)methyl)-1H-benzo[d]imidazole-2-carbonyl)-5-methoxy-7-methyl-1H-indole-1-carboxylate and tert-butyl 4-(6-cyano-1-((2-(trimethylsilyl)ethoxy)methyl)-1H-benzo[d]imidazole-2-carbonyl)-5-methoxy-7-methyl-1H-indole-1-carboxylate (62 mg, 0.11 mmol) was dissolved in THF (1.1 mL) and then TBAF (1.1 mL, 1.1 mmol) was added and the reaction was heated at 65° C. for 17 hours. The mixture was then cooled to room temperature and treated with 10 mL of a saturated aq. solution of ammonium chloride and then diluted with EtOAc. The organic layer was separated and washed with water (3×100 mL). The organic extract was dried over magnesium sulfate and concentrated. The resulting residue was dissolved in MeOH (4 mL), cesium carbonate (48.9 mg, 0.15 mmol) was added and the reaction was heated at 60° C. for 1 h. The reaction was cooled to room temperature, a saturated aq. solution of ammonium chloride was added, followed by EtOAc. The organic layer was separated, washed with water and the organic extracts combined, dried over magnesium sulfate, filtered and concentrated. The resulting residue was purified by flash column chromatography (0-40% EtOAc in heptanes) to provide the title compound. $^1$H NMR (400 MHz, DMSO-d$_6$) δ ppm 13.73 (br. s., 1H) 11.33 (br. s., 1H) 8.29 (br. s.) 8.07 (br. s.) 7.60-7.90 (m, 2H) 7.45 (t, J=2.78 Hz, 1H) 6.89 (s, 1H) 6.42 (br. s., 1H) 3.56 (s, 3H) 2.54-2.63 (m, 3H). HRMS calcd. for $C_{19}H_{14}N_4O_2$ (M+H)$^+$ 331.119. found 331.1202.

Example 26

Example 26-A (±)-tert-Butyl 4-(1-(5-cyano-1-((2-(trimethylsilyl)ethoxy)methyl)-1H-benzo[d]imidazol-2-yl)-1-hydroxyethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-hydroxyethyl)-5-methoxy-7-methyl-1H-indole-1-carboxylate

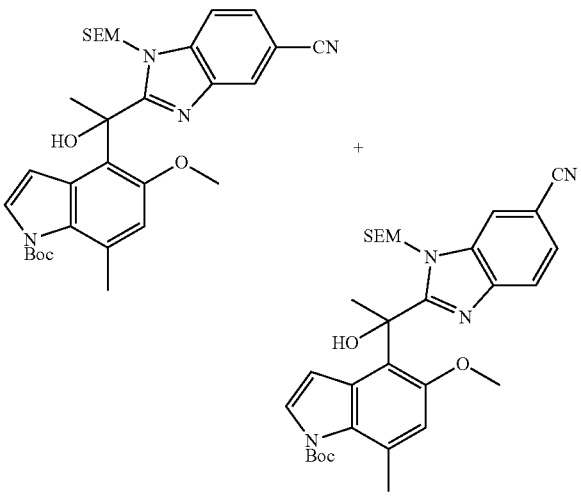

A mixture of tert-butyl 4-(5-cyano-1-((2-(trimethylsilyl)ethoxy)methyl)-1H-benzo[d]imidazole-2-carbonyl)-5-methoxy-7-methyl-1H-indole-1-carboxylate and tert-butyl 4-(6-cyano-1-((2-(trimethylsilyl)ethoxy)methyl)-1H-benzo[d]imidazole-2-carbonyl)-5-methoxy-7-methyl-1H-indole-1-carboxylate (1.9 g, 3.39 mmol) was dissolved in tetrahydrofuran (33.9 mL) and then cooled to 0° C. in an ice bath. Methylmagnesium chloride (3M, 1.35 mL, 4.07 mmol) was added and the mixture was stirred at 0° C. for 30 minutes. The reaction was then quenched with 15 mL aq. NH$_4$Cl and brine. The layers were separated and the aqueous layer was extracted with EtOAc. The organic extracts were combined, dried over Na$_2$SO$_4$, filtered, concentrated, and purified by flash chromatography (0-40% ethyl acetate in heptanes) to provide the mixture of title compounds. MS (ESI+) m/z 577.53 (M+H).

Example 26-B (±)-tert-Butyl 5-(benzyloxy)-4-(1-(5-cyano-1-((2-(trimethylsilyl)ethoxy)methyl)-1H-benzo[d]imidazol-2-yl)-1-hydroxyethyl)-7-methyl-1H-indole-1-carboxylate and (±)-tert-butyl 5-(benzyloxy)-4-(1-(6-cyano-1-((2-(trimethylsilyl)ethoxy)methyl)-1H-benzo[d]imidazol-2-yl)-1-hydroxyethyl)-7-methyl-1H-indole-1-carboxylate

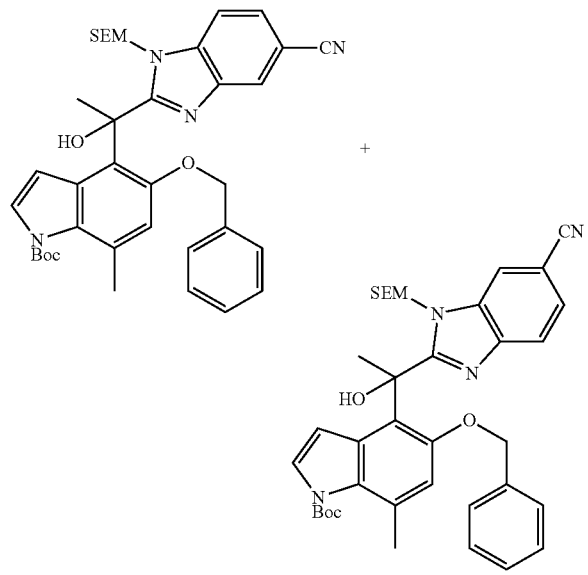

The mixture of title compounds was synthesized in a similar manner as described in Example 24, 25 and 26, starting from tert-butyl 5-(benzyloxy)-4-formyl-7-methyl-1H-indole-1-carboxylate (Example 19-H). MS (ESI+) m/z 653.2 (M+H).

Example 26-C a) (±)-2-(1-Hydroxy-1-(5-methoxy-7-methyl-1H-indol-4-yl)ethyl)-1H-benzo[d]imidazole-5-carbonitrile

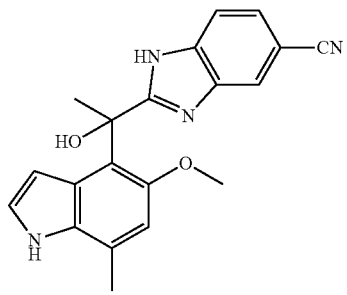 [SMILES: COc1cc(C)c2[nH]ccc2c1C(C)(O)c1nc2cc(C#N)ccc2[nH]1]

(±)-tert-Butyl 4-(1-(5-cyano-1-((2-(trimethylsilyl)ethoxy)methyl)-1H-benzo[d]imidazol-2-yl)-1-hydroxyethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-hydroxyethyl)-5-methoxy-7-methyl-1H-indole-1-carboxylate was converted in the title compound using the same procedure described in Example 24-B. $^1$H NMR (400 MHz, DMSO-$d_6$) δ ppm 12.30 (s, 1H) 10.86 (br. s., 1H) 8.10 (s) 7.63-7.84 (m) 7.38-7.55 (m, 2H) 7.21 (q, J=3.12 Hz, 1H) 6.47-6.77 (m, 1H) 6.00 (d, J=1.01 Hz, 1H) 3.26-3.30 (m, 3H) 2.40-2.45 (m, 3H) 2.03 (s, 3H). HRMS calcd. for $C_{20}H_{18}N_4O_2$ (M+H)$^+$ 347.1508. found 347.1510.

b) (+) and (−)-2-(1-hydroxy-1-(5-methoxy-7-methyl-1H-indol-4-yl)ethyl)-1H-benzo[d]imidazole-5-carbonitrile Resolution of the enantiomers of 2-(1-hydroxy-1-(5-methoxy-7-methyl-1H-indol-4-yl)ethyl)-1H-benzo[d]imidazole-5-carbonitrile is achieved by chiral HPLC using a CHIRALPAK® AD-H column with 30% ethanol (0.2% DEA) in heptanes to give (−)-2-(1-hydroxy-1-(5-methoxy-7-methyl-1H-indol-4-yl)ethyl)-1H-benzo[d]imidazole-5-carbonitrile ($t_r$=4.65 min) and (+)-2-(1-hydroxy-1-(5-methoxy-7-methyl-1H-indol-4-yl)ethyl)-1H-benzo[d]imidazole-5-carbonitrile=9.61 min).

The following compounds were prepared with similar method.

| | Structure/Chemical Name | $^1$H NMR | HRMS |
|---|---|---|---|
| 26-D a) | (±)-2-(1-(5-ethoxy-7-methyl-1H-indol-4-yl)-1-hydroxyethyl)-1H-benzo[d]imidazole-5-carbonitrile | $^1$H NMR (400 MHz, DMSO-$d_6$) δ ppm 12.11-12.32 (m, 1H) 10.82 (br. s., 1H) 8.08 (s, 1H) 7.65-7.81 (m) 7.37-7.56 (m) 7.11-7.28 (m) 6.70-6.78 (m, 1H) 6.64 (s, 1H) 5.79-6.07 (m, 1H) 3.70-3.82 (m, 1H) 3.39-3.50 (m, 1H) 2.42 (s, 3H) 2.00-2.08 (m, 3H) 0.57-0.68 (m, 3H). | calcd. for $C_{21}H_{20}N_4O_2$ (M + H)$^+$ 361.1659, found 361.1672. |

| Structure/Chemical Name | ¹H NMR | HRMS |
|---|---|---|

26-D b) (+) and (−)-2-(1-(5-ethoxy-7-methyl-1H-indol-4-yl)-1-hydroxyethyl)-1H-benzo[d]imidazole-5-carbonitrile Resolution of the enantiomers of 2-(1-(5-ethoxy-7-methyl-1H-indol-4-yl)-1-hydroxyethyl)-1H-benzo[d]imidazole-5-carbonitrile was achieved by chiral HPLC using a CHIRALPAK ® AD-H column with 40% ethanol (0.2% DEA) in heptanes to give (−)-2-(1-(5-ethoxy-7-methyl-1H-indol-4-yl)-1-hydroxyethyl)-1H-benzo[d]imidazole-5-carbonitrile ($t_r$ = 3.5 min) and (+)-2-(1-(5-ethoxy-7-methyl-1H-indol-4-yl)-1-hydroxyethyl)-1H-benzo[d]imidazole-5-carbonitrile ($t_r$ = 6.3 min).

26-E a)

(±)-2-(1-hydroxy-1-(5-isopropoxy-7-methyl-1H-indol-4-yl)ethyl)-1H-benzo[d]imidazole-5-carbonitrile (400 MHz, DICHLOROMETHANE-$d_2$) δ ppm 8.16 (br. s., 1H) 7.83 (s., 1H) 7.52-7.61 (m, 1H) 7.43-7.51 (m, 1H) 7.08 (t, J = 2.91 Hz, 1H) 6.73 (s, 1H) 6.24 (dd, J = 3.41, 2.15 Hz, 1H) 6.17 (s, 1H) 4.62 (dt, J = 12.13, 6.06 Hz, 1H) 2.44 (s, 3H) 2.19 (s, 3H) 1.22 (d, J = 6.06 Hz, 3H) 1.00 (d, J = 6.06 Hz, 3H).

calcd. for $C_{22}H_{22}N_4O_2$ $(M + H)^+$ 375.1816, found 375.1823.

26-E b) (+) and (−)-2-(1-hydroxy-1-(5-isopropoxy-7-methyl-1H-indol-4-yl)ethyl)-1H-benzo[d]imidazole-5-carbonitrile Resolution of the enantiomers of 2-(1-hydroxy-1-(5-isopropoxy-7-methyl-1H-indol-4-yl)ethyl)-1H-benzo[d]imidazole-5-carbonitrile was achieved by chiral HPLC using a CHIRALCEL ® OD column with 30% EtOH (0.2% DEA) in heptanes to give (−)-2-(1-hydroxy-1-(5-isopropoxy-7-methyl-1H-indol-4-yl)ethyl)-1H-benzo[d]imidazole-5-carbonitrile ($t_r$ = 4.08 min) and (+)-2-(1-hydroxy-1-(5-isopropoxy-7-methyl-1H-indol-4-yl)ethyl)-1H-benzo[d]imidazole-5-carbonitrile ($t_r$ = 7.72 min).

26-F a)

(Ethylmagnesium bromide was used in Example 26-A)

(±)-2-(1-hydroxy-1-(5-isopropoxy-7-methyl-1H-indol-4-yl)propyl)-1H-benzo[d]imidazole-5-carbonitrile (400 MHz, DICHLOROMETHANE-$d_2$) δ ppm 8.04 (br. s., 1H) 7.81 (br. s., 1H) 7.46-7.58 (m, 1H) 7.36-7.44 (m, 1H) 7.02 (t, J = 2.91 Hz, 1H) 6.69 (s, 1H) 6.29-6.44 (m, 2H) 4.63 (m, 1H) 2.60-2.75 (m, 1H) 2.45-2.58 (m, 1H) 2.38 (s, 3H) 1.24 (d, J = 6.06 Hz, 3H) 1.09 (d, J = 6.06 Hz, 3H) 0.89 (t, J = 7.33 Hz, 3H).

calcd. for $C_{23}H_{24}N_4O_2$ $(M + H)^+$ 389.1972, found 389.1977.

26-F b) (+) and (−)-2-(1-hydroxy-1-(5-isopropoxy-7-methyl-1H-indol-4-yl)propyl)-1H-benzo[d]imidazole-5-carbonitrile Resolution of the enantiomers of 2-(1-hydroxy-1-(5-isopropoxy-7-methyl-1H-indol-4-yl)propyl)-1H-benzo[d]imidazole-5-carbonitrile was achieved by chiral HPLC using a CHIRALCEL ® OD column with 30% EtOH (0.2% DEA) in heptane to give (−)-2-(1-hydroxy-1-(5-isopropoxy-7-methyl-1H-indol-4-yl)propyl)-1H-benzo[d]imidazole-5-carbonitrile ($t_r$ = 3.59 min) and (+)-2-(1-hydroxy-1-(5-isopropoxy-7-methyl-1H-indol-4-yl)propyl)-1H-benzo[d]imidazole-5-carbonitrile ($t_r$ = 6.46 min).

| Structure/Chemical Name | $^1$H NMR | HRMS |
|---|---|---|
| 26-G a) structure (±)-2-(1-(5-cyclopropylmethoxy)-7-methyl-1H-indol-4-yl)-1-hydroxyethyl)-1H-benzo[d]imidazole-5-carbonitrile | (400 MHz, DICHLOROMETHANE-$d_2$) δ ppm 8.08 (br. s., 1H) 7.75 (s, 1H) 7.42-7.55 (m, 1H) 7.27-7.43 (m, 1H) 7.00 (t, J = 2.91 Hz, 1H) 6.60 (s, 1H) 6.15 (dd, J = 3.28, 2.02 Hz, 1H) 6.02 (br. s., 1H) 3.75 (dd, J = 9.85, 7.33 Hz, 1H) 3.61 (dd, J = 9.85, 7.33 Hz, 1H) 2.34 (s, 3H) 2.12 (s, 3H) 0.85-1.05 (m, 1H) 0.39 (dd, J = 5.81, 2.02 Hz, 2H)-0.16-0.18 (m, 2H). | calcd. for $C_{23}H_{22}N_4O_2$ $(M + H)^+$ 387.1816, found 387.1823. |
| 26-G b) | (+) and (−)-2-(1-(5-(cyclopropylmethoxy)-7-methyl-1H-indol-4-yl)-1-hydroxyethyl)-1H-benzo[d]imidazole-5-carbonitrile Resolution of the enantiomers of 2-(1-(5-(cyclopropylmethoxy)-7-methyl-1H-indol-4-yl)-1-hydroxyethyl)-1H-benzo[d]imidazole-5-carbonitrile was achieved by chiral SFC using a CHIRALCEL ® OD-H column with 35% MeOH in $CO_2$ to give (−)-2-(1-(5-(cyclopropylmethoxy)-7-methyl-1H-indol-4-yl)-1-hydroxyethyl)-1H-benzo[d]imidazole-5-carbonitrile ($t_r$ = 2.3 min) and (+)-2-(1-(5-(cyclopropylmethoxy)-7-methyl-1H-indol-4-yl)-1-hydroxyethyl)-1H-benzo[d]imidazole-5-carbonitrile ($t_r$ = 3.9 min). | |

Example 27

Example 27-A (±)-tert-Butyl 4-(1-(5-cyano-1-((2-(trimethylsilyl)ethoxy)methyl)-1H-benzo[d]imidazol-2-yl)-1-methoxyethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-methoxyethyl)-5-methoxy-7-methyl-1H-indole-1-carboxylate

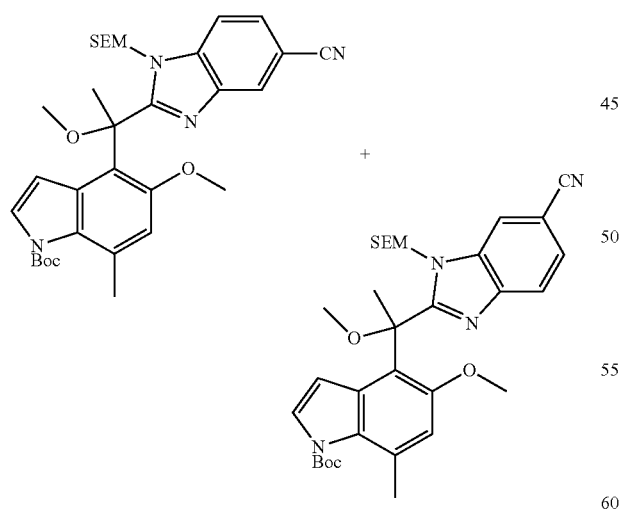

To a solution of a mixture of (±)-tert-butyl 4-(1-(5-cyano-1-((2-(trimethylsilyl)ethoxy)methyl)-1H-benzo[d]imidazol-2-yl)-1-hydroxy ethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-hydroxyethyl)-5-methoxy-7-methyl-1H-indole-1-carboxylate (Example 26-A) (0.82 g, 1.42 mmol) in DMF (14.22 mL) was added NaH (60%, 0.074 g, 1.85 mmol) at 0° C. The ice bath was removed and the reaction was allowed to stir at room temperature for 10 minutes. The reaction was then placed back in the ice bath and MeI (0.116 mL, 1.85 mmol) was added. After 10 minutes, additional NaH (60%, 50 mg) and MeI (0.1 mL) were added and the ice bath was removed. After 15 minutes the reaction mixture was quenched with 15 mL of a saturated solution of aq. ammonium chloride and then diluted with ethyl acetate. The layers were separated and the organic layer was removed and washed with water. The organic extract was then dried over magnesium sulfate, filtered and concentrated. The resulting residue was purified by flash chromatography (0-40% ethyl acetate in heptanes) to provide the mixture of title compounds. MS (ESI+) m/z 591.52 (M+H).

Example 27-B a) (±)-2-(1-Methoxy-1-(5-methoxy-7-methyl-1H-indol-4-yl)ethyl)-1H-benzo[d]imidazole-5-carbonitrile

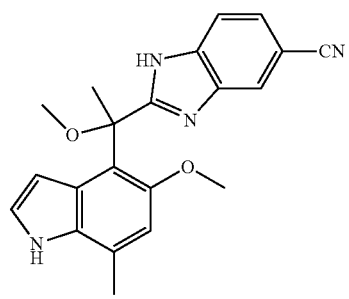 [SMILES: COc1cc(C)c2[nH]ccc2c1C(C)(OC)c1nc2cc(C#N)ccc2[nH]1]

To a mixture of (±)-tert-butyl 4-(1-(5-cyano-1-((2-(trimethylsilyl)ethoxy)methyl)-1H-benzo[d]imidazol-2-yl)-1- methoxy ethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-methoxyethyl)-5-methoxy-7-methyl-1H-indole-1-carboxylate (0.494 g, 0.836 mmol) in tetrahydrofuran (8.36 mL) was added TBAF (1M in THF, 8.36 mL, 8.36 mmol) and ethylenediamine (0.28 mL, 4.18 mmol). The reaction was heated at 65° C. for 26 hours. The reaction was cooled to room temperature and treated with 10 mL of a saturated solution of aq. ammonium chloride and then diluted with ethyl acetate. The layers were separated and the organic layer was washed with water (3×100 mL), dried over magnesium sulfate and concentrated. The resulting residue was dissolved in MeOH and cesium carbonate (1.38 g, 4.25 mmol) was added and the reaction was heated at 60° C. for 1.5 hours. The reaction was cooled to room temperature, diluted with EtOAc and then washed with a saturated solution of aq. ammonium chloride. The organic extract was dried over magnesium sulfate, filtered and concentrated. The resulting residues was purified by flash chromatography (0-10% MeOH in DCM) to provide the title compound. $^1$H NMR (400 MHz, DMSO-$d_6$ with about 5 μL TFA) δ ppm 11.14 (br. s., 1H) 8.23 (s, 1H) 7.66-8.01 (m, 2H) 7.39 (t, J=2.91 Hz, 1H) 6.48-6.88 (m, 2H) 3.28 (s, 3H) 3.17 (s, 3H) 2.48 (s, 3H) 2.13 (s, 3H). HRMS calcd. for $C_{21}H_{20}N_4O_2$ (M+H)$^+$ 361.1659. found 361.1675.

b) (+) and (−)-2-(1-methoxy-1-(5-methoxy-7-methyl-1H-indol-4-yl)ethyl)-1H-benzo[d]imidazole-5-carbonitrile Resolution of the enantiomers of 2-(1-methoxy-1-(5-methoxy-7-methyl-1H-indol-4-yl)ethyl)-1H-benzo[d]imidazole-5-carbonitrile was achieved by chiral SFC using a CHIRALPAK® AD-H column with 25% MeOH in $CO_2$ to give (−)-2-(1-methoxy-1-(5-methoxy-7-methyl-1H-indol-4-yl)ethyl)-1H-benzo[d]imidazole-5-carbonitrile ($t_r$=0.93 min) and (+)-2-(1-methoxy-1-(5-methoxy-7-methyl-1H-indol-4-yl)ethyl)-1H-benzo[d]imidazole-5-carbonitrile ($t_r$=1.58 min).

The following compounds were prepared with similar method.

| | Structure/Chemical Name | $^1$H NMR | HRMS |
|---|---|---|---|
| 27-C | (±)-2-(1-(5-isopropoxy-7-methyl-1H-indol-4-yl)-1-methoxyethyl)-1H-benzo[d]imidazole-5-carbonitrile | NMR (600 MHz, DMSO-$d_6$) δ ppm 12.39 (br. s., 1H) 10.84 (br. s., 1H) 8.12 (s) 7.70-7.81 (m) 7.42-7.56 (m) 7.25 (t, J = 2.80 Hz, 1H) 6.76 (d, J = 1.74 Hz, 1H) 6.61 (s, 1H) 4.32 (d, J = 5.96 Hz, 1H) 3.05 (s, 3H) 2.43 (s, 3H) 1.99 (s, 3H) 0.67-0.80 (m, 3H) 0.42-0.53 (m, 3H). | calcd. for $C_{23}H_{24}N_4O_2$ (M + H)$^+$ 389.1972, found 389.1972. |
| 27-D a) | (±)-2-(cyclopropyl(methoxy)(5-methoxy-7-methyl-1H-indol-4-yl)methyl)-1H-benzo[d]imidazole-5-carbonitrile | $^1$H NMR (400 MHz, DMSO-$d_6$) δ ppm 12.36 (d, J = 4.80 Hz, 1H) 10.89 (br. s., 1H) 8.11 (s) 7.95 (s) 7.68-7.83 (m) 7.41-7.57 (m) 7.18-7.33 (m, 1H) 6.70-6.82 (m, 1H) 6.66 (s, 1H) 3.11 (br. s., 3H) 3.07 (s, 3H) 2.45 (s, 3H) 2.20-2.31 (m, 1H) 0.52 (dd, J = 8.46, 1.64 Hz, 2H) 0.36-0.46 (m, 1H) 0.06-0.17 (m, 1H). | calcd. for $C_{23}H_{22}N_4O_2$ (M + H)$^+$ 387.1821, found 387.1815 |

27-D b) (+) and (−)-2-(cyclopropyl(methoxy)(5-methoxy-7-methyl-1H-indol-4-yl)methyl)-1H-benzo[d]imidazole-5-carbonitrile Resolution of the enantiomers of 2-(cyclopropyl(methoxy)(5-methoxy-7-methyl-1H-indol-4-yl)methyl)-1H-benzo[d]imidazole-5-carbonitrile was achieved by chiral HPLC, using a CHIRALCEL ® OD column with 20% EtOH (0.2% DEA) in heptanes to give (−)-2-(cyclopropyl(methoxy)(5-methoxy-7-methyl-1H-indol-4-yl)methyl)-1H-benzo[d]imidazole-5-carbonitrile ($t_r$ = 10.48 min) and (+)-2-(cyclopropyl(methoxy)(5-methoxy-7-methyl-1H-indol-4-yl)methyl)-1H-benzo[d]imidazole-5-carbonitrile ($t_r$ = 22.28 min).

| Structure/Chemical Name | $^1$H NMR | HRMS |
|---|---|---|
| 27-E a) 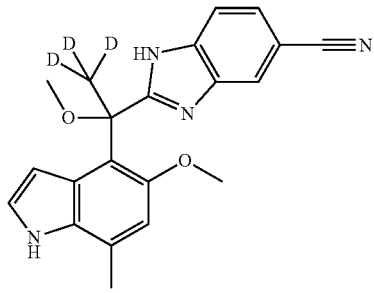<br><br>(±)-2-(($^2$H$_3$)methyl(methoxy)(5-methoxy-7-methyl-1H-indol-4-yl)methyl)-1H-benzo[d]imidazole-5-carbonitrile | (400 MHz, DMSO-d$_6$) δ ppm 12.23-12.62 (m, 1H) 10.89 (br. s., 1H) 8.10 (s) 7.64-7.87 (m) 7.41-7.57 (m) 7.26 (t, J = 2.84 Hz, 1H) 6.60-6.83 (m, 2H) 3.21-3.25 (m, 3H) 3.03-3.09 (m, 3H) 2.44 (s, 3H) | calcd. for C$_{21}$H$_{17}$D$_3$N$_4$O$_2$ (M + H)$^+$ 364.1848, found 364.1858 |
| 27-E b) | (+) and (−)-2-(($^2$H$_3$)methyl(methoxy)(5-methoxy-7-methyl-1H-indol-4-yl)methyl)-1H-benzo[d]imidazole-5-carbonitrile<br>Resolution of the enantiomers of 2-(($^2$H$_3$)methyl(methoxy)(5-methoxy-7-methyl-1H-indol-4-yl)methyl)-1H-benzo[d]imidazole-5-carbonitrile was achieved by chiral HPLC, using a CHIRALCEL ® OD column with 20% EtOH (0.2% DEA) in heptanes to give (+)-2-(($^2$H$_3$)methyl(methoxy)(5-methoxy-7-methyl-1H-indol-4-yl)methyl)-1H-benzo[d]imidazole-5-carbonitrile (t$_r$ = 6.96 min) and (−)-2-(($^2$H$_3$)methyl(methoxy)(5-methoxy-7-methyl-1H-indol-4-yl)methyl)-1H-benzo[d]imidazole-5-carbonitrile (t$_r$ = 11.52 min). | |
| 27-F a) 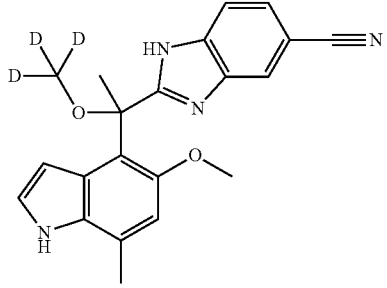<br><br>(±)-2-(1-($^2$H$_3$)methoxy-1-(5-methoxy-7-methyl-1H-indol-4-yl)ethyl)-1H-benzo[d]imidazole-5-carbonitrile | (400 MHz, DMSO-d$_6$) δ ppm 12.48 (s, 1H) 10.89 (s, 1H) 8.10 (s) 7.66-7.85 (m) 7.39-7.57 (m) 7.26 (t, J = 2.84 Hz, 1H) 6.58-6.78 (m, 2H) 3.20-3.24 (m, 3H) 2.44 (s, 3H) 1.97-2.04 (m, 3H) | calcd. for C$_{21}$H$_{17}$D$_3$N$_4$O$_2$ (M + H)$^+$ 364.1848, found 364.1847 |
| 27-F b) | (+) and (−)-2-(1-($^2$H$_3$)methoxy-1-(5-methoxy-7-methyl-1H-indol-4-yl)ethyl)-1H-benzo[d]imidazole-5-carbonitrile<br>Resolution of the enantiomers of 2-(1-($^2$H$_3$)methoxy-1-(5-methoxy-7-methyl-1H-indol-4-yl)ethyl)-1H-benzo[d]imidazole-5-carbonitrile was achieved by chiral SFC using a CHIRALPAK ® AD-H column with 17% MeOH in CO$_2$ to give (−)-2-(1-($^2$H$_3$)methoxy-1-(5-methoxy-7-methyl-1H-indol-4-yl)ethyl)-1H-benzo[d]imidazole-5-carbonitrile (t$_r$ = 5.5 min) and (+)-2-(1-($^2$H$_3$)methoxy-1-(5-methoxy-7-methyl-1H-indol-4-yl)ethyl)-1H-benzo[d]imidazole-5-carbonitrile (t$_r$ = 7.6 min). | |

Example 28

Example 28-A (±)-2-(Hydroxy(5-methoxy-7-methyl-1H-indol-4-yl)methyl)-1-((2-(trimethylsilyl)ethoxy)methyl)-1H-benzo[d]imidazole-5-carbonitrile and (±)-2-(hydroxy(5-methoxy-7-methyl-1H-indol-4-yl)methyl)-1-((2-(trimethylsilyl)ethoxy)methyl)-1H-benzo[d]imidazole-6-carbonitrile

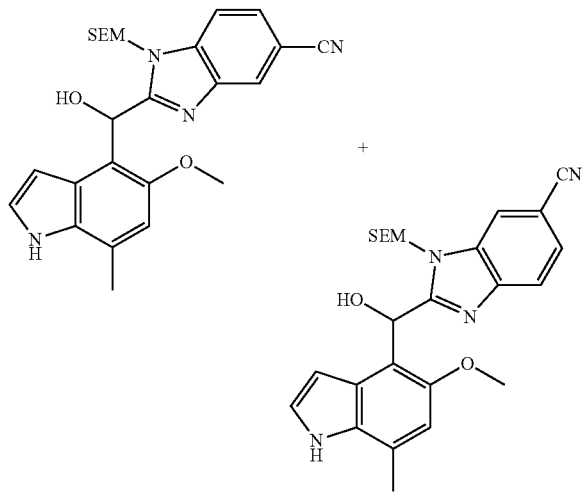

A mixture of (±)-tert-butyl 4-((5-cyano-1-((2-(trimethylsilyl)ethoxy)methyl)-1H-benzo[d]imidazol-2-yl)(hydroxy)methyl)-5-methoxy-7-methyl-1H-indole-1-carboxylate and (±)-tert-butyl 4-((6-cyano-1-((2-(trimethylsilyl)ethoxy)methyl)-1H-benzo[d]imidazol-2-yl)(hydroxy)methyl)-5-methoxy-7-methyl-1H-indole-1-carboxylate (Example 24-A) (1.01 g, 1.80 mmol) was dissolved in MeOH (9 mL) and then Cs₂CO₃ (2.94 g, 9.01 mmol) was added and the reaction was heated at 60° C. for 1 hour. The reaction was cooled to room temperature and then diluted with a saturated aq. solution of ammonium chloride, diluted with EtOAc and then washed with water. The organic extract was dried over magnesium sulfate, filtered, concentrated, and absorbed onto silica and purified by flash chromatography (0-10% MeOH in DCM) to provide the mixture of title compounds. MS (ESI+) m/z 463.41 (M+H).

Example 28-B (±)-2-((3-Chloro-5-methoxy-7-methyl-1H-indol-4-yl)(hydroxy)methyl)-1-((2-(trimethylsilyl)ethoxy)methyl)-1H-benzo[d]imidazole-5-carbonitrile and (±)-2-((3-chloro-5-methoxy-7-methyl-1H-indol-4-yl)(hydroxy)methyl)-1-((2-(trimethylsilyl)ethoxy)methyl)-1H-benzo[d]imidazole-6-carbonitrile

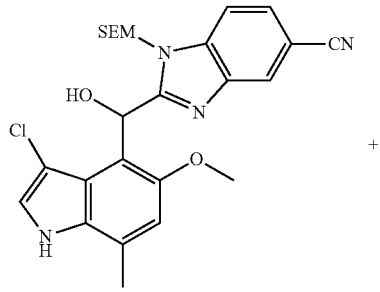

+

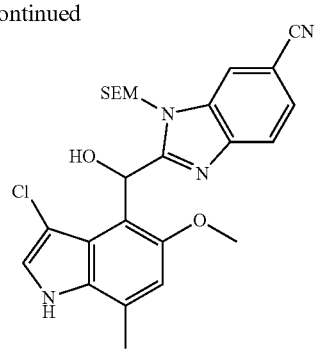

A mixture of (±)-2-(hydroxy(5-methoxy-7-methyl-1H-indol-4-yl)methyl)-1-((2-(trimethylsilyl)ethoxy)methyl)-1H-benzo[d]imidazole-5-carbonitrile and (±)-2-(hydroxy(5-methoxy-7-methyl-1H-indol-4-yl)methyl)-1-((2-(trimethylsilyl)ethoxy)methyl)-1H-benzo[d]imidazole-6-carbonitrile (0.67 g, 1.448 mmol) was dissolved in DMF (14.48 mL), and cooled to −15° C. NCS (0.24 g, 1.74 mmol) was then added. The ice bath was removed and the reaction was stirred for 2 hours at room temperature. The reaction was quenched with a saturated aq. solution of sodium thiosulfate and extracted with ethyl acetate. The organics layers were combined, dried over magnesium sulfate, filtered, concentrated and purified by flash chromatography (0-60% Ethyl acetate in heptanes) to provide the title compounds as a mixture. MS (ESI+) m/z 497.3 (M+H).

Example 28-C a) (±)-2-((3-Chloro-5-methoxy-7-methyl-1H-indol-4-yl)(hydroxy)methyl)-1H-benzo[d]imidazole-5-carbonitrile

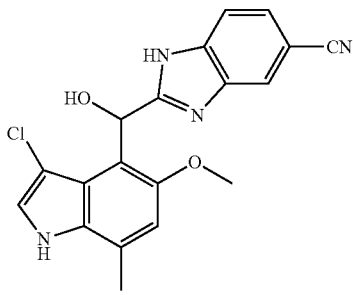 [SMILES: COc1cc(C)c2[nH]cc(Cl)c2c1C(O)c1nc2cc(C#N)ccc2[nH]1]

A mixture of (±)-2-((3-chloro-5-methoxy-7-methyl-1H-indol-4-yl)(hydroxy)methyl)-1-((2-(trimethylsilyl)ethoxy)methyl)-1H-benzo[d]imidazole-5-carbonitrile and (±)-2-((3-chloro-5-methoxy-7-methyl-1H-indol-4-yl)(hydroxy)methyl)-1-((2-(trimethylsilyl)ethoxy)methyl)-1H-benzo[d]imidazole-6-carbonitrile (0.2 g, 0.402 mmol) was dissolved in THF (4.02 mL) and treated with TBAF (1M in THF, 4.02 mL, 4.02 mmol) and ethylenediamine (0.272 mL, 4.02 mmol) and heated at 60° C. The reaction was cooled to room temperature, and treated with 10 mL of a saturated aq. solution of ammonium chloride and then diluted with EtOAc. The layers were separated and the organic layer was washed with water (3×100 mL). The organic extracts were combined, dried over magnesium sulfate, filtered and concentrated. The resulting residue was purified via FCC (0-100% EtOAc in heptanes) to obtain the title compound. ¹H NMR (400 MHz, DMSO-d₆) δ ppm 12.71 (d, J=6.57 Hz, 1H) 11.28 (br. s., 1H) 7.87 (d, J=6.19 Hz, 1H) 7.61 (m) 7.40-7.50 (m, 2H) 6.94-7.12 (m, 1H) 6.79 (s, 1H) 6.02-6.20 (m, 1H) 3.42-3.50 (m, 3H) 2.45 (s, 3H). HRMS calcd. for $C_{19}H_{16}ClN_4O_2$ (M+H)$^+$ 367.0957. found 367.096.

b) (+) and (−)-2-((3-chloro-5-methoxy-7-methyl-1H-indol-4-yl)(hydroxy)methyl)-1H-benzo[d]imidazole-6-carbonitrile Resolution of the enantiomers of 2-((3-chloro-5-methoxy-7-methyl-1H-indol-4-yl)(hydroxy)methyl)-1H-benzo[d]imidazole-6-carbonitrile is achieved by chiral SFC using a CHIRALPAK® AD-H column with 35% MeOH in $CO_2$ to give (+)-2-((3-chloro-5-methoxy-7-methyl-1H-indol-4-yl)(hydroxy)methyl)-1H-benzo[d]imidazole-5-carbonitrile ($t_r$=1.8 min) and (−)-2-((3-chloro-5-methoxy-7-methyl-1H-indol-4-yl)(hydroxy)methyl)-1H-benzo[d]imidazole-5-carbonitrile ($t_r$=2.5 min).

Example 29

Example 29-A (−) or (+)-2-(1-(3-Chloro-5-methoxy-7-methyl-1H-indol-4-yl)-1-hydroxyethyl)-1H-benzo[d]imidazole-5-carbonitrile

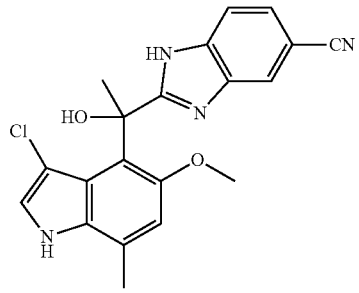 [SMILES: COc1cc(C)c2[nH]cc(Cl)c2c1C(C)(O)c1nc2cc(C#N)ccc2[nH]1]

To a solution of (−)-2-(1-hydroxy-1-(5-methoxy-7-methyl-1H-indol-4-yl)ethyl)-1H-benzo[d]imidazole-5-carbonitrile (Example 26-C) (20 mg, 0.058 mmol) in DMF (0.58 mL) was added NCS (14 mg, 0.1 mmol) at 0° C. The reaction was stirred in the ice bath for 1 hour. At this point, the reaction was quenched with a saturated solution of aq. $Na_2S_2O_3$ at 0° C., and then the mixture was extracted with EtOAc and then the EtOAc layer was dried, concentrated, absorbed onto silica and purified by flash column chromatography (0-100% EtOAc in heptanes) to provide the title compound. $^1$H NMR (400 MHz, DMSO-$d_6$) δ ppm 12.18-12.43 (m, 1H) 11.29 (br. s., 1H) 8.06 (s) 7.65-7.79 (m) 7.45-7.52 (m) 7.43 (d, J=3.03 Hz, 1H) 6.72 (s, 1H) 5.78-6.09 (m, 1H) 3.16 (s, 3H) 2.42 (s, 3H) 2.15 (s, 3H). HRMS calcd. for $C_{20}H_{17}ClN_4O_2$ (M+H)$^+$ 381.1113. found 381.1123.

Example 29-B (+) or (−)-2-(1-(3-chloro-5-methoxy-7-methyl-1H-indol-4-yl)-1-hydroxyethyl)-1H-benzo[d]imidazole-5-carbonitrile

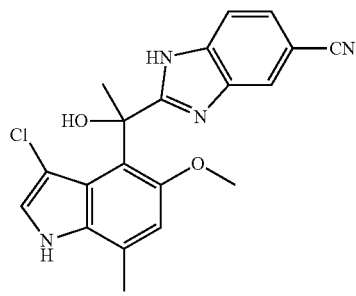 [SMILES: COc1cc(C)c2[nH]cc(Cl)c2c1C(C)(O)c1nc2cc(C#N)ccc2[nH]1]

The title compound was synthesized from (+)-2-(1-hydroxy-1-(5-methoxy-7-methyl-1H-indol-4-yl)ethyl)-1H-benzo[d]imidazole-5-carbonitrile (Example 26-C) in the same manner as described in Example 29-A. $^1$H NMR (400 MHz, DMSO-$d_6$) δ ppm 12.12-12.46 (m, 1H) 11.29 (br. s., 1H) 8.06 (s) 7.62-7.85 (m) 7.25-7.56 (m, 2H) 6.72 (s, 1H) 5.87-6.05 (m, 1H) 3.16 (s, 3H) 2.42 (s, 3H) 2.15 (s, 3H). HRMS calcd. for $C_{20}H_{17}ClN_4O_2$ (M+H)$^+$ 381.1113. found 381.1127.

Example 30

Example 30-A (±)-tert-Butyl 4-((5-cyano-1-((2-(trimethylsilyl)ethoxy)methyl)-1H-benzo[d]imidazol-2-yl)(methoxy)methyl)-5-methoxy-7-methyl-1H-indole-1-carboxylate and (±)-tert-butyl 4-((6-cyano-1-((2-(trimethylsilyl)ethoxy)methyl)-1H-benzo[d]imidazol-2-yl)(methoxy)methyl)-5-methoxy-7-methyl-1H-indole-1-carboxylate To a solution of a mixture of (±)-tert-butyl 4-((5-cyano-1-((2-(trimethylsilyl)ethoxy)methyl)-1H-benzo[d]imidazol-2-yl)(hydroxy)methyl)-5-methoxy-7-methyl-1H-indole-1-carboxylate and (±)-tert-butyl 4-((6-cyano-1-((2-(trimethylsilyl) ethoxy)methyl)-1H-benzo[d]imidazol-2-yl)(hydroxy) methyl)-5-methoxy-7-methyl-1H-indole-1-carboxylate (Example 24-A) (498 mg, 0.885 mmol) in DMF (2.5 mL) at 0° C. was added successively MeI (0.17 mL, 2.65 mmol) and NaH (60%, 53.1 mg, 1.32 mmol). The reaction mixture was stirred at 0° C. for 20 min. At this point, the reaction was quenched with a saturated aq. solution of NH$_4$Cl, then diluted with water and extracted with EtOAc. The layers were separated and the aqueous layer was extracted with EtOAc. The combined organic layers were dried over Na$_2$SO$_4$, filtered, concentrated and absorbed onto silica and purified by flash column chromatography (0-30% heptane in ethyl acetate) to provide a mixture of title compounds. MS (ESI+) m/z 577.37 (M+H).

Example 30-B (±)-2-(Methoxy(5-methoxy-7-methyl-1H-indol-4-yl) methyl)-1H-benzo[d]imidazole-5-carbonitrile

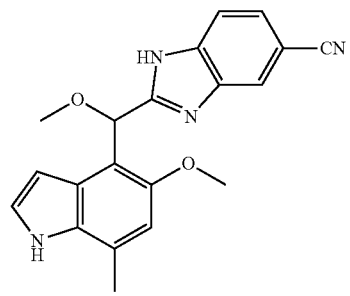 [SMILES: COc1cc(C)c2[nH]ccc2c1C(OC)c1nc2cc(C#N)ccc2[nH]1]

The title compound was synthesized from a mixture of (±)-tert-butyl 4-((5-cyano-1-((2-(trimethylsilyl)ethoxy)methyl)-1H-benzo[d]imidazol-2-yl)(methoxy)methyl)-5-methoxy-7-methyl-1H-indole-1-carboxylate and (±)-tert-butyl 4-((6-cyano-1-((2-(trimethylsilyl)ethoxy)methyl)-1H-benzo [d]imidazol-2-yl)methoxy)methyl)-5-methoxy-7-methyl-1H-indole-1-carboxylate as described in Example 24-B. $^1$H NMR (400 MHz, DMSO-d$_6$) δ ppm 12.91 (d, J=6.57 Hz, 1H) 10.92 (br. s., 1H) 7.91-7.97 (m) 7.88 (m) 7.55-7.66 (m, 1H) 7.42-7.54 (m, 1H) 7.18 (t, J=2.72 Hz, 1H) 6.78 (s, 1H) 6.24-6.30 (m, 2H) 3.80 (s, 3H) 3.33 (s, 3H) 2.46 (s, 3H). HRMS calcd. for C$_{20}$H$_{18}$N$_4$O$_2$ (M+H)$^+$ 347.1429. found 347.1516.

b) (+) and (−)-2-(methoxy(5-methoxy-7-methyl-1H-indol-4-yl)methyl)-1H-benzo[d]imidazole-5-carbonitrile Resolution of the enantiomers of 2-(methoxy(5-methoxy-7-methyl-1H-indol-4-yl)methyl)-1H-benzo[d]imidazole-5-carbonitrile was achieved by chiral SFC using a CHIRALPAK® AS-H column with 20% IPA (0.1% DEA) in CO$_2$ to give (+)-2-(methoxy(5-methoxy-7-methyl-1H-indol-4-yl) methyl)-1H-benzo[d]imidazole-5-carbonitrile (t$_r$=2.9 min) and (−)-2-(methoxy(5-methoxy-7-methyl-1H-indol-4-yl) methyl)-1H-benzo[d]imidazole-5-carbonitrile (t$_r$=6.0 min).

Example 31

Example 31-A (±)-tert-Butyl 4-(1-(5-cyano-1-((2-(trimethylsilyl) ethoxy)methyl)-1H-benzo[d]imidazol-2-yl)-1-hydroxyethyl)-5-hydroxy-7-methyl-1H-indole-1-carboxylate and (±)-tert-butyl 4-(1-(6-cyano-1-((2-(trimethylsilyl)ethoxy)methyl)-1H-benzo[d] imidazol-2-yl)-1-hydroxyethyl)-5-hydroxy-7-methyl-1H-indole-1-carboxylate

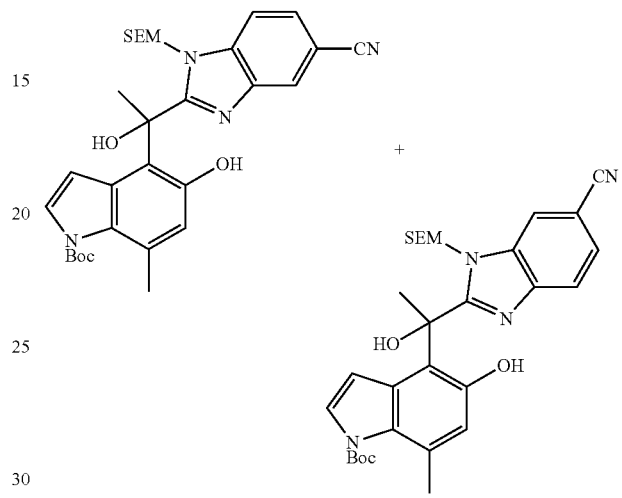

To a mixture of (±)-tert-butyl 5-(benzyloxy)-4-(1-(5-cyano-1-((2-(trimethylsilyl)ethoxy)methyl)-1H-benzo[d]imidazol-2-yl)-1-hydroxyethyl)-7-methyl-1H-indole-1-carboxylate and (±)-tert-butyl 5-(benzyloxy)-4-(1-(6-cyano-1-((2-(trimethylsilyl)ethoxy)methyl)-1H-benzo[d]imidazol-2-yl)-1-hydroxyethyl)-7-methyl-1H-indole-1-carboxylate (Example 26-B) (910 mg, 1.39 mmol) in THF (14 mL) was added Pd/C (10%, 222 mg), degassed twice with nitrogen and vacuum, and then stirred under hydrogen atmosphere overnight. The reaction was filtered, and rinsed with EtOAc, The volatiles were removed in vacuo to provide the title compounds as a mixture. MS (ESI+) m/z 563.0 (M+H).

Example 31-B (±)-tert-Butyl 5-(2-amino-2-oxoethoxy)-4-(1-(5-cyano-1-((2-(trimethylsilyl)ethoxy)methyl)-1H-benzo[d]imidazol-2-yl)-1-hydroxyethyl)-7-methyl-1H-indole-1-carboxylate and (±)-tert-butyl 5-(2-amino-2-oxoethoxy)-4-(1-(6-cyano-1-((2-(trimethylsilyl)ethoxy)methyl)-1H-benzo[d] imidazol-2-yl)-1-hydroxyethyl)-7-methyl-1H-indole-1-carboxylate

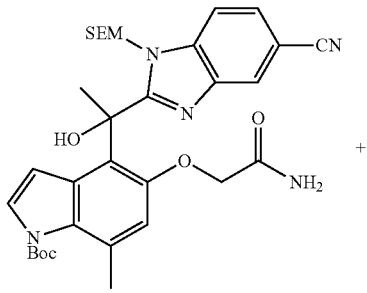

-continued

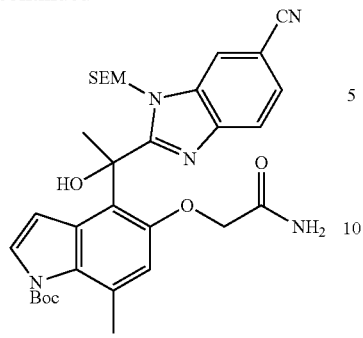

To a mixture of (±)-tert-butyl 4-(1-(5-cyano-1-((2-(trimethylsilyl)ethoxy)methyl)-1H-benzo[d]imidazol-2-yl)-1-hydroxyethyl)-5-hydroxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-hydroxyethyl)-5-hydroxy-7-methyl-1H-indole-1-carboxylate (43.2 mg, 0.313 mmol), was added 2-bromoacetamide (43.2 mg, 0.313 mmol) in $CH_3CN$ (2.9 mL) followed by $Cs_2CO_3$ (114 mg, 0.35 mmol). The reaction was stirred at 70° C. for 4 hours. The solid was filtered, and washed with EtOAc. The organics were concentrated and purified with FCC eluting with heptane/EtOAc (1:0 to 0:1) to provide a mixture of title compounds. MS (ESI+) m/z 620.2 (M+H).

Example 31-C (±)-2-((4-(1-(5-Cyano-1H-benzo[d]imidazol-2-yl)-1-hydroxyethyl)-7-methyl-1H-indol-5-yl)oxy)acetamide

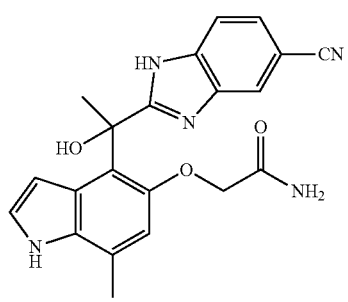 [SMILES: Cc1cc(OCC(N)=O)c(C(C)(O)c2nc3cc(C#N)ccc3[nH]2)c2cc[nH]c12]

The title compound was synthesized from a mixture of (±)-tert-butyl 5-(2-amino-2-oxoethoxy)-4-(1-(5-cyano-1-((2-(trimethylsilyl)ethoxy)methyl)-1H-benzo[d]imidazol-2-yl)-1-hydroxyethyl)-7-methyl-1H-indole-1-carboxylate and (±)-tert-butyl 5-(2-amino-2-oxoethoxy)-4-(1-(6-cyano-1-((2-(trimethylsilyl)ethoxy)methyl)-1H-benzo[d]imidazol-2-yl)-1-hydroxyethyl)-7-methyl-1H-indole-1-carboxylate as described in Example 24-B. $^1$H NMR (TFA salt, 400 MHz, MeOH-$d_4$) δ ppm 8.04 (s, 1H) 7.63-7.85 (m, 2H) 7.31 (d, J=3.28 Hz, 1H) 7.01 (d, J=3.28 Hz, 1H) 6.69 (s, 1H) 4.37-4.49 (m, 1H) 4.24-4.35 (m, 1H) 2.49 (s, 3H) 2.31 (s, 3H). HRMS calcd. for $C_{21}H_{19}N_5O_3$ (M+H)$^+$ 390.1561. found 390.1561.

Example 32

Example 32-A (±)-tert-Butyl 4-(1-(5-cyano-1-((2-(trimethylsilyl)ethoxy)methyl)-1H-benzo[d]imidazol-2-yl)-1-hydroxyethyl)-5-(2-methoxy-2-oxoethoxy)-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-hydroxyethyl)-5-(2-methoxy-2-oxoethoxy)-7-methyl-1H-indole-1-carboxylate

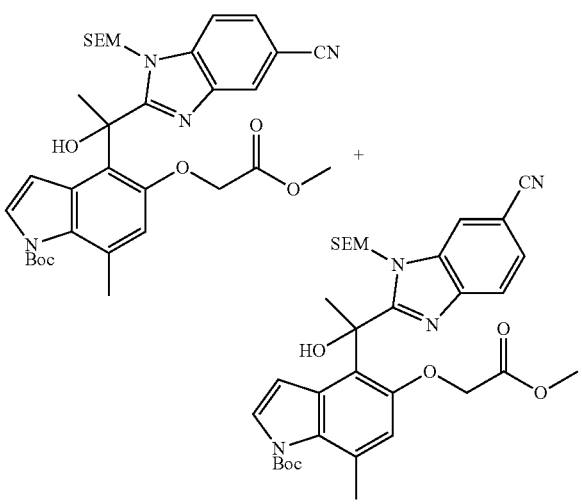

The title compounds were synthesized from a mixture of (±)-tert-butyl 4-(1-(5-cyano-1-((2-(trimethylsilyl)ethoxy)methyl)-1H-benzo[d]imidazol-2-yl)-1-hydroxyethyl)-5-hydroxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-hydroxyethyl)-5-hydroxy-7-methyl-1H-indole-1-carboxylate as described in Example 31-B using methyl 2-bromoacetate as electrophile in place to 2-bromoacetamide. MS (ESI+) m/z 635.4 (M+H).

Example 32-B (±)-2-((4-(1-(5-Cyano-1H-benzo[d]imidazol-2-yl)-1-hydroxyethyl)-7-methyl-1H-indol-5-yl)oxy)acetic acid

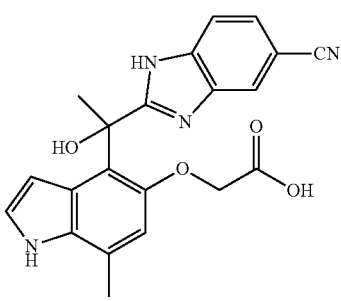

A mixture of (±)-tert-butyl 4-(1-(5-cyano-1-((2-(trimethylsilyl)ethoxy)methyl)-1H-benzo[d]imidazol-2-yl)-1-hydroxyethyl)-5-(2-methoxy-2-oxoethoxy)-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-hydroxyethyl)-5-(2-methoxy-2-oxoethoxy)-7-methyl-1H-indole-1-carboxylate was fully deprotected using the same procedure as described in Example 24-B to give the title compound. $^1$H NMR (TFA salt, 400 MHz, MeOH-$d_4$) δ ppm 8.06 (s, 1H) 7.79 (s, 2H) 7.31 (d, J=3.28 Hz, 1H) 6.92 (d, J=3.28 Hz, 1H) 6.70 (s, 1H) 4.49 (m, 2H) 2.50 (s, 3H) 2.30 (s, 3H). HRMS calcd. for $C_{21}H_{18}N_4O_4$ (M+H)$^+$ 391.1401. found 391.1394.

Example 33

Example 33-A (±)-tert-Butyl 4-(1-(5-cyano-1-((2-(trimethylsilyl)ethoxy)methyl)-1H-benzo[d]imidazol-2-yl)-2,2,2-trifluoro-1-hydroxyethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-2,2,2-trifluoro-1-hydroxyethyl)-5-methoxy-7-methyl-1H-indole-1-carboxylate

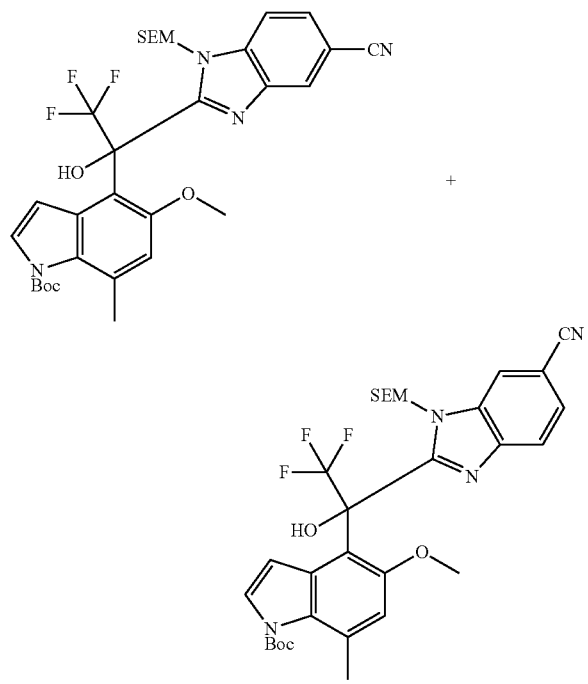

A mixture of tert-butyl 4-(5-cyano-1-((2-(trimethylsilyl)ethoxy)methyl)-1H-benzo[d]imidazole-2-carbonyl)-5-methoxy-7-methyl-1H-indole-1-carboxylate and tert-butyl 4-(6-cyano-1-((2-(trimethylsilyl)ethoxy)methyl)-1H-benzo[d]imidazole-2-carbonyl)-5-methoxy-7-methyl-1H-indole-1-carboxylate (Example 25-A) (1.30 g, 2.32 mmol) in THF (23 mL) at 0° C. was added trifluoromethyltrimethylsilane (3.62 mL, 23.18 mmol), followed by TBAF (1M in THF) (23.18 mL, 23.18 mmol). The reaction mixture was warmed to room temperature and stirred for 15 min. At this point the reaction mixture was cooled to 0° C. and diluted with water. The layers were separated and the aqueous layer was extracted with EtOAc. The organics extracts were combined, dried over $Na_2SO_4$, filtered, concentrated and purified by flash chromatography (0-50% ethyl acetate in heptane) to provide the mixture of title compounds. MS (ESI+) m/z 631.43 (M+H).

Example 33-B a) (±)-2-(2,2,2-Trifluoro-1-hydroxy-1-(5-methoxy-7-methyl-1H-indol-4-yl)ethyl)-1H-benzo[d]imidazole-5-carbonitrile

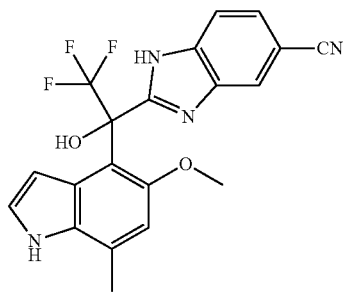 [SMILES: COc1cc(C)c2[nH]ccc2c1C(O)(c1nc2cc(C#N)ccc2[nH]1)C(F)(F)F]

A mixture of (±)-tert-butyl 4-(1-(5-cyano-1-((2-(trimethylsilyl)ethoxy)methyl)-1H-benzo[d]imidazol-2-yl)-2,2,2-trifluoro-1-hydroxyethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-2,2,2-trifluoro-1-hydroxyethyl)-5-methoxy-7-methyl-1H-indole-1-carboxylate (2.2 g, 3.49 mmol) was dissolved in 1.25 M HCl in MeOH (55.8 mL, 69.8 mmol) and heated at 60° C. for 17 hours. The reaction was cooled to room temperature and the solvent was removed in vacuo. The resulting residue was diluted with MeOH and basified by adding $NH_4OH$. The crude mixture was directly loaded onto a silica column and purified by flash chromatography (0-100% ethyl acetate in heptanes) to provide the title compound. $^1$H NMR (400 MHz, DMSO-$d_6$ with about 5 μL TFA) δ ppm 11.00 (br. s., 1H) 8.11 (s, 1H) 7.61-7.69 (m, 1H) 7.55-7.60 (m, 1H) 7.24 (t, J=2.84 Hz, 1H) 6.75 (s, 1H) 6.50 (br. s., 1H) 3.29 (s, 3H) 2.47 (d, J=0.51 Hz, 3H). HRMS calcd. for $C_{20}H_{16}F_3N_4O_2$ (M+H)$^+$ 401.122. found 401.1226.

b) (+) and (−)-2-(2,2,2-trifluoro-1-hydroxy-1-(5-methoxy-7-methyl-1H-indol-4-yl)ethyl)-1H-benzo[d]imidazole-5-carbonitrile Resolution of the enantiomers of 2-(2,2,2-trifluoro-1-hydroxy-1-(5-methoxy-7-methyl-1H-indol-4-yl)ethyl)-1H-benzo[d]imidazole-5-carbonitrile was achieved by chiral SFC using a CHIRALPAK® AD-H column with 20% MeOH in $CO_2$ to give (−)-2-(2,2,2-trifluoro-1-hydroxy-1-(5-methoxy-7-methyl-1H-indol-4-yl)ethyl)-1H-benzo[d]imidazole-5-carbonitrile ($t_r$=3.1 min) and (+)-2-(2,2,2-trifluoro-1-hydroxy-1-(5-methoxy-7-methyl-1H-indol-4-yl)ethyl)-1H-benzo[d]imidazole-5-carbonitrile ($t_r$=4.8 min).

The following compounds were prepared with similar method.

| Structure/Chemical Name | ¹H NMR | HRMS |
|---|---|---|
| 33-C a) 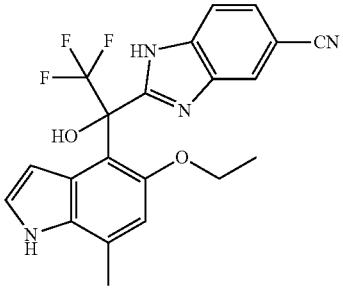<br>(±)-2-(1-(5-ethoxy-7-methyl-1H-indol-4-yl)-2,2,2-trifluoro-1-hydroxyethyl)-1H-benzo[d]imidazole-5-carbonitrile | (400 MHz, DMSO-d₆) δ 12.60-12.70 (m, 1H), 10.95 (br. s., 1H), 8.22-8.29 (m, 1H), 7.88 (m), 7.75-7.81 (m, 1H), 7.64 (s, 1H), 7.56 (dd, J = 1.52, 8.21 Hz, 1H), 7.48 (m), 7.24 (q, J = 2.65 Hz, 1H), 6.72 (s, 1H), 6.55-6.64 (m, 1H), 3.72-3.85 (m, 1H), 3.45-3.59 (m, 1H), 2.45 (s, 3H), 0.47-0.65 (m, 3H) | calcd. for C₂₁H₁₇F₃N₄O₂ (M + H)⁺ 415.1383, found 415.1377. |
| 33-C b) | (+) and (−)-2-(1-(5-ethoxy-7-methyl-1H-indol-4-yl)-2,2,2-trifluoro-1-hydroxyethyl)-1H-benzo[d]imidazole-5-carbonitrile<br>Resolution of the enantiomers of 2-(1-(5-ethoxy-7-methyl-1H-indol-4-yl)-2,2,2-trifluoro-1-hydroxyethyl)-1H-benzo[d]imidazole-5-carbonitrile was achieved by chiral SFC using a CHIRALPAK ® AD-H column with 20% methanol in CO₂ to give (−) or (+)-2-(1-(5-ethoxy-7-methyl-1H-indol-4-yl)-1-hydroxyethyl)-1H-benzo[d]imidazole-5-carbonitrile (t_r = 3 min) and (+) or (−)-2-(1-(5-ethoxy-7-methyl-1H-indol-4-yl)-1-hydroxyethyl)-1H-benzo[d]imidazole-5-carbonitrile (t_r = 5.1 min). | |
| 33-D 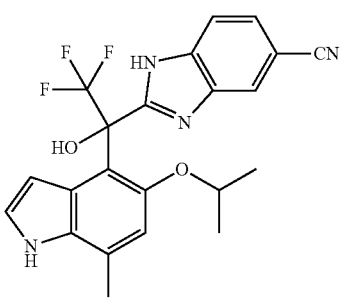<br>(±)-2-(2,2,2-trifluoro-1-hydroxy-1-(5-isopropoxy-7-methyl-1H-indol-4-yl)ethyl)-benzo[d]imidazole-5-carbonitrile | (TFA salt, 400 MHz, CD₃OD) δ ppm 8.05 (s, 1H), 7.73 (d, J = 8.46 Hz, 1H), 7.67 (app dd, J = 8.46, 1.26 Hz, 1H), 7.14 (m, 1H) 6.75 (s, 1H) 6.40 (d, J = 2.65 Hz, 1H) 4.56-4.64 (m, 1H) 2.51 (s, 3H) 1.06 (d, J = 6.06 Hz, 3H) 0.84 (d, J = 6.06 Hz, 3H). | calcd. for C₂₂H₁₉F₃N₄O₂ (M + H)⁺ 429.1533, found 429.1529. |

Example 34

Example 34-A (±)-tert-Butyl 4-(1-(5-cyano-1-((2-(trimethylsilyl)ethoxy)methyl)-1H-benzo[d]imidazol-2-yl)-2,2,2-trifluoro-1-methoxyethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-2,2,2-trifluoro-1-methoxyethyl)-5-methoxy-7-methyl-1H-indole-1-carboxylate

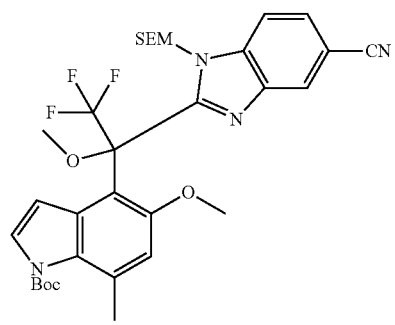

+

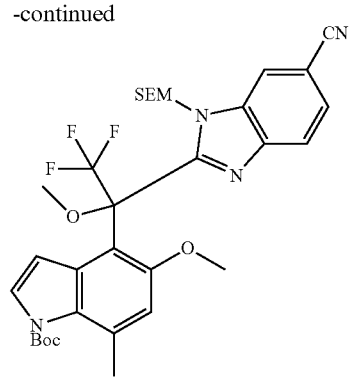

To a solution of (±)-tert-butyl 4-(1-(5-cyano-1-((2-(trimethylsilyl)ethoxy)methyl)-1H-benzo[d]imidazol-2-yl)-2,2,2-trifluoro-1-hydroxyethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-2,2,2-trifluoro-1-hydroxyethyl)-5-methoxy-7-methyl-1H-indole-1-carboxylate (100 mg, 0.159 mmol) in DMF (1.6 mL) was added successively MeI (0.3 mL, 4.8 mmol) and NaH (60%, 9.5 mg, 0.24 mmol) at 0° C. The reaction mixture was stirred at 0° C. for 15 min. At this point the reaction was quenched with 1.5 mL of a saturated aq. solution of NH₄Cl and extracted with EtOAc. The layers were separated and the organic layer was washed with water. The combined organic extracts were dried over Na₂SO₄, filtered and concentrated. The resulting residue was purified by flash chromatography (0-35% ethyl acetate in heptane) to provide the mixture of title compounds. MS (ESI+) m/z 645.44 (M+H).

Example 34-B a) (±)-2-(2,2,2-Trifluoro-1-methoxy-1-(5-methoxy-7-methyl-1H-indol-4-yl)ethyl)-1H-benzo[d]imidazole-5-carbonitrile

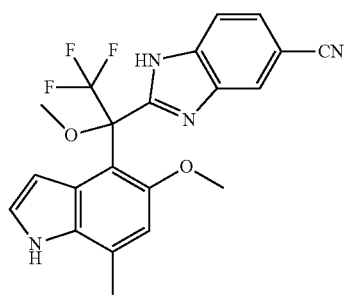 [SMILES: COc1cc(C)c2[nH]ccc2c1C(OC)(c1nc2cc(C#N)ccc2[nH]1)C(F)(F)F]

The title compound was synthesized from a mixture of (±)-tert-butyl 4-(1-(5-cyano-1-((2-(trimethylsilyl)ethoxy)methyl)-1H-benzo[d]imidazol-2-yl)-2,2,2-trifluoro-1-methoxyethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-2,2,2-trifluoro-1-methoxyethyl)-5-methoxy-7-methyl-1H-indole-1-carboxylate using the same procedure as described in Example 24-B. ¹H NMR (400 MHz, DMSO-d₆) δ ppm 12.76-13.01 (m, 1H) 11.06 (br. s., 1H) 8.27 (s) 7.82-7.92 (m) 7.50-7.66 (m, 2H) 7.36 (t, J=2.78 Hz, 1H) 6.65-6.79 (m, 2H) 3.19 (s, 3H) 3.10 (s, 3H). HRMS calcd. for $C_{21}H_{17}F_3N_4O_2$ (M+H)⁺ 415.1379. found 415.1376.

b) (+) and (−)-2-(2,2,2-trifluoro-1-methoxy-1-(5-methoxy-7-methyl-1H-indol-4-yl)ethyl)-1H-benzo[d]imidazole-5-carbonitrile Resolution of the enantiomers of 2-(2,2,2-trifluoro-1-methoxy-1-(5-methoxy-7-methyl-1H-indol-4-yl)ethyl)-1H-benzo[d]imidazole-5-carbonitrile was achieved by chiral SFC using a CHIRALPAK® AD-H column with 20% MeOH in CO₂ to give (−)-2-(2,2,2-trifluoro-1-methoxy-1-(5-methoxy-7-methyl-1H-indol-4-yl)ethyl)-1H-benzo[d]imidazole-5-carbonitrile ($t_r$=5.8 min) and (+)-2-(2,2,2-trifluoro-1-methoxy-1-(5-methoxy-7-methyl-1H-indol-4-yl)ethyl)-1H-benzo[d]imidazole-5-carbonitrile ($t_r$=7.5 min).

Example 35

Example 35-A (±)-tert-Butyl 4-(1-(5-cyano-1-((2-(trimethylsilyl)ethoxy)methyl)-1H-benzo[d]imidazol-2-yl)-2,2,2-trifluoro-1-(2-methoxy-2-oxoethoxy)ethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-2,2,2-trifluoro-1-(2-methoxy-2-oxoethoxy)ethyl)-5-methoxy-7-methyl-1H-indole-1-carboxylate

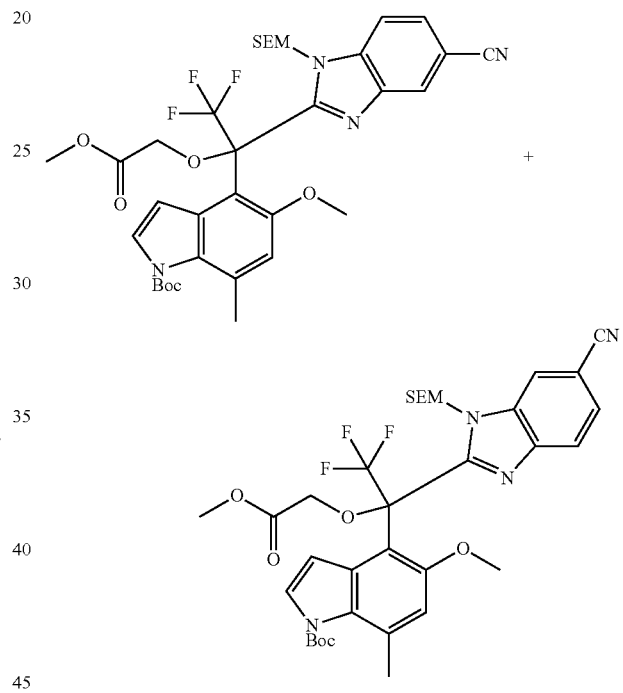

To a solution of a mixture of (±)-tert-butyl 4-(1-(5-cyano-1-((2-(trimethylsilyl)ethoxy)methyl)-1H-benzo[d]imidazol-2-yl)-2,2,2-trifluoro-1-hydroxyethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-2,2,2-trifluoro-1-hydroxyethyl)-5-methoxy-7-methyl-1H-indole-1-carboxylate (Example 33-A) (500 mg, 0.79 mmol) in DMF (8 mL), NaH (60%, 95 mg, 2.38 mmol) was added at 0° C. After stirring for 10 minutes, methyl 2-bromoacetate (0.26 mL, 2.38 mmol) was added at the same temperature. The reaction mixture was warmed to room temperature and then stirred at 50° C. for 3 hours. The reaction was quenched with sat. aq. NH₄Cl. The mixture was diluted with 80% EtOAc in heptanes. The layers were separated and the organic layer was washed with water. The organic extract was dried over magnesium sulfate, filtered and concentrated. The resulting residue was purified with FCC eluting with heptane/EtOAc (0-40%) to provide the mixture of title compounds. MS (ESI+) m/z 703.1 (M+H).

Example 35-B a) (±)-Methyl 2-(1-(5-cyano-1H-benzo[d]imidazol-2-yl)-2,2,2-trifluoro-1-(5-methoxy-7-methyl-1H-indol-4-yl)ethoxy)acetate

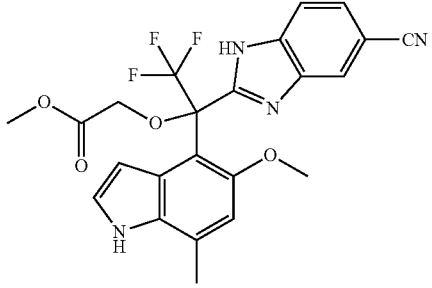 [SMILES: COC(=O)COC(c1nc2cc(C#N)ccc2[nH]1)(c1c(OC)cc(C)c2[nH]ccc12)C(F)(F)F]

A mixture of (±)-tert-butyl 4-(1-(5-cyano-1-((2-(trimethylsilyl)ethoxy)methyl)-1H-benzo[d]imidazol-2-yl)-2,2,2-trifluoro-1-(2-methoxy-2-oxoethoxy)ethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-2,2,2-trifluoro-1-(2-methoxy-2-oxoethoxy)ethyl)-5-methoxy-7-methyl-1H-indole-1-carboxylate (510 mg, 0.711 mmol) was dissolved in 1.25 N HCl in MeOH (8.6 mL, 10.75 mmol), and stirred at 60° C. for 7 hours. The reaction mixture was then concentrated to dryness, dissolved in EtOAc, basified with a 15% aq. NH₄OH solution at 0° C. and diluted with water. The organic layer was separated, dried over magnesium sulfate, filtered, concentrated and purified via FCC eluting with Heptane/EtOAc (0-60% of EtOAc) to provide the title compound. ¹H NMR (400 MHz, Acetone) δ ppm 11.86 (br. s., 1H) 10.15 (br. s., 1H) 7.54-8.07 (m) 7.48 (d, J=8.08 Hz, 1H) 7.25 (t, J=2.91 Hz, 1H) 6.91-7.05 (m, 1H) 6.64 (s, 1H) 4.31 (m, 1H) 3.92-4.05 (m, 1H) 3.30-3.45 (s, 3H) 2.97-3.13 (s, 3H) 2.35-2.46 (s, 3H) HRMS calcd. for $C_{23}H_{19}F_3N_4O_4$ (M+H)⁺ 473.1437. found 473.1438.

b) (+) and (−)-Methyl 2-(1-(5-cyano-1H-benzo[d]imidazol-2-yl)-2,2,2-trifluoro-1-(5-methoxy-7-methyl-1H-indol-4-yl)ethoxy)acetate Resolution of the enantiomers of methyl 2-(1-(5-cyano-1H-benzo[d]imidazol-2-yl)-2,2,2-trifluoro-1-(5-methoxy-7-methyl-1H-indol-4-yl)ethoxy)acetate was achieved by chiral SFC using a CHIRALPAK® IA column with 25% isopropanol in CO₂ to give (+) or (−)-methyl 2-(1-(5-cyano-1H-benzo[d]imidazol-2-yl)-2,2,2-trifluoro-1-(5-methoxy-7-methyl-1H-indol-4-yl)ethoxy)acetate ($t_r$=2.4 min) and (−) or (+)-methyl 2-(1-(5-cyano-1H-benzo[d]imidazol-2-yl)-2,2,2-trifluoro-1-(5-methoxy-7-methyl-1H-indol-4-yl)ethoxy)acetate ($t_r$=3.5 min).

Example 35-C

(+) and (−)-2-(1-(5-Cyano-1H-benzo[d]imidazol-2-yl)-2,2,2-trifluoro-1-(5-methoxy-7-methyl-1H-indol-4-yl)ethoxy)acetic acid

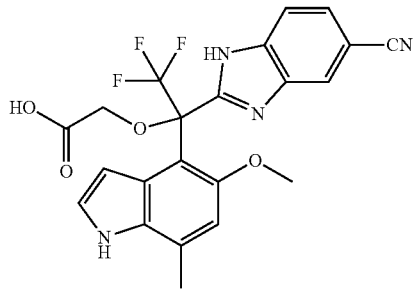 [SMILES: COc1cc(C)c2[nH]ccc2c1C(OCC(=O)O)(c1nc2cc(C#N)ccc2[nH]1)C(F)(F)F]

(+) or (−)-Methyl 2-(1-(5-cyano-1H-benzo[d]imidazol-2-yl)-2,2,2-trifluoro-1-(5-methoxy-7-methyl-1H-indol-4-yl)ethoxy)acetate ($t_r$=2.4 min—from Example 35-B) (116 mg, 0.246 mmol) was dissolved in THF (1.2 mL) and MeOH (1.2 mL). A 3N aq. NaOH solution (0.45 mL, 1.35 mmol) was added. The reaction was stirred at 40° C. for 1 hour. At this point the reaction mixture was concentrated. The residue was dissolved in MeOH, and purified with RP-HPLC(HC-A) to provide (−)-2-(1-(5-cyano-1H-benzo[d]imidazol-2-yl)-2,2,2-trifluoro-1-(5-methoxy-7-methyl-1H-indol-4-yl)ethoxy)acetic acid.

(−) or (+)-methyl 2-(1-(5-cyano-1H-benzo[d]imidazol-2-yl)-2,2,2-trifluoro-1-(5-methoxy-7-methyl-1H-indol-4-yl)ethoxy)acetate ($t_r$=3.5 min—from Example 35-B) (110 mg, 0.233 mmol) was dissolved in THF (1.2 mL) and MeOH (1.2 mL). A 3N aq. NaOH solution (0.45 mL, 1.35 mmol) was added. The reaction was stirred at 40° C. for 1 hour. At this point the reaction mixture was concentrated. The residue was dissolved in MeOH, and purified with RP-HPLC(HC-A) to provide (+)-2-(1-(5-cyano-1H-benzo[d]imidazol-2-yl)-2,2,2-trifluoro-1-(5-methoxy-7-methyl-1H-indol-4-yl)ethoxy)acetic acid.

¹H NMR (TFA salt, 400 MHz, Acetone-d₆) δ ppm 10.13 (br. s., 1H) 7.95 (s, 1H) 7.65 (d, J=8.34 Hz, 1H) 7.48 (dd, J=8.34, 1.52 Hz, 1H) 7.24 (t, J=2.91 Hz, 1H) 7.03 (t, J=2.53 Hz, 1H) 6.64 (s, 1H) 4.29 (d, J=16.17 Hz, 1H) 3.97 (d, J=16.17 Hz, 1H) 3.06 (s, 3H) 2.41 (s, 3H). HRMS calcd. for $C_{22}H_{17}F_3N_4O_4$ (M+H)⁺ 459.1275. found 459.1283.

Example 35-D

(+) or (−)-Ethyl 2-(1-(5-cyano-1H-benzo[d]imidazol-2-yl)-2,2,2-trifluoro-1-(5-methoxy-7-methyl-1H-indol-4-yl)ethoxy)acetate

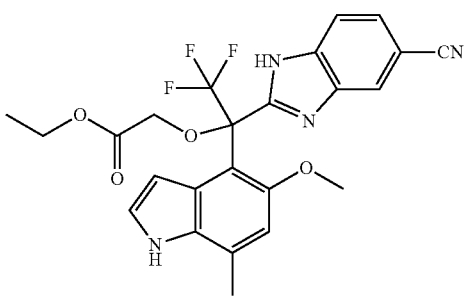 [SMILES: CCOC(=O)COC(c1nc2cc(C#N)ccc2[nH]1)(c1c(OC)cc(C)c2[nH]ccc12)C(F)(F)F]

(+) or (−)-Methyl 2-(1-(5-cyano-1H-benzo[d]imidazol-2-yl)-2,2,2-trifluoro-1-(5-methoxy-7-methyl-1H-indol-4-yl)ethoxy)acetate (t$_r$=3.5 min—from Example 35-B) (54 mg, 0.114 mmol) was dissolved in ethanol (2.0 mL). This solution was added to a mixture of acetyl chloride (1.0 mL) in ethanol (20.0 mL) at 0° C. This mixture was gradually warmed to room temperature and stirred for 16 hr. The reaction solution was basified with saturated sodium bicarbonate solution and the majority of the ethanol was removed in vacuo. The resulting reaction mixture was partitioned between ethyl acetate and water. The layers were separated and the organic layer was washed with brine, dried over sodium sulfate, filtered, and concentrated. This material was purified using FCC eluting with ethyl acetate/heptane (0-60%) to afford the title compound. $^1$H NMR (400 MHz, DMSO-d$_6$) δ ppm 12.89 (br.s., 1H) 11.09 (br. s., 1H) 8.26 (s, 1H) 7.83-8.06 (m, 1H) 7.49-7.73 (m, 1H) 7.38 (t, J=2.78 Hz, 1H) 6.91-6.96 (m, 1H) 6.74 (s, 1H) 3.98-4.36 (m, 2H) 3.73-3.97 (m, 2H) 3.04-3.06 (s, 3H) 2.47-2.50 (s, 3H) 0.97-1.08 (m, 3H) HRMS calcd. for C$_{24}$H$_{21}$F$_3$N$_4$O$_4$ (M+H)$^+$ 487.1548. found 487.1576.

Example 35-E (±)-Tert-butyl 4-(1-(5-cyano-1-((2-(trimethylsilyl)ethoxy)methyl)-1H-benzo[d]imidazol-2-yl)-1-(2-ethoxy-1-fluoro-2-oxoethoxy)-2,2,2-trifluoroethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-(2-ethoxy-1-fluoro-2-oxoethoxy)-2,2,2-trifluoroethyl)-5-methoxy-7-methyl-1H-indole-1-carboxylate

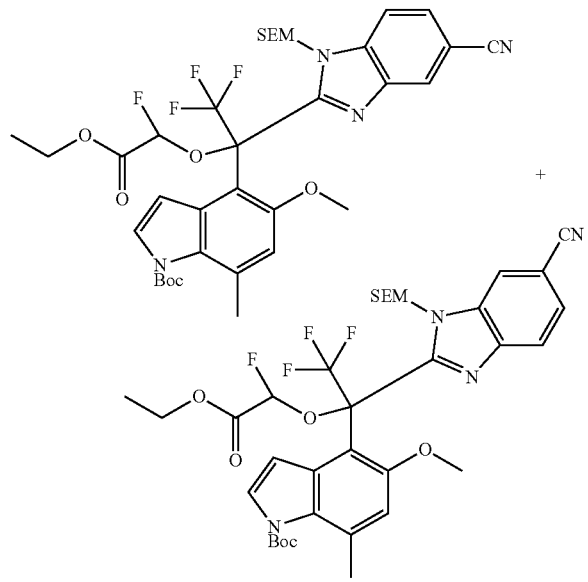

To a solution of a mixture of (±)-tert-butyl 4-(1-(5-cyano-1-((2-(trimethylsilyl)ethoxy)methyl)-1H-benzo[d]imidazol-2-yl)-2,2,2-trifluoro-1-hydroxyethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-2,2,2-trifluoro-1-hydroxyethyl)-5-methoxy-7-methyl-1H-indole-1-carboxylate (Example 33-A) (100 mg, 0.159 mmol) in DMF (1 mL), NaH (60%, 19 mg, 0.476 mmol) was added at 0° C. After stirring for 10 minutes, ethyl-2-bromo-2-fluoroacetate (0.056 mL, 0.476 mmol) was added at the same temperature. The reaction mixture was warmed to room temperature and then stirred at 50° C. for 3 hours. The reaction was quenched with sat. aq. NH$_4$Cl. The mixture was diluted with 80% EtOAc in heptanes. The layers were separated and the organic layer was washed with water. The organic extract was dried over sodium sulfate, filtered and concentrated. The resulting residue was purified with FCC eluting with ethyl acetate/heptane (0-40%) to provide the mixture of title compounds. MS (ESI+) m/z 735.5 (M+H).

Example 35-F (±)-Ethyl 2-(1-(5-cyano-1H-benzo[d]imidazol-2-yl)-2,2,2-trifluoro-1-(5-methoxy-7-methyl-1H-indol-4-yl)ethoxy)-2-fluoroacetate

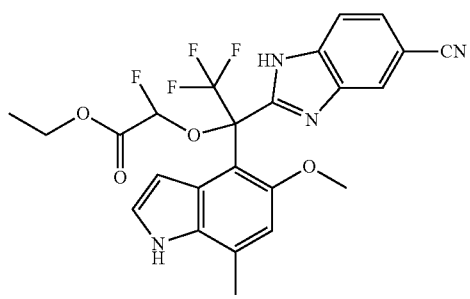 [SMILES: CCOC(=O)C(F)OC(c1nc2cc(C#N)ccc2[nH]1)(c1c(OC)cc(C)c2[nH]ccc12)C(F)(F)F]

To a solution of (±)-tert-butyl 4-(1-(5-cyano-1-((2-(trimethylsilyl)ethoxy)methyl)-1H-benzo[d]imidazol-2-yl)-1-(2-ethoxy-1-fluoro-2-oxoethoxy)-2,2,2-trifluoroethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-(2-ethoxy-1-fluoro-2-oxoethoxy)-2,2,2-trifluoroethyl)-5-methoxy-7-methyl-1H-indole-1-carboxylate (Example 35-E) (94 mg, 0.128 mmol) in dichloromethane (2.0 ml) at 0° C. was added SnCl$_4$ (1.0 M in DCM, 1.279 mL, 1.279 mmol); this mixture was stirred at 0° C. for 30 min followed by warming to room temperature and stirring for 1.0 hr additional. The reaction mixture was partitioned between EtOAc/saturated sodium bicarbonate solution upon which an emulsion formed. Both layers were filtered over a plug of Celite® and then returned to the separatory funnel as two distinct layers. The organic layer was washed with brine solution, dried over sodium sulfate, and concentrated in vacuo. The resulting residue was purified with FCC eluting with ethyl acetate/heptane (0-100%) to provide the title compound. MS (ESI+) m/z 505.2 (M+H).

Example 35-G (±)-2-(1-(5-Cyano-1H-benzo[d]imidazol-2-yl)-2,2,2-trifluoro-1-(5-methoxy-7-methyl-1H-indol-4-yl)ethoxy)-2-fluoroacetic acid

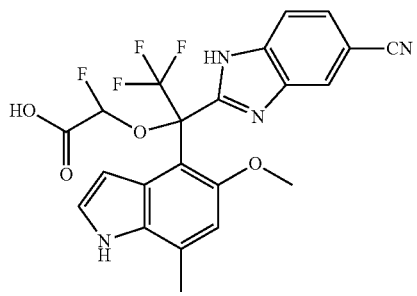 [SMILES: COc1cc(C)c2[nH]ccc2c1C(OC(F)C(=O)O)(c1nc2cc(C#N)ccc2[nH]1)C(F)(F)F]

To a solution of (±)-ethyl 2-(1-(5-cyano-1H-benzo[d]imidazol-2-yl)-2,2,2-trifluoro-1-(5-methoxy-7-methyl-1H-indol-4-yl)ethoxy)-2-fluoroacetate (Example 35-F) (60 mg, 0.119 mmol) in THF (1.0 mL), water (1.0 mL) and MeOH (0.20 mL) was added LiOH (25 mg, 0.595 mmol) and this mixture was stirred for 16 hr at room temperature. The reaction was partitioned between EtOAc and cold 1N HCl solution and the layers separated and the organic layer was washed with brine, dried over sodium sulfate, filtered, and concentrated. This material was purified with FCC eluting with dichloromethane/MeOH (0-10%) to afford the title compound. $^1$H NMR (400 MHz, DMSO-$d_6$) δ ppm 11.03 (br.s., 1H) 10.96 (br.s, 1H), 8.17-8.34 (br.s., 1H) 7.78-7.97 (br.s., 1H) 7.53-7.59 (m, 1H) 7.19-7.29 (m, 1H) 7.00-7.02 (br.s, 1H) 6.74-6.79 (br.s., 1H), 6.65 (s., 1H), 4.87-5.37 (m, 1H) 3.01 (s, 3H) 2.46 (s, 3H). HRMS calcd. for $C_{22}H_{16}F_4N_4O_4$ $(M+H)^+$ 477.1141. found 477.1154.

Example 35-H (±)-tert-Butyl 4-(1-(5-cyano-1-((2-(trimethylsilyl)ethoxy)methyl)-1H-benzo[d]imidazol-2-yl)-2,2,2-trifluoro-1-(2-ethoxy-2-oxoethoxy)ethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-2,2,2-trifluoro-1-(2-methoxy-2-oxoethoxy)ethyl)-5-methoxy-7-methyl-1H-indole-1-carboxylate

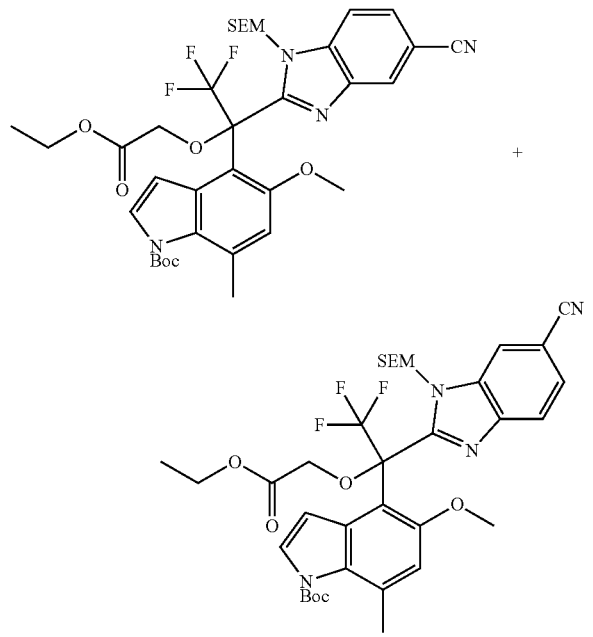

To a solution of a mixture of (±)-tert-butyl 4-(1-(5-cyano-1-((2-(trimethylsilyl)ethoxy)methyl)-1H-benzo[d]imidazol-2-yl)-2,2,2-trifluoro-1-hydroxyethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-2,2,2-trifluoro-1-hydroxyethyl)-5-methoxy-7-methyl-1H-indole-1-carboxylate (Example 33-A) (506 mg, 0.80 mmol) in DMF (5 mL), NaH (60%, 96 mg, 2.41 mmol) was added at 0° C. After stirring for 10 minutes, ethyl 2-bromoacetate (0.267 mL, 2.41 mmol) was added at the same temperature. The reaction mixture was warmed to room temperature and then stirred at 50° C. for 3 hours. The reaction was quenched with sat. aq. NH$_4$Cl. The mixture was diluted with 80% EtOAc in heptanes. The layers were separated and the organic layer was washed with water. The organic extract was dried over magnesium sulfate, filtered and concentrated. The resulting residue was purified with FCC eluting with ethyl acetate/heptane (0-40%) to provide the mixture of title compounds. MS (ESI+) m/z 717.4 (M+H).

Example 35-I (±)-2-(1-(1-(tert-Butoxycarbonyl)-5-methoxy-7-methyl-1H-indol-4-yl)-1-(5-cyano-1-((2-(trimethylsilyl)ethoxy)methyl)-1H-benzo[d]imidazol-2-yl)-2,2,2-trifluoroethoxy)acetic acid and (±)-2-(1-(1-(tert-butoxycarbonyl)-5-methoxy-7-methyl-1H-indol-4-yl)-1-(6-cyano-1-((2-(trimethylsilyl)ethoxy)methyl)-1H-benzo[d]imidazol-2-yl)-2,2,2-trifluoroethoxy)acetic acid

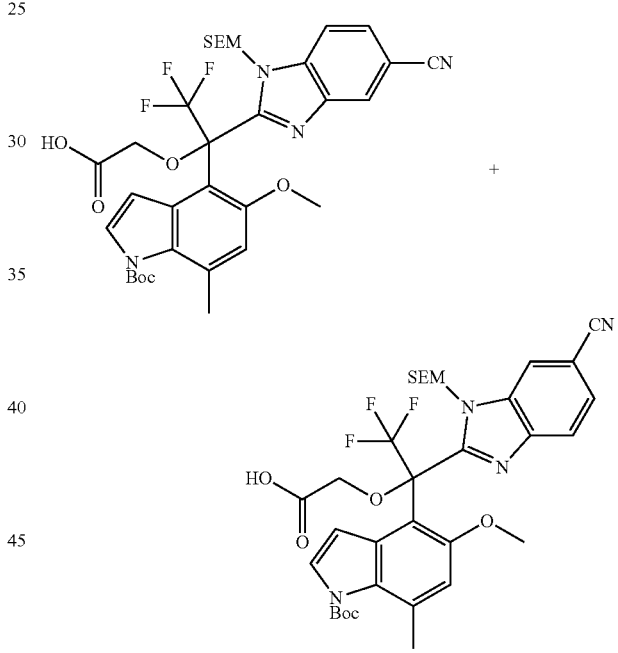

To a solution of (±)-tert-butyl 4-(1-(5-cyano-1-((2-(trimethylsilyl)ethoxy)methyl)-1H-benzo[d]imidazol-2-yl)-2,2,2-trifluoro-1-(2-ethoxy-2-oxoethoxy)ethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-2,2,2-trifluoro-1-(2-methoxy-2-oxoethoxy)ethyl)-5-methoxy-7-methyl-1H-indole-1-carboxylate (528 mg, 0.737 mmol) in THF (3.0 mL), water (3.0 mL) and EtOH(0.25 mL) was added LiOH(155 mg, 3.68 mmol) and this mixture was stirred for 16 hr at room temperature. The reaction was partitioned between EtOAc and cold 1N HCl solution and the layers separated and the organic layer was washed with brine, dried over sodium sulfate, filtered, and concentrated. This material was used without further purification to provide the mixture of title compounds. MS (ESI+) m/z 689.4 (M+H).

Example 35-J (±)-tert-butyl 4-(1-(2-(2-acetylhydrazinyl)-2-oxoethoxy)-1-(5-cyano-1-((2-(trimethylsilyl)ethoxy)methyl)-1H-benzo[d]imidazol-2-yl)-2,2,2-trifluoroethyl)-5-methoxy-7-methyl-1H-indole-1-carboxylate and (±)-tert-butyl 4-(1-(2-(2-acetylhydrazinyl)-2-oxoethoxy)-1-(6-cyano-1-((2-(trimethylsilyl)ethoxy)methyl)-1H-benzo[d]imidazol-2-yl)-2,2,2-trifluoroethyl)-5-methoxy-7-methyl-1H-indole-1-carboxylate

Example 35-K (±)-tert-Butyl 4-(1-(5-cyano-1-((2-(trimethylsilyl)ethoxy)methyl)-1H-benzo[d]imidazol-2-yl)-2,2,2-trifluoro-1-((5-methyl-1,3,4-oxadiazol-2-yl)methoxy)ethyl)-5-methoxy-7-methyl-1H-indole-1-carboxylate compound and (±)-tert-butyl 4-(1-(6-cyano-1-((2-(trimethylsilyl)ethoxy)methyl)-1H-benzo[d]imidazol-2-yl)-2,2,2-trifluoro-1-((5-methyl-1,3,4-oxadiazol-2-yl)methoxy)ethyl)-5-methoxy-7-methyl-1H-indole-1-carboxylate

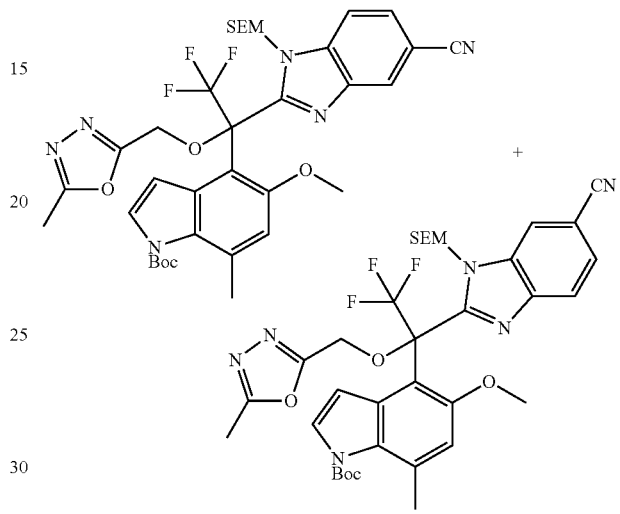

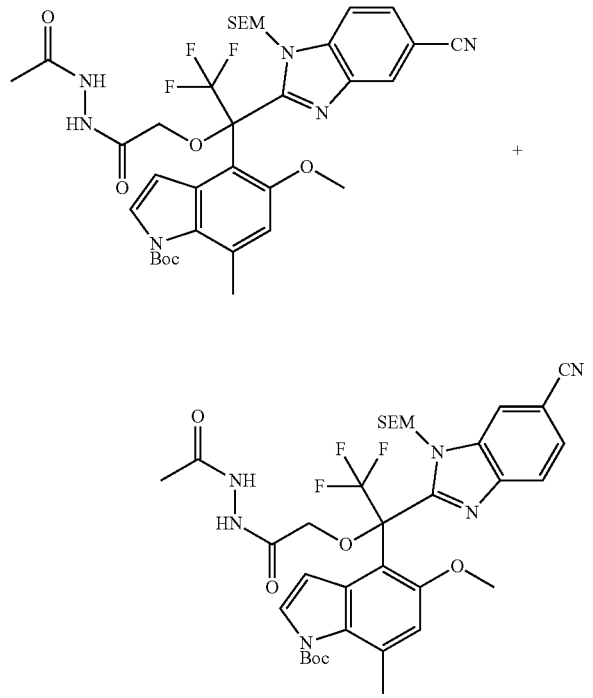 [SMILES: COc1cc(C)c2c(ccn2C(=O)OC(C)(C)C)c1C(OCC(=O)NNC(C)=O)(c1nc2cc(C#N)ccc2n1COCC[Si](C)(C)C)C(F)(F)F ; COc1cc(C)c2c(ccn2C(=O)OC(C)(C)C)c1C(OCC(=O)NNC(C)=O)(c1nc2ccc(C#N)cc2n1COCC[Si](C)(C)C)C(F)(F)F]

To a solution of (±)-2-(1-(1-(tert-butoxycarbonyl)-5-methoxy-7-methyl-1H-indol-4-yl)-1-(5-cyano-1-((2-(trimethylsilyl)ethoxy)methyl)-1H-benzo[d]imidazol-2-yl)-2,2,2-trifluoroethoxy)acetic acid and (±)-2-(1-(1-(tert-butoxycarbonyl)-5-methoxy-7-methyl-1H-indol-4-yl)-1-(6-cyano-1-((2-(trimethylsilyl)ethoxy)methyl)-1H-benzo[d]imidazol-2-yl)-2,2,2-trifluoroethoxy)acetic acid (Example 35-I) (100 mg, 0.145 mmol) in DMF (1.0 mL) was added acetohydrazide (27 mg, 0.218 mmol), 1-hydroxy-7-azabenzotriazole (30 mg, 0.218 mmol), diisopropylethylamine (0.051 mL, 0.29 mmol) and N-(3-dimethylaminopropyl)-N'-ethyl carbodiimide hydrochloride (42 mg, 0.218 mmol). This mixture was stirred at room temperature overnight. The reaction mixture was partitioned between ethyl acetate and cold 1N HCl solution and the layers were separated. The organic phase was washed with saturated sodium bicarbonate solution, brine, dried over sodium sulfate and concentrated in vacuo to afford the mixture of title compounds. The material was used as is for the next step without further purification. MS (ESI+) m/z 745.5 (M+H).

To a solution of (±)-tert-butyl 4-(1-(2-(2-acetylhydrazinyl)-2-oxoethoxy)-1-(5-cyano-1-((2-(trimethylsilyl)ethoxy)methyl)-1H-benzo[d]imidazol-2-yl)-2,2,2-trifluoroethyl)-5-methoxy-7-methyl-1H-indole-1-carboxylate and (±)-tert-butyl 4-(1-(2-(2-acetylhydrazinyl)-2-oxoethoxy)-1-(6-cyano-1-((2-(trimethylsilyl)ethoxy)methyl)-1H-benzo[d]imidazol-2-yl)-2,2,2-trifluoroethyl)-5-methoxy-7-methyl-1H-indole-1-carboxylate (Example 35-J) (108 mg, 0.145 mmol) in THF (2.0 mL) was added methyl N-(triethylammoniumsulfonyl)carbamate (70 mg, 0.290 mmol). This mixture was stirred and heated at 60° C. for 24 hours. The reaction mixture was concentrated down and purified directly by using FCC eluting with ethyl acetate/heptane (0-100%) to afford the mixture of title compound. MS (ESI+) m/z 727.4 (M+H).

Example 35-L (±)-2-(2,2,2-Trifluoro-1-(5-methoxy-7-methyl-1H-indol-4-yl)-1-((5-methyl-1,3,4-oxadiazol-2-yl)methoxy)ethyl)-1H-benzo[d]imidazole-5-carbonitrile

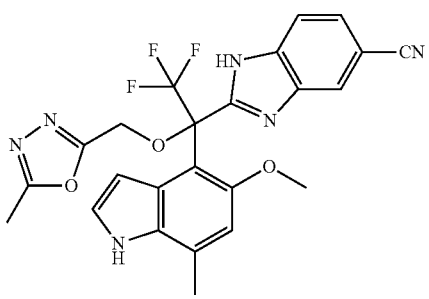 [SMILES: COc1cc(C)c2[nH]ccc2c1C(OCc1nnc(C)o1)(c1nc2cc(C#N)ccc2[nH]1)C(F)(F)F]

To a solution of (±)-tert-butyl 4-(1-(5-cyano-1-((2-(trimethylsilyl)ethoxy)methyl)-1H-benzo[d]imidazol-2-yl)-2,2,2-trifluoro-1-((5-methyl-1,3,4-oxadiazol-2-yl)methoxy)ethyl)-5-methoxy-7-methyl-1H-indole-1-carboxylate compound and (±)-tert-butyl 4-(1-(6-cyano-1-((2-(trimethylsilyl)ethoxy)methyl)-1H-benzo[d]imidazol-2-yl)-2,2,2-trifluoro-1-((5-methyl-1,3,4-oxadiazol-2-yl)methoxy)ethyl)-5-methoxy-7-methyl-1H-indole-1-carboxylate (Example 35-K) (38 mg, 0.051 mmol) in dichloromethane (1.0 mL) at 0° C. was added a 1.0M solution of SnCl$_4$ in dichloromethane (0.51 mL, 0.51 mmol). This mixture was stirred at 0° C. for 30 min and then warmed to room temperature and stirred for an additional 1.0 hr. The crude reaction mixture was diluted with ethyl acetate and a saturated sodium bicarbonate solution and the layers were passed over Celite® and then separated. The organic phase was washed with brine solution, dried over sodium sulfate, and concentrated in vacuo. The crude product was purified using FCC eluting with ethyl acetate/heptane (0-100%) to afford the title compound. $^1$H NMR (400 MHz, DMSO-d$_6$) δ ppm 13.00 (br.s., 1H) 11.10 (br. s., 1H) 8.30 (s, 1H) 7.82-7.93 (m, 1H) 7.49-7.64 (m, 1H) 7.36 (t, J=2.91 Hz, 1H) 6.76 (s, 1H) 6.68 (br. s., 1H) 4.47-4.82 (m, 2H) 3.11 (s, 3H) 2.40 (s, 3H) 1.24 (s, 3H). HRMS calcd. for C$_{24}$H$_{19}$F$_3$N$_6$O$_3$ (M+H)$^+$ 497.1535. found 497.1504.

Example 36

Example 36-A (±)-tert-Butyl 5-methoxy-7-methyl-4-(2,2,2-trifluoro-1-hydroxyethyl)-1H-indole-1-carboxylate

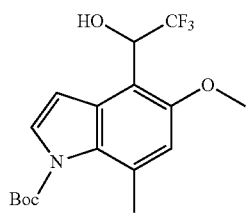 [SMILES: COc1cc(C)c2c(ccn2C(=O)OC(C)(C)C)c1C(O)C(F)(F)F]

To a solution of tert-butyl 4-formyl-5-methoxy-7-methyl-1H-indole-1-carboxylate (Example 19-D) (0.44 g, 1.52 mmol) in THF (7.24 mL), trimethyl(trifluoromethyl)silane (0.71 mL, 4.56 mmol) and then TBAF (1M in THF, 4.56 mL, 4.56 mmol) were added at 0° C., and the reaction was stirred at room temperature. After 20 minutes the reaction mixture was diluted with aq. NH$_4$Cl and brine, extracted with EtOAc, and the organic extract was dried over MgSO$_4$, filtered and concentrated. The resulting residue was purified by flash chromatography (0-70% EtOAc in heptanes) to provide the title compound. MS (ESI+) m/z 360.1 (M+H).

Example 36-B tert-Butyl 5-methoxy-7-methyl-4-(2,2,2-trifluoroacetyl)-1H-indole-1-carboxylate

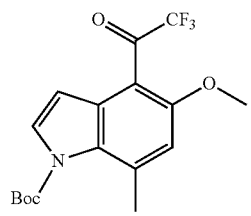 [SMILES: COc1cc(C)c2c(ccn2C(=O)OC(C)(C)C)c1C(=O)C(F)(F)F]

To a solution of (±)-tert-butyl 5-methoxy-7-methyl-4-(2,2,2-trifluoro-1-hydroxyethyl)-1H-indole-1-carboxylate (0.46 g, 1.28 mmol) in DCM (13 mL), Dess-Martin periodinane (0.814 g, 1.920 mmol) was added, and the reaction was stirred at room temperature. After 10 minutes the reaction mixture was quenched with aq. NaHCO$_3$ and aq. sodium thiosulfate. The layers were separated and the aqueous layer was extracted with DCM. The combined organic extracts were dried over MgSO$_4$, filtered and concentrated. The resulting residue was purified by flash chromatography (0-50% EtOAc in heptanes) to provide the title compound. MS (ESI+) m/z 358.3 (M+H).

Example 36-C (±)-tert-Butyl 4-(1-((tert-butylsulfinyl)imino)-2,2,2-trifluoroethyl)-5-methoxy-7-methyl-1H-indole-1-carboxylate

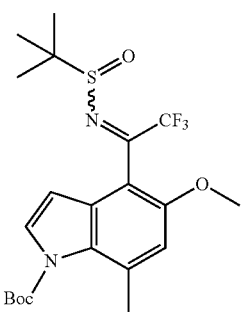 [SMILES: COc1cc(C)c2c(ccn2C(=O)OC(C)(C)C)c1C(=NS(=O)C(C)(C)C)C(F)(F)F]

To a solution of tert-butyl 5-methoxy-7-methyl-4-(2,2,2-trifluoroacetyl)-1H-indole-1-carboxylate (0.45 g, 1.26 mmol) and 2-methyl-2-propanesulfinamide (0.46 g, 3.78 mmol) in toluene (12.6 mL), Zr(O-t-Bu)$_4$ (2.52 mL, 6.30 mmol) was added at room temperature, and the reaction was heated to 100° C. After 15 minutes the reaction mixture was cooled to room temperature and diluted with EtOAc and sat. aq. brine. The resulting mixture was filtered and the layers separated. The aqueous layer was extracted with EtOAc. The combined organic extracts were dried over MgSO$_4$, filtered and concentrated. The resulting residue was purified by flash chromatography (0-50% EtOAc in heptanes) to provide the title compound. MS (ESI+) m/z 461.3 (M+H).

Example 36-D (±)-tert-Butyl 4-(1-(5-cyano-1-((2-(trimethylsilyl)ethoxy)methyl)-1H-benzo[d]imidazol-2-yl)-1-(1,1-dimethylethylsulfinamido)-2,2,2-trifluoroethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-(1,1-dimethylethylsulfinamido)-2,2,2-trifluoroethyl)-5-methoxy-7-methyl-1H-indole-1-carboxylate

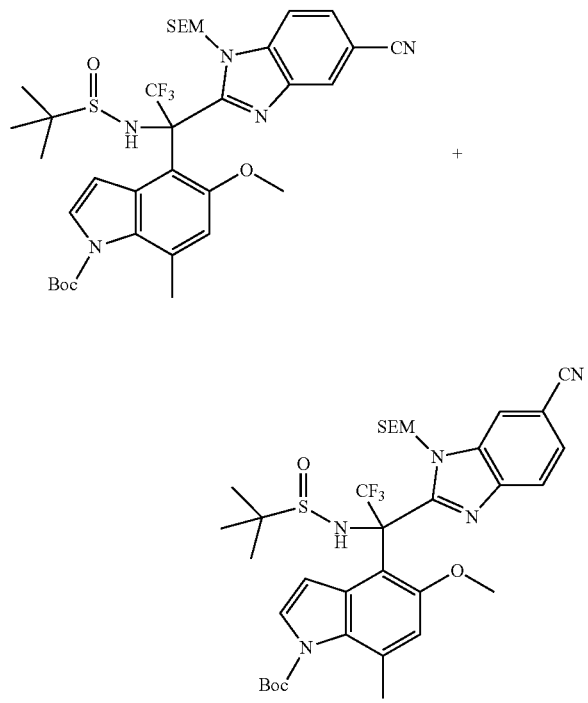 [SMILES: COc1cc(C)c2c(ccn2C(=O)OC(C)(C)C)c1C(NS(=O)C(C)(C)C)(c1nc2cc(C#N)ccc2n1COCC[Si](C)(C)C)C(F)(F)F ; COc1cc(C)c2c(ccn2C(=O)OC(C)(C)C)c1C(NS(=O)C(C)(C)C)(c1nc2ccc(C#N)cc2n1COCC[Si](C)(C)C)C(F)(F)F]

To a solution of a mixture of 1-((2-(trimethylsilyl)ethoxy)methyl)-1H-benzo[d]imidazole-5-carbonitrile and 1-((2-(trimethylsilyl)ethoxy)methyl)-1H-benzo[d]imidazole-6-carbonitrile (0.62 g, 2.26 mmol) in THF (10 mL), LDA in heptane/THF/ethylbenzene (1.8M, 1.13 mL, 2.03 mmol) was added at −78° C. After stirring for 30 min., a solution of (±)-tert-butyl 4-(1-((tert-butylsulfinyl)imino)-2,2,2-trifluoroethyl)-5-methoxy-7-methyl-1H-indole-1-carboxylate (0.52 g, 1.129 mmol) in THF (5 mL) was added to the reaction mixture. After stirring for 10 minutes the reaction mixture was warmed to 0° C., stirred for 2 minutes, then successively diluted with MeOH (2 mL), sat. aq. NH₄Cl (10 mL), sat. aq. brine (10 mL) and EtOAc (30 mL). The layers were separated and the aqueous layer was extracted twice with EtOAc. The organic layers were combined, washed with brine, dried over MgSO₄, filtered, and concentrated. The resulting residue was purified by flash column chromatography (0-100% EtOAc in heptanes) to provide a mixture of the title compounds. MS (ESI+) m/z 734.4 (M+H).

Example 36-E a) (±)-2-(1-Amino-2,2,2-trifluoro-1-(5-methoxy-7-methyl-1H-indol-4-yl)ethyl)-1H-benzo[d]imidazole-5-carbonitrile

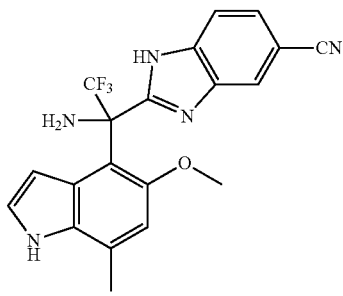 [SMILES: COc1cc(C)c2[nH]ccc2c1C(N)(c1nc2cc(C#N)ccc2[nH]1)C(F)(F)F]

A mixture of (±)-tert-butyl 4-(1-(5-cyano-1-((2-(trimethylsilyl)ethoxy)methyl)-1H-benzo[d]imidazol-2-yl)-1-(1,1-dimethylethylsulfinamido)-2,2,2-trifluoroethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-(1,1-dimethylethylsulfinamido)-2,2,2-trifluoroethyl)-5-methoxy-7-methyl-1H-indole-1-carboxylate (0.50 g, 0.68 mmol) was dissolved in 1.25M HCl in MeOH (10.9 mL, 13.63 mmol) and the mixture was heated at 60° C. After 4 hours the reaction was cooled to room temperature and concentrated. The residue was dissolved in MeOH (6.81 mL) and Cs₂CO₃ (2.22 g, 6.81 mmol) was added, and the mixture was stirred at 60° C. After 30 minutes additional Cs₂CO₃ (1.11 g, 3.4 mmol) was added. After 10 minutes the reaction was diluted with sat. aq. NH₄Cl and the layers separated. The aqueous layer was extracted with EtOAc, dried over MgSO₄, filtered and concentrated. The resulting residues was purified by flash column chromatography (0-100% EtOAc in heptanes) to provide the title compound. ¹H NMR (400 MHz, DMSO-d₆ with about 5 μL TFA) δ ppm 11.19 (br. s., 1H) 8.27 (br. s., 1H) 7.78 (d, J=7.96 Hz, 1H) 7.69 (dd, J=8.46, 1.52 Hz, 1H) 7.13 (t, J=2.91 Hz, 1H) 6.94 (s, 1H) 5.09 (br. s., 1H) 3.77 (s, 3H). HRMS calcd. for $C_{20}H_{16}F_3N_6O$ (M+H)⁺ 400.138. found 400.1385.

b) (+) and (−)-2-(1-amino-2,2,2-trifluoro-1-(5-methoxy-7-methyl-1H-indol-4-yl)ethyl)-1H-benzo[d]imidazole-5-carbonitrile Resolution of the enantiomers of 2-(1-amino-2,2,2-trifluoro-1-(5-methoxy-7-methyl-1H-indol-4-yl)ethyl)-1H-benzo[d]imidazole-5-carbonitrile was achieved by chiral SFC using a CHIRALPAK® AD-H column with 20% MeOH in CO₂ to give (−)-2-(1-amino-2,2,2-trifluoro-1-(5-methoxy-7-methyl-1H-indol-4-yl)ethyl)-1H-benzo[d]imidazole-5-carbonitrile ($t_r$=3.6 min) (MP=255° C., when crystallized from a 1.5:1 mixture of EtOH:H₂O) and (+)-2-(1-amino-2,2,2-trifluoro-1-(5-methoxy-7-methyl-1H-indol-4-yl)ethyl)-1H-benzo[d]imidazole-5-carbonitrile ($t_r$=6.2 min).

Example 36-F (+)-2-(6-methoxy-8-methyl-5-(trifluoromethyl)-1,3,4,5-tetrahydropyrrolo[4,3,2-de]isoquinolin-5-yl)-1H-benzo[d]imidazole-5-carbonitrile

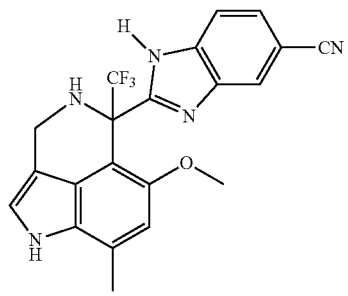 [SMILES: COc1cc(C)c2[nH]cc3c2c1C(c1nc2cc(C#N)ccc2[nH]1)(C(F)(F)F)NC3]

The title compound was isolated from the reaction mixture leading to Example 36-E b) (−), which was synthesized as described in Example 36-A to 36-E using (R)-(+)-2-methyl-2-propanesulfinamide in Example 36-C, as a minor product (<1% yield) using SFC with a Whelk-O (R,R) column (25% IPA in $CO_2$) followed by flash chromatography (0-60% EtOAc:DCM). $^1$H NMR (400 MHz, DMSO-$d_6$) δ ppm 12.36-12.51 (m, 1H) 10.84 (s, 1H) 8.15-8.28 (m) 7.84 (m) 7.75 (m) 7.54 (dd, J=8.21, 1.39 Hz, 1H) 7.47 (m) 7.14 (s, 1H) 6.68 (s, 1H) 4.07-4.29 (m, 2H) 3.72-3.82 (m, 1H) 3.22 (s, 3H) 2.47 (s, 3H). HRMS calcd for $C_{21}H_{16}F_3N_6O$ $(M+H)^+$ 412.1385. found 412.1382.

Example 37

(±)-2-(1-Amino-2,2,2-trifluoro-1-(5-isopropoxy-7-methyl-1H-indol-4-yl)ethyl)-1H-benzo[d]imidazole-5-carbonitrile

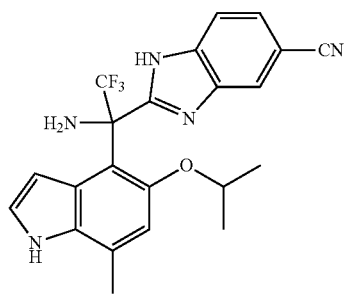 [SMILES: Cc1cc(OC(C)C)c(C(N)(c2nc3cc(C#N)ccc3[nH]2)C(F)(F)F)c2cc[nH]c12]

The title compound was synthesized as described in Example 36-A to 36-E starting from tert-butyl 4-formyl-5-isopropoxy-7-methyl-1H-indole-1-carboxylate (Example 19-G). $^1$H NMR (TFA salt, 400 MHz, $CD_3OD$) δ ppm 8.03 (br.s, 1H) 7.70 (d, J=8.34 Hz, 1H) 7.64 (d, J=8.34 Hz, 1H) 7.25 (app d, J=2.78 Hz, 1H) 6.81 (s, 1H) 6.32 (br.s, 1H) 4.65-4.58 (m, 1H) 2.53 (s, 3H) 0.96 (d, J=5.94 Hz, 3H) 0.82 (d, J=5.94 Hz, 3H). HRMS calcd. for $C_{22}H_{20}F_3N_6O$ $(M+H)^+$ 428.1687. found 428.1696.

Example 38

Example 38-A (±)-tert-Butyl 4-(1-(5-cyano-1H-benzo[d]imidazol-2-yl)-2,2,2-trifluoro-1-(methylamino)ethyl)-5-methoxy-7-methyl-1H-indole-1-carboxylate and (±)-tert-butyl 4-(1-(5-cyano-1H-benzo[d]imidazol-2-yl)-1-(dimethylamino)-2,2,2-trifluoroethyl)-5-methoxy-7-methyl-1H-indole-1-carboxylate

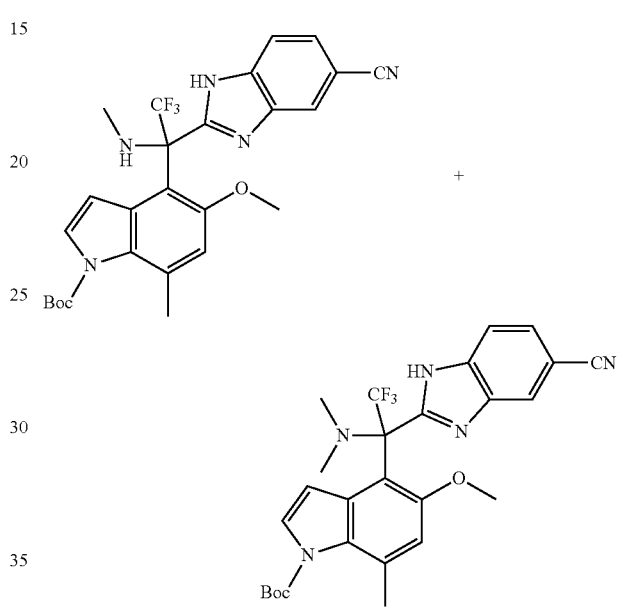

To a mixture of (±)-tert-butyl 4-(1-(5-cyano-1-((2-(trimethylsilyl)ethoxy)methyl)-1H-benzo[d]imidazol-2-yl)-2,2,2-trifluoro-1-hydroxyethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-2,2,2-trifluoro-1-hydroxyethyl)-5-methoxy-7-methyl-1H-indole-1-carboxylate (Example 33-A) (1.27 g, 2.014 mmol) was added 1.25 M HCl in MeOH (16.11 mL, 20.14 mmol) and the mixture was stirred at 60° C. After 40 minutes the reaction was cooled to room temperature and concentrated. The mixture was dissolved in $CHCl_3$ (40 mL), then was added thionyl chloride (1.47 mL, 20.14 mmol) and DMF (0.5 mL) and the mixture was heated at 70° C. After 10 minutes the reaction was cooled to room temperature and concentrated. At this point the reaction was dissolved in 33% methylamine in EtOH (25 mL, 201 mmol) and stirred at room temperature. After 5 minutes the mixture was concentrated and the resulting residue was purified directly by flash chromatography (0-100% EtOAc in heptanes) to provide (±)-tert-butyl 4-(1-(5-cyano-1H-benzo[d]imidazol-2-yl)-2,2,2-trifluoro-1-(methylamino)ethyl)-5-methoxy-7-methyl-1H-indole-1-carboxylate. MS (ESI+) m/z 514.3 (M+H). In addition, (±)-tert-butyl 4-(1-(5-cyano-1H-benzo[d]imidazol-2-yl)-1-(dimethylamino)-2,2,2-trifluoroethyl)-5-methoxy-7-methyl-1H-indole-1-carboxylate was also isolated. MS (ESI−) m/z 526.3 (M−H).

Example 38-B a) (±)-2-(2,2,2-Trifluoro-1-(5-methoxy-7-methyl-1H-indol-4-yl)-1-(methylamino)ethyl)-1H-benzo[d]imidazole-5-carbonitrile

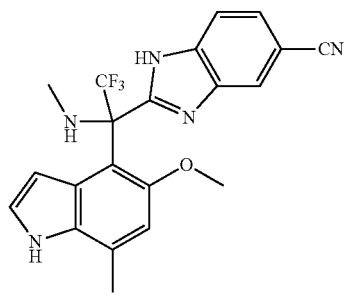 [SMILES: CNC(c1nc2cc(C#N)ccc2[nH]1)(c1c(OC)cc(C)c2[nH]ccc12)C(F)(F)F]

To a solution of (±)-tert-butyl 4-(1-(5-cyano-1H-benzo[d]imidazol-2-yl)-2,2,2-trifluoro-1-(methylamino)ethyl)-5-methoxy-7-methyl-1H-indole-1-carboxylate (0.87 g, 1.69 mmol) in MeOH (16.94 mL) at room temperature, Cs$_2$CO$_3$ (2.76 g, 8.47 mmol) was added and the reaction was stirred at 60° C. After 2.5 hours the reaction was cooled to room temperature, quenched with aq. NH$_4$Cl. The layers were separated and the aqueous layer was extracted with EtOAc. The organic layers were combined, dried over MgSO$_4$, filtered and concentrated. The resulting residue was purified by flash chromatography (0-100% EtOAc in heptanes) to provide the title compound. $^1$H NMR (400 MHz, DMSO-d$_6$ with about 5 μL TFA) δ ppm 11.14 (br. s., 1H) 8.21 (br. s., 1H) 7.72 (d, J=8.46 Hz, 1H) 7.64 (dd, J=8.40, 1.45 Hz, 1H) 7.18 (t, J=2.84 Hz, 1H) 6.89 (s, 1H) 5.56 (br. s., 1H) 3.57 (br. s., 3H) 2.31 (s, 3H). HRMS calcd. for C$_{21}$H$_{18}$F$_3$N$_5$O (M+H)$^+$ 414.1542. found 414.1542.

b) (+) and (−)-2-(2,2,2-trifluoro-1-(5-methoxy-7-methyl-1H-indol-4-yl)-1-(methylamino)ethyl)-1H-benzo[d]imidazole-5-carbonitrile Resolution of the enantiomers of 2-(2,2,2-trifluoro-1-(5-methoxy-7-methyl-1H-indol-4-yl)-1-(methylamino)ethyl)-1H-benzo[d]imidazole-5-carbonitrile was achieved by chiral SFC using a CHIRALCEL® OD-H column with 20% MeOH (0.2% DEA) in CO$_2$ to give (+)-2-(2,2,2-trifluoro-1-(5-methoxy-7-methyl-1H-indol-4-yl)-1-(methylamino)ethyl)-1H-benzo[d]imidazole-5-carbonitrile (t$_r$=2.7 min) and (−)-2-(2,2,2-trifluoro-1-(5-methoxy-7-methyl-1H-indol-4-yl)-1-(methylamino)ethyl)-1H-benzo[d]imidazole-5-carbonitrile (t$_r$=4.1 min).

Example 38-C

(±)-2-(1-(Dimethylamino)-2,2,2-trifluoro-1-(5-methoxy-7-methyl-1H-indol-4-yl)ethyl)-1H-benzo[d]imidazole-5-carbonitrile

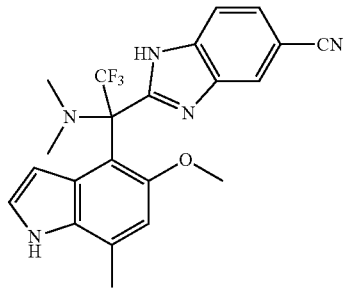 [SMILES: COc1cc(C)c2[nH]ccc2c1C(c1nc2cc(C#N)ccc2[nH]1)(N(C)C)C(F)(F)F]

The title compounds was synthesized starting from tert-butyl 4-(1-(5-cyano-1H-benzo[d]imidazol-2-yl)-1-(dimethylamino)-2,2,2-trifluoroethyl)-5-methoxy-7-methyl-1H-indole-1-carboxylate following a similar method as in Example 38-B. $^1$H NMR (400 MHz, DMSO-d$_6$) δ ppm 12.20-12.40 (m, 1H) 10.97 (br. s., 1H) 8.22 (m) 7.80-7.91 (m) 7.50-7.64 (m) 7.33 (br. s., 1H) 7.02 (br. s., 1H) 6.72 (s, 1H) 3.07 (s, 3H) 2.48 (br. s., 3H) 2.28 (s, 6H). HRMS calcd. for C$_{22}$H$_{20}$F$_3$N$_5$O (M+H)$^+$ 428.1698. found 428.1695.

Example 38-D a) (±)-2-(1-((2-aminoethyl)amino)-2,2,2-trifluoro-1-(5-methoxy-7-methyl-1H-indol-4-yl)ethyl)-1H-benzo[d]imidazole-5-carbonitrile

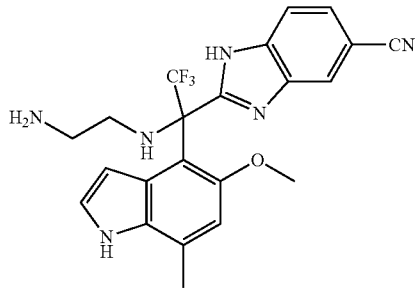 [SMILES: COc1cc(C)c2[nH]ccc2c1C(NCCN)(c1nc2cc(C#N)ccc2[nH]1)C(F)(F)F]

The title compound was synthesized as shown in the sequence in Example 38-A and B. Ethylenediamine was used in place of methylamine in Example 38-A. $^1$H NMR (400 MHz, DMSO-d$_6$ with about 5 μL TFA) δ ppm 11.04 (br. s., 1H) 8.16 (br. s., 1H) 7.67 (br. s., 1H) 7.60 (dd, J=8.34, 1.52 Hz, 1H) 7.49 (br. s., 1H) 7.14 (br. s., 1H) 6.84 (s, 1H) 3.52 (br. s., 3H) 2.72-2.95 (m, 3H) 2.47 (s, 3H) 2.14-2.31 (m, 1H). HRMS calcd. for C$_{22}$H$_{21}$F$_3$N$_6$O (M+H)$^+$ 443.1807. found 443.1793.

b) (+) and (−)-2-(1-((2-aminoethyl)amino)-2,2,2-trifluoro-1-(5-methoxy-7-methyl-1H-indol-4-yl)ethyl)-1H-benzo[d]imidazole-5-carbonitrile Resolution of the enantiomers of 2-(1-((2-aminoethyl)amino)-2,2,2-trifluoro-1-(5-methoxy-7-methyl-1H-indol-4- yl)ethyl)-1H-benzo[d]imidazole-5-carbonitrile was achieved by chiral SFC using a CHIRALPAK® IA column with 30% IPA+5% isopropylamine in $CO_2$ to give (−)-2-(1-((2-aminoethyl)amino)-2,2,2-trifluoro-1-(5-methoxy-7-methyl-1H-indol-4-yl)ethyl)-1H-benzo[d]imidazole-5-carbonitrile ($t_r$=2.9 min) and (+)-2-(1-((2-aminoethyl)amino)-2,2,2-trifluoro-1-(5-methoxy-7-methyl-1H-indol-4-yl)ethyl)-1H-benzo[d]imidazole-5-carbonitrile ($t_r$=3.5 min).

Example 39

Example 39-A (±)-tert-Butyl 4-(((tert-butylsulfinyl)imino)(5-cyano-1-((2-(trimethylsilyl)ethoxy)methyl)-1H-benzo[d]imidazol-2-yl)methyl)-5-methoxy-7-methyl-1H-indole-1-carboxylate and (±)-tert-butyl 4-(((tert-butylsulfinyl)imino)(6-cyano-1-((2-(trimethylsilyl)ethoxy)methyl)-1H-benzo[d]imidazol-2-yl)methyl)-5-methoxy-7-methyl-1H-indole-1-carboxylate

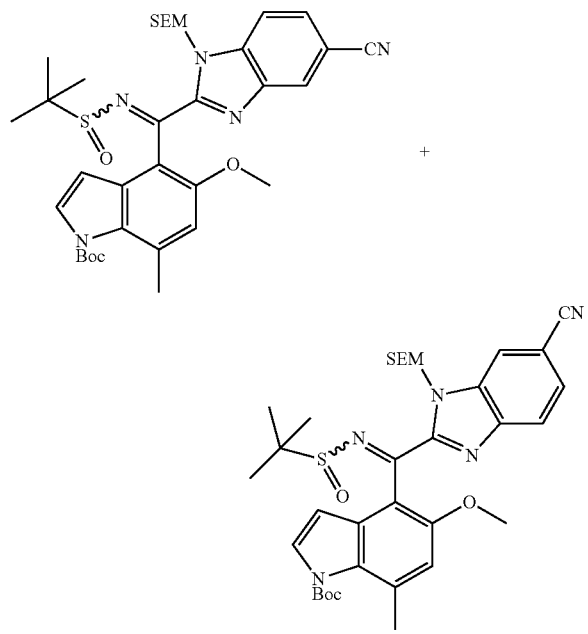

A mixture of tert-Butyl 4-(5-cyano-1-((2-(trimethylsilyl)ethoxy)methyl)-1H-benzo[d]imidazole-2-carbonyl)-5-methoxy-7-methyl-1H-indole-1-carboxylate and tert-butyl 4-(6-cyano-1-((2-(trimethylsilyl)ethoxy)methyl)-1H-benzo[d]imidazole-2-carbonyl)-5-methoxy-7-methyl-1H-indole-1-carboxylate (1 g, 1.78 mmol), 2-methylpropanesulfinamide (0.24 g, 1.96 mmol) and Ti(O-i-Pr)$_4$ (3.66 mL, 12.48 mmol) was stirred at 90° C. for 5 hours. The reaction was cooled to room temperature and diluted with EtOAc and brine. The resulting mixture was filtered and the layers were separated. The organic layer of the filtrate was dried over sodium sulfate, filtered, concentrated and purified by flash chromatography (0-50% EtOAc in heptanes) to provide the mixture of title compounds. MS (ESI+) m/z 664.6 (M+H).

Example 39-B (±)-tert-Butyl 4-((5-cyano-1-((2-(trimethylsilyl)ethoxy)methyl)-1H-benzo[d]imidazol-2-yl)(1,1-dimethylethylsulfinamido)methyl)-5-methoxy-7-methyl-1H-indole-1-carboxylate and (±)-tert-butyl 4-((6-cyano-1-((2-(trimethylsilyl)ethoxy)methyl)-1H-benzo[d]imidazol-2-yl)(1,1-dimethylethylsulfinamido)methyl)-5-methoxy-7-methyl-1H-indole-1-carboxylate

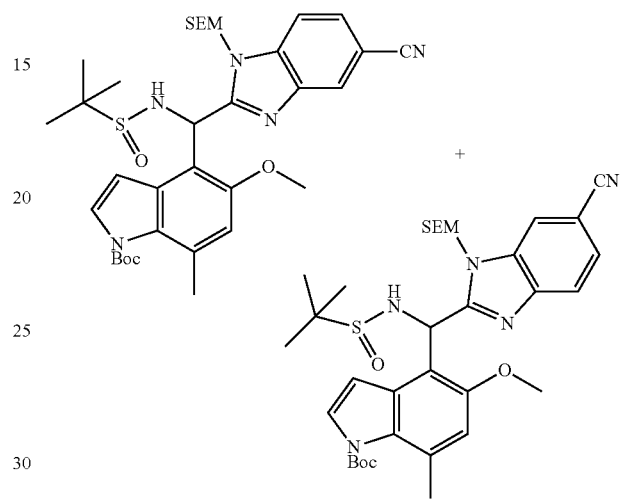

To a mixture of (±)-tert-butyl 4-(((tert-butylsulfinyl)imino)(5-cyano-1-((2-(trimethylsilyl)ethoxy)methyl)-1H-benzo[d]imidazol-2-yl)methyl)-5-methoxy-7-methyl-1H-indole-1-carboxylate and (±)-tert-butyl 4-(((tert-butylsulfinyl)imino)(6-cyano-1-((2-(trimethylsilyl)ethoxy)methyl)-1H-benzo[d]imidazol-2-yl)methyl)-5-methoxy-7-methyl-1H-indole-1-carboxylate (53 mg, 0.095 mmol) in MeOH (3 mL) was added NaBH$_4$ (71.5 mg, 1.89 mmol) at 0° C. and the reaction mixture was stirred at room temperature for 2 hours. The reaction mixture was diluted with DCM and water and filtered. The filtrate was washed with H$_2$O and brine, passed through a phase separator, concentrated and purified by flash chromatography (0-5% MeOH in DCM) to provide the mixture of title compounds. MS (ESI+) m/z 666.6 (M+H).

Example 39-C a) (±)-2-(Amino(5-methoxy-7-methyl-1H-indol-4-yl)methyl)-1H-benzo[d]imidazole-5-carbonitrile

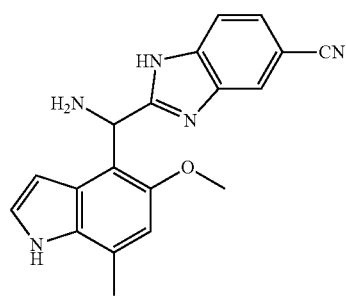

The title compound was synthesized from a mixture of (±)-tert-butyl 4-((5-cyano-1-((2-(trimethylsilyl)ethoxy)methyl)-1H-benzo[d]imidazol-2-yl)(1,1-dimethylethylsulfinamido)methyl)-5-methoxy-7-methyl-1H-indole-1-carboxylate and (±)-tert-butyl 4-((6-cyano-1-((2-(trimethylsilyl)ethoxy)methyl)-1H-benzo[d]imidazol-2-yl)(1,1-dimethylethylsulfinamido)methyl)-5-methoxy-7-methyl-1H-indole-1-carboxylate following the same procedure as described in Example 36-E. $^1$H NMR (400 MHz, DMSO-$d_6$) δ ppm 10.91 (br. s., 1H) 7.91 (s, 1H) 7.57 (d, J=8.08 Hz, 1H) 7.47 (dd, J=8.34, 1.52 Hz, 1H) 7.19 (t, J=2.78 Hz, 1H) 6.74 (s, 1H) 6.23 (dd, J=3.03, 2.02 Hz, 1H) 5.80 (s, 1H) 3.71 (s, 3H) 2.44 (s, 3H). HRMS calcd. for $C_{19}H_{17}N_5O$ (M+H)$^+$ 332.1506. found 332.1507.

b) (+) and (−)-2-(amino(5-methoxy-7-methyl-1H-indol-4-yl)methyl)-1H-benzo[d]imidazole-5-carbonitrile Resolution of the enantiomers of 2-(amino(5-methoxy-7-methyl-1H-indol-4-yl)methyl)-1H-benzo[d]imidazole-5-carbonitrile is achieved by chiral HPLC using a CHIRALPAK® AD-H column with 10% ethanol (0.2% DEA) in heptanes to give (−) or (+)-2-(amino(5-methoxy-7-methyl-1H-indol-4-yl)methyl)-1H-benzo[d]imidazole-5-carbonitrile ($t_r$=24.09 min) and (+) or (−)-2-(amino(5-methoxy-7-methyl-1H-indol-4-yl)methyl)-1H-benzo[d]imidazole-5-carbonitrile=30.56 min)

Example 40

(±)-2-(Amino(5-isopropoxy-7-methyl-1H-indol-4-yl)methyl)-1H-benzo[d]imidazole-5-carbonitrile

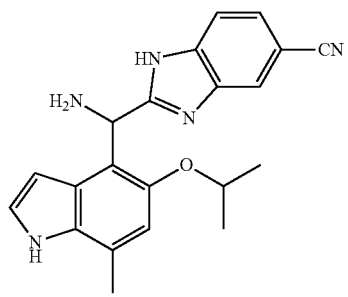 [SMILES: Cc1cc(OC(C)C)c(C(N)c2nc3cc(C#N)ccc3[nH]2)c2cc[nH]c12]

The title compound was synthesized as described in Example 39 starting from tert-butyl 4-formyl-5-isopropoxy-7-methyl-1H-indole-1-carboxylate. $^1$H NMR (400 MHz, CD$_3$OD) δ ppm 7.85 (br.s, 1H) 7.58 (d, J=8.38 Hz, 1H) 7.48 (app dd, J=8.38, 1.45 Hz, 1H) 7.20 (d, J=3.16 Hz, 1H) 6.75 (s, 1H) 6.34 (d, J=3.16 Hz, 1H) 5.80 (s, 1H) 4.57-4.48 (m, 1H) 2.48 (s, 3H) 1.22 (d, J=6.06 Hz, 3H) 0.83 (d, J=6.06 Hz, 3H). HRMS calcd. for $C_{22}H_{21}N_5O$ (M+H)$^+$ 360.1819. found 360.1811.

Example 41

Example 41-A (±)-tert-Butyl 4-(1-(5-cyano-1-((2-(trimethylsilyl)ethoxy)methyl)-1H-benzo[d]imidazol-2-yl)-1-(1,1-dimethylethylsulfinamido)ethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-(1,1-dimethylethylsulfinamido)ethyl)-5-methoxy-7-methyl-1H-indole-1-carboxylate

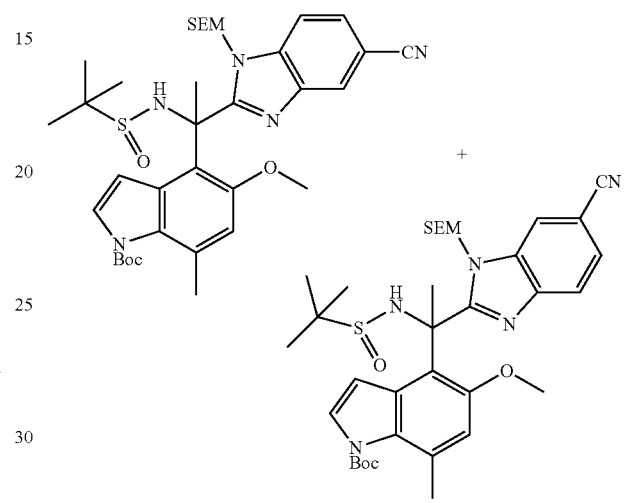

To a solution of a mixture of (±)-tert-butyl 4-(((tert-butylsulfinyl)imino)(5-cyano-1-((2-(trimethylsilyl)ethoxy)methyl)-1H-benzo[d]imidazol-2-yl)methyl)-5-methoxy-7-methyl-1H-indole-1-carboxylate and (±)-tert-butyl 4-(((tert-butylsulfinyl)imino)(6-cyano-1-((2-(trimethylsilyl)ethoxy)methyl)-1H-benzo[d]imidazol-2-yl)methyl)-5-methoxy-7-methyl-1H-indole-1-carboxylate (Example 39-A) (0.46 g, 0.69 mmol) in THF (6.93 mL), MeMgCl (3M in THF) (0.69 mL, 2.08 mmol) was added at 0° C. and stirred for 30 minutes. The reaction was quenched with aq. NH$_4$Cl and diluted with EtOAc. The layers were separated and the organic layer was removed, dried with sodium sulfate, filtered, concentrated and purified by flash chromatography (0-100% EtOAc in heptanes) to provide the mixture of title compounds. MS (ESI+) m/z 680.6 (M+H).

Example 41-B a) (±)-2-(1-Amino-1-(5-methoxy-7-methyl-1H-indol-4-yl)ethyl)-1H-benzo[d]imidazole-5-carbonitrile

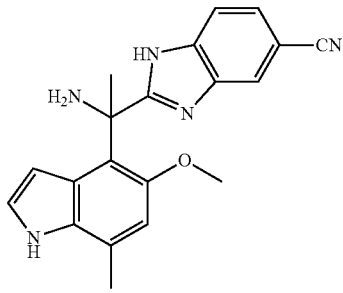 [SMILES: COc1cc(C)c2[nH]ccc2c1C(C)(N)c1nc2cc(C#N)ccc2[nH]1]

To a mixture of (±)-tert-butyl 4-(1-(5-cyano-1-((2-(trimethylsilyl)ethoxy)methyl)-1H-benzo[d]imidazol-2-yl)-1-(1,1-dimethylethylsulfinamido)ethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-(1,1-dimethylethylsulfinamido)ethyl)-5-methoxy-7-methyl-1H-indole-1-carboxylate (0.52 g, 0.76 mmol) was added 1.25 M HCl in MeOH (6.12 mL, 7.65 mmol) and heated at 60° C. for 30 minutes. The reaction was concentrated and then diluted with MeOH (5 mL). Cs$_2$CO$_3$ (4 g, 12.28 mmol) was added and the reaction was heated at 60° C. After 2 hours the reaction was complete. Reaction was then cooled and quenched with 10 mL of a saturated aq. solution of ammonium chloride and diluted with 50 mL of ethyl acetate. The layers were separated and the aqueous layer was extracted with EtOAc. The combined organics layers were dried over magnesium sulfate, concentrated and purified by flash chromatography [0-10% (10% ammonium hydroxide in MeOH)-DCM] to provide the title compound. $^1$H NMR (400 MHz, DMSO-d$_6$ with ~5 μL TFA) δ ppm 11.23 (br. s., 1H) 8.82 (br. s., 3H) 7.47-7.76 (m, 1H) 7.35 (t, J=2.97 Hz, 1H) 6.87 (s, 1H) 5.94 (dd, J=3.16, 1.77 Hz, 1H) 3.50 (s, 3H) 2.04-2.37 (m, 3H). HRMS calcd. for C$_{20}$H$_{13}$N$_6$O (M+H)$^+$ 346.1663. found 346.1663.

b) (+) and (−)-2-(1-amino-1-(5-methoxy-7-methyl-1H-indol-4-yl)ethyl)-1H-benzo[d]imidazole-5-carbonitrile Resolution of the enantiomers of 2-(1-amino-1-(5-methoxy-7-methyl-1H-indol-4-yl)ethyl)-1H-benzo[d]imidazole-5-carbonitrile was achieved by chiral SFC using a CHIRALPAK® AD-H column with 15% MeOH in CO$_2$ to give (−)-2-(1-amino-1-(5-methoxy-7-methyl-1H-indol-4-yl)ethyl)-1H-benzo[d]imidazole-5-carbonitrile (t$_r$=4.2 min) (MP=201° C., when crystallized from a 3:1 mixture of MeOH:H$_2$O), and (+)-2-(1-amino-1-(5-methoxy-7-methyl-1H-indol-4-yl)ethyl)-1H-benzo[d]imidazole-5-carbonitrile (t$_r$=7.1 min).

Example 42

Example 42-A (±)-tert-Butyl 4-(1-amino-1-(5-cyano-1-((2-(trimethylsilyl)ethoxy)methyl)-1H-benzo[d]imidazol-2-yl)ethyl)-5-methoxy-7-methyl-1H-indole-1-carboxylate and (±)-tert-butyl 4-(1-amino-1-(6-cyano-1-((2-(trimethylsilyl)ethoxy)methyl)-1H-benzo[d]imidazol-2-yl)ethyl)-5-methoxy-7-methyl-1H-indole-1-carboxylate

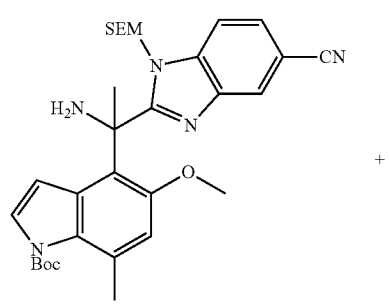

+

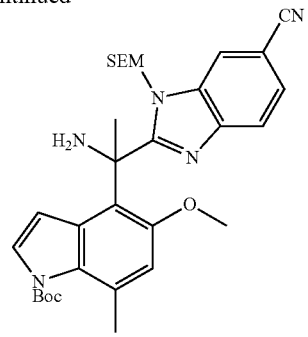

To a solution of a mixture of (±)-tert-butyl 4-(1-(5-cyano-1-((2-(trimethylsilyl)ethoxy)methyl)-1H-benzo[d]imidazol-2-yl)-1-(1,1-dimethylethylsulfinamido)ethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-(1,1-dimethylethylsulfinamido)ethyl)-5-methoxy-7-methyl-1H-indole-1-carboxylate (0.54 g, 0.79 mmol) in anhydrous MeOH (1.6 mL) was added 1.25 M HCl in MeOH (3.18 mL, 3.97 mmol) and stirred at room temperature for 5 hours. The reaction was diluted with MeOH and 2M aq. Na$_2$CO$_3$ (6 mL). The mixture was concentrated to remove the MeOH and then aqueous layer was extracted with EtOAc. The organic extract was dried over Na$_2$SO$_4$, filtered, concentrated and purified by flash column chromatography (0-10% MeOH in DCM) to provide the mixture of title compounds. MS (ESI+) m/z 576.5 (M+H).

Example 42-B (±)-tert-Butyl 4-(1-((tert-butoxycarbonyl)amino)-1-(5-cyano-1-((2-(trimethylsilyl)ethoxy)methyl)-1H-benzo[d]imidazol-2-yl)ethyl)-5-methoxy-7-methyl-1H-indole-1-carboxylate and (±)-tert-butyl 4-(1-((tert-butoxycarbonyl)amino)-1-(6-cyano-1-((2-(trimethylsilyl)ethoxy)methyl)-1H-benzo[d]imidazol-2-yl)ethyl)-5-methoxy-7-methyl-1H-indole-1-carboxylate

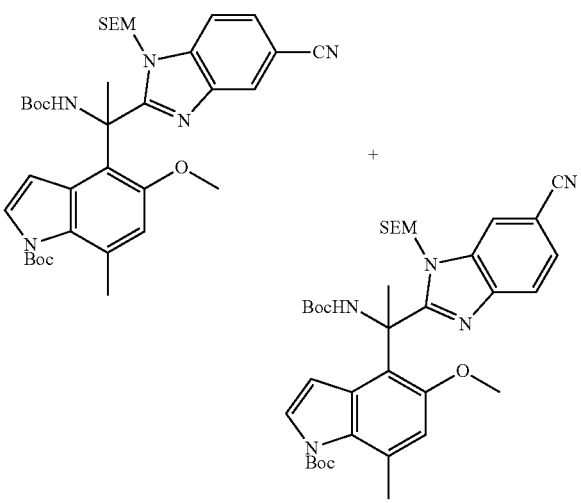

A mixture of (±)-tert-butyl 4-(1-amino-1-(5-cyano-1-((2-(trimethylsilyl)ethoxy)methyl)-1H-benzo[d]imidazol-2-yl)

ethyl)-5-methoxy-methyl-1H-indole-1-carboxylate and (±)-tert-butyl 4-(1-amino-1-(6-cyano-1-((2-(trimethylsilyl)ethoxy)methyl)-1H-benzo[d]imidazol-2-yl)ethyl)-5-methoxy-7-methyl-1H-indole-1-carboxylate (0.29 g, 0.504 mmol) and Boc$_2$O (1.099 g, 5.04 mmol) was allowed to stir at 60° C. for 14 hours. The reaction was cooled to room temperature and purified by flash column chromatography on silica gel (0-50% EtOAc in heptanes) to obtain the title compounds as a mixture. MS (ESI+) m/z 676.5 (M+H).

Example 42-C (±)-tert-Butyl 4-(1-((tert-butoxycarbonyl)(methyl)amino)-1-(5-cyano-1-((2-(trimethylsilyl)ethoxy)methyl)-1H-benzo[d]imidazol-2-yl)ethyl)-5-methoxy-7-methyl-1H-indole-1-carboxylate and (±)-tert-butyl 4-(1-((tert-butoxycarbonyl)(methyl)amino)-1-(6-cyano-1-((2-(trimethylsilyl)ethoxy)methyl)-1H-benzo[d]imidazol-2-yl)ethyl)-5-methoxy-7-methyl-1H-indole-1-carboxylate

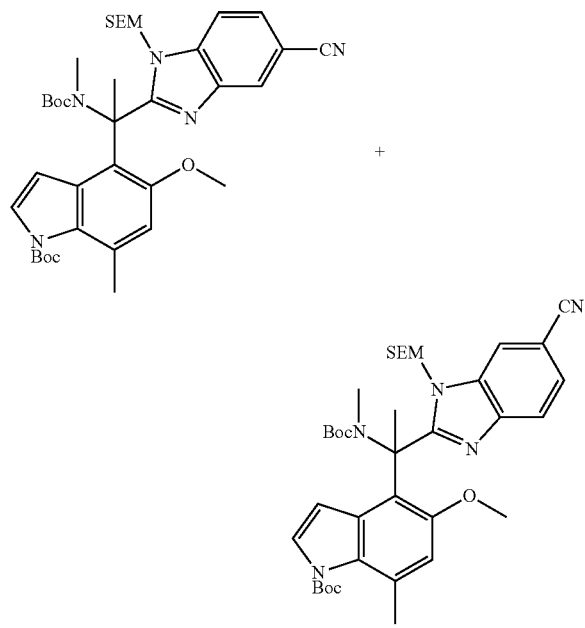

To a mixture of (±)-tert-butyl 4-(1-((tert-butoxycarbonyl)amino)-1-(5-cyano-1-((2-(trimethylsilyl)ethoxy)methyl)-1H-benzo[d]imidazol-2-yl)ethyl)-5-methoxy-7-methyl-1H-indole-1-carboxylate and (±)-tert-butyl 4-(1-((tert-butoxycarbonyl)amino)-1-(6-cyano-1-((2-(trimethylsilyl)ethoxy)methyl)-1H-benzo[d]imidazol-2-yl)ethyl)-5-methoxy-7-methyl-1H-indole-1-carboxylate (0.3 g, 0.44 mmol) in DMF (4.5 mL), NaH (60%, 0.053 g, 1.33 mmol) and then MeI (0.083 mL, 1.33 mmol) were added at 0° C. and the reaction was then stirred at room temperature. After 30 minutes the reaction was cooled in an ice bath and quenched with 5 mL of saturated aq. ammonium chloride and then diluted with EtOAc. The layers were separated and the organic layer was dried over magnesium sulfate, concentrated and purified by flash chromatography (0-50% EtOAc in heptanes) to provide the mixture of title compounds. MS (ESI+) m/z 690.5 (M+H).

Example 42-D a) (±)-2-(1-(5-Methoxy-7-methyl-1H-indol-4-yl)-1-(methylamino)ethyl)-1H-benzo[d]imidazole-5-carbonitrile

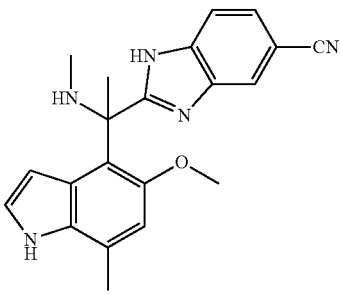 [SMILES: CNC(C)(c1nc2cc(C#N)ccc2[nH]1)c1c(OC)cc(C)c2[nH]ccc12]

A mixture of (±)-tert-butyl 4-(1-((tert-butoxycarbonyl)(methyl)amino)-1-(5-cyano-1-((2-(trimethylsilyl)ethoxy)methyl)-1H-benzo[d]imidazol-2-yl)ethyl)-5-methoxy-7-methyl-1H-indole-1-carboxylate and (±)-tert-butyl 4-(1-((tert-butoxycarbonyl)(methyl)amino)-1-(6-cyano-1-((2-(trimethylsilyl)ethoxy)methyl)-1H-benzo[d]imidazol-2-yl)ethyl)-5-methoxy-7-methyl-1H-indole-1-carboxylate (0.21 g, 0.304 mmol) was dissolved in anhydrous MeOH (0.61 mL) and cooled to 0° C. A 4 M HCl solution in dioxane (1.52 mL, 6.09 mmol) was added and the reaction was stirred in the ice bath for 5 hours. Anhydrous MeOH (0.6 mL) was added to the reaction followed by cesium carbonate (2.98 g, 9.13 mmol). The mixture was heated at 60° C. for 1 hour. At this point the reaction was concentrated and diluted with a saturated solution of aq. ammonium chloride and ethyl acetate. The layers were separated and the organic phase was dried over magnesium sulfate, concentrated and purified by flash chromatography [0-5% MeOH (containing 10% ammonium hydroxide) in DCM] to provide the title compound. $^1$H NMR (400 MHz, DMSO-d$_6$) δ ppm 10.87 (br. s., 1H) 7.93 (m) 7.56 (m) 7.43-7.50 (m, 1H) 7.22 (br. s., 1H) 6.69 (s, 1H) 6.57 (br. s., 1H) 3.22 (s, 3H) 2.44 (s, 3H) 2.06 (s, 3H) 1.91 (s, 3H). HRMS calcd. for $C_{21}H_{21}N_5O$ (M+H) 360.1824. found 360.1831.

b) (+) and (−)-2-(1-(5-methoxy-7-methyl-1H-indol-4-yl)-1-(methylamino)ethyl)-1H-benzo[d]imidazole-5-carbonitrile Resolution of the enantiomers of 2-(1-(5-methoxy-7-methyl-1H-indol-4-yl)-1-(methylamino)ethyl)-1H-benzo[d]imidazole-5-carbonitrile was achieved by chiral HPLC using a CHIRALPAK® AD-H column with 15% Ethanol (0.05% DEA) in heptanes to give (−)-2-(1-(5-methoxy-7-methyl-1H-indol-4-yl)-1-(methylamino)ethyl)-1H-benzo[d]imidazole-5-carbonitrile=6.96 min) and (+)-2-(1-(5-methoxy-7-methyl-1H-indol-4-yl)-1-(methylamino)ethyl)-1H-benzo[d]imidazole-5-carbonitrile (t$_r$=9.23 min).

Example 43

Example 43-A (±)-tert-Butyl 4-((5-cyano-1-((2-(trimethylsilyl)ethoxy)methyl)-1H-benzo[d]imidazol-2-yl)(methylimino)methyl)-5-methoxy-7-methyl-1H-indole-1-carboxylate and (±)-tert-butyl 4-((6-cyano-1-((2-(trimethylsilyl)ethoxy)methyl)-1H-benzo[d]imidazol-2-yl)(methylimino)methyl)-5-methoxy-7-methyl-1H-indole-1-carboxylate

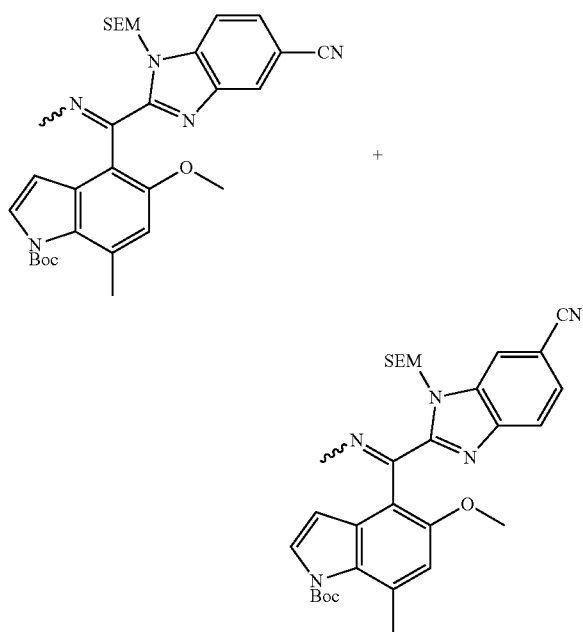

A mixture of tert-butyl 4-(5-cyano-1-((2-(trimethylsilyl)ethoxy)methyl)-1H-benzo[d]imidazole-2-carbonyl)-5-methoxy-7-methyl-1H-indole-1-carboxylate and tert-butyl 4-(6-cyano-1-((2-(trimethylsilyl)ethoxy)methyl)-1H-benzo[d]imidazole-2-carbonyl)-5-methoxy-7-methyl-1H-indole-1-carboxylate (Example 25-A) (0.22 g, 0.39 mmol) was dissolved in a 2 M methyl amine in THF solution (3.98 mL, 7.96 mmol). Titanium(IV) isopropoxide (0.350 mL, 1.194 mmol) was added at 0° C. The reaction was then removed from the ice bath and left stirring for 15 minutes. The reaction was cooled in an ice bath and quenched with brine and then diluted with EtOAc. The layers were separated and the aqueous layer was extracted with EtOAc. The combined organic layers were dried over magnesium sulfate and concentrated. The resulting residue was purified by flash column chromatography (0-30% EtOAc in heptanes) to provide the mixture of title compounds. (ESI+) m/z 574.4 (M+H).

Example 43-B (±)-tert-Butyl 4-((5-cyano-1-((2-(trimethylsilyl)ethoxy)methyl)-1H-benzo[d]imidazol-2-yl)(dimethylamino)methyl)-5-methoxy-7-methyl-1H-indole-1-carboxylate and tert-butyl 4-((6-cyano-1-((2-(trimethylsilyl)ethoxy)methyl)-1H-benzo[d]imidazol-2-yl)(dimethylamino)methyl)-5-methoxy-7-methyl-1H-indole-1-carboxylate

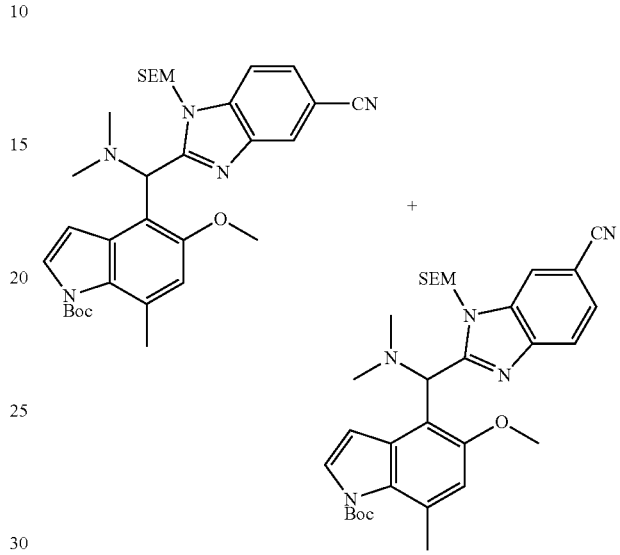

A mixture of (±)-tert-butyl 4-((5-cyano-1-((2-(trimethylsilyl)ethoxy)methyl)-1H-benzo[d]imidazol-2-yl)methylimino)methyl)-5-methoxy-7-methyl-1H-indole-1-carboxylate and (±)-tert-butyl 4-((6-cyano-1-((2-(trimethylsilyl)ethoxy)methyl)-1H-benzo[d]imidazol-2-yl)(methylimino)methyl)-5-methoxy-7-methyl-1H-indole-1-carboxylate (50 mg, 0.044 mmol) was dissolved in THF (0.44 mL) and cooled to 0° C. Methyl magnesium chloride (3 M, 0.1 mL, 0.30 mmol) was added dropwise to the yellow solution and stirred for 30 minutes. The reaction was quenched with saturated aq. ammonium chloride. The layers were separated and the aqueous layer was then extracted with EtOAc. The organic phases were combined, dried over magnesium sulfate and concentrated to obtain the mixture of title compounds. MS (ESI+) m/z 590.6 (M+H).

Example 43-C (±)-2-((Dimethylamino)(5-methoxy-7-methyl-1H-indol-4-yl)methyl)-1H-benzo[d]imidazole-5-carbonitrile

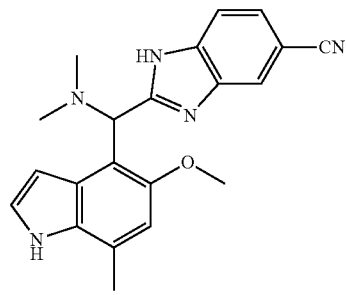 [SMILES: COc1cc(C)c2[nH]ccc2c1C(c1nc2cc(C#N)ccc2[nH]1)N(C)C]

The title compound was synthesized from a mixture of (±)-tert-butyl 4-((5-cyano-1-((2-(trimethylsilyl)ethoxy)methyl)-1H-benzo[d]imidazol-2-yl)(dimethylamino)methyl)-5-methoxy-7-methyl-1H-indole-1-carboxylate and (±)-tert-butyl 4-((6-cyano-1-((2-(trimethylsilyl)ethoxy)methyl)-1H-benzo[d]imidazol-2-yl)(dimethylamino)methyl)-5-methoxy-7-methyl-1H-indole-1-carboxylate as described in Example 36-E. $^1$H NMR (400 MHz, DMSO-d$_6$) δ ppm 12.60 (s, 1H) 10.88 (s, 1H) 7.90 (s) 7.54-7.60 (m) 7.46 (m) 7.22 (t, J=2.78 Hz, 1H) 6.74 (s, 1H) 6.69 (dd, J=2.97, 1.96 Hz, 1H) 5.38 (s, 1H) 3.79 (s, 3H) 2.41 (d, J=0.63 Hz, 3H) 2.22 (s, 6H). MS (ESI−) m/z 358.2 (M−H).

Example 44

Example 44-A tert-Butyl 4-(1-(5-cyano-1-((2-(trimethylsilyl)ethoxy)methyl)-1H-benzo[d]imidazol-2-yl)vinyl)-5-ethoxy-7-methyl-1H-indole-1-carboxylate and tert-butyl 4-(1-(6-cyano-1-((2-(trimethylsilyl)ethoxy)methyl)-1H-benzo[d]imidazol-2-yl)vinyl)-5-ethoxy-7-methyl-1H-indole-1-carboxylate

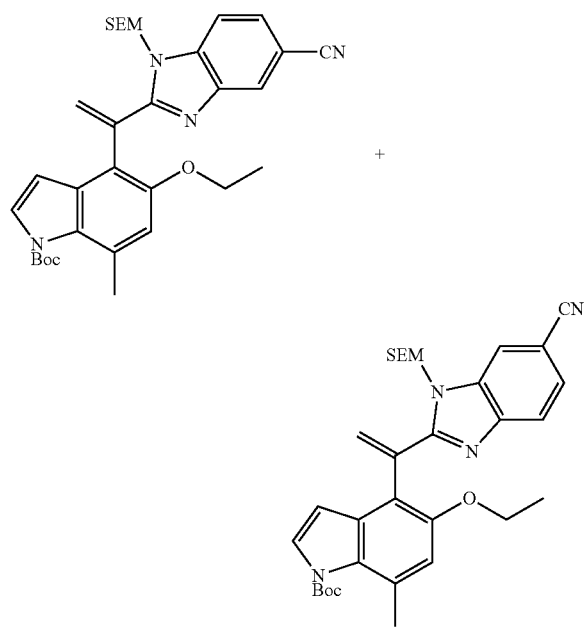

To a solution of (±)-tert-butyl 4-(1-(5-cyano-1-((2-(trimethylsilyl)ethoxy)methyl)-1H-benzo[d]imidazol-2-yl)-1-hydroxyethyl)-5-ethoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-hydroxyethyl)-5-ethoxy-7-methyl-1H-indole-1-carboxylate [synthesized as in Example 24-B, 25-A and 26-A starting from tert-butyl 5-ethoxy-4-formyl-7-methyl-1H-indole-1-carboxylate (Example 19-F)] (0.37 g, 0.65 mmol) in DCM (6.48 mL) was added DMAP (7.92 mg, 0.065 mmol) and TEA (4.52 mL, 32.4 mmol). At this point the reaction was cooled to 0° C. and MsCl (2.021 mL, 25.9 mmol) was added and the reaction stirred in an ice bath for 10 minutes. The reaction was then diluted with water and EtOAc. The layers were separated and the organic extract was dried over magnesium sulfate, filtered and concentrated. The resulting residue was purified by flash column chromatography (0-100% EtOAc in heptanes) to provide a mixture of title compounds. (ESI+) m/z 573.5 (M+H).

Example 44-B (±)-tert-Butyl 4-(2-amino-1-(5-cyano-1-((2-(trimethylsilyl)ethoxy)methyl)-1H-benzo[d]imidazol-2-yl)ethyl)-5-ethoxy-7-methyl-1H-indole-1-carboxylate and (±)-tert-butyl 4-(2-amino-1-(6-cyano-1-((2-(trimethylsilyl)ethoxy)methyl)-1H-benzo[d]imidazol-2-yl)ethyl)-5-ethoxy-7-methyl-1H-indole-1-carboxylate

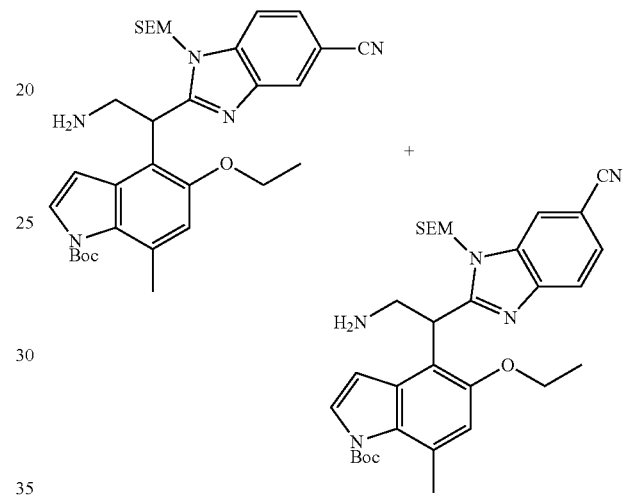

To a mixture of tert-butyl 4-(1-(5-cyano-1-((2-(trimethylsilyl)ethoxy)methyl)-1H-benzo[d]imidazol-2-yl)vinyl)-5-ethoxy-7-methyl-1H-indole-1-carboxylate and tert-butyl 4-(1-(6-cyano-1-((2-(trimethylsilyl)ethoxy)methyl)-1H-benzo[d]imidazol-2-yl)vinyl)-5-ethoxy-7-methyl-1H-indole-1-carboxylate (0.28 g, 0.489 mmol) was added 7 N ammonia in MeOH (4.89 mmol) and heated in a sealed tube at 80° C. for 15 hours. The reaction was concentrated to provide a mixture of title compounds. (ESI+) m/z 590.6 (M+H).

Example 44-C (±)-2-(2-amino-1-(5-ethoxy-7-methyl-1H-indol-4-yl)ethyl)-1H-benzo[d]imidazole-5-carbonitrile

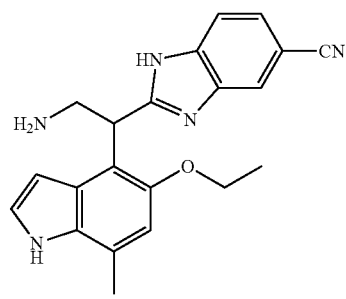 [SMILES: CCOc1cc(C)c2[nH]ccc2c1C(CN)c1nc2cc(C#N)ccc2[nH]1]

The title compound was obtained from a mixture of (±)-tert-butyl 4-(2-amino-1-(5-cyano-1-((2-(trimethylsilyl)ethoxy)methyl)-1H-benzo[d]imidazol-2-yl)ethyl)-5-ethoxy-7-methyl-1H-indole-1-carboxylate and (±)-tert-butyl 4-(2-amino-1-(6-cyano-1-((2-(trimethylsilyl)ethoxy)methyl)-1H-benzo[d]imidazol-2-yl)ethyl)-5-ethoxy-7-methyl-1H-indole-1-carboxylate as described in Example 24-B. $^1$H NMR (400 MHz, DMSO-$d_6$) δ ppm 10.87 (br. s., 1H) 7.96 (s, 1H) 7.53-7.61 (m, 1H) 7.44-7.52 (m, 1H) 7.12 (t, J=2.65 Hz, 1H) 6.76 (s, 1H) 5.98 (br. s., 1H) 5.34 (br. s., 2H) 4.86 (dd, J=8.08, 5.56 Hz, 1H) 3.98-4.08 (m, 1H) 3.89 (dd, J=9.35, 7.07 Hz, 1H) 3.66 (dd, J=12.63, 8.08 Hz, 1H) 3.03 (dd, J=12.63, 5.56 Hz, 1H) 2.43 (s, 3H) 1.16 (t, J=6.95 Hz, 3H). HRMS calcd. for $C_{21}H_{21}N_5O$ (M+H) 360.1824. found 360.1823.

Example 45

(±)-2-(1-(5-ethoxy-7-methyl-1H-indol-4-yl)-2-(methylamino)ethyl)-1H-benzo[d]imidazole-5-carbonitrile

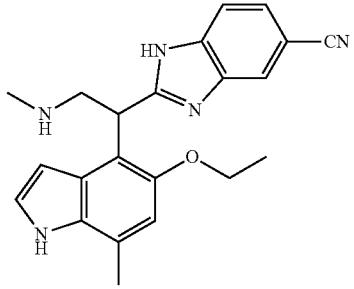 [SMILES: CCOc1cc(C)c2[nH]ccc2c1C(CNC)c1nc2cc(C#N)ccc2[nH]1]

The title compound was synthesized as described in Example 44, methylamine (2 M in THF) was used instead of ammonia in Example 44-B. $^1$H NMR (400 MHz, DMSO-$d_6$) δ ppm 11.08 (br. s., 1H) 8.02 (br. s., 1H) 7.46-7.65 (m) 7.24 (t, J=2.78 Hz, 1H) 6.82 (s, 1H) 6.01 (br. s., 1H) 5.25 (dd, J=8.72, 5.43 Hz, 1H) 3.94-4.15 (m, 2H) 3.87 (dd, J=9.22, 7.20 Hz, 1H) 3.25-3.31 (m, 1H) 2.68 (s, 3H) 2.47 (s, 3H) 0.98-1.16 (m, 3H). HRMS calcd. for $C_{22}H_{23}N_5O$ (M+H)$^+$ 374.1976. found 374.1978.

Example 46

Example 46-A 5,7-Dimethyl-4-nitro-1-tosyl-1H-indole

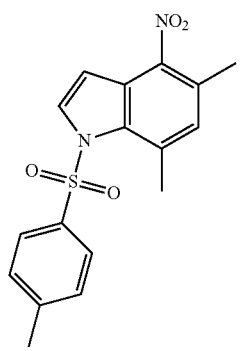

To a solution of 5,7-dimethyl-4-nitro-1H-indole (CAS; 1190314-35-2, 10 g, 52.6 mmol) in DMF (200 mL) was added portionwise NaH (3.2 g, 60% in mineral oil, 79 mmol) at 0° C., and then the mixture was stirred at room temperature for 0.5 h. The mixture was cooled down to 0° C. To the red suspension was added TsCl (15.0 g, 79 mmol) at 0° C., and then the mixture was stirred at room temperature for 22 h. At this point, the reaction was quenched with half saturated aq. $KHSO_4$ solution. The mixture was diluted with $H_2O$, and then the whole mixture was stirred at room temperature for 1 h. The resulted solid was collected by filtration. The obtained brown solid was successively washed with $H_2O$, MeOH, and heptane. The solid was dried to give the title compound. MS (ESI+) m/z 345.1 (M+H).

Example 46-B 5,7-Dimethyl-1-tosyl-1H-indol-4-amine

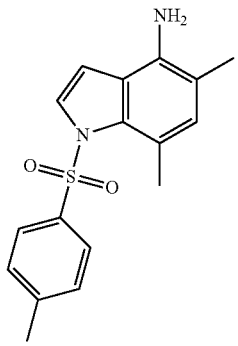 [SMILES: Cc1ccc(S(=O)(=O)n2ccc3c([N+](=O)[O-])c(C)cc(C)c32)cc1]

To a solution of 5,7-dimethyl-4-nitro-1-tosyl-1H-indole (17 g, 49.4 mmol) in MeOH (50 mL)/EtOAc (300 mL) was added Zn (16.1 g, 247 mmol). The suspension was cooled down to 0° C. To the suspension was added dropwise AcOH (30 mL) over 30 min, and then the mixture was stirred at 0° C. for 0.5 h. The flask was removed from the ice bath, and the mixture left stirring at room temperature for 18.5 h. The reaction mixture was poured into a mixture of Celite®/5% aq. $NaHCO_3$/EtOAc, and then the basic mixture was vigorously stirred for 0.5 h. The mixture was filtered through Celite®. The layers were separated and the aqueous layer was extracted with EtOAc. The combined organic phase was washed with 5% aq. $NaHCO_3$, $H_2O$, and brine, dried over $Na_2SO_4$, and then filtered. Concentration of the filtrate gave the title compound, without need of further purification. MS (ESI+) m/z 315.1 (M+H).

Example 46-C

4-Iodo-5,7-dimethyl-1-tosyl-1H-indole

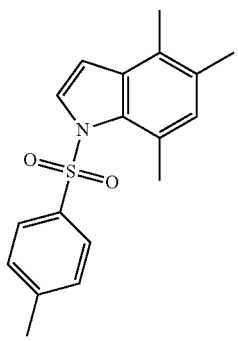 [SMILES: Cc1ccc(S(=O)(=O)n2ccc3c(C)c(C)cc(C)c32)cc1]

To a suspension of 5,7-dimethyl-1-tosyl-1H-indol-4-amine (7.70 g, 24.5 mmol) in H$_2$O (80 mL)/EtOAc (150 mL) was added conc. aq. HCl (4.3 mL, 49.0 mmol) at 0° C., and then the mixture was stirred at 0° C. To the suspension was added dropwise a solution of NaNO$_2$ (2.0 g, 29.4 mmol) in H$_2$O (20 mL) over 15 min while keeping the temperature below 5° C. Once the addition was complete, the mixture was stirred at 0° C. for 1 h. To the mixture was added dropwise a solution of KI (12.2 g, 73.5 mmol) in H$_2$O (20 mL) over 15 min, and then the mixture was stirred at 0° C. for 1 hr. The reaction was quenched by half saturated aqueous Na$_2$S$_2$O$_3$ solution, and then the whole mixture was stirred at room temperature overnight. The mixture was diluted with EtOAc, and then the layers were partitioned. The organic layer was washed with H$_2$O and brine, dried over Na$_2$SO$_4$, and then filtered and concentrated. The resulting residue was purified by FCC [heptane/(30% EtOAc in CH$_2$Cl$_2$)=91/9 to 85/15)]. The resulting residue was triturated with Et$_2$O, and then the solid was collected by filtration to give the title compound. $^1$H NMR (400 MHz, DMSO-d$_6$) δ 7.92 (d, J=3.80 Hz, 1H), 7.61 (d, J=8.60 Hz, 2H), 7.40 (dd, J=0.50, 8.60 Hz, 2H), 7.04 (s, 1H), 6.72 (d, J=3.79 Hz, 1H), 2.41 (s, 3H), 2.37 (s, 3H), 2.34 (s, 3H).

Example 46-D 5,7-Dimethyl-1-tosyl-1H-indole-4-carbaldehyde

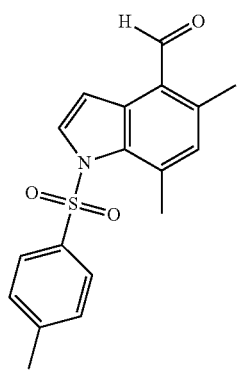 [SMILES: Cc1ccc(S(=O)(=O)n2ccc3c(C=O)c(C)cc(C)c32)cc1]

To a solution of 4-iodo-5,7-dimethyl-1-tosyl-1H-indole (950 mg, 2.1 mmol) and DMF (0.33 mL, 4.2 mmol) in cyclopentyl methyl ether (22 mL), n-butyllithium in hexane (2.2 M, 1.3 mL, 2.8 mmol) was added at −78° C. After stirring for 1 h, additional n-butyllithium in hexane (2.2 M, 0.19 mL, 0.42 mmol) was added. After stirring for 15 min, the reaction was quenched with MeOH (2 mL) and 1M aq. NaHSO$_4$ (4.5 mL), and diluted with EtOAc and brine. The layers were separated and the aqueous layer was extracted with EtOAc. The organic layers were combined, washed with brine, dried over Na$_2$SO$_4$, and then filtered. Concentration of the filtrate gave a residue that was purified by FCC [(10% DCM/heptane)/(20% EtOAc/DCM)=100/0 to 50/50] to give the title compound. MS (ESI+) m/z 328.2 (M+H).

Example 47

Example 47-A (2-Chloro-4-methyl-5-nitrophenyl)methanol

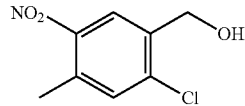

To a solution of 2-chloro-4-methyl-5-nitrobenzoic acid (CAS; 101580-96-5, 15 g, 69.6 mmol) and triethylamine (11.1 mL, 80 mmol) in THF (200 mL) was added 1,1,1-trichloro-2-methylpropan-2-yl carbonochloridate (19.2 g, 80 mmol) at 0° C., and then the mixture was stirred at 0° C. for 1 hr. The resulting white solid was filtered off through Celite®. The solid was washed by THF (20 mL). To the filtrate was added NaBH$_4$ (3.2 g, 83 mmol) at 0° C., followed by H$_2$O (50 mL). The mixture was stirred at 0° C. for 0.5 h, and then stirred at room temperature for 1.25 h. The reaction was quenched by half satd. KHSO$_4$. The layers were separated and the aqueous layer was extracted with CH$_2$Cl$_2$. The organic layers were combined, washed with H$_2$O and brine, dried over Na$_2$SO$_4$, and then filtered through a silica pad. The SiO$_2$ cake was washed with EtOAc. The residue was concentrated and then triturated with heptane. The resulting solid was collected by filtration to give the title compound. $^1$H NMR (400 MHz, ACETONITRILE-d$_3$) δ 8.11 (s, 1H), 7.47 (s, 1H), 4.68 (s, 2H), 2.53 (s, 3H).

Example 47-B (±)-2-((2-Chloro-4-methyl-5-nitrobenzyl)oxy)tetrahydro-2H-pyran

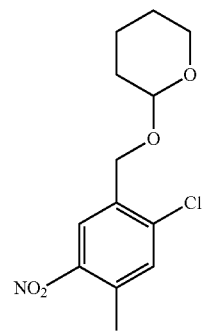 [SMILES: Cc1cc(Cl)c(COC2CCCCO2)cc1[N+](=O)[O-]]

To a solution of (2-chloro-4-methyl-5-nitrophenyl)methanol (23 g, 114 mmol) and 3,4-dihydro-2H-pyran (20.9 mL, 228 mmol) in CH$_2$Cl$_2$ (500 mL) was added pyridinium p-toluenesulfonate (5.7 g, 22.8 mmol), and then the mixture was stirred at room temperature for 11 h. The reaction was quenched by 5% aq. NaHCO$_3$. The layers were separated and the aqueous layer was extracted with CH$_2$Cl$_2$. The organic layers were combined and washed with H$_2$O and brine, dried over Na$_2$SO$_4$, filtered and concentrated. The resulting residue was purified by SiO$_2$ column chromatography (heptane/EtOAc=96/4, isocratic) to give the title compound. $^1$H NMR (400 MHz, ACETONITRILE-d$_3$) δ 8.10 (s, 1H), 7.49 (s, 1H), 4.81 (d, J=13.64 Hz, 1H), 4.72-4.78 (m, 1H), 4.59 (d, J=13.64

Hz, 1H), 3.77-3.92 (m, 1H), 3.34-3.60 (m, 1H), 2.54 (s, 3H), 1.68-1.91 (m, 2H), 1.43-1.68 (m, 4H).

Example 47-C (±)-5-Chloro-7-methyl-4-(((tetrahydro-2H-pyran-2-yl)oxy)methyl)-1H-indole

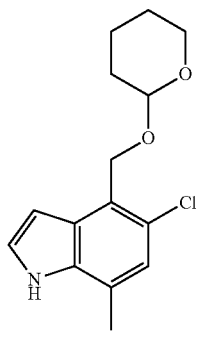 [SMILES: Cc1cc(Cl)c(COC2CCCCO2)c2cc[nH]c12]

To a suspension of vinylmagnesium bromide (1M in THF, 200 mL, 200 mmol) was added dropwise (±)-2-((2-chloro-4-methyl-5-nitrobenzyl)oxy)tetrahydro-2H-pyran (14 g, 49.0 mmol) in THF (40 mL) below −20° C. After completion of the addition, the flask was removed from the ice bath with stirring. After 2 h, the reaction mixture was cooled to below −20° C. The reaction was quenched with MeOH with maintaining the temperature below 0° C. The mixture was diluted with CH$_2$Cl$_2$ and H$_2$O. The mixture was filtered through Celite®. The Celite® cake was washed with CH$_2$Cl$_2$. The layers were separated and the organic phase was washed with H$_2$O and brine, dried over Na$_2$SO$_4$, and then filtered. Concentration of the filtrate gave the title compound, which was used in the next reaction without any further purification. For an analytical purpose, the crude was purified by SiO$_2$ column chromatography [heptane/(30% EtOAc in CH$_2$Cl$_2$)]=69/31] to afford the title compound. $^1$H NMR (400 MHz, ACETONITRILE-d$_3$) δ 9.43 (br. s., 1H), 7.29-7.36 (m, 1H), 6.99 (s, 1H), 6.58-6.70 (m, 1H), 5.05 (d, J=11.12 Hz, 1H), 4.84 (d, J=11.10 Hz, 1H), 4.67-4.77 (m, 1H), 3.89-4.03 (m, 1H), 3.46-3.60 (m, 1H), 2.47 (s, 3H), 1.59-1.75 (m, 2H), 1.43-1.59 (m, 4H)

Example 47-D (±)-5-Chloro-7-methyl-4-(((tetrahydro-2H-pyran-2-yl)oxy)methyl)-1-tosyl-1H-indole

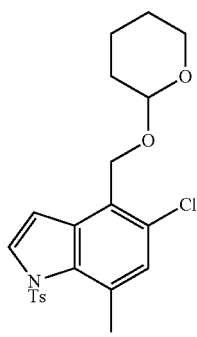 [SMILES: Cc1ccc(S(=O)(=O)n2ccc3c(COC4CCCCO4)c(Cl)cc(C)c32)cc1]

To a solution of (±)-5-chloro-7-methyl-4-(((tetrahydro-2H-pyran-2-yl)oxy)methyl)-1H-indole (8.95 g, 32 mmol) in CH$_2$Cl$_2$ (150 mL), at 0° C. was added NaOH (2.56 g, 64.0 mmol), followed by triethylbenzylammonium chloride (0.729 g, 3.20 mmol) and TsCl (12.20 g, 64.0 mmol). The mixture was then stirred at room temperature. After 17 h, additional NaOH (1.28 g, 32.0 mmol), and TsCl (6.10 g, 32.0 mmol) were added. The mixture was stirred at room temperature for 1.5 h. The reaction mixture was diluted with H$_2$O, and was vigorously stirred for 1 h. The mixture was diluted with CH$_2$Cl$_2$ and the organic layer was successively washed with H$_2$O and brine, dried over Na$_2$SO$_4$, and then filtered. Concentration of the filtrate gave the crude product, which was purified by FCC [heptane/(30% EtOAc in CH$_2$Cl$_2$)=82/18 then 79/21] to give the title compound. $^1$H NMR (400 MHz, ACETONITRILE-d$_3$) δ 7.84 (d, J=3.79 Hz, 1H), 7.67 (d, J=8.20 Hz, 1H), 7.59 (d, J=8.59 Hz, 1H), 7.48 (d, J=8.20 Hz, 1H), 7.33 (d, J=8.50 Hz, 1H), 7.13 (s, 1H), 6.97 (d, J=3.79 Hz, 1H), 4.97 (d, J=11.37 Hz, 1H), 4.76 (d, J=11.37 Hz, 1H), 4.61-4.70 (m, 1H), 3.79-3.91 (m, 1H), 3.40-3.52 (m, 1H), 2.53 (s, 3H), 2.36 (s, 3H), 1.58-1.75 (m, 2H), 1.38-1.58 (m, 4H).

Example 47-E (5-Chloro-7-methyl-1-tosyl-1H-indol-4-yl)methanol

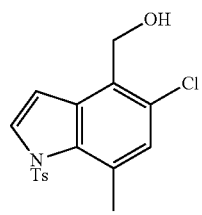 [SMILES: Cc1ccc(S(=O)(=O)n2ccc3c(CO)c(Cl)cc(C)c32)cc1]

A solution of (±)-5-chloro-7-methyl-4-(((tetrahydro-2H-pyran-2-yl)oxy)methyl)-1-tosyl-1H-indole (4.1 g, 9.5 mmol) and TsOH.H$_2$O (359 mg, 1.9 mmol) in EtOH (50 mL) was stirred at room temperature for 21 h. The reaction mixture was concentrated. The mixture was diluted with CH$_2$Cl$_2$. The organic phase was successively washed with 5% aq. NaHCO$_3$, H$_2$O and brine, dried over Na$_2$SO$_4$, and then filtered. Concentration of the filtrate gave the title compound, without need of further purification. $^1$H NMR (400 MHz, ACETONITRILE-d$_3$) δ 7.84 (d, J=3.79 Hz, 1H), 7.59 (d, J=8.34 Hz, 2H), 7.33 (d, J=8.34 Hz, 2H), 7.10 (s, 1H), 7.00 (d, J=3.79 Hz, 1H), 4.84 (d, J=5.81 Hz, 2H), 3.14 (t, J=5.81 Hz, 1H), 2.52 (s, 3H), 2.37 (s, 3H).

Example 47-F

5-Chloro-7-methyl-1-tosyl-1H-indole-4-carbaldehyde

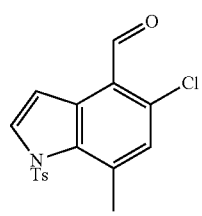 [SMILES: Cc1ccc(S(=O)(=O)n2ccc3c(C=O)c(Cl)cc(C)c32)cc1]

To a solution of (5-chloro-7-methyl-1-tosyl-1H-indol-4-yl)methanol (3.3 g, 9.5 mmol) and N-ethyl-diisopropylamine (8.3 mL, 47.3 mmol) in CH$_2$Cl$_2$ (20 mL)/DMSO (1 mL) was added SO$_3$.Py (4.5 g, 28.4 mmol) at 0° C. The mixture was stirred at 0° C. for 2.5 h, and then stirred at room temperature for 15 h. The reaction was quenched by MeOH. The mixture was stirred for 1 h. The mixture was partially concentrated. The mixture was diluted with H$_2$O, and then the resulted solid was collected by filtration. The resulting residue was triturated with MeOH to give the title compound. $^1$H NMR (400 MHz, ACETONITRILE-d$_3$) δ 10.56 (s, 1H), 8.00 (d, J=3.80 Hz, 1H), 7.62 (d, J=3.80 Hz, 1H), 7.60 (d, J=8.60 Hz, 2H), 7.35 (d, J=8.60 Hz, 2H), 7.22 (s, 1H), 2.60 (s, 3H), 2.37 (s, 3H).

Example 48

Example 48-A (±)-5-Ethyl-7-methyl-4-(((tetrahydro-2H-pyran-2-yl)oxy)methyl)-1-tosyl-1H-indole

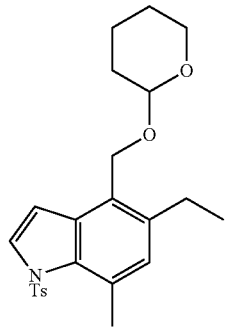 [SMILES: CCc1cc(C)c2c(ccn2S(=O)(=O)c2ccc(C)cc2)c1COC1CCCCO1]

To a suspension of (±)-5-chloro-7-methyl-4-(((tetrahydro-2H-pyran-2-yl)oxy)methyl)-1-tosyl-1H-indole (Example 47-D) (200 mg, 0.46 mmol), cesium carbonate (601 mg, 1.8 mmol), potassium ethyltrifluoroborate (125 mg, 0.92 mmol) in dioxane (3 mL)/H$_2$O (0.3 mL) Pd(OAc)$_2$ (21 mg, 0.092 mmol) and Ru-Phos (CAS 787618-22-8, 86 mg, 0.18 mmol) were added and then the mixture was stirred at 90° C. for 15 h. The reaction mixture was cooled to room temperature, and diluted with CH$_2$Cl$_2$. The organic phase was separated and washed with H$_2$O, and brine, dried over Na$_2$SO$_4$, and then filtered. Concentration of the filtrate gave a residue that was purified by SiO$_2$ column chromatography (heptane/EtOAc=1/0 to 3/2) to give the title compound. $^1$H NMR (400 MHz, ACETONITRILE-d$_3$) δ 7.75 (d, J=3.79 Hz, 1H), 7.57 (d, J=8.34 Hz, 2H), 7.31 (d, J=8.34 Hz, 2H), 6.95 (s, 1H), 6.91 (d, J=3.79 Hz, 1H), 4.90 (d, J=11.24 Hz, 1H), 4.65 (d, J=11.24 Hz, 1H), 4.61-4.64 (m, 1H), 3.79-3.92 (m, 1H), 3.41-3.54 (m, 1H), 2.71 (q, J=7.58 Hz, 2H), 2.53 (s, 3H), 2.35 (s, 3H), 1.56-1.75 (m, 2H), 1.38-1.56 (m, 4H), 1.16 (t, J=7.58 Hz, 3H).

Example 48-B (5-Ethyl-7-methyl-1-tosyl-1H-indol-4-yl)methanol

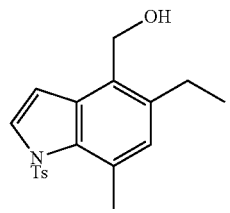 [SMILES: CCc1cc(C)c2c(ccn2S(=O)(=O)c2ccc(C)cc2)c1CO]

The title compound was synthesized by deprotection of (±)-5-ethyl-7-methyl-4-(((tetrahydro-2H-pyran-2-yl)oxy)methyl)-1-tosyl-1H-indole as described in Example 47-E. $^1$H NMR (400 MHz, ACETONITRILE-d$_3$) δ 7.76 (d, J=3.79 Hz, 1H), 7.58 (d, J=8.59 Hz, 2H), 7.31 (d, J=8.59 Hz, 2H), 6.94 (d, J=3.79 Hz, 1H), 6.91-6.93 (m, 1H), 4.76 (d, J=5.31 Hz, 2H), 2.92 (t, J=5.37 Hz, 1H), 2.72 (q, J=7.58 Hz, 2H), 2.52 (s, 3H), 2.35 (s, 3H), 1.17 (t, J=7.58 Hz, 3H).

Example 48-C

5-Ethyl-7-methyl-1-tosyl-1H-indole-4-carbaldehyde

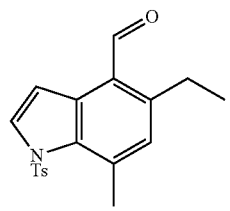 [SMILES: CCc1cc(C)c2c(ccn2S(=O)(=O)c2ccc(C)cc2)c1C=O]

The title compound was synthesized by oxidation of (5-ethyl-7-methyl-1-tosyl-1H-indol-4-yl)methanol as described in Example 47-F. MS (ESI+) m/z 342.1 (M+H).

Example 48-D

5-Cyclopropyl-7-methyl-1-tosyl-1H-indole-4-carbaldehyde

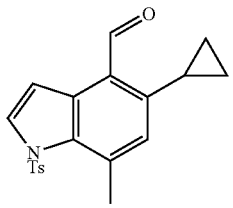 [SMILES: Cc1ccc(S(=O)(=O)n2ccc3c(C=O)c(C4CC4)cc(C)c32)cc1]

The title compound was synthesized starting from 5-chloro-7-methyl-4-(((tetrahydro-2H-pyran-2-yl)oxy)methyl)-1-tosyl-1H-indole as described in Example 48-A to 48-C using potassium cyclopropyltrifluoroborate in place of potassium ethylrifluoroborate in Example 48-A. MS (ESI+) m/z 354.2 (M+H).

Example 49

Example 49-A (±)-5-Isobutyl-7-methyl-4-(((tetrahydro-2H-pyran-2-yl)oxy)methyl)-1-tosyl-1H-indole

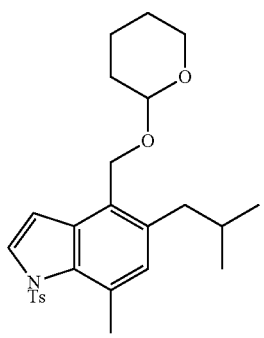 [SMILES: Cc1ccc(S(=O)(=O)n2ccc3c(COC4CCCCO4)c(CC(C)C)cc(C)c32)cc1]

To a solution of (±)-5-chloro-7-methyl-4-(((tetrahydro-2H-pyran-2-yl)oxy)methyl)-1-tosyl-1H-indole (Example 47-D) (2.7 g, 6.2 mmol) in isobutylzinc(II) bromide in THF (0.5 M, 24.9 mL, 12.4 mmol) was added Pd[(t-Bu)$_3$P]$_2$ (0.5 g, 0.98 mmol), and then the mixture was stirred at 70° C. for 14 h. The mixture was then stirred under reflux for 7 h. The reaction was then diluted with H$_2$O and EtOAc. The mixture was then filtered through a Celite® pad. The filtrate was partitioned. The organic phase was washed with H$_2$O, and brine, dried over Na$_2$SO$_4$, filtered and concentrated. The resulting residue was purified by SiO$_2$ column chromatography (heptane/EtOAc=88/12) to afford the title compound. $^1$H NMR (400 MHz, ACETONITRILE-d$_3$) δ 7.74 (d, J=3.79 Hz, 1H), 7.58 (d, J=8.59 Hz, 2H), 7.31 (d, J=8.60 Hz, 2H), 6.86-6.94 (m, 2H), 4.90 (d, J=11.12 Hz, 1H), 4.64 (d, J=11.12 Hz, 1H), 4.60-4.64 (m, 1H), 3.81-3.91 (m, 1H), 3.45-3.54 (m, 1H), 2.57 (d, J=7.33 Hz, 2H), 2.52 (s, 3H), 2.35 (s, 3H), 1.79-1.88 (m, 1H), 1.56-1.75 (m, 2H), 1.39-1.55 (m, 4H), 0.84-0.89 (m, 6H).

Example 49-B

5-Isobutyl-7-methyl-1-tosyl-1H-indole-4-carbaldehyde

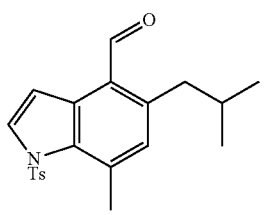 [SMILES: Cc1ccc(S(=O)(=O)n2ccc3c(C=O)c(CC(C)C)cc(C)c32)cc1]

The title compound was synthesized as described in Example 47-E and 47-F from (±)-5-isobutyl-7-methyl-4-(((tetrahydro-2H-pyran-2-yl)oxy)methyl)-1-tosyl-1H-indole. MS (ESI+) m/z 370.2 (M+H).

Example 50

Example 50-A

5-Isopropyl-7-methyl-1-tosyl-1H-indole-4-carbaldehyde and 7-methyl-5-propyl-1-tosyl-1H-indole-4-carbaldehyde

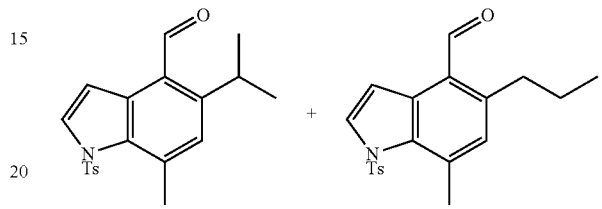

A mixture of 5-isopropyl-7-methyl-1-tosyl-1H-indole-4-carbaldehyde and 7-methyl-5-propyl-1-tosyl-1H-indole-4-carbaldehyde, isolated as a 5:1 mixture respectively, were synthesized by a coupling reaction of 5-chloro-7-methyl-1-tosyl-1H-indole-4-carbaldehyde (Example 47-F) with isopropylzinc(II) bromide following the procedure in Example 49-A. MS (ESI+) m/z 356.2 (M+H).

Example 51

Example 51-A (±)-7-Methyl-4-(((tetrahydro-2H-pyran-2-yl)oxy)methyl)-1-tosyl-5-vinyl-1H-indole

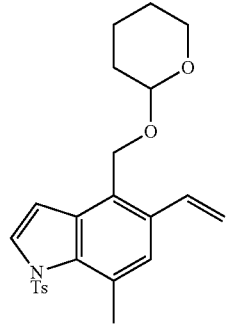 [SMILES: C=Cc1cc(C)c2c(ccn2S(=O)(=O)c2ccc(C)cc2)c1COC1CCCCO1]

To a suspension of (±)-5-chloro-7-methyl-4-(((tetrahydro-2H-pyran-2-yl)oxy)methyl)-1-tosyl-1H-indole (Example 47-D) (2.1 g, 4.8 mmol), vinylboronic anhydride pyridine complex (3.5 g, 14.5 mmol) and K$_2$CO$_3$ (6.7 g, 48.4 mmol) in toluene (10 mL)/H$_2$O (4 mL) were added Pd(OAc)$_2$ (0.22 g, 0.97 mmol) and S-Phos (CAS; 657408-07-6) (0.80 g, 1.9 mmol), and then the mixture was stirred at 90° C. under N$_2$ atmosphere for 4 h. The reaction mixture was cooled to room temperature, diluted with CH$_2$Cl$_2$ and partitioned. The organic phase was washed with H$_2$O and brine, dried over Na$_2$SO$_4$, and then filtered. Concentration of the filtrate gave a residue that was purified by SiO$_2$ column chromatography (heptane/EtOAc=95/5 to 7/3) to give the title compound. $^1$H NMR (400 MHz, ACETONITRILE-d$_3$) δ 7.78 (d, J=3.79 Hz, 1H), 7.58 (d, J=8.59 Hz, 2H), 7.26-7.38 (m, 3H), 7.13 (dd, J=11.12, 17.43 Hz, 1H), 6.95 (d, J=3.79 Hz, 1H), 5.70 (dd, J=1.26, 17.43 Hz, 1H), 5.31 (dd, J=1.26, 11.12 Hz, 1H), 4.93 (d, J=11.37 Hz, 1H), 4.72 (d, J=11.37 Hz, 1H), 4.56-4.66 (m, 1H), 3.78-3.92 (m, 1H), 3.35-3.57 (m, 1H), 2.57 (s, 3H), 2.35 (s, 3H), 1.56-1.75 (m, 2H), 1.38-1.56 (m, 4H).

Example 51-B

7-Methyl-1-tosyl-5-vinyl-1H-indole-4-carbaldehyde

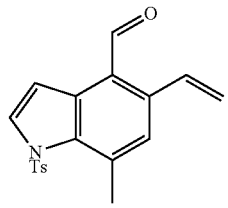 [SMILES: C=Cc1cc(C)c2c(ccn2S(=O)(=O)c2ccc(C)cc2)c1C=O]

The title compound was synthesized following Example 47-E and 47-F from (±)-7-methyl-4-(((tetrahydro-2H-pyran-2-yl)oxy)methyl)-1-tosyl-5-vinyl-1H-indole. MS (ESI+) m/z 340.1 (M+H).

Example 52

Example 52-A (±)-1-(7-Methyl-4-(((tetrahydro-2H-pyran-2-yl)oxy)methyl)-1-tosyl-1H-indol-5-yl)ethane-1,2-diol

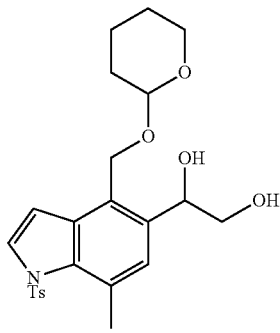 [SMILES: Cc1ccc(S(=O)(=O)n2ccc3c(COC4CCCCO4)c(C(O)CO)cc(C)c32)cc1]

To a suspension of (±)-7-methyl-4-(((tetrahydro-2H-pyran-2-yl)oxy)methyl)-1-tosyl-5-vinyl-1H-indole (1.8 g, 4.2 mmol) in tert-BuOH (70 mL)/H$_2$O (70 mL) was added AD-mix-alpha (5 g, 4.2 mmol), and then the mixture was stirred at room temperature for 24 h. The reaction was quenched by aq. Na$_2$S$_2$O$_3$, and the whole mixture was stirred for 0.25 h. The mixture was diluted with CH$_2$Cl$_2$ and partitioned. The organic phase was washed with H$_2$O and brine, dried over Na$_2$SO$_4$, filtered and concentrated. The resulting residue was purified by SiO$_2$ column chromatography (CH$_2$Cl$_2$/MeOH=94/6) to give the title compound. $^1$H NMR (400 MHz, DMSO-d$_6$) δ 7.84 (d, J=3.79 Hz, 1H), 7.62 (d, J=8.34 Hz, 2H), 7.40 (d, J=8.34 Hz, 2H), 7.18 (s, 1H), 6.95-6.98 (m, 1H), 5.14 (dd, J=3.92, 6.95 Hz, 1H), 4.69-5.03 (m, 3H), 4.52-4.68 (m, 2H), 3.74-3.92 (m, 1H), 3.44-3.55 (m, 1H), 2.46 (s, 3H), 2.34 (s, 3H), 1.34-1.74 (m, 6H).

Example 52-B (±)-7-Methyl-4-(((tetrahydro-2H-pyran-2-yl)oxy)methyl)-1-tosyl-1H-indole-5-carbaldehyde

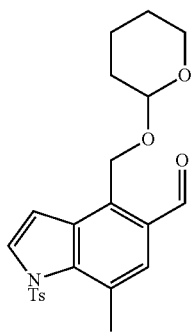 [SMILES: Cc1ccc(S(=O)(=O)n2ccc3c(COC4CCCCO4)c(C=O)cc(C)c32)cc1]

To a suspension of (±)-1-(7-methyl-4-(((tetrahydro-2H-pyran-2-yl)oxy)methyl)-1-tosyl-1H-indol-5-yl)ethane-1,2-diol (238 mg, 0.52 mmol) in THF (5 mL)/H$_2$O (1 mL) was added NaIO$_4$ (443 mg, 2.1 mmol) at 0° C., and then the mixture was stirred at 0° C. for 1.25 h. The reaction mixture was diluted with EtOAc. The bi-layer was partitioned. The organic phase was washed with half satd. Na$_2$S$_2$O$_3$, H$_2$O and brine, dried over Na$_2$SO$_4$, and then filtered. Concentration of the filtrate gave the title compound with no need of any further purification. $^1$H NMR (400 MHz, DMSO-d$_6$) δ 10.35 (s, 1H), 8.02 (d, J=4.04 Hz, 1H), 7.68 (d, J=8.59 Hz, 2H), 7.55 (s, 1H), 7.43 (d, J=8.59 Hz, 2H), 7.20 (d, J=4.04 Hz, 1H), 5.27 (d, J=11.62 Hz, 1H), 5.09 (d, J=11.62 Hz, 1H), 4.69-4.76 (m, 1H), 3.68-3.81 (m, 1H), 3.37-3.51 (m, 1H), 2.52 (s, 3H), 2.36 (s, 3H), 1.53-1.70 (m, 2H), 1.32-1.53 (m, 4H).

Example 52-C (±)-(7-Methyl-4-(((tetrahydro-2H-pyran-2-yl)oxy)methyl)-1-tosyl-1H-indol-5-yl)methanol

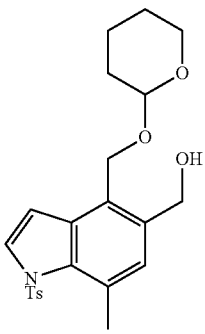 [SMILES: Cc1ccc(S(=O)(=O)n2ccc3c(COC4CCCCO4)c(CO)cc(C)c32)cc1]

A suspension of (±)-7-methyl-4-(((tetrahydro-2H-pyran-2-yl)oxy)methyl)-1-tosyl-1H-indole-5-carbaldehyde (221 mg, 0.52 mmol) and NaBH$_4$ (98 mg, 2.6 mmol) in EtOH (5 mL) was stirred at 0° C. for 0.5 h. The reaction mixture was diluted with CH$_2$Cl$_2$. The mixture was washed with H$_2$O, half satd. KHSO$_4$ aqueous solution, H$_2$O, and brine, dried over Na₂SO₄, and then filtered. Concentration of the filtrate gave the title compound, which was used in the next reaction without any further purification. ¹H NMR (400 MHz, DMSO-d₆) δ 7.83 (d, J=3.79 Hz, 1H), 7.60 (d, J=8.34 Hz, 2H), 7.38 (d, J=8.34 Hz, 2H), 7.14 (s, 1H), 6.98 (d, J=3.79 Hz, 1H), 5.01 (t, J=5.56 Hz, 1H), 4.87 (d, J=11.37 Hz, 1H), 4.67 (d, J=11.37 Hz, 1H), 4.55-4.63 (m, 3H), 3.73-3.85 (m, 1H), 3.37-3.51 (m, 1H), 2.34 (s, 3H), 2.08 (s, 3H), 1.51-1.71 (m, 2H), 1.30-1.51 (m, 4H).

Example 52-D (7-Methyl-1-tosyl-5-(((2-(trimethylsilyl)ethoxy)methoxy)methyl)-1H-indol-4-yl)methanol

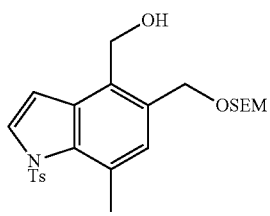

To a solution (±)-(7-methyl-4-(((tetrahydro-2H-pyran-2-yl)oxy)methyl)-1-tosyl-1H-indol-5-yl)methanol (200 mg, 0.466 mmol) and iPr₂EtN (0.16 mL, 0.93 mmol) in CH₂Cl₂ (2 mL) was added SEMCl (0.124 mL, 0.69 mmol), and then the mixture was stirred at 40° C. for 1 hr. The reaction mixture was concentrated (during the concentration, the THP group was partially removed) and then purified by SiO₂ column chromatography (heptane/EtOAc=1/0 to 1/3) to give the title compound. ¹H NMR (400 MHz, ACETONITRILE-d₃) δ 7.81 (d, J=3.79 Hz, 1H), 7.58 (d, J=8.30 Hz, 2H), 7.32 (d, J=8.30 Hz, 2H), 7.08 (s, 1H), 6.99 (d, J=3.79 Hz, 1H), 4.79 (d, J=5.81 Hz, 2H), 4.68 (s, 2H), 4.67 (s, 2H), 3.54-3.63 (m, 2H), 3.05 (t, J=5.80 Hz, 1H), 2.54 (s, 3H), 2.35 (s, 3H), 0.82-0.96 (m, 2H), 0.01 (s, 9H).

Example 52-E

7-Methyl-1-tosyl-5-(((2-(trimethylsilyl)ethoxy)methoxy)methyl)-1H-indole-4-carbaldehyde

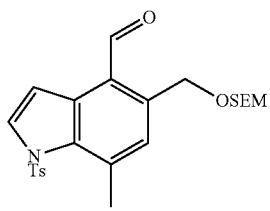

The title compound was synthesized by oxidation of (7-methyl-1-tosyl-5-(((2-(trimethylsilyl)ethoxy)methoxy)methyl)-1H-indol-4-yl)methanol as described in Example 47-F. ¹H NMR (400 MHz, DMSO-d₆) δ 10.51 (s, 1H), 8.08 (d, J=3.79 Hz, 1H), 7.64 (d, J=8.34 Hz, 2H), 7.58 (d, J=3.79 Hz, 1H), 7.41 (d, J=8.34 Hz, 2H), 7.26 (s, 1H), 4.94 (s, 2H), 4.70 (s, 2H), 3.47-3.55 (m, 2H), 2.56 (s, 3H), 2.35 (s, 3H), 0.76-0.84 (m, 2H), 0.05 (s, 9H).

Example 53

Example 53-A 2-((4-(Hydroxymethyl)-7-methyl-1-tosyl-1H-indol-5-yl)methyl)isoindoline-1,3-dione

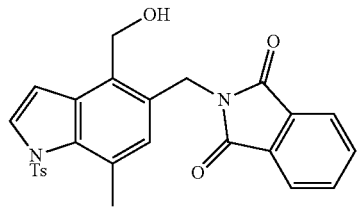 [SMILES: Cc1ccc(S(=O)(=O)n2ccc3c(CO)c(CN4C(=O)c5ccccc5C4=O)cc(C)c32)cc1]

To a solution of (±)-(7-methyl-4-(((tetrahydro-2H-pyran-2-yl)oxy)methyl)-1-tosyl-1H-indol-5-yl)methanol (Example 52-C) (210 mg, 0.49 mmol), phthalimide (144 mg, 0.98 mmol), and PPh₃ (385 mg, 1.47 mmol) in THF (5 mL) was added DIAD (0.29 mL, 1.48 mmol) at 0° C., and then the mixture was stirred at room temperature for 3.5 h. The reaction was then concentrated and partially purified by SiO₂ column chromatography (heptane/EtOAc=1/0 to 6/4). A solution of the resulting residue and 4M HCl in dioxane (4 mL) in MeOH (10 mL) was stirred at room temperature for 0.5 h. The reaction mixture was poured into 5% aq. NaHCO₃. The basic mixture was extracted with CH₂Cl₂. The organics extract was washed with H₂O and brine, dried over Na₂SO₄, and then filtered. Concentration of the filtrate gave a residue which was purified by SiO₂ column chromatography (heptane/EtOAc=6/4 to 3/7) to give the title compound. ¹H NMR (400 MHz, DMSO-d₆) δ 7.76-7.95 (m, 5H), 7.59 (d, J=8.34 Hz, 2H), 7.38 (d, J=8.34 Hz, 2H), 7.06 (d, J=4.04 Hz, 1H), 6.90 (s, 1H), 5.08 (t, J=5.31 Hz, 1H), 4.91 (s, 2H), 4.85 (d, J=5.31 Hz, 2H), 2.38 (s, 3H), 2.33 (s, 3H).

Example 53-B 5-((1,3-Dioxoisoindolin-2-yl)methyl)-7-methyl-1-tosyl-1H-indole-4-carbaldehyde

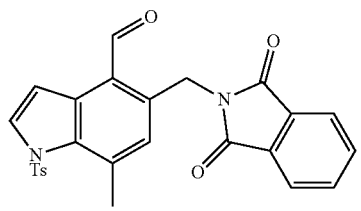 [SMILES: Cc1ccc(S(=O)(=O)n2ccc3c(C=O)c(CN4C(=O)c5ccccc5C4=O)cc(C)c32)cc1]

A suspension of 2-((4-(hydroxymethyl)-7-methyl-1-tosyl-1H-indol-5-yl)methyl)isoindoline-1,3-dione (180 mg, 0.38 mmol) and MnO₂ (165 mg, 1.9 mmol) in toluene (20 mL) was stirred at 80° C. for 11 h. The reaction mixture was cooled to room temperature. The reaction mixture was filtered off through Celite®. The Celite® cake was washed with CH₂Cl₂.

The combined filtrate was concentrated to give the title compound, with no need of further purification. MS (ESI+) m/z 473.1 (M+H).

Example 54

Example 54-A (±)-5-(Methoxymethyl)-7-methyl-4-(((tetrahydro-2H-pyran-2-yl)oxy)methyl)-1-tosyl-1H-indole

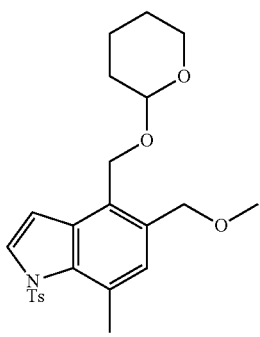 [SMILES: COCc1cc(C)c2c(ccn2S(=O)(=O)c2ccc(C)cc2)c1COC1CCCCO1]

To a solution of (±)-(7-methyl-4-(((tetrahydro-2H-pyran-2-yl)oxy)methyl)-1-tosyl-1H-indol-5-yl)methanol (Example 52-C) (170 mg, 0.40 mmol) in DMF (1 mL) was added NaH (31.7 mg, 60% in mineral oil, 0.79 mmol) at room temperature, and then the mixture was stirred for 10 min. To the mixture was added MeI (25 uL, 0.40 mmol) at room temperature, and then the mixture was stirred for 2.5 h. The reaction was quenched by half saturated aqueous solution of $KHSO_4$, and diluted with EtOAc. The bi-layer was partitioned. The organic phase was washed successively $H_2O$ and brine, dried over $Na_2SO_4$, and then filtered. Concentration of the filtrate gave the title compound, without need of any further purification. $^1$H NMR (400 MHz, DMSO-$d_6$) δ 7.86 (d, J=3.79 Hz, 1H), 7.62 (d, J=8.34 Hz, 2H), 7.39 (d, J=8.34 Hz, 2H), 7.08 (s, 1H), 6.99 (d, J=3.79 Hz, 1H), 4.87 (d, J=11.37 Hz, 1H), 4.67 (d, J=11.37 Hz, 1H), 4.60-4.64 (m, 1H), 4.44-4.54 (m, 2H), 3.73-3.86 (m, 1H), 3.41-3.52 (m, 1H), 3.30 (s, 3H), 2.47 (s, 3H), 2.34 (s, 3H), 1.51-1.78 (m, 2H), 1.34-1.51 (m, 4H).

Example 54-B 5-(Methoxymethyl)-7-methyl-1-tosyl-1H-indole-4-carbaldehyde

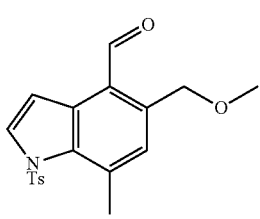 [SMILES: COCc1cc(C)c2c(ccn2S(=O)(=O)c2ccc(C)cc2)c1C=O]

The title compound was synthesized from (±)-5-(methoxymethyl)-7-methyl-4-(((tetrahydro-2H-pyran-2-yl)oxy) methyl)-1-tosyl-1H-indole following Example 47-E and 47-F. MS (ESI+) m/z 358.1 (M+H).

Example 55

Example 55-A

5-Bromo-7-methyl-1H-indole-4-carbonitrile

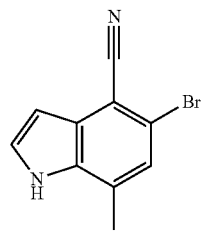

The title compound was synthesized from 2-bromo-4-methyl-5-nitrobenzonitrile (CAS; 1202858-65-8) as described in Example 47-C. MS (ES) m/z 233.1, 235.1. (M−H).

Example 55-B

5-Bromo-7-methyl-1-tosyl-1H-indole-4-carbonitrile

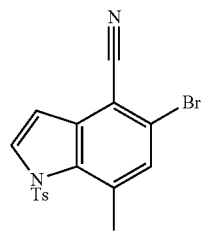 [SMILES: Cc1ccc(S(=O)(=O)n2ccc3c(C#N)c(Br)cc(C)c32)cc1]

The title compound was synthesized from 5-bromo-7-methyl-1H-indole-4-carbonitrile as described in Example 47-D. MS (ESI−) m/z 387.2, 389.2. (M−H).

Example 55-C

5-Bromo-7-methyl-1-tosyl-1H-indole-4-carbaldehyde

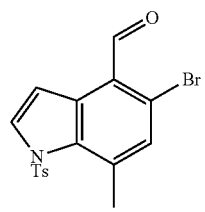 [SMILES: Cc1ccc(S(=O)(=O)n2ccc3c(C=O)c(Br)cc(C)c32)cc1]

To a solution of 5-bromo-7-methyl-1H-indole-4-carbonitrile (3.2 g, 8.2 mmol) in 80 mL of toluene (80 mL) at −78° C., diisobutylaluminium hydride in toluene solution (1M, 9.7 mL, 9.7 mmol) was added slowly. The mixture was stirred at −78° C. for 30 min, and then −60° C. for 30 min. The reaction was quenched by 1N aqueous HCl solution (10 mL) at −60° C., then was warmed to 0° C. At this point, 1N aqueous HCl (40 mL) was added. The reaction mixture was stirred for 30 min at room temperature and the organic layer was separated. The aqueous layer was extracted with ethyl acetate. The combined organic layers were dried over $Na_2SO_4$, filtered and concentrated. The resulting residue was purified by $SiO_2$ column chromatography [heptane/(30% EtOAc in $CH_2Cl_2$) =1/0 to 0/1] to give the title compound. $^1$H NMR (400 MHz, DICHLOROMETHANE-$d_2$) δ 10.47 (s, 1H), 7.95 (d, J=3.8 Hz, 1H), 7.68 (d, J=3.8 Hz, 1H), 7.54 (d, J=8.5 Hz, 2H), 7.30 (d, J=8.5 Hz, 2H), 7.27 (s, 1H), 2.59 (s, 3H), 2.38 (s, 3H).

Example 56

Intermediate 2

Example 56-A 4,5-Diamino-2-fluorobenzonitrile

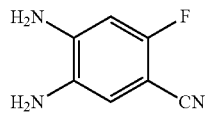

To a solution of 2,4-difluoro-5-nitrobenzonitrile (CAS #: 67152-20-9) (5.0 g, 27.2 mmol) in EtOH (100 mL) was added $NH_4OH$ (100 mL) slowly at room temperature. The mixture was stirred for 30 min, then concentrated under reduced pressure to about 100 mL. The yellow product was filtered and washed with water, and then dried. To a solution of the residue (3.96 g, 22 mmol) in EtOAc (150 mL) and acetic acid (25 mL) was added zinc (14.3 g, 219 mmol). The mixture was stirred at room temperature for 2 hour. The reaction mixture was diluted with EtOAc and filtered through a pad of Celite®. The Celite® pad was washed with EtOAc. The filtrate was concentrated, and the residue was dissolved in MeOH (50 mL) and $NH_4OH$ (100 mL). The mixture was then concentrated to around 100 mL and the mixture was left standing at room temperature overnight. The precipitate was filtered and washed with water, and then dried to give the title compound. MS (ESI+) m/z 152.1 (M+H).

Example 56-B

6-Fluoro-1-((2-(trimethylsilyl)ethoxy)methyl)-1H-benzo[d]imidazole-5-carbonitrile and 5-fluoro-1-((2-(trimethylsilyl)ethoxy)methyl)-1H-benzo[d]imidazole-6-carbonitrile

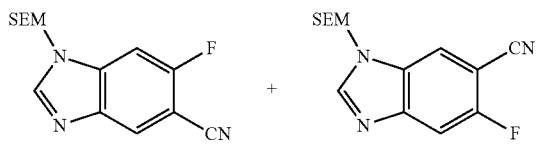 [SMILES: C[Si](C)(C)CCOCn1cnc2cc(C#N)c(F)cc21 ; C[Si](C)(C)CCOCn1cnc2cc(F)c(C#N)cc21]

A solution of 4,5-diamino-2-fluorobenzonitrile (2.4 g, 15.9 mmol) in formic acid (40 mL) was heated to reflux for 2 hours. The reaction was concentrated. MS (ESI+) m/z 152.1 (M+H).

To a solution of the residue (15.9 mmol) obtained above in DMF (40 mL) was added NaH (60%, 3.2 g, 79 mmol) at 0° C. The mixture was stirred at 0° C. for 1 hour. Then 2-(trimethylsilyl)ethoxy)methylchloride (3.1 mL, 17.5 mmol) was added. The mixture was stirred at 0° C. for another 2 hours. MeOH (20 mL) was added to the mixture. The mixture was diluted with $Et_2O$. The organic layer was separated and washed with water and brine, dried over $Na_2SO_4$, and filtered. Concentration of the filtrate gave a residue, which was purified by flash column chromatography (0% to 100% EtOAc in heptane) to give a mixture of title compounds. $^1$H NMR (400 MHz, METHANOL-d4) δ 8.57 (s, 1H), 8.49 (s, 1H), 8.13-8.17 (m, 1H), 8.11 (d, J=5.56 Hz, 1H), 7.69 (d, J=8.84 Hz, 1H), 7.63 (d, J=9.60 Hz, 1H), 5.69 (d, J=10.99 Hz, 4H), 3.50-3.65 (m, 4H), 0.83-0.96 (m, 4H)-0.06 (s, 18H).

Example 57

Intermediate 3

Example 57-A

N-(3-cyano-2-methyl-6-nitrophenyl)acetamide

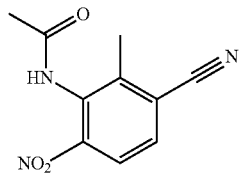 [SMILES: CC(=O)Nc1c([N+](=O)[O-])ccc(C#N)c1C]

To a solution of N-(3-cyano-2-methylphenyl)acetamide (CAS #: 70946-79-1) (1.8 g, 10.33 mmol) in conc. sulfuric acid (20 mL) at –10° C., potassium nitrate (2.08 g, 20.67 mmol) in 5 mL of conc. sulfuric acid was added slowly. After addition, the reaction was stirred at –10° C. for 30 min, then at 0° C. for 3.5 hr. The reaction mixture was poured onto ice, and then the precipitate was collected by filtration. The solid was washed with water and then purified by silica gel flash column chromatography (heptanes/EtOAc=1/0 to 1/1) to give the title compound. MS (ESI–) m/z 218.0 (M–H).

Example 57-B

3-Amino-2-methyl-4-nitrobenzonitrile

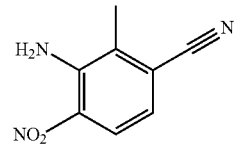

N-(3-cyano-2-methyl-6-nitrophenyl)acetamide (0.37 g, 1.7 mmol) was added to a 2N aq. $H_2SO_4$ solution (10 mL). The reaction was heated to 100° C. for 6 hr. The reaction mixture was cooled to rt and poured into iced water. The solid precipitate was collected by filtration, and then washed with water several times to give the title compound. MS (ESI–) m/z 176.1 (M–H).

Example 57-C 3,4-Diamino-2-methylbenzonitrile

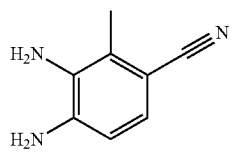

To a solution of 3-amino-2-methyl-4-nitrobenzonitrile (250 mg, 1.41 mmol) in methanol (15 mL), palladium-activated carbon ethylene diamine complex (255 mg, 3.5%-6.5% Pd, 0.071 mmol) was added. The reaction was stirred at rt under hydrogen atmosphere for 2 hr. The catalyst was removed by filtration through Celite® pad. The Celite® pad was washed with MeOH. The collected filtrate was concentrated to give the title compound. MS (ESI+) m/z 148.0 (M+H).

Example 58

Example 58-A 4-(2,2-Dibromovinyl)-5,7-dimethyl-1-tosyl-1H-indole

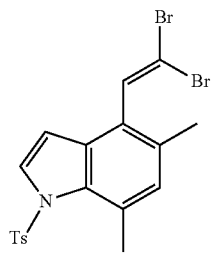 [SMILES: Cc1ccc(S(=O)(=O)n2ccc3c(C=C(Br)Br)c(C)cc(C)c32)cc1]

To a solution of 5,7-dimethyl-1-tosyl-1H-indole-4-carbaldehyde (Example 46-D) (1.5 g, 4.58 mmol) and CBr$_4$ (3.04 g, 9.16 mmol) in CH$_2$Cl$_2$ (50 mL) was added PPh$_3$ (3.61 g, 13.74 mmol) at 0° C., and then the mixture was stirred at room temperature for 1 hr. The reaction mixture was directly purified by silica gel flash chromatography (heptanes/EtOAc=1/0 to 1/1) to give the title compound. MS (ESI+) m/z 483.9, 485.9, 481.9, 487.1 (M+H).

Example 58-B 2-((5,7-dimethyl-1-tosyl-1H-indol-4-yl)methyl)-1H-benzo[d]imidazole-5-carbonitrile

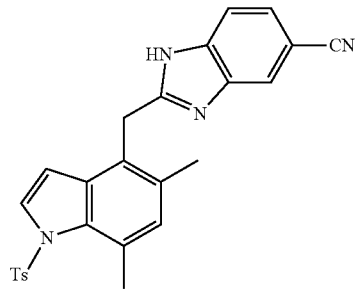 [SMILES: Cc1ccc(S(=O)(=O)n2ccc3c(Cc4nc5cc(C#N)ccc5[nH]4)c(C)cc(C)c32)cc1]

A solution of 4-(2,2-dibromovinyl)-5,7-dimethyl-1-tosyl-1H-indole (130 mg, 0.269 mmol), 3,4-diaminobenzonitrile (46.6 mg, 0.350 mmol), and DABCO (75 mg, 0.673 mmol) in NMP (0.5 mL) was stirred at 100° C. for 19 h. The reaction mixture was cooled to room temperature. The reaction mixture was concentrated and purified by silica gel flash column chromatography (heptanes/EtOAc=1/3 to 0/1) to give the title compound. MS (ESI+) m/z 455.2 (M+H).

Example 58-C 2-((5,7-Dimethyl-1H-indol-4-yl)methyl)-1H-benzo[d]imidazole-5-carbonitrile

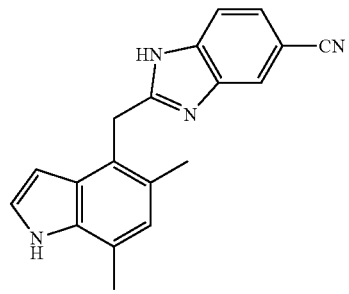 [SMILES: Cc1cc(C)c2[nH]ccc2c1Cc1nc2cc(C#N)ccc2[nH]1]

A mixture of 2-((5,7-dimethyl-1-tosyl-1H-indol-4-yl)methyl)-1H-benzo[d]imidazole-5-carbonitrile (370 mg, 0.814 mmol), KOH (457 mg, 8.14 mmol), and isoamylamine (1.892 mL, 16.28 mmol) in EtOH (15 mL) was stirred at 100° C. under microwave irradiation for 2 hr. The reaction mixture was diluted with CH$_2$Cl$_2$. The mixture was filtered through SiO$_2$ pad. The SiO$_2$ cake was washed with a mixture of CH$_2$Cl$_2$/MeOH (c.a. 6/1). The organic solution was concentrated and purified by silica gel flash column chromatography [(5% 2,2,2-trifluoroethanol in CH$_2$Cl$_2$)/MeOH=1/0 to 85/15] to give the title compound. $^1$H NMR (400 MHz, DMSO-d$_6$, with about 5 μL TFA) δ ppm 11.01 (br. s., 1H), 8.05 (s, 1H), 7.67 (br. d, J=8.30 Hz, 1H), 7.62 (br. d, J=8.30 Hz, 1H), 7.26 (t, J=2.80 Hz, 1H), 6.79 (s, 1H), 6.43 (dd, J=1.80, 2.80 Hz, 1H), 4.53 (s, 2H), 2.43 (s, 3H), 2.35 (s, 3H). HRMS calcd. for C$_{19}$H$_{16}$N$_4$ (M+H)$^+$ 301.1448. found 301.1459.

Example 59

Example 59-A 2-((7-Methyl-1-tosyl-5-(((2-(trimethylsilyl)ethoxy)methoxy)methyl)-1H-indol-4-yl)methyl)-1H-benzo[d]imidazole-5-carbonitrile

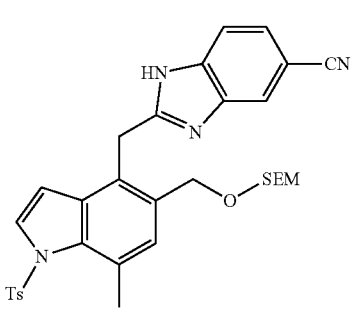 [SMILES: Cc1ccc(S(=O)(=O)n2ccc3c(Cc4nc5cc(C#N)ccc5[nH]4)c(COCOCC[Si](C)(C)C)cc(C)c32)cc1]

The title compound was synthesized from 7-methyl-1-tosyl-5-(((2-(trimethylsilyl)ethoxy)methoxy)methyl)-1H-indole-4-carbaldehyde (Example 52-A) analogously to Example 58-B. MS (ESI+) m/z 601.3 (M+H).

Example 59-B 2-((5-(Hydroxymethyl)-7-methyl-1-tosyl-1H-indol-4-yl)methyl)-1H-benzo[d]imidazole-5-carbonitrile

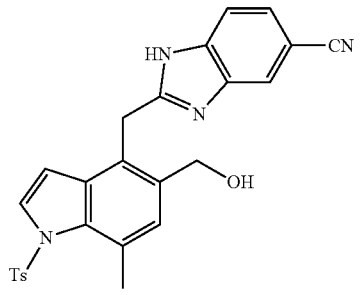 [SMILES: Cc1ccc(S(=O)(=O)n2ccc3c(Cc4nc5cc(C#N)ccc5[nH]4)c(CO)cc(C)c32)cc1]

To a solution of 2-((7-methyl-1-tosyl-5-(((2-(trimethylsilyl)ethoxy)methoxy)methyl)-1H-indol-4-yl)methyl)-1H-benzo[d]imidazole-5-carbonitrile (133 mg, 0.221 mmol) in CH$_2$Cl$_2$ (10 mL) was added BF$_3$-OEt$_2$ (0.084 mL, 0.664 mmol) at 0° C. The whole mixture was stirred at 0° C. for 1.5 h, and then at room temperature for 2.5 h. The reaction was quenched by 5% aq. NaHCO$_3$ and stirred for 0.5 h. The layers were separated and the aqueous layer was extracted with CH$_2$Cl$_2$. The organic layers were combined and washed with H$_2$O and brine, dried over Na$_2$SO$_4$, and filtered. Concentration of the filtrate gave the title compound, without need of further purification. MS (ESI+) m/z 471.1 (M+H).

Example 59-C 2-((5-(Hydroxymethyl)-7-methyl-1H-indol-4-yl)methyl)-1H-benzo[d]imidazole-5-carbonitrile

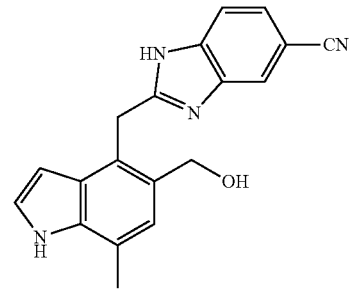 [SMILES: Cc1cc(CO)c(Cc2nc3cc(C#N)ccc3[nH]2)c2cc[nH]c12]

The title compound was synthesized by a deprotection of 2-((5-(hydroxymethyl)-7-methyl-1-tosyl-1H-indol-4-yl)methyl)-1H-benzo[d]imidazole-5-carbonitrile analogously to Example 58-C. $^1$H NMR (400 MHz, DMSO-d$_6$ with about 5 µL TFA) δ ppm 11.10 (br. s., 1H), 8.08 (s, 1H), 7.69 (d, J=8.60 Hz, 1H), 7.62 (dd, J=1.50, 8.60 Hz, 1H), 7.30 (dd, J=2.80, 3.00 Hz, 1H), 6.97 (s, 1H), 6.53 (dd, J=1.77, 3.03 Hz, 1H), 4.67 (s, 2H), 4.63 (s, 2H), 2.45 (s, 3H). HRMS calcd. for C$_{13}$H$_{16}$N$_4$O (M+H)$^+$ 317.1397. found 317.1407.

Example 60

Example 60-A 2-((5-((1,3-Dioxoisoindolin-2-yl)methyl)-7-methyl-1-tosyl-1H-indol-4-yl)methyl)-1H-benzo[d]imidazole-5-carbonitrile

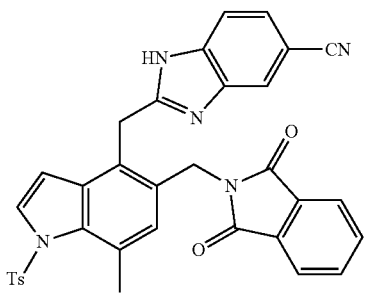 [SMILES: Cc1ccc(S(=O)(=O)n2ccc3c(Cc4nc5cc(C#N)ccc5[nH]4)c(CN4C(=O)c5ccccc5C4=O)cc(C)c32)cc1]

The title compound was synthesized from 5-((1,3-dioxoisoindolin-2-yl)methyl)-7-methyl-1-tosyl-1H-indole-4-carbaldehyde (Example 53-B) analogously to Example 58-B. MS (ESI+) m/z 600.1 (M+H).

Example 60-B 2-((5-(Aminomethyl)-7-methyl-1H-indol-4-yl)methyl)-1H-benzo[d]imidazole-5-carbonitrile

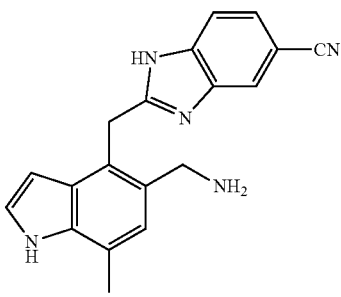

A mixture of 2-((5-((1,3-dioxoisoindolin-2-yl)methyl)-7-methyl-1-tosyl-1H-indol-4-yl)methyl)-1H-benzo[d]imidazole-5-carbonitrile (60 mg, 0.100 mmol) and hydrazine hydrate (5.01 mg, 0.100 mmol) in EtOH (2 mL) was stirred at 100° C. under microwave irradiation for 0.5 hr. To the mixture was added KOH (56.1 mg, 1.001 mmol), and then the mixture was stirred at 100° C. under the microwave irradiation for 1.75 h. The reaction mixture was diluted with CH$_2$Cl$_2$/2,2,2-trifluoroethanol (c.a. 9/1). The layers were separated and the organic layer was washed successively by H$_2$O and brine, dried over Na$_2$SO$_4$, and filtered. After concentration, the residue was purified by silica gel flash column chromatography (CH$_2$Cl$_2$/2M NH$_3$ in MeOH=94/6) to give the title compound. $^1$H NMR (400 MHz, DMSO-d$_6$ with about 5 µL TFA) δ ppm 11.28 (br. s., 1H), 8.53 (br. s., 3H), 8.09 (s, 1H), 7.68 (d, J=8.34 Hz, 1H), 7.55 (dd, J=1.00, 8.30 Hz, 1H), 7.38 (t, J=2.80 Hz, 1H), 7.06 (s, 1H), 6.76-6.84 (m, 1H), 4.61 (s, 2H),

Example 61

N-((4-((5-cyano-1H-benzo[d]imidazol-2-yl)methyl)-7-methyl-1H-indol-5-yl)methyl)acetamide

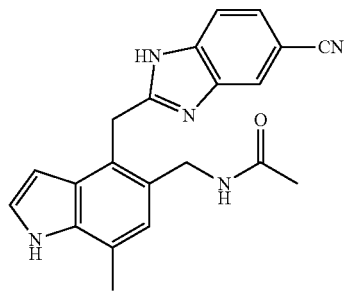 [SMILES: CC(=O)NCc1cc(C)c2[nH]ccc2c1Cc1nc2cc(C#N)ccc2[nH]1]

To a mixture of 2-((5-(aminomethyl)-7-methyl-1H-indol-4-yl)methyl)-1H-benzo[d]imidazole-5-carbonitrile (20 mg, 0.063 mmol) in CH$_2$Cl$_2$ (1 mL)/5% aq. NaHCO$_3$ (2 mL) was added acetyl chloride (45 µL, 0.634 mmol), and then the mixture was stirred at room temperature for 1 hr. The reaction was quenched by methylamine in EtOH (33%, 2 mL), and then stirred for 0.5 h. The layers were separated and the aqueous layer was extracted with CH$_2$Cl$_2$. The combined organics were washed with H$_2$O and brine, dried over Na$_2$SO$_4$, and filtered. After concentration the residue was purified by silica gel flash column chromatography (CH$_2$Cl$_2$/2M NH$_3$ in MeOH=94/6) to give the title compound. $^1$H NMR (400 MHz, DMSO-d$_6$ with about 5 µL TFA) δ ppm 11.16 (br. s., 1H), 8.47 (t, J=5.31 Hz, 1H), 8.10 (s, 1H), 7.69 (d, J=8.30 Hz, 1H), 7.65 (dd, J=1.00, 8.30 Hz, 1H), 7.30 (dd, J=2.80, 3.00 Hz, 1H), 6.91 (s, 1H), 6.49 (dd, J=1.80, 3.00 Hz, 1H), 4.64 (s, 2H), 4.42 (d, J=5.31 Hz, 2H), 2.45 (s, 3H), 1.79 (s, 3H). HRMS calcd. for C$_{21}$H$_{19}$N$_5$O (M+H)$^+$ 358.1662. found 358.1660.

Example 62

Example 62-A

5-Bromo-2-((5,7-dimethyl-1H-indol-4-yl)methyl)-7-fluoro-1H-benzo[d]imidazole

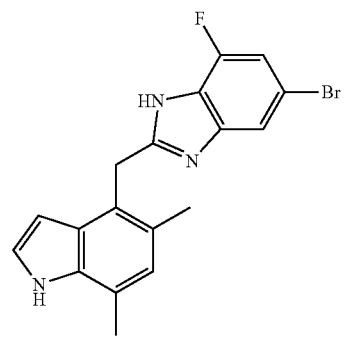 [SMILES: Cc1cc(C)c2[nH]ccc2c1Cc1nc2cc(Br)cc(F)c2[nH]1]

The title compound was synthesized using 5-bromo-3-fluorobenzene-1,2-diamine (CAS: 517920-69-3) analogously to Example 58-B. MS (ESI+) m/z 372.0, 374.0 (M+H).

Example 62-B 2-((5,7-Dimethyl-1H-indol-4-yl)methyl)-7-fluoro-1H-benzo[d]imidazole-5-carbonitrile

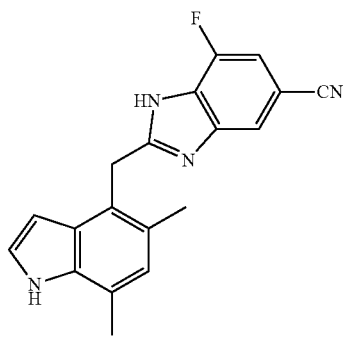 [SMILES: Cc1cc(C)c2[nH]ccc2c1Cc1nc2cc(C#N)cc(F)c2[nH]1]

Zinc cyanide (44 mg, 0.375 mmol) was weighed into a 50 mL flask, a degassed solution of 5-bromo-2-((5,7-dimethyl-1H-indol-4-yl)methyl)-7-fluoro-1H-benzo[d]imidazole (45 mg, 0.121 mmol) in DMF (4 mL) was added followed by Pd(Ph$_3$P)$_4$ (14 mg, 0.012 mmol). The reaction mixture was heated at 120° C. for 2 hours. Additional portions of zinc dust, dppf, and Pd$_2$(dba)$_3$ were added followed by heating to 130° C. until no starting material remained by LC-MS. The reaction was diluted with EtOAc and a saturated solution of NaHCO$_3$, then filtered through a Celite® pad. The filtrate was extracted with EtOAc. The combined organic layers were dried over Na$_2$SO$_4$, filtered and concentrated to dryness. The residue was purified by reverse phase HPLC (HC-B) to afford the title compound. $^1$H NMR (400 MHz, DMSO-d6) δ ppm 10.98 (br. s., 1H) 7.78 (s, 1H) 7.52-7.67 (m, 1H) 7.48 (d, J=10.61 Hz, 1H) 7.24 (t, J=2.78 Hz, 1H) 6.76 (s, 1H) 6.46 (dd, J=3.03, 2.02 Hz, 1H) 4.44 (s, 2H) 2.41 (s, 3H) 2.36 (s, 3H). HRMS calculated for C$_{19}$H$_{15}$FN$_4$(M+H)$^+$ 319.1354. found 319.1361.

Example 63

The following compounds were prepared with similar method as described in Example 58 using the appropriate aldehydes and dianilines.

| Structure/Chemical Name | $^1$H NMR | HRMS |
|---|---|---|
| 63-A 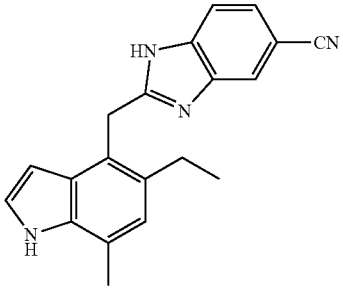<br>2-((5-ethyl-7-methyl-1H-indol-4-yl)methyl)-1H-benzo[d]imidazole-5-carbonitrile | (400 MHz, ACETONITRILE-$d_3$ with about 5 μL TFA) δ ppm 9.34 (br. s., 1H), 7.95 (dd, J = 0.84, 1.39 Hz, 1H), 7.67 (dd, J = 0.84, 8.50 Hz, 1H), 7.63 (dd, J = 1.40, 8.50 Hz, 1H), 7.24 (dd, J = 2.90, 3.03 Hz, 1H), 6.92 (s, 1H), 6.39 (dd, J = 2.02, 3.03 Hz, 1H), 4.69 (s, 2H), 2.70 (q, J = 7.58 Hz, 2H), 2.48 (d, J = 0.63 Hz, 3H), 1.12 (t, J = 7.58 Hz, 3H). | calcd. for $C_{20}H_{18}N_4$ $(M + H)^+$ 315.1604, found 315.1601. |
| 63-B 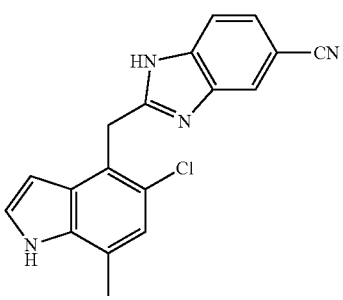<br>2-((5-chloro-7-methyl-1H-indol-4-yl)methyl)-1H-benzo[d]imidazole-5-carbonitrile | (400 MHz, DMSO-$d_6$ with about 5 μL TFA) δ ppm 11.33 (br. s., 1H), 7.96 (s, 1H), 7.59 (d, J = 8.30 Hz, 1H), 7.51 (d, J = 8.30 Hz, 1H), 7.36 (dd, J = 2.50, 2.80 Hz, 1H), 6.99 (s, 1H), 6.48 (dd, J = 2.00, 2.50 Hz, 1H), 4.58 (s, 2H), 2.47 (s, 3H). TFA) | calcd. for $C_{18}H_{13}ClN_4$ $(M + H)^+$ 321.0902, found 321.0909. |
| 63-C 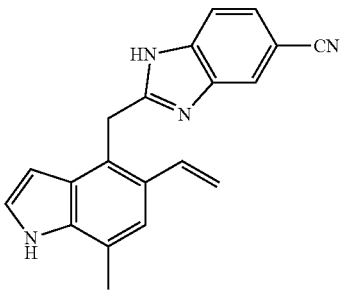<br>2-((5-vinyl-7-methyl-1H-indol-4-yl)methyl)-1H-benzo[d]imidazole-5-carbonitrile | (400 MHz, ACETONITRILE-$d_3$) δ ppm 9.48 (br. s., 1H), 7.92 (s, 1H), 7.65 (d, J = 8.60 Hz, 1H), 7.59-7.64 (m, 1H), 7.29 (s, 1H), 7.26 (dd, J = 2.80, 3.03 Hz, 1H), 7.07 (dd, J = 11.12, 17.25 Hz, 1H), 6.51 (dd, J = 2.02, 3.03 Hz, 1H), 5.64 (dd, J = 1.06, 17.25 Hz, 1H), 5.18 (dd, J = 1.06, 11.12 Hz, 1H), 4.76 (s, 2H), 2.50 (s, 3H). | calcd. for $C_{20}H_{16}N_4$ $(M + H)^+$ 313.1448, found 313.1454. |
| 63-D 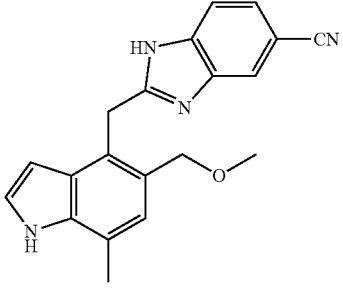<br>2-((5-methoxymethyl-7-methyl-1H-indol-4-yl)methyl)-1H-benzo[d]imidazole-5-carbonitrile | (400 MHz, DMSO-$d_6$ with about 5 μL TFA) δ ppm 11.27 (br. s., 1H), 8.19 (s, 1H), 7.77 (br. s., 2H), 7.37 (dd, J = 2.80, 3.00 Hz, 1H), 6.96 (s, 1H), 6.51 (dd, J = 2.02, 3.03 Hz, 1H), 4.72 (s, 2H), 4.53 (s, 2H), 3.10 (s, 3H), 2.49 (s, 3H). | calcd. for $C_{20}H_{18}N_4O$ $(M + H)^+$ 331.1553, found 331.1561. |

-continued

| Structure/Chemical Name | ¹H NMR | HRMS |
|---|---|---|
| 63-E 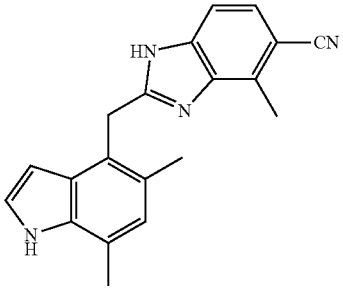<br>2-((5,7-dimethyl-1H-indol-4-yl)methyl)-4-methyl-1H-benzo[d]imidazole-5-carbonitrile | (400 MHz, DMSO-$d_6$) δ ppm 12.20 (br. s., 1H), 10.96 (br. s., 1H), 7.27-7.45 (m, 2H), 7.23 (br. s., 1H), 6.76 (s, 1H), 6.46 (dd, J = 3.2, 1.9 Hz, 1H), 4.41 (s, 2H), 2.66 (s, 3H), 2.41 (s, 3H), 2.37 (s, 3H). | calcd. for $C_{20}H_{18}N_4$ $(M + H)^+$ 315.1610, found 315.1614 |
| 63-F 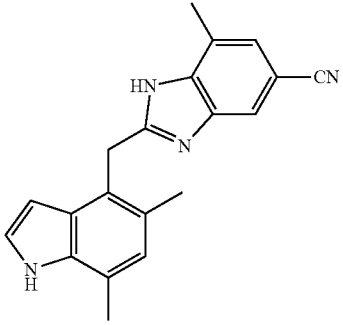<br>2-((5,7-dimethyl-1H-indol-4-yl)methyl)-7-methyl-1H-benzo[d]imidazole-5-carbonitrile | (400 MHz, DMSO-$d_6$) δ ppm 10.83-10.98 (m, 1H), 7.58-7.81 (m, 1H), 7.29 (d, J = 8.1 Hz, 1H), 7.21 (dt, J = 13.2, 2.9 Hz, 1H), 6.75 (d, J = 11.6 Hz, 1H), 6.41-6.49 (m, 1H), 4.41 (d, J = 16.2 Hz, 2H), 2.41 (d, J = 5.6 Hz, 3H), 2.38 (s, 3H), 2.35 (s, 3H). | calcd. for $C_{20}H_{18}N_4$ $(M + H)^+$ 315.1604, found 315.1610. |
| 63-G 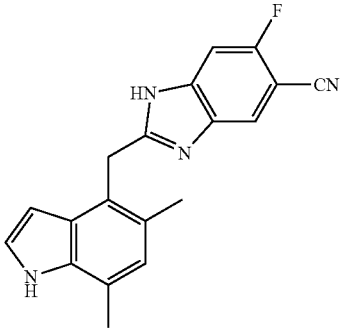<br>2-((5,7-dimethyl-1H-indol-4-yl)methyl)-6-fluoro-1H-benzo[d]imidazole-5-carbonitrile | (400 MHz, ACETONITRILE-$d_3$) δ 9.26 (br. s., 1H), 7.77 (d, J = 4.42 Hz, 1H), 7.30 (d, J = 9.85 Hz, 1H), 7.22 (t, J = 2.91 Hz, 1H), 6.85 (s, 1H), 6.45 (dd, J = 2.02, 3.16 Hz, 1H), 4.47 (s, 2H), 2.45 (s, 3H), 2.35 (s, 3H). | calcd. for $C_{19}H_{15}FN_4$ $(M + H)^+$ 319.1354, found 319.1352. |
| 63-H 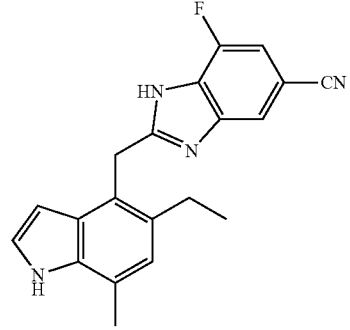<br>2-((5-ethyl-7-methyl-1H-indol-4-yl)methyl)-6-fluoro-1H-benzo[d]imidazole-5-carbonitrile | (400 MHz, ACETONITRILE-$d_3$) δ 9.17 (br. s., 1H), 7.66 (d, J = 5.68 Hz, 1H), 7.19 (d, J = 9.85 Hz, 1H), 7.12 (s, 1H), 6.79 (s, 1H), 6.33 (dd, J = 2.02, 3.16 Hz, 1H), 4.39 (s, 2H), 2.63 (q, J = 7.58 Hz, 2H), 2.37 (d, J = 0.63 Hz, 3H), 1.02 (t, J = 7.58 Hz, 3H). | calcd. for $C_{20}H_{17}FN_4$ $(M + H)^+$ 333.151, found 333.1512. |

| Structure/Chemical Name | ¹H NMR | HRMS |
|---|---|---|
| 63-I 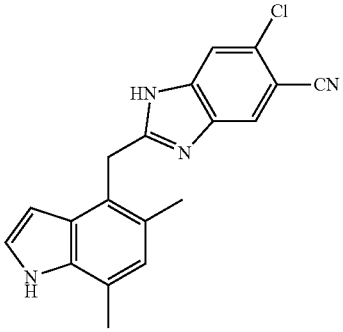 6-chloro-2-((5,7-dimethyl-1H-indol-4-yl)methyl)-1H-benzo[d]imidazole-5-carbonitrile | (400 MHz, DMSO-$d_6$) δ ppm 12.56 (br. s., 1H), 10.97 (br. s., 1H), 8.06 (br. s., 1H), 7.73 (br. s., 1H), 7.23 (t, J = 2.8 Hz, 1H), 6.75 (s, 1H), 6.45 (dd, J = 3.0, 1.8 Hz, 1H), 4.42 (s, 2H), 2.41 (s, 3H), 2.34 (s, 3H). | calcd. for $C_{19}H_{15}ClN_4$ $(M + H)^+$ 335.1058, found 335.1060. |
| 63-J 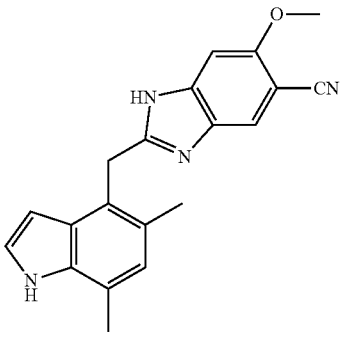 2-((5,7-dimethyl-1H-indol-4-yl)methyl)-6-methoxy-1H-benzo[d]imidazole-5-carbonitrile | (400 MHz, DMSO-$d_6$) δ ppm 11.02 (br. s., 1H), 7.94 (s, 1H), 7.26 (dd, J = 2.70, 3.00 Hz, 1H), 7.21 (s, 1H), 6.79 (s, 1H), 6.41 (dd, J = 1.77, 3.03 Hz, 1H), 4.51 (s, 2H), 3.91 (s, 3H), 2.43 (s, 3H), 2.34 (s, 3H). | calcd. for $C_{20}H_{18}N_4O$ $(M + H)^+$ 331.1554, found 331.1559. |

Example 64

Example 64-A (±)-2-((5,7-Dimethyl-1-tosyl-1H-indol-4-yl)(hydroxy)methyl)-1-((2-(trimethylsilyl)ethoxy)methyl)-1H-benzo[d]imidazole-5-carbonitrile and (±)-2-((5,7-dimethyl-1-tosyl-1H-indol-4-yl)(hydroxy)methyl)-1-((2-(trimethylsilyl)ethoxy)methyl)-1H-benzo[d]imidazole-6-carbonitrile

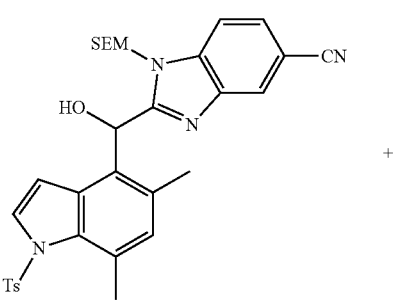

+

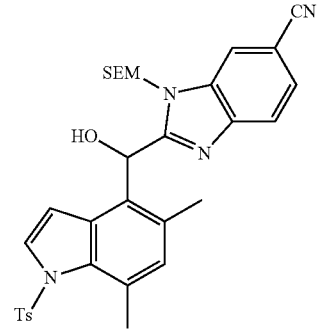

To a solution of 1-((2-(trimethylsilyl)ethoxy)methyl)-1H-benzo[d]imidazole-5-carbonitrile and 1-((2-(trimethylsilyl)ethoxy)methyl)-1H-benzo[d]imidazole-6-carbonitrile (110 mg, 0.402 mmol) in THF (2 mL), 2 M LDA in heptane/THF/ethylbenzene (0.221 mL, 0.443 mmol) was added at −78° C. After stirring for 45 min., a solution of 5,7-dimethyl-1-tosyl-1H-indole-4-carbaldehyde (Example 46-D) (132 mg, 0.402 mmol) in THF (2 mL) was added to the reaction mixture at the same temperature. After stirring for 1 h, the reaction mixture was diluted with MeOH (0.1 mL), aq. NH$_4$Cl (0.5 mL), brine (3 mL) and EtOAc (5 mL). The layers were separated and the aqueous layer was extracted with EtOAc. The organic layer was washed with brine, dried over Na$_2$SO$_4$, filtered, and concentrated. The residue was purified by flash column chromatography on silica gel (CH$_2$Cl$_2$/MeOH=100:0 to 50:50) to give title compounds as a mixture. MS (ESI+) m/z 601.1 (M+H).

Example 64-B (±)-2-((5,7-Dimethyl-1-tosyl-1H-indol-4-yl)(hydroxy)methyl)-1H-benzo[d]imidazole-5-carbonitrile

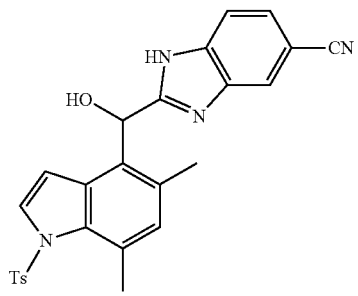 [SMILES: Cc1ccc(S(=O)(=O)n2ccc3c(C(O)c4nc5cc(C#N)ccc5[nH]4)c(C)cc(C)c32)cc1]

To a solution of (±)-2-((5,7-dimethyl-1-tosyl-1H-indol-4-yl)(hydroxy)methyl)-1-((2-(trimethylsilyl)ethoxy)methyl)-1H-benzo[d]imidazole-5-carbonitrile and (±)-2-((5,7-dimethyl-1-tosyl-1H-indol-4-yl)(hydroxy)methyl)-1-((2-(trimethylsilyl)ethoxy)methyl)-1H-benzo[d]imidazole-6-carbonitrile (90 mg, 0.150 mmol) in CH$_2$Cl$_2$ (1.5 mL), BF$_3$.OEt$_2$ (0.095 mL, 0.749 mmol) was added at 0° C. After stirring for 5 min., the mixture was warmed to room temperature. After stirring for 1 h, the reaction mixture was diluted with 2M aq. Na$_2$CO$_3$ and EtOAc. The layers were separated and the aqueous layer was extracted with EtOAc. The combined organic layers were washed with brine, dried over Na$_2$SO$_4$, filtered, and concentrated to give the title compound, without need of further purification. MS (ESI+) m/z 471 (M+H).

Example 64-C a) (±)-2-((5,7-Dimethyl-1H-indol-4-yl)(hydroxy)methyl)benzo[d]imidazole-5-carbonitrile

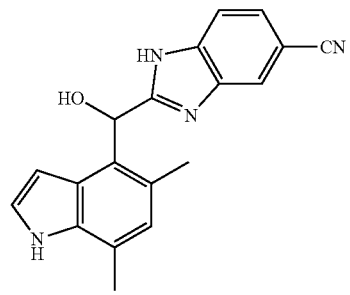 [SMILES: Cc1cc(C)c2[nH]ccc2c1C(O)c1nc2cc(C#N)ccc2[nH]1]

A mixture of (±)-2-((5,7-dimethyl-1-tosyl-1H-indol-4-yl)(hydroxy)methyl)-1H-benzo[d]imidazole-5-carbonitrile, KOH (84 mg, 1.50 mmol) and isoamylamine (0.35 mL, 3 mmol) in EtOH (1.5 mL) was heated at 100° C. for 1 h under the microwave irradiation. The reaction mixture was concentrated. The residue was diluted with CH$_2$Cl$_2$ and brine. The layers were separated and the aqueous layer was extracted with CH$_2$Cl$_2$. The combined organic extracts were dried over NaSO$_3$, filtered and evaporated. The resulting residue was purified by flash column chromatography on NH-modified silica gel (CH$_2$Cl$_2$:MeOH=100:0 to 10:1) to give the title compound. $^1$H NMR (400 MHz, DMSO-d$_6$) δ ppm 12.90 (br.s, 1H) 10.84 (s, 1H) 7.87-7.91 (m, 1H) 7.56-7.61 (m, 1H) 7.45-7.50 (m, 1H) 7.14 (t, J=2.65 Hz, 1H) 6.71 (s, 1H) 6.44-6.45 (m, 1H) 6.35-6.36 (m, 1H) 2.43 (s, 3H) 2.39 (s, 3H). HRMS calcd. for C$_{22}$H$_{20}$N$_5$O (M+H)$^+$ 317.1397. found 317.1404.

b) (+) and (−)-2-((5,7-dimethyl-1H-indol-4-yl)(hydroxy)methyl)benzo[d]imidazole-5-carbonitrile Resolution of the enantiomers of 2-((5,7-dimethyl-1H-indol-4-yl)(hydroxy)methyl)benzo[d]imidazole-5-carbonitrile was achieved by chiral HPLC using a CHIRALCEL® OD-H column with 20% MeOH and 20% EtOH in heptane to give (+)-2-((5,7-dimethyl-1H-indol-4-yl)(hydroxy)methyl)benzo[d]imidazole-5-carbonitrile (t$_r$=4.8 min) and (−)-2-((5,7-dimethyl-1H-indol-4-yl)(hydroxy)methyl)benzo[d]imidazole-5-carbonitrile (t$_r$=9.3 min).

Example 65

Example 65-A 7-(±)-Methyl-4-(((tetrahydro-2H-pyran-2-yl)oxy)methyl)-1-tosyl-5-(((triisopropylsilyl)oxy)methyl)-1H-indole

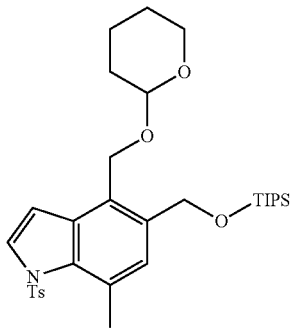

To a solution of (±)-(7-methyl-4-(((tetrahydro-2H-pyran-2-yl)oxy)methyl)-1-tosyl-1H-indol-5-yl)methanol (Example 52-C) (1 g, 2.30 mmol) in DMF (10 mL) was added imidazole (239 mg, 3.51 mmol), followed by TIPSCl (0.496 mL, 2.339 mmol). The whole mixture was stirred at room temperature for 24 h. The reaction was then quenched by MeOH. The mixture was then stirred at room temperature for 0.25 h. The mixture was then diluted with EtOAc. The organic phase was successively washed with H$_2$O and brine, dried over Na$_2$SO$_4$, filtered, and concentrated. The resulting residue was purified by SiO$_2$ chromatography (heptane/EtOAc=1/0 to 7/3) to afford the title compound. $^1$H NMR (400 MHz, ACETONITRILE-d$_3$) δ 7.76 (d, J=3.92 Hz, 1H), 7.56 (d, J=8.34 Hz, 2H), 7.29 (d, J=8.34 Hz, 2H), 7.24 (s, 1H), 6.93 (d, J=3.92 Hz, 1H), 4.94 (s, 2H), 4.89 (d, J=11.62 Hz, 1H), 4.69 (d, J=11.62 Hz, 1H), 4.57 (s, 1H), 3.72-3.88 (m, 1H), 3.38-3.54 (m, 1H), 2.56 (s, 3H), 2.34 (s, 3H), 1.35-1.74 (m, 6H), 1.11-1.22 (m, 3H), 1.00-1.10 (m, 18H).

Example 65-B

7-Methyl-1-tosyl-5-(((triisopropylsilyl)oxy)methyl)-1H-indole-4-carbaldehyde

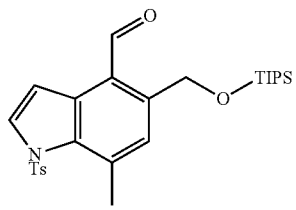

The title compound was prepared from 7-(±)-methyl-4-(((tetrahydro-2H-pyran-2-yl)oxy)methyl)-1-tosyl-5-(((triisopropylsilypoxy)methyl)-1H-indole following the procedures shown in Example 47-E and 47-F. MS (ESI+) m/z 500.3 (M+H).

Example 65-C

(±)-2-(hydroxy(7-methyl-1-tosyl-5-(((triisopropylsilyl)oxy)methyl)-1H-indol-4-yl)methyl)-1-((2-(trimethylsilyl)ethoxy)methyl)-1H-benzo[d]imidazole-5-carbonitrile and (±)-2-(hydroxy(7-methyl-1-tosyl-5-(((triisopropylsilyl)oxy)methyl)-1H-indol-4-yl)methyl)-1-((2-(trimethylsilyl)ethoxy)methyl)-1H-benzo[d]imidazole-6-carbonitrile

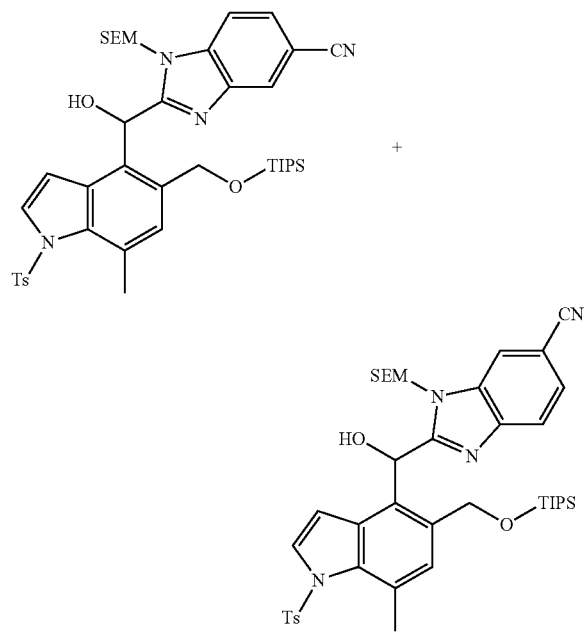

A mixture of title compounds was synthesized from 7-methyl-1-tosyl-5-(((triisopropylsilypoxy)methyl)-1H-indole-4-carbaldehyde analogously to Example 64-A. MS (ESI+) m/z 773.4 (M+H).

Example 65-D a) (±)-2-(Hydroxy(5-(hydroxymethyl)-7-methyl-1H-indol-4-yl)methyl)-1H-benzo[d]imidazole-5-carbonitrile

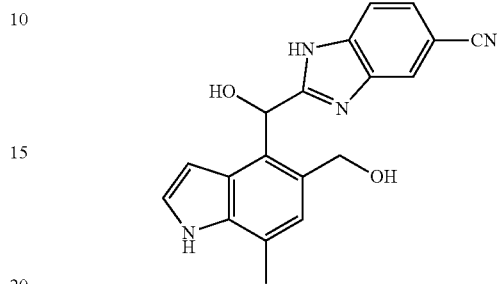

To a solution of (±)-2-(hydroxy(7-methyl-1-tosyl-5-(((triisopropylsilypoxy)methyl)-1H-indol-4-yl)methyl)-1-((2-(trimethylsilyl)ethoxy)methyl)-1H-benzo[d]imidazole-5-carbonitrile and (±)-2-(hydroxy(7-methyl-1-tosyl-5-(((triisopropylsilypoxy)methyl)-1H-indol-4-yl)methyl)-1-((2-(trimethylsilyl)ethoxy)methyl)-1H-benzo[d]imidazole-6-carbonitrile (263 mg, 0.340 mmol) in $CH_2Cl_2$ (10 mL) was added $BF_3$—$OEt_2$ (0.215 mL, 1.70 mmol) at 0° C., and then the mixture was stirred at room temperature for 2.5 h. The reaction was quenched by 7N $NH_3$ in MeOH. The mixture was filtered off through $SiO_2$. The $SiO_2$ cake was washed with $CH_2Cl_2$/MeOH (c.a. 6/1). Combined organics were concentrated. The resulting residue was mixed with isoamylamine (148 mg, 1.70 mmol), and KOH (95 mg, 1.70 mmol) in EtOH (10 mL) and stirred at 100° C. under microwave irradiation for 1 hr. The reaction mixture was diluted with $CH_2Cl_2$. The mixture was filtered through $SiO_2$. The $SiO_2$ cake was washed with a mixture of $CH_2Cl_2$/MeOH (c.a. 6/1). The filtrate was concentrated and purified by RP-HPLC (HC-A) to give the title compound. $^1$H NMR (400 MHz, ACETONITRILE-$d_3$ with about 5 μL TFA) δ ppm 9.46 (br. s., 1H), 8.08-8.19 (m, 1H), 7.86 (d, J=8.60 Hz, 1H), 7.80 (dd, J=1.30, 8.60 Hz, 1H), 7.27 (dd, J=2.80, 3.00 Hz, 1H), 7.02 (s, 1H), 6.89 (s, 1H), 6.71 (dd, J=2.02, 3.00 Hz, 1H), 5.05 (d, J=11.87 Hz, 1H), 4.76 (d, J=11.87 Hz, 1H), 2.48 (s, 3H). HRMS calcd. for $C_{19}H_{16}N_4O_2$ (M+H)$^+$ 333.1352. found 333.1352.

b) (+) and (−)-2-(hydroxy(5-(hydroxymethyl)-7-methyl-1H-indol-4-yl)methyl)-1H-benzo[d]imidazole-5-carbonitrile Resolution of the enantiomers of 2-(hydroxy(5-(hydroxymethyl)-7-methyl-1H-indol-4-yl)methyl)-1H-benzo[d]imidazole-5-carbonitrile was achieved by chiral SFC using a CHIRALCEL® OD-H column with 35% MeOH in $CO_2$ to give (+)-2-(hydroxy(5-(hydroxymethyl)-7-methyl-1H-indol-4-yl)methyl)-1H-benzo[d]imidazole-5-carbonitrile ($t_r$=2.7 min) and (−)-2-(hydroxy(5-(hydroxymethyl)-7-methyl-1H-indol-4-yl)methyl)-1H-benzo[d]imidazole-5-carbonitrile ($t_r$=4.6 min).

Example 66

Example 66-A

7-Methyl-5-(phenoxymethyl)-1-tosyl-1H-indole-4-carbaldehyde

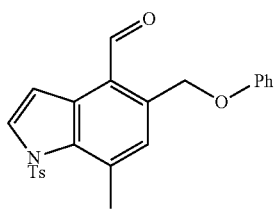 [SMILES: Cc1ccc(S(=O)(=O)n2ccc3c(C=O)c(COc4ccccc4)cc(C)c32)cc1]

The title compound was prepared from (±)-(7-methyl-4-((((tetrahydro-2H-pyran-2-yl)oxy)methyl)-1-tosyl-1H-indol-5-yl)methanol (Example 52-C) using phenol instead of phthalimide in the method depicted in Example 53. MS (ESI+) m/z 420.1 (M+H).

Example 66-B (±)-2-(Hydroxy(7-methyl-5-(phenoxymethyl)-1-tosyl-1H-indol-4-yl)methyl)-1-((2-(trimethylsilyl)ethoxy)methyl)-1H-benzo[d]imidazole-5-carbonitrile and (±)-2-(hydroxy(7-methyl-5-(phenoxymethyl)-1-tosyl-1H-indol-4-yl)methyl)-1-((2-(trimethylsilyl)ethoxy)methyl)-1H-benzo[d]imidazole-6-carbonitrile

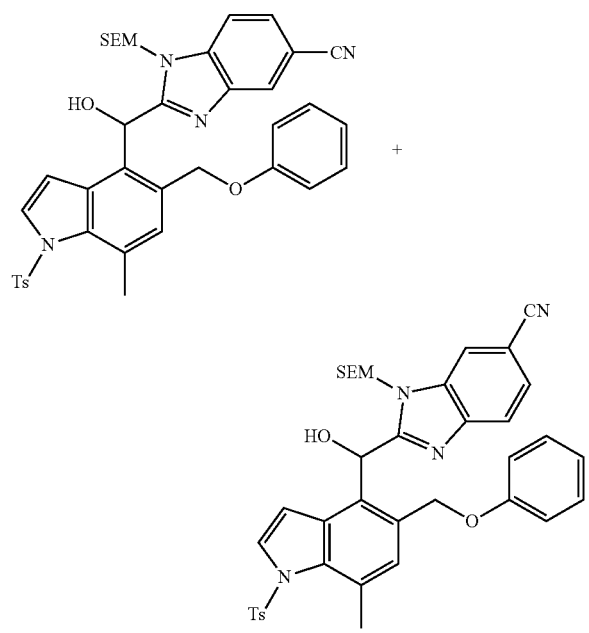

A mixture of title compounds was synthesized from 7-methyl-5-(phenoxymethyl)-1-tosyl-1H-indole-4-carbaldehyde analogously to Example 64-A MS (ESI+) m/z 693.3 (M+H).

Example 66-C (±)-2-(Hydroxy(7-methyl-5-(phenoxymethyl)-1-tosyl-1H-indol-4-yl)methyl)-1H-benzo[d]imidazole-5-carbonitrile

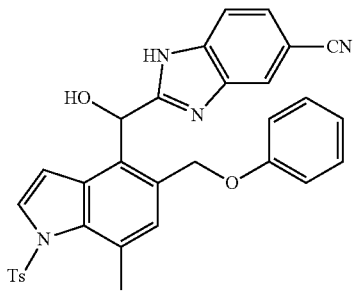 [SMILES: Cc1ccc(S(=O)(=O)n2ccc3c(C(O)c4nc5cc(C#N)ccc5[nH]4)c(COc4ccccc4)cc(C)c32)cc1]

To a solution of (±)-2-(hydroxy(7-methyl-5-(phenoxymethyl)-1-tosyl-1H-indol-4-yl)methyl)-1-((2-(trimethylsilyl)ethoxy)methyl)-1H-benzo[d]imidazole-5-carbonitrile and (±)-2-(hydroxy(7-methyl-5-(phenoxymethyl)-1-tosyl-1H-indol-4-yl)methyl)-1-((2-(trimethylsilyl)ethoxy)methyl)-1H-benzo[d]imidazole-6-carbonitrile (160 mg, 0.231 mmol) in $CH_2Cl_2$ (2 mL) was added $BF_3$—$OEt_2$ (0.059 mL, 0.462 mmol) at 0° C., and then the mixture was stirred at room temperature for 2.5 h. The reaction was quenched by 7N $NH_3$ in MeOH. The mixture was filtered off through $SiO_2$. The $SiO_2$ cake was washed with $CH_2Cl_2$/MeOH (c.a. 6/1). The combined organics were concentrated to give the title compound, without need of further purification. MS (ESI+) m/z 563.3 (M+H).

Example 66-D a) (±)-2-((5-(Ethoxymethyl)-7-methyl-1H-indol-4-yl)(hydroxy)methyl)-1H-benzo[d]imidazole-5-carbonitrile

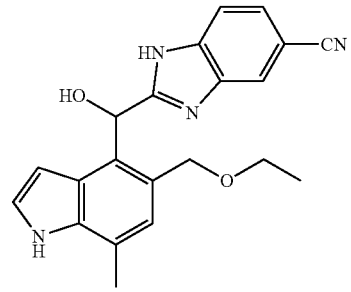 [SMILES: CCOCc1cc(C)c2[nH]ccc2c1C(O)c1nc2cc(C#N)ccc2[nH]1]

To a solution of 2-(hydroxy(7-methyl-5-(phenoxymethyl)-1-tosyl-1H-indol-4-yl)methyl)-1H-benzo[d]imidazole-5-carbonitrile (130 mg, 0.23 mmol) in EtOH (3 mL), isoamylamine (101 mg, 1.15 mmol), and KOH (64.8 mg, 1.15 mmol) were added and the reaction stirred at 100° C. for 1.5 h under microwave irradiation. The reaction mixture was diluted with $CH_2Cl_2$ filtered through $SiO_2$. The $SiO_2$ cake was washed with a mixture of $CH_2Cl_2$/MeOH (c.a. 6/1). The organic solution was concentrated and purified by RP-HPLC (HC-A) to give the title compound. $^1H$ NMR (400 MHz, ACETONITRILE-$d_3$ with about 5 μL TFA) δ ppm 9.45 (br. s., 1H), 8.08

(s, 1H), 7.79 (d, J=8.60 Hz, 1H), 7.75 (dd, J=1.30, 8.60 Hz, 1H), 7.25 (dd, J=2.80, 3.00 Hz, 1H), 7.02 (s, 1H), 6.76 (s, 1H), 6.62 (dd, J=2.02, 3.03 Hz, 1H), 4.80 (d, J=10.86 Hz, 1H), 4.63 (d, J=10.86 Hz, 1H), 3.56-3.73 (m, 2H), 2.48 (s, 3H), 1.13 (t, J=6.95 Hz, 3H). HRMS calcd. for $C_{21}H_{20}N_4O_2$ $(M+H)^+$ 361.1665. found 361.1658.

b) (+) and (−)-2-((5-(ethoxymethyl)-7-methyl-1H-indol-4-yl)(hydroxy)methyl)-1H-benzo[d]imidazole-5-carbonitrile Resolution of the enantiomers of 2-((5-(ethoxymethyl)-7-methyl-1H-indol-4-yl)(hydroxy)methyl)-1H-benzo[d]imidazole-5-carbonitrile was achieved by normal phase HPLC using a CHIRALPAK® AS column with 10% (0.2% diethylamine in EtOH) in heptane to give (−)-2-((5-(ethoxymethyl)-7-methyl-1H-indol-4-yl)(hydroxy)methyl)-1H-benzo[d]imidazole-5-carbonitrile ($t_r$=18.0 min) and (+)-2-((5-(ethoxymethyl)-7-methyl-1H-indol-4-yl)(hydroxy)methyl)-1H-benzo[d]imidazole-5-carbonitrile ($t_r$=21.1 min).

Example 67

The following compounds were prepared with similar method as described in Example 64.

| | Structure/Chemical Name | $^1$H NMR | HRMS |
|---|---|---|---|
| 67-A a) | 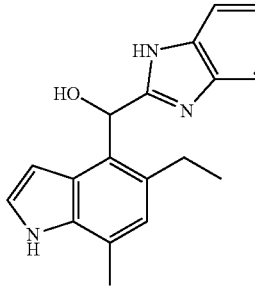<br>(±)-2-((5-ethyl-7-methyl-1H-indol-4-yl)(hydroxy)methyl)-1H-benzo[d]imidazole-5-carbonitrile | (400 MHz, ACETONITRILE-$d_3$ with about 5 μL TFA) δ ppm 9.24 (br. s., 1H), 7.86 (s, 1H), 7.62 (dd, J = 0.50, 8.30 Hz, 1H), 7.55 (dd, J = 1.50, 8.30 Hz, 1H), 7.09 (dd, J = 2.80, 3.00 Hz, 1H), 6.83 (s, 1H), 6.54 (s, 1H), 6.19 (dd, J = 2.02, 3.03 Hz, 1H), 2.69-2.88 (m, 2H), 2.43 (d, J = 0.76 Hz, 3H), 1.19 (t, J = 7.58 Hz, 3H). | calcd. for $C_{20}H_{18}N_4O$ $(M + H)^+$ 331.1553, found 331.1555. |
| 67-A b) | (+) and (−)-2-((5-ethyl-7-methyl-1H-indol-4-yl)(hydroxy)methyl)-1H-benzo[d]imidazole-5-carbonitrile<br><br>Resolution of the enantiomers of 2-((5-ethyl-7-methyl-1H-indol-4-yl)(hydroxy)methyl)-1H-benzo[d]imidazole-5-carbonitrile was achieved by normal phase chiral HPLC using a CHIRALCEL ® OD column with 15% MeOH and 15% EtOH in heptane to give (+)-2-((5-ethyl-7-methyl-1H-indol-4-yl)(hydroxy)methyl)-1H-benzo[d]imidazole-5-carbonitrile ($t_r$ = 4.5 min) and (−)-2-((5-ethyl-7-methyl-1H-indol-4-yl)(hydroxy)methyl)-1H-benzo[d]imidazole-5-carbonitrile ($t_r$ = 11.3 min). | | |
| 67-B | 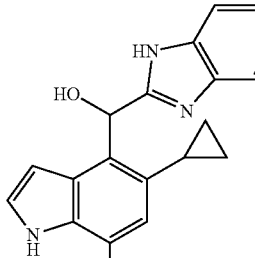<br>(±)-2-((5-cyclopropyl-7-methyl-1H-indol-4-yl)(hydroxy)methyl)-1H-benzo[d]imidazole-5-carbonitrile | (400 MHz, DICHLOROMETHANE-$d_2$) δ ppm 8.26 (br. s., 1H), 7.77 (br. s., 1H), 7.54 (d, J = 8.3 Hz, 1H), 7.43-7.49 (m, 1H), 7.12 (t, J = 2.9 Hz, 1H), 6.99 (s, 1H), 6.83 (s, 1H), 6.29 (dd, J = 3.0, 2.0 Hz, 1H), 2.45 (s, 3H), 2.10-2.22 (m, 1H), 1.26 (s, 1H), 0.78-0.95 (m, 3H), 0.59-0.67 (m, 1H). | calcd. for $C_{21}H_{18}N_4O$ $(M + H)^+$ 343.1559, found 343.1557. |

| | Structure/Chemical Name | ¹H NMR | HRMS |
|---|---|---|---|
| 67-C a) | (±)-2-(hydroxy(5-(isobutyl)-7-methyl-1H-indol-4-yl)methyl)-1H-benzo[d]imidazole-5-carbonitrile | (400 MHz, ACETONITRILE-$d_3$ with about 5 μL TFA) δ ppm 9.24 (br. s., 1H), 7.93 (s, 1H), 7.66 (d, J = 8.30 Hz, 1H), 7.61 (dd, J = 1.30, 8.30 Hz, 1H), 7.08 (dd, J = 2.80, 3.00 Hz, 1H), 6.83 (s, 1H), 6.56 (s, 1H), 6.12 (dd, J = 2.00, 3.00 Hz, 1H), 2.78 (dd, J = 7.30, 13.89 Hz, 1H), 2.60 (dd, J = 7.33, 13.89 Hz, 1H), 2.45 (s, 3H), 1.85-1.91 (m, 1H), 0.93 (d, J = 6.57 Hz, 6H). | calcd. for $C_{22}H_{22}N_4O$ $(M + H)^+$ 359.1867, found 359.1867. |
| 67-C b) | (+) and (−)-2-(hydroxy(5-(isobutyl)-7-methyl-1H-indol-4-yl)methyl)-1H-benzo[d]imidazole-5-carbonitrile Resolution of the enantiomers of 2-(hydroxy(5-(isobutyl)-7-methyl-1H-indol-4-yl)methyl)-1H-benzo[d]imidazole-5-carbonitrile was achieved by normal phase chiral HPLC using a CHIRALCEL ® OD column with 30% (0.2% diethylamine in EtOH) in heptane to give (+)-2-(hydroxy(5-(isobutyl)-7-methyl-1H-indol-4-yl)methyl)-1H-benzo[d]imidazole-5-carbonitrile ($t_r$ = 4.1 min) and (−)-2-(hydroxy(5-(isobutyl)-7-methyl-1H-indol-4-yl)methyl)-1H-benzo[d]imidazole-5-carbonitrile ($t_r$ = 7.3 min). | | |
| 67-D a) | (±)-2-(hydroxy(5-isopropyl-7-methyl-1H-indol-4-yl)methyl)-1H-benzo[d]imidazole-5-carbonitrile | (400 MHz, ACETONITRILE-$d_3$ with about 5 μL TFA) δ ppm 9.28 (br. s., 1H), 7.94 (s, 1H), 7.69 (d, J = 8.30 Hz, 1H), 7.65 (dd, J = 1.30, 8.30 Hz, 1H), 7.14 (t, J = 2.80 Hz, 1H), 7.01 (s, 1H), 6.72 (s, 1H), 6.19-6.26 (m, 1H), 3.24-3.39 (m, 1H), 2.46 (s, 3H), 1.28 (d, J = 6.82 Hz, 3H), 1.09 (d, J = 6.82 Hz, 3H). | calcd. for $C_{21}H_{20}N_4O$ $(M + H)^+$ 345.1710, found 345.1710. |
| 67-D b) | (+) and (−)-2-(hydroxy(5-isopropyl-7-methyl-1H-indol-4-yl)methyl)-1H-benzo[d]imidazole-5-carbonitrile Resolution of the enantiomers of 2-(hydroxy(5-isopropyl-7-methyl-1H-indol-4-yl)methyl)-1H-benzo[d]imidazole-5-carbonitrile was achieved by chiral SFC using a CHIRALCEL ® OD-H column with 40% (0.2% diethylamine in MeOH) in $CO_2$ to give (+)-2-(hydroxy(5-isopropyl-7-methyl-1H-indol-4-yl)methyl)-1H-benzo[d]imidazole-5-carbonitrile ($t_r$ = 1.8 min) and (−)-2-(hydroxy(5-isopropyl-7-methyl-1H-indol-4-yl)methyl)-1H-benzo[d]imidazole-5-carbonitrile ($t_r$ = 3.1 min) | | |
| 67-E a) | (±)-2-((5-chloro-7-methyl-1H-indol-4-yl)(hydroxy)methyl)-1H-benzo[d]imidazole-5-carbonitrile | (400 MHz, ACETONITRILE-$d_3$ with about 5 μL TFA) δ ppm 9.48 (br. s., 1H), 7.84 (s, 1H), 7.63 (d, J = 8.30 Hz, 1H), 7.60 (dd, J = 1.30, 8.30 Hz, 1H), 7.19 (m, 1H), 6.95 (s, 1H), 6.77 (s, 1H), 6.28 (dd, J = 2.02, 3.03 Hz, 1H), 2.42 (s, 3H). | calcd. for $C_{18}H_{13}ClN_4O$ $(M + H)^+$ 337.0856, found 337.0858. |
| 67-E b) | (+) and (−)-2-((5-chloro-7-methyl-1H-indol-4-yl)(hydroxy)methyl)-1H-benzo[d]imidazole-5-carbonitrile Resolution of the enantiomers of 2-((5-chloro-7-methyl-1H-indol-4-yl)(hydroxy)methyl)-1H-benzo[d]imidazole-5-carbonitrile was achieved by chiral SFC using a CHIRALCEL ® OD-H | | |

| Structure/Chemical Name | ¹H NMR | HRMS |
|---|---|---| column with 35% MeOH in CO₂ to give (+)-2-((5-chloro-7-methyl-1H-indol-4-yl)(hydroxy)methyl)-1H-benzo[d]imidazole-5-carbonitrile (t$_r$ = 2.3 min) and (−)-2-((5-chloro-7-methyl-1H-indol-4-yl)(hydroxy)methyl)-1H-benzo[d]imidazole-5-carbonitrile (t$_r$ = 3.3 min).

67-F

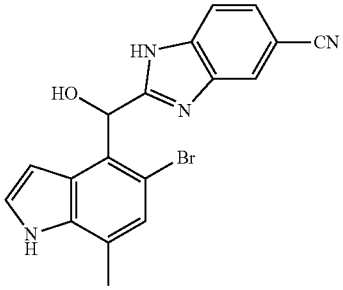

(±)-2-((5-bromo-7-methyl-1H-indol-4-yl)(hydroxy)methyl)-1H-benzo[d]imidazole-5-carbonitrile (400 MHz, ACETONITRILE-d₃) δ ppm 11.06 (br. s., 1H), 9.43 (br. s., 1H), 7.85-7.98 (m, 1H), 7.55-7.69 (m, 1H), 7.42-7.54 (m, 1H), 7.20 (d, J = 0.5 Hz, 1H), 7.15 (t, J = 2.8 Hz, 1H), 6.71 (d, J = 4.5 Hz, 1H), 6.30 (br. s., 1H), 4.58 (d, J = 4.5 Hz, 1H), 2.47 (d, J = 0.8 Hz, 3H).

calcd. for C₁₈H₁₃BrN₄O (M + H)⁺ 381.0346, found 381.0343.

67-G a)

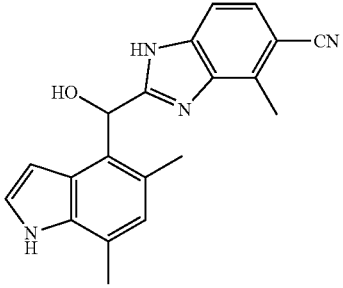

(±)-2-((5,7-dimethyl-1H-indol-4-yl)(hydroxy)methyl)-4-methyl-1H-benzo[d]imidazole-5-carbonitrile (400 MHz, DMSO-d₆) δ ppm 12.75-13.06 (m, 1H), 10.77-10.94 (m, 1H), 7.32-7.47 (m, 2H), 7.10-7.20 (m, 2H), 6.72 (s, 1H), 6.41-6.49 (m, 2H), 6.29-6.37 (m, 1H), 2.56 (s, 3H), 2.44 (s, 3H), 2.40 (s, 3H).

calcd. for C₂₀H₁₈N₄O (M + H)⁺ 331.1553, found 331.1559.

67-G b)

(+) and (−)-2-((5,7-dimethyl-1H-indol-4-yl)(hydroxy)methyl)-4-methyl-1H-benzo[d]imidazole-5-carbonitrile Resolution of the enantiomers of 2-((5,7-dimethyl-1H-indol-4-yl)(hydroxy)methyl)-4-methyl-1H-benzo[d]imidazole-5-carbonitrile was achieved by chiral HPLC using a CHIRALCEL ® OD column with 40% ethanol in heptane to give (+)-2-((5,7-dimethyl-1H-indol-4-yl)(hydroxy)methyl)-4-methyl-1H-benzo[d]imidazole-5-carbonitrile (t$_r$ = 4.22 min) and (−)-2-((5,7-dimethyl-1H-indol-4-yl)(hydroxy)methyl)-4-methyl-1H-benzo[d]imidazole-5-carbonitrile (t$_r$ = 10.07 min).

67-H

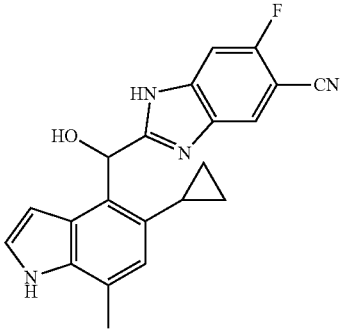

(±)-2-((5-cyclopropyl-7-methyl-1H-indol-4-yl)(hydroxy)methyl)-6-fluoro-1H-benzo[d]imidazole-5-carbonitrile (400 MHz, ACETONITRILE-d₃) δ 9.03 (br. s., 1H), 7.66 (d, J = 5.81 Hz, 1H), 7.19 (d, J = 10.11 Hz, 1H), 6.98 (t, J = 2.84 Hz, 1H), 6.79 (s, 1H), 6.67 (s, 1H), 6.20 (dd, J = 2.02, 3.16 Hz, 1H), 2.32 (s, 3H), 2.10-2.21 (m, 1H), 0.72-0.84 (m, 3H), 0.43-0.54 (m, 1H).

calcd. for C₂₁H₁₇FN₄O (M + H)⁺ 361.1465, found 361.1463.

Example 68

Example 68-A (±)-2-((5,7-Dimethyl-1-tosyl-1H-indol-4-yl)(methoxy)methyl)-1-((2-(trimethylsilyl)ethoxy)methyl)-1H-benzo[d]imidazole-5-carbonitrile and (±)-2-((5,7-dimethyl-1-tosyl-1H-indol-4-yl)(methoxy)methyl)-1-((2-(trimethylsilyl)ethoxy)methyl)-1H-benzo[d]imidazole-6-carbonitrile

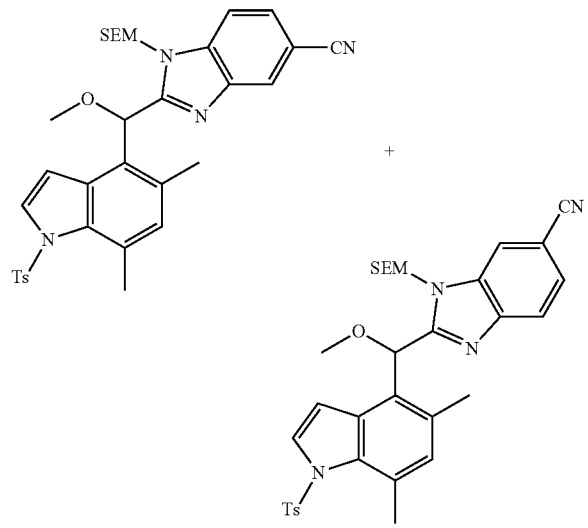

To a suspension of (±)-2-((5,7-dimethyl-1-tosyl-1H-indol-4-yl)(hydroxy)methyl)-1-((2-(trimethylsilyl)ethoxy)methyl)-1H-benzo[d]imidazole-5-carbonitrile and (±)-2-((5,7-dimethyl-1-tosyl-1H-indol-4-yl)(hydroxy)methyl)-1-((2-(trimethylsilyl)ethoxy)methyl)-1H-benzo[d]imidazole-6-carbonitrile (Example 64-A) (22 mg, 0.037 mmol) and NaH (oil dispersion, 60%) (2.93 mg, 0.073 mmol) in THF (0.4 mL), MeI (2.7 μl, 0.044 mmol) was added at 0° C. After stirring for 1.5 h at the same temperature, the mixture was allowed to reach room temperature and then stirred overnight. The mixture was diluted with aq. NH₄Cl and EtOAc. The layers were separated and the aqueous layer extracted with EtOAc. The combined organic phase was washed with brine, dried over Na₂SO₄, filtered, and concentrated to give the mixture of title compounds without need of further purification. MS (ESI+) m/z 615.2 (M+H).

Example 68-B (±)-2-((5,7-Dimethyl-1H-indol-4-yl)(methoxy)methyl)-1H-benzo[d]imidazole-5-carbonitrile

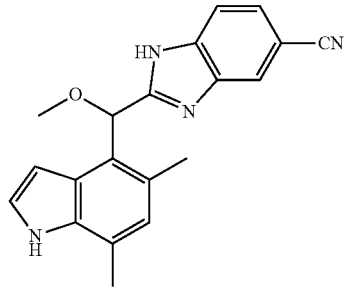 [SMILES: COC(c1nc2cc(C#N)ccc2[nH]1)c1c(C)cc(C)c2[nH]ccc12]

The title compound was synthesized from a mixture of (±)-2-((5,7-dimethyl-1-tosyl-1H-indol-4-yl)(methoxy)methyl)-1-((2-(trimethylsilyl)ethoxy)methyl)-1H-benzo[d]imidazole-5-carbonitrile and (±)-2-((5,7-dimethyl-1-tosyl-1H-indol-4-yl)(methoxy)methyl)-1-((2-(trimethylsilyl)ethoxy)methyl)-1H-benzo[d]imidazole-6-carbonitrile as described in Example 64-B and 64-C. $^1$H NMR (400 MHz, DMSO-$d_6$) δ ppm 10.96 (s, 1H) 7.96 (s, 1H) 7.63 (d, J=8.34 Hz, 1H) 7.53 (d, J=8.34 Hz, 1H) 7.20 (t, J=2.65 Hz, 1H) 6.75 (s, 1H) 6.49 (br.s, 1H) 6.21 (s, 1H) 3.35 (s, 3H) 2.43 (s, 3H) 2.42 (s, 3H). HRMS calcd. for $C_{20}H_{18}N_4O$ (M+H)$^+$ 331.1553. found 331.1559.

Example 69

(±)-2-((5-cyano-1H-benzo[d]imidazol-2-yl)(5,7-dimethyl-1H-indol-4-yl)methoxy)acetic acid

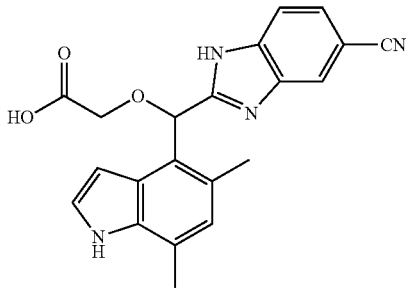 [SMILES: Cc1cc(C)c2[nH]ccc2c1C(OCC(=O)O)c1nc2cc(C#N)ccc2[nH]1]

The title compound was synthesized from a mixture of (±)-2-((5,7-dimethyl-1-tosyl-1H-indol-4-yl)(hydroxy)methyl)-1-((2-(trimethylsilyl)ethoxy)methyl)-1H-benzo[d]imidazole-5-carbonitrile and (±)-2-((5,7-dimethyl-1-tosyl-1H-indol-4-yl)(hydroxy)methyl)-1-((2-(trimethylsilyl)ethoxy)methyl)-1H-benzo[d]imidazole-6-carbonitrile (Example 64-A) as described in Example 68 using methyl 2-bromoacetate as electrophile instead of methyl iodide. $^1$H NMR (TFA salt, 400 MHz, DMSO-$d_6$) δ ppm 11.00 (br.s, 1H) 7.97 (s, 1H) 7.64 (d, J=8.33 Hz, 1H) 7.51-7.54 (m, 1H) 7.21 (t, J=2.78 Hz, 1H) 6.76 (s, 1H) 6.48-6.51 (m, 2H) 4.14 (A of AB, J=16.55 Hz, 1H) 3.99 (B of AB, J=16.55 Hz, 1H) 2.42 (s, 3H) 2.40 (s, 3H). HRMS calcd. for $C_{21}H_{18}N_4O_3$ (M+H)$^+$ 375.1452. found 375.1465.

Example 70

Example 70-A (±)-2-((5-Ethyl-7-methyl-1-tosyl-1H-indol-4-yl)(hydroxy)methyl)-1-((2-(trimethylsilyl)ethoxy)methyl)-1H-benzo[d]imidazole-5-carbonitrile and (±)-2-((5-ethyl-7-methyl-1-tosyl-1H-indol-4-yl)(hydroxy)methyl)-1-((2-(trimethylsilyl)ethoxy)methyl)-1H-benzo[d]imidazole-6-carbonitrile

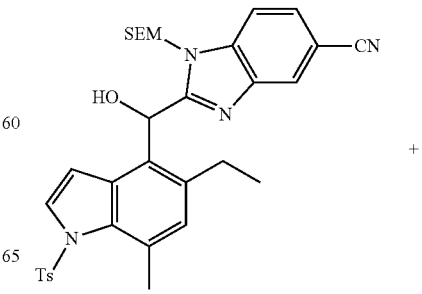

-continued

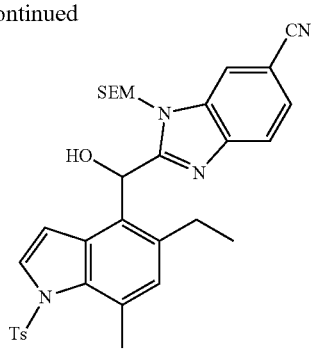

A mixture of title compounds was synthesized from 5-ethyl-7-methyl-1-tosyl-1H-indole-4-carbaldehyde analogously to Example 64-A. MS (ESI+) m/z 615.4 (M+H).

Example 70-B (±)-2-((5-Ethyl-7-methyl-1-tosyl-1H-indol-4-yl)(methoxy)methyl)-1-((2-(trimethylsilyl)ethoxy)methyl)-1H-benzo[d]imidazole-5-carbonitrile and (±)-2-((5-ethyl-7-methyl-1-tosyl-1H-indol-4-yl)(methoxy)methyl)-1-((2-(trimethylsilyl)ethoxy)methyl)-1H-benzo[d]imidazole-6-carbonitrile

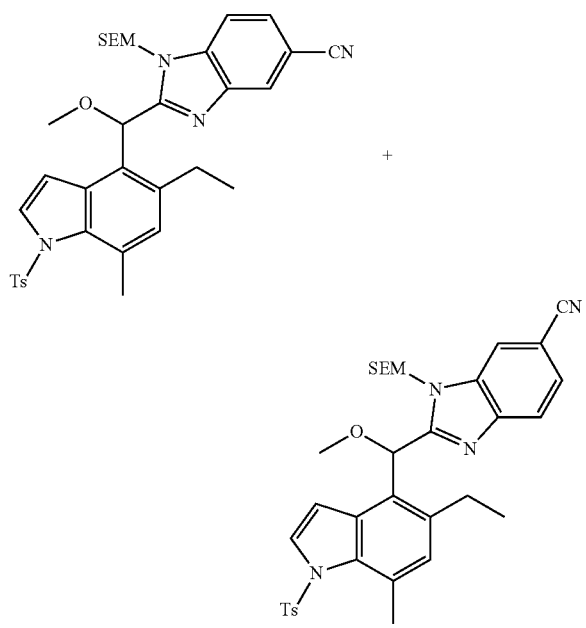

To a solution of a mixture of (±)-2-((5-ethyl-7-methyl-1-tosyl-1H-indol-4-yl)(hydroxy)methyl)-1-((2-(trimethylsilyl)ethoxy)methyl)-1H-benzo[d]imidazole-5-carbonitrile and (±)-2-((5-ethyl-7-methyl-1-tosyl-1H-indol-4-yl)(hydroxy)methyl)-1-((2-(trimethylsilyl)ethoxy)methyl)-1H-benzo[d]imidazole-6-carbonitrile (1 g, 1.30 mmol) and MeI (0.122 mL, 1.952 mmol) in DMF (5 mL) was added NaH (60% in mineral oil, 78 mg, 1.952 mmol), and then the mixture was stirred at room temperature for 3 h. The reaction mixture was poured into a mixture of EtOAc/half satd. KHSO$_4$. The layers were separated and the aqueous layer was extracted with EtOAc. The combined organic phase was successively washed with H$_2$O and brine, dried over Na$_2$SO$_4$, filtered and concentrated. The resulting residue was purified by silica gel flash chromatography (heptanes/EtOAc 9/1 to 6/4) to give title compounds as a mixture. MS (ESI+) m/z 629.4 (M+H).

Example 70-C (±)-2-((5-Ethyl-7-methyl-1-tosyl-1H-indol-4-yl)(methoxy)methyl)-1H-benzo[d]imidazole-5-carbonitrile

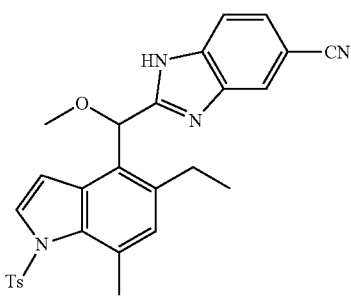 [SMILES: CCc1cc(C)c2c(ccn2S(=O)(=O)c2ccc(C)cc2)c1C(OC)c1nc2cc(C#N)ccc2[nH]1]

A mixture of (±)-2-((5-ethyl-7-methyl-1-tosyl-1H-indol-4-yl)(methoxy)methyl)-1-((2-(trimethylsilyl)ethoxy)methyl)-1H-benzo[d]imidazole-5-carbonitrile, (±)-2-((5-ethyl-7-methyl-1-tosyl-1H-indol-4-yl)(methoxy)methyl)-1-((2-(trimethylsilyl)ethoxy)methyl)-1H-benzo[d]imidazole-6-carbonitrile (mixture, 650 mg, 1.03 mmol) and LiBF$_4$ in CH$_3$CN (1M, 10 mL, 10 mmol)/H$_2$O (1 mL) was stirred at 75° C. for 14 h. The mixture was cooled to room temperature and poured into 5% NaHCO$_3$. The layers were separated and the aqueous layer was extracted with CH$_2$Cl$_2$. The combined organic phase was successively washed with H$_2$O and brine, dried over Na$_2$SO$_4$, filtered and concentrated. The resulting residue was purified by silica gel flash column chromatography (heptanes/EtOAc=55/45) to give the title compound. MS (ESI+) m/z 499.2 (M+H).

Example 70-D a) (±)-2-((5-Ethyl-7-methyl-1H-indol-4-yl)(methoxy)methyl)-1H-benzo[d]imidazole-5-carbonitrile

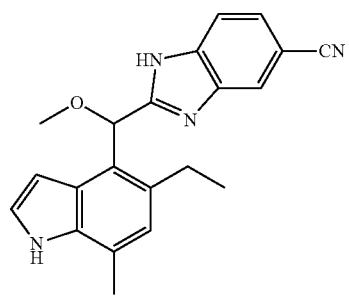 [SMILES: CCc1cc(C)c2[nH]ccc2c1C(OC)c1nc2cc(C#N)ccc2[nH]1]

The title compound was synthesized from (±)-2-((5-ethyl-7-methyl-1-tosyl-1H-indol-4-yl)(methoxy)methyl)-1H-benzo[d]imidazole-5-carbonitrile as described in Example 64-C. $^1$H NMR (400 MHz, ACETONITRILE-d$_3$ with about 5 µL TFA) δ ppm 9.33 (br. s., 1H), 7.99 (s, 1H), 7.72 (d, J=8.50 Hz, 1H), 7.68 (dd, J=1.30, 8.50 Hz, 1H), 7.17 (dd, J=2.80, 3.00 Hz, 1H), 6.94 (s, 1H), 6.30 (dd, J=2.02, 3.00 Hz, 1H), 6.26 (s, 1H), 3.42 (s, 3H), 2.73-2.86 (m, 2H), 2.48 (s, 3H), 1.21 (t, J=7.58 Hz, 3H). HRMS calcd. for $C_{21}H_{20}N_4O$ $(M+H)^+$ 345.171. found 345.1713.

b) (+) and (−)-2-((5-Ethyl-7-methyl-1H-indol-4-yl) (methoxy)methyl)-1H-benzo[d]imidazole-5-carbonitrile Resolution of the enantiomers of 2-((5-ethyl-7-methyl-1H-indol-4-yl)(methoxy)methyl)-1H-benzo[d]imidazole-5-carbonitrile was achieved by normal phase chiral HPLC using a CHIRALPAK® AD column with 30% IPA (0.2% diethylamine) in heptane to give (+)-2-((5-ethyl-7-methyl-1H-indol-4-yl)(methoxy)methyl)-1H-benzo[d]imidazole-5-carbonitrile ($t_r$=5.8 min) and (−)-2-((5-ethyl-7-methyl-1H-indol-4-yl)(methoxy)methyl)-1H-benzo[d]imidazole-5-carbonitrile=6.6 min).

Example 71 a) (±)-2-((5-isobutyl-7-methyl-1H-indol-4-yl)(methoxy)methyl)-1H-benzo[d]imidazole-5-carbonitrile

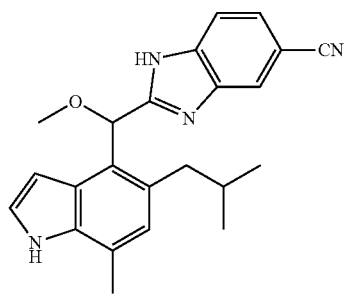 [SMILES: COC(c1nc2cc(C#N)ccc2[nH]1)c1c(CC(C)C)cc(C)c2[nH]ccc12]

The title compound was prepared with similar method as described in Example 70 starting from 5-Isobutyl-7-methyl-1-tosyl-1H-indole-4-carbaldehyde (Example 49-B). $^1$H NMR (400 MHz, DMSO-$d_6$ with about 5 μL TFA) δ ppm 10.96 (br. s., 1H), 7.96 (s, 1H), 7.63 (d, J=8.34 Hz, 1H), 7.53 (dd, J=1.26, 8.34 Hz, 1H), 7.16 (t, J=2.80 Hz, 1H), 6.75 (s, 1H), 6.42 (dd, J=1.80, 2.80 Hz, 1H), 6.19 (s, 1H), 3.37 (s, 3H), 2.73-2.84 (m, 1H), 2.55-2.65 (m, 1H), 2.43 (s, 3H), 1.81-2.02 (m, 1H), 0.93 (d, J=6.57 Hz, 3H), 0.89 (d, J=6.57 Hz, 3H). HRMS calcd. for $C_{23}H_{24}N_4O$ $(M+H)^+$ 373.2023. found 373.2025.

b) (+) and (−)-2-((5-isobutyl-7-methyl-1H-indol-4-yl)(methoxy)methyl)-1H-benzo[d]imidazole-5-carbonitrile Resolution of the enantiomers of 2-((5-isobutyl-7-methyl-1H-indol-4-yl)(methoxy)methyl)-1H-benzo[d]imidazole-5-carbonitrile was achieved by chiral SFC using a (R,R)-Whelk-O®1 column with 40% (0.2% diethylamine in EtOH) in heptane to give (+)-2-((5-isobutyl-7-methyl-1H-indol-4-yl)(methoxy)methyl)-1H-benzo[d]imidazole-5-carbonitrile ($t_r$=5.9 min) and (−)-2-((5-isobutyl-7-methyl-1H-indol-4-yl) (methoxy)methyl)-1H-benzo[d]imidazole-5-carbonitrile ($t_r$=9.0 min).

Example 72

Example 72-A (±)-2-((5,7-Dimethyl-1-tosyl-1H-indol-4-yl)(ethoxy) methyl)-1-((2-(trimethylsilyl)ethoxy)methyl)-1H-benzo[d]imidazole-5-carbonitrile and (±)-2-((5,7-dimethyl-1-tosyl-1H-indol-4-yl)(ethoxy)methyl)-1-((2-(trimethylsilyl)ethoxy)methyl)-1H-benzo[d] imidazole-6-carbonitrile

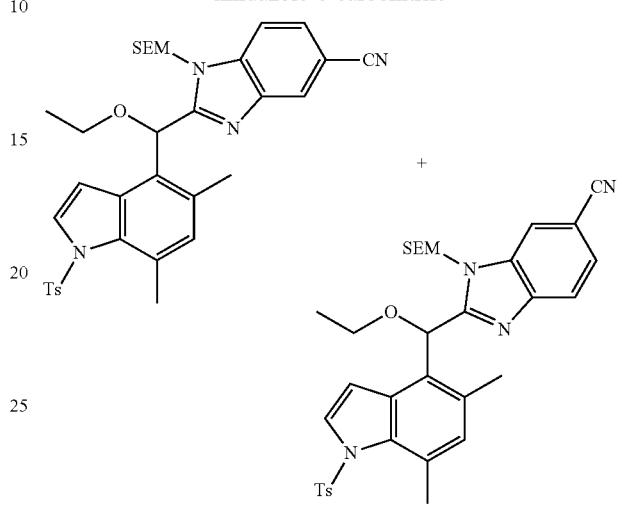

To a solution of a mixture of (±)-2-((5,7-dimethyl-1-tosyl-1H-indol-4-yl)(hydroxy)methyl)-1-((2-(trimethylsilyl)ethoxy)methyl)-1H-benzo[d]imidazole-5-carbonitrile and 2-((5,7-dimethyl-1-tosyl-1H-indol-4-yl)(hydroxy)methyl)-1-((2-(trimethylsilyl)ethoxy)methyl)-1H-benzo[d]imidazole-6-carbonitrile (Example 64-A) (82 mg, 0.136 mmol) and DIPEA (0.095 mL, 0.546 mmol) in toluene (1.3 mL), MsCl (0.021 mL, 0.273 mmol) was added at room temperature. After stirring for 1 h, EtOH (0.159 mL, 2.73 mmol) was added. The reaction mixture was allowed to stir at 80° C. for 13 h. To the reaction mixture, additional EtOH (0.79 mL, 13.65 mmol) was added. The mixture was allowed to stir at 80° C. for 4 h. The reaction mixture was cooled to room temperature, and concentrated. The residue was diluted with 2 M aq. $Na_2CO_3$, brine and $CH_2Cl_2$. The layers were separated and the aqueous layer was extracted with $CH_2Cl_2$. The organic layers were combined, dried over $Na_2SO_4$, filtered and concentrated to give title compounds as a mixture, without need of further purification. MS (ESI+) m/z 629.2 (M+H).

Example 73

(±)-2-((5,7-Dimethyl-1H-indol-4-yl)(ethoxy)methyl)-1H-benzo[d]imidazole-5-carbonitrile

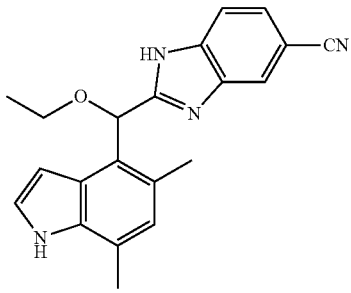 [SMILES: CCOC(c1nc2cc(C#N)ccc2[nH]1)c1c(C)cc(C)c2[nH]ccc12]

The title compound was synthesized from a mixture of (±)-2-((5,7-dimethyl-1-tosyl-1H-indol-4-yl)(ethoxy)methyl)-1-((2-(trimethylsilyl)ethoxy)methyl)-1H-benzo[d]imidazole-5-carbonitrile and (±)-2-((5,7-dimethyl-1-tosyl-1H-indol-4-yl)(ethoxy)methyl)-1-((2-(trimethylsilyl)ethoxy)methyl)-1H-benzo[d]imidazole-6-carbonitrile as described in Example 64-B and 64-C. $^1$H NMR (TFA salt, 400 MHz, DMSO-$d_6$) δ ppm 10.96 (br.s, 1H) 7.98 (s, 1H) 7.65 (d, J=8.25 Hz, 1H) 7.55 (m, 1H) 7.21 (t, J=2.78 Hz, 1H) 6.74 (s, 1H) 6.56 (dd, J=2.78, 2.02 Hz, 1H) 6.30 (s, 1H) 3.56-3.64 (m, 1H) 3.42-3.50 (m, 1H) 2.42 (s, 3H) 2.41 (s, 3H) 1.22 (t, J=6.95 Hz, 3H). HRMS calcd. for $C_{21}H_{20}N_4O$ (M+H)$^+$ 345.1710. found 345.1717.

Example 74

(±)-2-((5,7-Dimethyl-1H-indol-4-yl)(2-methoxyethoxy)methyl)benzo[d]imidazole-5-carbonitrile

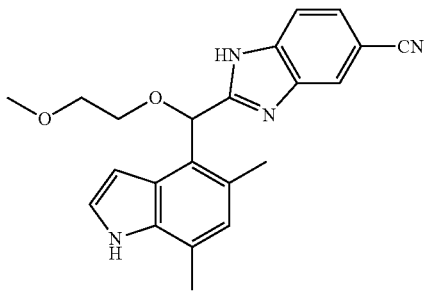 [SMILES: COCCOC(c1nc2cc(C#N)ccc2[nH]1)c1c(C)cc(C)c2[nH]ccc12]

The title compound was synthesized as in the Example 73 using 2-methoxyethanol instead of EtOH. $^1$H NMR (TFA salt, 400 MHz, DMSO-$d_6$) δ ppm 10.95 (br.s, 1H) 7.97 (s, 1H) 7.64 (d, J=8.34 Hz, 1H) 7.53 (dd, J=8.34, 1.01 Hz, 1H) 7.21 (t, J=2.65 Hz, 1H) 6.74 (s, 1H) 6.57-6.59 (m, 1H) 6.35 (s, 1H) 3.64-3.70 (m, 1H) 3.52-3.57 (m, 3H) 3.24 (s, 3H) 2.43 (s, 3H) 2.41 (s, 3H). HRMS calcd. for $C_{22}H_{22}N_4O_2$ (M+H)$^+$ 375.1816. found 375.0894.

Example 75

Example 75-A 2-(5,7-dimethyl-1-tosyl-1H-indole-4-carbonyl)-1-((2-(trimethylsilyl)ethoxy)methyl)-1H-benzo[d]imidazole-5-carbonitrile and 2-(5,7-dimethyl-1-tosyl-1H-indole-4-carbonyl)-1-((2-(trimethylsilyl)ethoxy)methyl)-1H-benzo[d]imidazole-6-carbonitrile

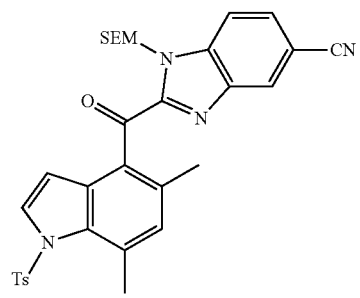

+

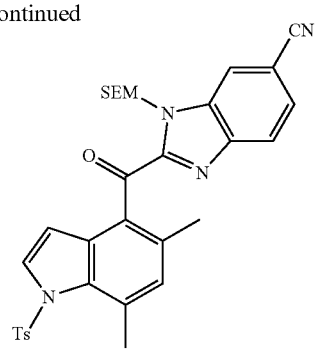

A suspension of a mixture of (±)-2-((5,7-dimethyl-1-tosyl-1H-indol-4-yl)(hydroxy)methyl)-1-((2-(trimethylsilyl)ethoxy)methyl)-1H-benzo[d]imidazole-5-carbonitrile and (±)-2-((5,7-dimethyl-1-tosyl-1H-indol-4-yl)(hydroxy)methyl)-1-((2-(trimethylsilyl)ethoxy)methyl)-1H-benzo[d]imidazole-6-carbonitrile (1.89 g, 2.99 mmol), and MnO$_2$ (1.53 g, 14.94 mmol) in CH$_2$Cl$_2$ (15 mL) was allowed to stir at 40° C. After stirring for 16 hr, additional MnO$_2$ (1.53 g, 14.94 mmol) was added. The reaction mixture was allowed to stir for further 5 h at the same temperature. The mixture was cooled to room temperature, and then passed through a pad of silica gel (20 g) by eluting with EtOAc (200 mL). The filtrate was concentrated and purified by flash column chromatography on silica gel (heptanes/EtOAc=100:0 to 60:40) to give title compounds as a mixture. MS (ESI+) m/z 599.3 (M+H).

Example 75-B 2-(1-(5,7-Dimethyl-1-tosyl-1H-indol-4-yl)vinyl)-1-((2-(trimethylsilyl)ethoxy)methyl)-1H-benzo[d]imidazole-5-carbonitrile and 2-(1-(5,7-dimethyl-1-tosyl-1H-indol-4-yl)vinyl)-1-((2-(trimethylsilyl)ethoxy)methyl)-1H-benzo[d]imidazole-6-carbonitrile

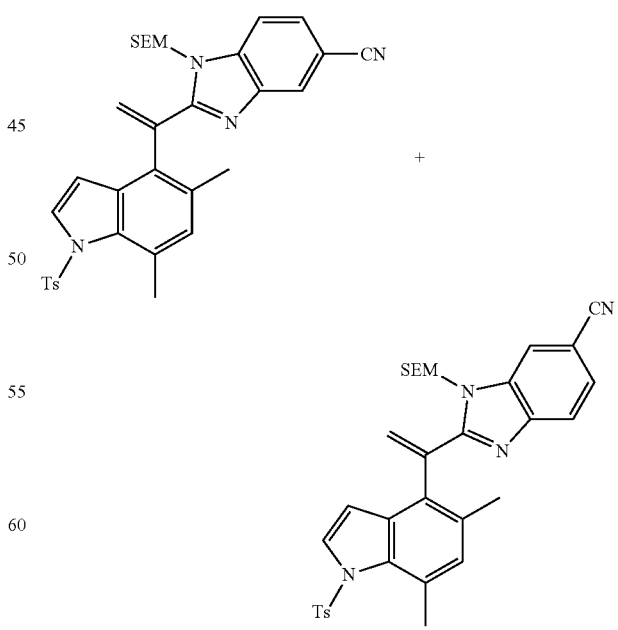

To a suspension of methyltriphenylphosphonium bromide (191 mg, 0.534 mmol) in THF (3.56 mL) at 0° C., NaHMDS (1.0M in THF, 0.534 mL, 0.534 mmol) was added. After stirring for 30 minutes, a solution of a mixture of 2-(5,7-dimethyl-1-tosyl-1H-indole-4-carbonyl)-1-((2-(trimethylsilyl)ethoxy)methyl)-1H-benzo[d]imidazole-5-carbonitrile and 2-(5,7-dimethyl-1-tosyl-1H-indole-4-carbonyl)-1-((2-(trimethylsilyl)ethoxy)methyl)-1H-benzo[d]imidazole-6-carbonitrile (213 mg, 0.356 mmol) in THF (1 mL) was added. The mixture was stirred at 0° C. for 10 minutes and then warmed to room temperature. After 3 days the reaction was quenched with sat. aq. NH$_4$Cl and brine, the layers separated and the aqueous layer extracted with EtOAc. The organic extract was dried over MgSO$_4$, filtered, and concentrated. The product was purified by flash chromatography (0-100% EtOAc in heptanes) to provide title compounds as a mixture. MS (ESI+) m/z 597.5 (M+H).

Example 75-C (±)-2-(1-(5,7-Dimethyl-1-tosyl-1H-indol-4-yl)ethyl)-1-((2-(trimethylsilyl)ethoxy)methyl)-1H-benzo[d]imidazole-5-carbonitrile and (±)-2-(1-(5,7-dimethyl-1-tosyl-1H-indol-4-yl)ethyl)-1-((2-(trimethylsilyl)ethoxy)methyl)-1H-benzo[d]imidazole-6-carbonitrile

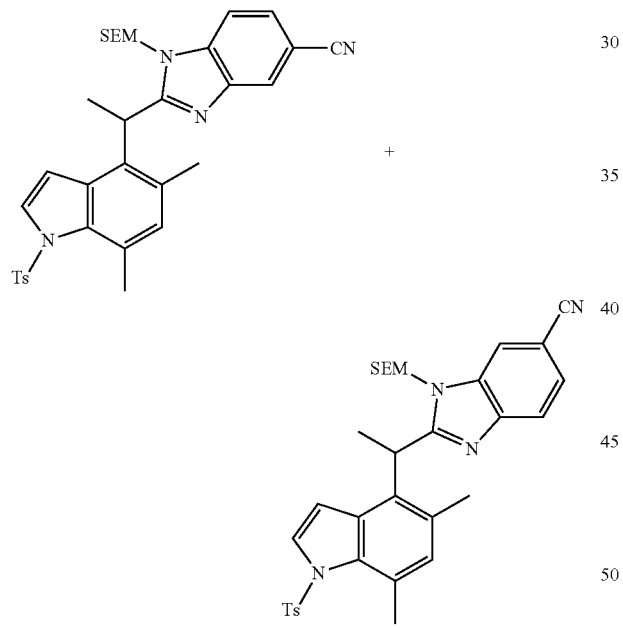

To a solution of a mixture of 2-(1-(5,7-dimethyl-1-tosyl-1H-indol-4-yl)vinyl)-1-((2-(trimethylsilyl)ethoxy)methyl)-1H-benzo[d]imidazole-5-carbonitrile and 2-(1-(5,7-dimethyl-1-tosyl-1H-indol-4-yl)vinyl)-1-((2-(trimethylsilyl)ethoxy)methyl)-1H-benzo[d]imidazole-6-carbonitrile (50 mg, 0.084 mmol) in EtOAc (1 mL) was added Pd/C (5% wet Degussa type, 8.9 mg, 4.19 μmol) and the reaction was stirred at room temperature under hydrogen. After 50 minutes additional Pd/C (5%, 27 mg) was added. After 4 hours total, the reaction was filtered through Celite®, rinsing with EtOAc, and concentrated. The residue was purified by flash chromatography (0-70% EtOAc in heptanes) to provide title compounds as a mixture. MS (ESI+) m/z 599.5 (M+H).

Example 75-D (±)-2-(1-(5,7-Dimethyl-1H-indol-4-yl)ethyl)-1H-benzo[d]imidazole-5-carbonitrile

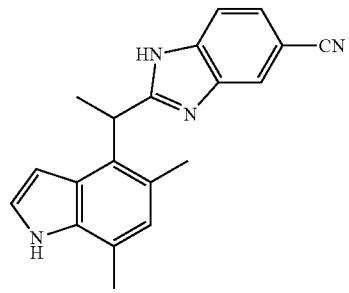 [SMILES: Cc1cc(C)c2[nH]ccc2c1C(C)c1nc2cc(C#N)ccc2[nH]1]

The title compound was synthesized from a mixture of (±)-2-(1-(5,7-dimethyl-1-tosyl-1H-indol-4-yl)ethyl)-1-((2-(trimethylsilyl)ethoxy)methyl)-1H-benzo[d]imidazole-5-carbonitrile and (±)-2-(1-(5,7-dimethyl-1-tosyl-1H-indol-4-yl)ethyl)-1-((2-(trimethylsilyl)ethoxy)methyl)-1H-benzo[d]imidazole-6-carbonitrile as described in Example 64-B and 64-C. $^1$H NMR (400 MHz, DMSO-d$_6$) δ ppm 12.22 (br. s., 1H) 10.86 (br. s., 1H) 8.13 (m) 7.69-7.84 (m) 7.36-7.54 (m) 7.05 (t, J=2.78 Hz, 1H) 6.76 (s, 1H) 5.83-5.96 (m, 1H) 4.72-4.90 (m, 1H) 2.39 (s, 3H) 2.37 (s, 3H) 1.76 (d, J=7.07 Hz, 3H). HRMS calcd. for C$_{20}$H$_{18}$N$_4$ (M+H)$^+$ 315.1610. found 315.1610.

Example 76

Example 76-A (±)-2-(1-(5,7-Dimethyl-1-tosyl-1H-indol-4-yl)-1-hydroxyethyl)-1-((2-(trimethylsilyl)ethoxy)methyl)-1H-benzo[d]imidazole-5-carbonitrile and (±)-2-(1-(5,7-dimethyl-1-tosyl-1H-indol-4-yl)-1-hydroxyethyl)-1-((2-(trimethylsilyl)ethoxy)methyl)-1H-benzo[d]imidazole-6-carbonitrile

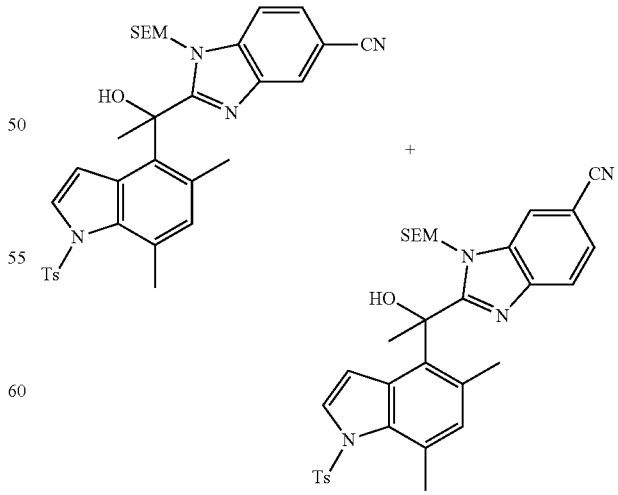

To a solution of a mixture of 2-(5,7-dimethyl-1-tosyl-1H-indole-4-carbonyl)-1-((2-(trimethylsilyl)ethoxy)methyl)-

1H-benzo[d]imidazole-5-carbonitrile and 2-(5,7-dimethyl-1-tosyl-1H-indole-4-carbonyl)-1-((2-(trimethylsilyl)ethoxy)methyl)-1H-benzo[d]imidazole-6-carbonitrile (Example 75-A) (1.25 g, 2.09 mmol) in THF (21 mL), 3 M MeMgBr in Et₂O (1.39 mL, 4.18 mmol) was added at 0° C. After stirring for 1 h, the reaction was quenched with aq. NH₄Cl and brine. The layers were separated and the aqueous layer was extracted with EtOAc. The organic layer was washed with brine, dried over Na₂SO₄, filtered, and concentrated to give crude. The crude was purified by flash column chromatography on silica gel (heptanes/EtOAc=100:0 to 45:55) to give title compounds as a mixture. MS (ESI+) m/z 615.4 (M+H).

Example 76-B a) (±)-2-(1-(5,7-Dimethyl-1H-indol-4-yl)-1-hydroxyethyl)-1H-benzo[d]imidazole-5-carbonitrile

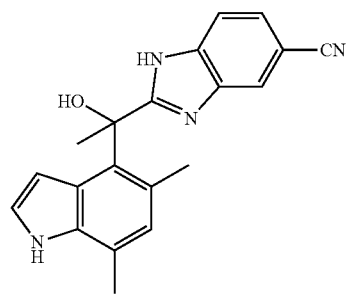 [SMILES: Cc1cc(C)c2[nH]ccc2c1C(C)(O)c1nc2cc(C#N)ccc2[nH]1]

The title compound was synthesized from a mixture of (±)-2-(1-(5,7-dimethyl-1-tosyl-1H-indol-4-yl)-1-hydroxyethyl)-1-((2-(trimethylsilyl)ethoxy)methyl)-1H-benzo[d]imidazole-5-carbonitrile and (±)-2-(1-(5,7-dimethyl-1-tosyl-1H-indol-4-yl)-1-hydroxyethyl)-1-((2-(trimethylsilyl)ethoxy)methyl)-1H-benzo[d]imidazole-6-carbonitrile following similar procedures as described in Example 64-B and 64-C. ¹H NMR (400 MHz, DMSO-d₆) δ ppm 12.30 (br.s, 1H) 10.80 (s, 1H) 8.18 (m) 7.77-7.82 (m) 7.48-7.54 (m) 7.07 (br. s, 1H) 6.63 (s, 1H) 6.23-6.25 (m) 5.96 (s, 1H) 2.38 (s, 3H) 2.11 (s, 3H) 2.07 (s, 3H). HRMS calcd. for C₂₀H₁₈N₄O (M+H)⁺ 331.1553. found 331.1559.

b) (+) and (−)-2-(1-(5,7-Dimethyl-1H-indol-4-yl)-1-hydroxyethyl)-1H-benzo[d]imidazole-5-carbonitrile Resolution of the enantiomers of 2-(1-(5,7-Dimethyl-1H-indol-4-yl)-1-hydroxyethyl)-1H-benzo[d]imidazole-5-carbonitrile was achieved by chiral HPLC using a CHIRALPAK® AS-H column with 20% EtOH (with DEA) in heptane to give (+)-2-(1-(5,7-Dimethyl-1H-indol-4-yl)-1-hydroxyethyl)-1H-benzo[d]imidazole-5-carbonitrile (t_r=7.7 min) and (−)-2-(1-(5,7-Dimethyl-1H-indol-4-yl)-1-hydroxyethyl)-1H-benzo[d]imidazole-5-carbonitrile (t_r=13.2 min).

Example 77

Example 77-A (±)-2-(1-(5-Ethyl-7-methyl-1-tosyl-1H-indol-4-yl)-1-hydroxyethyl)-1-((2-(trimethylsilyl)ethoxy)methyl)-1H-benzo[d]imidazole-5-carbonitrile and (±)-2-(1-(5-ethyl-7-methyl-1-tosyl-1H-indol-4-yl)-1-hydroxyethyl)-1-((2-(trimethylsilyl)ethoxy)methyl)-1H-benzo[d]imidazole-6-carbonitrile

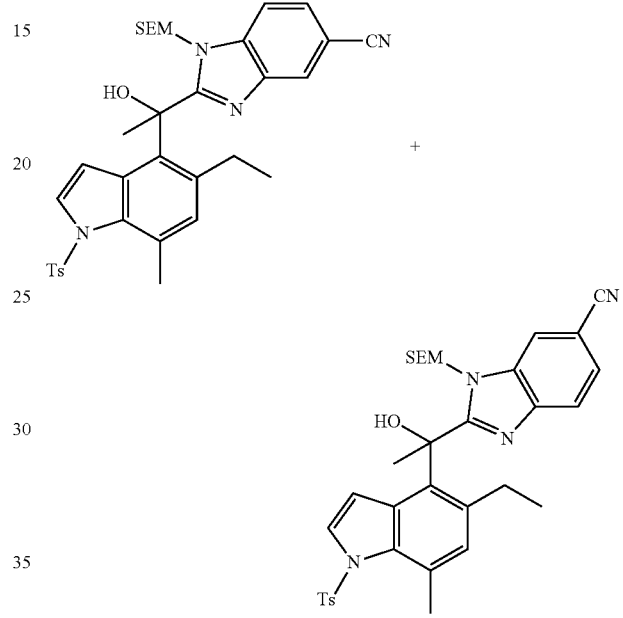

A mixture of title compounds was synthesized from a mixture of (±)-2-((5-ethyl-7-methyl-1-tosyl-1H-indol-4-yl)(hydroxy)methyl)-1-((2-(trimethylsilyl)ethoxy)methyl)-1H-benzo[d]imidazole-5-carbonitrile and (±)-2-((5-ethyl-7-methyl-1-tosyl-1H-indol-4-yl)(hydroxy)methyl)-1-((2-(trimethylsilyl)ethoxy)methyl)-1H-benzo[d]imidazole-6-carbonitrile (Example 70-A) analogously to Example 75-A and 76-A. MS (ESI+) m/z 629.4 (M+H).

Example 77-B (±)-2-(1-(5-Ethyl-7-methyl-1-tosyl-1H-indol-4-yl)-1-hydroxyethyl)-1H-benzo[d]imidazole-5-carbonitrile

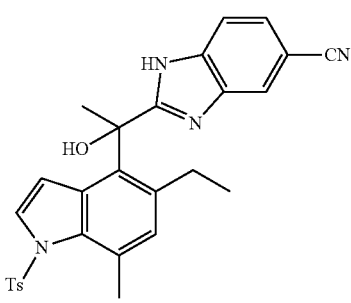 [SMILES: CCc1cc(C)c2c(ccn2S(=O)(=O)c2ccc(C)cc2)c1C(C)(O)c1nc2cc(C#N)ccc2[nH]1]

To a solution of a mixture of (±)-2-(1-(5-ethyl-7-methyl-1-tosyl-1H-indol-4-yl)-1-hydroxyethyl)-1-((2-(trimethylsilyl)ethoxy)methyl)-1H-benzo[d]imidazole-5-carbonitrile and (±)-2-(1-(5-ethyl-7-methyl-1-tosyl-1H-indol-4-yl)-1-hydroxyethyl)-1-((2-(trimethylsilyl)ethoxy)methyl)-1H-benzo[d]imidazole-6-carbonitrile (1.5 g, 2.38 mmol) and ethylenediamine (1.61 mL, 23.85 mmol) was added TBAF in THF (1M, 23.85 mL, 23.85 mmol), and then the mixture was stirred at 60° C. for 3 h. The reaction was quenched by H₂O. The layers were separated and the aqueous layer was extracted with EtOAc. The organic phase was successively washed with H₂O and brine, dried over Na₂SO₄, and filtered. After concentration of the filtrate the resulting residue was purified by silica gel flash chromatography (heptanes/EtOAc=66/34, isocratic) to give the title compound. MS (ESI+) m/z 499.3 (M+H).

Example 77-C a) (±)-2-(1-(5-Ethyl-7-methyl-1H-indol-4-yl)-1-hydroxyethyl)-1H-benzo[d]imidazole-5-carbonitrile

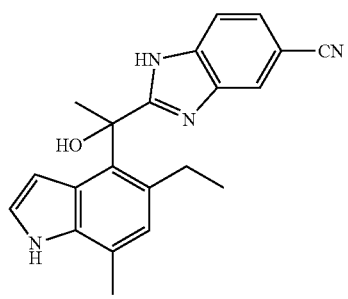 [SMILES: CCc1cc(C)c2[nH]ccc2c1C(C)(O)c1nc2cc(C#N)ccc2[nH]1]

The title compound was synthesized from (±)-2-(1-(5-Ethyl-7-methyl-1-tosyl-1H-indol-4-yl)-1-hydroxyethyl)-1H-benzo[d]imidazole-5-carbonitrile analogously to Example 64-C. $^1$H NMR (400 MHz, ACETONITRILE-$d_3$ with about 5 µL TFA) δ ppm 9.36 (br. s., 1H), 8.12 (s, 1H), 7.82 (d, J=0.76 Hz, 2H), 7.20 (dd, J=3.00, 3.30 Hz, 1H), 6.92 (s, 1H), 6.39 (dd, J=2.02, 3.28 Hz, 1H), 2.50-2.68 (m, 2H), 2.48 (s, 3H), 2.34 (s, 3H), 1.04 (t, J=7.45 Hz, 3H). HRMS calcd. for $C_{21}H_{20}N_4O$ (M+H)$^+$ 345.1715. found 345.1712.

b) (+) and (−)-2-(1-(5-ethyl-7-methyl-1H-indol-4-yl)-1-hydroxyethyl)-1H-benzo[d]imidazole-5-carbonitrile Resolution of the enantiomers of 2-(1-(5-ethyl-7-methyl-1H-indol-4-yl)-1-hydroxyethyl)-1H-benzo[d]imidazole-5-carbonitrile was achieved by chiral SFC using a CHIRALPAK® AD-H column with 35% MeOH in CO₂ to give (−)-2-(1-(5-ethyl-7-methyl-1H-indol-4-yl)-1-hydroxyethyl)-1H-benzo[d]imidazole-5-carbonitrile ($t_r$=2.2 min) and (+)-2-(1-(5-ethyl-7-methyl-1H-indol-4-yl)-1-hydroxyethyl)-1H-benzo[d]imidazole-5-carbonitrile ($t_r$=3.7 min).

Example 78

2-(5-Ethyl-7-methyl-1H-indole-4-carbonyl)-1H-benzo[d]imidazole-5-carbonitrile

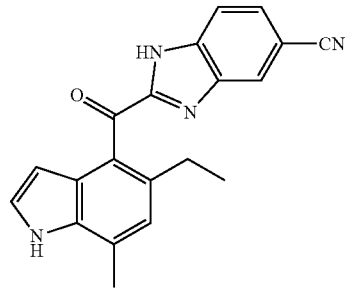 [SMILES: CCc1cc(C)c2[nH]ccc2c1C(=O)c1nc2cc(C#N)ccc2[nH]1]

The title compounds was synthesized as in Example 25A and 25-B from (±)-2-((5-ethyl-7-methyl-1-tosyl-1H-indol-4-yl)(hydroxy)methyl)-1-((2-(trimethylsilyl)ethoxy)methyl)-1H-benzo[d]imidazole-5-carbonitrile and (±)-2-((5-ethyl-7-methyl-1-tosyl-1H-indol-4-yl)(hydroxy)methyl)-1-((2-(trimethylsilyl)ethoxy)methyl)-1H-benzo[d]imidazole-6-carbonitrile (Example 70-A). $^1$H NMR (400 MHz, ACETONITRILE-$d_3$ with about 5 µL TFA) δ ppm 9.42 (br. s., 1H), 8.12 (dd, J=0.76, 1.39 Hz, 1H), 7.79 (dd, J=0.76, 8.59 Hz, 1H), 7.62 (dd, J=1.50, 8.60 Hz, 1H), 7.22 (dd, J=2.90, 3.03 Hz, 1H), 6.99 (s, 1H), 6.06 (dd, J=2.02, 3.03 Hz, 1H), 2.63 (q, J=7.58 Hz, 2H), 2.55 (d, J=0.88 Hz, 3H), 1.14 (t, J=7.58 Hz, 3H). HRMS calcd. for $C_{20}H_{16}N_4O$ (M+H)$^+$ 329.1397. found 329.1327.

Example 79

Example 79-A (±)-2-(1-Hydroxy-1-(5-isopropyl-7-methyl-1-tosyl-1H-indol-4-yl)ethyl)-1H-benzo[d]imidazole-5-carbonitrile and (±)-2-(1-hydroxy-1-(7-methyl-5-propyl-1-tosyl-1H-indol-4-yl)ethyl)-1H-benzo[d]imidazole-5-carbonitrile

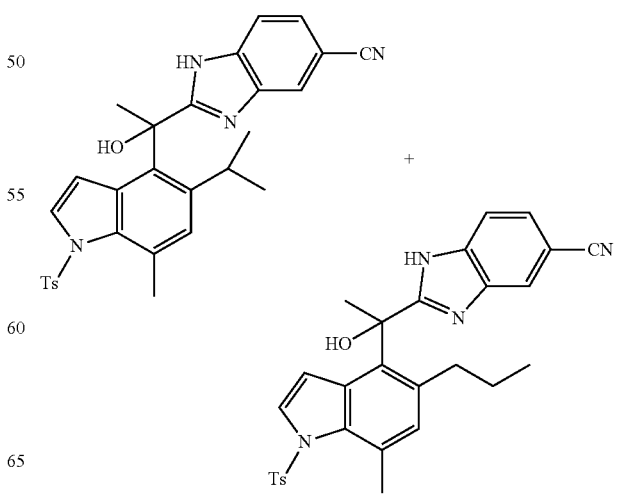

A mixture of title compounds was synthesized from a c.a. 5/1 mixture of 5-isopropyl-7-methyl-1-tosyl-1H-indole-4-carbaldehyde and 7-methyl-5-propyl-1-tosyl-1H-indole-4-carbaldehyde (Example 50-A) analogously to the preparation of (±)-2-(1-(5-ethyl-7-methyl-1-tosyl-1H-indol-4-yl)-1-hydroxyethyl)-1H-benzo[d]imidazole-5-carbonitrile (Example 77-B). MS (ESI+) m/z 513.2 (M+H).

Example 79-B a) (±)-2-(1-Hydroxy-1-(5-isopropyl-7-methyl-1H-indol-4-yl)ethyl)-1H-benzo[d]imidazole-5-carbonitrile and (±)-2-(1-hydroxy-1-(7-methyl-5-propyl-1H-indol-4-yl)ethyl)-1H-benzo[d]imidazole-5-carbonitrile

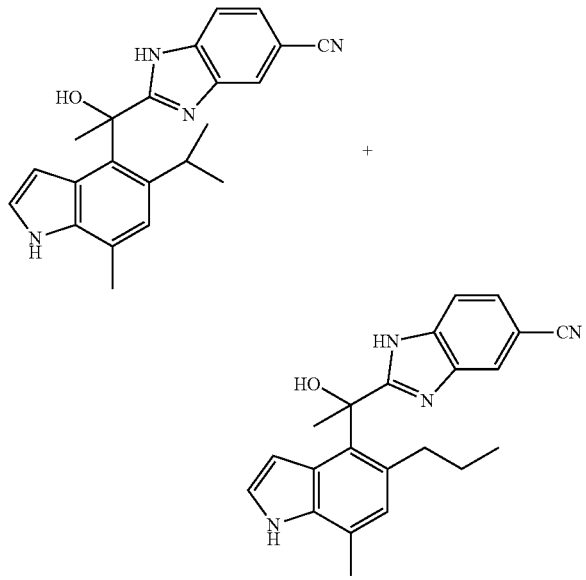

A mixture of (±)-2-(1-hydroxy-1-(5-isopropyl-7-methyl-1-tosyl-1H-indol-4-yl)ethyl)-1H-benzo[d]imidazole-5-carbonitrile and (±)-2-(1-hydroxy-1-(7-methyl-5-propyl-1-tosyl-1H-indol-4-yl)ethyl)-1H-benzo[d]imidazole-5-carbonitrile (110 mg, 0.215 mmol), isoamylamine (94 mg, 1.073 mmol), and KOH (60.2 mg, 1.073 mmol) was stirred at 100° C. for 0.75 h under the microwave irradiation. The reaction mixture was diluted with $CH_2Cl_2$. The mixture was filtered through $SiO_2$. The $SiO_2$ cake was washed with a mixture of $CH_2Cl_2$/MeOH (c.a. 6/1). Combined organic solution was concentrated and purified by silica gel flash column chromatography ($CH_2Cl_2$/EtOAc=82/18, isocratic) to give (±)-2-(1-hydroxy-1-(5-isopropyl-7-methyl-1H-indol-4-yl)ethyl)-1H-benzo[d]imidazole-5-carbonitrile as a pure isomeric form. $^1$H NMR (400 MHz, ACETONITRILE-$d_3$ with about 5 µL TFA) δ ppm 9.28 (br. s., 1H), 8.05 (s, 1H), 7.73 (d, J=8.60 Hz, 1H), 7.69 (dd, J=1.30, 8.60 Hz, 1H), 7.19 (dd, J=2.80, 2.90 Hz, 1H), 7.00 (s, 1H), 6.66 (dd, J=2.30, 3.00 Hz, 1H), 2.90-3.06 (m, 1H), 2.47 (s, 3H), 2.28 (s, 3H), 0.95 (d, J=6.82 Hz, 3H), 0.92 (d, J=6.57 Hz, 3H). HRMS calcd. for $C_{22}H_{22}N_4O$ (M+H)$^+$ 359.1867. found 359.1865.

Mixed fractions were concentrated separately and purified by RP-HPLC (HC-A) to give (±)-2-(1-hydroxy-1-(7-methyl-5-propyl-1H-indol-4-yl)ethyl)-1H-benzo[d]imidazole-5-carbonitrile. $^1$H NMR (400 MHz, ACETONITRILE-$d_3$ with about 5 µL TFA) δ ppm 9.37 (br. s., 1H), 8.09-8.19 (m, 1H), 7.76-7.88 (m, 2H), 7.20 (dd, J=3.00, 3.30 Hz, 1H), 6.90 (s, 1H), 6.40 (dd, J=2.02, 3.28 Hz, 1H), 2.42-2.59 (m, 5H), 2.34 (s, 3H), 1.43-1.54 (m, 1H), 1.31-1.42 (m, 1H), 0.74 (t, J=7.33 Hz, 3H). HRMS calcd. for $C_{22}H_{22}N_4O$ (M+H)$^+$ 359.1867. found 359.1864.

b) (+) and (−)-2-(1-hydroxy-1-(5-isopropyl-7-methyl-1H-indol-4-yl)ethyl)-1H-benzo[d]imidazole-5-carbonitrile Resolution of the enantiomers of 2-(1-hydroxy-1-(5-isopropyl-7-methyl-1H-indol-4-yl)ethyl)-1H-benzo[d]imidazole-5-carbonitrile was achieved by chiral SFC using a CHIRALPAK® AD-H column with 35% (0.2% diethylamine in MeOH) in $CO_2$ to give (−)-2-(1-hydroxy-1-(5-isopropyl-7-methyl-1H-indol-4-yl)ethyl)-1H-benzo[d]imidazole-5-carbonitrile ($t_r$=1.5 min) and (+)-2-(1-hydroxy-1-(5-isopropyl-7-methyl-1H-indol-4-yl)ethyl)-1H-benzo[d]imidazole-5-carbonitrile ($t_r$=2.9 min).

The following compounds were prepared with similar methods.

| | Structure/Chemical Name | $^1$H NMR | HRMS |
|---|---|---|---|
| 79-C a) | (±)-2-(1-(5-cyclopropyl-7-methyl-1H-indol-4-yl)-1-hydroxyethyl)-1H-benzo[d]imidazole-5-carbonitrile | (400 MHz, DICHLOROMETHANE-$d_2$) δ ppm 8.19 (br. s., 1H), 7.88 (br. s., 1H), 7.56 (d, J = 9.9 Hz, 1H), 7.45-7.52 (m, 1H), 7.15 (t, J = 2.8 Hz, 1H), 6.69 (s, 1H), 6.59-6.66 (m, 1H), 3.68 (br. s., 1H), 2.45 (s, 3H), 2.36 (s, 3H), 1.87-1.97 (m, 1H), 0.65-0.80 (m, 2H), 0.47-0.64 (m, 2H). | calcd. for $C_{22}H_{20}N_4O$ (M + H)$^+$ 357.1710, found 357.1713. |
| 79-C b) | (+) and (−)-2-(1-(5-cyclopropyl-7-methyl-1H-indol-4-yl)-1-hydroxyethyl)-1H-benzo[d]imidazole-5-carbonitrile Resolution of the enantiomers of 2-(1-(5-cyclopropyl-7-methyl-1H-indol-4-yl)-1-hydroxyethyl)-1H-benzo[d]imidazole-5-carbonitrile was achieved by chiral HPLC using a CHIRALPAK ® AS column with 30% ethanol with 0.2% diethylamine in | | |

-continued

| | Structure/Chemical Name | ¹H NMR | HRMS |
|---|---|---|---|
| | heptane to give (+)-2-(1-(5-cyclopropyl-7-methyl-1H-indol-4-yl)-1-hydroxyethyl)-1H-benzo[d]imidazole-5-carbonitrile (t$_r$ = 3.59 min) and (−)-2-(1-(5-cyclopropyl-7-methyl-1H-indol-4-yl)-1-hydroxyethyl)-1H-benzo[d]imidazole-5-carbonitrile (t$_r$ = 5.44 min). | | |
| 79-D a) | (±)-2-(1-hydroxy-1-(5-isobutyl-7-methyl-1H-indol-4-yl)-ethyl)-1H-benzo[d]imidazole-5-carbonitrile | (400 MHz, DMSO-d$_6$ with about 5 µL TFA) δ ppm 10.83 (br. s., 1H), 8.05 (br. s., 1H), 7.62 (d, J = 8.30 Hz, 1H), 7.55 (dd, J = 1.40, 8.30 Hz, 1H), 7.02 (dd, J = 2.80, 3.00 Hz, 1H), 6.69 (s, 1H), 5.98 (dd, J = 1.96, 3.09 Hz, 1H), 2.81-2.93 (m, 1H), 2.42-2.48 (m, 1H), 2.40 (s, 3H), 2.12 (s, 3H), 1.82-2.00 (m, 1H), 0.76 (d, J = 6.57 Hz, 6H). | calcd. for C$_{23}$H$_{24}$N$_4$O (M + H)$^+$ 373.2023, found 373.2033. |
| 79-D b) | (+) and (−)-2-(1-hydroxy-1-(5-isobutyl-7-methyl-1H-indol-4-yl)ethyl)-1H-benzo[d]imidazole-5-carbonitrile<br>Resolution of the enantiomers of 2-(1-hydroxy-1-(5-isobutyl-7-methyl-1H-indol-4-yl)ethyl)-1H-benzo[d]imidazole-5-carbonitrile was achieved by normal phase chiral HPLC using a CHIRALPAK ® AS column with 20% (0.2% diethylamine in EtOH) in heptane to give (+)-2-(1-hydroxy-1-(5-isobutyl-7-methyl-1H-indol-4-yl)ethyl)-1H-benzo[d]imidazole-5-carbonitrile (t$_r$ = 4.0 min) and (−)-2-(1-hydroxy-1-(5-isobutyl-7-methyl-1H-indol-4-yl)ethyl)-1H-benzo[d]imidazole-5-carbonitrile (t$_r$ = 5.9 min). | | |
| 79-E a) | (±)-2-(1-(5-chloro-7-methyl-1H-indol-4-yl)-1-hydroxyethyl)-1H-benzo[d]imidazole-5-carbonitrile | (400 MHz, DMSO-d$_6$ with about 5 µL TFA) δ ppm 11.29 (br. s., 1H), 8.08 (s, 1H), 7.67 (d, J = 8.60 Hz, 1H), 7.57-7.65 (m, 1H), 7.35-7.41 (m, 1H), 7.09 (dd, J = 2.02, 3.03 Hz, 1H), 6.85 (d, J = 0.51 Hz, 1H), 2.45 (d, J = 0.51 Hz, 3H), 2.14 (s, 3H). | calcd. for C$_{19}$H$_{15}$ClN$_4$O (M + H)$^+$ 351.1013, found 351.1014. |
| 79-E b) | (+) and (−)-2-(1-(5-chloro-7-methyl-1H-indol-4-yl)-1-hydroxyethyl)-1H-benzo[d]imidazole-5-carbonitrile<br>Resolution of the enantiomers of 2-(1-(5-chloro-7-methyl-1H-indol-4-yl)-1-hydroxyethyl)-1H-benzo[d]imidazole-5-carbonitrile was achieved by chiral SFC using a CHIRALPAK ® IA column with 35% MeOH in CO$_2$ to give (−)-2-(1-(5-chloro-7-methyl-1H-indol-4-yl)-1-hydroxyethyl)-1H-benzo[d]imidazole-5-carbonitrile (t$_r$ = 2.0 min) and (+)-2-(1-(5-chloro-7-methyl-1H-indol-4-yl)-1-hydroxyethyl)-1H-benzo[d]imidazole-5-carbonitrile (t$_r$ = 3.0 min). | | |
| 79-F a) | (±)-2-(1-(5-bromo-7-methyl-1H-indol-4-yl)-1-hydroxyethyl)-1H-benzo[d]imidazole-5-carbonitrile | (400 MHz, ACETONITRILE-d$_3$ with 5 µL TFA) δ ppm 9.66 (br. s., 1H), 8.19 (dd, J = 0.82, 1.33 Hz, 1H), 7.89-7.99 (m, 1H), 7.83-7.88 (m, 1H), 7.40 (s, 1H), 7.20 (d, J = 0.51 Hz, 1H), 7.11 (dd, J = 2.08, 3.35 Hz, 1H), 2.51 (d, J = 0.88 Hz, 3H), 2.34 (s, 3H). | calcd. for C$_{19}$H$_{15}$BrN$_4$O (M + H)$^+$ 395.0502, found 395.0510. |

| | Structure/Chemical Name | ¹H NMR | HRMS |
|---|---|---|---|
| 79-F b) | (+) and (−)-2-(1-(5-bromo-7-methyl-1H-indol-4-yl)-1-hydroxyethyl)-1H-benzo[d]imidazole-5-carbonitrile<br><br>Resolution of the enantiomers of 2-(1-(5-bromo-7-methyl-1H-indol-4-yl)-1-hydroxyethyl)-1H-benzo[d]imidazole-5-carbonitrile was achieved by chiral SFC using a CHIRALPAK ® IA column with 35% MeOH in CO₂ to give (+) or (−)-2-(1-(5-bromo-7-methyl-1H-indol-4-yl)-1-hydroxyethyl)-1H- benzo[d]imidazole-5-carbonitrile (t$_r$ = 2.2 min) and (−) or (+)-2-(1-(5-bromo-7-methyl-1H-indol-4-yl)-1-hydroxyethyl)-1H-benzo[d]imidazole-5-carbonitrile (t$_r$ = 3.8 min). | | |
| 79-G | (±)-2-(1-(5,7-dimethyl-1H-indol-4-yl)-1-hydroxypropyl)-1H-benzo[d]imidazole-5-carbonitrile | (400 MHz, DMSO-d₆) δ ppm 12.16 (s, 1H) 10.76 (br. s., 1H) 8.17 (m) 7.77-7.84 (m) 7.74 (m) 7.42-7.54 (m) 7.05 (br. s., 1H) 6.64 (s, 1H) 6.36 (br. s., 1H) 5.61-5.76 (m, 1H) 2.54-2.73 (m, 2H) 2.38 (s, 3H) 2.18 (s, 3H) 0.84 (t, J = 7.33 Hz, 3H). | calcd. for C$_{21}$H$_{20}$N$_4$O (M + H)⁺ 345.1715, found 345.1715. |
| 79-H | (±)-2-(cyclopropyl(5,7-dimethyl-1H-indol-4-yl)(hydroxy)methyl)-1H-benzo[d]imidazole-5-carbonitrile | (400 MHz, DMSO-d₆) δ ppm 12.43 (br. s., 1H) 10.80 (br. s., 1H) 8.05 (m) 7.80 (m) 7.65-7.72 (m) 7.44-7.56 (m) 7.14 (br. s., 1H) 6.69 (br. s., 1H) 6.62 (s, 1H) 5.67-5.79 (m, 1H) 2.39 (s, 3H) 2.04-2.12 (m, 1H) 2.02 (s, 3H) 0.38-0.74 (m, 4H). | calcd. for C$_{22}$H$_{20}$N$_4$O (M + H)⁺ 357.1715, found 357.1721. |
| 79-I | (±)-2-((5,7-dimethyl-1H-indol-4-yl)(hydroxy)(phenyl)methyl)-1H-benzo[d]imidazole-5-carbonitrile | (400 MHz, DMSO-d₆) δ ppm 12.68 (br. s., 1H) 10.79 (br. s., 1H) 8.09 (m) 7.87 (m) 7.67-7.75 (m) 7.45-7.62 (m, 3H) 7.19-7.34 (m, 3H) 6.93 (t, J = 3.03 Hz, 1H) 6.80 (s, 1H) 6.67 (s, 1H) 4.89 (m, 1H) 2.39 (s, 3H) 1.91-2.00 (m, 3H). | calcd. for C$_{25}$H$_{20}$N$_4$O (M + H)⁺ 393.1715, found 393.1708. |

Example 80

Example 80-A (±)-2-(1-(5-Ethyl-7-methyl-1-tosyl-1H-indol-4-yl)-2,2,2-trifluoro-1-hydroxyethyl)-1-((2-(trimethylsilyl)ethoxy)methyl)-1H-benzo[d]imidazole-5-carbonitrile and (±)-2-(1-(5-ethyl-7-methyl-1-tosyl-1H-indol-4-yl)-2,2,2-trifluoro-1-hydroxyethyl)-1-((2-(trimethylsilyl)ethoxy)methyl)-1H-benzo[d]imidazole-6-carbonitrile

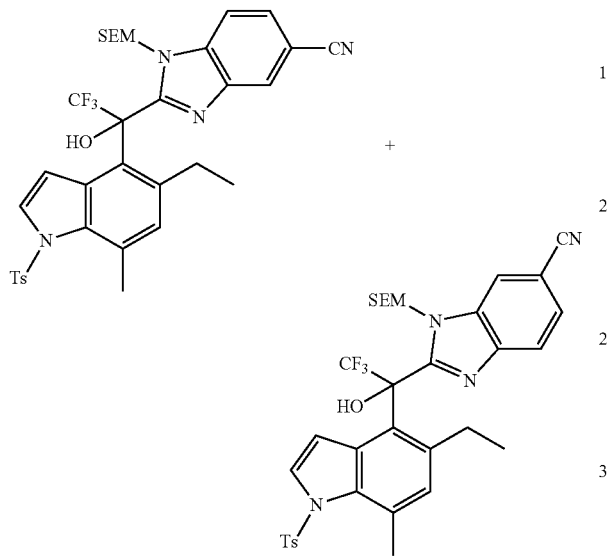

To a solution of a mixture of 2-(5-ethyl-7-methyl-1-tosyl-1H-indole-4-carbonyl)-1-((2-(trimethylsilyl)ethoxy)methyl)-1H-benzo[d]imidazole-5-carbonitrile and 2-(5-ethyl-7-methyl-1-tosyl-1H-indole-4-carbonyl)-1-((2-(trimethylsilyl)ethoxy)methyl)-1H-benzo[d]imidazole-6-carbonitrile (Example 117-A) (1.8 g, 2.94 mmol) and trimethyl(trifluoromethyl)silane (0.918 mL, 5.87 mmol) in THF (20 mL) was added TBAF in THF (1M, 8.81 mL, 8.81 mmol) at room temperature, and then the mixture was stirred at room temperature for 1.5 h. The reaction mixture was diluted with Et$_2$O. The mixture was successively washed by 5% aq. NaHCO$_3$, H$_2$O and brine, dried over Na$_2$SO$_4$, and filtered. Concentration of the filtrate gave title compounds as a mixture without need of further purification. MS (ESI+) m/z 683.5 (M+H).

Example 80-B (±)-2-(1-(5-Ethyl-7-methyl-1-tosyl-1H-indol-4-yl)-2,2,2-trifluoro-1-hydroxyethyl)-1H-benzo[d]imidazole-5-carbonitrile

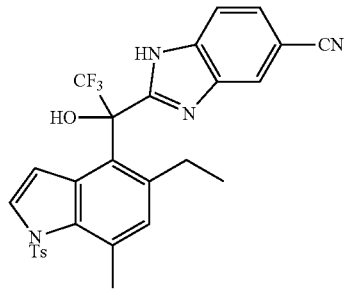 [SMILES: CCc1cc(C)c2c(ccn2S(=O)(=O)c2ccc(C)cc2)c1C(O)(c1nc2cc(C#N)ccc2[nH]1)C(F)(F)F]

A mixture of (±)-2-(1-(5-ethyl-7-methyl-1-tosyl-1H-indol-4-yl)-2,2,2-trifluoro-1-hydroxyethyl)-1-((2-(trimethylsilyl)ethoxy)methyl)-1H-benzo[d]imidazole-5-carbonitrile and (±)-2-(1-(5-ethyl-7-methyl-1-tosyl-1H-indol-4-yl)-2,2,2-trifluoro-1-hydroxyethyl)-1-((2-(trimethylsilyl)ethoxy)methyl)-1H-benzo[d]imidazole-6-carbonitrile (1.16 g, 1.69 mmol) and HCl in MeOH (1.25 M, 13.59 mL, 16.99 mmol) was allowed to stir at 60° C. for 0.5 h. The reaction mixture was cooled to rt and concentrated. The residue was dissolved in a small amount of EtOAc, and then diluted with heptanes. The precipitated solid was collected on a Kiriyama funnel, washed with hexane, dried under reduced pressure to give the title compound. MS (ESI+) m/z 553.3 (M+H).

Example 80-C a) (±)-2-(1-(5-Ethyl-7-methyl-1H-indol-4-yl)-2,2,2-trifluoro-1-hydroxyethyl)-1H-benzo[d]imidazole-5-carbonitrile

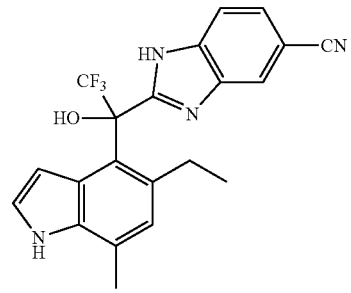 [SMILES: CCc1cc(C)c2[nH]ccc2c1C(O)(c1nc2cc(C#N)ccc2[nH]1)C(F)(F)F]

To a solution of a mixture of 2-(5-ethyl-7-methyl-1-tosyl-1H-indole-4-carbonyl)-1-((2-(trimethylsilyl)ethoxy)methyl)-1H-benzo[d]imidazole-5-carbonitrile and 2-(5-ethyl-7-methyl-1-tosyl-1H-indole-4-carbonyl)-1-((2-(trimethylsilyl)ethoxy)methyl)-1H-benzo[d]imidazole-6-carbonitrile (400 mg, 0.653 mmol) and trimethyl(trifluoromethyl)silane (0.204 mL, 1.30 mmol) in THF (1 mL) was added dropwise TBAF in THF (1M, 1.95 mL, 1.95 mmol) at 0° C., and then the mixture was stirred at room temperature for 0.5 hr. To the mixture were added ethylenediamine (0.441 mL, 6.53 mmol) and TBAF in THF (1M, 6.53 mL, 6.53 mmol), and then the mixture was stirred at 60° C. for 77 h. The reaction mixture was cooled to room temperature. The reaction mixture was diluted with EtOAc and successively washed by 5% aq. NaHCO$_3$, H$_2$O and brine, dried over Na$_2$SO$_4$, and filtered. After concentration the residue was purified by silica gel flash chromatography [heptanes/(30% EtOAc in CH$_2$Cl$_2$)=44/55] to give the title compound. $^1$H NMR (400 MHz, ACETONITRILE-d$_3$ with about 5 μL TFA) δ ppm 9.25 (br. s., 1H), 8.10 (s, 1H), 7.67 (d, J=8.30 Hz, 1H), 7.61 (dd, J=1.30, 8.30 Hz, 1H), 7.04 (t, J=3.00 Hz, 1H), 6.97 (s, 1H), 6.02 (br. s., 1H), 5.32 (br. s., 1H), 2.92-3.04 (m, 1H), 2.51-2.59 (m, 1H), 2.50 (d, J=0.76 Hz, 3H), 1.12 (t, J=7.33 Hz, 3H). HRMS calcd. for C$_{21}$H$_{17}$F$_3$N$_4$O (M+H)$^+$ 399.1427. found 399.1420.

b) (+) and (−)-2-(1-(5-ethyl-7-methyl-1H-indol-4-yl)-2,2,2-trifluoro-1-hydroxyethyl)-1H-benzo[d]imidazole-5-carbonitrile Resolution of the enantiomers of 2-(1-(5-ethyl-7-methyl-1H-indol-4-yl)-2,2,2-trifluoro-1-hydroxyethyl)-1H-benzo[d]imidazole-5-carbonitrile was achieved by chiral SFC using a CHIRALPAK® AD-H column with 15% MeOH in $CO_2$ to give (−)-2-(1-(5-ethyl-7-methyl-1H-indol-4-yl)-2,2,2-trifluoro-1-hydroxyethyl)-1H-benzo[d]imidazole-5-carbonitrile ($t_r$=3.2 min) and (+)-2-(1-(5-ethyl-7-methyl-1H-indol-4-yl)-2,2,2-trifluoro-1-hydroxyethyl)-1H-benzo[d]imidazole-5-carbonitrile ($t_r$=6.9 min).

The following compounds were prepared with similar methods.

| | Structure/Chemical Name | $^1$H NMR | HRMS |
|---|---|---|---|
| 80-D a) | (±)-2-(1-(5,7-dimethyl-1H-indol-4-yl)-2,2,2-trifluoro-1-hydroxyethyl)-1H-benzo[d]imidazole-5-carbonitrile | (400 MHz, DMSO-$d_6$) δ ppm 12.72 (br. s., 1H) 10.91 (br. s., 1H) 8.35 (m) 7.92-7.99 (m) 7.80 (m) 7.55-7.63 (m) 7.46-7.52 (m) 7.08 (t, J = 2.91 Hz, 1H) 6.72 (s, 1H) 6.05 (br. s., 1H) 2.41 (s, 3H) 2.14 (s, 3H). | calcd. for $C_{20}H_{15}F_3N_4O$ $(M + H)^+$ 385.1271, found 385.1287. |

80-D b) (+) and (−)-2-(1-(5,7-dimethyl-1H-indol-4-yl)-2,2,2-trifluoro-1-hydroxyethyl)-1H-benzo[d]imidazole-5-carbonitrile Resolution of the enantiomers of 2-(1-(5,7-dimethyl-1H-indol-4-yl)-2,2,2-trifluoro-1-hydroxyethyl)-1H-benzo[d]imidazole-5-carbonitrile was achieved by chiral SFC using a CHIRALPAK ® AD-H column with 15% MeOH in $CO_2$ to give (−)-2-(1-(5,7-dimethyl-1H-indol-4-yl)-2,2,2-trifluoro-1-hydroxyethyl)-1H-benzo[d]imidazole-5-carbonitrile ($t_r$ = 3.8 min) and (+)-2-(1-(5,7-dimethyl-1H-indol-4-yl)-2,2,2-trifluoro-1-hydroxyethyl)-1H-benzo[d]imidazole-5-carbonitrile ($t_r$ = 8.5 min).

| | Structure/Chemical Name | $^1$H NMR | HRMS |
|---|---|---|---|
| 80-E a) | (±)-2-(1-(5-cyclopropyl-7-methyl-1H-indol-4-yl)-2,2,2-trifluoro-1-hydroxyethyl)-1H-benzo[d]imidazole-5-carbonitrile | (400 MHz, ACETONITRILE-d3 with about 5 μL TFA) δ ppm 9.43 (br. s., 1H), 8.23 (t, J = 1.07 Hz, 1H), 7.89 (d, J = 1.14 Hz, 2H), 7.28 (t, J = 2.97 Hz, 1H), 6.54-6.70 (m, 2H), 2.49 (d, J = 0.76 Hz, 3H), 1.52-1.71 (m, 1H), 0.60-0.74 (m, 1H), 0.41-0.57 (m, 2H), 0.11-0.26 (m, 1H). | calcd. for $C_{22}H_{17}F_3N_4O$ $(M + H)^+$ 411.1427, found 411.1424. |

80-E b) (+) and (−)-2-(1-(5-cyclopropyl-7-methyl-1H-indol-4-yl)-2,2,2-trifluoro-1-hydroxyethyl)-1H-benzo[d]imidazole-5-carbonitrile Resolution of the enantiomers of 2-(1-(5-cyclopropyl-7-methyl-1H-indol-4-yl)-2,2,2-trifluoro-1-hydroxyethyl)-1H-benzo[d]imidazole-5-carbonitrile was achieved by chiral SFC using a CHIRALPAK ® AD-H column with 17-27% MeOH and 5 mM $NH_4OH$ in $CO_2$ to give (−)-2-(1-(5-cyclopropyl-7-methyl-1H-indol-4-yl)-2,2,2-trifluoro-1-hydroxyethyl)-1H-benzo[d]imidazole-5-carbonitrile ($t_r$ = 2.87 min) and (+)-2-(1-(5-cyclopropyl-7-methyl-1H-indol-4-yl)-2,2,2-trifluoro-1-hydroxyethyl)-1H-benzo[d]imidazole-5-carbonitrile ($t_r$ = 3.8 min).

| Structure/Chemical Name | ¹H NMR | HRMS |
|---|---|---|
| 80-F a) ![structure] (±)-2-(2,2,2-trifluoro-1-hydroxy-1-(5-isopropyl-7-methyl-1H-indol-4-yl)ethyl)-1H-benzo[d]imidazole-5-carbonitrile | (400 MHz, ACETONITRILE-$d_3$ with about 5 μL TFA) δ ppm 9.23 (br. s., 1H), 8.05 (s, 1H), 7.63 (d, J = 8.30 Hz, 1H), 7.57 (dd, J = 1.50, 8.30 Hz, 1H), 7.09 (t, J = 3.00 Hz, 1H), 7.04 (s, 1H), 6.42 (br. s., 1H), 5.27 (br. s., 1H), 3.19-3.30 (m, 1H), 2.48 (d, J = 0.76 Hz, 3H), 1.10 (d, J = 6.57 Hz, 3H), 0.78 (d, J = 6.82 Hz, 3H). | calcd. for $C_{22}H_{19}F_3N_4O$ $(M + H)^+$ 413.1584, found 413.158. |
| 80-F b) | (+) and (−)-2-(2,2,2-trifluoro-1-hydroxy-1-(5-isopropyl-7-methyl-1H-indol-4-yl)ethyl)-1H-benzo[d]imidazole-5-carbonitrile Resolution of the enantiomers of 2-(2,2,2-trifluoro-1-hydroxy-1-(5-isopropyl-7-methyl-1H-indol-4-yl)ethyl)-1H-benzo[d]imidazole-5-carbonitrile was achieved by chiral SFC using a CHIRALPAK ® AD-H column with 10 to 25% MeOH in $CO_2$ to give (−)-2-(2,2,2-trifluoro-1-hydroxy-1-(5-isopropyl-7-methyl-1H-indol-4-yl)ethyl)-1H-benzo[d]imidazole-5-carbonitrile ($t_r$ = 3.0 min) and (+)-2-(2,2,2-trifluoro-1-hydroxy-1-(5-isopropyl-7-methyl-1H-indol-4-yl)ethyl)-1H-benzo[d]imidazole-5-carbonitrile ($t_r$ = 3.9 min). | |

Example 81

Example 81-A 2-(5-Bromo-7-methyl-1-tosyl-1H-indole-4-carbonyl)-1-((2-(trimethylsilyl)ethoxy)methyl)-1H-benzo[d]imidazole-5-carbonitrile and 2-(5-bromo-7-methyl-1-tosyl-1H-indole-4-carbonyl)-1-((2-(trimethylsilyl)ethoxy)methyl)-1H-benzo[d]imidazole-6-carbonitrile

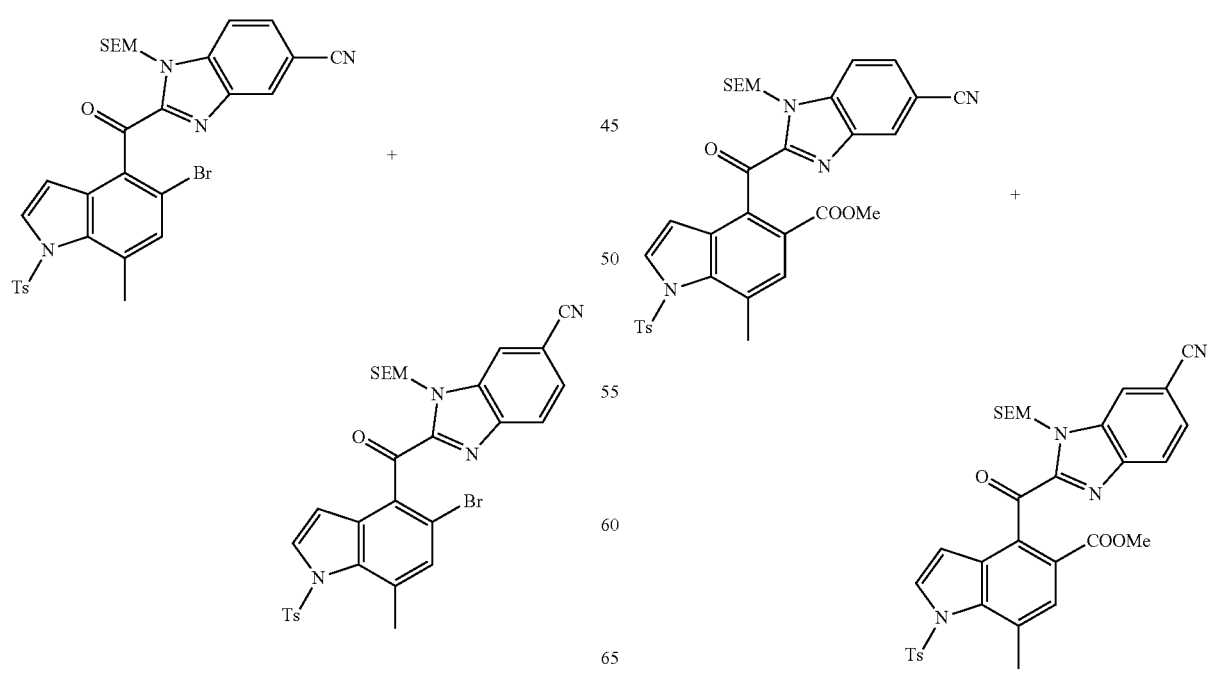

A mixture of title compounds was prepared from 5-bromo-7-methyl-1-tosyl-1H-indole-4-carbaldehyde (Example 55-C) analogously to the preparation of title compound in Example 75-A. MS (ESI+) m/z 663.3, 665.3 (M+H).

Example 81-B

Methyl 4-(5-cyano-1-((2-(trimethylsilyl)ethoxy)methyl)-1H-benzo[d]imidazole-2-carbonyl)-7-methyl-1-tosyl-1H-indole-5-carboxylate and methyl 4-(6-cyano-1-((2-(trimethylsilyl)ethoxy)methyl)-1H-benzo[d]imidazole-2-carbonyl)-7-methyl-1-tosyl-1H-indole-5-carboxylate A septum-sealed flask containing a mixture of 2-(5-bromo-7-methyl-1-tosyl-1H-indole-4-carbonyl)-1-((2-(trimethylsilyl)ethoxy)methyl)-1H-benzo[d]imidazole-5-carbonitrile and 2-(5-bromo-7-methyl-1-tosyl-1H-indole-4-carbonyl)-1-((2-(trimethyl-silyl)ethoxy)methyl)-1H-benzo[d]imidazole-6-carbonitrile (1 g, 1.5 mmol), palladium acetate (0.034 g, 0.151 mmol), and Xantphos (0.174 g, 0.301 mmol) was evacuated and filled with CO gas and placed under CO atmosphere (balloon). Toluene (12 mL), methanol (3.05 mL, 75 mmol) and triethylamine (0.63 mL, 4.52 mmol) were then added to the reaction mixture. The reaction mixture was stirred at room temperature for 5 min and then stirred at 75° C. until the starting material had been completely consumed. The reaction mixture was allowed to cool to room temperature and diluted with ethyl acetate. The reaction mixture was filtered through a plug of Celite®, washed with ethyl acetate and concentrated under reduced pressure. The residue was purified via silica gel flash column chromatography (0 to 80% (30% EtOAc in $CH_2Cl_2$)-heptanes) to give a mixture of title compounds. MS (ESI+) m/z 643.6 (M+H).

Example 81-C (±)-2-(5-Methyl-3-oxo-1-(trifluoromethyl)-3,6-dihydro-1H-furo[3,4-e]indol-1-yl)-1-((2-(trimethylsilyl)ethoxy)methyl)-1H-benzo[d]imidazole-5-carbonitrile and (±)-2-(5-methyl-3-oxo-1-(trifluoromethyl)-3,6-dihydro-1H-furo[3,4-e]indol-1-yl)-1-((2-(trimethyl-silyl)ethoxy)methyl)-1H-benzo[d]imidazole-6-carbonitrile

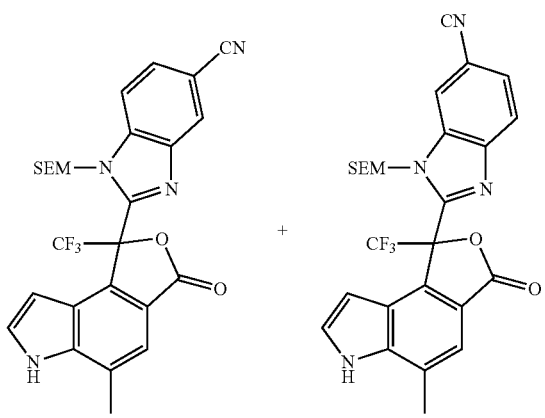

To a solution of a mixture of methyl 4-(5-cyano-1-((2-(trimethylsilyl)ethoxy)methyl)-1H-benzo[d]imidazole-2-carbonyl)-7-methyl-1-tosyl-1H-indole-5-carboxylate and methyl 4-(6-cyano-1-((2-(trimethylsilyl)ethoxy)methyl)-1H-benzo[d]imidazole-2-carbonyl)-7-methyl-1-tosyl-1H-indole-5-carboxylate (460 mg, 0.69 mmol) and trimethyl(trifluoromethyl)silane (0.22 mL, 1.39 mmol) in THF (7 mL) at 0° C., TBAF (1M in THF, 2.08 mL, 2.08 mmol) was added slowly. After addition, the reaction was stirred at 0° C. for 10 min, then warmed to room temperature for 20 min. The reaction was quenched with a sat. aq. $NaHCO_3$ solution, the layers were separated and the aqueous layer extracted with ethyl acetate and dried over $Na_2SO_4$. After concentration under reduced pressure, the residue was purified via silica gel flash column chromatography (heptane/(30% EtOAc in $CH_2Cl_2$) =0 to 60%) to give title compounds as a mixture. MS (ESI+) m/z 527.5 (M+H).

Example 81-D (±)-2-(5-Methyl-3-oxo-1-(trifluoromethyl)-3,6-dihydro-1H-furo[3,4-e]indol-1-yl)-1H-benzo[d]imidazole-5-carbonitrile

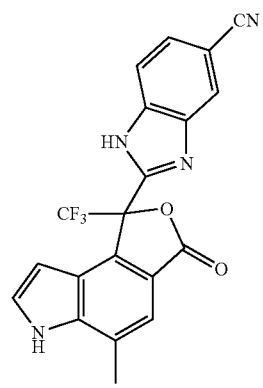 [SMILES: Cc1cc2c(c3cc[nH]c13)C(c1nc3cc(C#N)ccc3[nH]1)(C(F)(F)F)OC2=O]

To a solution of a mixture of (±)-2-(5-methyl-3-oxo-1-(trifluoromethyl)-3,6-dihydro-1H-furo[3,4-e]indol-1-yl)-1-((2-(trimethylsilyl)ethoxy)methyl)-1H-benzo[d]imidazole-5-carbonitrile and (±)-2-(5-methyl-3-oxo-1-(trifluoromethyl)-3,6-dihydro-1H-furo[3,4-e]indol-1-yl)-1-((2-(trimethylsilyl)ethoxy)methyl)-1H-benzo[d]imidazole-6-carbonitrile (36 mg, 0.068 mmol) in THF (0.5 mL), TBAF (1M in THF, 1.37 mL, 1.37 mmol) was added. The reaction was stirred at 75° C. for 30 min. The reaction mixture was cooled to room temperature, diluted with brine, and the layers were separated. The aqueous layer was extracted with ethyl acetate and dried over $Na_2SO_4$. After concentration, the residue was purified via silica gel flash chromatography (heptanes/((30% EtOAc in $CH_2Cl_2$)=0 to 100%) to give the title compound. $^1$H NMR (400 MHz, ACETONITRILE-$d_3$) δ ppm 10.09 (br. s., 1H), 8.06 (s, 1H), 7.70 (d, J=8.5 Hz, 1H), 7.58 (dd, J=8.5, 1.5 Hz, 1H), 7.54-7.57 (m, 1H), 7.53 (d, J=0.8 Hz, 1H), 7.00-7.04 (m, 1H), 2.63 (d, J=0.8 Hz, 3H). HRMS calcd. for $C_{20}H_{11}F_3N_4O_2$ (M+H)$^+$ 397.0907. found 397.0902.

Example 81-E (±)-2-(2,2,2-Trifluoro-1-hydroxy-1-(5-(hydroxymethyl)-7-methyl-1H-indol-4-yl)ethyl)-1H-benzo[d]imidazole-5-carbonitrile

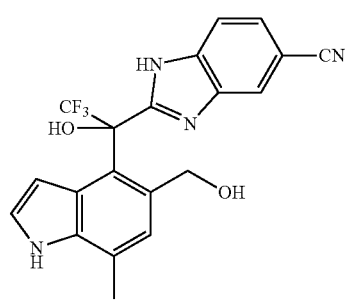 [SMILES: Cc1cc(CO)c(C(O)(c2nc3cc(C#N)ccc3[nH]2)C(F)(F)F)c2cc[nH]c12]

To a solution of (±)-2-(5-methyl-3-oxo-1-(trifluoromethyl)-3,6-dihydro-1H-furo[3,4-e]indol-1-yl)-1H-benzo[d]imidazole-5-carbonitrile (47 mg, 0.119 mmol) in THF (0.5 mL) at 0° C., LiBH₄ (2N in THF, 1.19 mL, 2.38 mmol) was added, followed by H₂O (43 μL, 2.38 mmol). The reaction was stirred at 50° C. for 16 hours and then cooled to 0° C. A NH₄Cl aqueous solution was added and the layers were separated. The aqueous layer was extracted with ethyl acetate. The combined organic layers were dried over Na₂SO₄. After concentration under reduced pressure, the residue was separated via silica gel flash column chromatography (CH₂Cl₂/EtOAc=0 to 100%) to give the title compound. ¹H NMR (400 MHz, ACETONITRILE-d₃ with about 3% METHANOL-d₄) δ ppm 8.05 (s, 1H), 7.54-7.70 (m, 2H), 7.13 (s, 1H), 6.97 (d, J=3.2 Hz, 1H), 5.54 (br. s., 1H), 5.20 (d, J=12.8 Hz, 1H), 4.68 (d, J=12.0 Hz, 1H), 2.48 (s, 3H). HRMS calcd. for C₂₀H₁₆F₃N₄O₂ (M+H)⁺ 401.122. found 401.1214.

Example 82

(±)-4-(1-(5-cyano-1H-benzo[d]imidazol-2-yl)-2,2,2-trifluoro-1-hydroxyethyl)-N,7-dimethyl-1H-indole-5-carboxamide

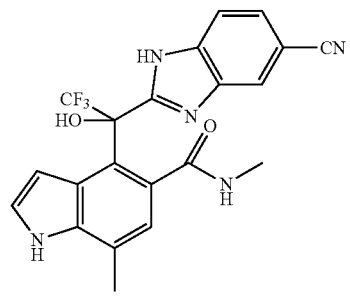 [SMILES: CNC(=O)c1cc(C)c2[nH]ccc2c1C(O)(c1nc2cc(C#N)ccc2[nH]1)C(F)(F)F]

To a suspension of methylamine hydrochloride (102 mg, 1.51 mmol) in THF (0.5 mL), 2N isopropylmagnesium chloride in THF (1.51 mL, 3.03 mmol) was added. The reaction was stirred at room temperature for 3 hr, then a solution of (±)-2-(5-methyl-3-oxo-1-(trifluoromethyl)-3,6-dihydro-1H-furo[3,4-e]indol-1-yl)-1H-benzo[d]imidazole-5-carbonitrile (30 mg, 0.076 mmol) in THF (0.5 mL) was added. The reaction was allowed to stir at room temperature for 16 hours. The reaction mixture was quenched with 1N HCl aqueous solution and then neutralized by adding NaHCO₃. The layers were separated and the aqueous layer was extracted with ethyl acetate. The combined organic layers were dried over Na₂SO₄. After concentration under reduced pressure, the residue was separated via silica gel flash column chromatography (CH₂Cl₂/EtOAc=0 to 100%) to give the title compound. ¹H NMR (400 MHz, DMSO-d₆, with about 3% METHANOL-d₄) δ ppm 7.85 (d, J=2.0 Hz, 1H), 7.41-7.46 (m, 2H), 7.39 (d, J=0.8 Hz, 1H), 7.19 (dd, J=8.3, 1.8 Hz, 1H), 6.50 (d, J=2.5 Hz, 1H), 2.96 (s, 3H), 2.58 (s, 3H). HRMS calcd. for C₂₁H₁₆F₃N₅O₂ (M+H)⁺ 428.1329. found 428.1333.

Example 83

Example 83-A 2-(7-Methyl-1-tosyl-5-(trifluoromethyl)-1H-indole-4-carbonyl)-1-((2-(trimethylsilyl)ethoxy)methyl)-1H-benzo[d]imidazole-5-carbonitrile and 2-(7-methyl-1-tosyl-5-(trifluoromethyl)-1H-indole-4-carbonyl)-1-((2-(trimethylsilyl)ethoxy)methyl)-1H-benzo[d]imidazole-6-carbonitrile

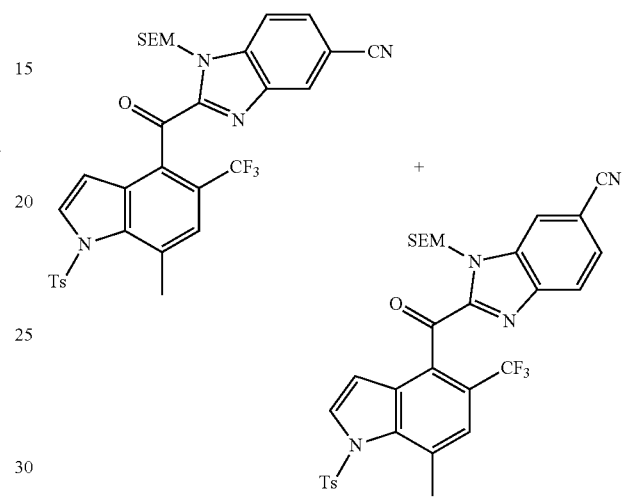

To methyl 2-(fluorosulfonyl)difluoroacetate (129 uL, 0.979 mmol), a mixture of 2-(5-bromo-7-methyl-1-tosyl-1H-indole-4-carbonyl)-1-((2-(trimethylsilyl)ethoxy)methyl)-1H-benzo[d]imidazole-6-carbonitrile and 2-(5-bromo-7-methyl-1-tosyl-1H-indole-4-carbonyl)-1-((2-(trimethylsilyl)ethoxy)methyl)-1H-benzo[d]imidazole-5-carbonitrile (Example 81-A) (260 mg, 0.392 mmol) in DMF (3.9 mL) was added CuI (8.95 mg, 0.047 mmol). The reaction mixture was stirred at 80° C. for 3 hours under microwave irradiation. After cooling the reaction was diluted with water, the layers separated and the aqueous layer was extracted with 80% EtOAc in Heptane. The organic phase was washed with water and concentrated. The residue was purified with Heptane-(30% EtOAc in DCM) to provide a mixture of title compounds. MS (ESI+) m/z 653.2 (M+H).

Example 83-B (±)-2-(1-hydroxy-1-(7-methyl-5-(trifluoromethyl)-1H-indol-4-yl)ethyl)-1H-benzo[d]imidazole-5-carbonitrile

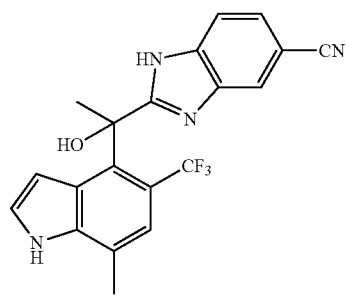 [SMILES: Cc1cc(C(F)(F)F)c(C(C)(O)c2nc3cc(C#N)ccc3[nH]2)c2cc[nH]c12]

The title compound was synthesized from a mixture of 2-(7-methyl-1-tosyl-5-(trifluoromethyl)-1H-indole-4-carbonyl)-1-((2-(trimethylsilyl)ethoxy)methyl)-1H-benzo[d]imidazole-5-carbonitrile and 2-(7-methyl-1-tosyl-5-(trifluoromethyl)-1H-indole-4-carbonyl)-1-((2-(trimethylsilyl)ethoxy)methyl)-1H-benzo[d]imidazole-6-carbonitrile using the same procedures as described in Example 64-B and 64-C. $^1$H NMR (400 MHz, DICHLOROMETHANE-d$_2$ with 5% of METHANOL-d$_4$) δ ppm 9.24 (br. s., 1H) 7.92 (s, 1H) 7.57-7.65 (m, 1H) 7.51-7.55 (m, 1H) 7.47 (s, 1H) 6.99-7.12 (m, 1H) 5.96 (dd, J=3.41, 1.89 Hz, 1H) 2.53 (s, 3H) 2.34 (s, 3H). HRMS calcd. for $C_{20}H_{15}F_3N_4O$ (M+H)$^+$ 385.1271. found 385.1277.

Example 84

Example 84-A (±)-2-(1-(5,7-Dimethyl-1-tosyl-1H-indol-4-yl)-1-methoxyethyl)-1-((2-(trimethylsilyl)ethoxy)methyl)-1H-benzo[d]imidazole-5-carbonitrile and (±)-2-(1-(5,7-dimethyl-1-tosyl-1H-indol-4-yl)-1-methoxyethyl)-1-((2-(trimethylsilyl)ethoxy)methyl)-1H-benzo[d]imidazole-6-carbonitrile

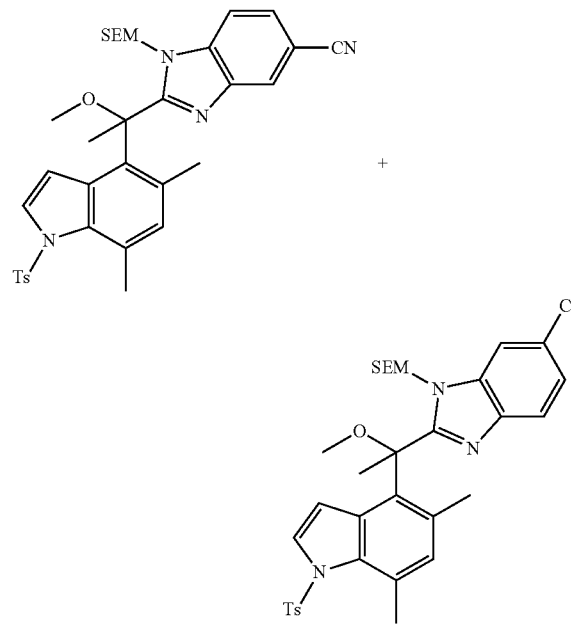

A mixture of title compounds was synthesized by alkylation of a mixture of (±)-2-(1-(5,7-dimethyl-1-tosyl-1H-indol-4-yl)-1-hydroxyethyl)-1-((2-(trimethylsilyl)ethoxy)methyl)-1H-benzo[d]imidazole-5-carbonitrile and (±)-2-(1-(5,7-dimethyl-1-tosyl-1H-indol-4-yl)-1-hydroxyethyl)-1-((2-(trimethylsilyl)ethoxy)methyl)-1H-benzo[d]imidazole-6-carbonitrile (Example 76-A) analogously to Example 25-A. MS (ESI+) m/z 629.2 (M+H).

Example 84-B a) (±)-2-(1-(5,7-Dimethyl-1H-indol-4-yl)-1-methoxyethyl)-1H-benzo[d]imidazole-5-carbonitrile

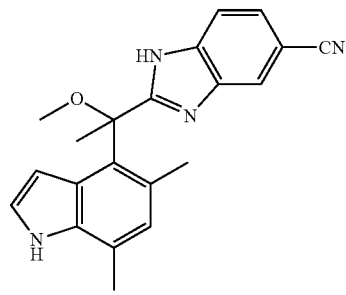 [SMILES: COC(C)(c1nc2cc(C#N)ccc2[nH]1)c1c(C)cc(C)c2[nH]ccc12]

The title compound was synthesized from a mixture of (±)-2-(1-(5,7-dimethyl-1-tosyl-1H-indol-4-yl)-1-methoxyethyl)-1-((2-(trimethylsilyl)ethoxy)methyl)-1H-benzo[d]imidazole-5-carbonitrile and (±)-2-(1-(5,7-dimethyl-1-tosyl-1H-indol-4-yl)-1-methoxyethyl)-1-((2-(trimethylsilyl)ethoxy)methyl)-1H-benzo[d]imidazole-6-carbonitrile analogously to Example 64-B and 64-C. $^1$H NMR (TFA salt, 400 MHz, DMSO-d$_6$) δ ppm 10.89 (s, 1H) 8.07 (s, 1H) 7.55-7.64 (m, 2H) 7.12 (t, J=2.78 Hz, 1H) 6.67 (s, 1H) 6.08 (dd, J=3.03, 2.02 Hz, 1H) 3.05 (s, 3H) 2.39 (s, 3H) 2.05 (s, 3H) 2.03 (s, 3H). HRMS calcd. for $C_{21}H_{20}N_4O$ (M+H)$^+$ 345.1710. found 345.1715.

b) (+) and (−)-2-(1-(5,7-dimethyl-1H-indol-4-yl)-1-methoxyethyl)-1H-benzo[d]imidazole-5-carbonitrile Resolution of the enantiomers of 2-(1-(5,7-dimethyl-1H-indol-4-yl)-1-methoxyethyl)-1H-benzo[d]imidazole-5-carbonitrile was achieved by normal phase chiral HPLC using a CHIRALPAK® IC column with 30% EtOH in heptane to give (−)-2-(1-(5,7-dimethyl-1H-indol-4-yl)-1-methoxyethyl)-1H-benzo[d]imidazole-5-carbonitrile (t$_r$=5.5 min) and (+)-2-(1-(5,7-dimethyl-1H-indol-4-yl)-1-methoxyethyl)-1H-benzo[d]imidazole-5-carbonitrile (t$_r$=8.3 min).

The following compounds were prepared with similar methods.

| Structure/Chemical Name | ¹H NMR | HRMS |
|---|---|---|
| 84-C a) 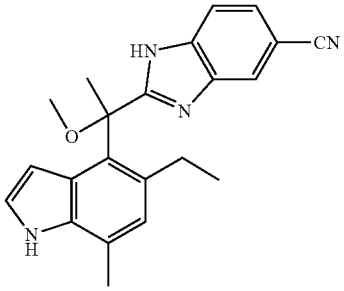 (±)-2-(1-(5-ethyl-7-methyl-1H-indol-4-yl)-1-methoxyethyl)-1H-benzo[d]imidazole-5-carbonitrile | (400 MHz, ACETONITRILE-$d_3$ with about 5 μL TFA) δ ppm 9.42 (br. s., 1H), 8.12 (s, 1H), 7.83 (dd, J = 1.30, 8.60 Hz, 1H), 7.80 (dd, J = 0.80, 8.60 Hz, 1H), 7.27 (t, J = 3.00 Hz, 1H), 6.96 (s, 1H), 6.54 (dd, J = 2.02, 3.00 Hz, 1H), 3.21 (s, 3H), 2.46-2.54 (m, 5H), 2.34 (s, 3H), 0.97 (t, J = 7.45 Hz, 3H). | calcd. for $C_{22}H_{22}N_4O$ $(M+H)^+$ 359.1867, found 359.1882. |
| 84-C b) | (+) and (−)-2-(1-(5-ethyl-7-methyl-1H-indol-4-yl)-1-methoxyethyl)-1H-benzo[d]imidazole-5-carbonitrile Resolution of the enantiomers of 2-(1-(5-ethyl-7-methyl-1H-indol-4-yl)-1-methoxyethyl)-1H-benzo[d]imidazole-5-carbonitrile was achieved by normal phase chiral HPLC using a CHIRALPAK ® IC column with 15% (0.2% diethylamine in EtOH) in heptane to give (−)-2-(1-(5-ethyl-7-methyl-1H-indol-4-yl)-1-methoxyethyl)-1H-benzo[d]imidazole-5-carbonitrile ($t_r$ = 6.5 min) and (+)-2-(1-(5-ethyl-7-methyl-1H-indol-4-yl)-1-methoxyethyl)-1H-benzo[d]imidazole-5-carbonitrile ($t_r$ = 8.9 min). | |
| 84-D a) 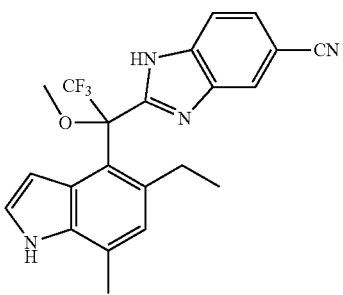 (±)-2-(1-(5-ethyl-7-methyl-1H-indol-4-yl)-2,2,2-trifluoro-1-methoxyethyl)-1H-benzo[d]imidazole-5-carbonitrile | (TFA salt, 400 MHz, ACETONITRILE-$d_3$) δ ppm 9.16 (br. s., 1H), 8.01 (br. s., 1H), 7.54-7.62 (m, 1H), 7.51 (dd, J = 1.50, 8.60 Hz, 1H), 6.97 (t, J = 2.80 Hz, 1H), 6.87 (s, 1H), 5.91 (br. s., 1H), 3.12 (d, J = 1.01 Hz, 3H), 2.63 (br. s., 1H), 2.39 (s, 3H), 2.19-2.35 (m, 1H), 0.98 (t, J = 7.33 Hz, 3H). | calcd. for $C_{22}H_{19}F_3N_4O$ $(M+H)^+$ 413.1573, found 413.1577. |
| 84-D b) | (+) and (−)-2-(1-(5-ethyl-7-methyl-1H-indol-4-yl)-2,2,2-trifluoro-1-methoxyethyl)-1H-benzo[d]imidazole-5-carbonitrile Resolution of the enantiomers of 2-(1-(5-ethyl-7-methyl-1H-indol-4-yl)-2,2,2-trifluoro-1-methoxyethyl)-1H-benzo[d]imidazole-5-carbonitrile was achieved by chiral SFC using a CHIRALPAK ® IC column with 20% IPA in $CO_2$ to give (−)-2-(1-(5-ethyl-7-methyl-1H-indol-4-yl)-2,2,2-trifluoro-1-methoxyethyl)-1H-benzo[d]imidazole-5-carbonitrile ($t_r$ = 6.1 min) and (+)-2-(1-(5-ethyl-7-methyl-1H-indol-4-yl)-2,2,2-trifluoro-1-methoxyethyl)-1H-benzo[d]imidazole-5-carbonitrile ($t_r$ = 7.2 min). | |
| 84-E a) 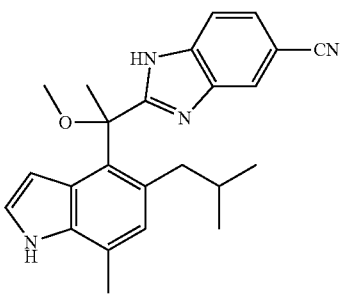 (±)-2-(1-(5-isobutyl-7-methyl-1H-indol-4-yl)-1-methoxyethyl)-1H-benzo[d]imidazole-5-carbonitrile | NMR (400 MHz, ACETONITRILE-$d_3$ with about 5 μL TFA) δ ppm 9.18 (br. s., 1H), 8.01 (d, J = 0.76 Hz, 1H), 7.64 (d, J = 8.60 Hz, 1H), 7.58 (dd, J = 1.50, 8.60 Hz, 1H), 7.04 (dd, J = 2.80, 3.00 Hz, 1H), 6.84 (s, 1H), 6.11 (dd, J = 2.00, 3.00 Hz, 1H), 3.11 (s, 3H), 2.55-2.69 (m, 1H), 2.41-2.54 (m, 4H), 2.18 (s, 3H), 0.81 (d, J = 6.57 Hz, 3H), 0.75 (d, J = 6.82 Hz, 3H). | calcd. for $C_{24}H_{26}N_4O$ $(M+H)^+$ 387.2180, found 387.2186. |
| 84-E b) | (+) and (−)-2-(1-(5-isobutyl-7-methyl-1H-indol-4-yl)-1-methoxyethyl)-1H-benzo[d]imidazole-5-carbonitrile Resolution of the enantiomers of 2-(1-(5-isobutyl-7-methyl-1H-indol-4-yl)-1-methoxyethyl)-1H-benzo[d]imidazole-5-carbonitrile was achieved by normal phase chiral HPLC using a CHIRALPAK ® IC column with 15% (0.2% diethylamine in EtOH) | |

-continued in heptane to give (−)-2-(1-(5-isobutyl-7-methyl-1H-indol-4-yl)-1-methoxyethyl)-1H-benzo[d]imidazole-5-carbonitrile (t$_r$ = 5.4 min) and (+)-2-(1-(5-isobutyl-7-methyl-1H-indol-4-yl)-1-methoxyethyl)-1H-benzo[d]imidazole-5-carbonitrile (t$_r$ = 10.5 min).

Example 85

2-((3-bromo-5,7-dimethyl-1H-indol-4-yl)methyl)-1H-benzo[d]imidazole-5-carbonitrile

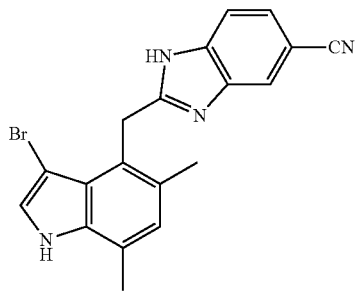 [SMILES: Cc1cc(C)c2[nH]cc(Cl)c2c1Cc1nc2cc(C#N)ccc2[nH]1]

2-((5,7-Dimethyl-1H-indol-4-yl)methyl)-1H-benzo[d]imidazole-5-carbonitrile (Example 58-C) (61 mg, 0.203 mmol) was dissolved in DMF (2 mL) and NBS (40.1 mg, 0.225 mmol) was added at 0° C. and the reaction stirred for 1 hour. The reaction was then quenched with saturated aq. sodium thiosulfate and saturated aq. NaHCO$_3$. The layers were separated and the aqueous layer was extracted with ethyl acetate. The organic phase was dried over MgSO$_4$, concentrated and purified by flash column chromatography (0-40% EtOAc in heptanes) to provide the title compound. $^1$H NMR (400 MHz, DMSO-d$_6$) δ ppm 12.33 (br. s., 1H) 11.39 (br. s., 1H) 7.97 (s, 1H) 7.83 (s, 1H) 7.41-7.64 (m, 2H) 6.86 (s, 1H) 4.82 (d, J=4.55 Hz, 2H) 2.43 (s, 3H) 2.21 (s, 3H). HRMS calcd. for C$_{19}$H$_{15}$BrN$_4$ (M+H)$^+$ 379.0553. found 379.0557.

Example 86

2-((3-Chloro-5,7-dimethyl-1H-indol-4-yl)methyl)-1H-benzo[d]imidazole-5-carbonitrile

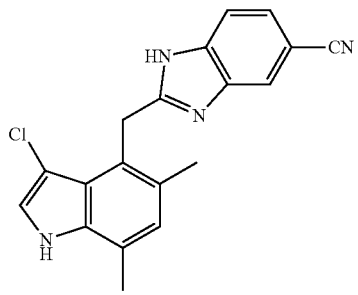

The title compound was synthesized by a chlorination of 2-((5,7-dimethyl-1H-indol-4-yl)methyl)-1H-benzo[d]imidazole-5-carbonitrile using NCS analogously to the preparation of Example 85. $^1$H NMR (400 MHz, DMSO-d$_6$) δ ppm 12.38 (s, 1H) 11.29 (br. s., 1H) 7.98 (d, J=0.76 Hz, 1H) 7.75-7.87 (m, 1H) 7.61 (d, J=8.34 Hz, 1H) 7.44-7.55 (m) 7.39-7.44 (m) 6.86 (s, 1H) 4.75 (d, J=4.55 Hz, 2H) 2.42 (s, 3H) 2.24 (s, 3H). HRMS calcd. for C$_{13}$H$_{16}$ClN$_4$ (M+H)$^+$ 335.1058. found 335.1062.

Example 87

(±)-2-((3-Chloro-5-ethyl-7-methyl-1H-indol-4-yl)(hydroxy)methyl)-1H-benzo[d]imidazole-5-carbonitrile

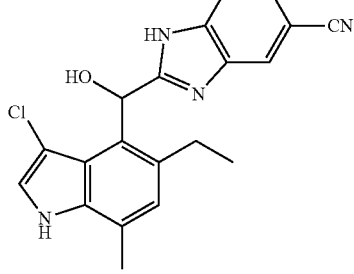

The title compound was synthesized from (±)-2-((5-ethyl-7-methyl-1H-indol-4-yl)(hydroxy)methyl)-1H-benzo[d]imidazole-5-carbonitrile (Example 67-A) as described in Example 86. $^1$H NMR (400 MHz, DICHLOROMETHANE-d$_2$ with about 5 μL TFA) δ ppm 8.47 (br. s., 1H), 8.01 (s, 1H), 7.81 (d, J=8.60 Hz, 1H), 7.76 (br. d, J=8.60 Hz, 1H), 7.32 (br. s., 1H), 7.25 (s, 1H), 7.05 (s, 1H), 2.62-2.82 (m, 2H), 2.51 (s, 3H), 1.18 (t, J=7.45 Hz, 3H). HRMS calcd. for C$_{20}$H$_{17}$ClN$_4$O (M+H)$^+$ 365.1164. found 365.1167.

Example 88

(+)-2-(1-(5-Ethyl-7-methyl-3-(trifluoromethyl)-1H-indol-4-yl)-1-hydroxyethyl)-1H-benzo[d]imidazole-5-carbonitrile

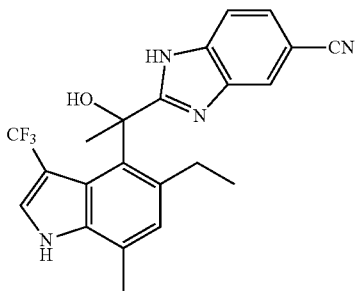 [SMILES: CCc1cc(C)c2[nH]cc(C(F)(F)F)c2c1C(C)(O)c1nc2cc(C#N)ccc2[nH]1]

To a suspension of (+)-2-(1-(5-ethyl-7-methyl-1H-indol-4-yl)-1-hydroxyethyl)-1H-benzo[d]imidazole-5-carbonitrile (Example 77-C) (20 mg, 0.058 mmol) and K$_2$CO$_3$ (56.2 mg, 0.406 mmol) in DMF (0.5 mL) was added 5-(trifluoromethyl)-5H-dibenzo[b,d]thiophenium trifluoromethanesulfonate (117 mg, 0.290 mmol), and then the mixture was stirred at 70° C. for 2 h. The reaction was quenched by 5% aq. NaHCO$_3$. The layers were separated and the aqueous layer was extracted with EtOAc. The organic layer was washed with H$_2$O and brine, dried over Na$_2$SO$_4$, and filtered. After concentration, the residue was purified by silica gel column chromatography (CH$_2$Cl$_2$/EtOAc=94/6 to 51/49) to give the title compound. $^1$H NMR (400 MHz, ACETONITRILE-d$_3$ with about 5 μL TFA) δ ppm 9.86 (br. s., 1H), 8.00 (dd, J=0.68, 1.44 Hz, 1H), 7.66 (dd, J=0.68, 8.50 Hz, 1H), 7.62 (dd, J=1.44, 8.50 Hz, 1H), 7.21-7.25 (m, 1H), 7.02 (s, 1H), 2.48 (d, J=0.76 Hz, 3H), 2.41 (q, J=7.45 Hz, 2H), 2.22 (s, 3H), 0.91 (t, J=7.45 Hz, 3H). HRMS calcd. for C$_{22}$H$_{19}$F$_3$N$_4$O (M+H)$^+$ 413.1584. found 413.1588.

Example 89

Example 89-A 2-(5,7-Dimethyl-1H-indole-4-carbonyl)-1H-benzo[d]imidazole-5-carbonitrile

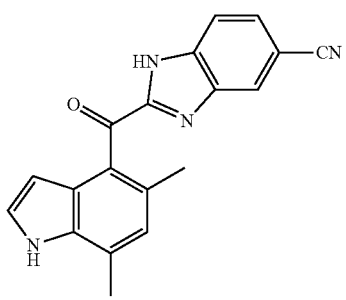 [SMILES: Cc1cc(C)c2[nH]ccc2c1C(=O)c1nc2cc(C#N)ccc2[nH]1]

The title compound was synthesized from a mixture of 2-(5,7-dimethyl-1-tosyl-1H-indole-4-carbonyl)-1-((2-(trimethylsilyl)ethoxy)methyl)-1H-benzo[d]imidazole-5-carbonitrile and 2-(5,7-dimethyl-1-tosyl-1H-indole-4-carbonyl)-1-((2-(trimethylsilyl)ethoxy)methyl)-1H-benzo[d]imidazole-6-carbonitrile (Example 75-A) analogously to Example 64-B and 64-C. MS (ESI+) m/z 315.1 (M+H).

Example 89-B 2-(3-Formyl-5,7-dimethyl-1H-indole-4-carbonyl)-1H-benzo[d]imidazole-5-carbonitrile

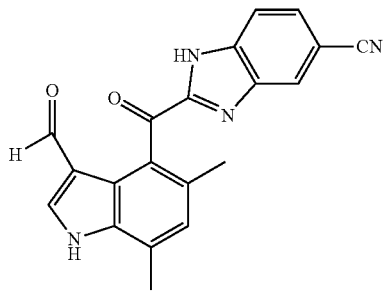 [SMILES: Cc1cc(C)c2[nH]cc(C=O)c2c1C(=O)c1nc2cc(C#N)ccc2[nH]1]

To a suspension of 2-(5,7-dimethyl-1H-indole-4-carbonyl)-1H-benzo[d]imidazole-5-carbonitrile (79 mg, 0.251 mmol) in CH$_2$Cl$_2$ (20 mL) was added N-(chloromethylene)-N-methylmethanaminium chloride (48.3 mg, 0.377 mmol) at room temperature, and then the mixture was stirred at room temperature for 2.5 h. To the mixture was added N-(chloromethylene)-N-methylmethanaminium chloride (32.2 mg, 0.251 mmol), and then the mixture was stirred at room temperature for another 6 h. The reaction was quenched by 5M aq. HCl (2 mL), followed by MeOH. The mixture was stirred at room temperature for 17 h. The mixture was basified by 5% aq. NaHCO$_3$, the layers were separated and the aqueous layer was extracted with CH$_2$Cl$_2$/2,2,2-trifluoroethanol (c.a. 9/1). The organic phase was washed with H$_2$O and brine, dried over Na$_2$SO$_4$, and filtered. Concentration of the filtrate gave crude, which was purified by silica gel flash column chromatography (CH$_2$Cl$_2$/EtOAc=1/0 to 54/46 then hold) to give the title compound. MS (ESI+) m/z 343.1 (M+H).

Example 89-C 2-(3,5,7-Trimethyl-1H-indole-4-carbonyl)-1H-benzo[d]imidazole-5-carbonitrile

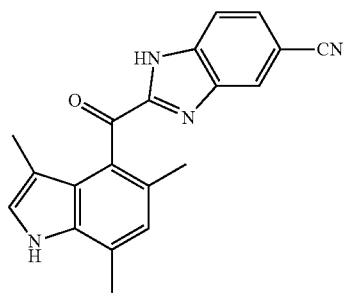 [SMILES: Cc1cc(C)c2[nH]cc(C)c2c1C(=O)c1nc2cc(C#N)ccc2[nH]1]

To a solution of 2-(3-formyl-5,7-dimethyl-1H-indole-4-carbonyl)-1H-benzo[d]imidazole-5-carbonitrile (20 mg, 0.058 mmol) in MeOH (2 mL) was added NaBH$_4$ (11.05 mg, 0.292 mmol), and then the mixture was stirred at room temperature for 1 hr. The reaction mixture was diluted with EtOAc/2,2,2-trifluoroethanol (c.a. 9/1). The organic phase was successively washed by H$_2$O and brine, dried over Na$_2$SO$_4$, and filtered. Concentration of the filtrate gave the title compound, which was used in the next reaction without any further purification. MS (ESI+) m/z 329.1 (M+H).

Example 89-D (±)-2-(Hydroxy(3,5,7-trimethyl-1H-indol-4-yl)methyl)-1H-benzo[d]imidazole-5-carbonitrile

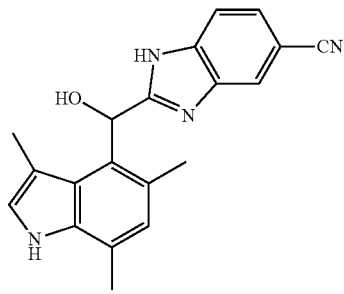 [SMILES: Cc1cc(C)c2[nH]cc(C)c2c1C(O)c1nc2cc(C#N)ccc2[nH]1]

A solution of 2-(3,5,7-trimethyl-1H-indole-4-carbonyl)-1H-benzo[d]imidazole-5-carbonitrile (20 mg, 0.061 mmol) and LiBH₄ in THF (2M, 2 mL, 4.00 mmol) was stirred at 50° C. for 2 h. The reaction mixture was cooled to room temperature. The mixture was quenched by half satd. aq. KHSO₄ and basified by 5% NaHCO₃. The layers were separated and the aqueous layer was extracted with CH₂Cl₂/2,2,2-trifluoroethanol (c.a. 9/1). The organic phase was washed with H₂O and brine, dried over Na₂SO₄, and filtered. After concentration of the filtrate the resulting residue was purified by RP-HPLC (HC-A) to give the title compound. ¹H NMR (400 MHz, ACETONITRILE-d₃ with about 5 μL TFA) δ ppm 9.10 (br. s., 1H), 8.08 (s, 1H), 7.73-7.82 (m, 2H), 7.06 (s, 1H), 6.96 (s, 1H), 6.84 (s, 1H), 2.45 (s, 3H), 2.21 (br. s., 3H), 2.19 (s, 3H). HRMS calcd. for $C_{20}H_{18}N_4O$ (M+H)⁺ 331.1554. found 331.1555.

Example 90

2-((3-Cyano-5-ethyl-7-methyl-1H-indol-4-yl)methyl)-1H-benzo[d]imidazole-5-carbonitrile

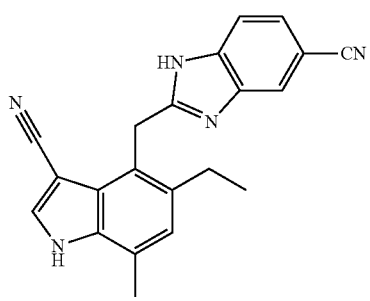 [SMILES: CCc1cc(C)c2[nH]cc(C#N)c2c1Cc1nc2cc(C#N)ccc2[nH]1]

To a suspension of 2-((5-ethyl-7-methyl-1H-indol-4-yl)methyl)-1H-benzo[d]imidazole-5-carbonitrile (15 mg, 0.048 mmol) in DMF (1 mL) was added chlorosulfonyl isocyanate (17 μL, 0.191 mmol) at 0° C., and then the mixture was stirred at 0° C. for 1.5 h. The mixture was allowed to warm up to room temperature with stirring. After 13.5 h, the reaction was quenched by 28% aq. NH₄OH. The mixture was stirred for 0.25 h and then extracted with EtOAc/2,2,2-trifluoroethanol (c.a. 9/1). The organic layer was washed with H₂O and brine, dried over Na₂SO₄, and filtered. After concentration, the resulting residue was purified by silica gel flash column chromatography [CH₂Cl₂/(2M NH₃ in MeOH)=98/2, isocratic] to give the title compound. ¹H NMR (400 MHz, ACETONITRILE-d₃ with about 5 μL TFA) δ ppm 10.22 (br. s., 1H), 8.07 (dd, J=1.00, 1.10 Hz, 1H), 7.91 (d, J=3.16 Hz, 1H), 7.71-7.85 (m, 2H), 7.15 (s, 1H), 5.02 (s, 2H), 2.71 (q, J=7.60 Hz, 2H), 2.54 (d, J=0.63 Hz, 3H), 1.14 (t, J=7.58 Hz, 3H). HRMS calcd. for $C_{21}H_{17}N_5$ (M+H)⁺ 340.1557. found 340.1556.

Example 91

(−)-2-((3-Cyano-5-ethyl-7-methyl-1H-indol-4-yl)(methoxy)methyl)-1H-benzo[d]imidazole-5-carbonitrile

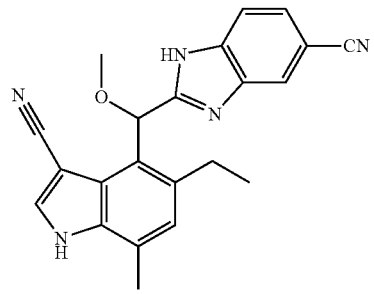 [SMILES: CCc1cc(C)c2[nH]cc(C#N)c2c1C(OC)c1nc2cc(C#N)ccc2[nH]1]

The title compound was synthesized from (−)-2-((5-ethyl-7-methyl-1H-indol-4-yl)(methoxy)methyl)-1H-benzo[d]imidazole-5-carbonitrile as described in Example 90. ¹H NMR (400 MHz, ACETONITRILE-d₃ with about 5 μL TFA) δ ppm 10.12 (br. s., 1H), 7.93 (s, 1H), 7.80 (d, J=3.28 Hz, 1H), 7.65 (dd, J=0.60, 8.60 Hz, 1H), 7.60 (dd, J=1.50, 8.60 Hz, 1H), 7.03 (s, 1H), 6.46 (s, 1H), 3.36 (s, 3H), 2.58-2.71 (m, 2H), 2.44 (d, J=0.76 Hz, 3H), 1.01 (t, J=7.58 Hz, 3H). HRMS calcd. for $C_{22}H_{19}N_5O$ (M+H)⁺ 370.1663. found 370.1661.

Example 92

Example 92-A 2-((5-Ethyl-7-methyl-3-(2,2,2-trifluoroacetyl)-1H-indol-4-yl)methyl)-1H-benzo[d]imidazole-5-carbonitrile

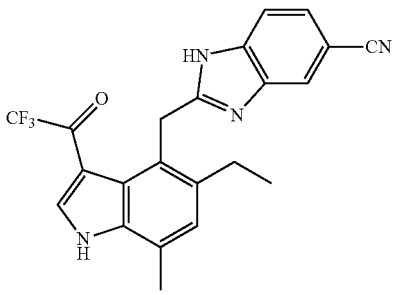 [SMILES: CCc1cc(C)c2[nH]cc(C(=O)C(F)(F)F)c2c1Cc1nc2cc(C#N)ccc2[nH]1]

To a suspension of 2-((5-ethyl-7-methyl-1H-indol-4-yl)methyl)-1H-benzo[d]imidazole-5-carbonitrile (200 mg, 0.382 mmol) in CH₂Cl₂ (10 mL) was added trifluoroacetic anhydride (162 μL, 1.145 mmol), and then the mixture was stirred at room temperature for 0.75 hr. The reaction mixture was cooled to 0° C. The solid that was generated was collected by filtration to give the title compound, without need of further purification. MS (ESI+) m/z 411.3 (M+H).

Example 92-B (±)-2-((5-Ethyl-7-methyl-3-(2,2,2-trifluoro-1-hydroxyethyl)-1H-indol-4-yl)methyl)-1H-benzo[d]imidazole-5-carbonitrile

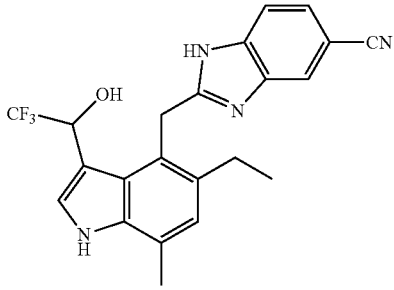 [SMILES: CCc1cc(C)c2[nH]cc(C(O)C(F)(F)F)c2c1Cc1nc2cc(C#N)ccc2[nH]1]

To a solution of 2-((5-ethyl-7-methyl-3-(2,2,2-trifluoroacetyl)-1H-indol-4-yl)methyl)-1H-benzo[d]imidazole-5-carbonitrile (60 mg, 0.114 mmol) in MeOH (10 mL) was added portionwise NaBH$_4$ (21.6 mg, 0.572 mmol). The mixture was stirred at room temperature for 3 h, and then for 16 h at 60° C. The reaction mixture was diluted with H$_2$O. The layers were separated and the aqueous layer was extracted with CH$_2$Cl$_2$. The combined organic phase was washed with H$_2$O and brine, dried over Na$_2$SO$_4$, filtered and concentrated. The resulting residue was purified by silica gel flash column chromatography [CH$_2$Cl$_2$/(2M NH$_3$ in MeOH)=94/6, isocratic] to give the title compound. $^1$H NMR (400 MHz, ACETONITRILE-d$_3$ with about 5 μL TFA) δ ppm 9.50 (br. s., 1H), 7.83 (s, 1H), 7.54 (d, J=8.30 Hz, 1H), 7.47 (d, J=8.30 Hz, 1H), 7.42 (br. s., 1H), 6.95 (s, 1H), 5.56 (q, J=7.28 Hz, 1H), 4.78 (d, J=17.40 Hz, 1H), 4.64 (d, J=17.43 Hz, 1H), 2.74 (q, J=7.45 Hz, 2H), 2.45 (s, 3H), 1.12 (t, J=7.52 Hz, 3H). HRMS calcd. for C$_{22}$H$_{19}$F$_3$N$_4$O (M+H)$^+$ 413.1584. found 413.1583.

Example 93

Example 93-A 1-(5,7-Dimethyl-1-tosyl-1H-indol-4-yl)prop-2-en-1-one

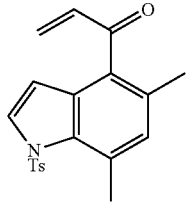 [SMILES: C=CC(=O)c1c(C)cc(C)c2c1ccn2S(=O)(=O)c1ccc(C)cc1]

To a solution of 5,7-dimethyl-1-tosyl-1H-indole-4-carbaldehyde (Example 46-D) (500 mg, 1.53 mmol) in THF (15 mL) at −78° C., vinylmagnesium bromide (2.29 mL, 2.29 mmol) was added and the reaction was stirred for 15 minutes. At this point a saturated water solution of NH$_4$Cl was added. The layers were separated and the aqueous layer was extracted with ethyl acetate. The combined organics were dried over MgSO$_4$ and evaporated. The resulting residue was dissolved in DCM (4 mL), and Dess-Martin Periodinane (1.19 g, 2.81 mmol) was added. After 15 minutes the reaction was complete. The reaction was quenched with a sat. aq. solution of NaHCO$_3$ and sodium thiosulfate. The layers were separated and the aqueous layer was extracted with DCM. It was purified using FCC eluting with heptane/EtOAc 1:1 to give the title compound. $^1$H NMR (400 MHz, DMSO-d$_6$) δ 7.85 (d, J=3.79 Hz, 1H), 7.50-7.66 (m, J=8.34 Hz, 2H), 7.30-7.45 (m, J=8.34 Hz, 2H), 7.01 (s, 1H), 6.71 (dd, J=10.48, 17.56 Hz, 1H), 6.59 (d, J=4.04 Hz, 1H), 6.14 (d, J=10.86 Hz, 1H), 5.88 (d, J=17.43 Hz, 1H), 2.35 (s, 3H), 2.21 (s, 3H).

Example 93-B 6,8-Dimethyl-1-tosylbenzo[cd]indol-5(1H)-one

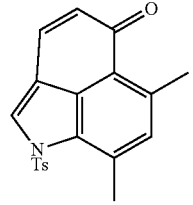 [SMILES: Cc1ccc(S(=O)(=O)n2cc3c4c(c(C)cc(C)c42)C(=O)C=C3)cc1]

To a mixture of 1-(5,7-dimethyl-1-tosyl-1H-indol-4-yl)prop-2-en-1-one (240 mg, 0.679 mmol), PdOAc$_2$ (152 mg, 0.679 mmol) and P-CHLORANIL (167 mg, 0.679 mmol), AcOH (7 mL) was added and the reaction heated to 100° C. for 1.5 h. The reaction was stopped and filtered to remove precipitated salts. The AcOH was removed in vacuo and then the resulting residue was purified using FCC eluting with heptane:EtOAc 1:1 to give the title compound. MS (ESI+) m/z 352.3 (M+H).

Example 93-C (±)-2-(5-hydroxy-6,8-dimethyl-1-tosyl-1,5-dihydrobenzo[cd]indol-5-yl)-1-((2-(trimethylsilyl)ethoxy)methyl)-1H-benzo[d]imidazole-6-carbonitrile and (±)-2-(5-hydroxy-6,8-dimethyl-1-tosyl-1,5-dihydrobenzo[cd]indol-5-yl)-1-((2-(trimethylsilyl)ethoxy)methyl)-1H-benzo[d]imidazole-5-carbonitrile

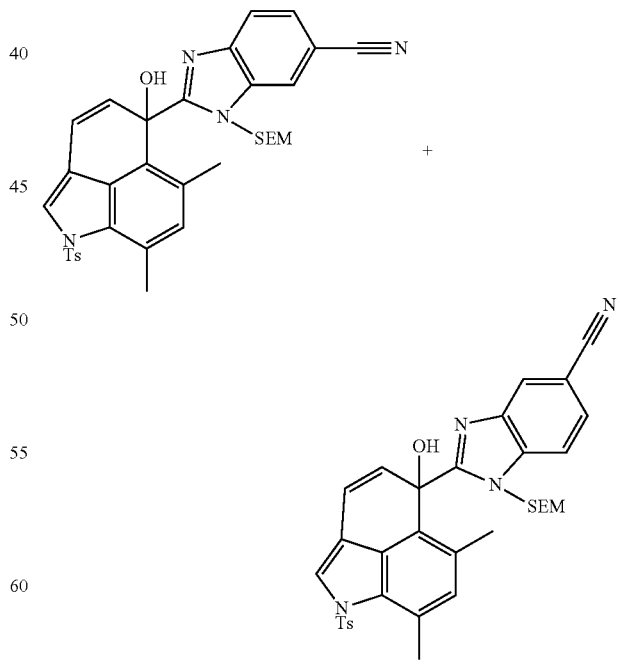

To a solution of a mixture of 1-((2-(trimethylsilyl)ethoxy)methyl)-1H-benzo[d]imidazole-5-carbonitrile and 1-((2-(trimethylsilyl)ethoxy)methyl)-1H-benzo[d]imidazole-6-carbonitrile (467 mg, 1.707 mmol) in THF (9 mL), LDA (0.785 mL, 1.571 mmol) was added and the reaction left stirring at −78° C. for 30 minutes. 6,8-Dimethyl-1-tosylbenzo[cd]indol-5(1H)-one (240 mg, 0.683 mmol) in THF was added and the reaction allowed to stir for 1 h at −78° C. The reaction was quenched with a saturated aq. solution of ammonium chloride, extracted with EtOAc and evaporated to give the crude product. The resulting residue was purified using heptane/EtOAc 1:1 to give the mixture of title compounds. MS (ESI+) m/z 625.5 (M+H).

Example 93-D (±)-2-(5-Hydroxy-6,8-dimethyl-1-tosyl-1,3,4,5-tetrahydrobenzo[cd]indol-5-yl)-1-((2-(trimethylsilyl)ethoxy)methyl)-1H-benzo[d]imidazole-6-carbonitrile and (±)-2-(5-hydroxy-6,8-dimethyl-1-tosyl-1,3,4,5-tetrahydrobenzo[cd]indol-5-yl)-1-((2-(trimethylsilyl)ethoxy)methyl)-1H-benzo[d]imidazole-5-carbonitrile

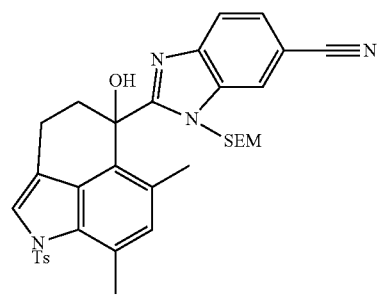

+

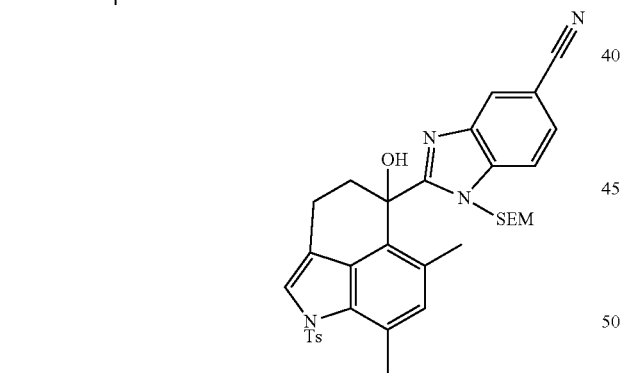

A solution of a mixture of (±)-2-(5-hydroxy-6,8-dimethyl-1-tosyl-1,5-dihydrobenzo[cd]indol-5-yl)-1-((2-(trimethylsilyl)ethoxy)methyl)-1H-benzo[d]imidazole-6-carbonitrile and (±)-2-(5-hydroxy-6,8-dimethyl-1-tosyl-1,5-dihydrobenzo[cd]indol-5-yl)-1-((2-(trimethylsilyl)ethoxy)methyl)-1H-benzo[d]imidazole-5-carbonitrile (50 mg, 0.080 mmol) in MeOH was charged with Pd/C (10%, 5 mg). The atmosphere was changed from $N_2$ to $H_2$ (balloon) and stirred for 2 h, at this point more Pd/C (10%, 5 mg) was added and the reaction was complete after 2 more hours. The mixture was filtered and evaporated to give the mixture of title compounds. MS (ESI+) m/z 628.5 (M+2H).

Example 93-E (±)-2-(5-Hydroxy-6,8-dimethyl-1-tosyl-1,3,4,5-tetrahydrobenzo[cd]indol-5-yl)-1H-benzo[d]imidazole-5-carbonitrile

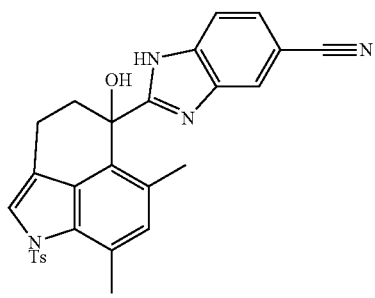 [SMILES: Cc1ccc(S(=O)(=O)n2cc3c4c(c(C)cc(C)c42)C(O)(c2nc4cc(C#N)ccc4[nH]2)CC3)cc1]

To a mixture of (±)-2-(5-hydroxy-6,8-dimethyl-1-tosyl-1,3,4,5-tetrahydrobenzo[cd]indol-5-yl)-1-((2-(trimethylsilyl)ethoxy)methyl)-1H-benzo[d]imidazole-6-carbonitrile and (±)-2-(5-hydroxy-6,8-dimethyl-1-tosyl-1,3,4,5-tetrahydrobenzo[cd]indol-5-yl)-1-((2-(trimethylsilyl)ethoxy)methyl)-1H-benzo[d]imidazole-5-carbonitrile (50 mg, 0.08 mmol), lithium tetrafluoroborate (1.5 mL, 1.5 mmol) and $H_2O$ (0.15 mL) were added. The reaction was heated to 70° C. overnight. It was quenched with a sat. $NaHCO_3$ solution. The layers were separated and the aqueous layer was extracted with EtOAc. It was purified using FCC eluting with heptane:EtOAc 1:2 to give the title compound. MS (ESI+) m/z 497.4 (M+H).

Example 93-F a) (±)-2-(5-Hydroxy-6,8-dimethyl-1,3,4,5-tetrahydrobenzo[cd]indol-5-yl)-1H-benzo[d]imidazole-5-carbonitrile

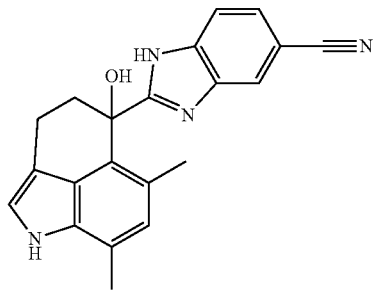 [SMILES: Cc1cc(C)c2[nH]cc3c2c1C(O)(c1nc2cc(C#N)ccc2[nH]1)CC3]

(±)-2-(5-Hydroxy-6,8-dimethyl-1-tosyl-1,3,4,5-tetrahydrobenzo[cd]indol-5-yl)-1H-benzo[d]imidazole-5-carbonitrile (41 mg, 0.083 mmol) in EtOH (0.83 mL) was treated with isomylamine (190 μL, 1.65 mmol) and KOH (46.3 mg, 0.826 mmol) and heated in a microwave for 30 minutes at 100° C. After 30 minutes an additional aliquot of isomylamine (190 μL, 1.65 mmol) and KOH (46.3 mg, 0.826 mmol) were added and the reaction heated in a microwave. After 30 minutes the reaction was complete. It was directly loaded onto a column and purified using FCC eluting with heptane:EtOAc 1:2 to give the title compound. $^1$H NMR (400 MHz, DMSO-$d_6$) δ 12.79 (s, 1H), 10.59 (br. s., 1H), 7.89-7.95 (m, 1H), 7.55-7.72 (m, 1H), 7.34-7.55 (m, 1H), 7.01 (s, 1H), 6.56 (s, 1H), 6.15 (m, 1H), 2.89-2.90 (m, 2H), 2.27-2.45 (m, 5H). HRMS calcd. for $C_{21}H_{18}N_4O$ (M+H)$^+$ 343.1554. found 343.156.

b) (+) and (−)-2-(5-hydroxy-6,8-dimethyl-1,3,4,5-tetrahydrobenzo[cd]indol-5-yl)-1H-benzo[d]imidazole-5-carbonitrile Resolution of the enantiomers of 2-(5-hydroxy-6,8-dimethyl-1,3,4,5-tetrahydrobenzo[cd]indol-5-yl)-1H-benzo[d]imidazole-5-carbonitrile was achieved by chiral SFC using a CHIRALPAK® AD-H column with 35% (0.2% diethylamine in MeOH) in $CO_2$ to give (+) or (−)-2-(5-hydroxy-6,8-dimethyl-1,3,4,5-tetrahydrobenzo[cd]indol-5-yl)-1H-benzo[d]imidazole-5-carbonitrile ($t_r$=7.2 min) and (−) or (+)-2-(5-hydroxy-6,8-dimethyl-1,3,4,5-tetrahydrobenzo[cd]indol-5-yl)-1H-benzo[d]imidazole-5-carbonitrile ($t_r$=10.2 min).

Example 94 a) (±)-2-(6-ethyl-5-hydroxy-8-methyl-1,3,4,5-tetrahydrobenzo[cd]indol-5-yl)-1H-benzo[d]imidazole-5-carbonitrile

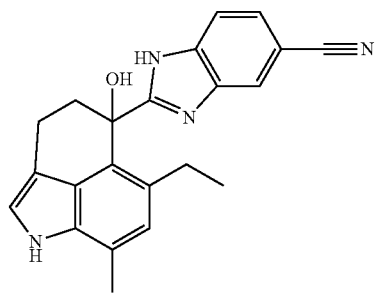 [SMILES: CCc1cc(C)c2[nH]cc3c2c1C(O)(c1nc2cc(C#N)ccc2[nH]1)CC3]

The title compound was synthesized starting from 5-ethyl-7-methyl-1-tosyl-1H-indole-4-carbaldehyde following same procedures as described in Example 93. $^1$H NMR (400 MHz, DMSO-$d_6$) δ 12.78 (s, 1H), 10.59 (s, 1H), 7.87-7.93 (m, 1H), 7.54-7.65 (m, 1H), 7.42-7.54 (m, 1H), 7.01 (s, 1H), 6.63 (s, 1H), 6.11-6.24 (m, 1H), 2.87 (m, 2H), 2.41 (s, 3H), 2.21-2.38 (m, 4H), 0.72-0.89 (m, 3H). HRMS calcd. for $C_{22}H_{20}N_4O$ (M+H)$^+$ 357.171. found 357.1718.

b) (+) and (−)-2-(6-ethyl-5-hydroxy-8-methyl-1,3,4,5-tetrahydrobenzo[cd]indol-5-yl)-1H-benzo[d]imidazole-5-carbonitrile Resolution of the enantiomers of 2-(6-ethyl-5-hydroxy-8-methyl-1,3,4,5-tetrahydrobenzo[cd]indol-5-yl)-1H-benzo[d]imidazole-5-carbonitrile was achieved by chiral SFC using a CHIRALCEL® OD-H column with 25% (0.2% diethylamine in MeOH) in $CO_2$ to give (+) or (−)-2-(6-ethyl-5-hydroxy-8-methyl-1,3,4,5-tetrahydrobenzo[cd]indol-5-yl)-1H-benzo[d]imidazole-5-carbonitrile ($t_r$=4.5 min) and (−) or (+)-2-(6-ethyl-5-hydroxy-8-methyl-1,3,4,5-tetrahydrobenzo[cd]indol-5-yl)-1H-benzo[d]imidazole-5-carbonitrile ($t_r$=6.3 min).

Example 95

Example 95-A (±)-N-((5-cyano-1-((2-(trimethylsilyl)ethoxy)methyl)-1H-benzo[d]imidazol-2-yl)(5,7-dimethyl-1-tosyl-1H-indol-4-yl)methyl)-2,2,2-trifluoroacetamide and (±)-N-((6-cyano-1-((2-(trimethylsilyl)ethoxy)methyl)-1H-benzo[d]imidazol-2-yl)(5,7-dimethyl-1-tosyl-1H-indol-4-yl)methyl)-2,2,2-trifluoroacetamide

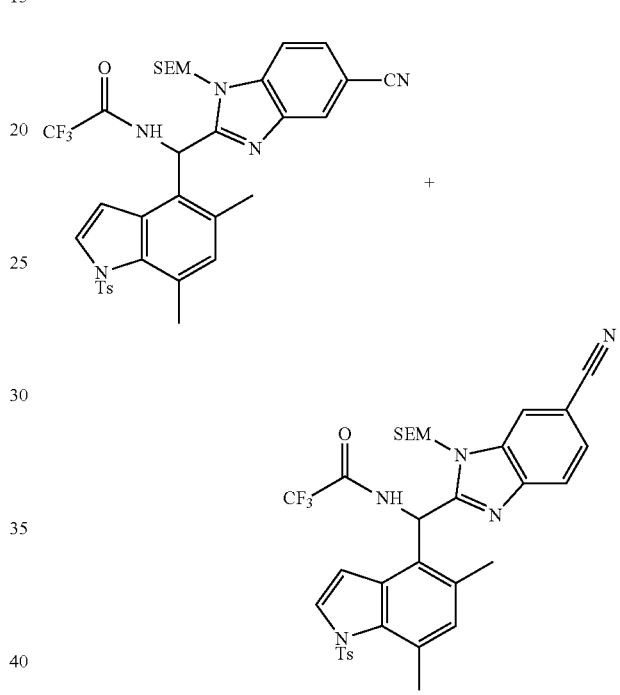

A solution of a mixture of (±)-2-((5,7-dimethyl-1-tosyl-1H-indol-4-yl)(hydroxy)methyl)-1-((2-(trimethylsilyl)ethoxy)methyl)-1H-benzo[d]imidazole-5-carbonitrile and (±)-2-((5,7-dimethyl-1-tosyl-1H-indol-4-yl)(hydroxy)methyl)-1-((2-(trimethylsilyl)ethoxy)methyl)-1H-benzo[d]imidazole-6-carbonitrile (Example 64-A) (240 mg, 0.399 mmol), DBU (0.18 mL, 1.198 mmol), and DPPA (0.26 mL, 1.19 mmol) in toluene (4 mL) was allowed to stir at rt for 16 h. The reaction mixture was diluted with 2M aq. $Na_2CO_3$ and EtOAc. The layers were separated and the aqueous layer was extracted with EtOAc. The combined organic phase was washed with 1M aq. $KHSO_4$ and brine, dried over $Na_2SO_4$, filtered, and concentrated.

A resulting residue was dissolved in EtOH (8 mL) and hydrogenated using H-Cube® apparatus (1 atm, rt, 10% Pd/C, 1 mL/min.) until the reaction completed. The reaction mixture was concentrated and the resulting residue was dissolved in $CH_2Cl_2$ (4 mL), and DIPEA (0.14 mL, 0.8 mmol) and $(CF_3CO)_2O$ (0.084 mL, 0.599 mmol) were added at rt. After stirring for 5 min, the reaction mixture was diluted with brine and $CH_2Cl_2$. The layers were separated and the organic layer was dried over $MgSO_4$, filtered and evaporated. The residue was purified by flash column chromatography on silica gel (heptanes/EtOAc=100:0 to 55:45) to give the mixture of title compounds. MS (ESI+) m/z 696.28 (M+H).

Example 95-B a) (±)-2-(Amino(5,7-dimethyl-1H-indol-4-yl)methyl)-1H-benzo[d]imidazole-5-carbonitrile

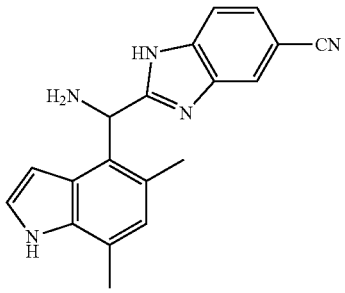 [SMILES: Cc1cc(C)c2[nH]ccc2c1C(N)c1nc2cc(C#N)ccc2[nH]1]

The title compound was synthesized from a mixture of (±)-N-((5-cyano-1-((2-(trimethylsilyl)ethoxy)methyl)-1H-benzo[d]imidazol-2-yl)(5,7-dimethyl-1-tosyl-1H-indol-4-yl)methyl)-2,2,2-trifluoroacetamide and (±)-N-((6-cyano-1-((2-(trimethylsilyl)ethoxy)methyl)-1H-benzo[d]imidazol-2-yl)(5,7-dimethyl-1-tosyl-1H-indol-4-yl)methyl)-2,2,2-trifluoroacetamide as described in Example 64-B and 64-C. $^1$H NMR (400 MHz, DMSO-$d_6$) δ ppm. $^1$H NMR (400 MHz, DMSO-$d_6$) δ ppm 10.88 (s, 1H) 7.93 (s, 1H) 7.59 (d, J=8.08 Hz, 1H) 7.48 (app dd, J=8.34, 1.26 Hz, 1H) 7.11 (t, J=2.78 Hz, 1H) 6.73 (s, 1H) 6.19 (s, 1H) 5.77 (s, 1H) 2.43 (s, 3H) 2.39 (s, 3H). HRMS calcd. for $C_{19}H_{17}N_5$ (M+H)$^+$ 316.1557. found 316.1563.

b) (+) and (−)-2-(amino(5,7-dimethyl-1H-indol-4-yl)methyl)-1H-benzo[d]imidazole-5-carbonitrile Resolution of the enantiomers of 2-(amino(5,7-dimethyl-1H-indol-4-yl)methyl)-1H-benzo[d]imidazole-5-carbonitrile was achieved by chiral SFC using a CHIRALCEL® OD-H column with 50% i-PrOH (with 0.2% DEA) in $CO_2$ to give (+)-2-(amino(5,7-dimethyl-1H-indol-4-yl)methyl)benzo[d]imidazole-5-carbonitrile ($t_r$=0.6 min) and (−)-2-(amino(5,7-dimethyl-1H-indol-4-yl)methyl)benzo[d]imidazole-5-carbonitrile ($t_r$=1.2 min).

Example 96

Example 96-A (±)-N-((5-cyano-1-((2-(trimethylsilyl)ethoxy)methyl)-1H-benzo[d]imidazol-2-yl)(5-ethyl-7-methyl-1-tosyl-1H-indol-4-yl)methyl)-2-methylpropane-2-sulfinamide and (±)-N-((6-cyano-1-((2-(trimethylsilyl)ethoxy)methyl)-1H-benzo[d]imidazol-2-yl)(5-ethyl-7-methyl-1-tosyl-1H-indol-4-yl)methyl)-2-methylpropane-2-sulfinamide

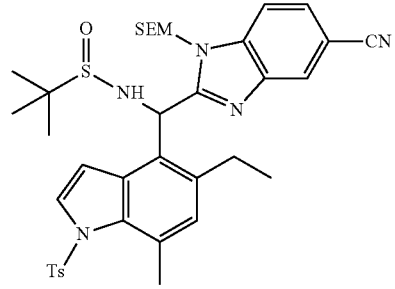
+
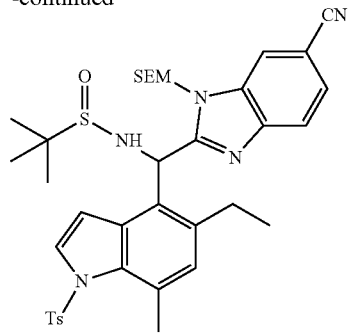

A suspension of a mixture of 2-(5-ethyl-7-methyl-1-tosyl-1H-indole-4-carbonyl)-1-((2-(trimethylsilyl)ethoxy)methyl)-1H-benzo[d]imidazole-5-carbonitrile and 2-(5-ethyl-7-methyl-1-tosyl-1H-indole-4-carbonyl)-1-((2-(trimethylsilyl)ethoxy)methyl)-1H-benzo[d]imidazole-6-carbonitrile (Example 117-A) (500 mg, 0.816 mmol), and (±)-2-methylpropane-2-sulfinamide (129 mg, 1.061 mmol) in Ti(O-iPr)$_4$ (1.43 mL, 4.90 mmol) was stirred at 90° C. for 5 h. The reaction mixture was cooled down to 0° C., and then diluted with MeOH (30 mL). To the mixture was added portionwise NaBH$_4$ (617 mg, 16.32 mmol) at 0° C., and then the mixture was stirred at room temperature for 18 h. The reaction mixture was diluted with $CH_2Cl_2$. Celite® was added to the mixture, and then the mixture was diluted with $H_2O$ with stirring. The mixture was filtered. The Celite® cake was washed with $CH_2Cl_2$. The combined organic phase was washed successively by $H_2O$ and brine, dried over $Na_2SO_4$, and filtered. Concentration of the filtrate gave the title compounds as a mixture, without need of further purification. MS (ESI+) m/z 718.6 (M+H).

Example 96-B (±)-2-(Amino(5-ethyl-7-methyl-1-tosyl-1H-indol-4-yl)methyl)-1H-benzo[d]imidazole-5-carbonitrile

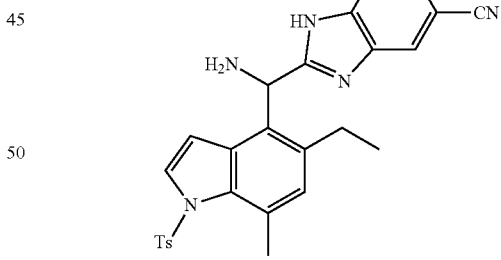

A solution of a mixture of (±)-N-((5-cyano-1-((2-(trimethylsilyl)ethoxy)methyl)-1H-benzo[d]imidazol-2-yl)(5-ethyl-7-methyl-1-tosyl-1H-indol-4-yl)methyl)-2-methylpropane-2-sulfinamide and (±)-N-((6-cyano-1-((2-(trimethylsilyl)ethoxy)methyl)-1H-benzo[d]imidazol-2-yl)(5-ethyl-7-methyl-1-tosyl-1H-indol-4-yl)methyl)-2-methylpropane-2-sulfinamide (574 mg, 0.8 mmol) in 1M HCl in MeOH (10 mL) was stirred at room temperature for 1.5 h, and then at 60° C. for 18 h. The reaction mixture was basified by 5% aq. NaHCO$_3$. The layers were separated and the aqueous layer was extracted with $CH_2Cl_2$. The organic phase was successively washed with $H_2O$ and brine, dried over $Na_2SO_4$, and filtered. After concentration the residue was purified by silica gel flash column chromatography (heptanes/EtOAc=1/1 to 0/1) to give the title compound. MS (ESI+) m/z 484.2 (M+H).

Example 96-C a) (±)-2-(Amino(5-ethyl-7-methyl-1H-indol-4-yl)methyl)-1H-benzo[d]imidazole-5-carbonitrile

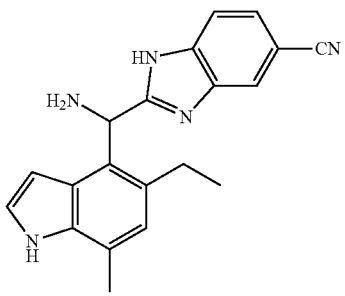 [SMILES: CCc1cc(C)c2[nH]ccc2c1C(N)c1nc2cc(C#N)ccc2[nH]1]

The title compound was synthesized from (±)-2-(amino(5-ethyl-7-methyl-1-tosyl-1H-indol-4-yl)methyl)-1H-benzo[d]imidazole-5-carbonitrile as described in Example 64-C. $^1$H NMR (400 MHz, ACETONITRILE-$d_3$ with about 5 μL TFA) δ ppm 9.50 (br. s., 1H), 8.00 (s, 1H), 7.56-7.60 (m, 1H), 7.12 (t, J=3.00 Hz, 1H), 7.02 (s, 1H), 6.42 (s, 1H), 5.75-5.83 (m, 1H), 2.92-3.02 (m, 1H), 2.81-2.91 (m, 1H), 2.51 (d, J=0.76 Hz, 3H), 1.29 (t, J=7.58 Hz, 3H). HRMS calcd. for $C_{20}H_{19}N_5$ (M+H)$^+$ 330.1713. found 330.1707.

b) (+) and (−)-2-(Amino(5-ethyl-7-methyl-1H-indol-4-yl)methyl)-1H-benzo[d]imidazole-5-carbonitrile Resolution of the enantiomers of 2-(amino(5-ethyl-7-methyl-1H-indol-4-yl)methyl)-1H-benzo[d]imidazole-5-carbonitrile was achieved by normal phase chiral HPLC using a CHIRALCEL® OD column with 0.2% diethylamine in EtOH to give (+)-2-(amino(5-ethyl-7-methyl-1H-indol-4-yl)methyl)-1H-benzo[d]imidazole-5-carbonitrile ($t_r$=6.6 min) and (−)-2-(amino(5-ethyl-7-methyl-1H-indol-4-yl)methyl)-1H-benzo[d]imidazole-5-carbonitrile ($t_r$=9.4 min).

Example 97 a) (±)-2-(Amino(5-isopropyl-7-methyl-1H-indol-4-yl)methyl)-1H-benzo[d]imidazole-5-carbonitrile

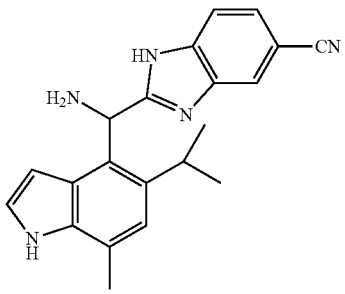 [SMILES: Cc1cc(C(C)C)c(C(N)c2nc3cc(C#N)ccc3[nH]2)c2cc[nH]c12]

The title compound was synthesized following the same procedures that led to 2-(amino(5-ethyl-7-methyl-1H-indol-4-yl)methyl)-1H-benzo[d]imidazole-5-carbonitrile (Example 96) starting from 5-Isopropyl-7-methyl-1-tosyl-1H-indole-4-carbaldehyde (Example 50-A). $^1$H NMR (400 MHz, ACETONITRILE-$d_3$ with about 5 μL TFA) δ ppm 9.50 (br. s., 1H), 8.00 (s, 1H), 7.60 (d, J=8.30 Hz, 1H), 7.56 (dd, J=1.50, 8.30 Hz, 1H), 7.05-7.20 (m, 2H), 6.55 (s, 1H), 5.71-5.88 (m, 1H), 3.33-3.48 (m, 1H), 2.52 (s, 3H), 1.36 (d, J=6.82 Hz, 3H), 1.21-1.33 (m, 3H). HRMS calcd. for $C_{21}H_{21}N_5$ (M+H)$^+$ 344.1870. found 344.1865.

b) (+) and (−)-2-(Amino(5-isopropyl-7-methyl-1H-indol-4-yl)methyl)-1H-benzo[d]imidazole-5-carbonitrile Resolution of the enantiomers of 2-(amino(5-isopropyl-7-methyl-1H-indol-4-yl)methyl)-1H-benzo[d]imidazole-5-carbonitrile was achieved by normal phase chiral HPLC using a CHIRALCEL® OD column with 15% EtOH in heptane to give (+) or (−)-2-(amino(5-isopropyl-7-methyl-1H-indol-4-yl)methyl)-1H-benzo[d]imidazole-5-carbonitrile ($t_r$=10.5 min) and (−) or (+)-2-(amino(5-isopropyl-7-methyl-1H-indol-4-yl)methyl)-1H-benzo[d]imidazole-5-carbonitrile ($t_r$=19.4 min).

Example 98

Example 98-A (±)-N-((5-cyano-1-((2-(trimethylsilyl)ethoxy)methyl)-1H-benzo[d]imidazol-2-yl)(5,7-dimethyl-1-tosyl-1H-indol-4-yl)methyl)-2,2,2-trifluoro-N-methylacetamide and (±)-N-((6-cyano-1-((2-(trimethylsilyl)ethoxy)methyl)-1H-benzo[d]imidazol-2-yl)(5,7-dimethyl-1-tosyl-1H-indol-4-yl)methyl)-2,2,2-trifluoro-N-methylacetamide

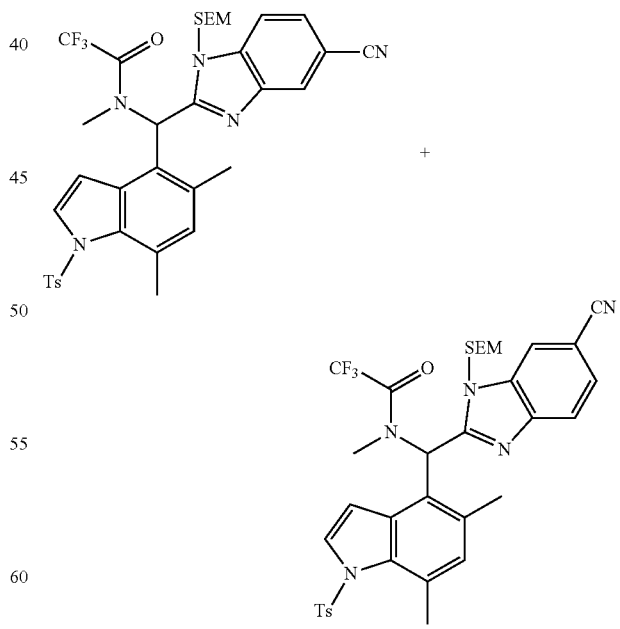

To a solution of a mixture of (±)-N-((5-cyano-1-((2-(trimethylsilyl)ethoxy)methyl)-1H-benzo[d]imidazol-2-yl)(5,7-dimethyl-1-tosyl-1H-indol-4-yl)methyl)-2,2,2-trifluoroacetamide and (±)-N-((6-cyano-1-((2-(trimethylsilyl)ethoxy)

methyl)-1H-benzo[d]imidazol-2-yl)(5,7-dimethyl-1-tosyl-1H-indol-4-yl)methyl)-2,2,2-trifluoroacetamide (Example 95-A) (300 mg, 0.431 mmol) in anhydrous DMF (4 mL), NaH (60% oil dispersion, 22.42 mg, 0.560 mmol) was added at 0° C. After stirring for 15 min at rt, MeI (0.054 mL, 0.862 mmol) was added at 0° C. After stirring for 16 h at rt, the reaction was quenched with aq. NH₄Cl. The layers were separated and the aqueous layer was extracted with EtOAc. The organic layer was washed with brine, dried over Na₂SO₄, filtered, and concentrated. The residue was purified by flash column chromatography on silica gel (heptanes/EtOAc=100:0 to 65:35) to give the title compounds as a mixture. MS (ESI+) m/z 710.43 (M+H).

Example 98-B (±)-2-((5,7-Dimethyl-1H-indol-4-yl)(methylamino)methyl)-1H-benzo[d]imidazole-5-carbonitrile

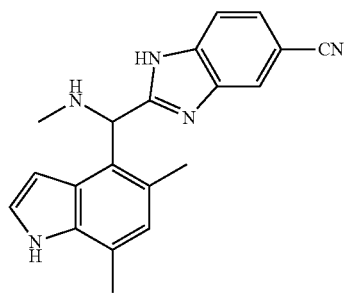 [SMILES: CNC(c1nc2cc(C#N)ccc2[nH]1)c1c(C)cc(C)c2[nH]ccc12]

The title compound was synthesized from a mixture of (±)-N-((5-cyano-1-((2-(trimethylsilyl)ethoxy)methyl)-1H-benzo[d]imidazol-2-yl)(5,7-dimethyl-1-tosyl-1H-indol-4-yl)methyl)-2,2,2-trifluoro-N-methylacetamide and (±)-N-((6-cyano-1-((2-(trimethylsilyl)ethoxy)methyl)-1H-benzo[d]imidazol-2-yl)(5,7-dimethyl-1-tosyl-1H-indol-4-yl)methyl)-2,2,2-trifluoro-N-methylacetamide as described in Example 64-B and 64-C. ¹H NMR (TFA salt, 400 MHz, ACETONITRILE-d₃) δ ppm 9.52 (br. s, 1H) 8.00 (s, 1H) 7.54-7.62 (m, 2H) 7.16 (s, 1H) 6.98 (s, 1H) 6.33 (s, 1H) 6.06 (s, 1H) 2.68 (s, 3H) 2.55 (s, 3H) 2.49 (s, 3H). HRMS calcd. for C₂₀H₁₉N₅ (M+H)⁺ 330.1713. found 330.1716.

Example 99

Example 99-A (±)-N-((5-cyano-1-((2-(trimethylsilyl)ethoxy)methyl)-1H-benzo[d]imidazol-2-yl)(5,7-dimethyl-1-tosyl-1H-indol-4-yl)methyl)methanesulfonamide and
(±)-N-((6-cyano-1-((2-(trimethylsilyl)ethoxy)methyl)-1H-benzo[d]imidazol-2-yl)(5,7-dimethyl-1-tosyl-1H-indol-4-yl)methyl)methanesulfonamide

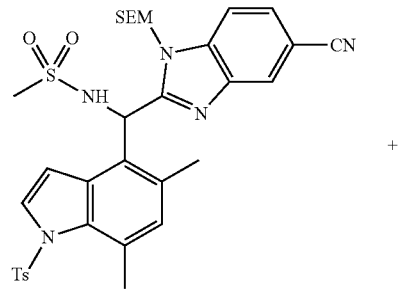

+

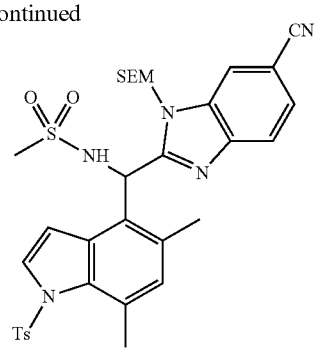

To a solution of a mixture of (±)-2-((5,7-dimethyl-1-tosyl-1H-indol-4-yl)(hydroxy)methyl)-1-((2-(trimethylsilyl)ethoxy)methyl)-1H-benzo[d]imidazole-5-carbonitrile, (±)-2-((5,7-dimethyl-1-tosyl-1H-indol-4-yl)(hydroxy)methyl)-1-((2-(trimethylsilyl)ethoxy)methyl)-1H-benzo[d]imidazole-6-carbonitrile (114 mg, 0.190 mmol), and DBU (0.086 mL, 0.569 mmol) in toluene (1.9 mL), DPPA (0.123 mL, 0.569 mmol) was added at rt. After stirring for 15 h at rt, additional DBU (0.029 mL, 0.190 mmol) and DPPA (0.041 mL, 0.190 mmol) were added. After stirring for 3 h, the reaction mixture was diluted with 2 M aq. Na₂CO₃ and EtOAc. The layers were separated and the aqueous layer was extracted with EtOAc. The organic layer was washed with 1 M aq. KHSO₄ and then with brine, dried over Na₂SO₄, filtered, and concentrated. A solution of the resulting residue was dissolved in EtOH (4 mL) and was hydrogenated by using the H-Cube® apparatus (1 atm, rt, 10% Pd/C, 1 mL/min.) for 1.5 h. The mixture was concentrated and dissolved in CH₂Cl₂ (1.9 mL) to which DIPEA (0.066 mL, 0.380 mmol) and Ms₂O (49.6 mg, 0.285 mmol) were added at rt. After stirring for 1 h, additional DIPEA (0.066 mL, 0.380 mmol) and Ms₂O (49.6 mg, 0.285 mmol) were added. After stirring for 1 h, the mixture was diluted with brine and CH₂Cl₂. The layers were separated and the organic layer was collected, dried over MgSO₄, filtered and concentrated. The residue was purified by flash column chromatography on silica gel (heptanes/EtOAc=100:0 to 30:70) to give the title compounds as a mixture. MS (ESI+) m/z 678.4 (M+H).

Example 99-B (±)-N-((5-cyano-1H-benzo[d]imidazol-2-yl)(5,7-dimethyl-1H-indol-4-yl)methyl)methanesulfonamide

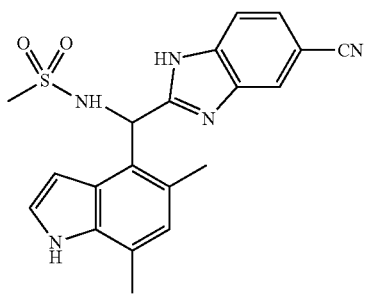 [SMILES: Cc1cc(C)c2[nH]ccc2c1C(NS(C)(=O)=O)c1nc2cc(C#N)ccc2[nH]1]

The title compound was synthesized from a mixture of (±)-N-((5-cyano-1-((2-(trimethylsilyl)ethoxy)methyl)-1H-benzo[d]imidazol-2-yl)(5,7-dimethyl-1-tosyl-1H-indol-4-yl)methyl)methanesulfonamide and (±)-N-((6-cyano-1-((2-

(trimethylsilyl)ethoxy)methyl)-1H-benzo[d]imidazol-2-yl) (5,7-dimethyl-1-tosyl-1H-indol-4-yl)methyl) methanesulfonamide as described in Example 64-B and 64-C. $^1$H NMR (400 MHz, DMSO-d$_6$) δ ppm 11.01 (s, 1H) 7.97 (br. s, 1H) 7.58-7.60 (m, 1H) 7.49 (m, 1H) 7.18 (t, J=2.78 Hz, 1H) 6.78 (s, 1H) 6.35-6.37 (m, 2H) 2.82 (s, 3H) 2.44 (s, 3H) 2.42 (s, 3H). HRMS calcd. for C$_{20}$H$_{19}$N$_6$O$_2$S (M+H)$^+$ 394.1332. found 394.1332.

Example 100

(±)-N-((5-cyano-1H-benzo[d]imidazol-2-yl)(5,7-dimethyl-1H-indol-4-yl)methyl)acetamide

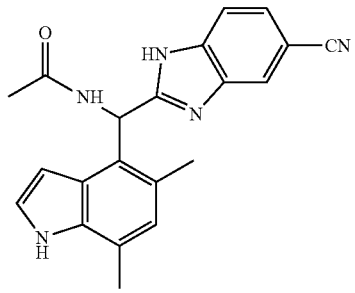 [SMILES: CC(=O)NC(c1nc2cc(C#N)ccc2[nH]1)c1c(C)cc(C)c2[nH]ccc12]

The title compound was synthesized as described in Example 99 using Ac$_2$O in the place of Ms$_2$O in Example 99-A. $^1$H NMR (400 MHz, DMSO-d$_6$) δ ppm 10.96 (s, 1H) 8.71 (d, J=7.33, 1H) 7.99 (br. s, 1H) 7.58 (br. s, 1H) 7.51 (app dd, J=8.34, 1.52 Hz, 1H) 7.12 (app t, J=2.91 Hz, 1H) 6.77 (s, 1H) 6.72 (d, J=7.33 Hz, 1H) 6.05 (dd, J=3.03, 1.77 Hz, 1H) 2.41 (s, 3H) 2.39 (s, 3H) 1.97 (s, 3H). HRMS calcd. for C$_{21}$H$_{19}$N$_5$O (M+H)$^+$ 358.1663. found 358.1663.

Example 101

Example 101-A (±)-N-((5-cyano-1-((2-(trimethylsilyl)ethoxy)methyl)-1H-benzo[d]imidazol-2-yl)(5,7-dimethyl-1-tosyl-1H-indol-4-yl)methylene)-2-methylpropane-2-sulfinamide and (±)-N-((6-cyano-1-((2-(trimethylsilyl)ethoxy)methyl)-1H-benzo[d]imidazol-2-yl)(5,7-dimethyl-1-tosyl-1H-indol-4-yl)methylene)-2-methylpropane-2-sulfinamide

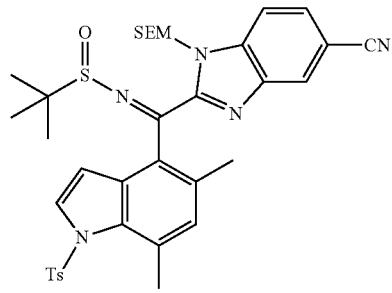

+

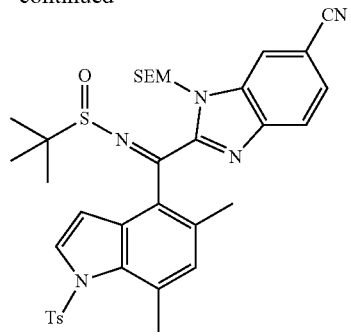

A suspension of a mixture of 2-(5,7-dimethyl-1-tosyl-1H-indole-4-carbonyl)-1-((2-(trimethylsilyl)ethoxy)methyl)-1H-benzo[d]imidazole-5-carbonitrile and 2-(5,7-dimethyl-1-tosyl-1H-indole-4-carbonyl)-1-((2-(trimethylsilyl)ethoxy)methyl)-1H-benzo[d]imidazole-6-carbonitrile (Example 75-A) (96 mg, 0.769 mmol), and Ti(O-i-Pr)$_4$ (1.4 mL, 4.89 mmol) was allowed to stir at 90° C. After stirring for 18 h, the reaction mixture was cooled to rt and diluted with EtOAc and brine. The resulting mixture was filtered and the organic layer of the filtrate was separated. The organic layer was dried over Na$_2$SO$_4$, filtered, and concentrated. The residue was purified by flash column chromatography on silica gel (heptanes/EtOAc=100:0 to 30:70) to give title compounds as a mixture. MS (ESI+) m/z 702.54 (M+H).

Example 101-B (±)-N-(1-(5-cyano-1-((2-(trimethylsilyl)ethoxy)methyl)-1H-benzo[d]imidazol-2-yl)-1-(5,7-dimethyl-1-tosyl-1H-indol-4-yl)ethyl)-2-methylpropane-2-sulfinamide and (±)-N-(1-(6-cyano-1-((2-(trimethylsilyl)ethoxy)methyl)-1H-benzo[d]imidazol-2-yl)-1-(5,7-dimethyl-1-tosyl-1H-indol-4-yl)ethyl)-2-methylpropane-2-sulfinamide

+

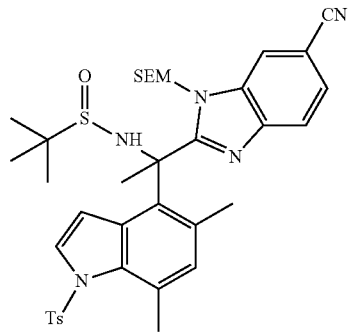

To a solution of (±)-N-(1-(5-cyano-1-((2-(trimethylsilyl)ethoxy)methyl)-1H-benzo[d]imidazol-2-yl)-1-(5,7-dimethyl-1-tosyl-1H-indol-4-yl)ethyl)-2-methylpropane-2-sulfinamide and (±)-N-(1-(6-cyano-1-((2-(trimethylsilyl)ethoxy)methyl)-1H-benzo[d]imidazol-2-yl)-1-(5,7-dimethyl-1-tosyl-1H-indol-4-yl)ethyl)-2-methylpropane-2-sulfinamide (410 mg, 0.584 mmol) in THF (5 mL), MeMgCl (3 M in THF, 0.584 mL, 1.752 mmol) was added the reaction was allowed to stir at rt for 50 min. The mixture was diluted with aq. NH$_4$Cl and EtOAc. The layers were separated and the aqueous layer was extracted with EtOAc. The combined organic layers were washed with brine, dried over Na$_2$SO$_4$, filtered, and concentrated to give title compounds as a mixture. MS (ESI+) m/z 718.73 (M+H).

Example 101-C (±)-N-(1-(5-cyano-1H-benzo[d]imidazol-2-yl)-1-(5,7-dimethyl-1-tosyl-1H-indol-4-yl)ethyl)-2-methylpropane-2-sulfinamide

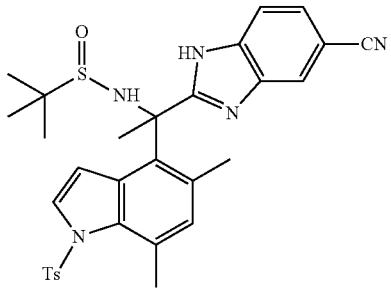 [SMILES: Cc1ccc(S(=O)(=O)n2ccc3c(C(C)(NS(=O)C(C)(C)C)c4nc5cc(C#N)ccc5[nH]4)c(C)cc(C)c32)cc1]

The title compound was synthesized from a mixture of (±)-N-(1-(5-cyano-1-((2-(trimethylsilyl)ethoxy)methyl)-1H-benzo[d]imidazol-2-yl)-1-(5,7-dimethyl-1-tosyl-1H-indol-4-yl)ethyl)-2-methylpropane-2-sulfinamide and (±)-N-(1-(6-cyano-1-((2-(trimethylsilyl)ethoxy)methyl)-1H-benzo[d]imidazol-2-yl)-1-(5,7-dimethyl-1-tosyl-1H-indol-4-yl)ethyl)-2-methylpropane-2-sulfinamide as described in Example 64-B. MS (ESI+) m/z 598.47 (M+H).

Example 101-D (±)-2-(1-Amino-1-(5,7-dimethyl-1-tosyl-1H-indol-4-yl)ethyl)-1H-benzo[d]imidazole-5-carbonitrile

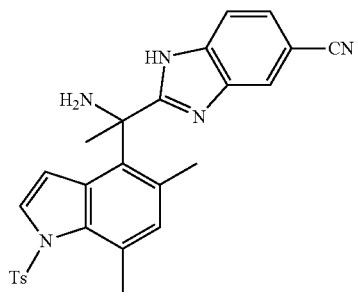 [SMILES: Cc1ccc(S(=O)(=O)n2ccc3c(C(C)(N)c4nc5cc(C#N)ccc5[nH]4)c(C)cc(C)c32)cc1]

A solution of (±)-N-(1-(5-cyanobenzo[d]imidazol-2-yl)-1-(5,7-dimethyl-1-tosyl-1H-indol-4-yl)ethyl)-2-methylpropane-2-sulfinamide (97 mg, 0.165 mmol) and HCl (1.25 M in MeOH) (792 µL, 0.990 mmol) was allowed to stir at rt for 17 h. The mixture was concentrated and then diluted with 1 M aq. NaOH, brine and CH$_2$Cl$_2$. The organic layer was separated and concentrated. The residue was purified by flash column chromatography on silica gel (CH$_2$Cl$_2$/MeOH=100:0 to 10:1) to give the title compound. MS (ESI+) m/z 484.44 (M+H).

Example 101-E a) (±)-2-(1-Amino-1-(5,7-dimethyl-1H-indol-4-yl)ethyl)-1H-benzo[d]imidazole-5-carbonitrile

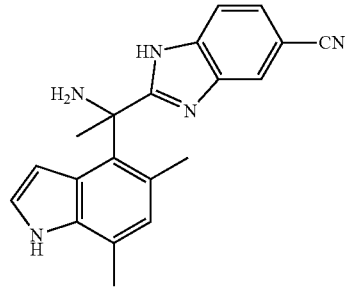 [SMILES: Cc1cc(C)c2[nH]ccc2c1C(C)(N)c1nc2cc(C#N)ccc2[nH]1]

The title compound was synthesized from (±)-2-(1-amino-1-(5,7-dimethyl-1-tosyl-1H-indol-4-yl)ethyl)benzo[d]imidazole-5-carbonitrile as described in Example 64-C. $^1$H NMR (400 MHz, DMSO-d$_6$) δ ppm 10.78 (s, 1H) 7.91 (s, 1H) 7.53 (br. d, J=8.34 Hz, 1H) 7.41 (br. d, J=7.73 Hz, 1H) 7.09 (t, J=2.78 Hz, 1H) 6.58-6.59 (m, 2H) 2.37 (s, 3H) 1.98 (s, 3H) 1.95 (s, 3H). HRMS calcd. for C$_{20}$H$_{19}$N$_6$ (M+H)$^+$ 330.1713. found 330.1718.

b) (+) and (−)-2-(1-Amino-1-(5,7-dimethyl-1H-indol-4-yl)ethyl)-1H-benzo[d]imidazole-5-carbonitrile Resolution of the enantiomers of 2-(1-amino-1-(5,7-dimethyl-1H-indol-4-yl)ethyl)benzo[d]imidazole-5-carbonitrile was achieved by chiral SFC using a CHIRALCEL® OD-H column with 30% MeOH (with 0.2% DEA) in CO$_2$ to give (+)-2-(1-amino-1-(5,7-dimethyl-1H-indol-4-yl)ethyl)benzo[d]imidazole-5-carbonitrile (t$_r$=1.6 min) and (−)-2-(1-amino-1-(5,7-dimethyl-1H-indol-4-yl)ethyl)benzo[d]imidazole-5-carbonitrile (t$_r$=2.2 min).

Example 102

Example 102-A (±)-N-(1-(5-cyano-1-((2-(trimethylsilyl)ethoxy)methyl)-1H-benzo[d]imidazol-2-yl)-1-(5-ethyl-7-methyl-1-tosyl-1H-indol-4-yl)ethyl)-2-methylpropane-2-sulfinamide and (±)-N-(1-(6-cyano-1-((2-(trimethylsilyl)ethoxy)methyl)-1H-benzo[d]imidazol-2-yl)-1-(5-ethyl-7-methyl-1-tosyl-1H-indol-4-yl)ethyl)-2-methylpropane-2-sulfinamide

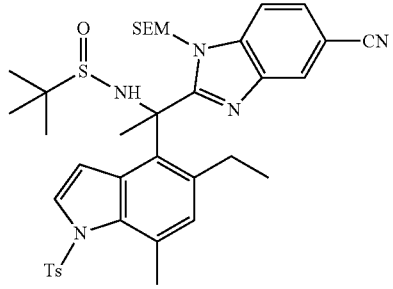

+

-continued

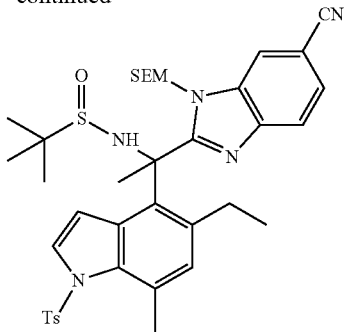

A mixture of title compounds was synthesized from a mixture of 2-(5-ethyl-7-methyl-1-tosyl-1H-indole-4-carbonyl)-1-((2-(trimethylsilyl)ethoxy)methyl)-1H-benzo[d]imidazole-5-carbonitrile and 2-(5-ethyl-7-methyl-1-tosyl-1H-indole-4-carbonyl)-1-((2-(trimethylsilyl)ethoxy)methyl)-1H-benzo[d]imidazole-6-carbonitrile (Example 117-A) analogously to the preparation of Example 101-B. MS (ESI+) m/z 732.7 (M+H).

Example 102-B (±)-2-(1-Amino-1-(5-ethyl-7-methyl-1-tosyl-1H-indol-4-yl)ethyl)-1H-benzo[d]imidazole-5-carbonitrile

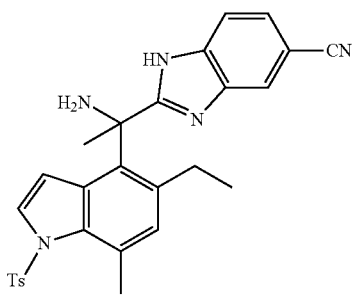 [SMILES: CCc1cc(C)c2c(ccn2S(=O)(=O)c2ccc(C)cc2)c1C(C)(N)c1nc2cc(C#N)ccc2[nH]1]

A solution of (±)-N-(1-(5-cyano-1-((2-(trimethylsilyl)ethoxy)methyl)-1H-benzo[d]imidazol-2-yl)-1-(5-ethyl-7-methyl-1-tosyl-1H-indol-4-yl)ethyl)-2-methylpropane-2-sulfinamide and (±)-N-(1-(6-cyano-1-((2-(trimethylsilyl)ethoxy)methyl)-1H-benzo[d]imidazol-2-yl)-1-(5-ethyl-7-methyl-1-tosyl-1H-indol-4-yl)ethyl)-2-methylpropane-2-sulfinamide (330 mg, 0.451 mmol) in 1M HCl in MeOH (5 mL) was stirred at 60° C. for 6 h. The reaction mixture was neutralized with 5% aq. NaHCO$_3$. The layers were separated and the aqueous layer was extracted with CH$_2$Cl$_2$. The organic phase was successively washed by H$_2$O and brine, dried over Na$_2$SO$_4$, and filtered. After concentration, the residue was purified by silica gel flash column chromatography (CH$_2$Cl$_2$/EtOH=1/0 to 9/1) to give the title compound. MS (ESI−) m/z 496.4 (M−H).

Example 102-C a) (±)-2-(1-Amino-1-(5-ethyl-7-methyl-1H-indol-4-yl)ethyl)-1H-benzo[d]imidazole-5-carbonitrile

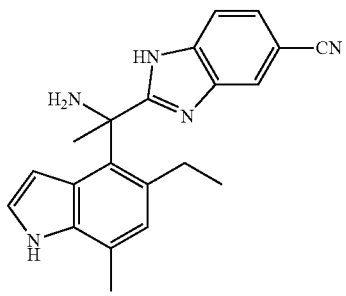 [SMILES: CCc1cc(C)c2[nH]ccc2c1C(C)(N)c1nc2cc(C#N)ccc2[nH]1]

The title compound was synthesized from (±)-2-(1-amino-1-(5-ethyl-7-methyl-1-tosyl-1H-indol-4-yl)ethyl)-1H-benzo[d]imidazole-5-carbonitrile as described in Example 64-C. $^1$H NMR (400 MHz, ACETONITRILE-d$_3$ with about 5 μL TFA) δ ppm 9.47 (br. s., 1H), 8.01 (s, 1H), 7.61 (d, J=8.60 Hz, 1H), 7.56 (dd, J=1.50, 8.60 Hz, 1H), 7.20 (t, J=3.00 Hz, 1H), 6.93 (s, 1H), 6.13 (dd, J=2.00, 3.00 Hz, 1H), 2.49-2.60 (m, 1H), 2.47 (d, J=0.76 Hz, 3H), 2.43-2.52 (m, 1H), 2.42 (s, 3H), 0.98 (t, J=7.33 Hz, 3H). HRMS calcd. for C$_{21}$H$_{21}$N$_5$ (M+H)$^+$ 344.1870. found 344.1876.

b) (+) and (−)-2-(1-amino-1-(5-ethyl-7-methyl-1H-indol-4-yl)ethyl)-1H-benzo[d]imidazole-5-carbonitrile Resolution of the enantiomers of 2-(1-amino-1-(5-ethyl-7-methyl-1H-indol-4-yl)ethyl)-1H-benzo[d]imidazole-5-carbonitrile was achieved by normal phase chiral HPLC using a CHIRALCEL® OD column with 15% EtOH to give (+)-2-(1-amino-1-(5-ethyl-7-methyl-1H-indol-4-yl)ethyl)-1H-benzo[d]imidazole-5-carbonitrile (t$_r$=12.0 min) and (−)-2-(1-amino-1-(5-ethyl-7-methyl-1H-indol-4-yl)ethyl)-1H-benzo[d]imidazole-5-carbonitrile (t$_r$=15.6 min).

The following compounds were prepared with similar methods.

| | Structure/Chemical Name | $^1$H NMR | HRMS |
|---|---|---|---|
| 102-D a) | (±)-2-(1-amino-1-(5-cyclopropyl-7-methyl-1H-indol-4-yl)ethyl)-1H-benzo[d]imidazole-5-carbonitrile | (400 MHz, ACETONITRILE-d3 with about 5% TFA) δ ppm 8.08 (dd, J = 0.88, 1.39 Hz, 1H), 7.57-7.78 (m, 2H), 7.25 (t, J = 3.03 Hz, 1H), 6.97 (s, 1H), 6.04 (dd, J = 1.89, 3.41 Hz, 1H), 2.61 (s, 3H) 2.52 (s, 3H), 1.72-1.88 (m, 1H), 0.58-1.08 (m, 4H). | calcd. for C$_{22}$H$_{21}$N$_5$ (M + H)$^+$ 356.187, found 356.1876. |

| Structure/Chemical Name | ¹H NMR | HRMS |
|---|---|---|
| 102-D b) | (+) and (−)-2-(1-amino-1-(5-cyclopropyl-7-methyl-1H-indol-4-yl)ethyl)-1H-benzo[d]imidazole-5-carbonitrile<br>Resolution of the enantiomers of 2-(1-amino-1-(5-cyclopropyl-7-methyl-1H-indol-4-yl)ethyl)-1H-benzo[d]imidazole-5-carbonitrile was achieved by normal phase chiral HPLC using a CHIRALPAK ® AD column with 15% EtOH in heptane to give (−)-2-(1-amino-1-(5-cyclopropyl-7-methyl-1H-indol-4-yl)ethyl)-1H-benzo[d]imidazole-5-carbonitrile ($t_r$ = 9.95 min) and (+)-2-(1-amino-1-(5-cyclopropyl-7-methyl-1H-indol-4-yl)ethyl)-1H-benzo[d]imidazole-5-carbonitrile ($t_r$ = 14.66 min). | |
| 102-E a) 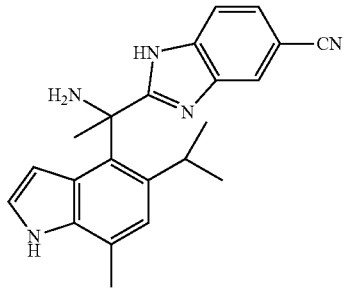<br>(±)-2-(1-amino-1-(5-isopropyl-7-methyl-1H-indol-4-yl)ethyl)-1H-benzo[d]imidazole-5-carbonitrile | (400 MHz, ACETONITRILE-$d_3$ with about 5 μL TFA) δ ppm 9.55 (br. s., 1H), 8.02 (d, J = 0.76 Hz, 1H), 7.62 (d, J = 8.30 Hz, 1H), 7.59 (dd, J = 1.30, 8.30 Hz, 1H), 7.29-7.36 (m, 1H), 7.08 (s, 1H), 6.46 (dd, J = 2.02, 3.28 Hz, 1H), 2.67-2.81 (m, 1H), 2.51 (s, 3H), 2.48 (s, 3H), 1.04 (d, J = 6.57 Hz, 3H), 0.85 (d, J = 6.57 Hz, 3H). | calcd. for $C_{22}H_{23}N_5$ $(M + H)^+$ 358.2026, found 358.2021. |
| 102-E b) | (+) and (−)-2-(1-amino-1-(5-isopropyl-7-methyl-1H-indol-4-yl)ethyl)-1H-benzo[d]imidazole-5-carbonitrile<br>Resolution of the enantiomers of 2-(1-amino-1-(5-isopropyl-7-methyl-1H-indol-4-yl)ethyl)-1H-benzo[d]imidazole-5-carbonitrile was achieved by normal phase chiral HPLC using a CHIRALCEL ® OD column with 15% EtOH to give (+) or (−)-2-(1-amino-1-(5-isopropyl-7-methyl-1H-indol-4-yl)ethyl)-1H-benzo[d]imidazole-5-carbonitrile ($t_r$ = 7.0 min) and (−) or (+)-2-(1-amino-1-(5-isopropyl-7-methyl-1H-indol-4-yl)ethyl)-1H-benzo[d]imidazole-5-carbonitrile ($t_r$ = 10.0 min). | |

Example 103

Example 103-A (±)-2-(1-Amino-1-(5,7-dimethyl-1-tosyl-1H-indol-4-yl)ethyl)-1-((2-(trimethylsilyl)ethoxy)methyl)-1H-benzo[d]imidazole-5-carbonitrile and (±)-2-(1-amino-1-(5,7-dimethyl-1-tosyl-1H-indol-4-yl)ethyl)-1-((2-(trimethylsilyl)ethoxy)methyl)-1H-benzo[d]imidazole-6-carbonitrile

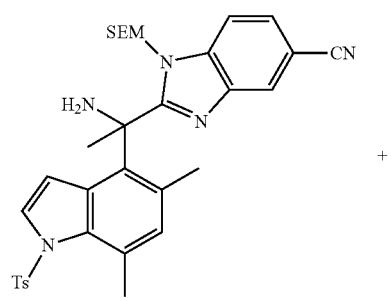

+

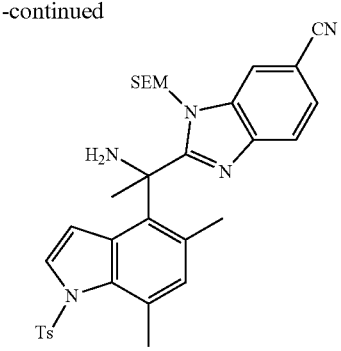

To a solution of a mixture of (±)-N-(1-(5-cyano-1-((2-(trimethylsilyl)ethoxy)methyl)-1H-benzo[d]imidazol-2-yl)-1-(5,7-dimethyl-1-tosyl-1H-indol-4-yl)ethyl)-2-methylpropane-2-sulfinamide and (±)-N-(1-(6-cyano-1-((2-(trimethylsilyl)ethoxy)methyl)-1H-benzo[d]imidazol-2-yl)-1-(5,7-dimethyl-1-tosyl-1H-indol-4-yl)ethyl)-2-methylpropane-2-sulfinamide (280 mg) in anhydrous MeOH (1.07 mL), HCl (1.25 M in MeOH) (0.683 mL, 0.854 mmol) was added at rt. After stirring for 1 h, additional HCl (1.25 M in MeOH) (0.683 mL, 0.854 mmol) was added. After stirring for further 2.5 h, the reaction was diluted with 2 M aq. $Na_2CO_3$, brine and EtOAc. The layers were separated and the aqueous layer was extracted with EtOAc. The organic layer was washed with brine, dried over $Na_2SO_4$, filtered, and concentrated. The residue was purified by flash column chromatography on silica gel (heptanes/EtOAc=100:0 to 40:60) to give the mixture of title compounds. MS (ESI+) m/z 614.35 (M+H).

Example 103-B (±)-tert-Butyl (1-(5-cyano-1-((2-(trimethylsilyl)ethoxy)methyl)-1H-benzo[d]imidazol-2-yl)-1-(5,7-dimethyl-1-tosyl-1H-indol-4-yl)ethyl)carbamate and (±)-tert-butyl 1-(6-cyano-1-((2-(trimethylsilyl)ethoxy)methyl)-1H-benzo[d]imidazol-2-yl)-1-(5,7-dimethyl-1-tosyl-1H-indol-4-yl)ethyl)carbamate

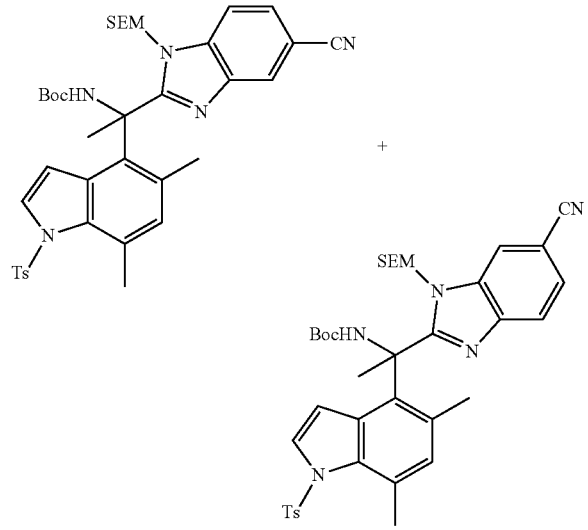

A mixture of (±)-2-(1-amino-1-(5,7-dimethyl-1-tosyl-1H-indol-4-yl)ethyl)-1-((2-(trimethylsilyl)ethoxy)methyl)-1H-benzo[d]imidazole-5-carbonitrile and (±)-2-(1-amino-1-(5,7-dimethyl-1-tosyl-1H-indol-4-yl)ethyl)-1-((2-(trimethylsilyl)ethoxy)methyl)-1H-benzo[d]imidazole-6-carbonitrile (153 mg, 0.249 mmol) and Boc$_2$O (544 mg, 2.492 mmol) was allowed to stir at 60° C. for 6.5 h. The reaction mixture was cooled to rt, and then purified by flash column chromatography on silica gel (eluent: heptane/EtOAc=100:0 to 65:35) to give the title compounds as a mixture. MS (ESI+) m/z 714.64 (M+H).

Example 103-C (±)-tert-Butyl 1-(5-cyano-1-((2-(trimethylsilyl)ethoxy)methyl)-1H-benzo[d]imidazol-2-yl)-1-(5,7-dimethyl-1-tosyl-1H-indol-4-yl)ethyl(methyl)carbamate and (±)-tert-butyl 1-(6-cyano-1-((2-(trimethylsilyl)ethoxy)methyl)-1H-benzo[d]imidazol-2-yl)-1-(5,7-dimethyl-1-tosyl-1H-indol-4-yl)ethyl(methyl)carbamate

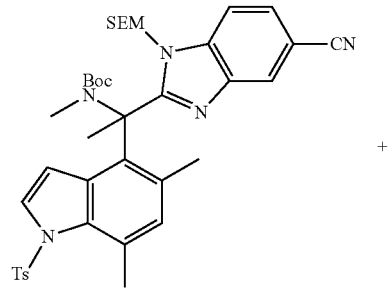

+

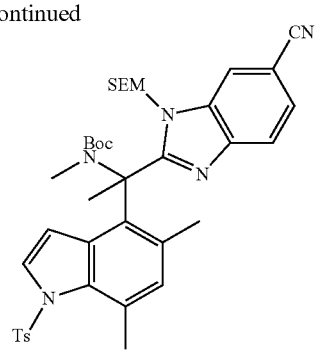

To a mixture of (±)-tert-butyl 1-(5-cyano-1-((2-(trimethylsilyl)ethoxy)methyl)-1H-benzo[d]imidazol-2-yl)-1-(5,7-dimethyl-1-tosyl-1H-indol-4-yl)ethylcarbamate and (±)-tert-butyl 1-(6-cyano-1-((2-(trimethylsilyl)ethoxy)methyl)-1H-benzo[d]imidazol-2-yl)-1-(5,7-dimethyl-1-tosyl-1H-indol-4-yl)ethylcarbamate (146 mg, 0.204 mmol) and NaH (60%, 16.36 mg, 0.409 mmol) in DMF (2 mL), MeI (0.023 mL, 0.368 mmol) was added at rt. After stirring for 1.5 h, additional NaH (60%, 16.36 mg, 0.409 mmol) and MeI (0.023 mL, 0.368 mmol) were added. After stirring for 30 min, the reaction mixture was diluted with sat. aq. NH$_4$Cl and EtOAc. The layers were separated and the aqueous layer was extracted twice with EtOAc. The organic layer was washed with H$_2$O and then with brine, dried over Na$_2$SO$_4$, filtered, and concentrated. The mixture was purified by flash column chromatography on silica gel (heptane/EtOAc=100:0 to 60:40) to give the title compounds as a mixture. MS (ESI+) m/z 728.54 (M+H).

Example 103-D (±)-2-(1-(5,7-Dimethyl-1-tosyl-1H-indol-4-yl)-1-(methylamino)ethyl)-1H-benzo[d]imidazole-5-carbonitrile

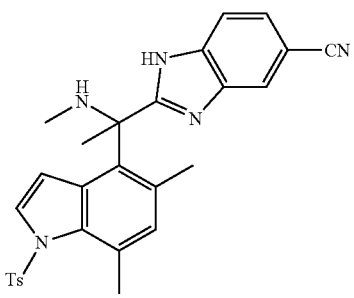 [SMILES: CNC(C)(c1nc2cc(C#N)ccc2[nH]1)c1c(C)cc(C)c2c1ccn2S(=O)(=O)c1ccc(C)cc1]

A solution of (±)-tert-butyl 1-(5-cyano-1-((2-(trimethylsilyl)ethoxy)methyl)-1H-benzo[d]imidazol-2-yl)-1-(5,7-dimethyl-1-tosyl-1H-indol-4-yl)ethyl(methyl)carbamate and (±)-tert-butyl 1-(6-cyano-1-((2-(trimethylsilyl)ethoxy)methyl)-1H-benzo[d]imidazol-2-yl)-1-(5,7-dimethyl-1-tosyl-1H-indol-4-yl)ethyl(methyl)carbamate (95 mg, 0.130 mmol) in MeOH (326 μL) was mixed with 4 M HCl in dioxane (0.65 mL, 2.61 mmol) and the reaction stirred at 50° C. for 0.5 h. The reaction mixture was cooled to rt and diluted with 2 M aq. Na$_2$CO$_3$, brine and EtOAc. The products were extracted with EtOAc. The organic layer was washed with brine, dried over Na$_2$SO$_4$, filtered, and concentrated. The residue was purified by flash column chromatography on silica gel (heptane/EtOAc=100:0 to 40:60) to give the title compound. MS (ESI) m/z 496.34(M−1).

Example 103-E (±)-2-(1-(5,7-Dimethyl-1H-indol-4-yl)-1-(methylamino)ethyl)-1H-benzo[d]imidazole-5-carbonitrile

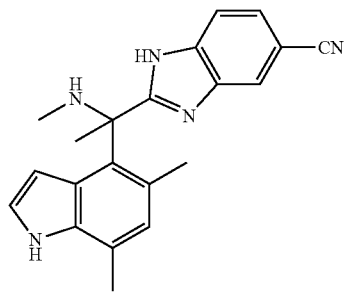 [SMILES: CNC(C)(c1nc2cc(C#N)ccc2[nH]1)c1c(C)cc(C)c2[nH]ccc12]

The title compound was synthesized from (±)-2-(1-(5,7-dimethyl-1-tosyl-1H-indol-4-yl)-1-(methylamino)ethyl)-1H-benzo[d]imidazole-5-carbonitrile following a similar procedure as described in Example 64-C. $^1$H NMR (TFA salt, 400 MHz, CD$_3$OD) δ ppm 10.93 (br. s, 1H), 8.03 (br. s, 1H), 7.56-7.63 (br. m, 2H), 7.20-7.21 (m, 1H), 6.91 (s, 1H), 6.12 (d, J=3.16 Hz, 1H), 2.56 (s, 3H), 2.50 (s, 3H), 2.45 (s, 3H), 2.34 (s, 3H). HRMS calcd. for C$_{22}$H$_{21}$N$_5$ (M+H)$^+$ 344.1870. found 344.1867.

Example 104

Example 104-A (±)-2-(1-(5,7-dimethyl-1-tosyl-1H-indol-4-yl)-1-(dimethylamino)ethyl)-1-((2-(trimethylsilyl)ethoxy)methyl)-1H-benzo[d]imidazole-5-carbonitrile and
(±)-2-(1-(5,7-dimethyl-1-tosyl-1H-indol-4-yl)-1-(dimethylamino)ethyl)-1-((2-(trimethylsilyl)ethoxy)methyl)-1H-benzo[d]imidazole-6-carbonitrile

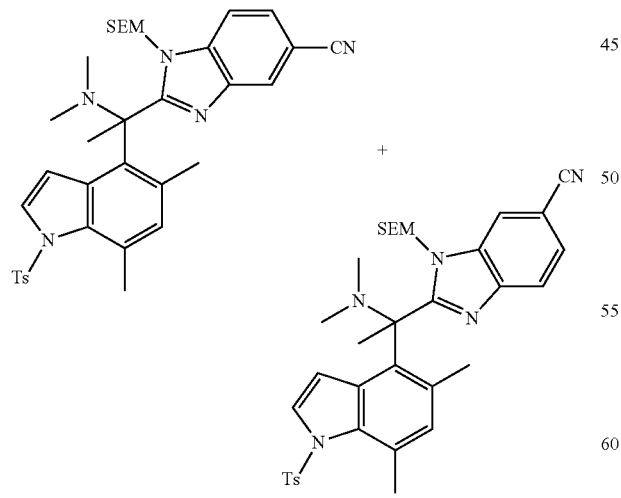

A solution of a mixture of (±)-2-(1-amino-1-(5,7-dimethyl-1-tosyl-1H-indol-4-yl)ethyl)-1-((2-(trimethylsilyl)ethoxy)methyl)-1H-benzo[d]imidazole-5-carbonitrile and (±)-2-(1-amino-1-(5,7-dimethyl-1-tosyl-1H-indol-4-yl)ethyl)-1-((2-(trimethylsilyl)ethoxy)methyl)-1H-benzo[d]imidazole-6-carbonitrile (Example 103-A) (150 mg, 0.244 mmol), K$_2$CO$_3$ (169 mg, 1.222 mmol) and MeI (0.076 mL, 1.222 mmol) in DMF (2.4 mL) was allowed to stir at 45° C. for 17.5 h. The reaction was cooled to rt and diluted with 2 M Na$_2$CO$_3$ aq., brine and EtOAc. The layers were separated and the aqueous layer was extracted with EtOAc. The organic layer was washed with brine, dried over Na$_2$SO$_4$, filtered, and concentrated. The residue was purified by flash column chromatography on silica gel (heptanes/EtOAc=100:0 to 60:40) to give the title compounds as a mixture. MS (ESI+) m/z 642.52 (M+H).

Example 104-B (±)-2-(1-(5,7-dimethyl-1H-indol-4-yl)-1-(dimethylamino)ethyl)-1H-benzo[d]imidazole-5-carbonitrile

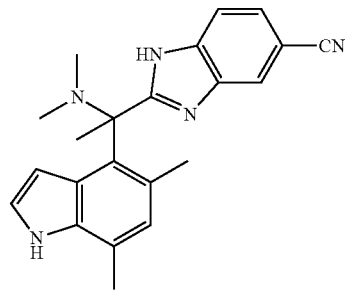

The title compound was synthesized from a mixture of (±)-2-(1-(5,7-dimethyl-1-tosyl-1H-indol-4-yl)-1-(dimethylamino)ethyl)-1-((2-(trimethylsilyl)ethoxy)methyl)-1H-benzo[d]imidazole-5-carbonitrile and (±)-2-(1-(5,7-dimethyl-1-tosyl-1H-indol-4-yl)-1-(dimethylamino)ethyl)-1-((2-(trimethylsilyl)ethoxy)methyl)-1H-benzo[d]imidazole-6-carbonitrile as described in Example 102-B and 64-C. $^1$H NMR (400 MHz, CD$_3$OD) δ ppm 7.56-8.08 (br. m, 2H), 7.55 (m, J=8.15, 1.20 Hz, 1H), 7.03 (d, J=3.23 Hz, 1H) 6.72 (s, 1H) 6.28 (d, J=3.23 Hz, 1H) 2.43 (s, 3H) 2.23 (s, 3H) 2.06 (s, 3H) 2.05 (s, 3H). HRMS calcd. for C$_{23}$H$_{26}$N$_5$ (M+H)$^+$ 358.2026. found 358.2010.

Example 105

Example 105-A (±)-2-(1-Amino-1-(5-bromo-7-methyl-1-tosyl-1H-indol-4-yl)-2,2,2-trifluoroethyl)-1H-benzo[d]imidazole-5-carbonitrile

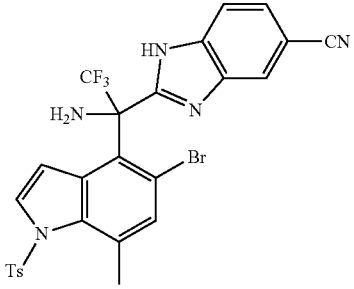 [SMILES: Cc1ccc(S(=O)(=O)n2ccc3c(C(N)(c4nc5cc(C#N)ccc5[nH]4)C(F)(F)F)c(Br)cc(C)c32)cc1]

The title compound was synthesized starting from 2-(5-Bromo-7-methyl-1-tosyl-1H-indole-4-carbonyl)-1-((2-(trimethylsilyl)ethoxy)methyl)-1H-benzo[d]imidazole-5-carbonitrile and 2-(5-bromo-7-methyl-1-tosyl-1H-indole-4-carbonyl)-1-((2-(trimethylsilyl)ethoxy)methyl)-1H-benzo[d]imidazole-6-carbonitrile (Example 81-A) following the same procedures as in Example 33-A and 38-A. MS (ESI+) m/z 602.0, 603.9 (M+H).

Example 105-B a) (±)-2-(1-Amino-1-(5-bromo-7-methyl-1H-indol-4-yl)-2,2,2-trifluoroethyl)-1H-benzo[d]imidazole-5-carbonitrile

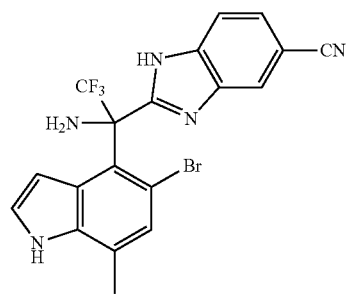 [SMILES: Cc1cc(Br)c(C(N)(c2nc3cc(C#N)ccc3[nH]2)C(F)(F)F)c2cc[nH]c12]

To (±)-2-(1-amino-1-(5-bromo-7-methyl-1-tosyl-1H-indol-4-yl)-2,2,2-trifluoroethyl)-1H-benzo[d]imidazole-5-carbonitrile (203 mg, 0.337 mmol) in EtOH (3.3 mL) was added sodium ethoxide (22% solution in EtOH) (2.5 mL, 6.74 mmol) and the mixture was stirred at 60° C. After 3 hours the reaction mixture was purified directly by flash chromatography (0-100% EtOAc in heptanes) to give the title compound. $^1$H NMR (400 MHz, DMSO-$d_6$) δ ppm 12.61 (br. s., 1H) 11.37 (br. s., 1H) 8.25 (m) 7.94 (m) 7.83-7.90 (m) 7.51-7.61 (m) 7.33 (br. s., 1H) 7.16 (s, 1H) 6.92 (br. s., 1H) 3.22 (s, 2H) 2.46 (d, J=0.51 Hz, 3H). HRMS calcd. for $C_{19}H_{13}BrF_3N_5$ (M+H)$^+$ 448.0379. found 448.0389.

b) (+) and (−)-2-(1-amino-1-(5-bromo-7-methyl-1H-indol-4-yl)-2,2,2-trifluoroethyl)-1H-benzo[d]imidazole-5-carbonitrile Resolution of the enantiomers of 2-(1-amino-1-(5-bromo-7-methyl-1H-indol-4-yl)-2,2,2-trifluoroethyl)-1H-benzo[d]imidazole-5-carbonitrile was achieved by chiral SFC using a CHIRALPAK® AD-H column with 25% MeOH in $CO_2$ to give (−)-2-(1-amino-1-(5-bromo-7-methyl-1H-indol-4-yl)-2,2,2-trifluoroethyl)-1H-benzo[d]imidazole-5-carbonitrile ($t_r$=2.9 min) and (+)-2-(1-amino-1-(5-bromo-7-methyl-1H-indol-4-yl)-2,2,2-trifluoroethyl)-1H-benzo[d]imidazole-5-carbonitrile ($t_r$=7.9 min).

Example 106 a) (±)-2-(1-(5-Bromo-7-methyl-1H-indol-4-yl)-2,2,2-trifluoro-1-(methylamino)ethyl)-1H-benzo[d]imidazole-5-carbonitrile

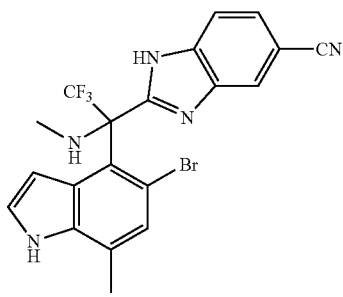 [SMILES: CNC(c1nc2cc(C#N)ccc2[nH]1)(c1c(Br)cc(C)c2[nH]ccc12)C(F)(F)F]

The title compound was synthesized as described in Example 105, methylamine in MeOH was used instead of ammonia in ethanol in Example 105-A. $^1$H NMR (400 MHz, ACETONITRILE-$d_3$, with 1% of TFA) δ ppm 8.11 (s, 1H), 7.72-7.78 (m, 1H), 7.63-7.70 (m, 1H), 7.34 (t, J=3.0 Hz, 1H), 7.27 (d, J=0.5 Hz, 1H), 7.14 (br. s., 1H), 2.51 (d, J=0.8 Hz, 3H), 2.19 (d, J=0.6 Hz, 3H); HRMS calcd. for $C_{20}H_{15}BrF_3N_5$ (M+H)$^+$ 462.0536. found 462.0544.

b) (+) and (−)-2-(1-(5-bromo-7-methyl-1H-indol-4-yl)-2,2,2-trifluoro-1-(methylamino)ethyl)-1H-benzo[d]imidazole-5-carbonitrile Resolution of the enantiomers of 2-(1-(5-bromo-7-methyl-1H-indol-4-yl)-2,2,2-trifluoro-1-(methylamino)ethyl)-1H-benzo[d]imidazole-5-carbonitrile was achieved by chiral HPLC using a CHIRALPAK® AD-H column with 10% ethanol (with 0.2% diethylamine) in heptane to give (+)-2-(1-(5-bromo-7-methyl-1H-indol-4-yl)-2,2,2-trifluoro-1-(methylamino)ethyl)-1H-benzo[d]imidazole-5-carbonitrile ($t_r$=13.04 min) and (−)-2-(1-(5-bromo-7-methyl-1H-indol-4-yl)-2,2,2-trifluoro-1-(methylamino)ethyl)-1H-benzo[d]imidazole-5-carbonitrile ($t_r$=18.92 min).

Example 107

Example 107-A (±)-2-(1-(5-Ethyl-7-methyl-1-tosyl-1H-indol-4-yl)-2,2,2-trifluoro-1-(methylamino)ethyl)-1H-benzo[d]imidazole-5-carbonitrile

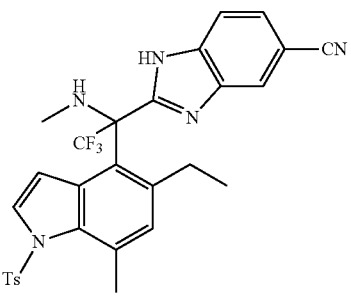 [SMILES: CCc1cc(C)c2c(ccn2S(=O)(=O)c2ccc(C)cc2)c1C(NC)(c1nc2cc(C#N)ccc2[nH]1)C(F)(F)F]

The title compound was synthesized from a mixture of (±)-2-(1-(5-ethyl-7-methyl-1-tosyl-1H-indol-4-yl)-2,2,2-trifluoro-1-hydroxyethyl)-1-((2-(trimethylsilyl)ethoxy)methyl)-1H-benzo[d]imidazole-5-carbonitrile and (±)-2-(1-(5-ethyl-7-methyl-1-tosyl-1H-indol-4-yl)-2,2,2-trifluoro-1-hydroxyethyl)-1-((2-(trimethylsilyl)ethoxy)methyl)-1H-benzo[d]imidazole-6-carbonitrile as described in Example 105-A, methylamine in MeOH was used instead of ammonia in ethanol. MS (ESI+) m/z 566.79 (M+H).

Example 107-B a) (±)-2-(1-(5-Ethyl-7-methyl-1H-indol-4-yl)-2,2,2-trifluoro-1-(methylamino)ethyl)-1H-benzo[d]imidazole-5-carbonitrile

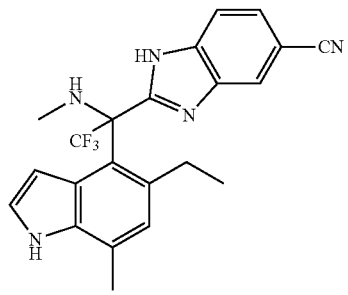 [SMILES: CCc1cc(C)c2[nH]ccc2c1C(NC)(c1nc2cc(C#N)ccc2[nH]1)C(F)(F)F]

The title compound was synthesized from (±)-2-(1-(5-ethyl-7-methyl-1-tosyl-1H-indol-4-yl)-2,2,2-trifluoro-1-(methylamino)ethyl)benzo[d]imidazole-5-carbonitrile following a similar procedure as described in Example 64-C $^1$H NMR (TFA salt, 400 MHz, CD$_3$OD) δ ppm 8.02 (d, J=0.63 Hz, 1H), 7.69 (d, J=8.42 Hz, 1H) 7.61 (app dd, J=8.42, 1.45 Hz, 1H) 7.10 (d, J=3.16 Hz, 1H) 6.94 (s, 1H) 6.42 (br. s, 1H) 2.45-2.62 (m, 5H), 2.18 (s, 3H) 1.00 (t, J=7.33 Hz, 3H). HRMS calcd. for C$_{22}$H$_{20}$F$_3$N$_5$ (M+H)$^+$ 412.1744. found 412.1745.

b) (+) and (−)-2-(1-(5-Ethyl-7-methyl-1H-indol-4-yl)-2,2,2-trifluoro-1-(methylamino)ethyl)-1H-benzo[d]imidazole-5-carbonitrile Resolution of the enantiomers of 2-(1-(5-Ethyl-7-methyl-1H-indol-4-yl)-2,2,2-trifluoro-1-(methylamino)ethyl)-1H-benzo[d]imidazole-5-carbonitrile was achieved by chiral SFC using a CHIRALCEL® OD-H column with 5-55% MeOH (with DEA) in CO$_2$ to give (+)-2-(1-(5-ethyl-7-methyl-1H-indol-4-yl)-2,2,2-trifluoro-1-(methylamino)ethyl)-1H-benzo[d]imidazole-5-carbonitrile (t$_r$=2.2 min) and (−)-2-(1-(5-ethyl-7-methyl-1H-indol-4-yl)-2,2,2-trifluoro-1-(methylamino)ethyl)-1H-benzo[d]imidazole-5-carbonitrile (t$_r$=2.4 min).

The following compounds were prepared with similar methods.

| | Structure/Chemical Name | $^1$H NMR | HRMS |
|---|---|---|---|
| 107-C a) | (±)-2-(1-amino-1-(5-ethyl-7-methyl-1H-indol-4-yl)-2,2,2-trifluoroethyl)-1H-benzo[d]imidazole-5-carbonitrile | (400 MHz, CD$_3$OD) δ 8.10 (br. s), 7.86 (br. d, J = 8.36 Hz), 7.75 (br. s), 7.55 (app d, J = 8.71 Hz, 1H), 7.48 (app d, J = 8.11 Hz), 7.05 (d, J = 3.29 Hz, 1H), 6.90 (s, 1H), 6.35 (br. s, 1H), 2.79-2.83 (m, 1H), 2.42-2.53 (m, 4H), 1.03 (t, J = 7.39 Hz, 3H). | calcd. for C$_{21}$H$_{18}$F$_3$N$_5$ (M + H)$^+$ 398.1590, found 398.1585. |

107-C b) (+) and (−)-2-(1-amino-1-(5-ethyl-7-methyl-1H-indol-4-yl)-2,2,2-trifluoroethyl)-1H-benzo[d]imidazole-5-carbonitrile Resolution of the enantiomers of 2-(1-amino-1-(5-ethyl-7-methyl-1H-indol-4-yl)-2,2,2-trifluoroethyl)-1H-benzo[d]imidazole-5-carbonitrile was achieved by chiral HPLC using a Lux ® Cellulose-2 column with 30% EtOH in heptane to give (+)-2-(1-amino-1-(5-ethyl-7-methyl-1H-indol-4-yl)-2,2,2-trifluoroethyl)-1H-benzo[imidazole-5-carbonitrile (t$_r$ = 4.2 min) and (−)-2-(1-amino-1-(5-ethyl-7-methyl-1H-indol-4-yl)-2,2,2-trifluoroethyl)-1H-benzo[d]imidazole-5-carbonitrile (t$_r$ = 6.2 min).

| Structure/Chemical Name | ¹H NMR | HRMS |
|---|---|---|
| 107-D a) 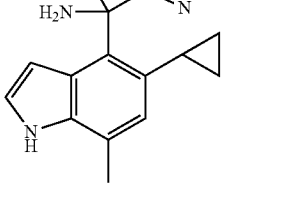<br>(±)-2-(1-amino-1-(5-cyclopropyl-7-methyl-1H-indol-4-yl)-2,2,2-trifluoroethyl)-1H-benzo[d]imidazole-5-carbonitrile | (400 MHz, ACETONITRILE-$d_3$ with about 5% TFA) δ 9.45 (br. s., 1H), 8.20 (t, J = 1.07 Hz, 1H), 7.86 (d, J = 1.14 Hz, 2H), 7.23 (t, J = 2.97 Hz, 1H), 6.65 (s, 1H), 6.56 (br. s., 1H), 2.49 (d, J = 0.76 Hz, 3H), 1.60-1.74 (m, 1H), 0.77-0.89 (m, 1H), 0.66-0.76 (m, 1H), 0.49-0.60 (m, 1H), 0.17-0.29 (m, 1H). | calcd. for $C_{22}H_{18}F_3N_5$ $(M+H)^+$ 410.1593, found 410.1589. |
| 107-D b) | (+) and (−)-2-(1-amino-1-(5-cyclopropyl-7-methyl-1H-indol-4-yl)-2,2,2-trifluoroethyl)-1H-benzo[d]imidazole-5-carbonitrile<br>Resolution of the enantiomers of 2-(1-amino-1-(5-cyclopropyl-7-methyl-1H-indol-4-yl)-2,2,2-trifluoroethyl)-1H-benzo[d]imidazole-5-carbonitrile was achieved by chiral separation using a Lux ® Cellulose-2 with 20% EtOH in heptane to give (+)-2-(1-amino-1-(5-cyclopropyl-7-methyl-1H-indol-4-yl)-2,2,2-trifluoroethyl)-1H-benzo[d]imidazole-5-carbonitrile ($t_r$ = 5.95 min) and (−)-2-(1-amino-1-(5-cyclopropyl-7-methyl-1H-indol-4-yl)-2,2,2-trifluoroethyl)-1H-benzo[d]imidazole-5-carbonitrile ($t_r$ = 10.6 min). | |
| 107-E a) 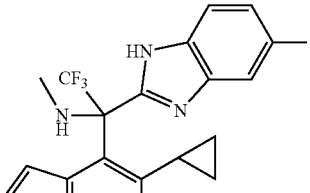<br>(±)-2-(1-(5-cyclopropyl-7-methyl-1H-indol-4-yl)-2,2,2-trifluoro-1-(methylamino)ethyl)-1H-benzo[d]imidazole-5-carbonitrile | (400 MHz, ACETONITRILE-$d_3$ with about 5% TFA) δ 9.46 (br. s., 1H), 8.16-8.34 (m, 1H), 7.80-7.97 (m, 2H), 7.29 (t, J = 3.03 Hz, 1H), 6.64 (br. s., 1H), 6.56 (s, 1H), 2.52 (d, J = 0.76 Hz, 3H), 2.28 (s, 3H), 1.51-1.69 (m, 1H), 0.79-0.91 (m, 1H), 0.68-0.78 (m, 1H), 0.53-0.65 (m, 1H), 0.19-0.34 (m, 1H). | calcd. for $C_{23}H_{20}F_3N_5$ $(M+H)^+$ 424.1749, found 424.1750. |
| 107-E b) | (+) and (−)-2-(1-(5-cyclopropyl-7-methyl-1H-indol-4-yl)-2,2,2-trifluoro-1-(methylamino)ethyl)-1H-benzo[d]imidazole-5-carbonitrile<br>Resolution of the enantiomers of 2-(1-(5-cyclopropyl-7-methyl-1H-indol-4-yl)-2,2,2-trifluoro-1-(methylamino)ethyl)-1H-benzo[d]imidazole-5-carbonitrile was achieved by chiral separation using a CHIRALPAK ® AD column with 15% EtOH in heptane to give (+)-2-(1-(5-cyclopropyl-7-methyl-1H-indol-4-yl)-2,2,2-trifluoro-1-(methylamino)ethyl)-1H-benzo[d]imidazole-5-carbonitrile ($t_r$ = 4.5 min) and (−)-2-(1-(5-cyclopropyl-7-methyl-1H-indol-4-yl)-2,2,2-trifluoro-1-(methylamino)ethyl)-1H-benzo[d]imidazole-5-carbonitrile ($t_r$ = 6.6 min). | |

Example 108

Example 108-A 2-((5,7-Dimethyl-1-tosyl-1H-indol-4-yl)methyl)-1-((2-(trimethylsilyl)ethoxy)methyl)-1H-benzo[d]imidazole-5-carbonitrile and 2-((5,7-dimethyl-1-tosyl-1H-indol-4-yl)methyl)-1-((2-(trimethylsilyl)ethoxy)methyl)-1H-benzo[d]imidazole-6-carbonitrile

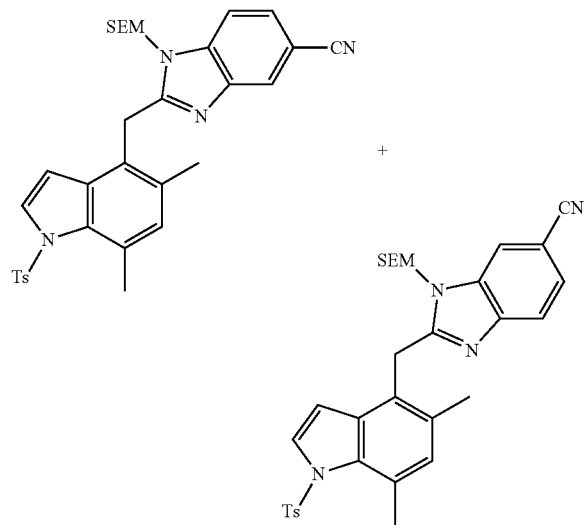

Sodium hydride (60% dispersion in mineral oil, 201 mg, 5.02 mmol) was added to a solution of 2-((5,7-dimethyl-1-tosyl-1H-indol-4-yl)methyl)-1H-benzo[d]imidazole-5-carbonitrile (Example 58-B) (1.9 g, 4.18 mmol) in THF (90 mL) at 0° C. After 5 min, SEMCl (0.890 mL, 5.02 mmol) was added and the reaction mixture was allowed to warm to room temperature over an hour. The reaction mixture was then partitioned between EtOAc and brine. The aqueous layer was extracted with EtOAc. The combined organics were washed over MgSO$_4$, filtered and concentrated. The residue was purified by silica gel chromatography (0-60% EtOAc in heptane) to provide the mixture of title compounds. MS (ESI+) m/z 585.4 (M+H).

Example 108-B (±)-Ethyl 2-(5-cyano-1-((2-(trimethylsilyl)ethoxy)methyl)-1H-benzo[d]imidazol-2-yl)-2-(5,7-dimethyl-1-tosyl-1H-indol-4-yl)acetate and (±)-ethyl 2-(6-cyano-1-((2-(trimethylsilyl)ethoxy)methyl)-1H-benzo[d]imidazol-2-yl)-2-(5,7-dimethyl-1-tosyl-1H-indol-4-yl)acetate

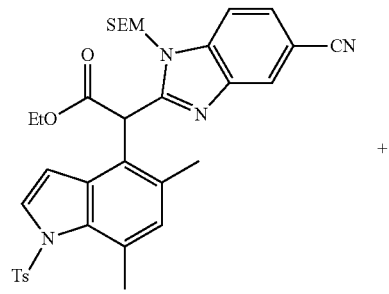

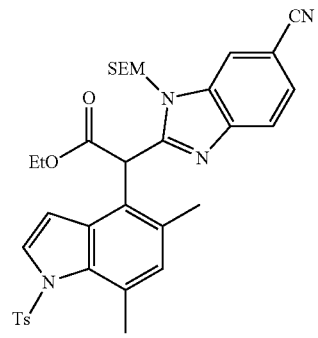

LHMDS (1.0 M in THF, 2.29 mL, 2.29 mmol) was added to a solution of a mixture of 2-((5,7-dimethyl-1-tosyl-1H-indol-4-yl)methyl)-1-((2-(trimethylsilyl)ethoxy)methyl)-1H-benzo[d]imidazole-5-carbonitrile and 2-((5,7-dimethyl-1-tosyl-1H-indol-4-yl)methyl)-1-((2-(trimethylsilyl)ethoxy)methyl)-1H-benzo[d]imidazole-6-carbonitrile (535 mg, 0.915 mmol) and ethyl chloroformate (1.76 mL, 18.3 mmol) in THF (10 mL) at 78° C. The reaction mixture was allowed to warm to room temperature over 1 h and stirred at room temperature overnight. Sat. aq. NH$_4$Cl was added to quench excess base. The layers were separated and the aqueous layer was extracted with EtOAc. The combined organics were washed with brine, dried (Na$_2$SO$_4$) and concentrated to give title compounds as a mixture. MS (ESI+) m/z 657.3 (M+H).

Example 108-C (±)-Ethyl 2-(5-cyano-1H-benzo[d]imidazol-2-yl)-2-(5,7-dimethyl-1-tosyl-1H-indol-4-yl)acetate

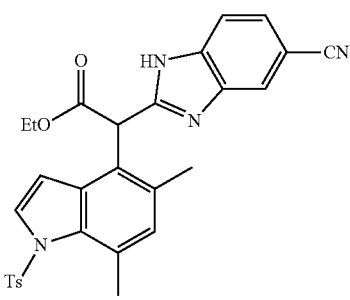 [SMILES: CCOC(=O)C(c1nc2cc(C#N)ccc2[nH]1)c1c(C)cc(C)c2c1ccn2S(=O)(=O)c1ccc(C)cc1]

HCl in dioxane (4 M, 2.28 mL, 9.13 mmol) was added to a solution of a mixture of (±)-ethyl 2-(5-cyano-1-((2-(trimethylsilyl)ethoxy)methyl)-1H-benzo[d]imidazol-2-yl)-2-(5,7-dimethyl-1-tosyl-1H-indol-4-yl)acetate and (±)-ethyl 2-(6-cyano-1-((2-(trimethylsilyl)ethoxy)methyl)-1H-benzo[d]imidazol-2-yl)-2-(5,7-dimethyl-1-tosyl-1H-indol-4-yl)acetate (600 mg, 0.913 mmol) in EtOH (12 mL) at room temperature. The resulting mixture was stirred at 60° C. overnight then partitioned between EtOAc and sat. aq. NaHCO$_3$. The aqueous layer was extracted with EtOAc. The combined organics were washed with brine, dried, and concentrated to give the title compound. The residue was taken onto the next step without further purification. MS (ESI+) m/z 527.3 (M+H).

Example 108-D (±)-2-(1-(5,7-Dimethyl-1-tosyl-1H-indol-4-yl)-2-hydroxyethyl)-1H-benzo[d]imidazole-5-carbonitrile

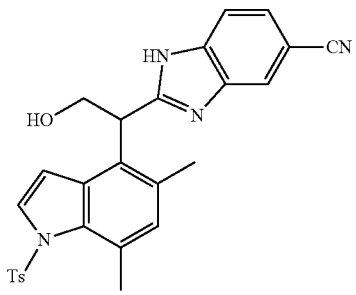 [SMILES: Cc1ccc(S(=O)(=O)n2ccc3c(C(CO)c4nc5cc(C#N)ccc5[nH]4)c(C)cc(C)c32)cc1]

NaBH$_4$ (518 mg, 13.7 mmol) was added to a solution of (±)-ethyl 2-(5-cyano-1H-benzo[d]imidazol-2-yl)-2-(5,7-dimethyl-1-tosyl-1H-indol-4-yl)acetate (481 mg, 0.913 mmol) in MeOH (10 mL) at 23° C. The mixture was stirred at room temperature for 2 h. An additional aliquot of NaBH$_4$ (1.03 g, 27.4 mmol) was added to the mixture. After 1 hr, sat. aq. NH$_4$Cl was added and the resulting mixture was separated. The aqueous layer was extracted with EtOAc. The combined organic layers were dried (Na$_2$SO$_4$) and concentrated. The residue was purified by silica gel chromatography (0-100% EtOAc in heptane) to provide the title compound. MS (ESI+) m/z 485.2 (M+H).

Example 108-E (±)-2-(1-(5,7-Dimethyl-1H-indol-4-yl)-2-hydroxyethyl)-1H-benzo[d]imidazole-5-carbonitrile

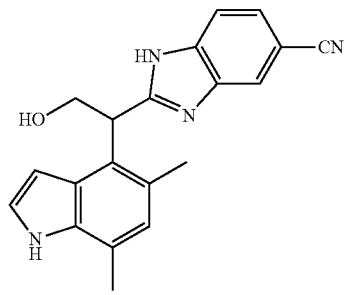 [SMILES: Cc1cc(C)c2[nH]ccc2c1C(CO)c1nc2cc(C#N)ccc2[nH]1]

A mixture of (±)-2-(1-(5,7-dimethyl-1-tosyl-1H-indol-4-yl)-2-hydroxyethyl)-1H-benzo[d]imidazole-5-carbonitrile, isoamylamine (103 mg, 1.18 mmol) and KOH (66.0 mg, 1.18 mmol) in EtOH (2 mL) was stirred at 100° C. for 30 min under microwave irradiation. The reaction mixture was concentrated and the residue was partitioned between EtOAc and sat. aq. NH$_4$Cl. The aqueous layer was extracted with EtOAc. The combined organics were washed with brine, dried over sodium sulfate and concentrated. The residue was purified with reverse phase HPLC (HC-B) to provide the title compound. $^1$H NMR (400 MHz, ACETONITRILE-d$_3$) 9.18 (br. s., 1H) 7.87 (br. s., 1H) 7.47 (d, J=7.07 Hz, 2H) 7.01 (t, J=2.84 Hz, 1H) 6.85 (s, 1H) 5.79-5.86 (m, 1H) 4.92 (dd, J=8.91, 5.49 Hz, 1H) 4.59 (dd, J=10.99, 9.09 Hz, 1H) 3.92 (dd, J=11.05, 5.49 Hz, 1H) 2.42 (s, 6H). MS (ESI+) m/z 331.3 (M+H).

Example 109

Example 109-A (±)-Ethyl 2-(1-(5-cyano-1-((2-(trimethylsilyl)ethoxy)methyl)-1H-benzo[d]imidazol-2-yl)-1-(5-ethyl-7-methyl-1-tosyl-1H-indol-4-yl)-2,2,2-trifluoroethoxy)acetate and (±)-ethyl 2-(1-(6-cyano-1-((2-(trimethylsilyl)ethoxy)methyl)-1H-benzo[d]imidazol-2-yl)-1-(5-ethyl-7-methyl-1-tosyl-1H-indol-4-yl)-2,2,2-trifluoroethoxy)acetate

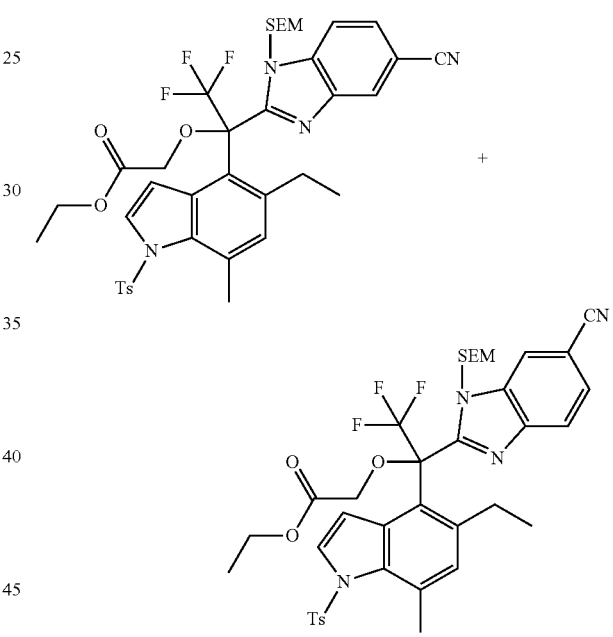

To a solution of a mixture of (±)-2-(1-(5-ethyl-7-methyl-1-tosyl-1H-indol-4-yl)-2,2,2-trifluoro-1-hydroxyethyl)-1-((2-(trimethylsilyl)ethoxy)methyl)-1H-benzo[d]imidazole-5-carbonitrile and (±)-2-(1-(5-ethyl-7-methyl-1-tosyl-1H-indol-4-yl)-2,2,2-trifluoro-1-hydroxyethyl)-1-((2-(trimethylsilyl)ethoxy)methyl)-1H-benzo[d]imidazole-6-carbonitrile (Example 80-A) (150 mg, 0.220 mmol) in THF (2.2 mL), NaH (60%, 26.4 mg, 0.659 mmol) was added at 0° C. After stirring for 30 min., ethyl 2-bromoacetate (0.122 mL, 1.098 mmol) was added at the same temperature. After stirring for 17 h, the reaction mixture was diluted with aq. NH$_4$Cl and brine. The layers were separated and the aqueous layer extracted with EtOAc. The organic layer was washed with brine, dried over Na$_2$SO$_4$, filtered, and concentrated. The residue was purified by flash column chromatography on silica gel (heptane/EtOAc=100:0 to 65:35) to give the mixture of title compounds. MS (ESI+) m/z 769.6 (M+H).

Example 109-B (±)-2-(1-(5-cyano-1H-benzo[d]imidazol-2-yl)-1-(5-ethyl-7-methyl-1H-indol-4-yl)-2,2,2-trifluoroethoxy)acetic acid

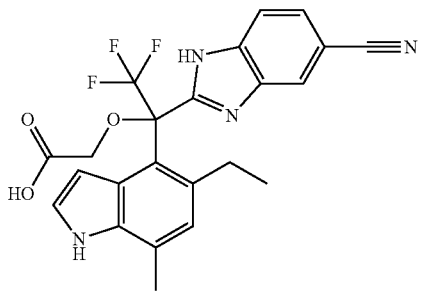 [SMILES: CCc1cc(C)c2[nH]ccc2c1C(OCC(=O)O)(c1nc2cc(C#N)ccc2[nH]1)C(F)(F)F]

A solution of a mixture of (±)-ethyl 2-(1-(5-cyano-1-((2-(trimethylsilyl)ethoxy)methyl)-1H-benzo[d]imidazol-2-yl)-1-(5-ethyl-7-methyl-1-tosyl-1H-indol-4-yl)-2,2,2-trifluoroethoxy)acetate and (±)-ethyl 2-(1-(6-cyano-1-((2-(trimethylsilyl)ethoxy)methyl)-1H-benzo[d]imidazol-2-yl)-1-(5-ethyl-7-methyl-1-tosyl-1H-indol-4-yl)-2,2,2-trifluoroethoxy)acetate (153 mg, 0.199 mmol) and HCl (1.25 M in MeOH) (1592 μL, 1.990 mmol) was allowed to stir at 60° C. for 0.5 h. The reaction was cooled to rt and concentrated. A suspension of the residue and KOH (112 mg, 1.99 mmol) in EtOH (2 mL) was allowed to stir at 100° C. for 1 h under microwave irradiation. The reaction mixture was concentrated. The crude was purified by HPLC (HC-A) to give the title compound. $^1$H NMR (TFA salt, 400 MHz, CD$_3$OD) δ 8.05 (s, 1H), 7.71 (br. d, J=8.34 Hz, 1H), 7.61 (dd, J=1.51, 8.59 Hz, 1H), 7.06 (br. s, 1H), 6.92 (s, 1H), 6.11 (br. s, 1H), 4.17 (d, J=16.17 Hz, 1H), 3.95 (d, J=16.17 Hz, 1H), 2.70-2.85 (br. m, 1H), 2.49 (s, 3H), 2.33-2.44 (br. m, 1H) 1.06 (br. t, 3H). HRMS calcd. for C$_{23}$H$_{19}$F$_3$N$_4$O$_3$ (M+H)$^+$ 457.1488. found 457.1474.

Example 109-C (±)-2-(1-(5-Cyano-1H-benzo[d]imidazol-2-yl)-1-(5-cyclopropyl-7-methyl-1H-indol-4-yl)-2,2,2-trifluoroethoxy)acetic acid

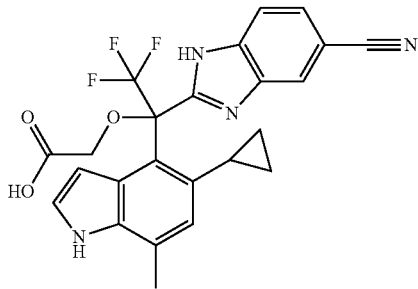 [SMILES: Cc1cc(C2CC2)c(C(OCC(=O)O)(c2nc3cc(C#N)ccc3[nH]2)C(F)(F)F)c2cc[nH]c12]

The title compound was synthesized using similar procedures as shown in Example 109-A and B using 5-cyclopropyl-7-methyl-1-tosyl-1H-indole-4-carbaldehyde (Example 48-D) in Example 70-A. $^1$H NMR (400 MHz, ACETONITRILE-d$_3$) δ 9.28 (br. s., 1H) 8.07 (br. s., 1H) 7.68 (br. s., 1H) 7.55-7.62 (m, 1H) 7.19 (s, 1H) 6.62 (br. s., 1H) 6.45 (s, 1H) 4.10-4.21 (m, 1H) 3.94-4.04 (m, 1H) 2.46 (s, 3H) 1.62 (br. s., 1H) 0.65-0.77 (m, 1H) 0.52-0.64 (m, 1H) 0.27-0.41 (m, 1H) ppm −0.09-0.07 (m, 1H). MS (ESI+) m/z 469.3 (M+H).

Example 110

Example 110-A

4-Nitro-1-tosyl-1H-indole

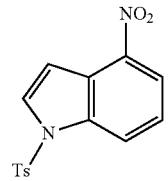

To a suspension of 4-nitro-1H-indole (CAS #: 4769-97-5) (10.4 g, 64.1 mmol) in DMF (401 mL) at 0° C. was added NaH (60% in mineral oil, 3.85 g, 96 mmol), and the mixture was stirred at 0° C. After 15 minutes, to the red suspension was added TsCl (14.67 g, 77 mmol). The reaction turned yellow and was warmed to room temperature. After 15 minutes the reaction was quenched by ice/H$_2$O, and the mixture was stirred for 30 minutes at room temperature. The precipitate was collected by filtration to provide the title compound, which was used in the next reaction without any further purification. $^1$H NMR (400 MHz, DMSO-d$_6$) δ ppm 8.43 (d, J=8.34 Hz, 1H) 8.15-8.29 (m, 2H) 7.96 (m, 2H) 7.60 (t, J=8.21 Hz, 1H) 7.42 (m, J=7.83 Hz, 2H) 7.26-7.38 (m, 1H) 2.33 (s, 3H)

Example 110-B

1-Tosyl-1H-indol-4-amine

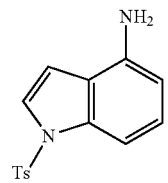 [SMILES: Cc1ccc(S(=O)(=O)n2ccc3c([N+](=O)[O-])cccc32)cc1]

To 4-nitro-1-tosyl-1H-indole (20.2 g, 63.9 mmol) in EtOAc (639 mL) was added 10% Pd/C (6.80 g, 6.39 mmol) and the mixture was stirred under hydrogen. After 4 hours the reaction was filtered through Celite®, rinsing with EtOAc. The filtrate was concentrated and purified by flash chromatography (0-70% EtOAc in heptanes) to provide the title compound. MS (ESI+) m/z 287.1 (M+H).

Example 110-C

5-Bromo-1-tosyl-1H-indol-4-amine

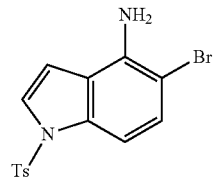 [SMILES: Cc1ccc(S(=O)(=O)n2ccc3c(N)c(Br)ccc32)cc1]

To 1-tosyl-1H-indol-4-amine (9.1 g, 31.8 mmol) in DMF (300 mL) at −20° C. was added NBS (5.60 g, 31.5 mmol) and the mixture was stirred at −20° C. After 5 minutes the reaction was quenched with sat. aq. NaHCO3, then with sat. sodium thiosulfate, extracted with EtOAc (three times), dried over MgSO$_4$, filtered and concentrated. The product was purified by flash chromatography (0-100% EtOAc in heptanes) to provide the title compound. MS (ESI+) m/z 364.9, 366.9 (M+H).

Example 110-D tert-Butyl (5-bromo-1-tosyl-1H-indol-4-yl)carbamate

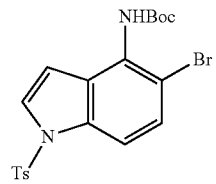 [SMILES: Cc1ccc(S(=O)(=O)n2ccc3c(NC(=O)OC(C)(C)C)c(Br)ccc32)cc1]

To a solution of 5-bromo-1-tosyl-1H-indol-4-amine (12.2 g, 33.4 mmol) in THF (167 mL) was added Boc$_2$O (21.8 g, 100 mmol) and then DMAP (0.61 g, 5.01 mmol), and the mixture was stirred at 60° C. After 2 hours the reaction was cooled to room temperature, diluted with water, extracted with EtOAc, washed with brine, dried over MgSO$_4$, filtered and concentrated to provide 24.9 g of a brown oil. The mixture was dissolved in DCM (300 mL) and TFA (6.78 mL, 88 mmol) was added and the mixture was stirred at room temperature. After 40 minutes additional TFA (3.4 mL, 44 mmol) was added. After 1 hour total the reaction was basified with sat. aq. NaHCO$_3$, extracted with DCM, dried over MgSO$_4$, filtered and concentrated. The product was purified by flash chromatography (0-100% EtOAc in heptanes) to provide the title compound. $^1$H NMR (400 MHz, DMSO-d$_6$) δ ppm 8.99 (br. s., 1H) 7.87 (d, J=8.34 Hz, 2H) 7.80 (d, J=3.79 Hz, 1H) 7.75 (d, J=8.84 Hz, 1H) 7.55 (d, J=8.84 Hz, 1H) 7.39 (d, J=8.08 Hz, 2H) 6.61 (d, J=3.79 Hz, 1H) 2.32 (s, 3H) 1.41 (s, 9H).

Example 110-E tert-Butyl (5-methyl-1-tosyl-1H-indol-4-yl)carbamate

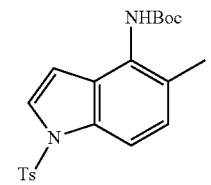 [SMILES: Cc1ccc(S(=O)(=O)n2ccc3c(NC(=O)OC(C)(C)C)c(C)ccc32)cc1]

To a solution of tert-butyl (5-bromo-1-tosyl-1H-indol-4-yl)carbamate (9.95 g, 21.38 mmol) in toluene (194 mL) was added potassium methyltrifluoroborate (13 g, 107 mmol) and PdCl$_2$(dppf).CH$_2$Cl$_2$ adduct (1.75 g, 2.138 mmol) and Cs$_2$CO$_3$ (20.90 g, 64.1 mmol) and finally water (19.44 mL), and the mixture was stirred at 100° C. After stirring overnight the reaction was cooled to room temperature and 1N HCl (100 mL) was added. The layers were separated and the aqueous layer was extracted with EtOAc, washed with 1N HCl, dried over MgSO$_4$, filtered and concentrated to provide the title compound, which was used in the next reaction without any further purification. MS (ESI−) m/z 399.2 (M−H).

Example 110-F

5-Methyl-1-tosyl-1H-indol-4-amine

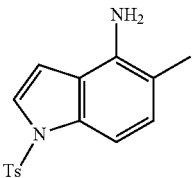 [SMILES: Cc1ccc(S(=O)(=O)n2ccc3c(N)c(C)ccc32)cc1]

To a solution of tert-butyl (5-methyl-1-tosyl-1H-indol-4-yl)carbamate (10.5 g, 26.2 mmol) in DCM (197 mL) was added TFA (65.5 mL), and the mixture was stirred at room temperature. After 20 minutes the reaction was concentrated, dissolved in EtOAc, washed with sat. aq. NaHCO$_3$, dried over MgSO$_4$, filtered and concentrated. The resulting residue was purified by flash chromatography (0-70% EtOAc in heptanes) to provide the title compound. MS (ESI+) m/z 301.1 (M+H).

Example 110-G

7-Chloro-5-methyl-1-tosyl-1H-indol-4-amine

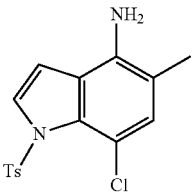

To a solution of 5-methyl-1-tosyl-1H-indol-4-amine (0.52 g, 1.731 mmol) in acetonitrile (17.31 mL) was added NCS (0.231 g, 1.731 mmol), and the mixture was stirred at 50° C. After 2 hours the reaction was cooled to room temperature, quenched with sat. aq. NaHCO$_3$, and with sat. sodium thiosulfate. The layers were separated and the aqueous layer extracted with EtOAc (twice), dried over MgSO$_4$, filtered and concentrated. The resulting residue was purified by flash chromatography (0-80% EtOAc in heptanes) to provide the title compound. MS (ESI+) m/z 335.0 (M+H).

Example 110-H

7-Chloro-4-iodo-5-methyl-1-tosyl-1H-indole

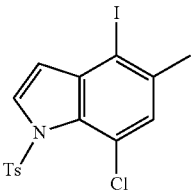

To a suspension of 7-chloro-5-methyl-1-tosyl-1H-indol-4-amine (0.35 g, 1.04 mmol) in EtOAc (6.18 mL) and water (4.12 mL) at 0° C. was added conc. HCl (0.181 mL, 2.091 mmol) and then dropwise a solution of sodium nitrite (0.087 g, 1.254 mmol) in water (0.4 mL). After 25 minutes a solution of KI (0.521 g, 3.14 mmol) in water (1 mL) was added and the reaction was warmed to room temperature. After stirring overnight, the reaction was quenched with sat. aq. sodium thiosulfate. The layers were separated and the aqueous layer was extracted three times with EtOAc, and the organic extract was dried over MgSO$_4$, filtered and concentrated. The resulting residue was purified by flash chromatography (0-100% EtOAc in heptanes) to provide the title compound. $^1$H NMR (400 MHz, DMSO-d$_6$) δ ppm 8.07 (d, J=3.79 Hz, 1H) 7.73 (d, J=8.34 Hz, 2H) 7.43 (d, J=8.08 Hz, 2H) 7.30 (s, 1H) 6.79 (d, J=4.04 Hz, 1H) 2.41 (s, 3H) 2.37 (s, 3H).

Example 110-I

7-Chloro-5-methyl-1-tosyl-1H-indole-4-carbaldehyde

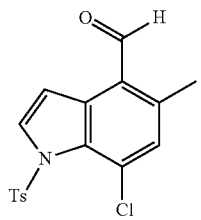 [SMILES: Cc1ccc(S(=O)(=O)n2ccc3c(C=O)c(C)cc(Cl)c32)cc1]

To a solution of 7-chloro-4-iodo-5-methyl-1-tosyl-1H-indole (98 mg, 0.220 mmol) and DMF (34 μL, 0.440 mmol) in cyclopentyl methyl ether (2 mL) at −78° C., was added n-butyllithium (2.5 M in hexanes, 114 μL, 0.286 mmol). After 80 minutes additional n-butyllithium (2.5 M in hexanes, 0.11 mL, 0.286 mmol) was added. After 15 more minutes the reaction was quenched with MeOH (0.5 mL) and sat. aq. NH$_4$Cl. The layers were separated and the aqueous layer was extracted with EtOAc, washed with brine, dried over MgSO$_4$, filtered and concentrated. The resulting residue was purified by flash chromatography (0-50% EtOAc in heptanes) to provide the title compound. MS (ESI+) m/z 347.9 (M+H).

Example 110-J

7-Chloro-4-(2,2-dibromovinyl)-5-methyl-1-tosyl-1H-indole

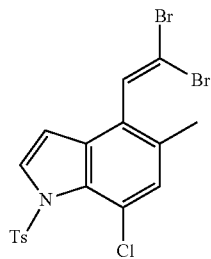 [SMILES: Cc1ccc(S(=O)(=O)n2ccc3c(C=C(Br)Br)c(C)cc(Cl)c32)cc1]

To a solution of 7-chloro-5-methyl-1-tosyl-1H-indole-4-carbaldehyde (48 mg, 0.138 mmol) and PPh$_3$ (109 mg, 0.414 mmol) in DCM (1.4 mL) at 0° C., was added CBr$_4$ (68.6 mg, 0.207 mmol) and the reaction was warmed to room temperature. After 10 minutes the reaction mixture was loaded onto silica gel and was purified by flash chromatography (0-50% EtOAc in heptanes) to provide the title compound. $^1$H NMR (400 MHz, DMSO-d$_6$) δ ppm 8.00 (d, J=3.79 Hz, 1H) 7.88 (s, 1H) 7.73 (m, J=8.59 Hz, 2H) 7.42 (m, J=7.83 Hz, 2H) 7.23 (s, 1H) 6.71 (d, J=3.79 Hz, 1H) 2.37 (s, 3H) 2.23 (s, 3H).

Example 110-K 2-((7-Chloro-5-methyl-1H-indol-4-yl)methyl)-1H-benzo[d]imidazole-5-carbonitrile

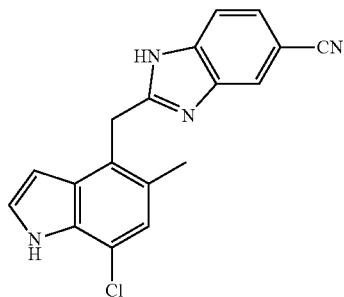 [SMILES: Cc1cc(Cl)c2[nH]ccc2c1Cc1nc2cc(C#N)ccc2[nH]1]

A solution of 7-chloro-4-(2,2-dibromovinyl)-5-methyl-1-tosyl-1H-indole (67 mg, 0.133 mmol), 3,4-diaminobenzonitrile (26.6 mg, 0.200 mmol) and DABCO (44.8 mg, 0.399 mmol) in NMP (0.5 mL) was stirred at 110° C. After stirring overnight, the reaction mixture was loaded onto silica gel and was purified by flash chromatography (0-100% EtOAc in heptanes) to provide 2-((7-chloro-5-methyl-1-tosyl-1H-indol-4-yl)methyl)-1H-benzo[d]imidazole-5-carbonitrile. The obtained compound was dissolved in EtOH (5.0 mL), and KOH (0.118 g, 2.105 mmol) and isoamylamine (0.489 mL, 4.21 mmol) were added, and the mixture was stirred at 100° C. in the microwave for 30 minutes. The reaction mixture was loaded onto silica gel and was purified by flash chromatography (0-100% EtOAc in heptanes) to provide the title compound. $^1$H NMR (400 MHz, DMSO-d$_6$) δ ppm 12.50 (s, 1H) 11.33 (br. s., 1H) 7.93 (s, 1H) 7.57 (d, J=8.84 Hz, 1H) 7.47 (dd, J=8.34, 1.52 Hz, 1H) 7.33 (t, J=2.78 Hz, 1H) 7.06 (s, 1H) 6.52-6.63 (m, 1H) 4.45 (s, 2H) 2.39 (s, 3H). HRMS calcd. for C$_{18}$H$_{13}$ClN$_4$ (M+H)$^+$ 321.0902. found 321.0906.

Example 111

Example 111-A

5-Methyl-1-tosyl-7-vinyl-1H-indole-4-carbaldehyde

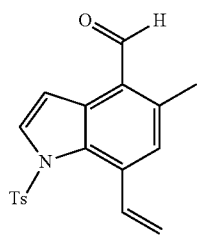 [SMILES: C=Cc1cc(C)c(C=O)c2ccn(S(=O)(=O)c3ccc(C)cc3)c12]

To a suspension of 7-chloro-5-methyl-1-tosyl-1H-indole-4-carbaldehyde (Example 110-E) (73 mg, 0.210 mmol) and vinylboronic anhydride pyridine complex (152 mg, 0.630 mmol) and $K_2CO_3$ (290 mg, 2.09 mmol) in toluene (1.7 mL) water (0.7 mL) $Pd(OAc)_2$ (4.71 mg, 0.021 mmol) and S-Phos (CAS#657408-07-6) (17.2 mg, 0.042 mmol) were added, and the reaction was stirred at 80° C. After 1 hour the reaction was diluted with EtOAc. The organics were washed with water, dried over $MgSO_4$, filtered and concentrated. The mixture was loaded onto silica gel and purified by flash chromatography (0-40% EtOAc in heptanes) to the title compound. MS (ESI+) m/z 340.1 (M+H).

Example 111-B 4-(2,2-Dibromovinyl)-5-methyl-1-tosyl-7-vinyl-1H-indole

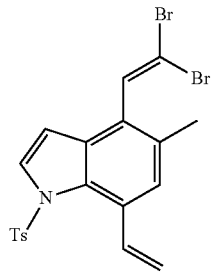 [SMILES: C=Cc1cc(C)c(C=C(Br)Br)c2ccn(S(=O)(=O)c3ccc(C)cc3)c12]

To a solution of 5-methyl-1-tosyl-7-vinyl-1H-indole-4-carbaldehyde (50 mg, 0.147 mmol) and $PPh_3$ (116 mg, 0.442 mmol) in DCM (1.5 mL) at 0° C., was added $CBr_4$ (73.3 mg, 0.221 mmol) and the reaction was warmed to room temperature. After 10 minutes the reaction mixture was loaded onto silica gel and was purified by flash chromatography (0-50% EtOAc in heptanes) to provide the title compound. $^1$H NMR (400 MHz, DMSO-$d_6$) d ppm 7.76-7.91 (m, 2H) 7.43-7.61 (m, 3H) 7.17-7.43 (m, 3H) 6.63-6.70 (m, 1H) 5.59 (dd, J=17.18, 1.26 Hz, 1H) 5.27 (dd, J=10.99, 1.14 Hz, 1H) 2.28-2.35 (m, 3H) 2.18-2.28 (m, 3H).

Example 111-C.

2-((5-Methyl-1-tosyl-7-vinyl-1H-indol-4-yl)methyl)-1H-benzo[d]imidazole-5-carbonitrile

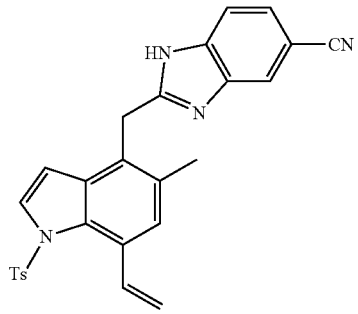 [SMILES: C=Cc1cc(C)c(Cc2nc3cc(C#N)ccc3[nH]2)c2ccn(S(=O)(=O)c3ccc(C)cc3)c12]

A solution of 4-(2,2-dibromovinyl)-5-methyl-1-tosyl-7-vinyl-1H-indole (57 mg, 0.115 mmol) and 3,4-diaminobenzonitrile (23 mg, 0.173 mmol) and DABCO (38.7 mg, 0.345 mmol) in NMP (0.5 mL) was stirred at 110° C. After 80 minutes the mixture was slowly cooled to room temperature overnight, and then heated again at 110° C. for 4 hours. The reaction was cooled to room temperature and loaded onto silica gel and purified by flash chromatography (0-100% EtOAc in heptanes) to provide the title compound. MS (ESI+) m/z 467.2 (M+H).

Example 111-D 2-((5-Methyl-7-vinyl-1H-indol-4-yl)methyl)-1H-benzo[d]imidazole-5-carbonitrile

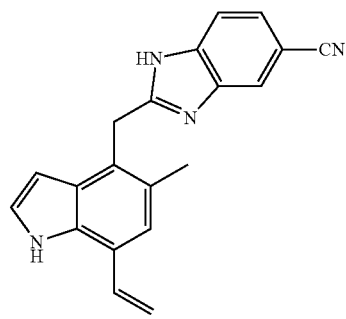 [SMILES: C=Cc1cc(C)c(Cc2nc3cc(C#N)ccc3[nH]2)c2cc[nH]c12]

2-((5-Methyl-1-tosyl-7-vinyl-1H-indol-4-yl)methyl)-1H-benzo[d]imidazole-5-carbonitrile (23 mg, 0.049 mmol) was dissolved in EtOH (1 mL) and KOH (27.7 mg, 0.493 mmol) and isoamylamine (0.11 mL, 0.986 mmol) were added and the mixture was stirred at 100° C. in the microwave for 30 minutes. The mixture was then stirred at 100° C. in the microwave for another 15 minutes. The reaction was purified directly by flash chromatography (0-100% EtOAc in heptanes) to provide the title compound. MS (ESI+) m/z 313.1 (M+H).

Example 111-E 2-((7-Ethyl-5-methyl-1H-indol-4-yl)methyl)-1H-benzo[d]imidazole-5-carbonitrile

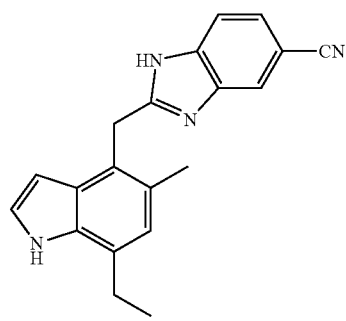 [SMILES: CCc1cc(C)c(Cc2nc3cc(C#N)ccc3[nH]2)c2cc[nH]c12]

To a solution of 2-((5-methyl-7-vinyl-1H-indol-4-yl)methyl)-1H-benzo[d]imidazole-5-carbonitrile (11 mg, 0.035 mmol) in EtOAc (0.7 mL) was added Pd/C (5%, 3.75 mg) and the reaction was stirred at room temperature under hydrogen. After 10 minutes the reaction was filtered through Celite®, rinsing with EtOAc, and concentrated. The resulting residue was purified directly by RP-HPLC (HC-A) to provide the title compound. $^1$H NMR (TFA salt, 400 MHz, DMSO-$d_6$) δ ppm 10.97 (br. s., 1H) 7.98 (s, 1H) 7.61 (d, J=8.34 Hz, 1H) 7.53 (d, J=8.34 Hz, 1H) 7.23 (t, J=2.78 Hz, 1H) 6.79 (s, 1H) 6.45 (dd, J=3.16, 1.89 Hz, 1H) 4.46 (s, 2H) 2.81 (q, J=7.58 Hz, 2H) 2.37 (s, 3H) 1.25 (t, J=7.45 Hz, 3H). HRMS calcd. for $C_{20}H_{18}N_4$ (M+H)$^+$ 315.1604. found 315.1609.

Example 112

Example 112-A

7-Bromo-5-methyl-1-tosyl-1H-indol-4-amine

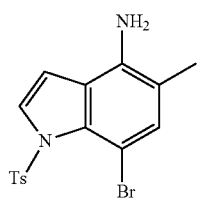 [SMILES: Cc1ccc(S(=O)(=O)n2ccc3c(N)c(C)cc(Br)c32)cc1]

To a solution of 5-methyl-1-tosyl-1H-indol-4-amine (Example 110-F) (1.06 g, 3.53 mmol) in DMF (35.3 mL) at 0° C. was added NBS (0.628 g, 3.53 mmol), and the mixture was stirred at 0° C. After 5 minutes the reaction was quenched with sat. aq. NaHCO$_3$, then with sat. aq. sodium thiosulfate, extracted with EtOAc (2×), dried over MgSO$_4$, filtered and concentrated. The resulting residue was purified by flash chromatography (0-80% EtOAc in heptanes) to provide the title compound, which was used in the next reaction without any further purification. MS (ESI+) m/z 379.0, 380.9 (M+H).

Example 112-B

7-Bromo-4-iodo-5-methyl-1-tosyl-1H-indole

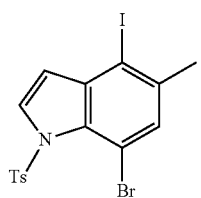 [SMILES: Cc1ccc(S(=O)(=O)n2ccc3c(I)c(C)cc(Br)c32)cc1]

To a suspension of 7-bromo-5-methyl-1-tosyl-1H-indol-4-amine (0.83 g, 2.19 mmol) in EtOAc (12.16 mL) and water (8.11 mL) at 0° C. was added conc. HCl (0.380 mL, 4.38 mmol) and then dropwise a solution of sodium nitrite (0.181 g, 2.63 mmol) in water (1.0 mL). After 10 minutes a solution of KI (1.09 g, 6.57 mmol) in water (2 mL) was added and the reaction was warmed to room temperature. After 2 hours the reaction was quenched with sat. aq. sodium thiosulfate; the layers were separated and the aqueous layer was extracted with EtOAc. The organic extract was dried over MgSO$_4$, filtered and concentrated. The resulting residues was purified by flash chromatography (0-40% EtOAc in heptanes) to provide the title compound. $^1$H NMR (400 MHz, DMSO-d$_6$) δ ppm 8.06 (d, J=3.79 Hz, 1H) 7.73 (m, J=8.34 Hz, 2H) 7.49 (s, 1H) 7.42 (m, J=8.08 Hz, 2H) 6.80 (d, J=3.79 Hz, 1H) 2.41 (s, 3H) 2.38 (s, 3H).

Example 112-C

7-Bromo-5-methyl-1-tosyl-4-((trimethylsilyl)ethynyl)-1H-indole

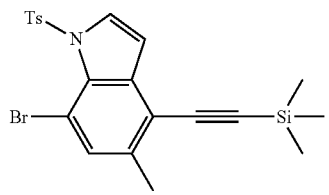 [SMILES: Cc1ccc(S(=O)(=O)n2ccc3c(C#C[Si](C)(C)C)c(C)cc(Br)c32)cc1]

To a suspension of 7-bromo-4-iodo-5-methyl-1-tosyl-1H-indole (90 mg, 0.184 mmol), CuI (5.60 mg, 0.029 mmol) and Pd(PPh$_3$)$_4$ (16.9 mg, 0.015 mmol) in triethylamine (3 mL) was added trimethylsilylacetylene (0.036 mL, 0.257 mmol) and the mixture was stirred at room temperature. After 3 hours the reaction was purified directly by flash chromatography (0-40% EtOAc in heptanes) to provide the title compound. $^1$H NMR (400 MHz, DMSO-d$_6$) δ ppm 8.03 (d, J=3.79 Hz, 1H) 7.70 (d, J=8.34 Hz, 2H) 7.34-7.48 (m, 3H) 6.85 (d, J=3.79 Hz, 1H) 2.38 (s, 3H) 2.37 (s, 3H) 0.27-0.31 (m, 9H).

Example 112-D

7-Bromo-4-(bromoethynyl)-5-methyl-1-tosyl-1H-indole

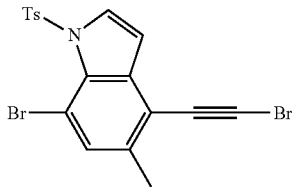 [SMILES: Cc1ccc(S(=O)(=O)n2ccc3c(C#CBr)c(C)cc(Br)c32)cc1]

To a suspension of 7-bromo-5-methyl-1-tosyl-4-((trimethylsilyl)ethynyl)-1H-indole (70 mg, 0.152 mmol) and AgNO$_3$ (7.75 mg, 0.046 mmol) in acetone (0.8 mL) at 0° C. was added a solution of NBS (38 mg, 0.213 mmol) in acetone (0.8 mL) and the mixture was warmed to room temperature. After stirring overnight the reaction was purified directly by flash chromatography (0-40% EtOAc in heptanes) to provide the title compound. $^1$H NMR (400 MHz, DMSO-d$_6$) δ ppm 8.03 (d, J=3.79 Hz, 1H) 7.72 (d, J=8.59 Hz, 2H) 7.37-7.48 (m, 3H) 6.91 (d, J=3.79 Hz, 1H) 2.38 (s, 3H) 2.37 (s, 3H).

Example 112-E 2-((7-Bromo-5-methyl-1H-indol-4-yl)methyl)-1H-benzo[d]imidazole-5-carbonitrile

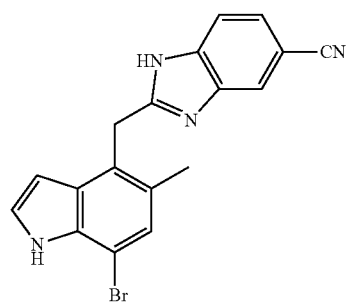 [SMILES: Cc1cc(Br)c2[nH]ccc2c1Cc1nc2cc(C#N)ccc2[nH]1]

A solution of 7-bromo-4-(bromoethynyl)-5-methyl-1-tosyl-1H-indole (35 mg, 0.075 mmol) and 3,4-diaminobenzonitrile (14.96 mg, 0.112 mmol) and DABCO (10.08 mg, 0.090 mmol) in NMP (0.3 mL) was stirred at 100° C. After stirring overnight the reaction mixture was loaded onto silica gel and was purified by flash chromatography (0-100% EtOAc in heptanes). The resulting residue was dissolved in EtOH (1.1 mL), KOH (51.8 mg, 0.924 mmol) and isoamylamine (0.21 mL, 1.85 mmol) were added, and the mixture was heated at 100° C. using microwave irradiation for 40 minutes. The resulting residue was purified directly by RP-HPLC (HC-A) to provide the title compound. $^1$H NMR (TFA salt, 400 MHz, DMSO-d$_6$) δ ppm 11.22 (br. s., 1H) 7.97 (s, 1H) 7.59 (d, J=7.83 Hz, 1H) 7.51 (dd, J=8.21, 1.39 Hz, 1H) 7.33 (t, J=2.91 Hz, 1H) 7.21 (s, 1H) 6.55-6.66 (m, 1H) 4.47 (s, 2H) 2.38 (s, 3H). HRMS calcd. for $C_{18}H_{13}BrN_4$ (M+H)$^+$ 365.0396. found 365.0408.

Example 113

Example 113-A 2-((7-Bromo-5-methyl-1-tosyl-1H-indol-4-yl)methyl)-1-((2-(trimethylsilyl)ethoxy)methyl)-1H-benzo[d]imidazole-5-carbonitrile and 2-((7-bromo-5-methyl-1-tosyl-1H-indol-4-yl)methyl)-1-((2-(trimethylsilyl)ethoxy)methyl)-1H-benzo[d]imidazole-6-carbonitrile

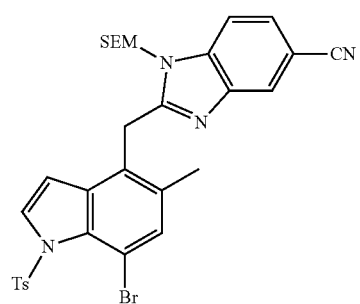

+

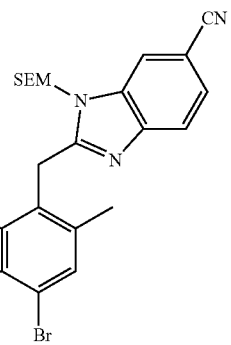

A solution of 7-bromo-4-(bromoethynyl)-5-methyl-1-tosyl-1H-indole (85 mg, 0.182 mmol) and 3,4-diaminobenzonitrile (36.3 mg, 0.273 mmol) and DABCO (24.5 mg, 0.218 mmol) in NMP (0.7 mL) was stirred at 110° C. After 3 hours the reaction mixture was loaded onto silica gel and was purified by flash chromatography (0-100% EtOAc in heptanes). The resulting residue was dissolved in THF (1.7 mL), cooled to 0° C., NaH (60% in mineral oil, 9.38 mg, 0.234 mmol) was added and the mixture was stirred at room temperature for 30 minutes. The mixture was cooled again to 0° C. and SEM-Cl (0.042 mL, 0.234 mmol) was added dropwise and the reaction was warmed to room temperature. After 30 minutes the reaction was quenched with MeOH, then water was added, the reaction was extracted with EtOAc (twice), dried over MgSO$_4$, filtered and concentrated. The resulting residue was purified by flash chromatography (0-100% EtOAc in heptanes) to provide the title compounds as a mixture. MS (ESI+) m/z 649.3, 651.2 (M+H).

Example 113-B 2-((5-Methyl-1-tosyl-7-vinyl-1H-indol-4-yl)methyl)-1-((2-(trimethylsilyl)ethoxy)methyl)-1H-benzo[d]imidazole-5-carbonitrile and 2-((5-methyl-1-tosyl-7-vinyl-1H-indol-4-yl)methyl)-1-((2-(trimethylsilyl)ethoxy)methyl)-1H-benzo[d]imidazole-6-carbonitrile

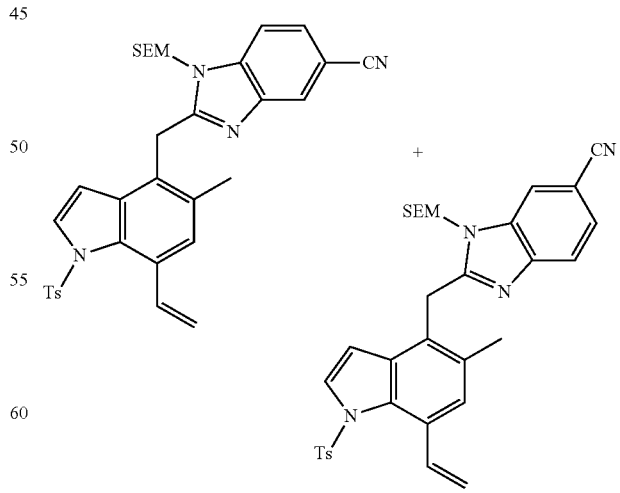

A mixture of 2-((7-bromo-5-methyl-1-tosyl-1H-indol-4-yl)methyl)-1-((2-(trimethylsilyl)ethoxy)methyl)-1H-benzo[d]imidazole-5-carbonitrile and 2-((7-bromo-5-methyl-1-tosyl-1H-indol-4-yl)methyl)-1-((2-(trimethylsilyl)ethoxy)methyl)-1H-benzo[d]imidazole-6-carbonitrile (55 mg, 0.085 mmol) was dissolved in DME (0.6 mL) and water (0.2 mL). Vinylboronic anhydride pyridine complex (26.5 mg, 0.110 mmol), Pd(PPh$_3$)$_4$ (9.8 mg, 8.5 μmol) and K$_2$CO$_3$ (11.7 mg, 0.085 mmol) were added and the reaction was heated at 100° C. using microwave irradiation for 1 hour. The reaction was diluted with water, extracted with EtOAc, and the organic extract was dried over MgSO$_4$, filtered and concentrated. The resulting residue was purified by flash chromatography (0-100% EtOAc in heptanes) to provide the title compounds as a mixture. MS (ESI+) m/z 597.5 (M+H).

Example 113-C 2-((7-Formyl-5-methyl-1-tosyl-1H-indol-4-yl)methyl)-1-((2-(trimethylsilyl)ethoxy)methyl)-1H-benzo[d]imidazole-5-carbonitrile and 2-((7-formyl-5-methyl-1-tosyl-1H-indol-4-yl)methyl)-1-((2-(trimethylsilyl)ethoxy)methyl)-1H-benzo[d]imidazole-6-carbonitrile

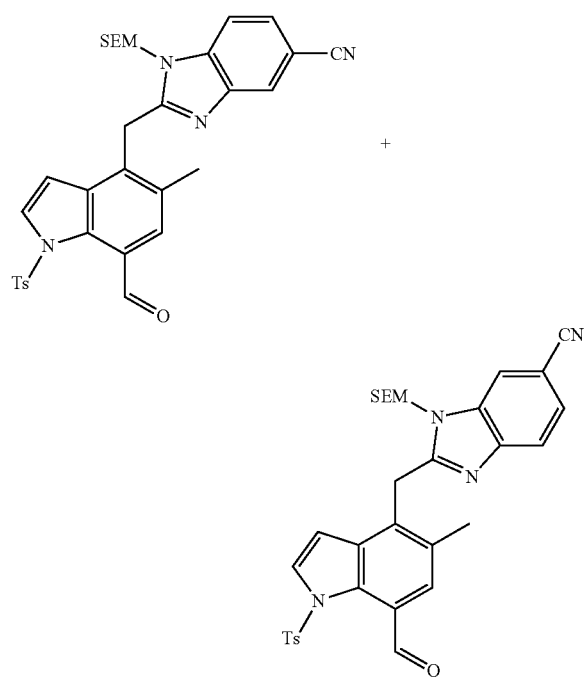

To a solution of 2-((5-methyl-1-tosyl-7-vinyl-1H-indol-4-yl)methyl)-1-((2-(trimethylsilyl)ethoxy)methyl)-1H-benzo[d]imidazole-5-carbonitrile and 2-((5-methyl-1-tosyl-7-vinyl-1H-indol-4-yl)methyl)-1-((2-(trimethylsilyl)ethoxy)methyl)-1H-benzo[d]imidazole-6-carbonitrile (43 mg, 0.072 mmol) in dioxane (0.54 mL) and water (0.18 mL) at 0° C. was added 2,6-lutidine (0.017 mL, 0.144 mmol), OsO$_4$ (2.5% in t-BuOH, 18 μL, 1.44 μmol) and NaIO$_4$ (61.6 mg, 0.288 mmol) and the reaction was stirred at room temperature. After 90 minutes the mixture was diluted with DCM and the layers separated. The organic layer was washed with sat. aq. NH$_4$Cl and water, dried over MgSO$_4$, filtered and concentrated. The resulting residue was purified by flash chromatography (0-100% EtOAc in heptanes) to provide the title compounds as a mixture. MS (ESI+) m/z 599.4 (M+H).

Example 113-D 2-((7-(Hydroxymethyl)-5-methyl-1-tosyl-1H-indol-4-yl)methyl)-1-((2-(trimethylsilyl)ethoxy)methyl)-1H-benzo[d]imidazole-5-carbonitrile and 2-((7-(hydroxymethyl)-5-methyl-1-tosyl-1H-indol-4-yl)methyl)-1-((2-(trimethylsilyl)ethoxy)methyl)-1H-benzo[d]imidazole-6-carbonitrile

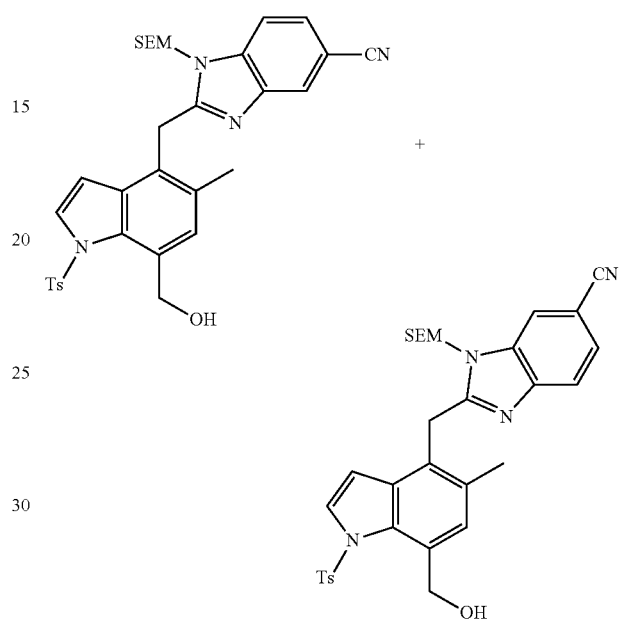

To a solution of 2-((7-formyl-5-methyl-1-tosyl-1H-indol-4-yl)methyl)-1-((2-(trimethylsilyl)ethoxy)methyl)-1H-benzo[d]imidazole-5-carbonitrile and 2-((7-formyl-5-methyl-1-tosyl-1H-indol-4-yl)methyl)-1-((2-(trimethylsilyl)ethoxy)methyl)-1H-benzo[d]imidazole-6-carbonitrile (26 mg, 0.043 mmol) in MeOH (0.9 mL) at 0° C. was added NaBH$_4$ (1.6 mg, 0.043 mmol). After 5 minutes the reaction was purified directly by flash chromatography (0-100% EtOAc in heptanes) to provide the title compounds as a mixture. MS (ESI+) m/z 601.4 (M+H).

Example 113-E 2-((7-(Hydroxymethyl)-5-methyl-1-tosyl-1H-indol-4-yl)methyl)-1H-benzo[d]imidazole-5-carbonitrile

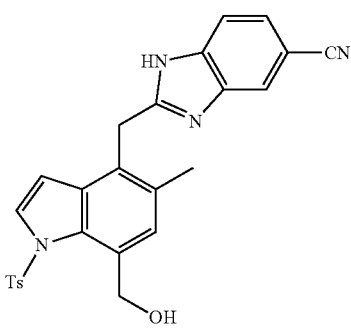 [SMILES: Cc1ccc(S(=O)(=O)n2ccc3c(Cc4nc5cc(C#N)ccc5[nH]4)c(C)cc(CO)c32)cc1]

To a solution of a mixture of 2-((7-(hydroxymethyl)-5-methyl-1-tosyl-1H-indol-4-yl)methyl)-1-((2-(trimethylsilyl)ethoxy)methyl)-1H-benzo[d]imidazole-5-carbonitrile and 2-((7-(hydroxymethyl)-5-methyl-1-tosyl-1H-indol-4-yl)methyl)-1-((2-(trimethylsilyl)ethoxy)methyl)-1H-benzo[d]imidazole-6-carbonitrile (14 mg, 0.023 mmol) in DCM (0.23 mL), BF$_3$.OEt$_2$ (15 μL, 0.117 mmol) was added at 0° C. After stirring for 5 minutes, the mixture was warmed up to room temperature. After 30 minutes the reaction mixture was diluted with sat. aq. NaHCO$_3$ and EtOAc, extracted with EtOAc, and the organic extract was dried over MgSO$_4$, filtered and concentrated to provide the title compound, which was used without further purification. MS (ESI+) m/z 471.2 (M+H).

Example 113-F 2-((7-(Hydroxymethyl)-5-methyl-1H-indol-4-yl)methyl)-1H-benzo[d]imidazole-5-carbonitrile

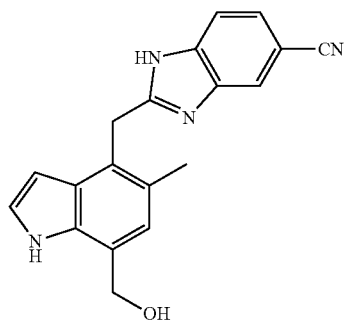 [SMILES: Cc1cc(CO)c2[nH]ccc2c1Cc1nc2cc(C#N)ccc2[nH]1]

A mixture of 2-((7-(hydroxymethyl)-5-methyl-1-tosyl-1H-indol-4-yl)methyl)-1H-benzo[d]imidazole-5-carbonitrile (13 mg, 0.028 mmol), KOH (15.5 mg, 0.276 mmol) and isoamylamine (64 μL, 0.553 mmol) in EtOH (0.8 mL) was stirred at 100° C. using microwave irradiation for 45 minutes. The mixture was directly purified using RP-HPLC (HC-A) to provide the title compound. $^1$H NMR (TFA salt, 400 MHz, DMSO-d$_6$) δ ppm 10.84 (s, 1H) 7.96 (s, 1H) 7.59 (d, J=8.34 Hz, 1H) 7.45-7.55 (m, 1H) 7.22 (t, J=2.78 Hz, 1H) 6.95 (s, 1H) 6.44-6.51 (m, 1H) 4.74 (s, 2H) 4.47 (s, 2H) 2.39 (s, 3H). HRMS calcd. for C$_{19}$H$_{16}$N$_4$O (M+H)$^+$ 317.1402. found 317.1404.

Example 114

Example 114-A 2-(1-(5-Ethyl-7-methyl-1-tosyl-1H-indol-4-yl)vinyl)-1-((2-(trimethylsilyl)ethoxy)methyl)-1H-benzo[d]imidazole-5-carbonitrile and 2-(1-(5-ethyl-7-methyl-1-tosyl-1H-indol-4-yl)vinyl)-1-((2-(trimethylsilyl)ethoxy)methyl)-1H-benzo[d]imidazole-6-carbonitrile

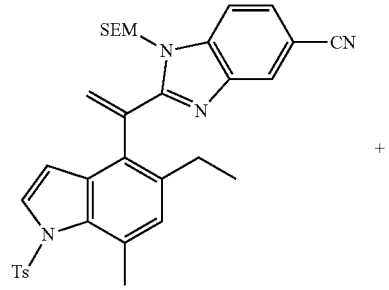

+

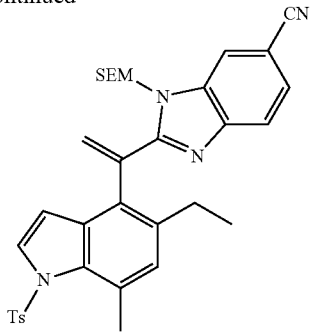

To a solution of (±)-2-(1-(5-ethyl-7-methyl-1-tosyl-1H-indol-4-yl)-1-hydroxyethyl)-1-((2-(trimethylsilyl)ethoxy)methyl)-1H-benzo[d]imidazole-5-carbonitrile and (±)-2-(1-(5-ethyl-7-methyl-1-tosyl-1H-indol-4-yl)-1-hydroxyethyl)-1-((2-(trimethylsilyl)ethoxy)methyl)-1H-benzo[d]imidazole-6-carbonitrile (Example 77-A) (302 mg, 0.480 mmol), DMAP (29.3 mg, 0.240 mmol) and Et$_3$N (0.666 mL, 4.80 mmol) in CH$_2$Cl$_2$ (3 mL) was added MsCl (0.112 mL, 1.441 mmol) at 0° C., and then the mixture was stirred at 0° C. for 1 hr. The reaction was allowed to warm up to room temperature and stirred for 15 h. To the mixture was added further aliquots of Et$_3$N (3.33 mL, 24.01 mmol), and MsCl (550 mg, 4.80 mmol). The mixture was then stirred at room temperature for 27 h. The reaction was quenched by 28% NH$_4$OH. The mixture was diluted with H$_2$O. The layers were separated and the aqueous layer was extracted with EtOAc. The combined organic phase was successively washed with H$_2$O and brine, dried over Na$_2$SO$_4$, and filtered. After concentration, the resulting residue was purified by SiO$_2$ flash column chromatography [CH$_2$Cl$_2$/(30% EtOAc in CH$_2$Cl$_2$)=45/55 to 35/65] to give title compounds as a mixture. MS (ESI+) m/z 611.3 (M+H).

Example 114-B 2-(1-(5-Ethyl-7-methyl-1-tosyl-1H-indol-4-yl)vinyl)-1H-benzo[d]imidazole-5-carbonitrile

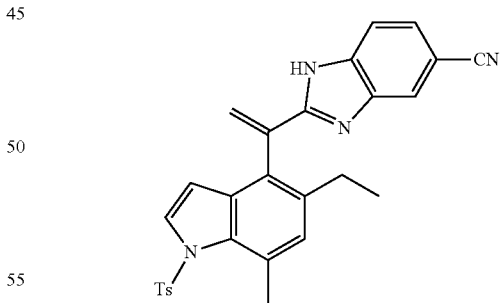

A solution of a mixture of 2-(1-(5-ethyl-7-methyl-1H-indol-4-yl)vinyl)-1-((2-(trimethylsilyl)ethoxy)methyl)-1H-benzo[d]imidazole-5-carbonitrile and 2-(1-(5-ethyl-7-methyl-1-tosyl-1H-indol-4-yl)vinyl)-1-((2-(trimethylsilyl)ethoxy)methyl)-1H-benzo[d]imidazole-6-carbonitrile (100 mg, 0.164 mmol) in 1M HCl in MeOH (10 mL) was stirred at 60° C. for 5 h. The reaction was cooled to room temperature. The reaction mixture was diluted with CH$_2$Cl$_2$. The layers were separated and the organic phase was successively washed with 5% aq. NaHCO$_3$, H$_2$O and brine, dried over Na$_2$SO$_4$, and filtered. Concentration of the filtrate gave the title compound, without need of any further purification. MS (ESI+) m/z 481.2 (M+H).

Example 114-C 2-(1-(5-Ethyl-7-methyl-1H-indol-4-yl)vinyl)-1H-benzo[d]imidazole-5-carbonitrile

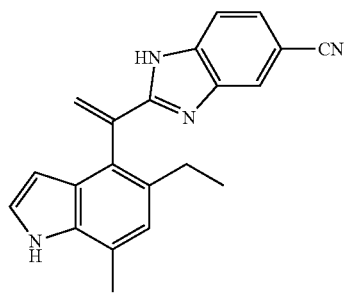

A mixture of 2-(1-(5-ethyl-7-methyl-1-tosyl-1H-indol-4-yl)vinyl)-1H-benzo[d]imidazole-5-carbonitrile (79 mg, 0.164 mmol) and KOH (46.1 mg, 0.822 mmol) in EtOH (3 mL) was stirred at 100° C. for 0.5 h under the microwave irradiation. The reaction mixture was diluted with CH$_2$Cl$_2$/2,2,2-trifluoroethanol (c.a. 9/1). The mixture was washed with H$_2$O, dried over Na$_2$SO$_4$, and filtered and concentrated. The resulting residue was purified by RP-HPLC (HC-A), then (HC-B) to give the title compound. $^1$H NMR (400 MHz, DICHLOROMETHANE-d$_2$ with about 5 µL TFA) δ ppm 8.46 (br. s., 1H), 8.04 (s, 1H), 7.86 (d, J=8.59 Hz, 1H), 7.73 (dd, J=1.14, 8.59 Hz, 1H), 7.37 (s, 1H), 7.27 (t, J=2.80 Hz, 1H), 7.07 (s, 1H), 6.25 (s, 2H), 2.47-2.65 (m, 5H), 1.14 (t, J=7.45 Hz, 3H). HRMS calcd. for C$_{21}$H$_{18}$N$_4$ (M+H)$^+$ 327.1610. found 327.1612.

Example 115

2-(1-(5-Methoxy-7-methyl-1H-indol-4-yl)vinyl)-1H-benzo[d]imidazole-5-carbonitrile

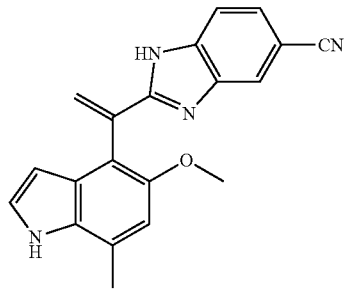

The title compound was synthesized from a mixture of (±)-tert-butyl 4-(1-(5-cyano-1-((2-(trimethylsilyl)ethoxy)methyl)-1H-benzo[d]imidazol-2-yl)-1-hydroxyethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-hydroxy ethyl)-5-methoxy-7-methyl-1H-indole-1-carboxylate (Example 26-A) in a similar manner as shown in Example 114. $^1$H NMR (400 MHz, DMSO-d$_6$) δ ppm 8.07 (s) 7.65-7.84 (m) 7.44-7.56 (m) 7.15-7.36 (m, 1H) 6.82 (d, J=2.91 Hz, 1H) 6.58 (dd, J=14.84, 1.71 Hz, 1H) 6.14 (dd, J=2.97, 1.96 Hz, 1H) 5.56-5.75 (m, 1H) 3.57 (d, J=0.88 Hz, 3H) 2.53 (br. s., 3H). HRMS calcd. for C$_{20}$H$_{16}$N$_4$O (M+H)$^+$ 329.1402. found 329.1395.

Example 116

Example 116-A 2-((5-Ethyl-7-methyl-1-tosyl-1H-indol-4-yl)methyl)-1H-benzo[d]imidazole-5-carbonitrile

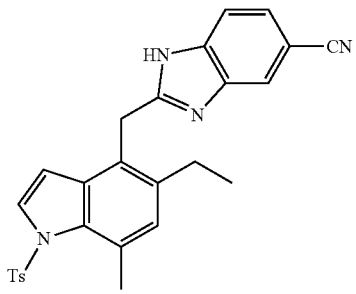 [SMILES: CCc1cc(C)c2c(ccn2S(=O)(=O)c2ccc(C)cc2)c1Cc1nc2cc(C#N)ccc2[nH]1]

2-((5-Ethyl-7-methyl-1-tosyl-1H-indol-4-yl)methyl)-1H-benzo[d]imidazole-5-carbonitrile was synthesized from 5-ethyl-7-methyl-1-tosyl-1H-indole-4-carbaldehyde (Example 48-C) analogously to the preparation of Example 58. MS (ESI+) m/z 469.5 (M+H).

Example 116-B 2-((5-Ethyl-7-methyl-1-tosyl-1H-indol-4-yl)methyl)-1-((2-(trimethylsilyl)ethoxy)methyl)-1H-benzo[d]imidazole-5-carbonitrile and 2-((5-ethyl-7-methyl-1-tosyl-1H-indol-4-yl)methyl)-1-((2-(trimethylsilyl)ethoxy)methyl)-1H-benzo[d]imidazole-6-carbonitrile

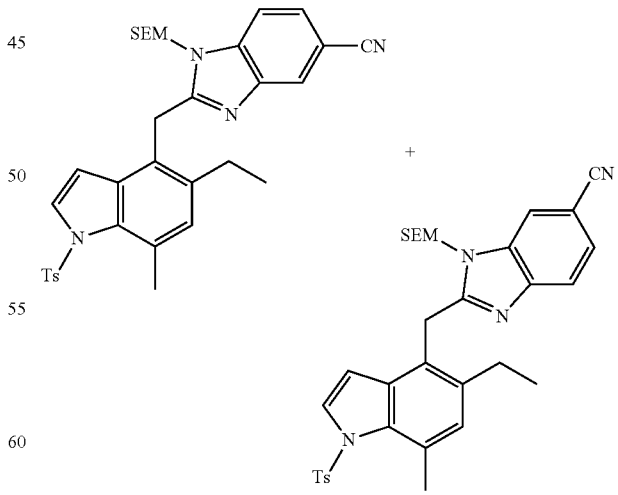

To a solution of 2-((5-ethyl-7-methyl-1-tosyl-1H-indol-4-yl)methyl)-1H-benzo[d]imidazole-5-carbonitrile (500 mg, 1.067 mmol) in THF (25 mL) was added NaH (60% in mineral oil, 171 mg, 4.27 mmol), and then the mixture was stirred at room temperature for 0.5 hr. To the mixture was added SEMCl (0.38 mL, 2.13 mmol) at room temperature, and then the mixture was stirred at room temperature for 1 hr. The reaction was quenched with MeOH at room temperature. The reaction mixture was diluted with $H_2O$, the layers were separated and the aqueous layer extracted with EtOAc. The organic phase was washed with $H_2O$ and brine, dried over $Na_2SO_4$, filtered and concentrated. The resulting residue was purified by silica gel flash column chromatography [heptane/(30% EtOAc in $CH_2Cl_2$)=53/47 then 56/44] to give the title compounds as a mixture. MS (ESI+) m/z 599.3 (M+H).

Example 116-C 2-((3-Bromo-5-ethyl-7-methyl-1-tosyl-1H-indol-4-yl)methyl)-1-((2-(trimethylsilyl)ethoxy)methyl)-1H-benzo[d]imidazole-5-carbonitrile and 2-((3-bromo-5-ethyl-7-methyl-1-tosyl-1H-indol-4-yl)methyl)-1-((2-(trimethylsilyl)ethoxy)methyl)-1H-benzo[d]imidazole-6-carbonitrile

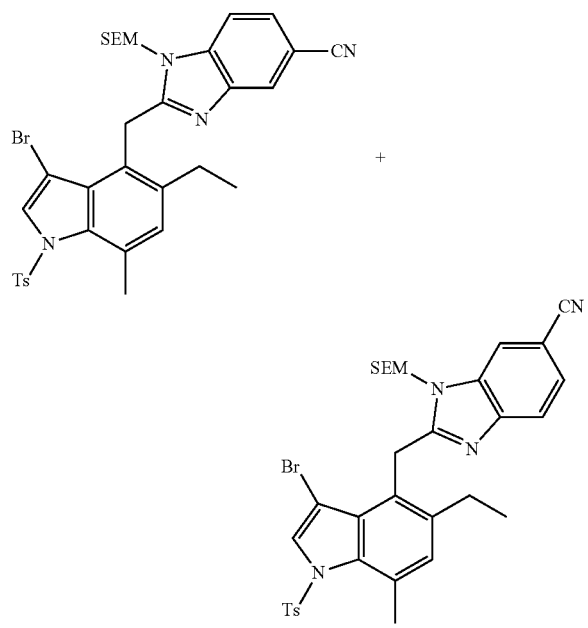

To a solution of a mixture of 2-((5-ethyl-7-methyl-1-tosyl-1H-indol-4-yl)methyl)-1-((2-(trimethylsilyl)ethoxy)methyl)-1H-benzo[d]imidazole-5-carbonitrile and 2-((5-ethyl-7-methyl-1-tosyl-1H-indol-4-yl)methyl)-1-((2-(trimethylsilyl)ethoxy)methyl)-1H-benzo[d]imidazole-6-carbonitrile (600 mg, 1 mmol) in DMF (10 mL) was added NBS (214 mg, 1.2 mmol), and then the mixture was stirred at 0° C. for 1 hr, and then stirred at room temperature for 19 h. The reaction was quenched by satd. aq. $Na_2S_2O_3/H_2O$ (c.a. 1/1), and then the mixture was stirred for 0.25 h and then diluted with $H_2O$. The layers were separated and the aqueous layer was extracted with EtOAc. The organic phase was washed with $H_2O$ and brine, dried over $Na_2SO_4$, filtered and concentrated. The resulting residue was purified by silica gel flash column chromatography [heptane/(30% EtOAc in $CH_2Cl_2$)=70/30 to 66/34] to give title compounds as a mixture. MS (ESI+) m/z 677.2, 679.3 (M+H).

Example 116-D 2-((5-Ethyl-7-methyl-1-tosyl-3-(1-((2-(trimethylsilyl)ethoxy)methyl)-1H-pyrazol-5-yl)-1H-indol-4-yl)methyl)-1-((2-(trimethylsilyl)ethoxy)methyl)-1H-benzo[d]imidazole-5-carbonitrile and 2-((5-ethyl-7-methyl-1-tosyl-3-(1-((2-(trimethylsilyl)ethoxy)methyl)-1H-pyrazol-5-yl)-1H-indol-4-yl)methyl)-1-((2-(trimethylsilyl)ethoxy)methyl)-1H-benzo[d]imidazole-6-carbonitrile

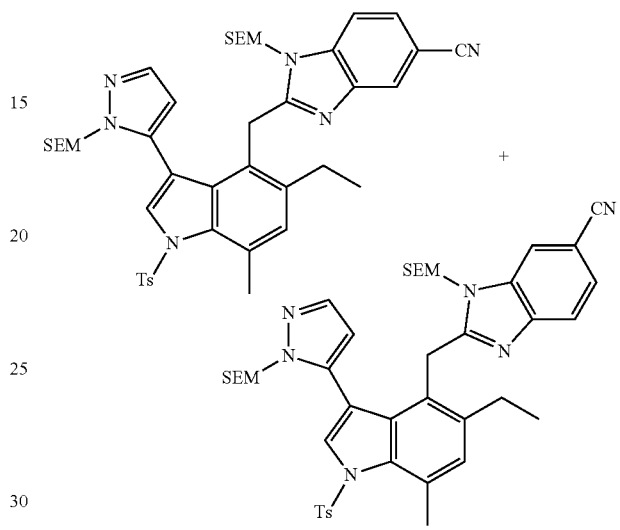

To a mixture of 2-((3-bromo-5-ethyl-7-methyl-1-tosyl-1H-indol-4-yl)methyl)-1-((2-(trimethylsilyl)ethoxy)methyl)-1H-benzo[d]imidazole-5-carbonitrile and 2-((3-bromo-5-ethyl-7-methyl-1-tosyl-1H-indol-4-yl)methyl)-1-((2-(trimethylsilyl)ethoxy)methyl)-1H-benzo[d]imidazole-6-carbonitrile (80 mg, 0.118 mmol), 1-(2-trimethylsilylethoxy)methyl-1H-pyrazole-5-boronic acid pinacol ester (CAS #: 903550-12-9, 77 mg, 0.236 mmol), and $K_3PO_4$ (50.1 mg, 0.236 mmol) in DME (2 mL)/$H_2O$ (0.5 mL) was added Pd(PPh$_3$)$_4$ (27.3 mg, 0.024 mmol), and then the mixture was stirred at 80° C. for 7 h. The reaction mixture was cooled to room temperature, and directly purified by silica gel flash column chromatography [heptane/(30% EtOAc in $CH_2Cl_2$)=9/1 to 0/1) to give the title compounds as a mixture. MS (ESI+) m/z 795.4 (M+H).

Example 116-E 2-((5-Ethyl-7-methyl-3-(1H-pyrazol-5-yl)-1-tosyl-1H-indol-4-yl)methyl)-1H-benzo[d]imidazole-5-carbonitrile

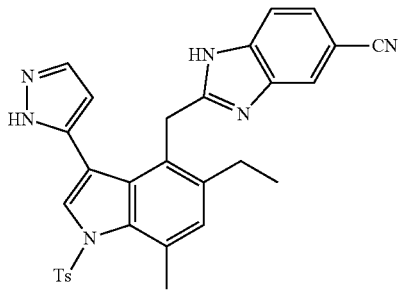 [SMILES: CCc1cc(C)c2c(c(-c3ccn[nH]3)cn2S(=O)(=O)c2ccc(C)cc2)c1Cc1nc2cc(C#N)ccc2[nH]1]

A solution of a mixture of 2-((5-ethyl-7-methyl-1-tosyl-3-(1-((2-(trimethylsilyl)ethoxy)methyl)-1H-pyrazol-5-yl)-1H- indol-4-yl)methyl)-1-((2-(trimethylsilyl)ethoxy)methyl)-1H-benzo[d]imidazole-5-carbonitrile and 2-((5-Ethyl-7-methyl-1-tosyl-3-(1-((2-(trimethylsilyl)ethoxy)methyl)-1H-pyrazol-5-yl)-1H-indol-4-yl)methyl)-1-((2-(trimethylsilyl)ethoxy)methyl)-1H-benzo[d]imidazole-6-carbonitrile (94 mg, 0.118 mmol) in 1M HCl in MeOH (5 mL) was stirred at 60° C. for 14 h. The reaction mixture was cooled to room temperature and diluted with CH$_2$Cl$_2$. The layers were separated and the organic phase was successively washed with 5% aq. NaHCO$_3$, H$_2$O and brine, dried over Na$_2$SO$_4$, and filtered. Concentration of the filtrate gave the title compound, without need of further purification. MS (ESI+) m/z 535.1 (M+H).

Example 116-F 2-((5-Ethyl-7-methyl-3-(1H-pyrazol-5-yl)-1H-indol-4-yl)methyl)-1H-benzo[d]imidazole-5-carbonitrile

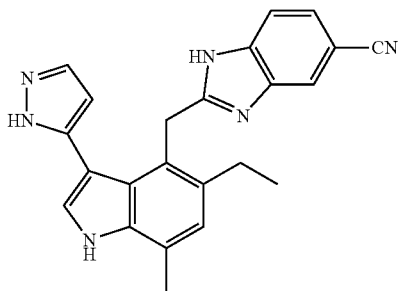 [SMILES: CCc1cc(C)c2[nH]cc(-c3ccn[nH]3)c2c1Cc1nc2cc(C#N)ccc2[nH]1]

A mixture of 2-((5-ethyl-7-methyl-3-(1H-pyrazol-5-yl)-1-tosyl-1H-indol-4-yl)methyl)-1H-benzo[d]imidazole-5-carbonitrile (63 mg, 0.118 mmol) and KOH (33.1 mg, 0.589 mmol) in EtOH (5 mL) was stirred at 100° C. for 0.5 h under microwave irradiation. The reaction mixture was diluted with CH$_2$Cl$_2$ and filtered through silica gel. The silica gel cake was washed with CH$_2$Cl$_2$/MeOH (c.a. 9/1). After concentration the resulting residue was purified by RP-HPLC (HC-A) to give the title compound. $^1$H NMR (TFA salt, 400 MHz, DMSO-d$_6$) δ ppm 10.13 (br. s., 1H), 8.53 (s, 1H), 8.23 (d, J=8.60 Hz, 1H), 8.18 (br. d, J=8.60 Hz, 1H), 8.05 (s, 1H), 7.96 (d, J=2.78 Hz, 1H), 7.54 (s, 1H), 6.72 (br. s., 1H), 5.32 (br. s., 2H), 3.38 (q, J=7.60 Hz, 2H), 3.06 (s, 3H), 1.69 (t, J=7.58 Hz, 3H). HRMS calcd. for C$_{23}$H$_{20}$N$_6$ (M+H)$^+$ 381.1828. found 381.1828.

Example 117

Example 117-A 2-(5-Ethyl-7-methyl-1-tosyl-1H-indole-4-carbonyl)-1-((2-(trimethylsilyl)ethoxy)methyl)-1H-benzo[d]imidazole-5-carbonitrile and 2-(5-ethyl-7-methyl-1-tosyl-1H-indole-4-carbonyl)-1-((2-(trimethylsilyl)ethoxy)methyl)-1H-benzo[d]imidazole-6-carbonitrile

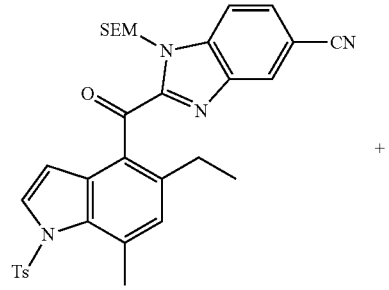

+

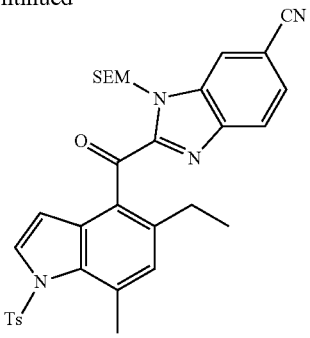

The mixture of title compounds was synthesized by oxidation of a mixture of (±)-2-((5-ethyl-7-methyl-1-tosyl-1H-indol-4-yl)(hydroxy)methyl)-1-((2-(trimethylsilyl)ethoxy)methyl)-1H-benzo[d]imidazole-5-carbonitrile and (±)-2-((5-ethyl-7-methyl-1-tosyl-1H-indol-4-yl)(hydroxy)methyl)-1-((2-(trimethylsilyl)ethoxy)methyl)-1H-benzo[d]imidazole-6-carbonitrile (Example 70-A) analogously to Example 75-A. MS (ESI+) m/z 613.3 (M+H).

Example 117-B 2-(3-Bromo-5-ethyl-7-methyl-1-tosyl-1H-indole-4-carbonyl)-1-((2-(trimethylsilyl)ethoxy)methyl)-1H-benzo[d]imidazole-5-carbonitrile and 2-(3-bromo-5-ethyl-7-methyl-1-tosyl-1H-indole-4-carbonyl)-1-((2-(trimethylsilyl)ethoxy)methyl)-1H-benzo[d]imidazole-6-carbonitrile

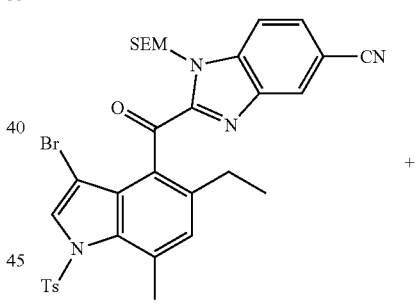

+

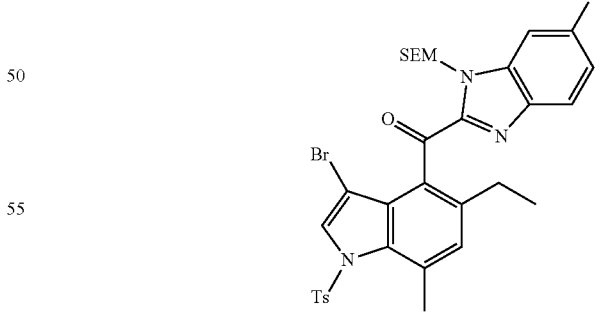

To a solution of 2-(5-ethyl-7-methyl-1-tosyl-1H-indole-4-carbonyl)-1-((2-(trimethylsilyl)ethoxy)methyl)-1H-benzo[d]imidazole-5-carbonitrile and 2-(5-ethyl-7-methyl-1-tosyl-1H-indole-4-carbonyl)-1-((2-(trimethylsilyl)ethoxy) methyl)-1H-benzo[d]imidazole-6-carbonitrile (150 mg, 0.245 mmol) in DMF (10 mL) was added NBS (65.3 mg, 0.367 mmol), and then the mixture was stirred at room temperature for 15 h. The reaction was quenched by satd. aq. Na$_2$S$_2$O$_3$/H$_2$O (c.a. 1/1), and then the mixture was stirred for 0.25 h. The mixture was diluted with H$_2$O and the layers were separated. The aqueous layer was extracted with EtOAc. The organic phase was washed with H$_2$O and brine, dried over Na$_2$SO$_4$, and filtered and concentrated. The resulting residue was purified by silica gel flash column chromatography [heptane/30% EtOAc=70/30 to 52/48] to give the title compounds as a mixture. MS (ESI+) m/z 693.3, 691.3 (M+H).

Example 117-C 2-(5-Ethyl-7-methyl-3-phenyl-1-tosyl-1H-indole-4-carbonyl)-1-((2-(trimethylsilyl)ethoxy)methyl)-1H-benzo[d]imidazole-5-carbonitrile and 2-(5-ethyl-7-methyl-3-phenyl-1-tosyl-1H-indole-4-carbonyl)-1-((2-(trimethylsilyl)ethoxy)methyl)-1H-benzo[d]imidazole-6-carbonitrile

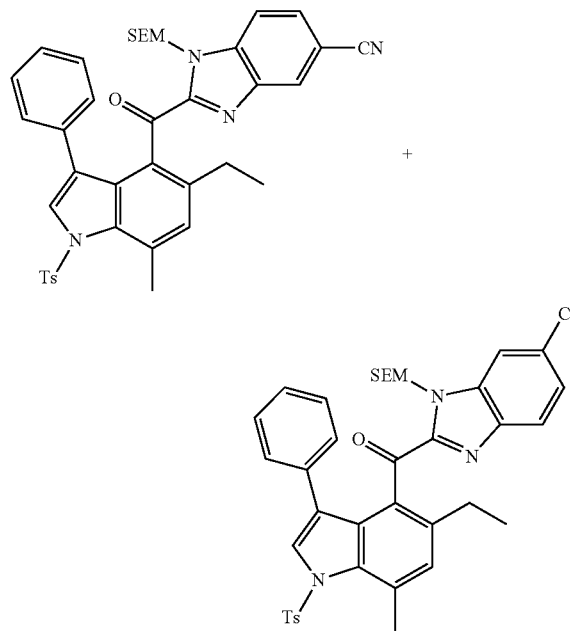

To a mixture of 2-(3-bromo-5-ethyl-7-methyl-1-tosyl-1H-indole-4-carbonyl)-1-((2-(trimethylsilyl)ethoxy)methyl)-1H-benzo[d]imidazole-5-carbonitrile and 2-(3-bromo-5-ethyl-7-methyl-1-tosyl-1H-indole-4-carbonyl)-1-((2-(trimethylsilyl)ethoxy)methyl)-1H-benzo[d]imidazole-6-carbonitrile (60 mg, 0.087 mmol), phenylboronic acid (21.15 mg, 0.173 mmol), and K$_3$PO$_4$ (55.2 mg, 0.260 mmol) in DME (1 mL)/H$_2$O (0.2 mL) was added Pd(OAc)$_2$ (1.947 mg, 8.67 µmol) and S-phos (CAS#657408-07-6) (7.12 mg, 0.017 mmol), and then the mixture was stirred at 80° C. for 13.5 h. Ba(OH)$_2$ H$_2$O (32.9 mg, 0.173 mmol) was then added and the mixture was stirred at the same temperature for 6 h. The reaction mixture was cooled to room temperature, and then directly purified by silica gel flash column chromatography (heptane/EtOAc=1/0 to 6/4) to give the title compounds as a mixture. MS (ESI+) m/z 689.3 (M+H).

Example 117-D (±)-2-((5-Ethyl-7-methyl-3-phenyl-1-tosyl-1H-indol-4-yl)(hydroxy)methyl)-1-((2-(trimethylsilyl)ethoxy)methyl)-1H-benzo[d]imidazole-5-carbonitrile and (±)-2-((5-ethyl-7-methyl-3-phenyl-1-tosyl-1H-indol-4-yl)(hydroxy)methyl)-1-((2-(trimethylsilyl)ethoxy)methyl)-1H-benzo[d]imidazole-6-carbonitrile

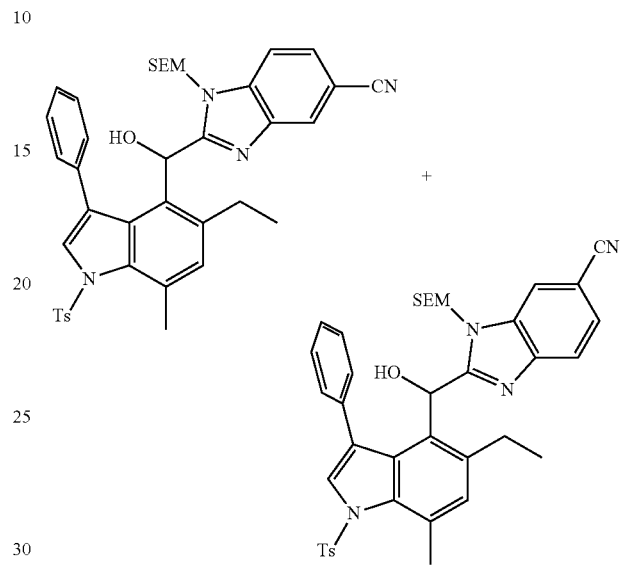

To a solution of 2-(5-ethyl-7-methyl-3-phenyl-1-tosyl-1H-indole-4-carbonyl)-1-((2-(trimethylsilyl)ethoxy)methyl)-1H-benzo[d]imidazole-5-carbonitrile and 2-(5-ethyl-7-methyl-3-phenyl-1-tosyl-1H-indole-4-carbonyl)-1-((2-(trimethylsilyl)ethoxy)methyl)-1H-benzo[d]imidazole-6-carbonitrile (45 mg, 0.065 mmol) in MeOH (2 mL), NaBH$_4$ (49.4 mg, 1.306 mmol) was added and the reaction was stirred at room temperature for 5 h. An additional aliquot of NaBH$_4$ (50 mg, 1.31 mmol) was added, and then the mixture was stirred at the same temperature for 1.5 h. The reaction mixture was diluted with CH$_2$Cl$_2$. The layers were separated and the organic layer was washed successively with H$_2$O and brine, dried over Na$_2$SO$_4$, and filtered. Concentration of the filtrate gave the title compounds as a mixture, without need of further purification. MS (ESI+) m/z 691.3 (M+H).

Example 117-E (±)-2-((5-Ethyl-7-methyl-3-phenyl-1-tosyl-1H-indol-4-yl)(hydroxy)methyl)-1H-benzo[d]imidazole-5-carbonitrile

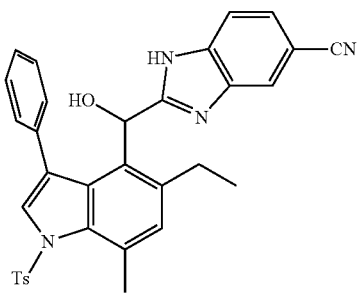 [SMILES: CCc1cc(C)c2c(c(-c3ccccc3)cn2S(=O)(=O)c2ccc(C)cc2)c1C(O)c1nc2cc(C#N)ccc2[nH]1]

A solution of a mixture of (±)-2-((5-ethyl-7-methyl-3-phenyl-1-tosyl-1H-indol-4-yl)(hydroxy)methyl)-1-((2-(trimethylsilyl)ethoxy)methyl)-1H-benzo[d]imidazole-5-carbonitrile and (±)-2-((5-ethyl-7-methyl-3-phenyl-1-tosyl-1H-indol-4-yl)(hydroxy)methyl)-1-((2-(trimethylsilyl)ethoxy)methyl)-1H-benzo[d]imidazole-6-carbonitrile (25 mg, 0.036 mmol) in 1M HCl in MeOH (2 mL) was stirred at 60° C. for 17 h. The reaction mixture was cooled to room temperature. The reaction mixture was diluted with EtOAc. The mixture was successively washed by 5% aq. NaHCO$_3$, H$_2$O and brine, dried over Na$_2$SO$_4$, and filtered. Concentration of the filtrate gave the title compound, which was used in the next reaction without any further purification. MS (ESI+) m/z 561.2 (M+H).

Example 117-F (±)-2-((5-Ethyl-7-methyl-3-phenyl-1H-indol-4-yl)(hydroxy)methyl)-1H-benzo[d]imidazole-5-carbonitrile

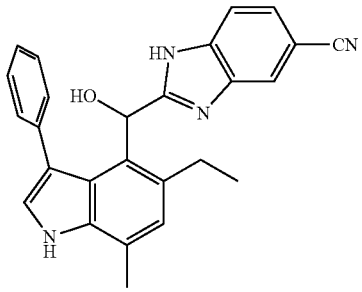 [SMILES: CCc1cc(C)c2[nH]cc(-c3ccccc3)c2c1C(O)c1nc2cc(C#N)ccc2[nH]1]

A mixture of (±)-2-((5-ethyl-7-methyl-3-phenyl-1-tosyl-1H-indol-4-yl)(hydroxy)methyl)-1H-benzo[d]imidazole-5-carbonitrile (20 mg, 0.036 mmol) and KOH (10 mg, 0.178 mmol) was stirred at 100° C. for 0.5 h under microwave irradiation. The reaction mixture was diluted with CH$_2$Cl$_2$. The mixture was filtered through silica gel. The silica gel cake was washed with CH$_2$Cl$_2$/MeOH (c.a. 9/1). After concentration, the filtrate was purified by silica gel flash column chromatography [CH$_2$Cl$_2$/(5% 2,2,2-trifluoroethanol in CH$_2$Cl$_2$)=95/5 to 40/60] to give the title compound. $^1$H NMR (400 MHz, ACETONITRILE-d$_3$) δ ppm 9.54 (br. s., 1H), 7.93 (s, 1H), 7.70 (dd, J=1.30, 8.60 Hz, 1H), 7.63 (d, J=8.60 Hz, 1H), 7.03-7.38 (m, 6H), 6.99 (s, 1H), 6.59 (s, 1H), 2.53-2.54 (m, 5H), 0.98 (t, J=7.33 Hz, 3H). HRMS calcd. for C$_{26}$H$_{22}$N$_4$O (M+H)$^+$ 407.1872. found 407.1868.

Example 118

Example 118-A

3-Bromo-5,7-dimethyl-1-tosyl-1H-indole-4-carbaldehyde

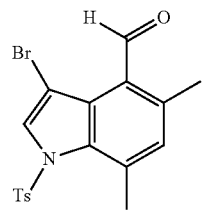 [SMILES: Cc1ccc(S(=O)(=O)n2cc(Br)c3c(C=O)c(C)cc(C)c32)cc1]

To a solution of 5,7-dimethyl-1-tosyl-1H-indole-4-carbaldehyde (Example 46-D) (2 g, 6.11 mmol) in DMF (10 mL) was added NBS (2.39 g, 13.44 mmol), and then the mixture was stirred at 60° C. for 18.5 h. The reaction mixture was cooled to room temperature. The mixture was diluted with H$_2$O, the layers were separated and the aqueous layer was extracted with EtOAc. The organic phase was washed with H$_2$O and brine, dried over Na$_2$SO$_4$, filtered and concentrated. The resulting residue was purified by silica gel flash column chromatography to give the title compound. MS (ESI+) m/z 406.0, 408.0 (M+H).

Example 118-B 5,7-Dimethyl-3-phenyl-1-tosyl-1H-indole-4-carbaldehyde

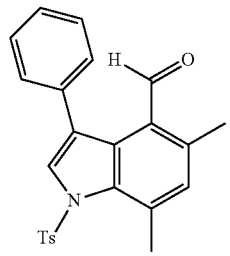 [SMILES: Cc1ccc(S(=O)(=O)n2cc(-c3ccccc3)c3c(C=O)c(C)cc(C)c32)cc1]

To a suspension of 3-bromo-5,7-dimethyl-1-tosyl-1H-indole-4-carbaldehyde (100 mg, 0.246 mmol), phenylboronic acid (60.0 mg, 0.492 mmol), and K$_3$PO$_4$ (157 mg, 0.738 mmol) in DME (1 mL)/H$_2$O (0.5 mL), Pd(OAc)$_2$ (5.53 mg, 0.025 mmol) and S-phos (CAS#657408-07-6) (20.21 mg, 0.049 mmol) were added the mixture was stirred at 80° C. for 15 h. The reaction mixture was cooled to room temperature and diluted with CH$_2$Cl$_2$ and water. The layers were partitioned. The organic layer was separated, dried over MgSO$_4$, filtered and concentrated. The resulting residue was purified by silica gel flash column chromatography [heptane/(30% EtOAc in CH$_2$Cl$_2$)=1/0 to 4/6] to give the title compound. MS (ESI+) m/z 404.1 (M+H).

Example 118-C a) (±)-2-((5,7-Dimethyl-3-phenyl-1H-indol-4-yl)(hydroxy)methyl)-1H-benzo[d]imidazole-5-carbonitrile

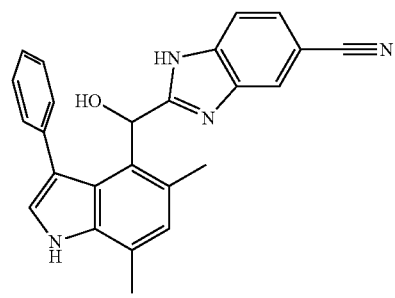 [SMILES: Cc1cc(C)c2[nH]cc(-c3ccccc3)c2c1C(O)c1nc2cc(C#N)ccc2[nH]1]

The title compound was synthesized from 5,7-dimethyl-3-phenyl-1-tosyl-1H-indole-4-carbaldehyde analogously to Example 64. $^1$H NMR (400 MHz, ACETONITRILE-d$_3$ with about 5 μL TFA) δ ppm 9.57 (br. s., 1H), 7.98 (s, 1H), 7.77 (dd, J=1.50, 8.60 Hz, 1H), 7.68 (d, J=8.60 Hz, 1H), 7.07-7.39 (m, 6H), 6.93 (s, 1H), 6.62 (s, 1H), 2.52 (s, 3H), 2.14 (br. s, 3H). HRMS calcd. for $C_{25}H_{20}N_4O$ (M+H)$^+$ 393.1715. found 393.1705.

b) (+) and (−)-2-((5,7-dimethyl-3-phenyl-1H-indol-4-yl)(hydroxy)methyl)-1H-benzo[d]imidazole-5-carbonitrile Resolution of the enantiomers of 2-((5,7-dimethyl-3-phenyl-1H-indol-4-yl)(hydroxy)methyl)-1H-benzo[d]imidazole-5-carbonitrile was achieved by chiral SFC using a CHIRALPAK® AD-H column with 30% (0.2% diethylamine in iPrOH) in $CO_2$ to give (+)- or (−)-2-((5,7-dimethyl-3-phenyl-1H-indol-4-yl)(hydroxy)methyl)-1H-benzo[d]imidazole-5-carbonitrile ($t_r$=4.6 min) and (−) or (+)-2-((5,7-dimethyl-3-phenyl-1H-indol-4-yl)(hydroxy)methyl)-1H-benzo[d]imidazole-5-carbonitrile ($t_r$=7.9 min).

Example 119 a) (±)-2-((5,7-Dimethyl-3-(1-methyl-1H-pyrazol-4-yl)-1H-indol-4-yl)(hydroxy)methyl)-1H-benzo[d]imidazole-5-carbonitrile

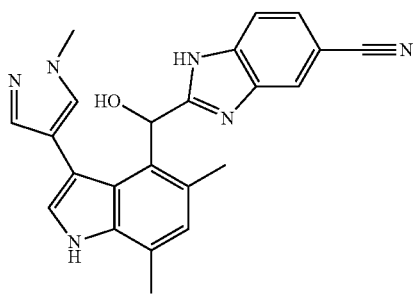 [SMILES: CN/C=C(\C=N)c1c[nH]c2c(C)cc(C)c(C(O)c3nc4cc(C#N)ccc4[nH]3)c12]

The title compound was synthesized form 3-bromo-5,7-dimethyl-1-tosyl-1H-indole-4-carbaldehyde (Example 118-A) using 1-methyl-4-(4,4,5,5-tetramethyl-1,3,2-dioxaborolan-2-yl)-1H-pyrazole (CAS #: 847818-74-0) analogously to the preparation of Example 118. $^1$H NMR (400 MHz, ACETONITRILE-$d_3$ with about 5 μL TFA) δ ppm 9.46 (br. s., 1H), 7.97 (s, 1H), 7.72 (dd, J=1.30, 8.60 Hz, 1H), 7.68 (d, J=8.60 Hz, 1H), 7.35 (br. s., 1H), 7.24 (br. s., 1H), 7.13 (d, J=2.53 Hz, 1H), 6.87 (s, 1H), 6.82 (br. s., 1H), 3.71 (s, 3H), 2.48 (s, 3H), 2.15 (br. s., 3H). HRMS calcd. for $C_{23}H_{20}N_6O$ (M+H)$^+$ 397.1777. found 397.1775.

b) (+) and (−)-2-((5,7-dimethyl-3-(1-methyl-1H-pyrazol-4-yl)-1H-indol-4-yl)(hydroxy)methyl)-1H-benzo[d]imidazole-5-carbonitrile Resolution of the enantiomers of 2-((5,7-dimethyl-3-(1-methyl-1H-pyrazol-4-yl)-1H-indol-4-yl)(hydroxy)methyl)-1H-benzo[d]imidazole-5-carbonitrile was achieved by chiral SFC using a CHIRALCEL® OJ-H column with 25% (0.2% diethylamine in MeOH) in $CO_2$ to give (+)- or (−)-2-((5,7-dimethyl-3-(1-methyl-1H-pyrazol-4-yl)-1H-indol-4-yl)(hydroxy)methyl)-1H-benzo[d]imidazole-5-carbonitrile ($t_r$=1.54 min) and (−) or (+)-2-((5,7-dimethyl-3-(1-methyl-1H-pyrazol-4-yl)-1H-indol-4-yl)(hydroxy)methyl)-1H-benzo[d]imidazole-5-carbonitrile ($t_r$=2.35 min).

Example 120 a) (±)-2-((5,7-Dimethyl-3-(pyridin-3-yl)-1H-indol-4-yl)(hydroxy)methyl)-1H-benzo[d]imidazole-5-carbonitrile

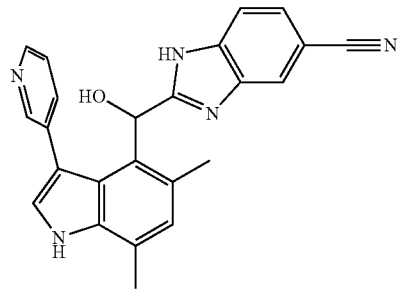 [SMILES: Cc1cc(C)c2[nH]cc(-c3cccnc3)c2c1C(O)c1nc2cc(C#N)ccc2[nH]1]

The title compound was synthesized form 3-bromo-5,7-dimethyl-1-tosyl-1H-indole-4-carbaldehyde (Example 118-A) using pyridin-3-ylboronic acid (CAS #: 1692-25-7) analogously to the preparation of Example 118. $^1$H NMR (400 MHz, ACETONITRILE-$d_3$ with about 5 μL TFA) δ ppm 9.84 (br. s., 1H), 8.66 (s, 1H), 8.37 (d, J=6.10 Hz, 1H), 8.00 (br. d, J=7.10 Hz, 1H), 7.83 (d, J=0.51 Hz, 1H), 7.59 (dd, J=1.30, 8.30 Hz, 1H), 7.52 (d, J=8.30 Hz, 1H), 7.39 (br. dd, J=6.10, 7.10 Hz, 1H), 7.25 (d, J=3.03 Hz, 1H), 6.99 (s, 1H), 6.44 (s, 1H), 2.52 (s, 3H), 2.36 (s, 3H). HRMS calcd. for $C_{24}H_{19}N_5O$ (M+H)$^+$ 394.1668. found 394.1674.

b) (+) and (−)-2-((5,7-Dimethyl-3-(pyridin-3-yl)-1H-indol-4-yl)(hydroxy)methyl)-1H-benzo[d]imidazole-5-carbonitrile Resolution of the enantiomers of 2-((5,7-Dimethyl-3-(pyridin-3-yl)-1H-indol-4-yl)(hydroxy)methyl)-1H-benzo[d]imidazole-5-carbonitrile was achieved by chiral SFC using a AS-H column with 30% (0.2% diethylamine in MeOH) in $CO_2$ to give (+)- or (−)-2-((5,7-dimethyl-3-(pyridin-3-yl)-1H-indol-4-yl)(hydroxy)methyl)-1H-benzo[d]imidazole-5-carbonitrile ($t_r$=2.25 min) and (−) or (+)-2-((5,7-dimethyl-3-(pyridin-3-yl)-1H-indol-4-yl)(hydroxy)methyl)-1H-benzo[d]imidazole-5-carbonitrile ($t_r$=3.20 min).

Example 121

Example 121-A

5,7-Dimethyl-1-tosyl-3-(1-((2-(trimethylsilyl)ethoxy)methyl)-1H-pyrazol-5-yl)-1H-indole-4-carbaldehyde

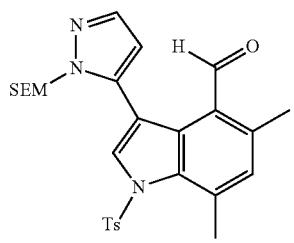 [SMILES: Cc1ccc(S(=O)(=O)n2cc(-c3ccnn3COCC[Si](C)(C)C)c3c(C=O)c(C)cc(C)c32)cc1]

To a suspension of 3-bromo-5,7-dimethyl-1-tosyl-1H-indole-4-carbaldehyde (100 mg, 0.246 mmol), 1-(2-trimethylsilylethoxy)methyl-1H-pyrazole-5-boronic acid pinacol ester (CAS #: 903550-12-9) (239 mg, 0.738 mmol), and K₃PO₄ (157 mg, 0.738 mmol) in DME (1 mL)/H₂O (0.5 mL) was added Pd(PPh₃)₄ (56.9 mg, 0.049 mmol), and then the mixture was stirred at 80° C. for 16 h. The reaction mixture was cooled down to room temperature. The mixture was diluted with CH₂Cl₂. The bi-phase layer was partitioned. The organic layer was separated, dried over MgSO₄, filtered and concentrated. The resulting residue was purified by silica gel flash column chromatography [heptane/(30% EtOAc in CH₂Cl₂)=1/0 to 4/6] to give the title compound. MS (ESI+) m/z 524.2 (M+H).

Example 121-B (±)-2-((5,7-Dimethyl-1-tosyl-3-(1-((2-(trimethylsilyl)ethoxy)methyl)-1H-pyrazol-5-yl)-1H-indol-4-yl)(hydroxy)methyl)-1-((2-(trimethylsilyl)ethoxy)methyl)-1H-benzo[d]imidazole-5-carbonitrile and (±)-2-((5,7-Dimethyl-1-tosyl-3-(1-((2-(trimethylsilyl)ethoxy)methyl)-1H-pyrazol-5-yl)-1H-indol-4-yl)(hydroxy)methyl)-1-((2-(trimethylsilyl)ethoxy)methyl)-1H-benzo[d]imidazole-6-carbonitrile

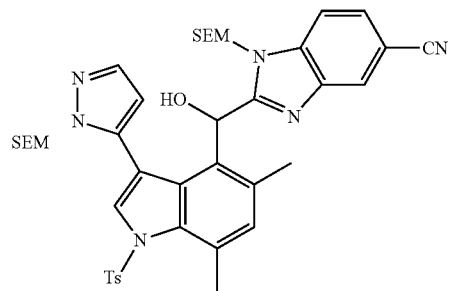

+

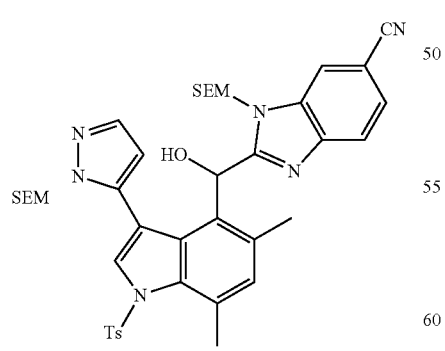

The title compounds were synthesized from 5,7-dimethyl-1-tosyl-3-(1-((2-(trimethylsilyl)ethoxy)methyl)-1H-pyrazol-5-yl)-1H-indole-4-carbaldehyde analogously to Example 64-A. MS (ESI+) m/z 797.3 (M+H).

Example 121-C (±)-2-((5,7-Dimethyl-3-(1H-pyrazol-5-yl)-1-tosyl-1H-indol-4-yl)(hydroxy)methyl)-1H-benzo[d]imidazole-5-carbonitrile

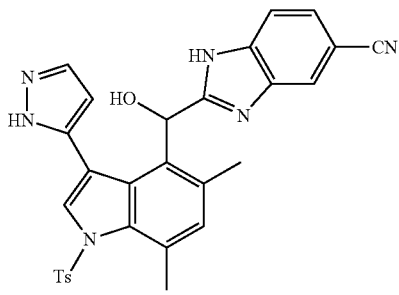 [SMILES: Cc1ccc(S(=O)(=O)n2cc(-c3ccn[nH]3)c3c(C(O)c4nc5cc(C#N)ccc5[nH]4)c(C)cc(C)c32)cc1]

A solution of a mixture of (±)-2-((5,7-dimethyl-1-tosyl-3-(1-((2-(trimethylsilyl)ethoxy)methyl)-1H-pyrazol-5-yl)-1H-indol-4-yl)(hydroxy)methyl)-1-((2-(trimethylsilyl)ethoxy)methyl)-1H-benzo[d]imidazole-5-carbonitrile and (±)-2-((5,7-dimethyl-1-tosyl-3-(1-((2-(trimethylsilyl)ethoxy)methyl)-1H-pyrazol-5-yl)-1H-indol-4-yl)(hydroxy)methyl)-1-((2-(trimethylsilyl)ethoxy)methyl)-1H-benzo[d]imidazole-6-carbonitrile (250 mg, 0.314 mmol) in 1M HCl in MeOH (2 mL) was stirred at 60° C. for 16 h. The reaction mixture was cooled to room temperature, and diluted with CH₂Cl₂. The layers were separated and the organic layer was washed with 5% aq. NaHCO₃, H₂O, and brine, dried over Na₂SO₄, and filtered. After concentration of the filtrate, the resulting residue was purified by silica gel flash column chromatography [CH₂Cl₂/(2M NH₃ in MeOH)=94/6 then 93/7] to give the title compound. MS (ESI+) m/z 537.1 (M+H).

Example 121-D (±)-2-((5,7-Dimethyl-3-(1H-pyrazol-5-yl)-1H-indol-4-yl)(hydroxy)methyl)-1H-benzo[d]imidazole-5-carbonitrile The title compound was synthesized from (±)-2-((5,7-dimethyl-3-(1H-pyrazol-5-yl)-1-tosyl-1H-indol-4-yl)(hydroxy)methyl)-1H-benzo[d]imidazole-5-carbonitrile following the same procedure as described in Example 64-C. ¹H NMR (400 MHz, ACETONITRILE-d₃ with about 5 µL TFA) δ ppm 9.73 (br. s., 1H), 7.94 (s, 1H), 7.74 (dd, J=1.50, 8.60 Hz, 1H), 7.64 (d, J=8.59 Hz, 1H), 7.40 (d, J=2.27 Hz, 1H), 7.29 (br. s., 1H), 7.01 (s, 1H), 6.66 (br. s., 1H), 5.80 (br. s., 1H), 2.53 (s, 3H), 2.48 (br. s., 3H). HRMS calcd. for $C_{22}H_{18}N_6O$ (M+H)$^+$ 383.1620. found 383.1626.

Example 122

Example 122-A 2-(5-methoxy-7-methyl-1-tosyl-1H-indole-4-carbonyl)-1-((2-(trimethylsilyl)ethoxy)methyl)-1H-benzo[d]imidazole-5-carbonitrile and 2-(5-methoxy-7-methyl-1-tosyl-1H-indole-4-carbonyl)-1-((2-(trimethylsilyl)ethoxy)methyl)-1H-benzo[d]imidazole-6-carbonitrile

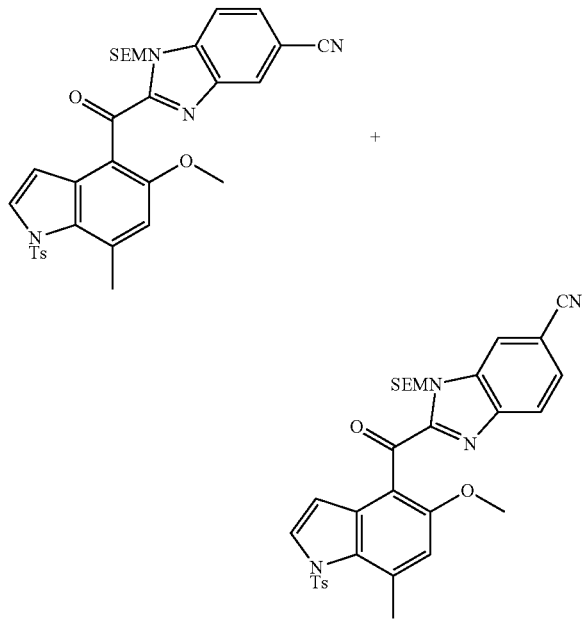

tert-Butyl 4-(5-cyano-1-((2-(trimethylsilyl)ethoxy)methyl)-1H-benzo[d]imidazole-2-carbonyl)-5-methoxy-7-methyl-1H-indole-1-carboxylate and tert-butyl 4-(6-cyano-1-((2-(trimethylsilyl)ethoxy)methyl)-1H-benzo[d]imidazole-2-carbonyl)-5-methoxy-7-methyl-1H-indole-1-carboxylate (Example 25-A) (314 mg, 0.56 mmol) was dissolved in MeOH (5.6 mL) at room temperature, then $Cs_2CO_3$ (912 mg, 2.80 mmol) was added and the reaction was stirred at 60° C. After 15 minutes, the reaction was cooled to room temperature, quenched with $NH_4Cl$ (sat. aq. solution) and extracted with EtOAc. The organic extract was dried over $MgSO_4$, filtered and concentrated. The resulting residue (250 mg) was dissolved in DMF (3.4 mL) at 0° C. and sodium hydride (60% in mineral oil, 43.4 mg, 1.086 mmol) was added in portions and the mixture was stirred at room temperature for 20 min. The reaction was then cooled to 0° C. and TsCl (145 mg, 0.760 mmol) was added, and the reaction was stirred at room temperature. After 1 hour the reaction was quenched with $H_2O$, the layers were separated and the aqueous layer was extracted with EtOAc. The organic layers were combined and washed with water, dried over $MgSO_4$, filtered and concentrated. The resulting residue was purified by flash chromatography (0-70% EtOAc:Heptanes) to give the title compounds as a mixture. MS (ESI+) m/z 615.3 (M+H).

Example 122-B 2-(2-(5-Methoxy-7-methyl-1-tosyl-1H-indol-4-yl)propan-2-yl)-1H-benzo[d]imidazole-5-carbonitrile

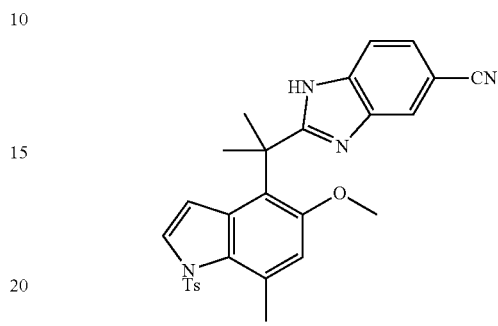

To DCM (1.4 mL) at −40° C. was added $TiCl_4$ (1.0M in DCM, 3.9 mL, 3.92 mmol) and then dimethylzinc (1.0M in Heptane, 3.92 mL, 3.92 mmol). After 15 minutes, a solution of a mixture of 2-(5-methoxy-7-methyl-1-tosyl-1H-indole-4-carbonyl)-1-((2-(trimethylsilyl)ethoxy)methyl)-1H-benzo[d]imidazole-5-carbonitrile and 2-(5-methoxy-7-methyl-1-tosyl-1H-indole-4-carbonyl)-1-((2-(trimethylsilyl)ethoxy)methyl)-1H-benzo[d]imidazole-6-carbonitrile (201 mg, 0.327 mmol) in DCM (2.0 mL) was added. The mixture was allowed to warm to room temperature. After stirring overnight the reaction was diluted with water, the layers were separated and the aqueous layer was extracted with EtOAc. The combined organic phases were dried over $MgSO_4$, filtered and concentrated. The resulting residue was purified by $SiO_2$ flash chromatography (0-80% EtOAc in heptanes) to provide the title compound. MS (ESI+) m/z 499.1 (M+H).

Example 122-C 2-(2-(5-Methoxy-7-methyl-1H-indol-4-yl)propan-2-yl)-1H-benzo[d]imidazole-5-carbonitrile

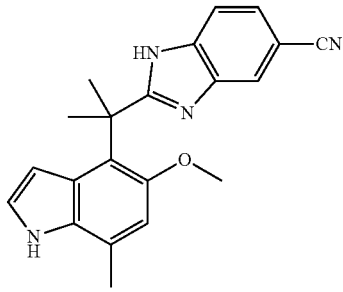 [SMILES: COc1cc(C)c2[nH]ccc2c1C(C)(C)c1nc2cc(C#N)ccc2[nH]1]

A solution of 2-(2-(5-methoxy-7-methyl-1-tosyl-1H-indol-4-yl)propan-2-yl)-1H-benzo[d]imidazole-5-carbonitrile (43 mg, 0.086 mmol) and KOH (48.4 mg, 0.862 mmol) and isoamylamine (150 μL, 1.29 mmol) in EtOH (1.2 mL) was heated at 100° C. under microwave irradiation for 2 h. The reaction mixture was loaded onto silica gel and was purified by silica gel flash chromatography (0-50% EtOAc:DCM), and then SFC using a 2-ethylpyridine column with 12%

MeOH+0.2% DEA in $CO_2$. $^1$H NMR (400 MHz, DMSO-$d_6$) δ ppm 12.19 (s, 1H) 10.88 (br. s., 1H) 8.08 (m) 7.66-7.76 (m) 7.37-7.53 (m) 7.04-7.18 (m, 1H) 6.73 (s, 1H) 5.89 (m) 5.83 (m) 3.45 (m) 3.43 (m) 2.43 (s, 3H) 1.90 (s, 6H). HRMS calcd. for $C_{21}H_{20}N_4O$ (M+H)$^+$ 345.1715. found 345.1724.

Example 123

2-((5,7-Dimethylindolin-4-yl)methyl)-1H-benzo[d]imidazole-5-carbonitrile

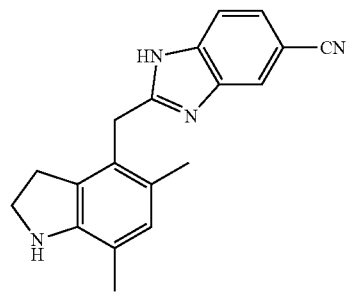 [SMILES: Cc1cc(C)c2c(c1Cc1nc3cc(C#N)ccc3[nH]1)CCN2]

2-((5,7-Dimethyl-1H-indol-4-yl)methyl)-1H-benzo[d]imidazole-5-carbonitrile (35 mg, 0.117 mmol) was suspended in DCM (1 mL), triethylsilane (0.37 mL, 2.33 mmol) and then TFA (0.5 mL) were added and the reaction was stirred at room temperature. After 1 hour the reaction was concentrated and then the resulting residue was dissolved in EtOAc and treated with 1 mL of aq. ammonium hydroxide. The residue was purified via FCC (0-100% EtOAc in heptanes) to obtain the title compound. $^1$H NMR (400 MHz, DMSO-$d_6$) δ ppm 12.47 (d, J=15.66 Hz, 1H) 8.02 (m) 7.88 (m) 7.56 (m) 7.50-7.54 (m) 6.60 (s, 1H) 5.08 (br. s., 1H) 4.08 (d, J=3.54 Hz, 2H) 3.40 (t, J=8.46 Hz, 2H) 2.91 (t, J=8.46 Hz, 2H) 2.09 (s, 3H) 1.94-2.03 (m, 3H). HRMS calcd. for $C_{19}H_{18}N_4$ (M+H)$^+$, 303.1604. found 303.1615.

Example 124 a) (±)-2-(1-Methoxy-1-(5-methoxy-7-methylindolin-4-yl)ethyl)-1H-benzo[d]imidazole-5-carbonitrile

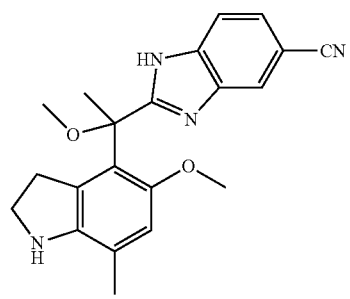 [SMILES: COc1cc(C)c2c(c1C(C)(OC)c1nc3cc(C#N)ccc3[nH]1)CCN2]

(±)-2-(1-Methoxy-1-(5-methoxy-7-methyl-1H-indol-4-yl)ethyl)-1H-benzo[d]imidazole-5-carbonitrile (Example 27-B) (0.213 g, 0.591 mmol) was dissolved in acetic acid (1.970 mL), and sodium cyanoborohydride (0.12 g, 1.910 mmol) was added at room temperature. The reaction was stirred at the same temperature for 1 hour. The reaction was placed in an ice bath and quenched with 1N aq. NaOH (20 mL) until pH>7. EtOAc was added and the organic layer was removed, dried over $MgSO_4$ and concentrated. The resulting residue was purified by flash chromatography (0-100% EtOAc in heptanes) to give the title compound. $^1$H NMR (400 MHz, CHLOROFORM-d) δ ppm 8.11 (s) 7.84 (m) 7.65 (s) 7.43-7.54 (m, 1H) 7.34-7.42 (m) 6.43 (s, 1H) 3.50-3.59 (m, 2H) 3.27-3.36 (m, 2H) 3.24 (s, 3H) 3.12 (s, 3H) 2.13 (s, 3H) 2.05 (s, 3H). HRMS calcd. for $C_{21}H_{22}N_4O_2$ (M+H)$^+$, 303.1604. found 303.1615 b) (+) and (−)-2-(1-Methoxy-1-(5-methoxy-7-methylindolin-4-yl)ethyl)-1H-benzo[d]imidazole-5-carbonitrile Resolution of the enantiomers of 2-(1-Methoxy-1-(5-methoxy-7-methylindolin-4-yl)ethyl)-1H-benzo[d]imidazole-5-carbonitrile was achieved by chiral SFC using a CHIRALPAK® AD-H column with 18% IPA (0.2% DEA) in $CO_2$ to give (−)-2-(1-methoxy-1-(5-methoxy-7-methylindolin-4-yl)ethyl)-1H-benzo[d]imidazole-5-carbonitrile ($t_r$=4.3 min) and (+)-2-(1-methoxy-1-(5-methoxy-7-methylindolin-4-yl)ethyl)-1H-benzo[d]imidazole-5-carbonitrile ($t_r$=5.2 min).

Example 125

Example 125-A (±)-tert-Butyl 4-((5-cyanobenzo[d]oxazol-2-yl)(hydroxy)methyl)-5-methoxy-7-methyl-1H-indole-1-carboxylate

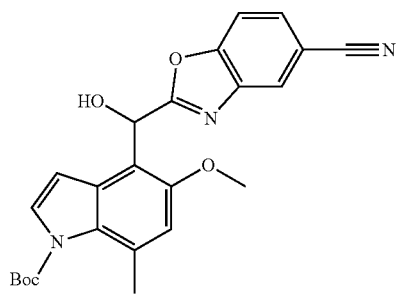 [SMILES: COc1cc(C)c2c(ccn2C(=O)OC(C)(C)C)c1C(O)c1nc2cc(C#N)ccc2o1]

To a solution of benzo[d]oxazole-5-carbonitrile (CAS #:132227-01-1) (0.996 g, 6.91 mmol) in THF (20 mL), TMP-MgCl.LiCl (1 M in THF) (6.91 mL, 6.91 mmol) was added at −78° C. After stirring for 30 min, tert-butyl 4-formyl-5-methoxy-7-methyl-1H-indole-1-carboxylate (Example 19-D) (1.00 g, 3.46 mmol) was added at −78° C. Then, the reaction mixture was warmed to rt. After stirring for 10 min, the reaction was heated at 50° C. After stirring for 1.5 h, the reaction mixture was cooled to rt, and diluted with aq. $NH_4Cl$ and brine. The layers were separated and the aqueous layer was extracted with EtOAc. The combined organic layers were washed with a 1:1 solution of 1M aq. $NaHSO_4$ and brine, dried over $Na_2SO_4$, filtered, and concentrated. The residue was purified by flash column chromatography on silica gel (heptane/EtOAc=100:0 to 40:60) to give the title compound. MS (ESI) m/z 432.3 (MH).

Example 125-B a) (±)-2-(hydroxy(5-methoxy-7-methyl-1H-indol-4-yl)methyl)benzo[d]oxazole-5-carbonitrile

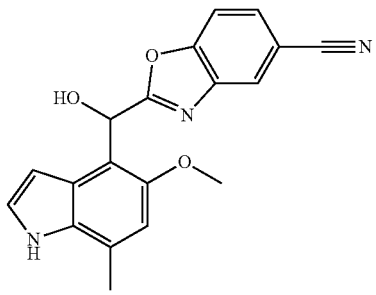 [SMILES: COc1cc(C)c2[nH]ccc2c1C(O)c1nc2cc(C#N)ccc2o1]

A suspension of tert-butyl 4-((5-cyanobenzo[d]oxazol-2-yl)(hydroxy)methyl)-5-methoxy-7-methyl-1H-indole-1-carboxylate (1.10 g, 2.54 mmol) and $Cs_2CO_3$ (1.65 g, 5.08 mmol) in MeOH (25 mL) was allowed to stir at 60° C. for 4 h. The reaction mixture was cooled to rt and diluted with EtOAc (50 mL). The mixture was concentrated to half of the initial volume. The mixture was then diluted with brine and 1M aq. $NaHSO_4$. The organic layer was separated. The aqueous layer was extracted with EtOAc. The combined organic phase was washed with brine, dried over $Na_2SO_4$, filtered, and concentrated. The residue was purified by flash column chromatography on silica gel (heptane/EtOAc=100:0 to 30:70) to give the title compound. $^1$H NMR (400 MHz, $CD_3OD$) δ ppm 8.08 (t, J=1.07 Hz, 1H), 7.68 (s, 2H), 7.17 (d, J=3.15 Hz, 1H), 6.77 (s, 1H), 6.69 (s, 1H), 6.53 (d, J=3.15 Hz, 1H), 3.81 (s, 3H), 2.50 (s, 3H). HRMS calcd. for $C_{19}H_{15}N_3O_3$ $(M+H)^+$ 334.1192. found 334.1191.

b) (+) and (−)-2-(hydroxy(5-methoxy-7-methyl-1H-indol-4-yl)methyl)benzo[d]oxazole-5-carbonitrile Resolution of the enantiomers of 2-(hydroxy(5-methoxy-7-methyl-1H-indol-4-yl)methyl)benzo[d]oxazole-5-carbonitrile was achieved by chiral HPLC using a CHIRALCEL®OD-H column with 30% EtOH in heptane to give (+)-2-(hydroxy(5-methoxy-7-methyl-1H-indol-4-yl)methyl)benzo[d]oxazole-5-carbonitrile ($t_r$=10.1 min) and (−)-2-(hydroxy(5-methoxy-7-methyl-1H-indol-4-yl)methyl)benzo[d]oxazole-5-carbonitrile ($t_r$=15.4 min).

Example 126

Example 126-A tert-Butyl 4-(5-cyanobenzo[d]oxazole-2-carbonyl)-5-methoxy-7-methyl-1H-indole-1-carboxylate

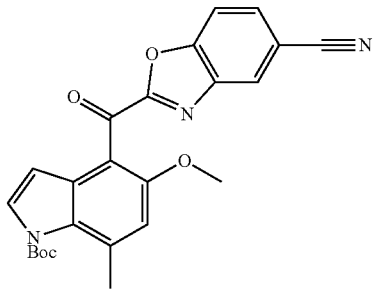 [SMILES: COc1cc(C)c2c(ccn2C(=O)OC(C)(C)C)c1C(=O)c1nc2cc(C#N)ccc2o1]

tert-Butyl-4-((5-cyanobenzo[d]oxazol-2-yl)(hydroxy)methyl)-5-methoxy-7-methyl-1H-indole-1-carboxylate (163 mg, 0.376 mmol) was dissolved in DCM (3.76 mL) and $MnO_2$ (327 mg, 3.76 mmol) was added. The reaction mixture was stirred at rt for 15 h. The reaction mixture was filtered through Celite® and washed three times with DCM. The filtrate was evaporated to dryness to give the title compound. MS (ESI+) m/z 432.16 (M+H).

Example 126-B (±)-tert-Butyl-4-(1-(5-cyanobenzo[d]oxazol-2-yl)-1-hydroxyethyl)-5-methoxy-7-methyl-1H-indole-1-carboxylate

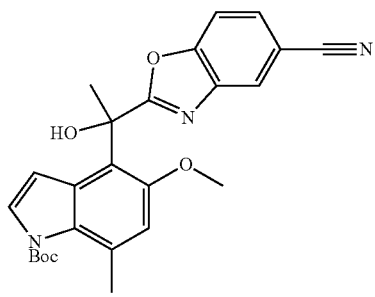 [SMILES: COc1cc(C)c2c(ccn2C(=O)OC(C)(C)C)c1C(C)(O)c1nc2cc(C#N)ccc2o1]

To a solution of tert-butyl 4-(5-cyanobenzo[d]oxazole-2-carbonyl)-5-methoxy-7-methyl-1H-indole-1-carboxylate (600 mg, 1.39 mmol) in THF (14 mL) at 0° C. methylmagnesium chloride, 3M in THF (1.39 mL, 4.17 mmol) was added. The reaction mixture was stirred for 15 min and then quenched with a saturated aq. solution of $NH_4Cl$ at 0° C. The layers were separated and the aqueous layer was extracted with EtOAc. The organic phase was dried over $MgSO_4$ filtered and concentrated. The resulting residue was absorbed onto silica and purified by flash chromatography (0-50% EtOAc:heptanes) to give the title compound. MS (ESI+) m/z 448.22 (M+H).

Example 126-C a) (±)-2-(1-hydroxy-1-(5-methoxy-7-methyl-1H-indol-4-yl)ethyl)benzo[d]oxazole-5-carbonitrile

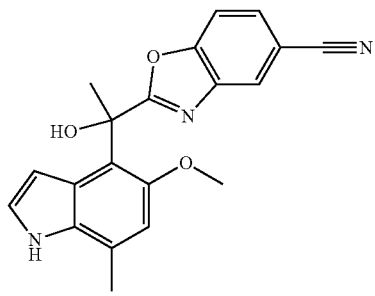 [SMILES: COc1cc(C)c2[nH]ccc2c1C(C)(O)c1nc2cc(C#N)ccc2o1]

A suspension of (±)-tert-butyl-4-(1-(5-cyanobenzo[d]oxazol-2-yl)-1-hydroxyethyl)-5-methoxy-7-methyl-1H-indole-1-carboxylate (6.5 mg, 0.019 mmol) and $Cs_2CO_3$ (146 mg, 0.447 mmol) in MeOH (0.5 mL) was heated at 60° C. and stirred for 30 min. The reaction mixture was cooled to rt, quenched with a saturated aq. solution of ammonium chloride, diluted with AcOEt and water. The layers were separated and the aq. layer was extracted with AcOEt. The combined organic layers were dried over MgSO$_4$, filtered and evaporated to dryness. The resulting residue was purified by flash chromatography (0-50% EtOAc:heptanes) to give the title compound. $^1$H NMR (400 MHz, DMSO-d$_6$) δ ppm 10.88 (br. s., 1H) 8.36 (dd, J=1.39, 0.76 Hz, 1H) 7.65-8.00 (m, 2H) 7.28 (t, J=2.84 Hz, 1H) 6.95 (dd, J=3.03, 2.02 Hz, 1H) 6.62 (s, 1H) 6.31 (s, 1H) 3.19 (s, 3H) 2.44 (d, J=0.51 Hz, 3H) 1.95-2.02 (m, 3H). MS (ESI+) m/z 348.1 (M+H).

b) (+) and (−)-2-(1-hydroxy-1-(5-methoxy-7-methyl-1H-indol-4-yl)ethyl)benzo[d]oxazole-5-carbonitrile Resolution of the enantiomers of 2-(1-hydroxy-1-(5-methoxy-7-methyl-1H-indol-4-yl)ethyl)benzo[d]oxazole-5-carbonitrile was achieved by chiral SFC using a CHIRALPAK® ID column with 25% IPA in CO$_2$ to give (−)-2-(1-hydroxy-1-(5-methoxy-7-methyl-1H-indol-4-yl)ethyl)benzo[d]oxazole-5-carbonitrile (t$_r$=4.6 min) and (+)-2-(1-hydroxy-1-(5-methoxy-7-methyl-1H-indol-4-yl)ethyl)benzo[d]oxazole-5-carbonitrile (t$_r$=7.2 min).

Example 127

Example 127-A (±)-tert-Butyl-4-(1-(5-cyanobenzo[d]oxazol-2-yl)-1-methoxyethyl)-5-methoxy-7-methyl-1H-indole-1-carboxylate

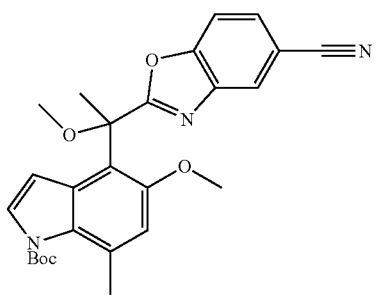 [SMILES: COc1cc(C)c2c(ccn2C(=O)OC(C)(C)C)c1C(C)(OC)c1nc2cc(C#N)ccc2o1]

To a solution of tert-butyl 4-(1-(5-cyanobenzo[d]oxazol-2-yl)-1-hydroxyethyl)-5-methoxy-7-methyl-1H-indole-1-carboxylate (250 mg, 0.559 mmol) in DMF (5.7 mL) at 0° C. was added successively MeI (0.105 mL, 1.676 mmol) and NaH (60% in mineral, 33.5 mg, 0.838 mmol). The reaction mixture was stirred at 0° C. for 1.5 h. The reaction mixture was quenched with 4 mL of saturated aq. solution of ammonium chloride and diluted with water and EtOAc. The layers were separated and the aqueous layer was extracted with EtOAc. The combined organic layers were dried over MgSO$_4$, filtered and concentrated. The resulting residue was purified by flash chromatography (0-30% EtOAc:heptanes) to obtain the title compound. $^1$H NMR (400 MHz, DMSO-d$_6$) δ ppm 8.43 (dd, J=1.52, 0.63 Hz, 1H) 7.79-7.97 (m, 2H) 7.63 (d, J=3.79 Hz, 1H) 7.05 (d, J=3.79 Hz, 1H) 6.83 (s, 1H) 3.23 (s, 3H) 3.17 (s, 3H) 1.81-2.08 (m, 3H) 1.60 (s, 9H).

Example 127-B a) (±)-2-(1-methoxy-1-(5-methoxy-7-methyl-1H-indol-4-yl)ethyl)benzo[d]oxazole-5-carbonitrile

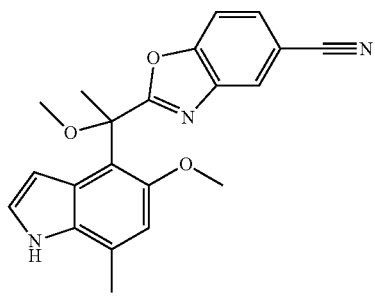

The title compound was synthesized from (±)-tert-butyl-4-(1-(5-cyanobenzo[d]oxazol-2-yl)-1-methoxyethyl)-5-methoxy-7-methyl-1H-indole-1-carboxylate with a similar method as described in Example 126-C. $^1$H NMR (400 MHz, DMSO-d$_6$) δ ppm 8.42 (dd, J=1.58, 0.69 Hz, 1H) 7.78-7.94 (m, 2H) 7.33 (t, J=2.91 Hz, 1H) 6.75 (dd, J=3.09, 1.96 Hz, 1H) 6.66 (s, 1H) 3.19 (s, 3H) 3.17 (s, 3H) 2.45 (s, 3H) 1.98 (s, 3H). MS (ESI−) m/z 360.14 (M−1).

b) (+) and (−)-2-(1-methoxy-1-(5-methoxy-7-methyl-1H-indol-4-yl)ethyl)benzo[d]oxazole-5-carbonitrile Resolution of the enantiomers of 2-(1-methoxy-1-(5-methoxy-7-methyl-1H-indol-4-yl)ethyl)benzo[d]oxazole-5-carbonitrile was achieved by chiral SFC using a CHIRALPAK® AD-H column with 60% EtOH (0.2% DEA) in CO$_2$ to give (+)-2-(1-hydroxy-1-(5-methoxy-7-methyl-1H-indol-4-yl)ethyl)benzo[d]oxazole-5-carbonitrile (t$_r$=6.31 min) and (−)-2-(1-hydroxy-1-(5-methoxy-7-methyl-1H-indol-4-yl) ethyl)benzo[d]oxazole-5-carbonitrile (t$_r$=11.01 min).

Example 128

Example 128-A tert-butyl 4-(1-(5-cyanobenzo[d]oxazol-2-yl)-2,2,2-trifluoro-1-hydroxyethyl)-5-methoxy-7-methyl-1H-indole-1-carboxylate

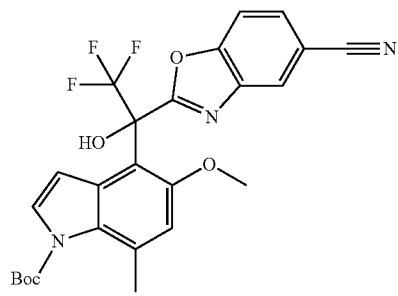 [SMILES: COc1cc(C)c2c(ccn2C(=O)OC(C)(C)C)c1C(O)(c1nc2cc(C#N)ccc2o1)C(F)(F)F]

The title compound was synthesized from tert-butyl 5-methoxy-7-methyl-4-(2,2,2-trifluoroacetyl)-1H-indole-1- carboxylate (Example 35-B) following as similar procedure as described in Example 125-A. MS (ESI+) m/z 502.3 (M+H).

Example 128-B a) (±)-2-(2,2,2-trifluoro-1-hydroxy-1-(5-methoxy-7-methyl-1H-indol-4-yl)ethyl)benzo[d]oxazole-5-carbonitrile

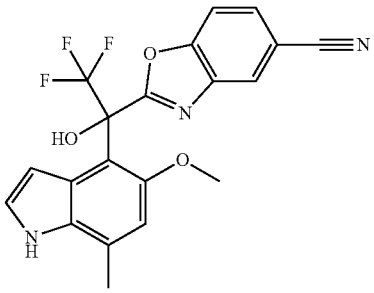

The title compound was synthesized from tert-butyl 4-(1-(5-cyanobenzo[d]oxazol-2-yl)-2,2,2-trifluoro-1-hydroxyethyl)-5-methoxy-7-methyl-1H-indole-1-carboxylate with a similar method as described in Example 126-C. $^1$H NMR (400 MHz, acetonitrile-D3 w/ about 5% $D_2O$) δ ppm 9.46 (br. s, 1H), 8.26 (m, 1H), 7.73-7.79 (m, 1H), 7.22 (d, J=3.28 Hz, 1H), 6.82 (s, 1H), 6.42 (br. d, J=3.16 Hz, 1H), 3.48 (s, 3H), 2.50 (s, 3H). HRMS calcd. for $C_{20}H_{14}F_3N_3O_3$ (M+H)$^+$ 402.1066. found 402.1051.

b) (+) and (−)-2-(2,2,2-trifluoro-1-hydroxy-1-(5-methoxy-7-methyl-1H-indol-4-yl)ethyl)benzo[d] oxazole-5-carbonitrile Resolution of the enantiomers of 2-(2,2,2-trifluoro-1-hydroxy-1-(5-methoxy-7-methyl-1H-indol-4-yl)ethyl)benzo [d]oxazole-5-carbonitrile was achieved by chiral SFC using a CHIRALPAK® ID column with 5-55% 2-propanol in $CO_2$ to give (−)-2-(2,2,2-trifluoro-1-hydroxy-1-(5-methoxy-7-methyl-1H-indol-4-yl)ethyl)benzo[d]oxazole-5-carbonitrile ($t_r$=2.0 min) and (+)-2-(2,2,2-trifluoro-1-hydroxy-1-(5-methoxy-7-methyl-1H-indol-4-yl)ethyl)benzo[d]oxazole-5-carbonitrile ($t_r$=2.3 min).

Example 129

Example 129-A (±)-tert-Butyl 4-(1-(5-cyanobenzo[d]oxazol-2-yl)-2,2,2-trifluoro-1-(2-methoxy-2-oxoethoxy)ethyl)-5-methoxy-7-methyl-1H-indole-1-carboxylate

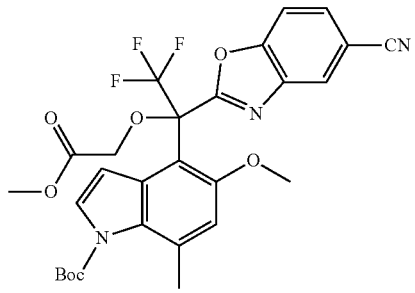 [SMILES: COC(=O)COC(c1nc2cc(C#N)ccc2o1)(c1c(OC)cc(C)c2c1ccn2C(=O)OC(C)(C)C)C(F)(F)F]

The title compound was synthesized from tert-butyl 4-(1-(5-cyanobenzo[d]oxazol-2-yl)-2,2,2-trifluoro-1-hydroxyethyl)-5-methoxy-7-methyl-1H-indole-1-carboxylate (Example 128-A) and methyl 2-bromoacetate following Example 109-A. MS (ESI+) m/z 574.3 (M+H).

Example 129-B (±)-2-(1-(5-cyanobenzo[d]oxazol-2-yl)-2,2,2-trifluoro-1-(5-methoxy-7-methyl-1H-indol-4-yl)ethoxy) acetic acid

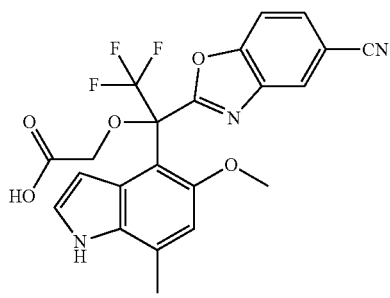 [SMILES: COc1cc(C)c2[nH]ccc2c1C(OCC(=O)O)(c1nc2cc(C#N)ccc2o1)C(F)(F)F]

To a solution of (±)-4-(1-(5-cyanobenzo[d]oxazol-2-yl)-2, 2,2-trifluoro-1-(2-methoxy-2-oxoethoxy)ethyl)-5-methoxy-7-methyl-1H-indole-1-carboxylate (90 mg, 0.157 mmol) in THF (1.5 mL) and MeOH (0.15 mL) was added 1 M aq. NaOH (0.47 mL, 0.47 mmol) and the reaction left to stir at rt for 1 h and then warmed up to 60° C. At this point, 2 M aq. NaOH (0.47 mL, 0.94 mmol) was added and the reaction mixture was stirred for 2 h. The reaction mixture was cooled to rt and diluted with 1M aq.KHSO$_4$, brine and EtOAc. The organic layer was separated, dried over Na$_2$SO$_4$, filtered, and concentrated. The resulting residue was purified by RP-HPLC (HC-A) to give the title compound. $^1$H NMR (TFA salt, 400 MHz, CD$_3$OD) δ ppm 8.21 (br. t, J=1.07 Hz, 1H), 7.80-7.81 (m, 2H), 7.35 (br. t, 1H), 6.82 (br. d, J=2.65 Hz, 1H), 6.72 (s, 1H), 4.32-4.46 (m, 2H) 3.20 (s, 3H), 2.54 (s, 3H). HRMS calcd. for $C_{22}H_{16}F_3N_3O_5$ (M+H)$^+$ 460.1120. found 460.1114.

Example 130

Example 130-A (±)-tert-Butyl 4-((tert-butylsulfinylimino)(5-cyanobenzo[d]oxazol-2-yl)methyl)-5-methoxy-7-methyl-1H-indole-1-carboxylate

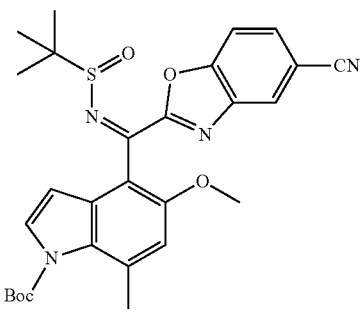 [SMILES: COc1cc(C)c2c(ccn2C(=O)OC(C)(C)C)c1/C(=N/S(=O)C(C)(C)C)c1nc2cc(C#N)ccc2o1]

To a solution of tert-butyl 4-(5-cyanobenzo[d]oxazole-2-carbonyl)-5-methoxy-7-methyl-1H-indole-1-carboxylate (Example 126-A) (711 mg, 1.648 mmol) and 2-methyl-2-propanesulfinamide (599 mg, 4.94 mmol) in toluene (16.5 mL), Zr(O-t-Bu)$_4$ (4.33 mL, 8.24 mmol) was added at room temperature. After 2 hours the reaction mixture was diluted with EtOAc and brine. The resulting mixture was filtered through Celite® and the organic layer of the filtrate was dried over MgSO$_4$, filtered, and concentrated. The resulting residue was purified by flash chromatography (0-80% EtOAc:Heptanes) to provide the title compound. MS (ESI+) m/z 535.2 (M+H).

Example 130-B (±)-2-(1-Amino-2,2,2-trifluoro-1-(5-methoxy-7-methyl-1H-indol-4-yl)ethyl)benzo[d]oxazole-5-carbonitrile

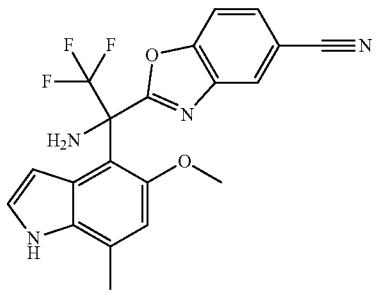 [SMILES: COc1cc(C)c2[nH]ccc2c1C(N)(c1nc2cc(C#N)ccc2o1)C(F)(F)F]

To a suspension of (±)-tert-butyl 4-((tert-butylsulfinylimino)(5-cyanobenzo[d]oxazol-2-yl)methyl)-5-methoxy-7-methyl-1H-indole-1-carboxylate (56 mg, 0.105 mmol) and tetramethylammonium fluoride (29.3 mg, 0.314 mmol) in THF (1 mL), TESCF$_3$ (38.6 mg, 0.209 mmol) was added at 0° C. Then, the reaction mixture was allowed to reach rt. After stirring for 2 h, additional tetramethylammonium fluoride (9.76 mg, 0.105 mmol) and TESCF$_3$ (38.6 mg, 0.209 mmol) were added. After stirring for 0.5 h at rt, the reaction was diluted with aq. NH$_4$Cl and brine. The layers were separated and the aqueous layer was extracted with EtOAc. The organic layer was washed with brine, dried over Na$_2$SO$_4$, filtered, and concentrated. The resulting residue was dissolved in HCl (1.25 M in MeOH) (0.840 mL, 1.050 mmol) and stirred at rt for 15 min. At this point the reaction was warmed to 50° C. and heated at this temperature for 45 minutes. The mixture was concentrated and the resulting residue was dissolved in MeOH (1 mL). Cs$_2$CO$_3$ (137 mg, 0.420 mmol) was added and the mixture was stirred at 60° C. for 1.5 h. At this point an additional aliquot of Cs$_2$CO$_3$ (137 mg, 0.420 mmol) was added. After stirring for 50 min, the reaction mixture was cooled to rt, concentrated, and then diluted with aq. NH$_4$Cl, brine and EtOAc. The layers were separated and the aqueous layer extracted with EtOAc. The combined organic layers were washed with brine, dried over Na$_2$SO$_4$, filtered, and concentrated. The resulting residue was purified by flash column chromatography on silica gel (heptane/EtOAc=100:0 to 35:65). $^1$H NMR (400 MHz, CD$_2$Cl$_2$) δ ppm 8.15-8.17 (br. m, 1H), 8.02 (d, J=1.26 Hz, 1H), 7.57 (m, 1H), 7.48 (m, 1H), 7.18 (dd, J=3.03, 2.78 Hz, 1H), 6.95 (br. s, 1H), 6.62 (s, 1H), 3.28 (s, 3H), 2.43 (s, 3H). HRMS calcd. for C$_{20}$H$_{15}$F$_3$N$_4$O$_2$ (M+H)$^+$ 401.1220. found 401.1221.

Example 131

Example 131-A (±)-tert-Butyl 4-(1-(5-cyanobenzo[d]oxazol-2-yl)-1-(1,1-dimethylethylsulfinamido)ethyl)-5-methoxy-7-methyl-1H-indole-1-carboxylate

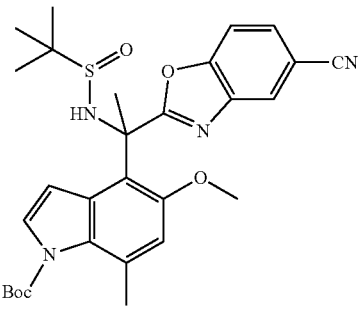 [SMILES: COc1cc(C)c2c(ccn2C(=O)OC(C)(C)C)c1C(C)(NS(=O)C(C)(C)C)c1nc2cc(C#N)ccc2o1]

To a solution of tert-butyl 4-((tert-butylsulfinyl)imino)(5-cyanobenzo[d]oxazol-2-yl)methyl)-5-methoxy-7-methyl-1H-indole-1-carboxylate (Example 130-A) (0.56 g, 1.047 mmol) in THF (10.47 mL), MeMgCl (3M in THF, 1.047 mL, 3.14 mmol) was added at 0° C. After 10 minutes the mixture was diluted with sat. aq. NH$_4$Cl and EtOAc. The aqueous layer was extracted with EtOAc, and the organic extract was dried over MgSO$_4$, filtered and concentrated. The product was purified by flash chromatography (0-100% EtOAc:Heptanes) to provide the title compound. MS (ESI+) m/z 551.2 (M+H).

Example 131-B a) (±)-2-(1-Amino-1-(5-methoxy-7-methyl-1H-indol-4-yl)ethyl)benzo[d]oxazole-5-carbonitrile

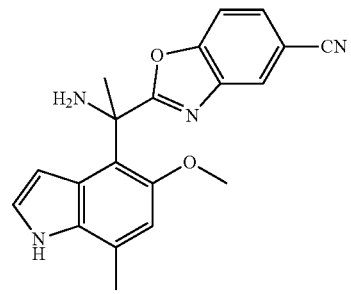 [SMILES: COc1cc(C)c2[nH]ccc2c1C(C)(N)c1nc2cc(C#N)ccc2o1]

To a solution of tert-butyl 4-(1-(5-cyanobenzo[d]oxazol-2-yl)-1-(1,1-dimethylethylsulfinamido)ethyl)-5-methoxy-7-methyl-1H-indole-1-carboxylate (120 mg, 0.218 mmol) in dioxane (1 mL) was added 4M HCl in dioxane (2.2 mL, 8.72 mmol) and the mixture was stirred at 60° C. After 2 hours the reaction was cooled in an ice bath and quenched with 30% aq. NH$_4$OH (2.18 mL). Water was added, the layers were separated and the aqueous layer was extracted with EtOAc, dried over MgSO$_4$, filtered and concentrated. The resulting residue was purified by flash chromatography (0-100% EtOAc:Heptanes) to provide the title compound. ¹H NMR (400 MHz, DMSO-d₆) δ ppm 10.92 (br. s., 1H) 8.29 (dd, J=1.39, 0.88 Hz, 1H) 7.72-7.85 (m, 2H) 7.28 (t, J=2.84 Hz, 1H) 7.05-7.16 (m, 1H) 6.64 (s, 1H) 3.19 (s, 3H) 2.59 (br. s., 2H) 2.43 (s, 3H) 1.90 (s, 3H). HRMS calcd. for $C_{20}H_{18}N_4O_2$ (M+H)⁺ 347.1503. found 347.1486.

b) (+) and (−)-2-(1-amino-1-(5-methoxy-7-methyl-1H-indol-4-yl)ethyl)benzo[d]oxazole-5-carbonitrile Resolution of the enantiomers of 2-(1-amino-1-(5-methoxy-7-methyl-1H-indol-4-yl)ethyl)benzo[d]oxazole-5-carbonitrile was achieved by chiral SFC using a (S,S)-Whelk-O® 1 column with 35% MeOH with 5 mM NH₄OH in CO₂ to give (+)-2-(1-amino-1-(5-methoxy-7-methyl-1H-indol-4-yl)ethyl)benzo[d]oxazole-5-carbonitrile ($t_r$=3.0 min) and (−)-2-(1-amino-1-(5-methoxy-7-methyl-1H-indol-4-yl)ethyl)benzo[d]oxazole-5-carbonitrile ($t_r$=4.4 min).

Example 132

Example 132-A (±)-tert-Butyl 4-((6-cyanobenzo[d]thiazol-2-yl)(hydroxy)methyl)-5-methoxy-7-methyl-1H-indole-1-carboxylate

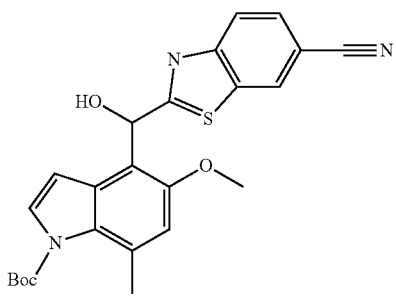

To a solution of 6-cyanobenzothiazol (CAS #:58249-61-9) (54.60 mg, 0.341 mmol) in THF (1.06 mL), LDA in Heptane/THF/Ethylbenzene (205 uL, 0.409 mmol) was added at −78° C. After 20 mins, a solution of tert-butyl 4-formyl-5-methoxy-7-methyl-1H-indole-1-carboxylate (Example 19-D) (79 mg, 0.273 mmol) in THF (1.68 mL) was added to the reaction mixture at −78° C. After stirring for 1.5 h, the reaction was quenched with MeOH, sat. aq. NH₄Cl solution and brine. The layers were separated and the aqueous layer was extracted with EtOAc. The combined organic layers were dried over MgSO₄, filtered, concentrated, and purified using FCC eluting with Heptane/EtOAc to provide the title compound. MS (ESI−) m/z 448 (M−H).

Example 132-B (±)-2-(hydroxy(5-methoxy-7-methyl-1H-indol-4-yl)methyl)benzo[d]thiazole-6-carbonitrile

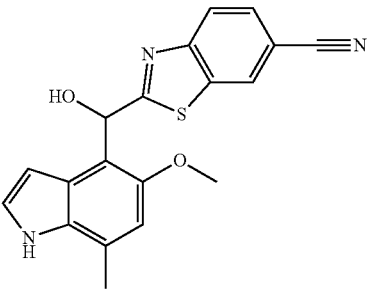 [SMILES: COc1cc(C)c2[nH]ccc2c1C(O)c1nc2ccc(C#N)cc2s1]

tert-Butyl 4-((6-cyanobenzo[d]thiazol-2-yl)(hydroxy)methyl)-5-methoxy-7-methyl-1H-indole-1-carboxylate (40 mg, 0.089 mmol) and Cs₂CO₃ (145 mg, 0.445 mmol) were mixed in THF (0.5 mL) and MeOH (0.5 mL), and stirred at 65° C. for 2 hours. NaBH₄ (67 mg, 1.78 mmol) was added to the reaction mixture and stirred at rt for 1 hour to reduce the oxidative by-products. The reaction mixture was then concentrated dissolved in MeOH and purified with HPLC (HC-B) to provide the title compound. ¹H NMR (400 MHz, CD₃OD) δ ppm 8.45 (d, J=1.01 Hz, 1H) 7.92 (d, J=8.59 Hz, 1H) 7.73 (dd, J=8.59, 1.52 Hz, 1H) 7.15 (d, J=3.28 Hz, 1H) 6.62-6.88 (m, 2H) 6.42 (d, J=3.03 Hz, 1H) 3.82 (s, 3H) 2.50 (s, 3H). HRMS calcd. for $C_{13}H_{15}N_3O_2S$ (M+H)⁺ 350.0958. found 350.096.

Example 133

Example 133-A (±)-tert-Butyl 4-((6-cyanobenzofuran-2-yl)(hydroxy)methyl)-5-methoxy-7-methyl-1H-indole-1-carboxylate

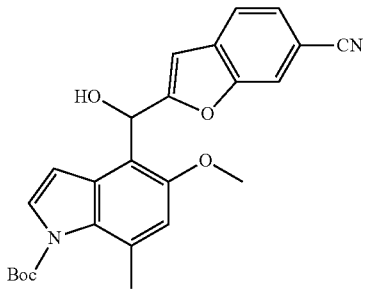 [SMILES: COc1cc(C)c2c(ccn2C(=O)OC(C)(C)C)c1C(O)c1cc2ccc(C#N)cc2o1]

To a solution of benzofuran-6-carbonitrile (CAS #: 17450-68-9) (29.7 mg, 0.207 mmol) in THF (1.7 mL), 1.8M LDA (heptane/THF/ethylbenzene, 0.125 mL, 0.225 mmol) was added at −78° C. After stirring for 30 min., a solution of tert-butyl 4-formyl-5-methoxy-7-methyl-1H-indole-1-carboxylate (Example 19-D) (50 mg, 0.173 mmol) in THF (1.0 mL) was added to the reaction mixture at the same temperature. After stirring for 5 minutes the reaction mixture was diluted with MeOH (1 mL), sat. aq. NH₄Cl (5 mL), brine (5 mL) and EtOAc (10 mL). The layers were separated and the aqueous layer was extracted with EtOAc. The organic layer was dried over MgSO$_4$, filtered, and concentrated. The resulting residue was purified by flash column chromatography to provide the title compound. $^1$H NMR (400 MHz, DMSO-d$_6$) δ ppm 8.07 (s, 1H) 7.68-7.80 (m, 1H) 7.60 (dd, J=8.08, 1.52 Hz, 1H) 7.52 (d, J=3.79 Hz, 1H) 6.91 (s, 1H) 6.72-6.86 (m, 2H) 6.49 (dd, J=4.80, 1.01 Hz, 1H) 6.32 (d, J=5.05 Hz, 1H) 3.85 (s, 3H) 2.53 (s, 3H) 1.51-1.61 (m, 9H).

Example 133-B (±)-2-(hydroxy(5-methoxy-7-methyl-1H-indol-4-yl)methyl)benzofuran-6-carbonitrile

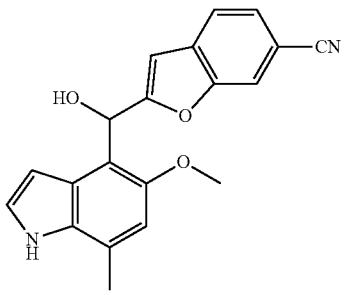 [SMILES: COc1cc(C)c2[nH]ccc2c1C(O)c1cc2ccc(C#N)cc2o1]

To a solution of tert-butyl 4-((6-cyanobenzofuran-2-yl)(hydroxy)methyl)-5-methoxy-7-methyl-1H-indole-1-carboxylate (28 mg, 0.065 mmol) in MeOH (0.65 mL) at room temperature, Cs$_2$CO$_3$ (105 mg, 0.324 mmol) was added and the reaction was stirred at 60° C. After 30 minutes the reaction was cooled to room temperature and quenched with sat. aq. NH$_4$Cl. The layers were separated and the aqueous layer was extracted with EtOAc. The combined organic phases were dried over MgSO$_4$, filtered and concentrated. The resulting residue was purified by flash chromatography (0-80% EtOAc:Heptanes) to provide the title compound. $^1$H NMR (400 MHz, DMSO-d$_6$) δ ppm 10.86 (br. s., 1H) 8.03 (s, 1H) 7.66-7.78 (m, 1H) 7.58 (dd, J=8.08, 1.39 Hz, 1H) 7.18 (t, J=2.78 Hz, 1H) 6.83 (t, J=1.07 Hz, 1H) 6.76 (s, 1H) 6.41-6.55 (m, 2H) 6.03 (d, J=4.93 Hz, 1H) 3.80 (s, 3H) 2.39-2.47 (m, 3H). HRMS calcd. for C$_{20}$H$_{16}$N$_2$O$_3$ (M+H)$^+$ 333.1234. found 333.1237.

Example 134

(±)-2-(hydroxy(5-methoxy-7-methyl-1H-indol-4-yl)methyl)benzofuran-5-carbonitrile

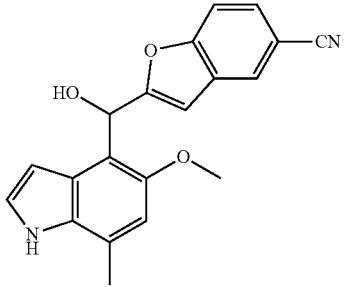 [SMILES: COc1cc(C)c2[nH]ccc2c1C(O)c1cc2cc(C#N)ccc2o1]

The title compound was prepared in the same manner as described in Example 133 using benzofuran-5-carbonitrile (CAS #: 79002-39-4) instead of benzofuran-6-carbonitrile in Example 133-A. $^1$H NMR (400 MHz, DMSO-d$_6$) δ ppm 10.86 (br. s., 1H) 8.08 (dd, J=1.52, 0.76 Hz, 1H) 7.56-7.71 (m, 2H) 7.19 (t, J=2.78 Hz, 1H) 6.70-6.79 (m, 2H) 6.43-6.54 (m, 2H) 6.01 (d, J=4.93 Hz, 1H) 3.80 (s, 3H) 2.41-2.47 (m, 3H). HRMS calcd. for C$_{20}$H$_{16}$N$_2$O$_3$ (M+H)$^+$ 333.1234. found 333.1235.

Example 135

Example 135-A

1((2-(trimethylsilyl)ethoxy)methyl)-1H-indole-6-carbonitrile

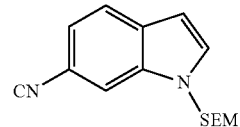

1H-Indole-6-carbonitrile (CAS #:15861-36-6) (1.47 g, 10.34 mmol) was dissolved in DMF (103 mL) and cooled to 0° C. NaH (60% in mineral oil, 0.620 g, 15.51 mmol) was added in one batch. The reaction was allowed to stir at room temperature for 15 minutes. SEMCl (2.38 mL, 13.44 mmol) was added at 0° C. and stirred for 20 minutes. The reaction was quenched with saturated ammonium chloride and then EtOAc was added. The organic layer was removed and the water layer was extracted again with EtOAc. The combined organics were washed with water, dried over MgSO$_4$ filtered and concentrated. The resulting residue was purified via flash chromatography (0-50% EtOAc:heptanes) to obtain title compound. MS (ESI+) m/z 273.23 (M+H).

Example 135-B (±)-tert-Butyl-4-((6-cyano-1-((2-(trimethylsilyl)ethoxy)methyl)-1H-indol-2-yl)(hydroxy)methyl)-5-methoxy-7-methyl-1H-indole-1-carboxylate

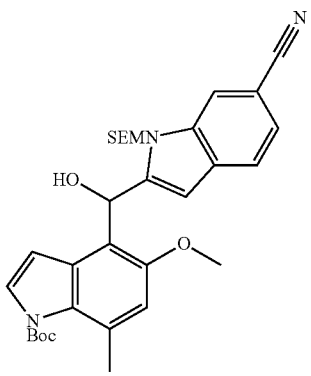 [SMILES: COc1cc(C)c2c(ccn2C(=O)OC(C)(C)C)c1C(O)c1cc2ccc(C#N)cc2n1COCC[Si](C)(C)C]

To a solution of 1-((2-(trimethylsilyl)ethoxy)methyl)-1H-indole-6-carbonitrile (424 mg, 1.55 mmol) in THF (0.7 mL), 1.8 M LDA in heptane/THF/ethylbenzene (139 mg, 1.29 mmol) was added at −78° C. The reaction was stirred at −78° C. for 30 minutes. tert-Butyl 4-formyl-5-methoxy-7-methyl-1H-indole-1-carboxylate (Example 19-D) (250 mg, 0.86 mmol) in THF (0.7 mL) was added at −78° C. The reaction was quenched with MeOH and then a saturated aq. ammonium chloride solution. The mixture was then diluted with EtOAc and the organic layer was removed, dried over MgSO$_4$, filtered and concentrated. The resulting residue was purified via flash chromatography (0-40% EtOAc:heptanes) to obtain the title compound. $^1$H NMR (400 MHz, DMSO-d$_6$) d ppm 8.06 (s, 1H) 7.61 (d, J=8.34 Hz, 1H) 7.51 (d, J=3.79 Hz, 1H) 7.34 (dd, J=8.21, 1.39 Hz, 1H) 6.91 (s, 1H) 6.79 (d, J=3.79 Hz, 1H) 6.63-6.71 (m, 1H) 6.20 (s, 1H) 6.09 (d, J=4.80 Hz, 1H) 5.57-5.74 (m, 2H) 3.81 (s, 3H) 3.40 (ddd, J=9.22, 6.82, 2.15 Hz, 2H) 2.55 (s, 3H) 1.50-1.63 (m, 9H) 0.78 (td, J=9.28, 6.95 Hz, 2H) −0.13--0.09 (m, 9H).

Example 135-C (±)-2-(hydroxy(5-methoxy-7-methyl-1H-indol-4-yl)methyl)-1H-indole-6-carbonitrile

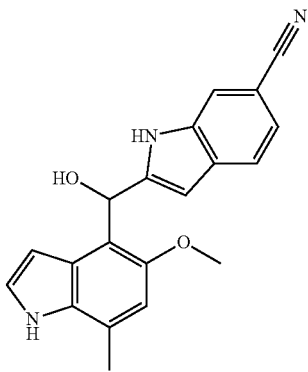 [SMILES: COc1cc(C)c2[nH]ccc2c1C(O)c1cc2ccc(C#N)cc2[nH]1]

tert-Butyl-4-((6-cyano-1-((2-(trimethylsilyl)ethoxy)methyl)-1H-indol-2-yl)(hydroxy)methyl)-5-methoxy-7-methyl-1H-indole-1-carboxylate (70 mg, 0.125 mmol) was dissolved in THF (1.3 mL) and TBAF (1.3 mL, 1.246 mmol) was added. Ethylenediamine (0.084 mL, 1.25 mmol) was then added. The reaction was heated at 65° C. for 4 days. The reaction cooled to room temperature and quenched with saturated aq. ammonium chloride (10 mL) and then diluted with DCM. The layers were separated and the organic layer was washed with water, dried over MgSO$_4$ filtered and concentrated. The resulting residue was absorbed onto silica and purified via flash chromatography (0-75% EtOAc:heptanes) to obtain the title compound. $^1$H NMR (400 MHz, DMSO-d$_6$) δ ppm 11.39 (s, 1H) 10.80 (s, 1H) 7.66-7.85 (m, 1H) 7.50 (d, J=8.08 Hz, 1H) 7.21 (dd, J=8.15, 1.45 Hz, 1H) 7.14 (t, J=2.78 Hz, 1H) 6.76 (s, 1H) 6.56 (d, J=4.42 Hz, 1H) 6.42 (dd, J=3.03, 2.02 Hz, 1H) 6.07-6.14 (m, 1H) 5.88 (d, J=4.55 Hz, 1H) 3.82 (s, 3H) 2.45 (d, J=0.63 Hz, 3H). MS (ESI−) m/z 330.05 (M−H).

Example 136

(±)-2-(hydroxy(5-methoxy-7-methyl-1H-indol-4-yl)methyl)-1H-indol-5-carbonitrile

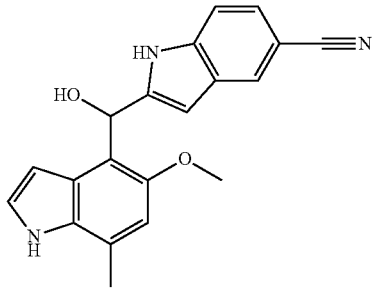 [SMILES: COc1cc(C)c2[nH]ccc2c1C(O)c1cc2cc(C#N)ccc2[nH]1]

The title compound was prepared in the same manner as described in Example 135 using 1H-indole-5-carbonitrile (CAS #: 15861-24-2) instead of 1H-Indole-6-carbonitrile in Example 135-A. $^1$H NMR (400 MHz, DMSO-d6) δ ppm 11.40 (s, 1H) 10.80 (s, 1H) 7.73-7.93 (m, 1H) 7.46 (d, J=8.34 Hz, 1H) 7.30 (dd, J=8.46, 1.64 Hz, 1H) 7.14 (t, J=2.78 Hz, 1H) 6.75 (s, 1H) 6.54 (dd, J=4.61, 0.95 Hz, 1H) 6.44 (dd, J=2.97, 1.96 Hz, 1H) 6.04-6.11 (m, 1H) 5.83 (d, J=4.55 Hz, 1H) 3.81 (s, 3H) 2.45 (d, J=0.63 Hz, 3H). MS (ESI−) m/z 330.05 (M−1).

Example 137

The following compounds were prepared as described in the examples above:

| | Structure/Chemical Name | $^1$H NMR | HRMS |
|---|---|---|---|
| 137-A a) | ![structure] (±)-2-(1-amino-1-(5-bromo-7-methyl-1H-indol-4-yl)ethyl)-1H-benzo[d]imidazole-5-carbonitrile | (400 MHz, DMSO-d$_6$) δ 12.38 (br. s., 1H), 11.26 (br. s., 1H), 8.00 (br. s., 1H), 7.55 (br. s., 1H), 7.46-7.51 (m, 1H), 7.33 (t, J = 2.9 Hz, 1H), 7.10 (br. s., 1H), 7.05 (s, 1H), 2.44 (s, 3H), 2.06 (s, 3H). | calcd. for C$_{19}$H$_{16}$N$_5$Br (M + H)$^+$ 394.0667, found 394.0660. |
| 137-A b) | (+) and (−)-2-(1-amino-1-(5-bromo-7-methyl-1H-indol-4-yl)ethyl)-1H-benzo[d]imidazole-5-carbonitrile Resolution of the enantiomers of 2-(1-amino-1-(5-bromo-7-methyl-1H-indol- | | |

-continued

| Structure/Chemical Name | ¹H NMR | HRMS |
|---|---|---|

4-yl)ethyl)-1H-benzo[d]imidazole-5-carbonitrile was achieved by chiral SFC using a CHIRALPAK ® AD-H column with 40% (0.2% diethylamine in MeOH) in $CO_2$ to give (+)-2-(1-amino-1-(5-bromo-7-methyl-1H-indol-4-yl)ethyl)-1H-benzo[d]imidazole-5-carbonitrile ($t_r$ = 2.2 min) and (−)-2-(1-amino-1-(5-bromo-7-methyl-1H-indol-4-yl)ethyl)-1H-benzo[d]imidazole-5-carbonitrile ($t_r$ = 3.90 min).

137-B a)

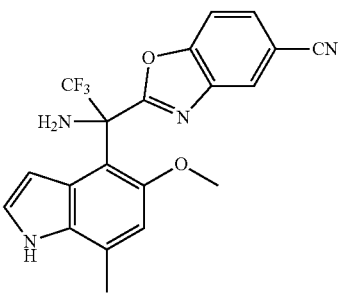

(±)-2-(1-amino-2,2,2-trifluoro-1-(5-methoxy-7-methyl-1H-indol-4-yl)ethyl)benzo[d]oxazole-5-carbonitrile (400 MHz, Dichloromethane-$d_2$) δ 9.45 (br. s., 1H), 8.20 (t, J = 1.07 Hz, 1H), 7.86 (d, J = 1.14 Hz, 2H), 7.23 (t, J = 2.97 Hz, 1H), 6.65 (s, 1H), 6.56 (br. s., 1H), 2.49 (d, J = 0.76 Hz, 3H), 1.60-1.74 (m, 1H), 0.77-0.89 (m, 1H), 0.66-0.76 (m, 1H), 0.49-0.60 (m, 1H), 0.17-0.29 (m, 1H).

calcd. for $C_{20}H_{15}F_3N_4O_2$ $(M - NH_2)^+$ 384.0960, found 384.0953.

137-B b)

(+) and (−)-2-(1-amino-2,2,2-trifluoro-1-(5-methoxy-7-methyl-1H-indol-4-yl)ethyl)benzo[d]oxazole-5-carbonitrile Resolution of the enantiomers of this compound was achieved by chiral SFC using a CHIRALPAK ® AD-H column with 25% MeOH (10 mM $NH_4OH$aq) in $CO_2$ to give (+) or (−)-2-(1-amino-2,2,2-trifluoro-1-(5-methoxy-7-methyl-1H-indol-4-yl)ethyl)benzo[d]oxazole-5-carbonitrile ($t_r$ = 2.7 min) and (−) or (+)-2-(1-amino-2,2,2-trifluoro-1-(5-methoxy-7-methyl-1H-indol-4-yl)ethyl)benzo[d]oxazole-5-carbonitrile ($t_r$ = 4.6 min).

137-C

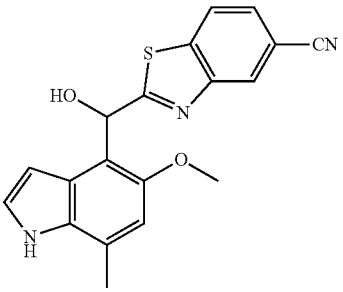

(±)-2-(hydroxy(5-methoxy-7-methyl-1H-indol-4-yl)methyl)benzo[d]thiazole-5-carbonitrile (400 MHz, METHANOL-$d_4$) δ ppm 8.10-8.18 (m, 2H), 7.64 (dd, J = 1.52, 8.34 Hz, 1H), 7.15 (d, J = 3.03 Hz, 1H), 6.78 (s, 1H), 6.74 (s, 1H), 6.42 (d, J = 3.03 Hz, 1H), 3.82 (s, 3H), 2.49 (s, 3H).

calcd. for $C_{19}H_{15}N_3O_2S$ $(M + H)^+$ 350.0958, found 350.0963.

137-D

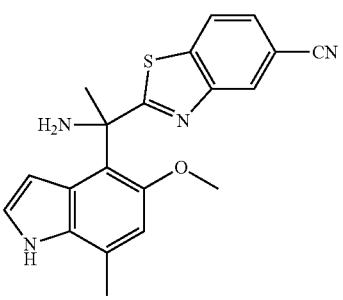

(±)-2-(1-amino-1-(5-methoxy-7-methyl-1H-indol-4-yl)ethyl)benzo[d]thiazole-5-carbonitrile (400 MHz, Acetone-$d_6$) δ ppm 10.07 (br. s., 1H), 8.06-8.09 (m, 1H), 7.99 (d, J = 1.58 Hz, 1H), 7.54 (dd, J = 1.58, 8.21 Hz, 1H), 7.21 (dd, J = 2.80, 3.03 Hz, 1H), 6.74 (dd, J = 2.02, 3.03 Hz, 1H), 6.64 (s, 1H), 3.23 (s, 3H), 2.89 (br. s., 2H), 2.38 (d, J = 0.76 Hz, 3H), 2.04 (s, 3H).

calcd. for $C_{20}H_{18}N_4OS$ $(M + H)^+$ 363.1274, found 363.1271.

| Structure/Chemical Name | ¹H NMR | HRMS |
|---|---|---|
| 137-E 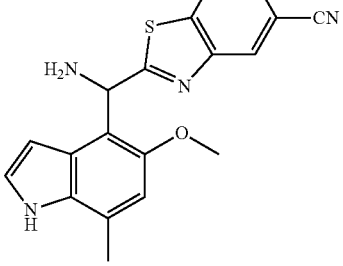 (±)-2-(amino(5-methoxy-7-methyl-1H-indol-4-yl)methyl)benzo[d]thiazole-5-carbonitrile | (400 MHz, Acetone-$d_6$) δ ppm 9.91 (br. s., 1H), 8.11 (d, J = 8.34 Hz, 1H), 8.02 (d, J = 1.39 Hz, 1H), 7.54 (dd, J = 1.39, 8.34 Hz, 1H), 7.00 (dd, J = 2.78, 3.03 Hz, 1H), 6.71 (s, 1H), 6.58 (s, 1H), 6.48 (dd, J = 2.02, 3.03 Hz, 1H), 3.88 (s, 3H), 2.34 (d, J = 0.76 Hz, 3H). | calcd. for $C_{19}H_{16}N_4OS$ $(M + H)^+$ 349.1118, found 349.1107. |
| 137-F a) 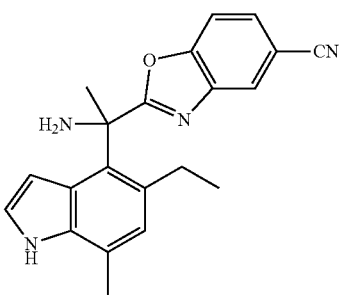 (±)-2-(1-amino-1-(5-ethyl-7-methyl-1H-indol-4-yl)ethyl)benzo[d]oxazole-5-carbonitrile | (400 MHz, ACETONITRILE-d3) δ ppm 9.19 (br. s., 1H), 8.09-8.22 (m, 1H), 7.69 (dd, J = 1.52, 8.34 Hz, 1H), 7.53-7.64 (m, 1H), 7.07 (dd, J = 2.80, 3.20 Hz, 1H), 6.83 (s, 1H), 6.53 (dd, J = 2.27, 3.20 Hz, 1H), 2.75-2.94 (m, 1H), 2.54-2.73 (m, 1H), 2.43 (d, J = 0.76 Hz, 3H), 2.33 (br. s., 2H), 2.14 (s, 3H), 1.02 (t, J = 7.45 Hz, 3H) | calcd. for $C_{21}H_{20}N_4O$ $(M - NH_2)$ 328.1444, found 328.1451. | b) (+) and (−)-2-(1-amino-1-(5-ethyl-7-methyl-1H-indol-4-yl)ethyl)benzo[d]oxazole-5-carbonitrile Resolution of the enantiomers of 2-(1-amino-1-(5-ethyl-7-methyl-1H-indol-4-yl)ethyl)benzo[d]oxazole-5-carbonitrile was achieved by chiral SFC using a CHIRALPAK ® AS-H column with 20% (10 mM NH$_4$OH in MeOH) in CO$_2$ to give (+) or (−)-2-(1-amino-1-(5-ethyl-7-methyl-1H-indol-4-yl)ethyl)benzo[d]oxazole-5-carbonitrile ($t_r$ = 3.3 min) and (−) or (+)-2-(1-amino-1-(5-ethyl-7-methyl-1H-indol-4-yl)ethyl)benzo[d]oxazole-5-carbonitrile ($t_r$ = 4.9 min).

| | | |
|---|---|---|
| 137-G 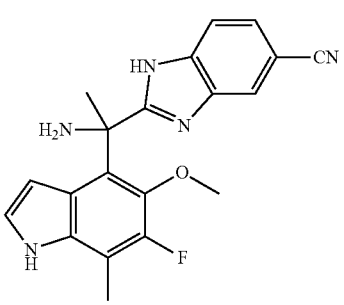 (±)-2-(1-amino-1-(6-fluoro-5-methoxy-7-methyl-1H-indol-4-yl)ethyl)-1H-benzo[d]imidazole-5-carbonitrile. | (400 MHz, DMSO-$d_6$) δ ppm 11.09 (br. s., 1H) 7.96 (br. s.) 7.59 (br. s) 7.50 (dd, J = 8.21, 1.52 Hz, 1H) 7.12-7.29 (m, 1H) 6.57 (br. s., 1H) 3.12-3.27 (m, 3H) 2.37 (d, J = 1.77 Hz, 3H) 2.00 (s, 3H). | calcd. for $C_{20}H_{18}FN_5O$ $(M + H)^+$ 364.1574, found 364.1577. |

-continued

| | Structure/Chemical Name | $^1$H NMR | HRMS |
|---|---|---|---|
| 137-H | 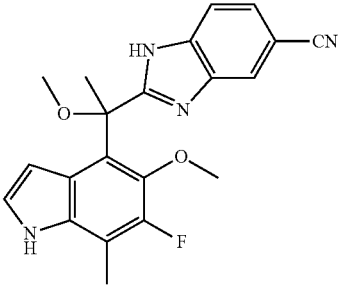<br>(±)-2-(1-(6-fluoro-5-methoxy-7-methyl-1H-indol-4-yl)-1-methoxyethyl)-1H-benzo[d]imidazole-5-carbonitrile | (400 MHz, DMSO-d$_6$) δ ppm 12.49-12.88 (m, 1H) 11.13 (br. s., 1H) 8.12 (s) 7.69-7.85 (m) 7.43-7.62 (m) 7.27 (t, J = 2.78 Hz, 1H) 6.66 (dd, J = 3.16, 1.89 Hz, 1H) 3.30 (d, J = 6.82 Hz, 3H) 3.09 (s, 3H) 2.37 (d, J = 1.77 Hz, 3H) 2.07 (s, 3H). | calcd. for C$_{21}$H$_{19}$FN$_4$O$_2$ (M + H)$^+$ 379.1570, found 379.1557. |
| 137-I a) | 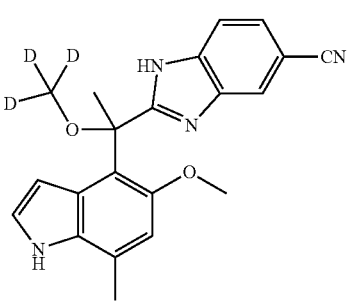<br>(±)-2-(1-($^2$H$_3$)methoxy-1-(5-methoxy-7-methyl-1H-indol-4-yl)ethyl)-1H-benzo[d]imidazole-5-carbonitrile | (400 MHz, DMSO-d$_6$) δ ppm 12.41-12.63 (m, 1H) 10.92 (br. s., 1H) 8.11 (s) 7.67-7.92 (m) 7.44 - 7.58 (m) 7.26 (t, J = 2.78 Hz, 1H) 6.59-6.80 (m, 2H) 3.19-3.25 (m, 3H) 2.44 (s, 3H) 1.94-2.04 (m, 3H). | calcd. for C$_{21}$H$_{17}$$^2$H$_3$N$_4$O$_2$ (M + H)$^+$ 364.1848, found 364.1855. |
| b) | (+) and (−)-2-(1-($^2$H$_3$)methoxy-1-(5-methoxy-7-methyl-1H-indol-4-yl)ethyl)-1H-benzo[d]imidazole-5-carbonitrile<br>Resolution of the enantiomers of 2-(1-($^2$H$_3$)methoxy-1-(5-methoxy-7-methyl-1H-indol-4-yl)ethyl)-1H-benzo[d]imidazole-5-carbonitrile was achieved by chiral SFC using a CHIRALPAK ® AD-H column with 17% MeOH + 0.2% DEA in CO$_2$ to give (−)-2-(1-($^2$H$_3$)methoxy-1-(5-methoxy-7-methyl-1H-indol-4-yl)ethyl)-1H-benzo[d]imidazole-5-carbonitrile (t$_r$ = 5.5 min) and (+)-2-(1-($^2$H$_3$)methoxy-1-(5-methoxy-7-methyl-1H-indol-4-yl)ethyl)-1H-benzo[d]imidazole-5-carbonitrile (t$_r$ = 7.7 min). | | |
| 137-J a) | 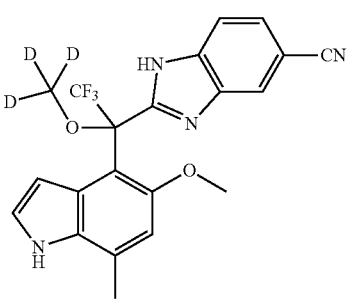<br>(±)-2-(2,2,2-trifluoro-1-($^2$H$_3$)-methoxy-1-(5-methoxy-7-methyl-1H-indol-4-yl)ethyl)-1H-benzo[d]imidazole-5-carbonitrile | (400 MHz, ACETONITRILE-d3) δ ppm 8.03-8.28 (m, 1H) 7.80 (d, J = 8.44 Hz, 1H) 7.67 (dd, J = 8.44, 1.47 Hz, 1H) 7.35 (t, J = 1.41 Hz, 1H) 6.75-6.84 (m, 2H) 3.21-3.28 (m, 3H) 2.51-2.57 (m, 3H). | calcd. for C$_{21}$H$_{14}$$^2$H$_3$F$_3$N$_4$O$_2$ (M + H)$^+$ 418.1565, found 418.157. |
| b) | (+) and (−)-2-(2,2,2-trifluoro-1-($^2$H$_3$)-methoxy-1-(5-methoxy-7-methyl-1H-indol-4-yl)ethyl)-1H-benzo[d]imidazole-5-carbonitrile<br>Resolution of the enantiomers of 2-(2,2,2-trifluoro-1-($^2$H$_3$)-methoxy-1-(5-methoxy-7-methyl-1H-indol-4-yl)ethyl)-1H-benzo[d]imidazole-5-carbonitrile was achieved by chiral SFC using a CHIRALPAK ® AD-H column with 20% IPA + 0.2% DEA in CO$_2$ to give (−)-2-(2,2,2-trifluoro-1-($^2$H$_3$)-methoxy-1-(5-methoxy-7-methyl-1H-indol-4-yl)ethyl)-1H-benzo[d]imidazole-5-carbonitrile (t$_r$ = 3.1 min) and (+)-2-(2,2,2-trifluoro-1-($^2$H$_3$)-methoxy-1-(5-methoxy-7-methyl-1H-indol-4-yl)ethyl)-1H-benzo[d]imidazole-5-carbonitrile (t$_r$ = 4.7 min). | | |

| Structure/Chemical Name | ¹H NMR | HRMS |
|---|---|---|
| 137-K a) 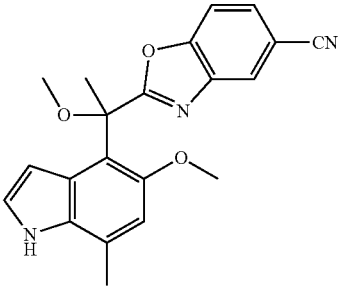<br><br>(±)-2-(1-methoxy-1-(5-methoxy-7-methyl-1H-indol-4-yl)ethyl)benzo[d]oxazole-5-carbonitrile | (400 MHz, DMSO-$d_6$) δ ppm 10.97 (br. s., 1H) 8.41 (dd, J = 1.58, 0.69 Hz, 1H) 7.76-8.01 (m, 2H) 7.33 (t, J = 2.78 Hz, 1H) 6.75 (dd, J = 3.03, 2.02 Hz, 1H) 6.66 (s, 1H) 3.19 (s, 3H) 3.17 (s, 3H) 2.45 (d, J = 0.63 Hz, 3H) 1.98 (s, 3H). | MS (ESI+) m/z 360.23 (M − H). |
| b) | (+) and (−)-2-(1-methoxy-1-(5-methoxy-7-methyl-1H-indol-4-yl)ethyl)benzo[d]oxazole-5-carbonitrile<br>Resolution of the enantiomers of 2-(hydroxy(5-methoxy-7-methyl-1H-indol-4-yl)methyl)-1H-benzo[d]imidazole-5-carbonitrile is achieved by chiral HPLC using a CHIRALPAK ® AD-H column with 60% ethanol (0.2% DEA) in heptane to give (+)-2-(1-methoxy-1-(5-methoxy-7-methyl-1H-indol-4-yl)ethyl)benzo[d]oxazole-5-carbonitrile ($t_r$ = 6.6 min) and (−)-2-(1-methoxy-1-(5-methoxy-7-methyl-1H-indol-4-yl)ethyl)benzo[d]oxazole-5-carbonitrile ($t_r$ = 11.6 min). | |
| 137-L a) 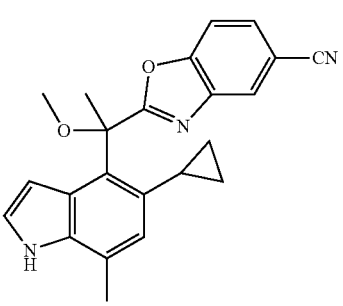<br><br>(±)-2-(1-(5-cyclopropyl-7-methyl-1H-indol-4-yl)-1-methoxyethyl)benzo[d]oxazole-5-carbonitrile | (400 MHz, DICHLOROMETHANE-$d_2$) δ ppm 8.16 (br. s., 1H) 8.11 (d, J = 1.01 Hz, 1H) 7.63-7.69 (m, 1H) 7.56-7.62 (m, 1H) 7.15-7.23 (m, 1H) 6.71 (dd, J = 3.35, 2.21 Hz, 1H) 6.62 (s, 1H) 3.24 (s, 3H) 2.45 (d, J = 0.76 Hz, 3H) 2.25 (s, 3H) 1.59 (tt, J = 8.42, 5.48 Hz, 1H) 0.60-0.69 (m, 1H) 0.45-0.56 (m, 1H) 0.33-0.44 (m, 1H) 0.19-0.31 (m, 1H). | calcd. for $C_{23}H_{21}N_3O_2$ $(M + H)^+$ 371.1628, found 371.1634. |
| b) | (+) and (−)-2-(1-(5-cyclopropyl-7-methyl-1H-indol-4-yl)-1-methoxyethyl)benzo[d]oxazole-5-carbonitrile<br>Resolution of the enantiomers of 2-(1-(5-cyclopropyl-7-methyl-1H-indol-4-yl)-1-methoxyethyl)benzo[d]oxazole-5-carbonitrile was achieved by chiral SFC using a CHIRALPAK ® OJ-H column with 30% MeOH in $CO_2$ to give (+)-2-(1-(5-cyclopropyl-7-methyl-1H-indol-4-yl)-1-methoxyethyl)benzo[d]oxazole-5-carbonitrile ($t_r$ = 2.7 min) and (−)-2-(1-(5-cyclopropyl-7-methyl-1H-indol-4-yl)-1-methoxyethyl)benzo[d]oxazole-5-carbonitrile ($t_r$ = 4.9 min). | |
| 137-M a) 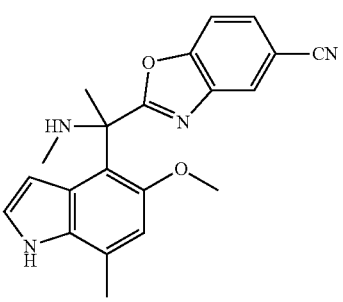<br><br>(±)-2-(1-(5-methoxy-7-methyl-1H-indol-4-yl)-1-(methylamino)ethyl)benzo[d]oxazole-5-carbonitrile | (400 MHz, DMSO-$d_6$) δ ppm 10.90 (br. s., 1H) 8.31 (d, J = 0.88 Hz, 1H) 7.71-7.90 (m, 2H) 7.28 (t, J = 2.84 Hz, 1H) 7.04-7.14 (m, 1H) 6.65 (s, 1H) 3.16 (s, 3H) 2.63 (br. s., 1H) 2.44 (s, 3H) 2.15 (br. s., 3H) 1.85 (s, 3H). | calcd. for $C_{21}H_{20}N_4O_2$ $(M + H)^+$ 361.1665, found 361.1632. |
| b) | (+) and (−)-2-(1-(5-methoxy-7-methyl-1H-indol-4-yl)-1-(methylamino)ethyl)benzo[d]oxazole-5-carbonitrile<br>Resolution of the enantiomers of 2-(1-(5-methoxy-7-methyl-1H-indol-4-yl)-1-(methylamino)ethyl)benzo[d]oxazole-5-carbonitrile was achieved by chiral SFC | |

| Structure/Chemical Name | ¹H NMR | HRMS |
|---|---|---| using a CHIRALPAK ® IC-H column with 30% IPA + 5 mM NH$_4$OH in CO$_2$ to give (+) or (−)-2-(1-(5-methoxy-7-methyl-1H-indol-4-yl)-1-(methylamino)ethyl)benzo[d]oxazole-5-carbonitrile (t$_r$ = 2.9 min) and (−) or (+)-2-(1-(5-methoxy-7-methyl-1H-indol-4-yl)-1-(methylamino)ethyl)benzo[d]oxazole-5-carbonitrile (t$_r$ = 4.5 min)

137-N a)

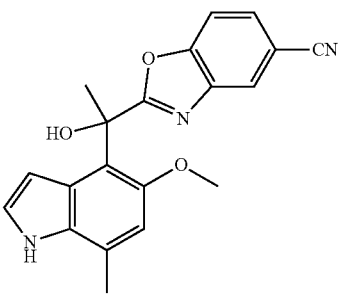

(±)-2-(1-hydroxy-1-(5-methoxy-7-methyl-1H-indol-4-yl)ethyl)benzo[d]oxazole-5-carbonitrile (400 MHz, DMSO-d$_6$) δ ppm 10.89 (br. s., 1H) 8.36 (dd, J = 1.39, 0.88 Hz, 1H) 7.63-7.96 (m, 2H) 7.28 (t, J = 2.84 Hz, 1H) 6.95 (dd, J = 2.97, 1.96 Hz, 1H) 6.62 (s, 1H) 6.31 (s, 1H) 3.11-3.23 (m, 3H) 2.44 (s, 3H) 1.99 (s, 3H).

calcd. for C$_{20}$H$_{17}$N$_3$O$_3$ (M + H)$^+$ 348.1348, found 348.1349.

b) (+) and (−)-2-(1-hydroxy-1-(5-methoxy-7-methyl-1H-indol-4-yl)ethyl)benzo[d]oxazole-5-carbonitrile
Resolution of the enantiomers 2-(1-hydroxy-1-(5-methoxy-7-methyl-1H-indol-4-yl)ethyl)benzo[d]oxazole-5-carbonitrile was achieved by chiral SFC using a CHIRALPAK ® AD-H column with 25% IPA + 0.2% DEA in CO$_2$ to give (−)-2-(1-hydroxy-1-(5-methoxy-7-methyl-1H-indol-4-yl)ethyl)benzo[d]oxazole-5-carbonitrile (t$_r$ = 4.8 min) and (+)-2-(1-hydroxy-1-(5-methoxy-7-methyl-1H-indol-4-yl)ethyl)benzo[d]oxazole-5-carbonitrile (t$_r$ = 7.2 min).

137-O

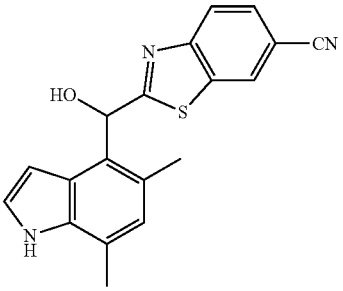

(±)-2-((5,7-dimethyl-1H-indol-4-yl)(hydroxy)methyl)benzo[d]thiazole-6-carbonitrile (400 MHz, DMSO-d$_6$) δ ppm 10.91 (br. s., 1H) 8.65-8.72 (m, 1H) 7.95 (d, J = 8.59 Hz, 1H) 7.81 (dd, J = 8.46, 1.64 Hz, 1H) 7.18 (t, J = 2.78 Hz, 1H) 6.88 (d, J = 4.29 Hz, 1H) 6.72 (s, 1H) 6.45-6.61 (m, 2H) 2.44 (s, 3H) 2.40 (s, 3H).

calcd. for C$_{19}$H$_{15}$N$_3$OS (M + H)$^+$ 334.1014, found 334.1014.

137-P

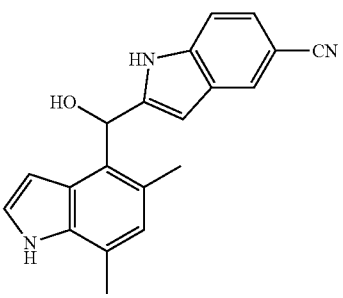

(±)-2-((5,7-dimethyl-1H-indol-4-yl)(hydroxy)methyl)-1H-indole-5-carbonitrile (400 MHz, DMSO-d$_6$) δ ppm 11.42 (s, 1H) 10.84 (br. s., 1H) 7.87 (d, J = 1.01 Hz, 1H) 7.47 (d, J = 8.34 Hz, 1H) 7.31 (dd, J = 8.40, 1.58 Hz, 1H) 7.15 (t, J = 2.78 Hz, 1H) 6.72 (s, 1H) 6.48 (dd, J = 3.03, 1.89 Hz, 1H) 6.39 (d, J = 2.40 Hz, 1H) 6.03 (s, 1H) 5.98 (d, J = 3.41 Hz, 1H) 2.42 (s, 3H) 2.36 (s, 3H).

MS (ESI−) m/z 314.2 (M − H).

-continued

| Structure/Chemical Name | ¹H NMR | HRMS |
|---|---|---|
| 137-Q 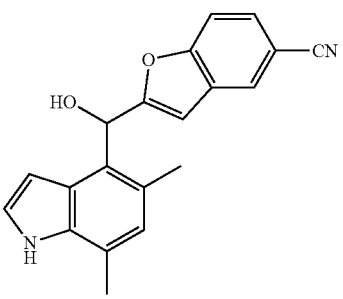 (±)-2-((5,7-dimethyl-1H-indol-4-yl)(hydroxy)methyl)benzofuran-5-carbonitrile | (400 MHz, DMSO-d₆) δ ppm 10.88 (br. s., 1H) 8.04-8.14 (m, 1H) 7.57-7.69 (m, 2H) 7.18 (t, J = 2.78 Hz, 1H) 6.77 (s, 1H) 6.71 (s, 1H) 6.57 (dd, J = 3.09, 1.96 Hz, 1H) 6.33 (br. s., 1H) 6.14 (br. s., 1H) 2.41 (s, 6H). | calcd. for $C_{20}H_{16}N_2O_2$ $(M + H)^+$ 317.1290, found 317.1291. |
| 137-R 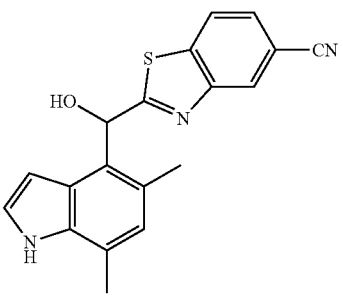 (±)-2-((5,7-dimethyl-1H-indol-4-yl)(hydroxy)methyl)benzo[d]thiazole-5-carbonitrile | (400 MHz, DMSO-d₆) δ ppm 10.91 (br. s., 1H) 8.21-8.46( m, 2H) 7.76 (d, J = 8.08 Hz, 1H) 7.18 (br. s., 1H) 6.86 (d, J = 3.66 Hz, 1H) 6.72 (s, 1H) 6.52 (br. s., 2H) 2.44 (br. s., 3H) 2.41 (br. s., 3H). | MS (ESI−) m/z 332.2 (M − H). |
| 137-S 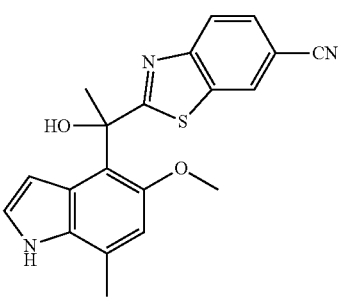 (±)-2-(1-hydroxy-1-(5-methoxy-7-methyl-1H-indol-4-yl)ethyl)benzo[d]thiazole-6-carbonitrile | (400 MHz, DMSO-d₆) δ ppm 10.89 (br. s., 1H) 8.60 (d, J = 1.64 Hz, 1H) 8.06 (d, J = 8.46 Hz, 1H) 7.84 (dd, J = 8.46, 1.64 Hz, 1H) 7.26 (t, J = 2.91 Hz, 1H) 6.87 (dd, J = 3.03, 2.02 Hz, 1H) 6.67 (s, 1H) 6.40 (s, 1H) 3.37 (s, 3H) 2.44 (s, 3H) 2.11 (s, 3H). | MS (ESI−) m/z 362.2 (M − H). |
| 137-T 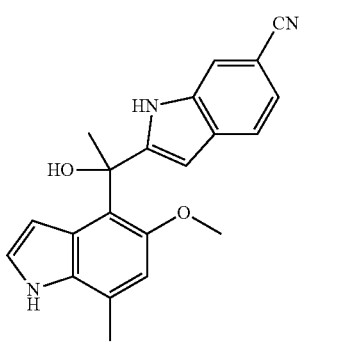 (±)-2-(1-hydroxy-1-(5-methoxy-7-methyl-1H-indol-4-yl)ethyl)-1H-indole-6-carbonitrile | (400 MHz, DMSO-d₆) δ ppm 11.16 (s, 1H) 10.79 (br. s., 1H) 7.64-7.70 (m, 1H) 7.59 (d, J = 8.21 Hz, 1H) 7.23 (dd, J = 8.21, 1.52 Hz, 1H) 7.15 (t, J = 2.84 Hz, 1H) 6.71 (s, 1H) 6.53 (dd, J = 3.16, 2.02 Hz, 1H) 6.39 (dd, J = 2.02, 0.76 Hz, 1H) 5.84 (s, 1H) 3.47 (s, 3H) 2.38-2.45 (m, 3H) 2.03 (s, 3H). | MS (ESI−) m/z 344.2 (M − H). |

-continued

| Structure/Chemical Name | ¹H NMR | HRMS |
|---|---|---|

137-U

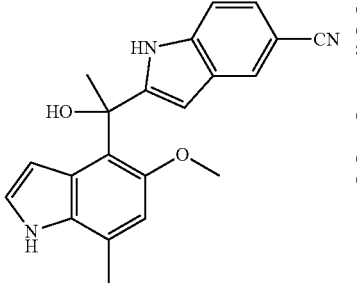

(±)-2-(1-hydroxy-1-(5-methoxy-7-methyl-1H-indol-4-yl)ethyl)-1H-indole-5-carbonitrile (400 MHz, DMSO-d$_6$) δ ppm 11.20 (s, 1H) 10.78 (br. s., 1H) 7.88-8.02 (m, 1H) 7.42 (d, J = 8.34 Hz, 1H) 7.30 (dd, J = 8.40, 1.58 Hz, 1H) 7.13 (t, J = 2.84 Hz, 1H) 6.72 (s, 1H) 6.45 (dd, J = 3.03, 2.02 Hz, 1H) 6.37 (d, J = 1.26 Hz, 1H) 5.83 (s, 1H) 3.50 (s, 3H) 2.37-2.45 (m, 3H) 2.03 (s, 3H).

MS (ESI−) m/z 344.2 (M − H).

137-V

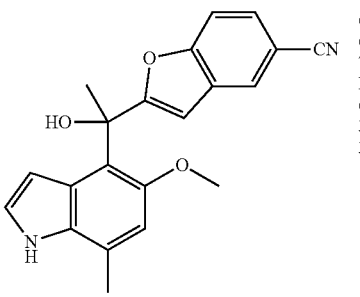

(±)-2-(1-hydroxy-1-(5-methoxy-7-methyl-1H-indol-4-yl)ethyl)benzofuran-5-carbonitrile (400 MHz, DMSO-d$_6$) δ ppm 10.82 (br. s., 1H) 8.07-8.18 (m, 1H) 7.57-7.72 (m, 2H) 7.22 (t, J = 2.84 Hz, 1H) 6.82-6.90 (m, 1H) 6.79 (s, 1H) 6.66 (s, 1H) 5.91 (s, 1H) 3.34 (s, 3H) 2.43 (s, 3H) 1.97 (s, 3H).

MS (ESI−) m/z 345.3 (M − H).

137-W

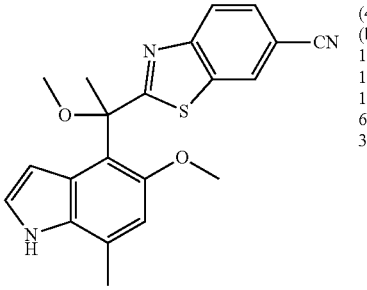

(±)-2-(1-methoxy-1-(5-methoxy-7-methyl-1H-indol-4-yl)ethyl)benzo[d]thiazole-6-carbonitrile (400 MHz, DMSO-d$_6$) δ ppm 10.95 (br. s., 1H) 8.64 (d, J = 1.64 Hz, 1H) 8.06 (dd, J = 8.46, 0.63 Hz, 1H) 7.84 (dd, J = 8.46, 1.77 Hz, 1H) 7.25 (t, J = 2.84 Hz, 1H) 6.58-6.78 (m, 2H) 3.44 (s, 3H) 3.15 (s, 3H) 2.45 (s, 3H) 2.10 (s, 3H).

MS (ESI−) m/z 376.3 (M − H).

137-X

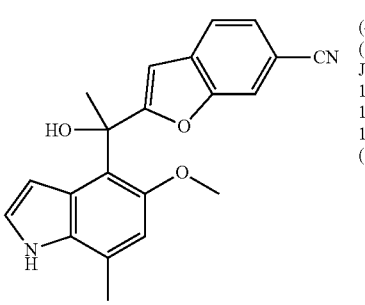

(±)-2-(1-hydroxy-1-(5-methoxy-7-methyl-1H-indol-4-yl)ethyl)benzofuran-6-carbonitrile (400 MHz, DMSO-d$_6$) δ ppm 10.82 (br. s., 1H) 8.04 (s, 1H) 7.77 (d, J = 8.08 Hz, 1H) 7.59 (dd, J = 8.08, 1.39 Hz, 1H) 7.22 (t, J = 2.84 Hz, 1H) 6.81-6.91 (m, 2H) 6.66 (s, 1H) 5.93 (s, 1H) 3.31 (s, 3H) 2.43 (s, 3H) 1.97 (s, 3H).

MS (ESI−) m/z 345.2 (M − H).

-continued

| Structure/Chemical Name | $^1$H NMR | HRMS |
|---|---|---|
| 137-Y (±)-2-(1-methoxy-1-(5-methoxy-7-methyl-1H-indol-4-yl)ethyl)benzofuran-6-carbonitrile | (400 MHz, DMSO-$d_6$) δ ppm 10.89 (br. s., 1H) 8.09 (s, 1H) 7.80 (d, J = 8.08 Hz, 1H) 7.62 (dd, J = 8.02, 1.33 Hz, 1H) 7.27 (t, J = 2.84 Hz, 1H) 7.00 (d, J = 0.88 Hz, 1H) 6.76 (dd, J = 3.03, 2.02 Hz, 1H) 6.69 (s, 1H) 3.30 (s, 3H) 3.10 (s, 3H) 2.45 (s, 3H) 1.95 (s, 3H). | MS (ESI–) m/z 359.2 (M – H). |
| 137-Z (±)-2-(1-methoxy-1-(5-methoxy-7-methyl-1H-indol-4-yl)ethyl)benzofuran-5-carbonitrile | (400 MHz, DMSO-$d_6$) δ ppm 10.88 (br. s., 1H) 8.16 (dd, J = 1.52, 0.88 Hz, 1H) 7.59-7.74 (m, 2H) 7.26 (t, J = 2.84 Hz, 1H) 6.94 (s, 1H) 6.75 (dd, J = 3.03, 2.02 Hz, 1H) 6.68 (s, 1H) 3.29 (s, 3H) 3.09 (s, 3H) 2.44 (s, 3H) 1.94 (s, 3H). | MS (ESI–) m/z 359.2 (M – H). |

Example 138

(±)-3-(1-(5-cyanobenzo[d]oxazol-2-yl)-2,2,2-trifluoro-1-(5-methoxy-7-methyl-1H-indol-4-yl)ethoxy)-2,2-dimethylpropanoic acid

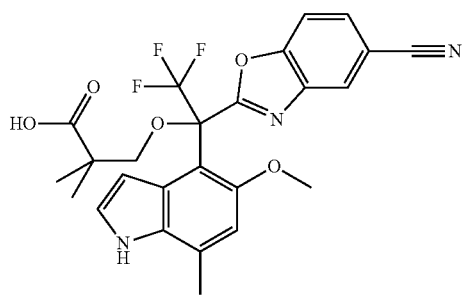 [SMILES: COc1cc(C)c2[nH]ccc2c1C(OCC(C)(C)C(=O)O)(c1nc2cc(C#N)ccc2o1)C(F)(F)F]

To a suspension of (±)-2-(2,2,2-trifluoro-1-hydroxy-1-(5-methoxy-7-methyl-1H-indol-4-yl)ethyl)benzo[d]oxazole-5-carbonitrile (Example 128-A) (50 mg, 0.100 mmol) in DMF (0.3 ml), NaH (oil dispersion, 60%) (11.96 mg, 0.299 mmol) was added at rt under nitrogen. After stirring for 15 min., 3-bromo-2,2-dimethylpropionic acid methyl ester (0.043 ml, 0.299 mmol; CAS#30452-00-7) was added at the same temperature. The mixture was warmed up to 90° C. After stirring for 2 h, the mixture was cooled to rt and diluted with EtOAc and 1M NaHSO$_4$aq. The organic layer was separated, dried over Na$_2$SO$_4$, filtered, and concentrated. To a solution of the resulting residue in THF (0.5 ml), potassium trimethylsilanolate (38.5 mg, 0.300 mmol) was added at rt under nitrogen. After stirring for 19 h, additional THF (0.5 ml) and potassium trimethylsilanolate were added. The mixture was heated at 50° C. for 1 h, and then the mixture was cooled to rt. The mixture was diluted with EtOAc, 1M HCl aq. and brine. The layers were separated and the aqueous layer extracted twice with EtOAc. The combined organic layer was washed with brine, dried over Na$_2$SO$_4$, filtered, and concentrated. The crude was purified by RP-HPLC (HC-A) to give the title compound as a 0.25-TFA salt.

$^1$H NMR (0.25 TFA salt, 400 MHz, methanol-$d_4$) δ ppm 8.25-8.26 (app t, 1H) 7.78-7.83 (m, 2H) 7.26-7.27 (m, 1H) 6.90 (d, J=3.03 Hz, 1H) 6.64 (s, 1H) 4.09 (d, J=8.59 Hz, 1H) 3.35 (d, J=8.84 Hz, 1H) 3.19 (s, 3H) 2.51 (s, 3H) 1.13 (s, 3H) 1.10 (s, 3H). HRMS calcd for $C_{25}H_{22}F_3N_3O_5$ (M+H)$^+$ 502.1590. found 502.1586.

Example 139

Example 139-A (±)-tert-Butyl 4-(1-amino-1-(5-cyano-1H-benzo[d]imidazol-2-yl)-2,2,2-trifluoroethyl)-5-methoxy-7-methyl-1H-indole-1-carboxylate

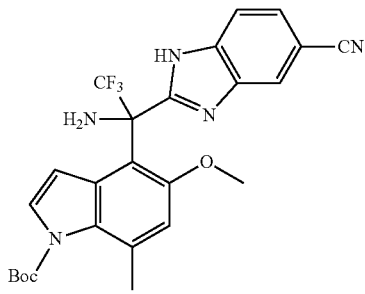 [SMILES: COc1cc(C)c2c(ccn2C(=O)OC(C)(C)C)c1C(N)(c1nc2cc(C#N)ccc2[nH]1)C(F)(F)F]

To a solution of a mixture of (±)-tert-butyl 4-(1-(5-cyano-1-((2-(trimethylsilyl)ethoxy)methyl)-1H-benzo[d]imidazol-2-yl)-1-(1,1-dimethylethylsulfinamido)-2,2,2-trifluoroethyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-1-(1,1-dimethylethylsulfinamido)-2,2,2-trifluoroethyl)-5-methoxy-7-methyl-1H-indole-1-carboxylate (Example 36-D) (0.37 g, 0.504 mmol) in dioxane (5.04 mL) was added HCl (4.0M in dioxane) (2.52 mL, 10.08 mmol) and this was stirred at room temperature. After 15 minutes this was cooled in an ice bath, neutralized with 30% aq. NH$_4$OH (2.52 mL), diluted with water, extracted twice with EtOAc, dried with MgSO$_4$, filtered and concentrated. The resulting residue was purified by flash chromatography (0-70% EtOAc in heptanes) to provide the title compound. MS (ESI+) m/z 500.2 (M+H).

Example 139-B (±)-tert-Butyl 4-(1-(5-cyano-1H-benzo[d]imidazol-2-yl)-2,2,2-trifluoro-1-((2-hydroxyethyl)amino)ethyl)-5-methoxy-7-methyl-1H-indole-1-carboxylate

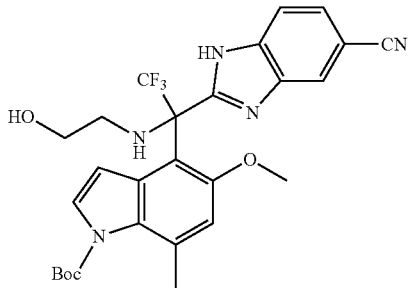 [SMILES: COc1cc(C)c2c(ccn2C(=O)OC(C)(C)C)c1C(NCCO)(c1nc2cc(C#N)ccc2[nH]1)C(F)(F)F]

A solution of (±)-tert-butyl 4-(1-amino-1-(5-cyano-1H-benzo[d]imidazol-2-yl)-2,2,2-trifluoroethyl)-5-methoxy-7-methyl-1H-indole-1-carboxylate (50 mg, 0.100 mmol) and ethyl glyoxylate (50% in toluene) (39.7 µL, 0.200 mmol) in DCE (1.00 mL) was stirred at room temperature. After 50 minutes MeOH (1 mL) was added followed by NaBH$_4$ (11.36 mg, 0.300 mmol). After 30 minutes additional NaBH$_4$ (4 mg, 0.106 mmol) was added. After 25 more minutes additional NaBH$_4$ (40 mg, 1.06 mmol) was added. After 15 more minutes the reaction was quenched with water, extracted twice with EtOAc, dried with MgSO$_4$, filtered and concentrated. The resulting residue was purified by flash chromatography (0-80% EtOAc in heptanes) to provide the title compound. MS (ESI+) m/z 544.2 (M+H).

Example 139-C (±)-2-(2,2,2-Trifluoro-1-((2-hydroxyethyl)amino)-1-(5-methoxy-7-methyl-1H-indol-4-yl)ethyl)-1H-benzo[d]imidazole-5-carbonitrile

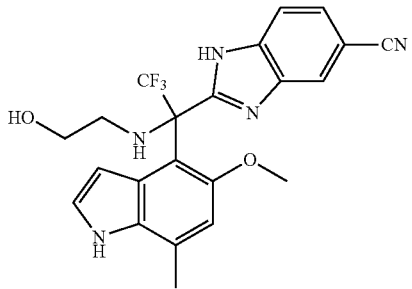 [SMILES: COc1cc(C)c2[nH]ccc2c1C(NCCO)(c1nc2cc(C#N)ccc2[nH]1)C(F)(F)F]

To a solution of (±)-tert-butyl 4-(1-(5-cyano-1H-benzo[d]imidazol-2-yl)-2,2,2-trifluoro-1-((2-hydroxyethyl)amino)ethyl)-5-methoxy-7-methyl-1H-indole-1-carboxylate (20 mg, 0.037 mmol) in MeOH (0.368 mL) at room temperature under nitrogen, Cs$_2$CO$_3$ (59.9 mg, 0.184 mmol) was added and the reaction was stirred at 60° C. After 90 minutes the reaction was cooled, quenched with NH$_4$Cl, extracted with EtOAc, dried with MgSO$_4$, filtered and concentrated. The resulting residue was purified by flash chromatography (0-100% EtOAc in heptanes) to provide the title compound. $^1$H NMR (400 MHz, DMSO-d$_6$) δ ppm 12.48-12.70 (m, 1H) 10.99 (br. s., 1H) 8.27 (m) 7.89 (m) 7.81 (m) 7.56 (dd, J=8.34, 1.52 Hz, 1H) 7.48 (m) 7.06-7.21 (m, 1H) 6.81 (s, 1H) 6.01 (br. s., 1H) 4.48 (t, J=5.24 Hz, 1H) 3.34-3.54 (m, 5H) 2.56-2.72 (m, 1H) 2.46 (s, 3H) 2.01 (br. s., 1H). HRMS calcd. for C$_{22}$H$_{20}$F$_3$N$_5$O$_2$ (M+H)$^+$ 444.1647. found 444.1656.

Example 140

Example 140-A (±)-tert-Butyl 4-(1-(5-cyano-1H-benzo[d]imidazol-2-yl)-1-((2-ethoxy-2-oxoethyl)amino)-2,2,2-trifluoroethyl)-5-methoxy-7-methyl-1H-indole-1-carboxylate

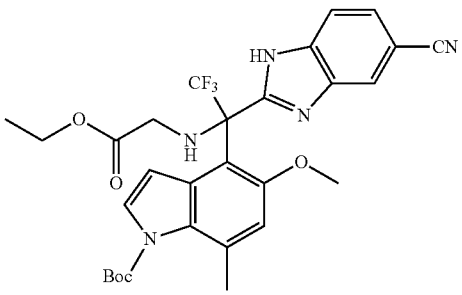 [SMILES: CCOC(=O)CNC(c1nc2cc(C#N)ccc2[nH]1)(c1c(OC)cc(C)c2c1ccn2C(=O)OC(C)(C)C)C(F)(F)F]

To a suspension of (±)-tert-butyl 4-(1-amino-1-(5-cyano-1H-benzo[d]imidazol-2-yl)-2,2,2-trifluoroethyl)-5-methoxy-7-methyl-1H-indole-1-carboxylate (Example 139-A) (117 mg, 0.234 mmol) in DCE (2.34 mL) was added ethyl glyoxylate (50% in toluene) (93 µL, 0.468 mmol) and this was stirred at 60° C. After 5 minutes this was cooled to room temperature, then sodium triacetoxyborohydride (298 mg, 1.405 mmol) was added and this was stirred again at 60° C. After stirring overnight the reaction was quenched with sat. aq. sodium bicarbonate, extracted with EtOAc, dried with MgSO$_4$, filtered and concentrated. The resulting residue was purified by flash chromatography (0-50% EtOAc in heptanes) to provide the title compound. MS (ESI+) m/z 586.3 (M+H).

Example 140-B (±)-2-((1-(5-cyano-1H-benzo[d]imidazol-2-yl)-2,2,2-trifluoro-1-(5-methoxy-7-methyl-1H-indol-4-yl)ethyl)amino)acetic acid

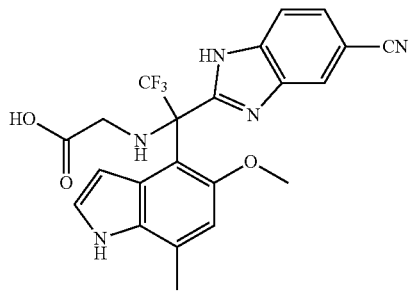 [SMILES: COc1cc(C)c2[nH]ccc2c1C(NCC(=O)O)(c1nc2cc(C#N)ccc2[nH]1)C(F)(F)F]

2To a solution of (±)-tert-butyl 4-(1-(5-cyano-1H-benzo[d]imidazol-2-yl)-1-((2-ethoxy-2-oxoethyl)amino)-2,2,2-trifluoroethyl)-5-methoxy-7-methyl-1H-indole-1-carboxylate (75 mg, 0.128 mmol) in EtOH (1.28 mL) at room temperature under nitrogen, $Cs_2CO_3$ (209 mg, 0.640 mmol) was added and the reaction was stirred at 60° C. After 95 minutes additional $Cs_2CO_3$ (209 mg, 0.640 mmol) was added. After 1 more hour the reaction was cooled, quenched with $NH_4Cl$, extracted with EtOAc (×5), dried with $MgSO_4$, filtered and concentrated. The resulting residue was purified by flash chromatography (0-30% MeOH in DCM, MeOH contains 10% ammonium hydroxide) to provide the title compound as the ammonium salt. $^1H$ NMR (ammonium salt, 400 MHz, DMSO-$d_6$ with about 5 μL TFA) δ ppm 11.05 (br. s., 1H) 8.12 (br. s., 1H) 7.65 (d, J=8.08 Hz, 1H) 7.58 (dd, J=8.34, 1.52 Hz, 1H) 7.20 (br. s., 1H) 6.81 (s, 1H) 6.15 (br. s., 1H) 3.40 (br. s., 3H) 3.27 (d, J=17.43 Hz, 1H) 2.87 (d, J=17.31 Hz, 1H) 2.44-2.48 (m, 3H). HRMS calcd. for $C_{22}H_{18}F_3N_5O_3$ $(M+H)^+$ 458.1440. found 458.1418.

Example 141

(+) or (−)-2-(1-amino-2,2,2-trifluoro-1-(5-hydroxy-7-methyl-1H-indol-4-yl)ethyl)-1H-benzo[d]imidazole-5-carbonitrile

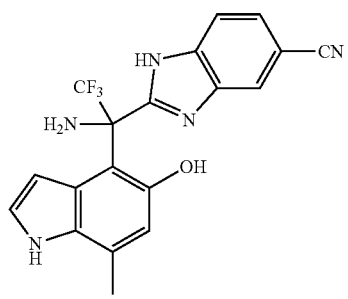 [SMILES: Cc1cc(O)c(C(N)(c2nc3cc(C#N)ccc3[nH]2)C(F)(F)F)c2cc[nH]c12]

To a suspension of (−)-2-(1-amino-2,2,2-trifluoro-1-(5-methoxy-7-methyl-1H-indol-4-yl)ethyl)-1H-benzo[d]imidazole-5-carbonitrile (Example 36-E-b) (63 mg, 0.158 mmol) in methylene chloride (Volume: 1.6 mL) at 0° C. was added 1 M $BBr_3$ in DCM (315 μl, 0.315 mmol). The reaction was stirred in ice bath for 5 minutes and then the suspension was allowed to stir at room temperature for 2 hours. The reaction was poured into ice water, treated with saturated a solution of sodium bicarbonate, and then diluted with EtOAc and the EtOAc layer was removed, dried, concentrated and absorbed onto silica to purify via FCC (0-5% MeOH containing 10% ammonium hydroxide:dcm) to obtain the title compound. $^1H$ NMR (400 MHz, DMSO-$d_6$) δ ppm 12.55-12.76 (m, 1H) 11.01-11.28 (m, 1H) 10.82 (br. s., 1H) 8.35 (s, 1H) 7.83-8.06 (m, 1H) 7.46-7.65 (m, 2H) 6.88 (t, J=2.91 Hz, 1H) 6.50 (s, 1H) 4.84 (br. s., 1H) 2.27-2.43 (m, 3H). MS (ESI+) m/z 386.3 (M+H).

Example 142

Example 142-A tert-Butyl 4-(1-(5-cyano-1-((2-(trimethylsilyl)ethoxy)methyl)-1H-benzo[d]imidazol-2-yl)-3-methoxy-3-oxoprop-1-en-1-yl)-5-methoxy-7-methyl-1H-indole-1-carboxylate and tert-butyl 4-(1-(6-cyano-1-((2-(trimethylsilyl)ethoxy)methyl)-1H-benzo[d]imidazol-2-yl)-3-methoxy-3-oxoprop-1-en-1-yl)-5-methoxy-7-methyl-1H-indole-1-carboxylate

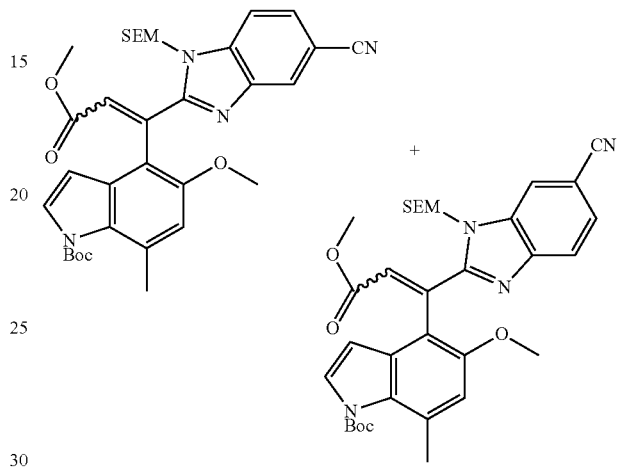

To a solution of tert-butyl 4-(5-cyano-1-((2-(trimethylsilyl)ethoxy)methyl)-1H-benzo[d]imidazole-2-carbonyl)-5-methoxy-7-methyl-1H-indole-1-carboxylate and tert-butyl 4-(6-cyano-1-((2-(trimethylsilyl)ethoxy)methyl)-1H-benzo[d]imidazole-2-carbonyl)-5-methoxy-7-methyl-1H-indole-1-carboxylate (Example 25A) (2.0 g, 3.57 mmol) in toluene (12 mL) was added methyl(triphenylphosphoranylidene)acetate (2.39 g, 7.13 mmol) and this mixture was stirred at 110° C. for overnight. The reaction was concentrated in vacuo and then this material was purified with FCC eluting with ethyl acetate/heptane (0-100%) to afford the mixture of title compounds. MS (ESI+) m/z 617.7 (M+H).

Example 142-B (±)-tert-Butyl 4-(1-(5-cyano-1-((2-(trimethylsilyl)ethoxy)methyl)-1H-benzo[d]imidazol-2-yl)-2-(methoxy carbonyl)cyclopropyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-2-(methoxycarbonyl)cyclopropyl)-5-methoxy-7-methyl-1H-indole-1-carboxylate

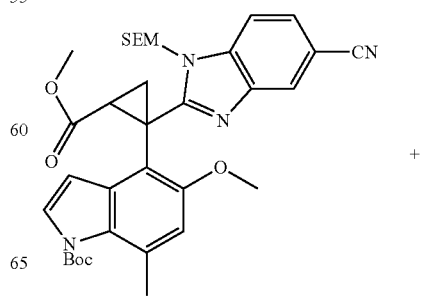

-continued

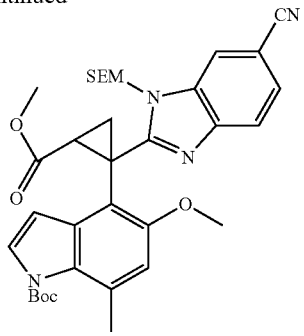

Trimethylsulfoxonium iodide (113 mg, 0.516 mmol) and NaH (60% dispersion, 22.7 mg, 0.567 mmol) were added to a dry round bottom flask; the flask was cooled to 0° C. under $N_2$. Then DMSO (0.5 mL) was added dropwise via syringe to this mixture. After 20 minutes, a solution of tert-butyl 4-(1-(5-cyano-1-((2-(trimethylsilyl)ethoxy)methyl)-1H-benzo[d]imidazol-2-yl)-3-methoxy-3-oxoprop-1-en-1-yl)-5-methoxy-7-methyl-1H-indole-1-carboxylate and tert-butyl 4-(1-(6-cyano-1-((2-(trimethylsilyl)ethoxy)methyl)-1H-benzo[d]imidazol-2-yl)-3-methoxy-3-oxoprop-1-en-1-yl)-5-methoxy-7-methyl-1H-indole-1-carboxylate (Example 142-A) (265 mg, 0.43 mmol) in DMSO (4.5 mL) was added dropwise and this mixture was stirred at room temperature overnight. The reaction mixture was partitioned between EtOAc/$H_2O$ and the layers separated. The organic phase was washed with brine, dried over sodium sulfate, and concentrated in vacuo to afford the crude product. This material was purified with FCC eluting with ethyl acetate/heptane (10-50%) to afford the mixture of title compounds. MS (ESI+) m/z 631.6 (M+H).

Example 142-C (±)-Methyl 2-(5-cyano-1H-benzo[d]imidazol-2-yl)-2-(5-methoxy-7-methyl-1H-indol-4-yl)cyclopropanecarboxylate

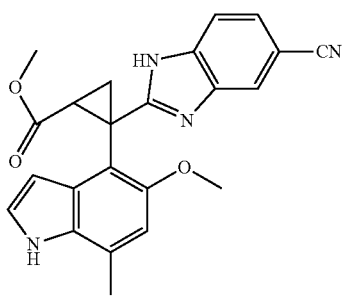 [SMILES: COC(=O)C1CC1(c1nc2cc(C#N)ccc2[nH]1)c1c(OC)cc(C)c2[nH]ccc12]

To a solution of (±)-tert-butyl 4-(1-(5-cyano-1-((2-(trimethylsilyl)ethoxy)methyl)-1H-benzo[d]imidazol-2-yl)-2-(methoxy carbonyl)cyclopropyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-2-(methoxy carbonyl)cyclopropyl)-5-methoxy-7-methyl-1H-indole-1-carboxylate (Example 142-B) (680 mg, 1.078 mmol) in dichloromethane (10.0 mL) at 0° C. was added a 1.0M solution of $SnCl_4$ in dichloromethane (10.78 mL, 10.78 mmol). This mixture was stirred for 30 min at 0° C. followed by 60 min at room temperature. The reaction was partitioned between EtOAc and a saturated aqueous sodium bicarbonate solution. The layers were filtered through Celite® to remove emulsion formed and then the layers were separated. The organic phase was brine washed, dried over $Na_2SO_4$ and concentrated in vacuo to afford the crude product. This material was purified using FCC eluting with ethyl acetate/heptane (30-100%) to afford the title compound. MS (ESI+) m/z 401.1 (M+H).

Example 142-D (±)-2-(5-Cyano-1H-benzo[d]imidazol-2-yl)-2-(5-methoxy-7-methyl-1H-indol-4-yl)cyclopropanecarboxylic acid

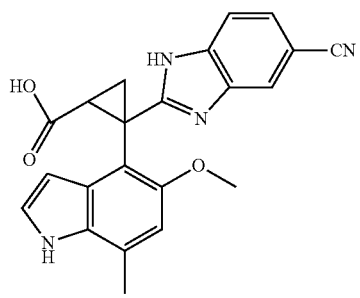

To a solution of (±)-methyl 2-(5-cyano-1H-benzo[d]imidazol-2-yl)-2-(5-methoxy-7-methyl-1H-indol-4-yl)cyclopropanecarboxylate (Example 142-C) (40 mg, 0.1 mmol) in pyridine (5.0 mL) was added lithium iodide (800 mg, 59.8 mmol) and this mixture was stirred at 125° C. overnight. The reaction was partitioned between EtOAc and cold 0.5N HCl solution and the layers separated. The organic layer was washed with brine, dried over sodium sulfate, filtered, and concentrated in vacuo. The crude product was purified by RP-HPLC (HC-B) to give the title compound. $^1$H NMR (400 MHz, METHANOL-$d_4$) δ ppm 7.75 (br.s., 1H), 7.55 (br.s., 1H) 7.27-7.55 (m, 1H) 7.17 (br.s., 1H) 6.79 (s, 1H) 6.50 (d, J=3.03 Hz, 1H) 3.81 (s, 3H) 2.52 (s, 3H) 2.22 (d, J=7.33 Hz, 1H) 1.30 (t, J=6.57 Hz, 1H), 0.88-0.92 (m, 1H). HRMS calcd. for $C_{22}H_{18}N_4O_3$ (M+H)$^+$ 387.1412. found 387.1443.

Example 143

(±)-2-(5-Cyanobenzo[d]oxazol-2-yl)-2-(5-methoxy-7-methyl-1H-indol-4-yl)cyclopropanecarboxylic acid

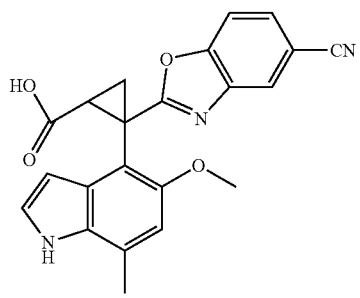 [SMILES: COc1cc(C)c2[nH]ccc2c1C1(c2nc3cc(C#N)ccc3o2)CC1C(=O)O]

The title compound was synthesized from tert-butyl 4-(5-cyanobenzo[d]oxazole-2-carbonyl)-5-methoxy-7-methyl- 1H-indole-1-carboxylate (Example 126-A) with similar methods as described in Example 142. $^1$H NMR (400 MHz, DMSO-d$_6$) δ ppm 11.03 (br.s., 1H) 8.08-8.40 (m, 1H) 7.61-7.90 (m, 3H) 7.39 (t, J=2.78 Hz, 1H) 6.55-6.93 (m, 2H) 3.80 (s, 3H) 2.44 (s, 3H) 1.73 (dd, J=8.21, 4.67 Hz, 1H) 1.1-1.35 (m, 1H) 0.86 (d, J=7.07 Hz, 1H). HRMS calcd. for C$_{22}$H$_{17}$N$_3$O$_4$ (M+H)$^+$ 388.1253. found 388.1282.

Example 144

Example 144-A tert-Butyl 4-((5-cyanobenzo[d]oxazol-2-yl)methyl)-5-methoxy-7-methyl-1H-indole-1-carboxylate

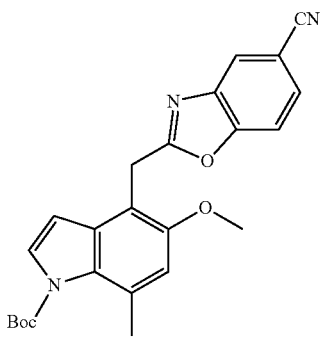 [SMILES: COc1cc(C)c2c(ccn2C(=O)OC(C)(C)C)c1Cc1nc2cc(C#N)ccc2o1]

A solution of tert-butyl 4-(2,2-dibromovinyl)-5-methoxy-7-methyl-1H-indole-1-carboxylate (Example 20-A) (0.720 g, 1.617 mmol) and 3-amino-4-hydroxybenzonitrile (0.325 g, 2.426 mmol) and DABCO (0.544 g, 4.85 mmol) in NMP (1.62 ml) was stirred at 100° C. for 16 hrs. The reaction mixture was cooled and loaded onto silica gel to purify via FCC eluting with Heptane/AcOEt:100/0 to 0/100 to obtain the title compound. MS (ESI+) m/z 418.34 (M+H).

Example 144-B (±)-tert-Butyl 4-(1-(5-cyanobenzo[d]oxazol-2-yl)-2-ethoxy-2-oxoethyl)-5-methoxy-7-methyl-1H-indole-1-carboxylate

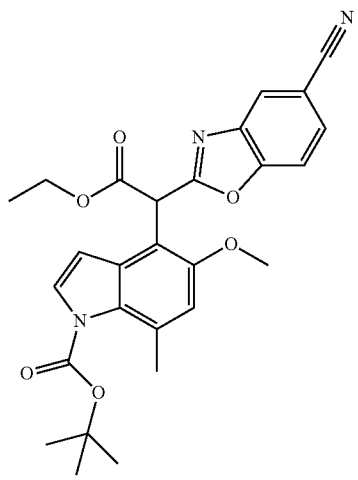 [SMILES: CCOC(=O)C(c1nc2cc(C#N)ccc2o1)c1c(OC)cc(C)c2c1ccn2C(=O)OC(C)(C)C]

To a solution of tert-butyl 4-((5-cyanobenzo[d]oxazol-2-yl)methyl)-5-methoxy-7-methyl-1H-indole-1-carboxylate (Example 144-A) (60 mg, 0.144 mmol) in THF (2.1 mL) under nitrogen at −78° C. was added LiHMDS (0.359 ml, 0.359 mmol) in THF. After 10 mins, ethyl chloroformate (0.276 mL, 2.87 mmol) was added and the reaction was warmed to room temperature. After 5 mins the reaction was quenched with sat. aq. NH$_4$Cl, the layers were separated and the aqueous layer extracted with EtOAc. The EtOAc layer was concentrated, purified via FCC with Hep/EtOAc to obtain the title compound. MS (ESI+) m/z 490.0 (M+H).

Example 144-C (±)-tert-Butyl 4-(2-(5-cyanobenzo[d]oxazol-2-yl)-1-ethoxy-1-oxopropan-2-yl)-5-methoxy-7-methyl-1H-indole-1-carboxylate

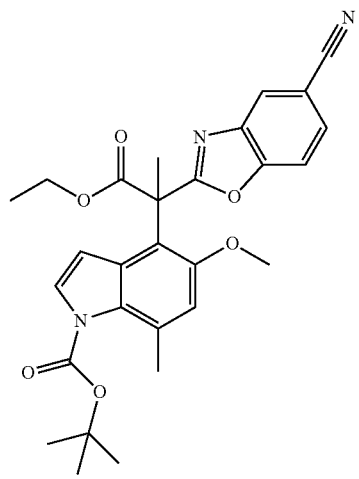 [SMILES: CCOC(=O)C(C)(c1nc2cc(C#N)ccc2o1)c1c(OC)cc(C)c2c1ccn2C(=O)OC(C)(C)C]

To a solution of (±)-tert-butyl 4-(1-(5-cyanobenzo[d]oxazol-2-yl)-2-ethoxy-2-oxoethyl)-5-methoxy-7-methyl-1H-indole-1-carboxylate (Example 144-B) (139.5 mg, 0.285 mmol) in DMF (2.850 mL) were added successively MeI (0.080 mL, 1.282 mmol) and NaH (34.2 mg, 0.855 mmol) at 0° C. After stirring for 2.5 hrs at this temperature another additional aliquot of MeI (0.045 mL, 0.57 mmol) were added to the mixture. The mixture was allowed to stir at room temperature overnight. The reaction mixture was quenched with a saturated aq. solution of ammonium chloride at 0° C. and the layers were separated. The aqueous layer was extracted with AcOEt and the combined organic layers were concentrated to give crude product that was purified via FCC: Heptane/AcOEt:100/0 to 50/50 to obtain the title compound. MS (ESI+) m/z 504.38 (M+H).

Example 144-D (±)-Ethyl 2-(5-cyanobenzo[d]oxazol-2-yl)-2-(5-methoxy-7-methyl-1H-indol-4-yl)propanoate

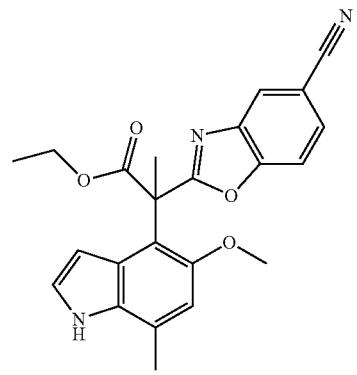 [SMILES: CCOC(=O)C(C)(c1nc2cc(C#N)ccc2o1)c1c(OC)cc(C)c2[nH]ccc12]

To a solution of (±)-tert-butyl 4-(2-(5-cyanobenzo[d]oxazol-2-yl)-1-ethoxy-1-oxopropan-2-yl)-5-methoxy-7-methyl-1H-indole-1-carboxylate (Example 144-C) (44 mg, 0.087 mmol) in EtOH (874 µL), was added cesium carbonate (142 mg, 0.437 mmol). The reaction mixture was heated up to 60° C. and stirred for 2 hrs. The reaction mixture was quenched with a saturated solution of sodium bicarbonate at 0° C. The layers were separated and the aqueous layer was extracted with EtOAc (2×). The combined organic layers were dried over magnesium sulfate and concentrated to give crude product that was purified via FCC (4 g column): Heptane/AcOEt: 100/0 to 50/50 to obtain the title compound. $^1$H NMR (600 MHz, DMSO-$d_6$) δ ppm 11.05 (br. s., 1H) 8.36-8.60 (m, 1H) 7.72-8.02 (m, 2H) 7.13 (t, J=2.93 Hz, 1H) 6.81 (s, 1H) 5.12 (dd, J=3.21, 1.83 Hz, 1H) 4.02-4.28 (m, 2H) 3.62 (s, 3H) 2.43-2.48 (m, 3H) 2.03 (s, 3H) 1.08 (t, J=7.11 Hz, 3H). HRMS calcd. for $C_{23}H_{21}N_3O_4$ (M+H)$^+$ 404.1610. found 404.1619.

Example 145

Example 145-A tert-Butyl 4-((5-cyano-1-((2-(trimethylsilyl)ethoxy)methyl)-1H-benzo[d]imidazol-2-yl)methyl)-5-methoxy-7-methyl-1H-indole-1-carboxylate and tert-butyl 4-((6-cyano-1-((2-(trimethylsilyl)ethoxy)methyl)-1H-benzo[d]imidazol-2-yl)methyl)-5-methoxy-7-methyl-1H-indole-1-carboxylate

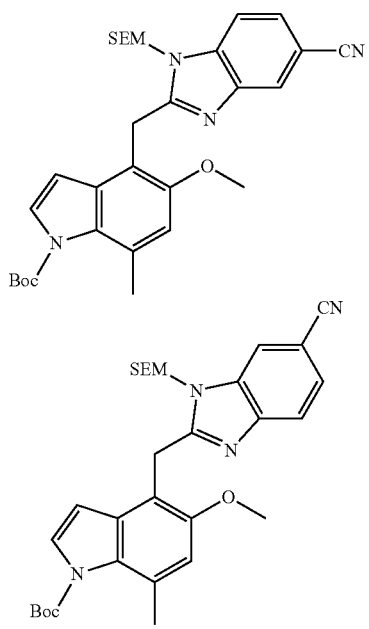

To a solution of tert-butyl 4-((5-cyano-1H-benzo[d]imidazol-2-yl)methyl)-5-methoxy-7-methyl-1H-indole-1-carboxylate (Example 20-B) (1.20 g, 2.88 mmol) in THF (Volume: 28.8 ml) at 0° C. was added NaH (0.173 g, 4.32 mmol). After 5 minutes SEM-Cl (1.022 ml, 5.76 mmol) was added at the same temperature. The reaction mixture was allowed to reach rt. After stirring for 2 hrs the reaction mixture was quenched with brine, extracted with AcOEt, passed through a phase separator and concentrated to give crude product that was purified via FCC with Heptane/AcOEt (100/0 to 50/50) to obtain the mixture of title compounds. MS (ESI+) m/z 547.37 (M+H).

Example 145-B (±)-tert-Butyl 4-(1-(5-cyano-1-((2-(trimethylsilyl)ethoxy)methyl)-1H-benzo[d]imidazol-2-yl)-3-methoxy-3-oxopropyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-3-methoxy-3-oxopropyl)-5-methoxy-7-methyl-1H-indole-1-carboxylate

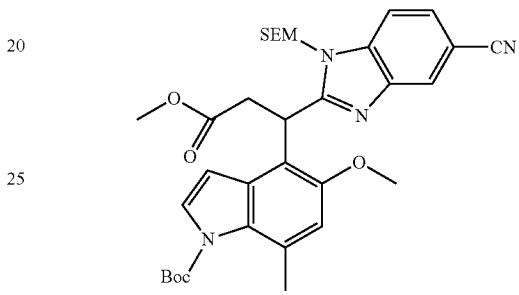

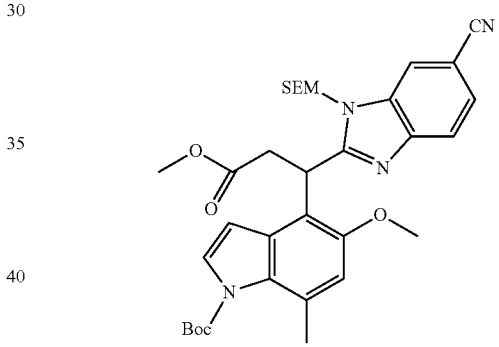

A solution of tert-butyl 4-((5-cyano-1-((2-(trimethylsilyl)ethoxy)methyl)-1H-benzo[d]imidazol-2-yl)methyl)-5-methoxy-7-methyl-1H-indole-1-carboxylate and tert-butyl 4-((6-cyano-1-((2-(trimethylsilyl)ethoxy)methyl)-1H-benzo[d]imidazol-2-yl)methyl)-5-methoxy-7-methyl-1H-indole-1-carboxylate (Example 145-A) (266 mg, 0.487 mmol) in THF (1.32 mL) was added to a mixture of potassium tert-butoxide (109 mg, 0.973 mmol) in THF (3.96 mL) under nitrogen at −78° C. After stirring for 15 min a solution 18-crown-6 (12.86 mg, 0.049 mmol) in THF (0.660 mL), that was degassed and placed under nitrogen, was added to the mixture at the same temperature and stirred for another 15 min. At this point, methyl bromoacetate (0.628 mL, 6.81 mmol) in THF (0.660 mL) was degassed and added dropwise. The reaction mixture was stirred at −78° C. for 1 hr and then allowed to reach rt over 1 hr and stirred at rt for 16 hrs. The reaction mixture was quenched with a saturated solution of ammonium chloride, diluted with DCM and water and passed through a phase separator and concentrated to give crude product that was purified via FCC with Heptane/AcOEt (100/0 to 50/50) to obtain the mixture of title compounds. MS (ESI+) m/z 619.47 (M+H).

Example 145-C (±)-Methyl 3-(5-cyano-1H-benzo[d]imidazol-2-yl)-3-(5-methoxy-7-methyl-1H-indol-4-yl)propanoate

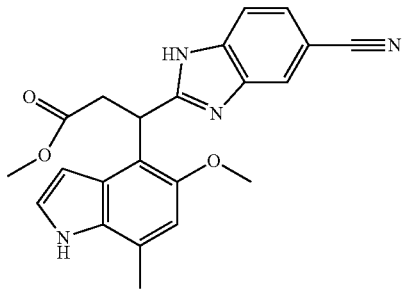 [SMILES: COC(=O)CC(c1nc2cc(C#N)ccc2[nH]1)c1c(OC)cc(C)c2[nH]ccc12]

A mixture of (±)-tert-butyl 4-(1-(5-cyano-1-((2-(trimethylsilyl)ethoxy)methyl)-1H-benzo[d]imidazol-2-yl)-3-methoxy-3-oxopropyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-3-methoxy-3-oxopropyl)-5-methoxy-7-methyl-1H-indole-1-carboxylate (Example 145-B) (400 mg, 0.646 mmol) was dissolved in 1.25M HCl in MeOH (20 mL, 25.00 mmol) and heated at 65° C. for 22 hrs. The reaction mixture was cooled down to 0° C. and neutralized with ammonium hydroxide. The layers were separated and the aqueous layer was extracted with AcOEt/heptanes (4:1) (3 x). The combined organic layers were dried over MgSO$_4$, filtered and concentrated to give crude product that was purified via FCC with Heptane/AcOEt (100/0 to 0/100) to obtain the title compound. MS (ESI+) m/z 389.36 (M+H).

Example 145-D (±)-3-(5-Cyano-1H-benzo[d]imidazol-2-yl)-3-(5-methoxy-7-methyl-1H-indol-4-yl)propanoic acid

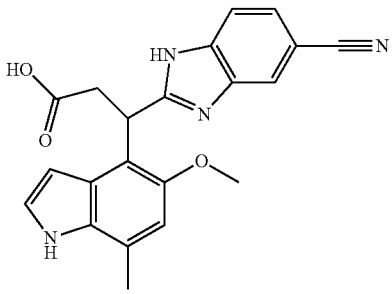 [SMILES: COc1cc(C)c2[nH]ccc2c1C(CC(=O)O)c1nc2cc(C#N)ccc2[nH]1]

To a solution of (±)-methyl 3-(5-cyano-1H-benzo[d]imidazol-2-yl)-3-(5-methoxy-7-methyl-1H-indol-4-yl)propanoate (Example 145-C) (254 mg, 0.248 mmol) in MeOH (6 mL) was added 1N NaOH (1.439 mL, 1.439 mmol) and the resulting solution was stirred at rt. After stirring for 1.5 hrs additional 1N NaOH (1.439 mL, 1.439 mmol) was added to the mixture and the mixture was stirred at rt for 16 hrs. At this point, additional 1N NaOH (1.439 mL, 1.439 mmol) was added and the mixture was heated to 60° C. for 3.5 hrs. The reaction mixture was then cooled to rt, diluted with water and the aqueous layer (pH=10) was washed AcOEt (4×). The water layer was acidified with 1N HCl (pH=2-3) and then extracted with AcOEt. The organic layer was washed with water (2×). The combined organic layers were passed through a phase separator and concentrated to give crude product that was purified via preparative HPLC (HC-B) to obtain the title compound. $^1$H NMR (400 MHz, DMSO-d$_6$) δ ppm 11.50-12.64 (m, 1H) 10.92 (br. s., 1H) 7.87-8.25 (m) 7.48 (d) 7.13 (t, J=2.78 Hz, 1H) 6.79 (s, 1H) 5.97 (dd, J=2.91, 1.89 Hz, 1H) 5.34 (dd, J=9.73, 4.67 Hz, 1H) 3.78 (s, 3H) 3.54-3.69 (m, 1H) 2.59-2.65 (m, 1H) 2.44 (s, 3H). HRMS calcd. for C$_{21}$H$_{18}$N$_4$O$_3$ (M+H)$^+$ 375.1457. found 375.1458.

Example 145-E (±)-2-(3-hydroxy-1-(5-methoxy-7-methyl-1H-indol-4-yl)propyl)-1H-benzo[d]imidazole-5-carbonitrile

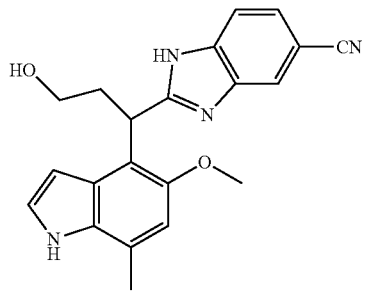 [SMILES: COc1cc(C)c2[nH]ccc2c1C(CCO)c1nc2cc(C#N)ccc2[nH]1]

To a solution of (±)-methyl 3-(5-cyano-1H-benzo[d]imidazol-2-yl)-3-(5-methoxy-7-methyl-1H-indol-4-yl)propanoate (Example 145-C) (50 mg, 0.129 mmol) in MeOH (1.3 mL) was added NaBH$_4$ (121 mg, 3.25 mmol) at 0° C. The reaction mixture was allowed to reach rt and stirred for 48 hrs. The reaction mixture was quenched with water at 0° C. and extracted with EtOAc (2×). The combined organic layers were passed through a phase separator and concentrated and absorbed onto silica to purify via FCC with DCM/MeOH (100/0 to 95/5) to obtain the title compound. $^1$H NMR (400 MHz, DMSO-d$_6$) δ ppm 12.04-12.30 (m, 1H) 10.89 (br. s., 1H) 8.10 (s, 1H) 7.68-7.77 (m, 1H) 7.38-7.51 (m, 1H) 6.99-7.21 (m, 1H) 6.78 (s, 1H) 6.10 (br. s., 1H) 4.99 (t, J=7.33 Hz, 1H) 4.36-4.57 (m, 1H) 3.74 (s, 3H) 3.42 (td, J=11.56, 5.68 Hz, 2H) 2.77 (dd, J=13.39, 6.82 Hz, 1H) 2.44 (s, 3H) 2.11-2.23 (m, 1H). HRMS calcd. for C$_{21}$H$_{20}$N$_4$O$_2$ (M+H)$^+$ 361.1651. found 361.1659.

Example 146

Example 146-A (±)-tert-butyl 4-(1-(5-cyano-1-((2-(trimethylsilyl)ethoxy)methyl)-1H-benzo[d]imidazol-2-yl)-4-methoxy-4-oxobutyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-4-methoxy-4-oxobutyl)-5-methoxy-7-methyl-1H-indole-1-carboxylate

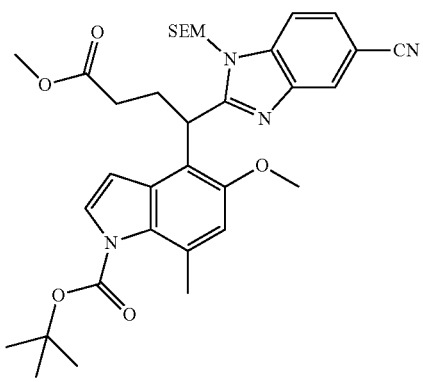

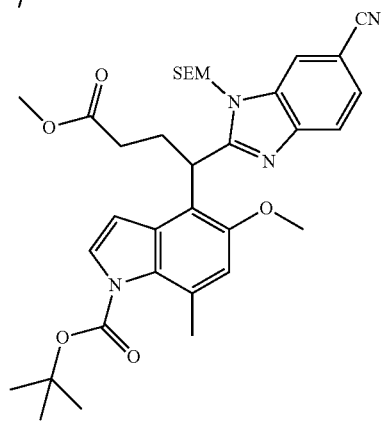

A solution of potassium tert-butoxide (66.5 mg, 0.593 mmol) in THF (1.2 mL) was added to a solution tert-butyl 4-((5-cyano-1-((2-(trimethylsilyl)ethoxy)methyl)-1H-benzo[d]imidazol-2-yl)methyl)-5-methoxy-7-methyl-1H-indole-1-carboxylate and tert-butyl 4-((6-cyano-1-((2-(trimethylsilyl)ethoxy)methyl)-1H-benzo[d]imidazol-2-yl)methyl)-5-methoxy-7-methyl-1H-indole-1-carboxylate (Example 145-A) (270 mg, 0.494 mmol) in THF (1.2 mL) under nitrogen at −78° C. After 15 min, 18-crown-6 (68 mg, 0.257 mmol) in THF (1.2 mL) was added to the mixture at the same temp and stirred. After 30 min methyl acrylate (71.6 μl, 0.790 mmol) in THF (1.2 mL) was added dropwise and stirred at the same temp for 2 hours. The reaction was quenched with a solution of saturated ammonium chloride, diluted with DCM, passed through a phase separator, concentrated and absorbed onto silica to purify via FCC with Heptane/AcOEt (100/0 to 50/50) to obtain the mixture of title compounds. MS (ESI+) m/z 633.7 (M+H).

Example 146-B (±)-Methyl 4-(5-cyano-1H-benzo[d]imidazol-2-yl)-4-(5-methoxy-7-methyl-1H-indol-4-yl)butanoate

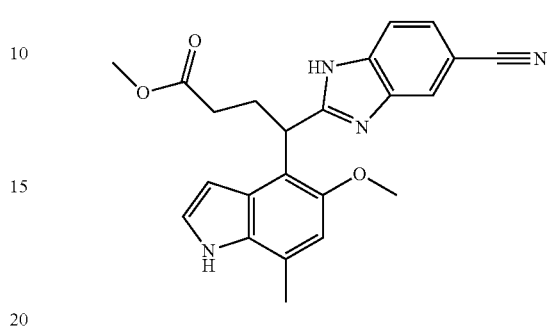

To a solution (±)-tert-butyl 4-(1-(5-cyano-1-((2-(trimethylsilyl)ethoxy)methyl)-1H-benzo[d]imidazol-2-yl)-4-methoxy-4-oxobutyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-4-methoxy-4-oxobutyl)-5-methoxy-7-methyl-1H-indole-1-carboxylate (Example 146-A) (0.21 g, 0.332 mmol) in DCM (3.32 ml) was added tin(IV) chloride (3.32 ml, 3.32 mmol) at 0° C. The solution was stirred at 0° C. for 30 minutes and then at room temperature for 1 hour. The reaction was concentrated and absorbed onto silica to purify via FCC (0-50% EtOAc:heptanes) to obtain the title compound. MS (ESI+) m/z 403.4 (M+H).

Example 146-C (±)-4-(5-Cyano-1H-benzo[d]imidazol-2-yl)-4-(5-methoxy-7-methyl-1H-indol-4-yl)butanoic acid

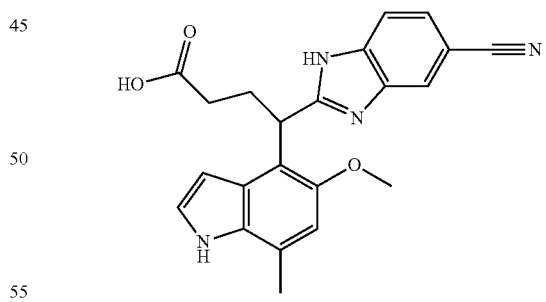

(±)-Methyl 4-(5-cyano-1H-benzo[d]imidazol-2-yl)-4-(5-methoxy-7-methyl-1H-indol-4-yl)butanoate (Example 146-B) (40 mg, 0.099 mmol) was dissolved in MeOH (1 mL) and then added 1 N NaOH (248 μl, 0.248 mmol). The reaction was stirred at room temperature for 3 h, concentrated and then directly purified via RP-HPLC (HC-B) to obtain the title compound. $^1$H NMR (400 MHz, DMSO-d6) d ppm 10.92 (br. s., 1H) 7.61-8.32 (m, 1H) 7.47-7.51 (m, 2H) 7.13 (d, J=5.56 Hz, 1H) 6.79 (s, 1H) 5.99 (br. s., 1H) 4.90 (dd, J=8.59, 5.81 Hz, 1H) 3.74 (s, 3H) 2.72-2.82 (m, 1H) 2.45 (s, 3H) 2.20-2.32

(m, 2H) 2.06-2.18 (m, 1H). HRMS calcd. for $C_{22}H_{20}N_4O_3$ (M+H)+ 389.1605. found 389.1604.

Example 147

Example 147-A (±)-tert-Butyl 4-(1-(5-cyano-1-((2-(trimethylsilyl)ethoxy)methyl)-1H-benzo[d]imidazol-2-yl)-3-methoxy-2-methyl-3-oxopropyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-3-methoxy-2-methyl-3-oxopropyl)-5-methoxy-7-methyl-1H-indole-1-carboxylate

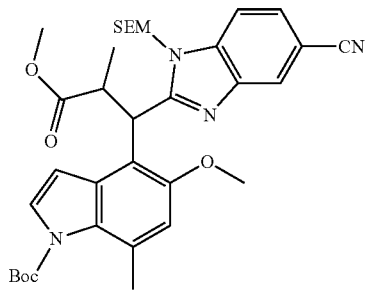

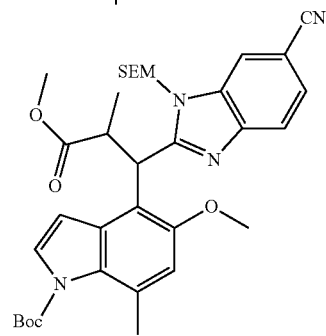

To tert-Butyl 4-((5-cyano-1-((2-(trimethylsilyl)ethoxy)methyl)-1H-benzo[d]imidazol-2-yl)methyl)-5-methoxy-7-methyl-1H-indole-1-carboxylate and tert-butyl 4-((6-cyano-1-((2-(trimethylsilyl)ethoxy)methyl)-1H-benzo[d]imidazol-2-yl)methyl)-5-methoxy-7-methyl-1H-indole-1-carboxylate (Example 145-A) (850 mg, 1.55 mmol) in THF (20 mL) at −78° C. was added 1 M LHMDS in THF (4.6 mL, 4.6 mmol) and the reaction was stirred for 30 minutes. Methyl 2-bromopropanoate (1.72 mL, 15.5 mmol) was then added and the reaction was allowed to stir at room temperature for 2 hours. The mixture was poured into a saturated aq. solution of NaHCO$_3$ (80 mL) and extracted with ethyl acetate, dried over sodium sulfate, concentrated, and purified via preparative HPLC(X-terra MS, C$_{18}$ column, 20 mL/min) to obtain (±)-tert-butyl 4-(1-(5-cyano-1-((2-(trimethylsilyl)ethoxy)methyl)-1H-benzo[d]imidazol-2-yl)-3-methoxy-2-methyl-3-oxopropyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-3-methoxy-2-methyl-3-oxopropyl)-5-methoxy-7-methyl-1H-indole-1-carboxylate as a single diastereomer (diastereomer A, t$_r$=16.9 min) and (±)-tert-butyl 4-(1-(5-cyano-1-((2-(trimethylsilyl)ethoxy)methyl)-1H-benzo[d]imidazol-2-yl)-3-methoxy-2-methyl-3-oxopropyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-3-methoxy-2-methyl-3-oxopropyl)-5-methoxy-7-methyl-1H-indole-1-carboxylate as a single diastereomer (diastereomer B, t$_r$=18.7 min). MS (ESI+) m/z 633.2 (M+H).

Example 147-B (±)-Methyl 3-(5-cyano-1H-benzo[d]imidazol-2-yl)-3-(5-methoxy-7-methyl-1H-indol-4-yl)-2-methylpropanoate (diastereomer A)

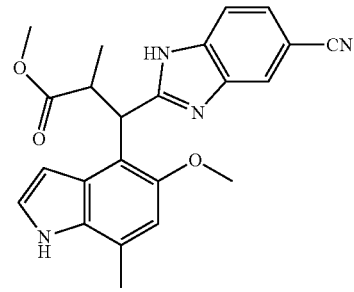 [SMILES: COC(=O)C(C)C(c1nc2cc(C#N)ccc2[nH]1)c1c(OC)cc(C)c2[nH]ccc12]

The title compound was synthesized from (±)-tert-butyl 4-(1-(5-cyano-1-((2-(trimethylsilyl)ethoxy)methyl)-1H-benzo[d]imidazol-2-yl)-3-methoxy-2-methyl-3-oxopropyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-3-methoxy-2-methyl-3-oxopropyl)-5-methoxy-7-methyl-1H-indole-1-carboxylate as a single diastereomer (diastereomer A, t$_r$=16.9 min from Example 147-A) following the procedure shown in Example 142-C. MS (ESI+) m/z 403.0 (M+H).

Example 147-C (±)-Methyl 3-(5-cyano-1H-benzo[d]imidazol-2-yl)-3-(5-methoxy-7-methyl-1H-indol-4-yl)-2-methylpropanoate (diastereomer B)

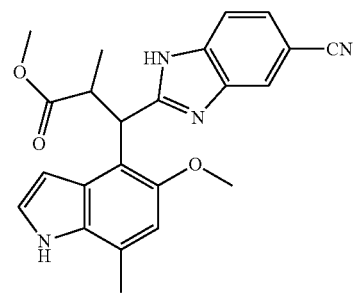 [SMILES: COC(=O)C(C)C(c1nc2cc(C#N)ccc2[nH]1)c1c(OC)cc(C)c2[nH]ccc12]

The title compound was synthesized from (±)-tert-butyl 4-(1-(5-cyano-1-((2-(trimethylsilyl)ethoxy)methyl)-1H-benzo[d]imidazol-2-yl)-3-methoxy-2-methyl-3-oxopropyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-3-methoxy-2-methyl-3-oxopropyl)-5-methoxy-7-methyl-1H-indole-1-carboxylate as a single diastereomer (diastereomer B, t$_r$=18.7 min from

Example 147-D (±)-3-(5-Cyano-1H-benzo[d]imidazol-2-yl)-3-(5-methoxy-7-methyl-1H-indol-4-yl)-2-methylpropanoic acid (Diastereomer A)

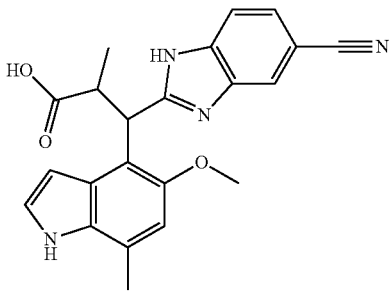

To (±)-methyl 3-(5-cyano-1H-benzo[d]imidazol-2-yl)-3-(5-methoxy-7-methyl-1H-indol-4-yl)-2-methylpropanoate (diastereomer A, Example 147-B) (45 mg, 0.11 mmol) was added LiOH (50 mg, 2.0 mmol) in MeOH/Water (3 mL:0.8 mL) and the reaction was heated at 60° C. overnight. The reaction was concentrated, diluted with ethyl acetate (100 mL) and 1 M HCl (20 mL). The organic layer was removed, dried over sodium sulfate and purified via RP-FCC (ACN/water) to afford the title compound. $^1$H NMR (400 MHz, DMSO-$d_6$) δ ppm 10.63-10.91 (m, 1H) 7.97 (br. s., 1H) 7.56 (br. s., 1H) 7.44-7.50 (m, 1H) 7.13-7.18 (m, 1H) 6.74 (s, 1H) 6.26 (br. s., 1H) 5.15 (d, J=9.29 Hz, 1H) 3.82 (s, 3H) 3.61-3.73 (m, 1H) 2.40 (s, 3H) 1.25 (d, J=6.97 Hz, 3H). HRMS calcd. for $C_{22}H_{20}N_4O_3$ (M+H)$^+$ 389.1605. found 389.1604.

Example 147-E (±)-3-(5-Cyano-1H-benzo[d]imidazol-2-yl)-3-(5-methoxy-7-methyl-1H-indol-4-yl)-2-methylpropanoic acid (Diastereomer B)

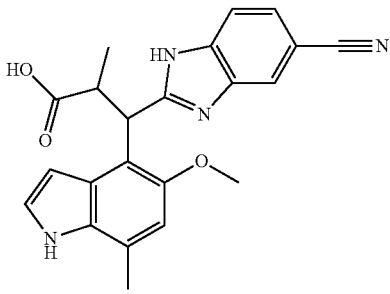 [SMILES: COc1cc(C)c2[nH]ccc2c1C(c1nc2cc(C#N)ccc2[nH]1)C(C)C(=O)O]

The title compound was synthesized from (±)-methyl 3-(5-cyano-1H-benzo[d]imidazol-2-yl)-3-(5-methoxy-7-methyl-1H-indol-4-yl)-2-methylpropanoate (diastereomer B, Example 147-C) using the same procedure shown in Example 147-D. $^1$H NMR (400 MHz, METHANOL-$d_4$) δ ppm 7.83 (s, 1H) 7.54 (d, J=8.34 Hz, 1H) 7.43 (dd, J=8.34, 1.26 Hz, 1H) 7.13 (d, J=3.03 Hz, 1H) 6.79 (s, 1H) 6.41 (d, J=3.03 Hz, 1H) 5.30 (d, J=11.37 Hz, 1H) 3.84-3.92 (m, 1H) 3.83 (s, 3H) 2.48 (s, 3H) 1.01 (d, J=7.07 Hz, 3H). HRMS calcd. for $C_{22}H_{20}N_4O_3$ (M+H)$^+$ 389.1605. found 389.1606.

Example 147-F (±)-2-(3-hydroxy-1-(5-methoxy-7-methyl-1H-indol-4-yl)-2-methylpropyl)-1H-benzo[d]imidazole-5-carbonitrile (Diastereomer B)

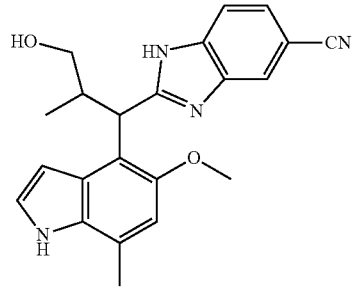 [SMILES: COc1cc(C)c2[nH]ccc2c1C(c1nc2cc(C#N)ccc2[nH]1)C(C)CO]

The title compound was synthesized from (±)-methyl 3-(5-cyano-1H-benzo[d]imidazol-2-yl)-3-(5-methoxy-7-methyl-1H-indol-4-yl)-2-methylpropanoate (diastereomer B, Example 147-C) following the same procedure as in Example 145-E. $^1$H NMR (400 MHz, DMSO-$d_6$) δ ppm 11.80-12.49 (m, 1H) 10.83 (br. s., 1H) 8.07 (s, 1H) 7.65-7.77 (m, 1H) 7.39-7.51 (m, 1H) 7.15 (br. s., 1H) 6.75 (s, 1H) 6.45 (br. s., 1H) 4.84 (d, J=10.15 Hz, 1H) 4.59 (br. s., 1H) 3.81 (s, 3H) 3.60 (dd, J=9.84, 4.22 Hz, 1H) 3.40-3.51 (m, 1H) 2.97-3.13 (m, 1H) 2.44 (s, 3H) 0.71 (d, J=6.85 Hz, 3H). MS (ESI+) m/z 375.33 (M+H).

Example 148

Example 148-A (±)-tert-Butyl 4-(1-(5-cyanobenzo[d]oxazol-2-yl)-3-methoxy-3-oxopropyl)-5-methoxy-7-methyl-1H-indole-1-carboxylate

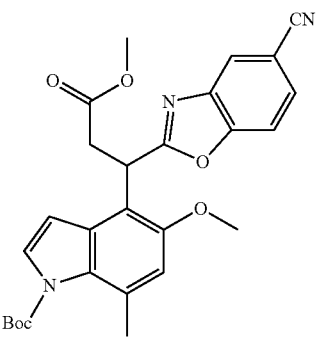 [SMILES: COC(=O)CC(c1nc2cc(C#N)ccc2o1)c1c(OC)cc(C)c2c1ccn2C(=O)OC(C)(C)C]

To a mixture of potassium tert-butoxide (108 mg, 0.958 mmol) in THF (0.715 mL) at −78° C. under nitrogen was added tert-butyl 4-((5-cyanobenzo[d]oxazol-2-yl)methyl)-5-methoxy-7-methyl-1H-indole-1-carboxylate (Example 144-A) (200 mg, 0.479 mmol) in THF (4.3 mL) under nitrogen. After stirring for 15 min a solution of 18-crown-6 (12.66 mg, 0.048 mmol) in THF (1.430 mL) was added to the mixture at the same temperature and stirred for another 15 min. Then a solution of methyl bromoacetate (0.618 mL, 6.71 mmol) in THF (0.715 mL) was degassed and added dropwise and stirred at the same temp for 10 min. The reaction mixture was quenched with a saturated solution of ammonium chloride, extracted with EtOAc (2×), passed through a phase separator and concentrated to give the title compound. MS (ESI+) m/z 490.32 (M+H).

Example 148-B (±)-3-(5-Cyanobenzo[d]oxazol-2-yl)-3-(5-methoxy-7-methyl-1H-indol-4-yl)propanoic acid

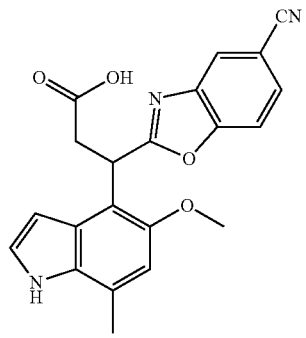 [SMILES: COc1cc(C)c2[nH]ccc2c1C(CC(=O)O)c1nc2cc(C#N)ccc2o1]

(±)-tert-Butyl 4-(1-(5-cyanobenzo[d]oxazol-2-yl)-3-methoxy-3-oxopropyl)-5-methoxy-7-methyl-1H-indole-1-carboxylate (Example 148-A) (0.3 g, 0.613 mmol) was dissolved in MeOH (6 ml). cesium carbonate (0.998 g, 3.06 mmol) was added and the reaction was heated at 65° C. for 2.5 hours. The reaction was then cooled to room temperature and treated with 1 N HCl until pH=~3. The mixture was then diluted with DCM and passed through a phase separator, concentrated and purified via preparative HPLC (HC-B) to give the title compound. $^1$H NMR (400 MHz, DMSO-$d_6$) δ ppm 11.00 (br. s., 1H) 8.34 (t, J=1.14 Hz, 1H) 7.58-7.92 (m, 2H) 7.22 (t, J=2.78 Hz, 1H) 6.77 (s, 1H) 6.22 (dd, J=3.03, 1.89 Hz, 1H) 5.39 (dd, J=9.85, 4.67 Hz, 1H) 3.72 (s, 3H) 3.57 (dd, J=16.67, 9.98 Hz, 1H) 2.74 (dd, J=16.67, 4.67 Hz, 1H) 2.44 (d, J=0.63 Hz, 3H). HRMS calcd. for $C_{21}H_{17}N_3O_4$ (M+H)$^+$ 376.1297. found 376.1290.

Example 148-C a) (±)-Methyl 3-(5-cyanobenzo[d]oxazol-2-yl)-3-(5-methoxy-7-methyl-1H-indol-4-yl)propanoate

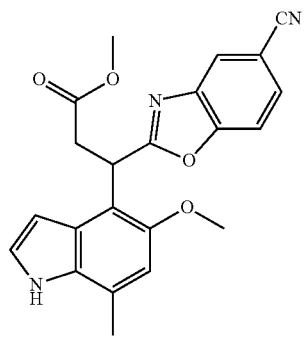 [SMILES: COC(=O)CC(c1nc2cc(C#N)ccc2o1)c1c(OC)cc(C)c2[nH]ccc12]

To a solution of (±)-3-(5-cyanobenzo[d]oxazol-2-yl)-3-(5-methoxy-7-methyl-1H-indol-4-yl)propanoic acid (Example 148-B) (60 mg, 0.160 mmol) in DCM (639 μl) were added MeOH (16.17 μl, 0.400 mmol), DMAP (3.91 mg, 0.032 mmol) and DCC (52.8 mg, 0.256 mmol) successively. The reaction mixture was stirred at rt overnight. The reaction mixture was quenched with a saturated solution of ammonium chloride, diluted with DCM and water and passed through a phase separator. The organic layer was concentrated to give crude product that was purified via FCC with Heptane/AcOEt (100/0 to 0/100) to obtain the title compound. (ESI+) m/z 390.4 (M+H).

b) (+) and (−)-methyl 3-(5-cyanobenzo[d]oxazol-2-yl)-3-(5-methoxy-7-methyl-1H-indol-4-yl)propanoate Resolution of the enantiomers of methyl 3-(5-cyanobenzo[d]oxazol-2-yl)-3-(5-methoxy-7-methyl-1H-indol-4-yl)propanoate was achieved by chiral SFC using a CHIRALPAK® AD-H column with 25% MeOH+0.2% NH$_4$OH in CO$_2$ to give (+) or (−)-methyl 3-(5-cyanobenzo[d]oxazol-2-yl)-3-(5-methoxy-7-methyl-1H-indol-4-yl)propanoate ($t_r$=3.8 min) and (−) or (+)-methyl 3-(5-cyanobenzo[d]oxazol-2-yl)-3-(5-methoxy-7-methyl-1H-indol-4-yl)propanoate ($t_r$=4.8 min).

Example 148-D (+)-3-(5-cyanobenzo[d]oxazol-2-yl)-3-(5-methoxy-7-methyl-1H-indol-4-yl)propanoic acid

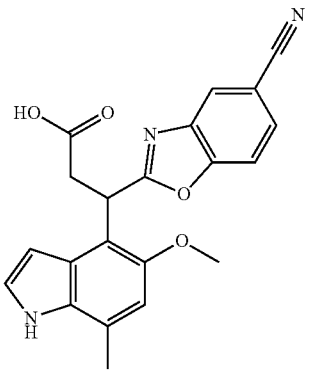 [SMILES: COc1cc(C)c2[nH]ccc2c1C(CC(=O)O)c1nc2cc(C#N)ccc2o1]

To (+) or (−)-methyl 3-(5-cyanobenzo[d]oxazol-2-yl)-3-(5-methoxy-7-methyl-1H-indol-4-yl)propanoate ($t_r$=3.8 min) (74 mg, 0.190 mmol) in THF (475 μl) and water (475 μl) was added NaOH (950 μl, 0.950 mmol) and the reaction stirred at room temperature for 4 hours. The reaction was directly purified via preparative HPLC (HC-B) to obtain the title compound. $^1$H NMR as in Example 148-B. HRMS calcd. for $C_{21}H_{17}N_3O_4$ (M+H)$^+$ 376.1297. found 376.1290.

Example 148-E (−)-3-(5-cyanobenzo[d]oxazol-2-yl)-3-(5-methoxy-7-methyl-1H-indol-4-yl)propanoic acid

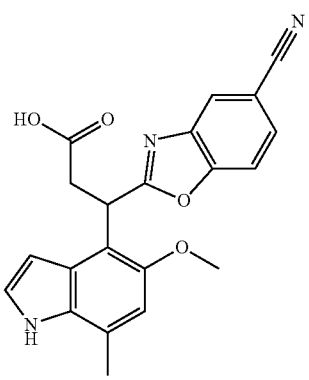 [SMILES: COc1cc(C)c2[nH]ccc2c1C(CC(=O)O)c1nc2cc(C#N)ccc2o1]

The title compound was synthesized starting from (−) or (+)-methyl 3-(5-cyanobenzo[d]oxazol-2-yl)-3-(5-methoxy-7-methyl-1H-indol-4-yl)propanoate ($t_r$=4.8 min) as shown in (Example 148-D). $^1$H NMR as in Example 148-B. HRMS calcd. for $C_{21}H_{17}N_3O_4$ (M+H)$^+$ 376.1297. found 376.1290.

Example 149

Example 149-A (±)-tert-Butyl 4-(1-(5-cyanobenzo[d]oxazol-2-yl)-4-ethoxy-4-oxobutyl)-5-methoxy-7-methyl-1H-indole-1-carboxylate

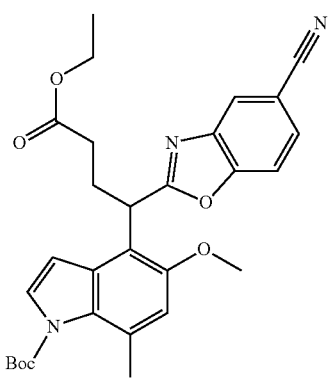 [SMILES: CCOC(=O)CCC(c1nc2cc(C#N)ccc2o1)c1c(OC)cc(C)c2c1ccn2C(=O)OC(C)(C)C]

A solution of tert-butyl 4-((5-cyanobenzo[d]oxazol-2-yl)methyl)-5-methoxy-7-methyl-1H-indole-1-carboxylate (Example 144-A) (189 mg, 0.453 mmol) in THF (1.7 mL) was added to a solution of potassium tert-butoxide (50.8 mg, 0.453 mmol) in THF (1.7 mL) under nitrogen at −78° C. After stirring for 15 min a solution 18-crown-6 (11.97 mg, 0.045 mmol) in THF (566 µl) was added to the mixture at the same temperature and the reaction was then stirred for another 15 min. At this point ethyl acrylate (61.5 µl, 0.679 mmol) in THF (566 µl) was added dropwise. After 25 minutes, the reaction mixture was poured into a solution of saturated ammonium chloride, extracted with EtOAc (2×), passed through a phase separator and concentrated and purified via FCC with Heptane/AcOEt (100/0 to 70/30) to afford the title compound. MS (ESI+) m/z 418.4 (M+H-Boc).

Example 149-B a) (±)-Ethyl 4-(5-cyanobenzo[d]oxazol-2-yl)-4-(5-methoxy-7-methyl-1H-indol-4-yl)butanoate

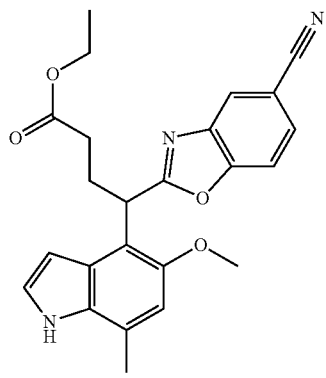 [SMILES: CCOC(=O)CCC(c1nc2cc(C#N)ccc2o1)c1c(OC)cc(C)c2[nH]ccc12]

The title compound was synthesized from (±)-tert-butyl 4-(1-(5-cyanobenzo[d]oxazol-2-yl)-4-ethoxy-4-oxobutyl)-5-methoxy-7-methyl-1H-indole-1-carboxylate (Example 149-A) as described in Example 35-F. MS (ESI+) m/z 418.4 (M+H).

b) (+) and (−)-Ethyl 4-(5-cyanobenzo[d]oxazol-2-yl)-4-(5-methoxy-7-methyl-1H-indol-4-yl)butanoate Resolution of the enantiomers of ethyl 4-(5-cyanobenzo[d]oxazol-2-yl)-4-(5-methoxy-7-methyl-1H-indol-4-yl)butanoate was achieved by chiral SFC using a CHIRALPAK® AD-H column with 40% MeOH in $CO_2$ to give (+) or (−)-ethyl 4-(5-cyanobenzo[d]oxazol-2-yl)-4-(5-methoxy-7-methyl-1H-indol-4-yl)butanoate ($t_r$=3.5 min) and (−) or (+)-ethyl 4-(5-cyanobenzo[d]oxazol-2-yl)-4-(5-methoxy-7-methyl-1H-indol-4-yl)butanoate ($t_r$=5.5 min).

Example 149-C (+)-4-(5-cyanobenzo[d]oxazol-2-yl)-4-(5-methoxy-7-methyl-1H-indol-4-yl)butanoic acid

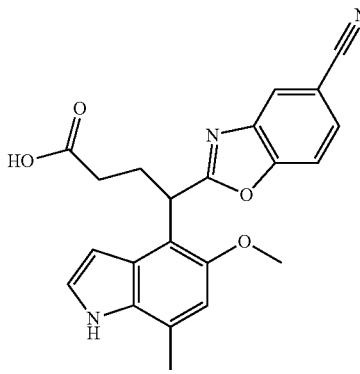

The title compounds was synthesized from (+) or (−)-ethyl 4-(5-cyanobenzo[d]oxazol-2-yl)-4-(5-methoxy-7-methyl-1H-indol-4-yl)butanoate ($t_r$=3.5 min) as described in Example 148-B. $^1$H NMR (400 MHz, DMSO-$d_6$) δ ppm 11.01 (br. s., 1H) 8.37 (t, J=1.01 Hz, 1H) 7.78 (d, J=1.01 Hz, 2H) 7.22 (t, J=2.78 Hz, 1H) 6.77 (s, 1H) 6.18 (dd, J=3.03, 1.77 Hz, 1H) 4.79-5.10 (m, 1H) 3.66 (s, 3H) 2.67-2.79 (m, 1H) 2.46 (s, 3H) 2.23-2.38 (m, 2H) 2.11-2.22 (m, 1H). HRMS calcd. for $C_{22}H_{19}N_3O_4$ (M+H)$^+$ 390.1454. found 390.1438.

Example 149-D (−)-4-(5-cyanobenzo[d]oxazol-2-yl)-4-(5-methoxy-7-methyl-1H-indol-4-yl)butanoic acid

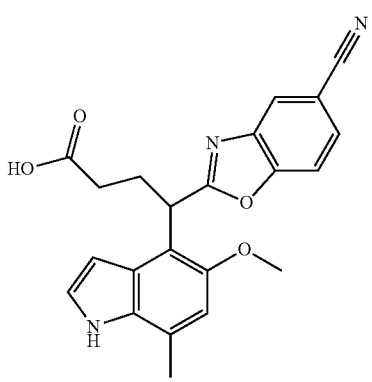 [SMILES: COc1cc(C)c2[nH]ccc2c1C(CCC(=O)O)c1nc2cc(C#N)ccc2o1]

The title compounds was synthesized from (−) or (+)-ethyl 4-(5-cyanobenzo[d]oxazol-2-yl)-4-(5-methoxy-7-methyl-1H-indol-4-yl)butanoate ($t_r$=5.5 min) as described in Example 148-B. $^1$H NMR (400 MHz, DMSO-$d_6$) δ ppm 11.01 (br. s., 1H) 8.24-8.45 (m, 1H) 7.78 (d, J=1.01 Hz, 2H) 7.22 (t, J=2.78 Hz, 1H) 6.77 (s, 1H) 6.18 (dd, J=2.91, 1.89 Hz, 1H) 4.88-5.07 (m, 1H) 3.67 (s, 3H) 2.65-2.77 (m, 1H) 2.46 (s, 3H) 2.23-2.38 (m, 2H) 2.11-2.22 (m, 1H). HRMS calcd. for $C_{22}H_{19}N_3O_4$ (M+H)$^+$ 390.1454. found 390.1438.

Example 150

Example 150-A (±)-tert-Butyl 4-(1-(5-cyanobenzo[d]oxazol-2-yl)ethyl)-5-methoxy-7-methyl-1H-indole-1-carboxylate

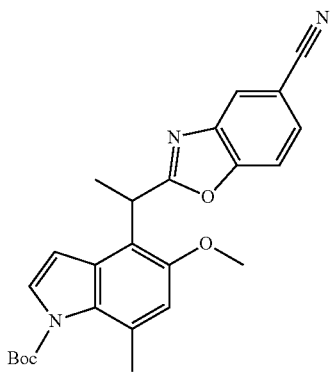 [SMILES: COc1cc(C)c2c(ccn2C(=O)OC(C)(C)C)c1C(C)c1nc2cc(C#N)ccc2o1]

To a solution of tert-butyl 4-((5-cyanobenzo[d]oxazol-2-yl)methyl)-5-methoxy-7-methyl-1H-indole-1-carboxylate (Example 144-A) (277 mg, 0.664 mmol) in THF (3.3 mL) was added MeI (0.050 mL, 0.796 mmol) at −78° C. At this point, LHMDS (0.730 mL, 0.730 mmol) was added at the same temperature and the reaction was allowed to warm up to rt over one hour and stirred at rt for 16 hrs. The reaction mixture was quenched at −78° C. with a saturated ammonium chloride (aq.) solution, diluted with water and DCM, passed through a phase separator, concentrated and purified via FCC (12 g column): Heptane/AcOEt:100/0 to 50/50 to obtain the title compound. MS (ESI+) m/z 432.4 (M+H).

Example 150-B (±)-tert-Butyl 4-(2-(5-cyanobenzo[d]oxazol-2-yl)-5-methoxy-5-oxopentan-2-yl)-5-methoxy-7-methyl-1H-indole-1-carboxylate

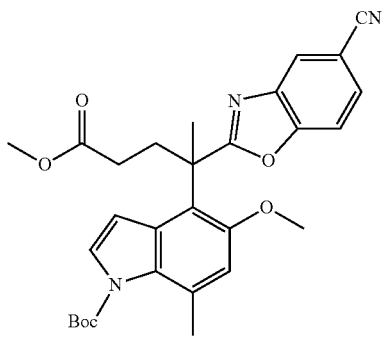 [SMILES: COC(=O)CCC(C)(c1nc2cc(C#N)ccc2o1)c1c(OC)cc(C)c2c1ccn2C(=O)OC(C)(C)C]

To a mixture of potassium tert-butoxide (15.60 mg, 0.139 mmol) in THF (329 μl) at −78° C. under nitrogen was added (±)-tert-butyl 4-(1-(5-cyanobenzo[d]oxazol-2-yl)ethyl)-5-methoxy-7-methyl-1H-indole-1-carboxylate (Example 150-A) (50 mg, 0.116 mmol) in THF (659 μL). After stirring for 5 min a solution of 18-crown-6 (3.06 mg, 0.012 mmol) in THF (412 μl) that was degassed and placed under nitrogen was added to the mixture at the same temperature and stirred for another 5 min. Then a solution of methyl acrylate (210 μl, 2.318 mmol) in THF (329 μl) was degassed and added dropwise and stirred at the same temp for 30 min. The reaction mixture was allowed to reach rt over 1 hr and then was stirred at rt for 30 hrs. The reaction mixture was quenched with a saturated solution of ammonium chloride, diluted with DCM and water, passed through a phase separator and concentrated to give the title compound that was taken to the next step without further purification. MS (ESI+) m/z 518.5 (M+H).

Example 150-C (±)-4-(5-cyanobenzo[d]oxazol-2-yl)-4-(5-methoxy-7-methyl-1H-indol-4-yl)pentanoic acid

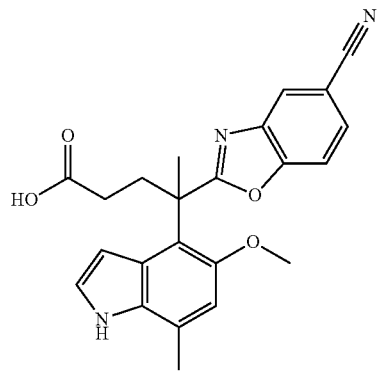 [SMILES: COc1cc(C)c2[nH]ccc2c1C(C)(CCC(=O)O)c1nc2cc(C#N)ccc2o1]

A mixture of (±)-tert-Butyl 4-(2-(5-cyanobenzo[d]oxazol-2-yl)-5-methoxy-5-oxopentan-2-yl)-5-methoxy-7-methyl-1H-indole-1-carboxylate (Example 150-B) (83 mg, 0.160 mmol) and cesium carbonate (261 mg, 0.802 mmol) in MeOH (1.6 mL) was heated to 60° C. and stirred for 2 hrs. The reaction was cooled down to rt and quenched with a saturated solution of ammonium chloride, MeOH was then removed in vacuo. The residue was diluted with AcOEt and water. The layers were separated and the water layer was extracted with AcOEt. The combined organic layers were passed through a phase separator and purified by preparative HPLC (HC-B) to provide the title compound. $^1$H NMR (400 MHz, DMSO-$d_6$) δ ppm 11.05 (br. s., 1H) 8.32 (d, J=1.26 Hz, 1H) 7.66-7.89 (m, 2H) 7.30 (t, J=2.91 Hz, 1H) 6.69 (s, 1H) 6.38 (dd, J=3.03, 1.77 Hz, 1H) 3.51 (s, 3H) 2.58-2.65 (m, 2H) 2.44 (s, 3H) 2.15 (dd, J=9.73, 6.69 Hz, 2H) 1.91 (s, 3H). HRMS calcd. for $C_{23}H_{21}N_3O_4$ (M+H)$^+$ 404.1610. found 404.1607.

Example 151

Example 151-A (±)-tert-Butyl 4-(1-(5-cyano-1-((2-(trimethylsilyl)ethoxy)methyl)-1H-benzo[d]imidazol-2-yl)-4-methoxy-3-methyl-4-oxobutyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-4-methoxy-3-methyl-4-oxobutyl)-5-methoxy-7-methyl-1H-indole-1-carboxylate

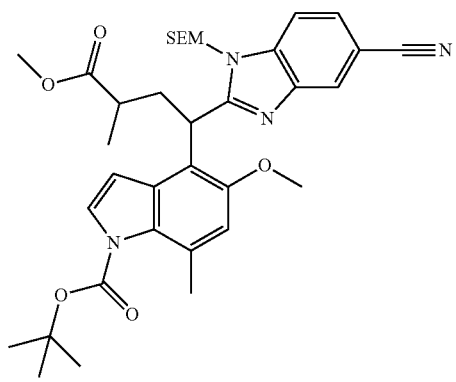

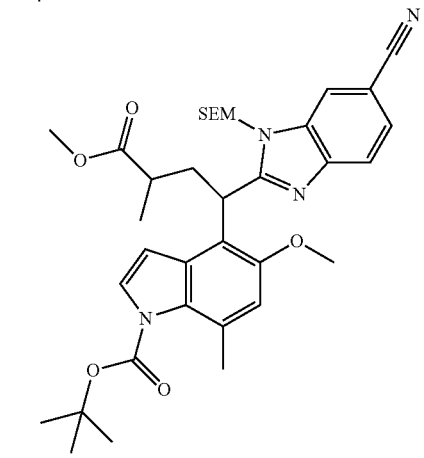

To (±)-tert-butyl 4-(1-(5-cyano-1-((2-(trimethylsilyl)ethoxy)methyl)-1H-benzo[d]imidazol-2-yl)-4-methoxy-4-oxobutyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-4-methoxy-4-oxobutyl)-5-methoxy-7-methyl-1H-indole-1-carboxylate (Example 146-A) (100 mg, 0.158 mmol) in THF (1 mL) at −78° C. was added LDA (2.0 M in heptane/THF/ethylbenzene, 0.1 mL, 0.205 mmol) and stirred for 30 minutes. The reaction was then allowed to reach 0° C. Methyl iodide (34 mg, 0.266 mmol) was added and the mixture was stirred for 30 minutes. The reaction was quenched with a saturated solution of ammonium chloride and then extracted with ethyl acetate, dried and concentrated and absorbed onto silica to purify via FCC (20-30% EtOAc:hexanes) to obtain the mixture of title compounds as mixture of diastereomers. MS (ESI+) m/z 647.2 (M+H).

Example 151-B (±)-Methyl 4-(5-cyano-1H-benzo[d]imidazol-2-yl)-4-(5-methoxy-7-methyl-1H-indol-4-yl)-2-methylbutanoate

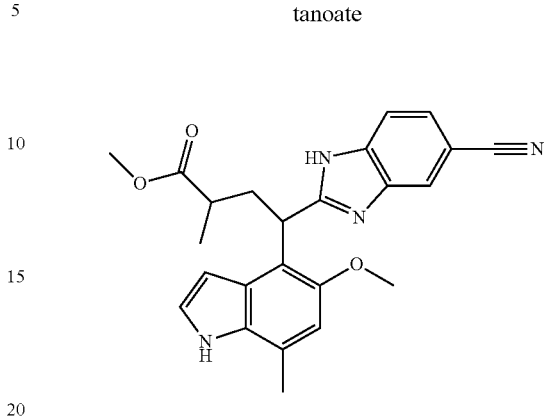

The title compound (as a mixture of diastereomers) was synthesized starting from (±)-tert-butyl 4-(1-(5-cyano-1-((2-(trimethylsilyl)ethoxy)methyl)-1H-benzo[d]imidazol-2-yl)-4-methoxy-3-methyl-4-oxobutyl)-5-methoxy-7-methyl-1H-indole-1-carboxylate and (±)-tert-butyl 4-(1-(6-cyano-1-((2-(trimethylsilyl)ethoxy)methyl)-1H-benzo[d]imidazol-2-yl)-4-methoxy-3-methyl-4-oxobutyl)-5-methoxy-7-methyl-1H-indole-1-carboxylate (Example 151-A) following the procedure shown in Example 142-C. MS (ESI+) m/z 417.4 (M+H).

Example 151-C (±)-2-(4-Hydroxy-1-(5-methoxy-7-methyl-1H-indol-4-yl)-3-methylbutyl)-1H-benzo[d]imidazole-5-carbonitrile

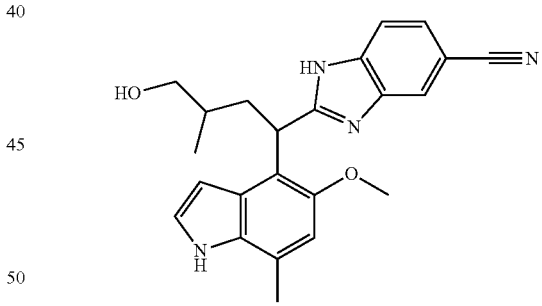

A solution of (±)-methyl 4-(5-cyano-1H-benzo[d]imidazol-2-yl)-4-(5-methoxy-7-methyl-1H-indol-4-yl)-2-methylbutanoate (Example 151-B) (95 mg, 0.228 mmol) in MeOH (3 mL) was treated with sodium borohydride (220 mg, 6.7 mmol) and heated at 60° C. for 4 hours. The reaction was cooled to room temperature and quenched with a saturated solution of ammonium chloride. The product was extracted with ethyl acetate, the organics were dried over sodium sulfate, concentrated and purified via reversed phase FCC(C18 gold column, 10-70% ACN:water) to obtain the title compound as a mixture of diastereomes. $^1$H NMR (400 MHz, DMSO-$d_6$) δ ppm 10.89 (br. s., 1H) 7.96 (br. s., 1H) 7.55 (br. s., 1H) 7.46-7.52 (m, 1H) 7.15 (t, J=2.75 Hz, 1H) 6.79 (s, 1H) 6.14 (d, J=1.96 Hz, 1H) 5.01 (dd, J=10.39, 4.89 Hz, 1H) 3.70-3.81 (m, 3H) 3.17-3.23 (m, 1H) 3.09-3.16 (m, 1H) 2.45

(d, J=0.61 Hz, 3H) 2.38 (ddd, J=13.57, 10.39, 3.67 Hz, 1H) 2.14-2.24 (m, 1H) 1.21-1.33 (m, 2H) 0.95 (d, J=6.60 Hz, 3H). HRMS calcd. for $C_{23}H_{24}N_4O_2$ $(M+H)^+$ 389.1975. found 389.1978.

Example 152

(±)-2-(1-(5-Methoxy-7-methyl-1H-indol-4-yl)-2-(2H-tetrazol-5-yl)ethyl)-1H-benzo[d]imidazole-5-carbonitrile

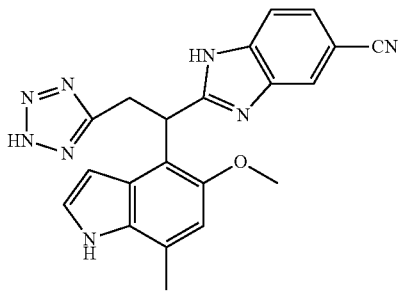 [SMILES: COc1cc(C)c2[nH]ccc2c1C(Cc1nn[nH]n1)c1nc2cc(C#N)ccc2[nH]1]

To a solution of ethyl 1H-tetrazole-5-carboxylate (2 g, 14.07 mmol) in DMF (100 mL), NaH (0.563 g, 14.07 mmol) and SEMCl (2.496 mL, 14.07 mmol) were added at 0° C. The reaction was allowed to warm to rt and stirred overnight. The reaction was quenched with a saturated aqueous solution of NH$_4$Cl, extracted with EtOAc, dried over Na$_2$SO$_4$ and evaporated to obtain a residue. To a solution of NaBH$_4$ (0.800 g, 21.15 mmol) in THF (70.5 ml)/EtOH (35.2 ml), was added CaCl$_2$ (1.76 g, 15.86 mmol) and the reaction stirred for 30 minutes. At this point the previously obtained residue (2.88 g, 10.57 mmol) was added and the reaction left stirring for 4 h at rt. The reaction was quenched with sat. aq. solution of NH$_4$Cl and extracted with EtOAc dried over Na$_2$SO$_4$ and evaporated. To the resulting residue (300 mg, 1.302 mmol) in DCM (10 mL) at 0° C., MsCl (0.203 mL, 2.60 mmol) was added and then Et$_3$N (0.722 mL, 5.21 mmol). The reaction was stirred at rt for 2 h. The reaction was quenched with brine and extracted with EtOAc. The crude product was dried, filtered and evaporated. It was then dissolved in acetone (suspension) and then NaI (293 mg, 1.954 mmol) was added at rt. The reaction was stirred at rt overnight. The reaction was quenched with brine, extracted with EtOAc dried over Na$_2$SO$_4$ and evaporated to give a crude residue. A solution of tert-butyl 4-((5-cyano-1-((2-(trimethylsilyl)ethoxy)methyl)-1H-benzo[d]imidazol-2-yl)methyl)-5-methoxy-7-methyl-1H-indole-1-carboxylate and tert-butyl 4-((6-cyano-1-((2-(trimethylsilyl)ethoxy)methyl)-1H-benzo[d]imidazol-2-yl)methyl)-5-methoxy-7-methyl-1H-indole-1-carboxylate (Example 145-A) (200 mg, 0.366 mmol) in THF (1.8 mL) was added to a mixture of potassium tert-butoxide (82 mg, 0.732 mmol) in THF (1.8 mL) under nitrogen at −78° C. After stirring for 15 min a solution 18-crown-6 (9.67 mg, 0.037 mmol) in THF (1.8 mL), was added. At this point, the previously obtained residue (373 mg, 1.097 mmol) in THF (1.8 mL) was degassed and added dropwise. The reaction mixture was stirred at −78° C. for 1 hr and then allowed to reach rt over 1 hr and stirred at rt for 16 hrs. The reaction mixture was quenched with a saturated solution of ammonium chloride, diluted with EtOAc; the layers were separated and the aqueous layer was extracted with EtOAc. The organic layer was dried over Na$_2$SO$_4$ and concentrated. To the crude product (400 mg, 0.527 mmol), HCl (1.25 M in MeOH, 8.5 mL, 10.54 mmol) was added and the reaction heated to 60° C. After 4 h, an addition aliquot of HCl in MeOH (8.5 mL, 10.54 mmol) was added. After 4 h the reaction was diluted with EtOAc, poured into water and extracted with EtOAc and then with DCM/iPrOH (4:1). The crude product was purified with preparative HLPC (HC-B). $^1$H NMR (400 MHz, DMSO-d$_6$) δ ppm 10.93 (br. s., 1H) 7.96 (br. s., 1H) 7.54 (br. s., 1H) 7.42-7.51 (m, 1H) 7.15 (t, J=2.84 Hz, 1H) 6.74 (s, 1H) 6.02 (dd, J=2.97, 1.83 Hz, 1H) 5.48 (t, J=7.52 Hz, 1H) 4.23 (dd, J=15.03, 7.45 Hz, 1H) 3.64 (s, 3H) 3.52 (dd, J=14.97, 7.64 Hz, 1H) 2.43 (s, 3H). HRMS calcd. for $C_{21}H_{18}N_8O$ $(M+H)^+$ 399.1682. found 399.1667.

Example 153

(±)-2-(1-(5-Methoxy-7-methyl-1H-indol-4-yl)-2-(2H-tetrazol-5-yl)ethyl)benzo[d]oxazole-5-carbonitrile

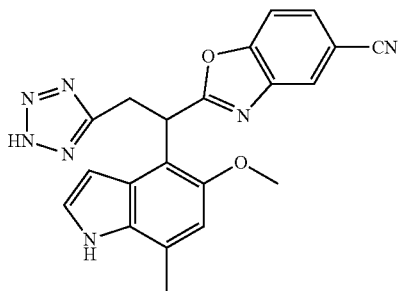 [SMILES: COc1cc(C)c2[nH]ccc2c1C(Cc1nn[nH]n1)c1nc2cc(C#N)ccc2o1]

The title compound was synthesized from tert-butyl 4-((5-cyanobenzo[d]oxazol-2-yl)methyl)-5-methoxy-7-methyl-1H-indole-1-carboxylate (Example 144-A) following the same protocol as shown in Example 152. However, for the deprotection of the Boc, the procedure used was the same as Example 142-C, whilst for the SEM deprotection, Example 135-C contained the protocol used. $^1$H NMR (400 MHz, DMSO-d$_6$) δ ppm 11.03 (br. s., 1H) 8.34 (t, J=1.14 Hz, 1H) 7.80 (d, J=1.26 Hz, 2H) 7.24 (t, J=2.91 Hz, 1H) 6.73 (s, 1H) 6.21 (dd, J=3.03, 2.02 Hz, 1H) 5.55 (t, J=7.58 Hz, 1H) 4.17 (dd, J=15.28, 7.71 Hz, 1H) 3.55-3.67 (m, 4H) 2.43 (s, 3H). MS (ESI+) m/z 400.2 (M+H).

Example 154

(±)-2-(2-(5-Methoxy-7-methyl-1H-indol-4-yl)-1-(2H-tetrazol-5-yl)propan-2-yl)benzo[d]oxazole-5-carbonitrile

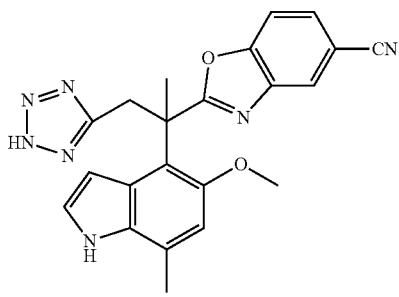 [SMILES: COc1cc(C)c2[nH]ccc2c1C(C)(Cc1nn[nH]n1)c1nc2cc(C#N)ccc2o1]

The title compound was synthesized from (±)-tert-butyl 4-(1-(5-cyanobenzo[d]oxazol-2-yl)ethyl)-5-methoxy-7-methyl-1H-indole-1-carboxylate (Example 150-A) using the same synthetic sequence as in Example 153. $^1$H NMR (400 MHz, DMSO-$d_6$) δ ppm 10.99 (br. s., 1H) 8.30 (s, 1H) 7.63-7.92 (m, 2H) 7.22 (t, J=2.84 Hz, 1H) 6.71 (s, 1H) 6.13 (d, J=3.03 Hz, 1H) 4.25 (d, J=14.15 Hz, 1H) 3.91 (d, J=14.15 Hz, 1H) 3.29-3.30 (m, 3H) 2.44 (s, 3H) 2.03 (s, 3H). MS (ESI+) m/z 414.2 (M+H).

Example 155

Example 155-A 2-(5-Methoxy-7-methyl-1H-indol-4-yl)acetonitrile

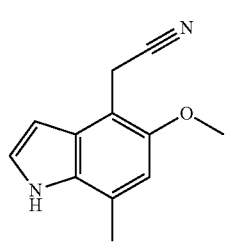

To a suspension of KOtBu (6.98 g, 62.2 mmol) in THF (50.0 mL) at −78° C. was added TOSMIC (8.10 g, 41.5 mmol) in THF (50.0 mL). The mixture was stirred at −78° for 15 minutes. To the mixture at −78° C. was then added a solution of tert-butyl 4-formyl-5-methoxy-7-methyl-1H-indole-1-carboxylate (Example 19-D) (6 g, 20.74 mmol) in THF (50 mL). The reaction was stirred at −78° C. for 1.5 hours. MeOH (10 ml) was then added and the reaction was removed from the dry ice bath. After 30 minutes the reaction was placed in a 40° C. water bath for 30 minutes. At this point, the reaction was cooled in an ice bath and was quenched with a saturated solution of ammonium chloride and then diluted with water and EtOAc. The layers were separated and the organics layer was dried, concentrated and absorbed onto silica to purify via FCC (0-50% EtOAc:heptanes) to afford the title compound. MS (ESI+) m/z 201.2 (M+H).

Example 155-B tert-Butyl 4-(cyanomethyl)-5-methoxy-7-methyl-1H-indole-1-carboxylate

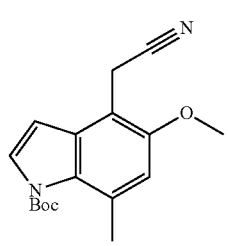 [SMILES: COc1cc(C)c2c(ccn2C(=O)OC(C)(C)C)c1CC#N]

To 2-(5-methoxy-7-methyl-1H-indol-4-yl)acetonitrile (Example 155-A) (3.8 g, 18.98 mmol) in CH$_3$CN (95 ml) was added Boc$_2$O (4.85 ml, 20.88 mmol) and DMAP (0.116 g, 0.949 mmol) and the reaction was stirred at room temperature. After 3 hours the reaction was concentrated and absorbed onto silica to purify via FCC (0-50% EtOAc:heptanes) to obtain the title compound. MS (ESI+) m/z 299.3 (M−H).

Example 155-C (±)-tert-Butyl 4-(1-cyano-2-methoxy-2-oxoethyl)-5-methoxy-7-methyl-1H-indole-1-carboxylate

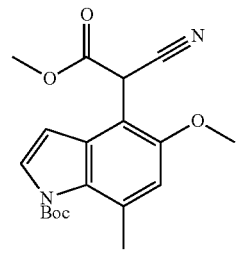

The title compound was synthesized from tert-Butyl 4-(cyanomethyl)-5-methoxy-7-methyl-1H-indole-1-carboxylate (Example 155-B) using the same procedure as in Example 148-A using methyl chloroformate in the place of methyl bromoacetate. MS (ESI+) m/z 359.4 (M+H).

Example 155-D (±)-tert-Butyl 4-(2-cyano-1-methoxy-1-oxopropan-2-yl)-5-methoxy-7-methyl-1H-indole-1-carboxylate

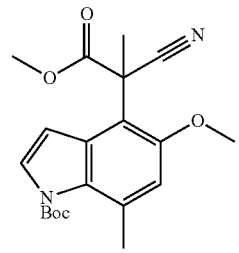

(±)-tert-Butyl 4-(1-cyano-2-methoxy-2-oxoethyl)-5-methoxy-7-methyl-1H-indole-1-carboxylate (Example 155-C) (1.1 g, 3.07 mmol) was dissolved in acetone (6.14 ml) and then added iodomethane (0.576 ml, 9.21 mmol) followed by potassium carbonate (0.636 g, 4.60 mmol) and stirred at room temperature for 2.5 hours. The reaction was then cooled in an ice bath and quenched with a saturated aqueous solution of ammonium chloride and diluted with DCM. The layers were separated and the organic layer was dried and concentrated to obtain the title compound. MS (ESI+) m/z 373.4 (M+H).

Example 155-E (±)-2-(1-(tert-Butoxycarbonyl)-5-methoxy-7-methyl-1H-indol-4-yl)-2-cyanopropanoic acid

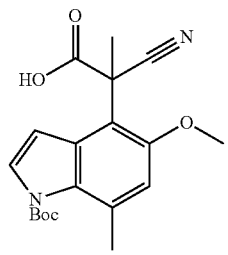 [SMILES: COc1cc(C)c2c(ccn2C(=O)OC(C)(C)C)c1C(C)(C#N)C(=O)O]

(±)-tert-Butyl 4-(2-cyano-1-methoxy-1-oxopropan-2-yl)-5-methoxy-7-methyl-1H-indole-1-carboxylate (Example 155-D) (0.35 g, 0.940 mmol) was dissolved in EtOH (4.70 ml), cooled to 0° C. and added 10% KOH (2.64 ml, 4.70 mmol) and stirred for 1 hour. At this point, the reaction was placed in an ice bath and quenched with 1 N HCl (4.70 ml, 4.70 mmol). The reaction was diluted with water and ethyl acetate. The layers were separated and the ethyl acetate layer was removed, dried over $Na_2SO_4$ and concentrated to obtain the title compound which was used directly in the next reaction without purification. MS (ESI+) m/z 359.4 (M+H).

Example 155-F (±)-2-(5-Bromo-1H-benzo[d]imidazol-2-yl)-2-(5-methoxy-7-methyl-1H-indol-4-yl)propanenitrile

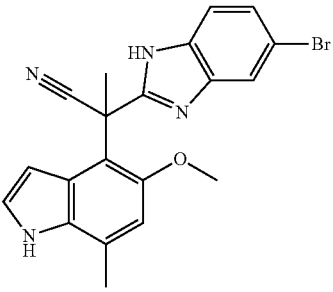 [SMILES: COc1cc(C)c2[nH]ccc2c1C(C)(C#N)c1nc2cc(Br)ccc2[nH]1]

To (±)-2-(1-(tert-butoxycarbonyl)-5-methoxy-7-methyl-1H-indol-4-yl)-2-cyanopropanoic acid (Example 155-E) (1.4 g, 3.91 mmol) in DCM (39.1 ml) at 0° C. was added DIPEA (2.05 ml, 11.72 mmol) followed by HBTU (1.926 g, 5.08 mmol) and 4-bromobenzene-1,2-diamine (1.096 g, 5.86 mmol) at 0° C. and stirred in the ice bath for 20 minutes. The ice bath was removed and the reaction was stirred at room temperature overnight. The reaction was diluted with water, the layers were separated and the organic layer was dried over $Na_2SO_4$ and concentrated. The residue was dissolved in acetic acid (7 mL) and heated at 85° C. for 4 hours. The reaction was cooled to 0° C. and quenched with a saturated solution of sodium bicarbonate, diluted with water and EtOAc. The layers were separated and the organic layer was removed, dried over $Na_2SO_4$ and concentrated. The crude product was purified via FCC (0-50% EtOAc:heptanes) to obtain the title compound. MS (ESI+) m/z 409.3, 411.3 (M+H).

Example 155-G (±)-2-(5-Bromo-1-((2-(trimethylsilyl)ethoxy)methyl)-1H-benzo[d]imidazol-2-yl)-2-(5-methoxy-7-methyl-1-((2-(trimethylsilyl)ethoxy)methyl)-1H-indol-4-yl)propanenitrile and (±)-2-(6-bromo-1-((2-(trimethylsilyl)ethoxy)methyl)-1H-benzo[d]imidazol-2-yl)-2-(5-methoxy-7-methyl-1-((2-(trimethylsilyl)ethoxy)methyl)-1H-indol-4-yl)propanenitrile

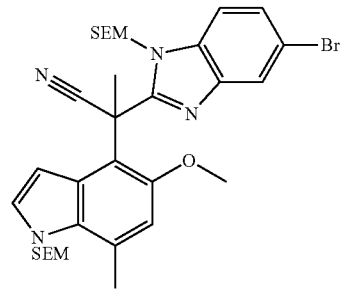

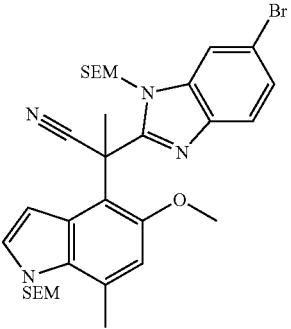

To (±)-2-(5-bromo-1H-benzo[d]imidazol-2-yl)-2-(5-methoxy-7-methyl-1H-indol-4-yl)propanenitrile (Example 155-F) (0.32 g, 0.782 mmol) in THF (7.82 ml) was added NaH (0.078 g, 1.955 mmol) at 0° C. and the reaction was stirred for 20 minutes. SEMCl (0.319 ml, 1.798 mmol) was added at 0° C. The reaction was allowed to reach room temperature and stir for 1 hour. At this point, an additional aliquot of NaH (0.078 g, 1.955 mmol) followed by SEMCl (0.319 ml, 1.798 mmol) were added at 0° C. The ice bath was removed and the reaction was allowed to warm to room temperature and stirred for 1 hour. The reaction was quenched with a saturated aq. solution of ammonium chloride, diluted with EtOAc and the layers were separated. The organic layer was dried over sodium sulfate, concentrated and absorbed onto silica to purify via FCC (0-30% EtOAc:heptanes) to give the mixture of title compounds. MS (ESI+) m/z 669.7, 671.6 (M+H).

Example 155-H (±)-2-(5-Bromo-1-((2-(trimethylsilyl)ethoxy)methyl)-1H-benzo[d]imidazol-2-yl)-2-(5-methoxy-7-methyl-1-((2-(trimethylsilyl)ethoxy)methyl)-1H-indol-4-yl)propanal and (±)-2-(6-bromo-1-((2-(trimethylsilyl)ethoxy)methyl)-1H-benzo[d]imidazol-2-yl)-2-(5-methoxy-7-methyl-1-((2-(trimethylsilyl)ethoxy)methyl)-1H-indol-4-yl)propanal

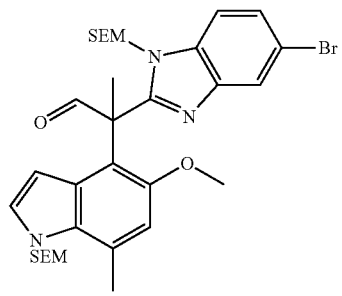

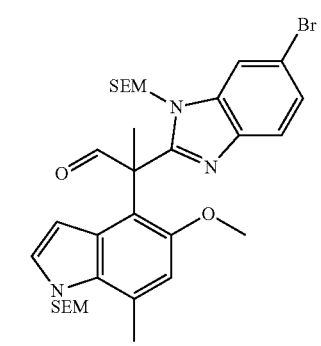

To (±)-2-(5-bromo-1-((2-(trimethylsilyl)ethoxy)methyl)-1H-benzo[d]imidazol-2-yl)-2-(5-methoxy-7-methyl-1-((2-(trimethylsilyl)ethoxy)methyl)-1H-indol-4-yl)propanenitrile and (±)-2-(6-bromo-1-((2-(trimethylsilyl)ethoxy)methyl)-1H-benzo[d]imidazol-2-yl)-2-(5-methoxy-7-methyl-1-((2-(trimethylsilyl)ethoxy)methyl)-1H-indol-4-yl)propanenitrile (Example 155-G) (0.41 g, 0.612 mmol) in DCM (6.12 ml) at −78° C. was added DIBAL-H (1M in DCM, 0.918 ml, 0.918 mmol) dropwise over 1 minute and stirred at this temperature for 1 hour. The reaction was quenched with MeOH (0.248 ml, 6.12 mmol) at −78° C. An ice bath was exchanged for the dry ice bath and the reaction was diluted with a saturated aq. solution of potassium sodium tartrate (6 mL), water (6 mL) and DCM (6 mL) and allowed to stir for 1 hour. The layers were separated and the aqueous layer was extracted with DCM. The combined organics were dried over sodium sulfate, evaporated and purified via FCC (0-30% EtOAc:heptanes) to obtain the mixture of title compounds. MS (ESI+) m/z 673.7, 675.6 (M+H).

Example 155-I (±)-Methyl 4-(5-bromo-1-((2-(trimethylsilyl)ethoxy)methyl)-1H-benzo[d]imidazol-2-yl)-4-(5-methoxy-7-methyl-1-((2-(trimethylsilyl)ethoxy)methyl)-1H-indol-4-yl)pent-2-enoate and (±)-methyl 4-(6-bromo-1-((2-(trimethylsilyl)ethoxy)methyl)-1H-benzo[d]imidazol-2-yl)-4-(5-methoxy-7-methyl-1-((2-(trimethylsilyl)ethoxy)methyl)-1H-indol-4-yl)pent-2-enoate

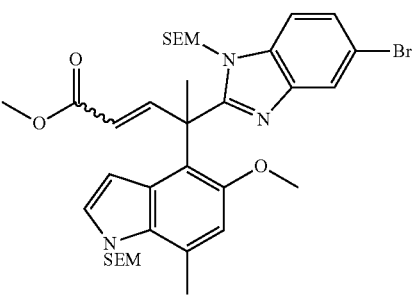

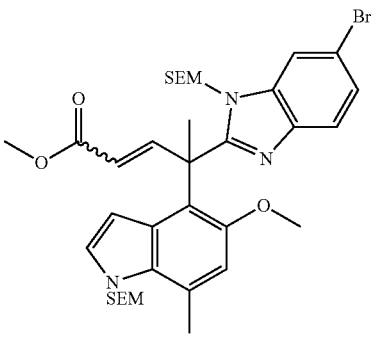

To (±)-2-(5-bromo-1-((2-(trimethylsilyl)ethoxy)methyl)-1H-benzo[d]imidazol-2-yl)-2-(5-methoxy-7-methyl-1-((2-(trimethylsilyl)ethoxy)methyl)-1H-indol-4-yl)propanal and (±)-2-(6-bromo-1-((2-(trimethylsilyl)ethoxy)methyl)-1H-benzo[d]imidazol-2-yl)-2-(5-methoxy-7-methyl-1-((2-(trimethylsilyl)ethoxy)methyl)-1H-indol-4-yl)propanal (Example 155-H) (0.42 g, 0.624 mmol) in toluene (6.24 ml) was added methyl(triphenylphosphoranylidene)acetate (2.08 g, 6.24 mmol) and the mixture was heated at 107° C. for 16 hours. The reaction mixture was then concentrated and absorbed onto silica to purify via FCC (0-40% EtOAc:heptanes) to give the mixture of title compounds. MS (ESI+) m/z 728.7, 730.7 (M+H).

Example 155-J (±)-Methyl 4-(5-cyano-1-((2-(trimethylsilyl)ethoxy)methyl)-1H-benzo[d]imidazol-2-yl)-4-(5-methoxy-7-methyl-1-((2-(trimethylsilyl)ethoxy)methyl)-1H-indol-4-yl)pent-2-enoate and (±)-methyl 4-(6-cyano-1-((2-(trimethylsilyl)ethoxy)methyl)-1H-benzo[d]imidazol-2-yl)-4-(5-methoxy-7-methyl-1-((2-(trimethylsilyl)ethoxy)methyl)-1H-indol-4-yl)pent-2-enoate

Example 155-K (±)-Methyl 4-(5-cyano-1-((2-(trimethylsilyl)ethoxy)methyl)-1H-benzo[d]imidazol-2-yl)-4-(5-methoxy-7-methyl-1-((2-(trimethylsilyl)ethoxy)methyl)-1H-indol-4-yl)pentanoate and (±)-methyl 4-(6-cyano-1-((2-(trimethylsilyl)ethoxy)methyl)-1H-benzo[d]imidazol-2-yl)-4-(5-methoxy-7-methyl-1-((2-(trimethylsilyl)ethoxy)methyl)-1H-indol-4-yl)pentanoate

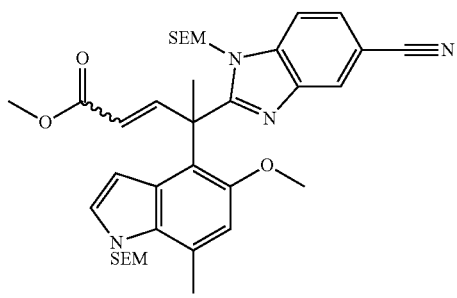

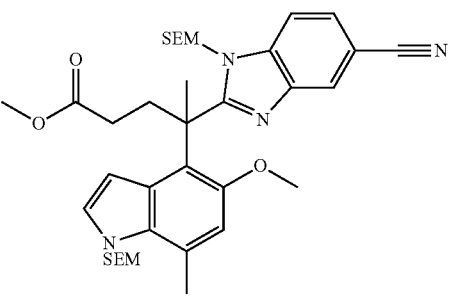

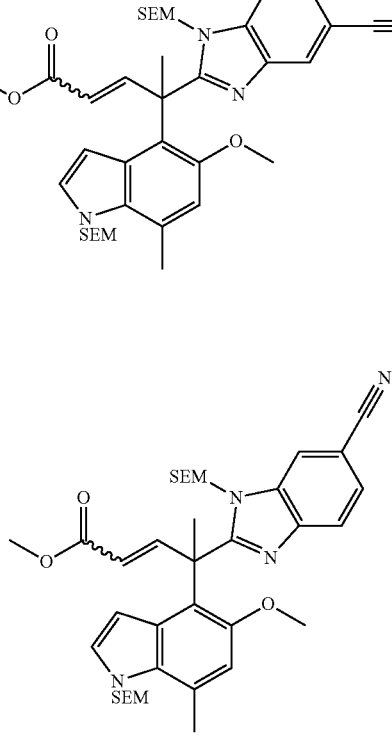

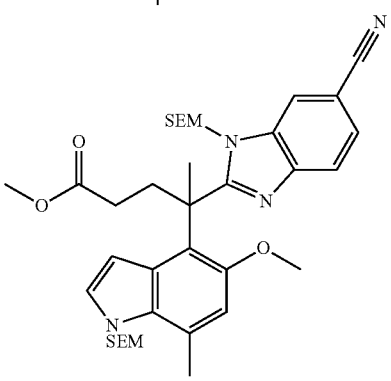

To (±)-methyl 4-(5-bromo-1-((2-(trimethylsilyl)ethoxy)methyl)-1H-benzo[d]imidazol-2-yl)-4-(5-methoxy-7-methyl-1-((2-(trimethylsilyl)ethoxy)methyl)-1H-indol-4-yl)pent-2-enoate and (±)-methyl 4-(6-bromo-1-((2-(trimethylsilyl)ethoxy)methyl)-1H-benzo[d]imidazol-2-yl)-4-(5-methoxy-7-methyl-1-((2-(trimethylsilyl)ethoxy)methyl)-1H-indol-4-yl)pent-2-enoate (Example 155-I) (0.21 g, 0.288 mmol) in DMF (2.88 mL) was added tetrakis(triphenylphosphine)palladium (0.033 g, 0.029 mmol) and dicyanozinc (0.034 g, 0.288 mmol) and the reaction heated at 145° C. for 30 minutes. At this point the reaction was cooled to room temperature and absorbed onto silica to purify via FCC (0-30% EtOAc:heptanes) to obtain the mixture of title compounds that was used directly in the next step. MS (ESI+) m/z 675.8 (M+H).

(±)-Methyl 4-(5-cyano-1-((2-(trimethylsilyl)ethoxy)methyl)-1H-benzo[d]imidazol-2-yl)-4-(5-methoxy-7-methyl-1-((2-(trimethylsilyl)ethoxy)methyl)-1H-indol-4-yl)pent-2-enoate and (±)-methyl 4-(6-cyano-1-((2-(trimethylsilyl)ethoxy)methyl)-1H-benzo[d]imidazol-2-yl)-4-(5-methoxy-7-methyl-1-((2-(trimethylsilyl)ethoxy)methyl)-1H-indol-4-yl)pent-2-enoate (Example 155-J) (13 mg, 0.019 mmol) was placed in MeOH (193 µl) and cooled to 0° C. Sodium borohydride (3 mg, 0.079 mmol) and NiCl$_2$ (4 mg, 0.031 mmol) were added and the reaction stirred in an ice bath for 2.5 hours. At this point further aliquots of NiCl$_2$ (4 mg, 0.031 mmol) and sodium borohydride (3 mg, 0.079 mmol) were added and the reaction was stirred at room temperature until reaction turned brown/black color. The reaction was then cooled in an ice bath and quenched with a saturated aq. solution of ammonium chloride and diluted with EtOAc. The layers were separated and the organic layer was dried over sodium sulfate, concentrated and absorbed onto silica to purify via FCC (0-50% EtOAc:heptanes) to obtain the mixture of title compounds that was used directly in the next step. MS (ESI+) m/z 677.8 (M+H).

Example 155-L (±)-Methyl 4-(5-cyano-1H-benzo[d]imidazol-2-yl)-4-(5-methoxy-7-methyl-1H-indol-4-yl)pentanoate

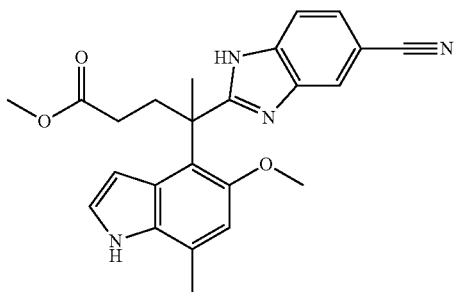 [SMILES: COC(=O)CCC(C)(c1nc2cc(C#N)ccc2[nH]1)c1c(OC)cc(C)c2[nH]ccc12]

(±)-Methyl 4-(5-cyano-1-((2-(trimethylsilyl)ethoxy)methyl)-1H-benzo[d]imidazol-2-yl)-4-(5-methoxy-7-methyl-1-((2-(trimethylsilyl)ethoxy)methyl)-1H-indol-4-yl)pentanoate and (±)-methyl 4-(6-cyano-1-((2-(trimethylsilyl)ethoxy)methyl)-1H-benzo[d]imidazol-2-yl)-4-(5-methoxy-7-methyl-1-((2-(trimethylsilyl)ethoxy)methyl)-1H-indol-4-yl)pentanoate (Example 155-K) (28 mg, 0.041 mmol) was dissolved in MeOH (700 µl) and then added 1.25 M HCl in MeOH (0.662 ml, 0.827 mmol) and heated at 65° C. After 30 minutes, an additional aliquot of 1.25 M HCl in MeOH (0.993 ml, 1.241 mmol) was added along with MeOH (700 uL) and the reaction left stirring for 17 hours. At this point an additional aliquot of 1.25 M HCl in MeOH (1.5 ml, 1.875 mmol) was added the reaction was heated at 75° C. for 3 hours and after additional 1.25 M HCl in MeOH (1.5 ml, 1.875 mmol) was added, the temperature was increased 85° C. and the reaction stirred for further 4 hours. At this point, an additional aliquot of 1.25 M HCl in MeOH (3 ml, 3.75 mmol) was added and the reaction was heated at 90° C. for 2 h. The reaction was then cooled to 0° C. and quenched with saturated sodium bicarbonate until pH=7 and then diluted with EtOAc. The layers were separated and the aqueous layer was extracted with EtOAc. The combined organics were dried over sodium sulfate and then concentrated. The resulting residue was absorbed onto silica to purify via FCC (0-60% EtOAc:heptanes) to obtain the title compound. MS (ESI+) m/z 417.18 (M+H).

Example 155-M (±)-4-(5-Cyano-1H-benzo[d]imidazol-2-yl)-4-(5-methoxy-7-methyl-1H-indol-4-yl)pentanoic acid

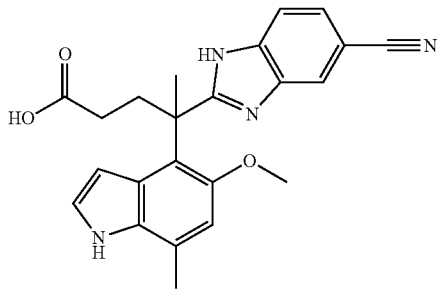 [SMILES: COc1cc(C)c2[nH]ccc2c1C(C)(CCC(=O)O)c1nc2cc(C#N)ccc2[nH]1]

(±)-Methyl 4-(5-cyano-1H-benzo[d]imidazol-2-yl)-4-(5-methoxy-7-methyl-1H-indol-4-yl)pentanoate (Example 155-L) (8.5 mg, 0.020 mmol) was dissolved in MeOH (300 µL) and then treated with 10% aq. KOH (70 µl, 0.125 mmol) and stirred at room temperature for 30 minutes. The reaction was directly purified using preparative HPLC (HC-B) to obtain the title compound. $^1$H NMR (400 MHz, DMSO-$d_6$) δ ppm 10.87 (br. s., 1H) 7.92 (br. s.) 7.53 (br. s.) 7.42-7.49 (m) 7.09 (t, J=2.78 Hz, 1H) 6.73 (s, 1H) 5.62 (br. s., 1H) 3.43 (s, 3H) 2.55-2.64 (m, 2H) 2.42 (s, 3H) 1.95-2.05 (m, 2H) 1.88 (s, 3H). MS (ESI+) m/z 403.3 (M+H).

Example 156

Example 156-A (±)-tert-Butyl 4-(1-cyanoethyl)-5-methoxy-7-methyl-1H-indole-1-carboxylate

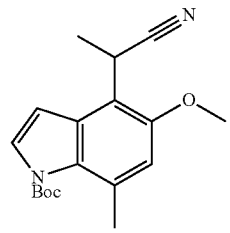 [SMILES: COc1cc(C)c2c(ccn2C(=O)OC(C)(C)C)c1C(C)C#N]

tert-Butyl 4-(cyanomethyl)-5-methoxy-7-methyl-1H-indole-1-carboxylate (Example 155-B) (1.2 g, 4.00 mmol) was dissolved in THF (40.0 ml), MeI (0.300 ml, 4.79 mmol) was then added at −78° C. At this point, lithium bis(trimethylsilyl)amide (4.39 ml, 4.39 mmol) was added and the reaction stirred for 10 minutes. The reaction was then quenched at −78° C. with a saturated aq. solution of ammonium chloride, diluted with water and EtOAc and the layers were separated. The organic layer was dried over $Na_2SO_4$ and concentrated and purified via FCC (0-50% EtOAc:heptanes) to obtain the title compound. MS (ESI+) m/z 313.5 (M−H).

Example 156-B (±)-tert-Butyl 4-(2-cyanopent-4-en-2-yl)-5-methoxy-7-methyl-1H-indole-1-carboxylate

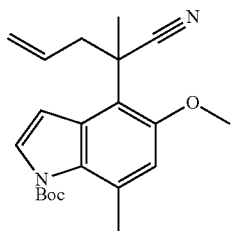 [SMILES: C=CCC(C)(C#N)c1c(OC)cc(C)c2c1ccn2C(=O)OC(C)(C)C]

To (±)-tert-butyl 4-(1-cyanoethyl)-5-methoxy-7-methyl-1H-indole-1-carboxylate (Example 156-A) (0.82 g, 2.61 mmol) in THF (13.04 ml) at −78° C. was added LiHMDS (1M in hexane, 3.13 ml, 3.13 mmol) and stirred for 7 minutes. At this point, allyl bromide (0.563 ml, 6.52 mmol) was added and the reaction stirred for 2 hours at −78° C. Reaction was then quenched with a saturated solution of aq. ammonium chloride and diluted with DCM. The layers were separated and the organic layer was dried over Na₂SO₄ and concentrated to an oil that was absorbed onto silica and purified via FCC (0-30% EtOAc:heptanes) to give the title compound. MS (ESI+) m/z 355.4 (M+H).

Example 156-C (±)-tert-Butyl 5-methoxy-7-methyl-4-(2-methyl-1-oxopent-4-en-2-yl)-1H-indole-1-carboxylate

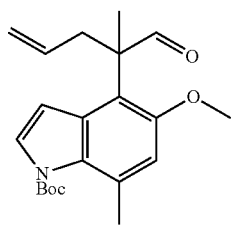 [SMILES: C=CCC(C)(C=O)c1c(OC)cc(C)c2c1ccn2C(=O)OC(C)(C)C]

To (±)-tert-butyl 4-(2-cyanopent-4-en-2-yl)-5-methoxy-7-methyl-1H-indole-1-carboxylate (Example 156-B) (0.92 g, 2.60 mmol) in DCM (26.0 mL) at -78° C. was added DIBAL-H (2.98 mL, 2.98 mmol) and the reaction was stirred for 30 minutes. At this point the reaction was quenched with MeOH (1.5 mL) followed by a saturated aq. solution of sodium potassium tartrate (5 mL). The mixture was then diluted with brine and DCM. The layers were separated and the aqueous layer was extracted with DCM (2×). The combined organics were dried over Na₂SO₄, concentrated and absorbed onto silica to purify via FCC (0-30% EtOAc:heptanes) to obtain the title compound. MS (ESI+) m/z 358.3 (M+H).

Example 156-D (±)-2-(1-(tert-Butoxycarbonyl)-5-methoxy-7-methyl-1H-indol-4-yl)-2-methylpent-4-enoic acid

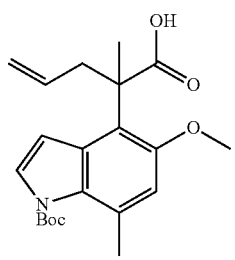 [SMILES: C=CCC(C)(C(=O)O)c1c(OC)cc(C)c2c1ccn2C(=O)OC(C)(C)C]

To (±)-tert-butyl 5-methoxy-7-methyl-4-(2-methyl-1-oxopent-4-en-2-yl)-1H-indole-1-carboxylate (Example 156-C) (2 g, 5.60 mmol) in tert-butanol (37.3 mL) and water (18.65 mL) was added 2-methyl-2-butene (5.93 ml, 56.0 mmol), sodium dihydrogen phosphate (2.69 g, 22.38 mmol) and then sodium chlorite (2.53 g, 22.38 mmol). The reaction was allowed to stir at room temperature overnight for 17 hours. At this point the reaction was diluted with EtOAc and water. The layers were separated and the aqueous layer was extracted with EtOAc. The combined organics were dried over MgSO₄ and concentrated to obtain the title compound that was use in the next step without further purification. MS (ESI+) m/z 374.3 (M+H).

Example 156-E (±)-tert-Butyl 4-(1-((2-amino-5-cyanophenyl)amino)-2-methyl-1-oxopent-4-en-2-yl)-5-methoxy-7-methyl-1H-indole-1-carboxylate

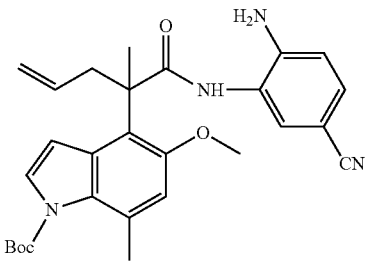 [SMILES: C=CCC(C)(C(=O)Nc1cc(C#N)ccc1N)c1c(OC)cc(C)c2c1ccn2C(=O)OC(C)(C)C]

To (±)-2-(1-(tert-butoxycarbonyl)-5-methoxy-7-methyl-1H-indol-4-yl)-2-methylpent-4-enoic acid (Example 156-D) (0.76 g, 2.035 mmol) in DCM (20.35 mL) was added DMF (7.88 µl, 0.102 mmol) and then oxalyl chloride (0.356 ml, 4.07 mmol). After 20 minutes the reaction was concentrated in vacuo. The crude product in THF (5 mL) was added to a mixture of 3,4-diaminobenzonitrile (0.48 g, 3.60 mmol) in THF (5 mL) and pyridine (0.494 ml, 6.11 mmol) at 0° C. After 10 minutes the reaction was stirred at room temperature. After 30 minutes the reaction was heated at 55° C. for 4 hours. At this point the volatiles were removed in vacuo and the crude product was absorbed onto silica to purify via FCC (0-50% EtOAc:heptanes) to obtain the title compound. MS (ESI+) m/z 489.5 (M+H).

Example 156-F (±)-2-(2-(5-methoxy-7-methyl-1H-indol-4-yl)pent-4-en-2-yl)-1H-benzo[d]imidazole-5-carbonitrile

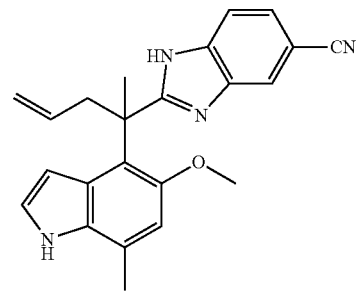 [SMILES: C=CCC(C)(c1nc2cc(C#N)ccc2[nH]1)c1c(OC)cc(C)c2[nH]ccc12]

(±)-tert-Butyl 4-(1-((2-amino-5-cyanophenyl)amino)-2-methyl-1-oxopent-4-en-2-yl)-5-methoxy-7-methyl-1H-indole-1-carboxylate (Example 156-E) (0.36 g, 0.737 mmol) was dissolved in toluene (2.76 mL) and dioxane (0.921 mL). p-Toluenesulfonic acid monohydrate (0.042 g, 0.221 mmol) was then added and the mixture heated at 135° C. for 3 hours. At this point another aliquot of p-toluenesulfonic acid monohydrate (0.030 g) was added and the reaction was heated for 1 hour. At this point another aliquot of p-toluenesulfonic acid monohydrate (0.025 g) was added and the reaction was heated for 1.5 hour. The reaction was then cooled to room temperature, concentrated and absorbed onto silica to purify via FCC(0-50% EtOAc:heptanes) to obtain the title compound that was used directly in the next step. MS (ESI+) m/z 371.4 (M+H).

Example 156-G (±)-2-(2-(5-methoxy-7-methylindolin-4-yl)pent-4-en-2-yl)-1H-benzo[d]imidazole-5-carbonitrile

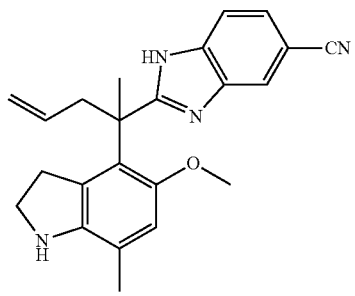 [SMILES: C=CCC(C)(c1nc2cc(C#N)ccc2[nH]1)c1c(OC)cc(C)c2c1CCN2]

To a solution of (±)-2-(2-(5-methoxy-7-methyl-1H-indol-4-yl)pent-4-en-2-yl)-1H-benzo[d]imidazole-5-carbonitrile (Example 156-F) (150 mg, 0.405 mmol) in acetic acid (2.025 mL) was added sodium cyanoborohydride (38.2 mg, 0.607 mmol) and the reaction was stirred at room temperature for 1 hour. At this point the mixture was placed in an ice bath and quenched with NaOH (17.61 mL, 35.2 mmol) and then diluted with DCM. The layers were separated and the organic layer was dried over sodium sulfate, concentrated and absorbed onto silica and purified via FCC (0-100% EtOAc:heptanes) to give the title compound. MS (ESI+) m/z 373.3 (M+H).

Example 156-H (±)-tert-Butyl 2-(2-(1-(tert-butoxycarbonyl)-5-methoxy-7-methylindolin-4-yl)pent-4-en-2-yl)-5-cyano-1H-benzo[d]imidazole-1-carboxylate and (±)-tert-butyl 2-(2-(1-(tert-butoxycarbonyl)-5-methoxy-7-methylindolin-4-yl)pent-4-en-2-yl)-6-cyano-1H-benzo[d]imidazole-1-carboxylate

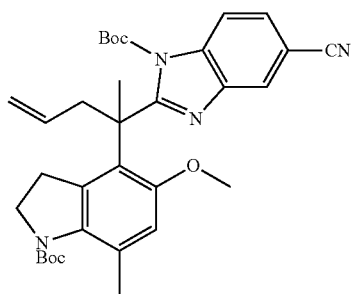

-continued

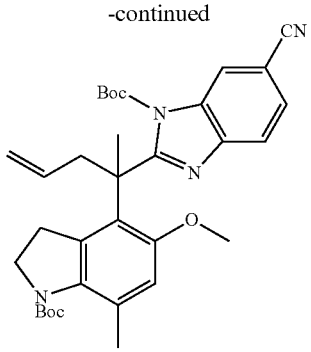

To (±)-2-(2-(5-methoxy-7-methylindolin-4-yl)pent-4-en-2-yl)-1H-benzo[d]imidazole-5-carbonitrile (Example 156-G) (77 mg, 0.207 mmol) in CH$_3$CN (689 μL) was added Boc-anhydride (120 μL, 0.517 mmol) and DMAP (2.53 mg, 0.021 mmol) and the reaction was stirred overnight at room temperature. The reaction was concentrated and absorbed onto silica to purify via FCC (0-50% EtOAc:heptanes) to obtain the mixture of title compounds. MS (ESI+) m/z 573.3 (M+H).

Example 156-I (±)-tert-Butyl 2-(2-(1-(tert-butoxycarbonyl)-5-methoxy-7-methylindolin-4-yl)-4-oxobutan-2-yl)-5-cyano-1H-benzo[d]imidazole-1-carboxylate and (±)-tert-butyl 2-(2-(1-(tert-butoxycarbonyl)-5-methoxy-7-methylindolin-4-yl)-4-oxobutan-2-yl)-6-cyano-1H-benzo[d]imidazole-1-carboxylate

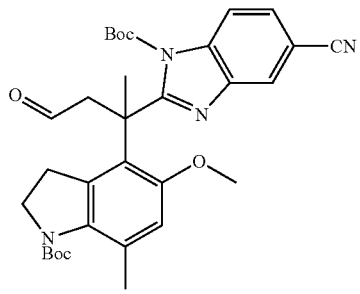

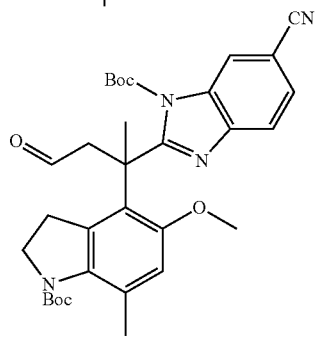

(±)-tert-Butyl 2-(2-(1-(tert-butoxycarbonyl)-5-methoxy-7-methylindolin-4-yl)pent-4-en-2-yl)-5-cyano-1H-benzo[d]imidazole-1-carboxylate and (±)-tert-butyl 2-(2-(1-(tert-butoxycarbonyl)-5-methoxy-7-methylindolin-4-yl)pent-4-en-2-yl)-6-cyano-1H-benzo[d]imidazole-1-carboxylate (Example 156-H) (66 mg, 0.115 mmol) was dissolved in dioxane (864 µL) and water (288 µL) and cooled to 0° C. 2,6-Lutidine (26.8 µl, 0.230 mmol) followed by osmium tetroxide (28.9 µl, 2.305 µmol) and sodium periodate (99 mg, 0.461 mmol) were added and the reaction was stirred for 30 minutes. The ice bath was removed and the reaction was allowed to warm to room temperature. After 2 hours the reaction was quenched with water, a saturated aq. solution of sodium thiosulfate and diluted with DCM. The layers were separated and the organic layer was dried over sodium sulfate and concentrated to obtain the mixture of title compounds which was used without further purification in the next step. MS (ESI+) m/z 575.6 (M+H).

Example 156-J (±)-3-(1-(tert-butoxycarbonyl)-5-cyano-1H-benzo[d]imidazol-2-yl)-3-(1-(tert-butoxycarbonyl)-5-methoxy-7-methylindolin-4-yl)butanoic acid and (±)-3-(1-(tert-butoxycarbonyl)-5-methoxy-7-methylindolin-4-yl)-3-(1-(tert-butoxycarbonyl)-6-cyano-1H-benzo[d]imidazol-2-yl)butanoic acid

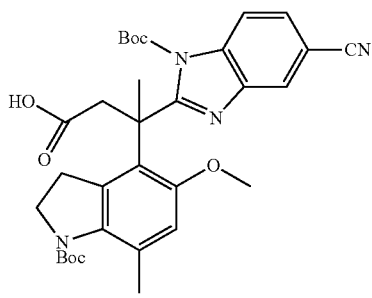

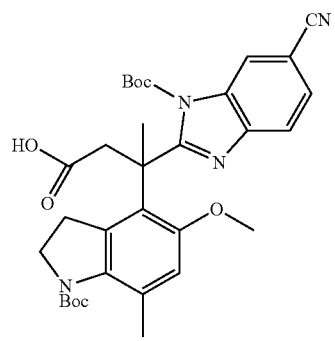

The mixture of title compounds was synthesized starting from (±)-tert-butyl 2-(2-(1-(tert-butoxycarbonyl)-5-methoxy-7-methylindolin-4-yl)-4-oxobutan-2-yl)-5-cyano-1H-benzo[d]imidazole-1-carboxylate and (±)-tert-butyl 2-(2-(1-(tert-butoxycarbonyl)-5-methoxy-7-methylindolin-4-yl)-4-oxobutan-2-yl)-6-cyano-1H-benzo[d]imidazole-1-carboxylate (Example 156-I) as shown in Example 156-D. MS (ESI+) m/z 591.4 (M+H).

Example 156-K (±)-Methyl 3-(5-cyano-1H-benzo[d]imidazol-2-yl)-3-(5-methoxy-7-methylindolin-4-yl)butanoate

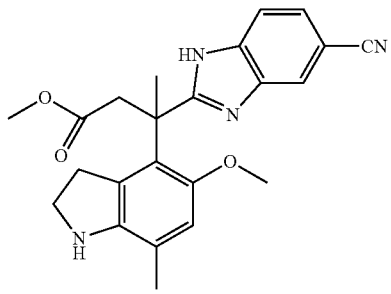 [SMILES: COC(=O)CC(C)(c1nc2cc(C#N)ccc2[nH]1)c1c(OC)cc(C)c2c1CCN2]

To (±)-3-(1-(tert-butoxycarbonyl)-5-cyano-1H-benzo[d]imidazol-2-yl)-3-(1-(tert-butoxycarbonyl)-5-methoxy-7-methylindolin-4-yl)butanoic acid and (±)-3-(1-(tert-butoxycarbonyl)-5-methoxy-7-methylindolin-4-yl)-3-(1-(tert-butoxycarbonyl)-6-cyano-1H-benzo[d]imidazol-2-yl)butanoic acid (Example 156-J) (115 mg, 0.195 mmol) in MeOH (1 mL) was added HCl (4M in dioxane, 973 µl, 3.89 mmol) and the reaction heated at 50° C. for 30 minutes. The reaction was cooled in an ice bath, quenched with ammonium hydroxide (505 µl, 3.89 mmol) and then diluted with DCM. The layers were separated, the organic layer was dried over sodium sulfate and concentrated to obtain the title compound that was used in the next step without further purification. MS (ESI+) m/z 405.3 (M+H).

Example 156-L (±)-3-(5-Cyano-1H-benzo[d]imidazol-2-yl)-3-(5-methoxy-7-methyl-1H-indol-4-yl)butanoic acid

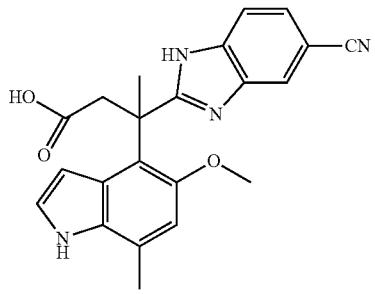 [SMILES: COc1cc(C)c2[nH]ccc2c1C(C)(CC(=O)O)c1nc2cc(C#N)ccc2[nH]1]

(±)-Methyl 3-(5-cyano-1H-benzo[d]imidazol-2-yl)-3-(5-methoxy-7-methylindolin-4-yl)butanoate (Example 156-K) (25 mg, 0.062 mmol) was dissolved in THF (0.371 mL), water (0.124 mL) and MeOH (0.124 mL). LiOH (13 mg, 0.304 mmol) was then added and the reaction was stirred for 18 hours at room temperature. At this point, NaOH (1 mL, 2.000 mmol), MeOH (1 mL) and THF (3 mL) were added and the reaction was stirred for further 4 hours. The reaction was then concentrated and diluted with EtOAc and water. The layers were separated, the aqueous layer was adjusted to pH=1 and directly purified using RP-HPLC (HC-A) to isolate the title compound. $^1$H NMR (TFA salt, 400 MHz, DMSO-$d_6$) δ ppm 11.01 (br. s., 1H) 8.11 (br. s., 1H) 7.68 (q, J=7.66 Hz, 2H) 7.22

(br. s., 1H) 6.74 (s, 1H) 5.95 (br. s., 1H) 3.55 (d, J=15.16 Hz, 1H) 3.43 (s, 1H) 3.39 (s, 3H) 2.44 (s, 3H) 1.99-2.15 (m, 3H). HRMS calcd. for $C_{22}H_{20}N_4O_3$ (M+H)$^+$ 389.1614. found 389.1609.

Example 157

(±)-5-(5-Cyano-1H-benzo[d]imidazol-2-yl)-5-(5-methoxy-7-methyl-1H-indol-4-yl)pentanoic acid

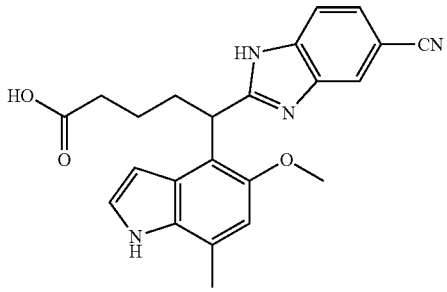 [SMILES: COc1cc(C)c2[nH]ccc2c1C(CCCC(=O)O)c1nc2cc(C#N)ccc2[nH]1]

tert-Butyl 4-((5-cyano-1-((2-(trimethylsilyl)ethoxy)methyl)-1H-benzo[d]imidazol-2-yl)methyl)-5-methoxy-7-methyl-1H-indole-1-carboxylate and tert-butyl 4-((6-cyano-1-((2-(trimethylsilyl)ethoxy)methyl)-1H-benzo[d]imidazol-2-yl)methyl)-5-methoxy-7-methyl-1H-indole-1-carboxylate (Example 145-A) (510 mg, 0.93 mmol) in THF (10 mL) was stirred at −78° C. and then LDA (2.0M in heptane/THF/ethylbenzene, 0.47 mL, 0.93 mmol) was added and the reaction was stirred for 10 minutes. At this point, methyl 4-iodobutanoate (0.5 mL, 3.7 mmol) was added and the dry ice bath was removed and the reaction was stirred for 2.5 hours at rt. The reaction was diluted with ethyl acetate (100 mL) and poured into saturated aq. solution of sodium chloride. The layers were separated and the organic layer was dried over $Na_2SO_4$, concentrated and absorbed onto silica to purify via FCC (0-20% EtOAc:hexanes). The resulting residue was deprotected of the SEM and Boc group using the conditions shown in Example 142-C. The resulting residue (170 mg, 0.408 mmol) was dissolved in MeOH (5 mL) and was added potassium carbonate (180 mg, 1.3 mmol), the reaction was heated at 65° C. overnight. The mixture was then poured into water (50 mL) and the pH was adjusted to ~1 with 3 M HCl. The layers were separated and the aqueous layer was extracted with ethyl acetate, dried over $Na_2SO_4$, and purified by reverse-phase FCC (0-50%) ACN:water to obtain the title compound. $^1$H NMR (400 MHz, DMSO-d$_6$) δ ppm 12.04-12.24 (m, 1H) 11.86-12.03 (m, 1H) 10.88 (s, 1H) 7.93-8.22 (m, 1H) 7.63-7.83 (m, 1H) 7.36-7.52 (m, 1H) 7.12 (t, J=2.81 Hz, 1H) 6.79 (s, 1H) 6.05 (br. s., 1H) 4.87 (dd, J=9.41, 5.62 Hz, 1H) 3.76 (s, 3H) 2.52-2.59 (m, 1H) 2.45 (s, 3H) 2.03-2.30 (m, 3H) 1.48-1.64 (m, 1H) 1.30-1.46 (m, 1H). HRMS calcd. for $C_{23}H_{22}N_4O_3$ (M+H)$^+$ 403.1770. found 403.1758.

Example 158

(±)-3-(5-Cyanobenzo[d]oxazol-2-yl)-3-(5-methoxy-7-methyl-1H-indol-4-yl)-2,2-dimethylpropanoic acid

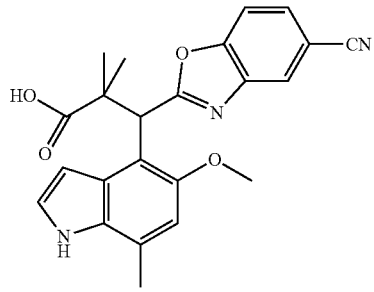 [SMILES: COc1cc(C)c2[nH]ccc2c1C(c1nc2cc(C#N)ccc2o1)C(C)(C)C(=O)O]

A solution of (±)-tert-butyl 4-((5-cyanobenzo[d]oxazol-2-yl)(hydroxy)methyl)-5-methoxy-7-methyl-1H-indole-1-carboxylate (Example 125-A) (133 mg, 0.31 mmol) in DCM (10 mL) was treated with TiCl$_4$ (1M in DCM, 1 mL, 1 mmol) at 0° C. The reaction mixture was stirred for 15 min, followed by the addition of ((1-methoxy-2-methylprop-1-en-1-yl)oxy)trimethylsilane (0.36 g, 2 mmol). The mixture was allowed to reach room temperature over 1 h. The reaction mixture was then poured into aqueous NaHCO$_3$. The organic layer was extracted with ethyl acetate (2×50 mL), and the combined organic layers were dried over Na$_2$SO$_4$, filtered and concentrated to provide a residue. The resulting residue was suspended in water (5 mL) and was treated wtih Dowex ion exchange resin (200% w/w) (washed with water twice). The reaction was stirred at 120° C. overnight in a sealed tube. Reaction was cooled, filtered and directly subjected to purification by FCC$_{1-5}$% (MeOH:DCM) to obtain the title compound. $^1$H NMR (400 MHz, CHLOROFORM-d) δ ppm 8.05 (br. s., 1H) 7.46-7.61 (m, 1H) 7.23 (t, J=2.78 Hz, 1H) 7.10 (d, J=8.34 Hz, 2H) 6.69 (s, 1H) 6.31-6.51 (m, 1H) 4.19 (s, 1H) 3.72 (s, 3H) 2.45 (s, 3H) 1.60 (s, 3H) 0.93 (s, 3H). HMRS calcd. for $C_{23}H_{21}N_3O_4$ (M+H)$^+$ 404.1602. found 404.1595.

Compounds of invention are active on factor B inhibition. Data on Table 1 collected using the assay of Biological Example 1.

TABLE 1

| Example number | IC$_{50}$ (nM) | Example number | IC$_{50}$ (nM) |
|---|---|---|---|
| 3-B a) 2$^{nd}$ compound | 2700 | 17-B b) (+) | 6860 |
| 3-B b) (+) | 820 | 17-B b) (−) | 1330 |
| 3-B b) (−) | 250 | 18-D (+) | 1240 |
| 4 | 570 | 18-D (−) | 150 |
| 5-E b) (+) | 420 | 20-C | 60 |
| 5-E b) (−) | 40 | 20-D | 80 |
| 6-B b) (+) | 140 | 20-E | 670 |
| 6-B b) (−) | 110 | 20-F | 5570 |
| 7 | 4240 | 20-G | 120 |
| 8-B b) (+) | 10 | 20-H | 4370 |
| 8-B b) (−) | 900 | 21-B | 3140 |
| 10-C | 1360 | 22 | 1140 |
| 11-C b) (t$_r$ = 3 min) | 90 | 23 | 2650 |
| 11-C b) (t$_r$ = 4.2 min) | 1020 | 24-B b) (+) | 370 |
| 12-B b) (t$_r$ = 3.5 min) | 13750 | 24-B b) (−) | 90 |
| 12-B b) (t$_r$ = 6.1 min) | 600 | 24-C b) (+) | 6050 |
| 13-E b) (+) | 250 | 24-C b) (−) | 600 |
| 13-E b) (−) | 1410 | 24-D b) (−) | 490 |
| 14-D b) (+) | 8410 | 24-D b) (+) | 1980 |
| 14-D b) (−) | 270 | 24-E | 1110 |
| 15-D b) (+) | 32680 | 25-B | 810 |

TABLE 1-continued

| Example number | IC$_{50}$ (nM) | Example number | IC$_{50}$ (nM) |
| --- | --- | --- | --- |
| 15-D b) (−) | 680 | 26-C b) (−) | 80 |
| 16-B b) (+) | 4740 | 26-C b) (+) | 50 |
| 16-B b) (−) | 180 | 26-D b) (−) | 440 |
| 26-D b) (+) | 360 | 33-C b) (t$_r$ = 3 min) | 490 |
| 26-E b) (−) | 170 | 33-C b) (t$_r$ = 5.1 min) | 5380 |
| 26-E b) (+) | 170 | 33-D | 310 |
| 26-F b) (−) | 380 | 34-B b) (−) | 10 |
| 26-F b) (+) | 230 | 34-B b) (+) | 50 |
| 26-G b) (−) | 4380 | 35-B a) | 70 |
| 26-G b) (+) | 4950 | 35-C (−) | 40 |
| 27-B b) (−) | 3 | 35-C (+) | 4870 |
| 27-B b) (+) | 60 | 36-E b) (−) | 40 |
| 27-C | 90 | 36-E b) (+) | 50 |
| 27-D | 20 | 37 | 30 |
| 27-E b) (+) | 90 | 38-B b) (+) | 140 |
| 27-E b) (−) | 4 | 38-B b) (−) | 8 |
| 27-F b) (−) | 9 | 38-C | 490 |
| 28-C b) (+) | 53900 | 39-C b) (t$_r$ = 24.1 min) | 8 |
| 28-C b) (−) | 140 | 39-C b) (t$_r$ = 30.6 min) | 190 |
| 29-A | 2030 | 40 | 50 |
| 29-B | 2570 | 41-B b) (−) | 9 |
| 30-B b) (+) | 220 | 41-B b) (+) | 190 |
| 30-B b) (−) | 160 | 42-D b) (−) | 5 |
| 31-C | 430 | 42-D b) (+) | 130 |
| 32-B | 1410 | 43-C | 1180 |
| 33-B b) (−) | 50 | 44-C | 870 |
| 33-B b) (+) | 430 | 45 | 1040 |
| 58-C | 200 | 67-C b) (+) | 8770 |
| 59-C | 1760 | 67-C b) (−) | 6750 |
| 60-B | 5780 | 67-D b) (+) | 3220 |
| 61 | 6620 | 67-D b) (−) | 60 |
| 62-B | 7610 | 67-E b) (+) | 2080 |
| 63-A | 160 | 67-E b) (−) | 1180 |
| 63-B | 260 | 67-F | 2000 |
| 63-C | 90 | 67-G b) (+) | 2980 |
| 63-D | 1100 | 67-G b) (−) | 570 |
| 63-E | 320 | 67-H | 1930 |
| 63-F | >100000 | 68-B | 200 |
| 63-G | 5550 | 69 | 3630 |
| 63-H | 1190 | 70-D b) (+) | 950 |
| 63-I | 72590 | 70-D b) (−) | 480 |
| 63-J | 83200 | 71 b) (+) | 4550 |
| 64-C b) (+) | 340 | 71 b) (−) | 4590 |
| 64-C b) (−) | 60 | 73 | 1270 |
| 65-D b) (+) | 6200 | 74 | 1870 |
| 65-D b) (−) | 270 | 75-D | 470 |
| 66-D b) (−) | 5110 | 76-B b) (+) | 290 |
| 66-D b) (+) | 30440 | 76-B b) (−) | 190 |
| 67-A b) (+) | 1160 | 77-C b) (−) | 20 |
| 67-A b) (−) | 160 | 77-C b) (+) | 40 |
| 67-B | 260 | 78 | 640 |
| 79-B a) 2$^{nd}$ compound | 150 | 84-B b) (−) | 50 |
| 79-B b) (+) | 260 | 84-B b) (+) | 710 |
| 79-B b) (−) | 1070 | 84-C b) (−) | 10 |
| 79-C b) (+) | 8 | 84-C b) (+) | 150 |
| 79-C b) (−) | 6 | 84-D b) (−) | 8 |
| 79-D b) (+) | 2240 | 84-D b) (+) | 460 |
| 79-D b) (−) | 310 | 84-E b) (−) | 260 |
| 79-E b) (−) | 350 | 84-E b) (+) | 1200 |
| 79-E b) (+) | 1120 | 85 | 220 |
| 79-F b) (t$_r$ = 2.2 min) | 60 | 86 | 270 |
| 79-F b) (t$_r$ = 3.8 min) | 270 | 87 | 380 |
| 79-G | 190 | 88 | 57950 |
| 79-H a) | 110 | 89-D | 2320 |
| 79-I | 660 | 90 | 110 |
| 80-C b) (−) | 10 | 91 | 420 |
| 80-C b) (+) | 380 | 92-B | 9750 |
| 80-D b) (−) | 70 | 93-F b) (t$_r$ = 7.2 min) | 33810 |
| 80-D b) (+) | 4330 | 93-F b) (t$_r$ = 10.2 min) | 950 |
| 80-E b) (−) | 10 | 94 b) (t$_r$ = 4.5 min) | 400 |
| 80-E b) (+) | 180 | 94 b) (t$_r$ = 6.3 min) | 1590 |
| 80-F b) (−) | 20 | 81-D | 2930 |
| 80-F b) (+) | 690 | 81-E | 1640 |
| 82 | 71940 | 96-C b) (+) | 2210 |
| 83-B | 1440 | 96-C b) (−) | 70 |
| 97 b) (t$_r$ = 10.5 min) | 3810 | 107-D b) (+) | 50 |
| 97 b) (t$_r$ = 19.4 min) | 70 | 107-D b) (−) | 8 |
| 98-B | 560 | 107-E b) (+) | 240 |
| 99-B | 750 | 107-E b) (−) | 3 |
| 100 | 1120 | 108-E | 80 |
| 101-E b) (+) | 80 | 109-B | 30 |
| 101-E b) (−) | 50 | 110-K | 3330 |
| 102-C b) (+) | 50 | 111-E | 22900 |
| 102-C b) (−) | 10 | 112-E | 4150 |
| 102-D b) (−) | 8 | 113-F | 9600 |
| 102-D b) (+) | 6 | 114-C | 70 |
| 102-E a) | 60 | 115 | 30 |
| 103-E | 50 | 116-F | 190 |
| 104-B | 260 | 117-F | 70 |
| 105-B b) (−) | 20 | 118-C b) (t$_r$ = 4.6 min) | 30 |
| 105-B b) (+) | 90 | 118-C b) (t$_r$ = 7.9 min) | 1750 |
| 106 b) (+) | 150 | 119 b) (t$_r$ = 1.54 min) | 130 |
| 106 b) (−) | 8 | 119 b) (t$_r$ = 2.35 min) | 12630 |
| 95-B b) (+) | 2140 | 120 b) (t$_r$ = 2.25 min) | 120 |
| 95-B b) (−) | 480 | 120 b) (t$_r$ = 3.20 min) | 29030 |
| 107-B b) (+) | 140 | 121-D | 480 |
| 107-B b) (−) | 3 | 122-C | 5 |
| 107-C b) (+) | 400 | 123 | 920 |
| 107-C b) (−) | 30 | 124 b) (−) | 11 |
| 124 b) (+) | 490 | | |
| 125-B b) (+) | 180 | | |
| 125-B b) (−) | 3 | | |
| 126-C a) | 8 | | |
| 127-B a) | 330 | | |
| 128-B b) (−) | 3 | | |
| 128-B b) (+) | 1990 | | |
| 129-B | 7860 | | |
| 130-B | 20 | | |
| 131-B b) (+) | 140 | | |
| 131-B b) (−) | 52 | | |
| 132-B | 70 | | |
| 133-B | 100 | | |
| 134 | 90 | | |
| 135-C | 20 | | |
| 136 | 20 | | |

Data on Table 2 collected using the assay of Biological Example 2.7.

TABLE 2

| Example number | IC$_{50}$ (nM) | Example number | IC$_{50}$ (nM) |
| --- | --- | --- | --- |
| 35-D | 24 | 137-M b) (t$_r$ = 2.9 min) | 370 |
| 35-G | 770 | 137-N b) (−) | 6 |
| 35-L | 240 | 137-N b) (+) | 40 |
| 36-F | 12 | 137-O | 3160 |
| 38-D b) (−) | 780 | 137-P | 980 |
| 38-D b) (+) | 2060 | 137-Q | 1350 |
| 109-C | 65 | 137-R | 790 |
| 137-A b) (+) | 120 | 137-S | 110 |
| 137-A b) (−) | 20 | 137-T | 50 |
| 137-B b) (t$_r$ = 2.7 min) | 20 | 137-U | 35 |
| 137-B b) (t$_r$ = 4.6 min) | 3210 | 137-V | 23 |
| 137-C | 62 | 137-W | 5220 |
| 137-D | 170 | 137-X | 190 |
| 137-E | 270 | 137-Y | 820 |
| 137-F b) (t$_r$ = 3.3 min) | 170 | 137-Z | 520 |
| 137-F b) (t$_r$ = 4.9 min) | 10 | 138 | 1220 |
| 137-G | 29 | 139-C | 120 |
| 137-H | 31 | 140-B | 340 |
| 137-I b) (−) | 10 | 141 | 150 |
| 137-I b) (+) | 110 | 142-D | 790 |
| 137-J b) (−) | 10 | 143 | 7200 |
| 137-J b) (+) | 1300 | 144-B | 7950 |
| 137-K b) (+) | 820 | 145-D | 41 |
| 137-K b) (−) | 200 | 145-E | 250 |
| 137-L b) (+) | 720 | 146-C | 59 |
| 137-L b) (−) | 270 | 147-D | 790 |
| 27-B b) (+) | 4 | | |
| 36-E b) (−) | 30 | | |
| 147-E | 160 | | |
| 147-F | 100 | | |
| 148-D | 340 | | |

427

TABLE 2-continued

| Example number | IC$_{50}$ (nM) | Example number | IC$_{50}$ (nM) |
|---|---|---|---|
| 148-E | 420 | | |
| 149-C | 160 | | |
| 149-D | 120 | | |
| 150-C | 1020 | | |
| 151-C | 92 | | |
| 152 | 67 | | |
| 153 | 1110 | | |
| 154 | 21100 | | |
| 155-M | 20 | | |
| 156-K | 130 | | |
| 157 | 39 | | |
| 158 | 20980 | | |
| 41-B b) (−) | 10 | | |

What is claimed is:

1. A compound, or salt or a tautomer thereof, according to Formula (I):

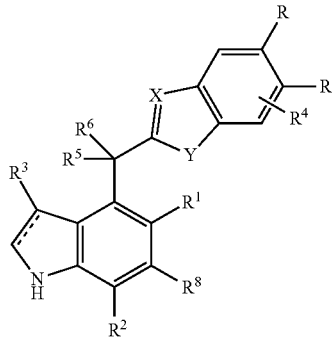

Wherein

⫽ is a single or double bond;
X is N;
Y is N(H);
one occurrence of R is cyano and the other occurrence of R is hydrogen or R$^4$;
R$^1$ is halogen, hydroxyl, C$_1$-C$_6$alkyl, C$_2$-C$_6$alkenyl, C$_3$-C$_6$cycloalkyl, C$_1$-C$_6$alkoxy, haloC$_1$-C$_6$alkyl, hydroxyC$_1$-C$_6$alkyl, aminoC$_1$-C$_6$alkyl, C$_1$-C$_6$alkoxyC$_1$-C$_6$alkyl, C$_1$-C$_6$alkoxyC$_1$-C$_6$alkoxy, C$_3$-C$_6$cycloalkylC$_1$-C$_6$alkoxy, haloC$_1$-C$_6$alkoxy, S(O)$_p$C$_1$-C$_6$alkyl, CH$_2$NHC(O)C$_1$-C$_4$alkyl or OCH$_2$C(O)R$^7$;
p is 0, 1, or 2;
R$^2$ is C$_1$-C$_6$alkyl, C$_1$-C$_6$alkoxy, hydroxyC$_1$-C$_6$alkyl or halogen;
R$^3$ is hydrogen, halogen, cyano, C$_1$-C$_4$alkyl, haloC$_1$-C$_4$alkyl, CH$_2$C(O)R$^7$, phenyl or 5 or 6 member heteroaryl having 1, 2 or 3 ring heteroatoms independently selected from N, O or S, wherein the phenyl or heteroaryl is optionally substituted with 0, 1, or 2 C$_1$-C$_4$alkyl groups, and wherein the alkyl and haloalkyl is optionally substituted with 0 or 1 hydroxy groups;
R$^4$ is 0, 1, or 2 substitutents independently selected at each occurrence from halogen and C$_1$-C$_6$alkyl;
R$^5$ is hydrogen, C$_1$-C$_6$alkyl, haloC$_1$-C$_6$alkyl, C$_3$-C$_6$cycloalkyl, phenyl or 5 or 6 member heteroaryl having 1, 2 or 3 ring heteroatoms independently selected from N, O or S;
or R$^3$ and R$^5$ taken in combination form a divalent —CH$_2$—CH$_2$— or —CH$_2$—N(H)— group;

R$^6$ is hydrogen, hydroxy, amino, C$_1$-C$_6$alkyl, C$_1$-C$_6$alkoxy, C$_1$-C$_6$alkoxyC$_1$-C$_6$alkoxy, mono- and di-C$_1$-C$_4$alkylamino, amino C$_1$-C$_6$alkylamino, [CR$^A{}_2$]$_n$R$^7$, [CR$^A{}_2$]$_n$C(O)R$^7$, O[CR$^A{}_2$]$_n$R$^7$, NHC(O)C$_1$-C$_6$alkyl, NHS(O$_2$)C$_1$-C$_6$alkyl, (CH$_2$)$_n$R$^9$, O(CH$_2$)$_n$R$^9$, C(O)R$^7$, N(H)[CR$^A{}_2$]$_n$R$^7$, O[CR$^A{}_2$]$_n$C(O)R$^7$, N(H)[CR$^A{}_2$]$_n$C(O)R$^7$ or tetrazolyl;
or CR$^5$R$^6$, taken in combination, form a divalent carbonyl group, a divalent =CH$_2$ group or cyclopropyl which cyclopropyl is optionally substituted by CO$_2$H or CH$_2$OH;
n is 1, 2, 3 or 4;
R$^A$ is independently selected at each occurrence from hydrogen, halogen or C$_1$-C$_4$alkyl;
R$^7$ is hydroxy, C$_1$-C$_4$alkoxy, amino or mono- and di-C$_1$-C$_4$alkylamino;
R$^8$ is hydrogen or halogen; and
R$^9$ is a 5 member heteroaryl having 1 to 4 ring heteroatoms selected from N, O or S and optionally substituted with 0, 1, or 2 C$_1$-C$_4$alkyl groups.

2. A compound, or salt or a tautomer thereof, according to Formula (I):

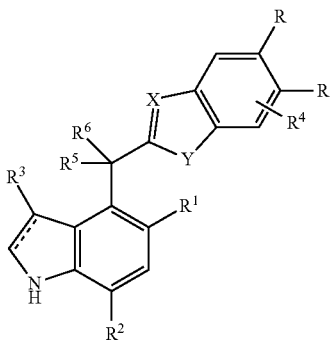

Wherein

⫽ is a single or double bond;
X is N;
Y is N(H);
one occurrence of R is cyano and the other occurrence of R is hydrogen or R$^4$;
R$^1$ is halogen, C$_1$-C$_6$alkyl, C$_2$-C$_6$alkenyl, C$_3$-C$_6$cycloalkyl, C$_1$-C$_6$alkoxy, haloC$_1$-C$_6$alkyl, hydroxyC$_1$-C$_6$alkyl, aminoC$_1$-C$_6$alkyl, C$_1$-C$_6$alkoxyC$_1$-C$_6$alkyl, C$_1$-C$_6$alkoxyC$_1$-C$_6$alkoxy, C$_3$-C$_6$cycloalkylC$_1$-C$_6$alkoxy, haloC$_1$-C$_6$alkoxy, S(O)$_p$C$_1$-C$_6$alkyl, CH$_2$NHC(O)C$_1$-C$_4$alkyl or OCH$_2$C(O)R$^7$;
p is 0, 1, or 2;
R$^2$ is C$_1$-C$_6$alkyl, C$_1$-C$_6$alkoxy, hydroxyC$_1$-C$_6$alkyl or halogen;
R$^3$ is hydrogen, halogen, cyano, C$_1$-C$_4$alkyl, haloC$_1$-C$_4$alkyl, CH$_2$C(O)R$^7$, phenyl or 5 or 6 member heteroaryl having 1, 2 or 3 ring heteroatoms independently selected from N, O or S, wherein the phenyl or heteroaryl is optionally substituted with 0, 1, or 2 C$_1$-C$_4$alkyl groups, and wherein the alkyl and haloalkyl is optionally substituted with 0 or 1 hydroxy groups;
R$^4$ is 0, 1, or 2 substitutents independently selected at each occurrence from halogen and C$_1$-C$_6$alkyl;
R$^5$ is hydrogen, C$_1$-C$_6$alkyl, haloC$_1$-C$_6$alkyl, C$_3$-C$_6$cycloalkyl, phenyl or 5 or 6 member heteroaryl having 1, 2 or 3 ring heteroatoms independently selected from N, O or S;

or R³ and R⁵ taken in combination form a divalent CH₂—CH₂— group;

R⁶ is hydrogen, hydroxy, amino, $C_1$-$C_6$alkyl, $C_1$-$C_6$alkoxy, $C_1$-$C_6$alkoxy$C_1$-$C_6$alkoxy, mono- and di-$C_1$-$C_4$alkylamino, amino $C_1$-$C_6$alkylamino, CH₂R⁷, NHC(O)$C_1$-$C_6$alkyl, NHS(O)₂$C_1$-$C_6$alkyl, C(O)NH₂, CO₂H, OCR⁴₂C(O)R⁷ or N(H)CR⁴₂C(O)R⁷;

or CR⁵R⁶, taken in combination, form a divalent carbonyl group or a divalent =CH₂ group;

R⁴ is independently selected at each occurrence from hydrogen or $C_1$-$C_4$alkyl; and R⁷ is hydroxy, $C_1$-$C_4$alkoxy, amino or mono- and di-$C_1$-$C_4$alkylamino.

3. The compound of claim 1, or salt or tautomer thereof, according to Formula (Ia):

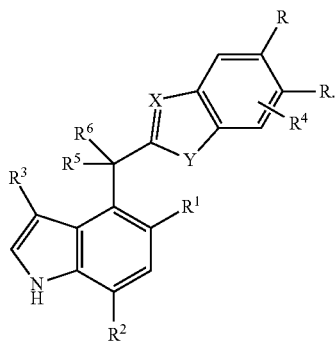

4. The compound of claim 1, or salt or tautomer thereof, wherein R⁴ is absent.

5. The compound of claim 1, or salt or tautomer thereof, wherein R³ is hydrogen, chloro or phenyl.

6. The compound of claim 1, or salt or tautomer thereof, wherein R³ is hydrogen.

7. The compound of claim 1, or a salt or tautomer thereof, wherein R² is methyl.

8. The compound of claim 1, or a salt or tautomer thereof, wherein R¹ is halogen, $C_1$-$C_4$alkyl, vinyl, cyclopropyl, $C_1$-$C_4$alkoxy, hydroxy$C_1$-$C_4$alkyl, $C_1$-$C_4$alkoxy$C_1$-$C_4$alkyl, $C_1$-$C_4$alkoxy$C_1$-$C_4$alkoxy, cyclopropyl$C_1$-$C_4$alkoxy, halo$C_1$-$C_4$alkoxy or S(O)₂$C_1$-$C_4$alkyl.

9. The compound of claim 1, or a salt or tautomer thereof, wherein R¹ is $C_1$-$C_4$alkyl, $C_1$-$C_4$alkoxy, cyclopropyl, bromo or difluoromethoxy.

10. The compound of claim 1, or a salt or tautomer thereof, wherein R⁵ is hydrogen, methyl, ethyl cyclopropyl or trifluoromethyl.

11. The compound of claim 1, or a salt or tautomer thereof, wherein R⁶ is hydrogen, hydroxy, methoxy, amino, mono- and di-methylamino or CH₂R⁷; and R⁷ is hydroxy, amino, N(H)CH₃ or N(CH₃)₂.

12. The compound of claim 1, or a salt or tautomer thereof, wherein R⁵ is methyl or trifluoromethyl;

R⁶ is hydroxy, methoxy, amino, methylamino or CH₂R⁷; and

R⁷ is hydroxy, amino, N(H)CH₃ or N(CH₃)₂.

13. The compound of claim 1, or a salt or tautomer thereof, wherein R⁸ is hydrogen.

14. The compound of claim 1, or a salt or tautomer thereof, wherein R⁸ is fluorine.

15. The compound of claim 1, or a salt or tautomer thereof, in which one occurrence of R is cyano and the other occurrence of R is hydrogen;

R¹ is methyl, hydroxyl or methoxy;

R² is methyl;

R³ is hydrogen, chloro or phenyl;

R⁴ is absent;

R⁵ is hydrogen, methyl, ethyl or trifluoromethyl;

R⁶ is amino, CO₂H, (CH₂)ₙC(O)R⁷ or (CH₂)ₙ-tetrazolyl; and n is 1, 2, or 3.

16. The compound of claim 1, or a salt or tautomer thereof, which compound is selected from the group consisting of
(±)-2-(((2-aminoethyl)amino)(5-(difluoromethoxy)-7-methyl-1H-indol-4-yl)methyl)-1H-benzo[d]imidazole-5-carbonitrile;
(+)-2-((5-(difluoromethoxy)-7-methyl-1H-indol-4-yl)(hydroxy)methyl)-1H-benzo[d]imidazole-5-carbonitrile;
(−)-2-((5-(difluoromethoxy)-7-methyl-1H-indol-4-yl)(hydroxy)methyl)-1H-benzo[d]imidazole-5-carbonitrile;
(±)-2-((5-(difluoromethoxy)-7-methyl-1H-indol-4-yl)(methylamino)methyl)-1H-benzo[d]imidazole-5-carbonitrile;
(+)-2-(1-amino-1-(5-(difluoromethoxy)-7-methyl-1H-indol-4-yl)ethyl)-1H-benzo[d]imidazole-5-carbonitrile;
(−)-2-(1-amino-1-(5-(difluoromethoxy)-7-methyl-1H-indol-4-yl)ethyl)-1H-benzo[d]imidazole-5-carbonitrile;
(+)-2-(1-(5-(difluoromethoxy)-7-methyl-1H-indol-4-yl)-1-hydroxyethyl)-1H-benzo[d]imidazole-5-carbonitrile;
(+) and (−)-2-(1-(5-(difluoromethoxy)-7-methyl-1H-indol-4-yl)-1-hydroxyethyl)-1H-benzo[d]imidazole-5-carbonitrile;
(+) or (−)-2-(1-(3-chloro-5-(difluoromethoxy)-7-methyl-1H-indol-4-yl)-1-hydroxyethyl)-1H-benzo[d]imidazole-5-carbonitrile;
(+)-2-(1-(5-(difluoromethoxy)-7-methyl-1H-indol-4-yl)-1-methoxyethyl)-1H-benzo[d]imidazole-5-carbonitrile;
(−)-2-(1-(5-(difluoromethoxy)-7-methyl-1H-indol-4-yl)-1-methoxyethyl)-1H-benzo[d]imidazole-5-carbonitrile;
(±)-2-(hydroxy(7-methyl-5-(methylsulfonyl)-1H-indol-4-yl)methyl)-1H-benzo[d]imidazole-5-carbonitrile;
(+)-2-(1-hydroxy-1-(7-methyl-5-(methylsulfonyl)-1H-indol-4-yl)ethyl)-1H-benzo[d]imidazole-5-carbonitrile;
(−)-2-(1-hydroxy-1-(7-methyl-5-(methylsulfonyl)-1H-indol-4-yl)ethyl)-1H-benzo[d]imidazole-5-carbonitrile;
(+)-2-(1-methoxy-1-(7-methyl-5-(methylsulfonyl)-1H-indol-4-yl)ethyl)-1H-benzo[d]imidazole-5-carbonitrile;
(−)-2-(1-methoxy-1-(7-methyl-5-(methylsulfonyl)-1H-indol-4-yl)ethyl)-1H-benzo[d]imidazole-5-carbonitrile;
(+)-2-(1-amino-1-(7-methyl-5-(methylsulfonyl)-1H-indol-4-yl)ethyl)-1H-benzo[d]imidazole-5-carbonitrile;
(−)-2-(1-amino-1-(7-methyl-5-(methylsulfonyl)-1H-indol-4-yl)ethyl)-1H-benzo[d]imidazole-5-carbonitrile;
(+)-2-(2,2,2-trifluoro-1-hydroxy-1-(7-methyl-5-(methylsulfonyl)-1H-indol-4-yl)ethyl)-1H-benzo[d]imidazole-5-carbonitrile;
(−)-2-(2,2,2-trifluoro-1-hydroxy-1-(7-methyl-5-(methylsulfonyl)-1H-indol-4-yl)ethyl)-1H-benzo[d]imidazole-5-carbonitrile;
(+)-2-(2,2,2-trifluoro-1-methoxy-1-(7-methyl-5-(methylsulfonyl)-1H-indol-4-yl)ethyl)-1H-benzo[d]imidazole-5-carbonitrile;

(−)-2-(2,2,2-trifluoro-1-methoxy-1-(7-methyl-5-(methylsulfonyl)-1H-indol-4-yl)ethyl)-1H-benzo[d]imidazole-5-carbonitrile;

(+)-2-(2,2,2-trifluoro-1-(7-methyl-5-(methylsulfonyl)-1H-indol-4-yl)-1-(methylamino)ethyl)-1H-benzo[d]imidazole-5-carbonitrile;

(−)-2-(2,2,2-trifluoro-1-(7-methyl-5-(methylsulfonyl)-1H-indol-4-yl)-1-(methylamino)ethyl)-1H-benzo[d]imidazole-5-carbonitrile;

(+)-2-(1-amino-2,2,2-trifluoro-1-(7-methyl-5-(methylsulfonyl)-1H-indol-4-yl)ethyl)-1H-benzo[d]imidazole-5-carbonitrile;

(−)-2-(1-amino-2,2,2-trifluoro-1-(7-methyl-5-(methylsulfonyl)-1H-indol-4-yl)ethyl)-1H-benzo[d]imidazole-5-carbonitrile;

(+)-2-(amino(7-methyl-5-(methylsulfonyl)-1H-indol-4-yl)methyl)-1H-benzo[d]imidazole-5-carbonitrile;

(−)-2-(amino(7-methyl-5-(methylsulfonyl)-1H-indol-4-yl)methyl)-1H-benzo[d]imidazole-5-carbonitrile;

2-((5-methoxy-7-methyl-1H-indol-4-yl)methyl)-1H-benzo[d]imidazole-5-carbonitrile;

2-((5-($^2H_3$) methoxy-7-methyl-1H indol-4-yl)methyl)-1H-benzo[d]imidazole-5-carbonitrile;

2-((5-isopropoxy-7-methyl-1H-indol-4-yl)methyl)-1H-benzo[d]imidazole-5-carbonitrile;

2-((5-(2-methoxyethoxy)-7-methyl-1H-indol-4-yl)methyl)-1H-benzo[d]imidazole-5-carbonitrile;

2-((7-fluoro-5-methoxy-1H-indol-4-yl)methyl)-1H-benzo[d]imidazole-5-carbonitrile;

2-((7-chloro-5-($^2H_3$)methoxy-1H-indol-4-yl)methyl)-1H-benzo[d]imidazole-5-carbonitrile; and (±)-2-((5-((1-methoxypropan-2-yl)oxy)-7-methyl-1H-indol-4-yl)methyl)-1H-benzo[d]imidazole-5-carbonitrile;

(+)-2-(hydroxy(5-methoxy-7-methyl-1H-indol-4-yl)methyl)-1H-benzo[d]imidazole-5-carbonitrile;

(−)-2-(hydroxy(5-methoxy-7-methyl-1H-indol-4-yl)methyl)-1H-benzo[d]imidazole-5-carbonitrile;

(+)-2-((5-ethoxy-7-methyl-1H-indol-4-yl)(hydroxy)methyl)-1H-benzo[d]imidazole-5-carbonitrile;

(−)-2-((5-ethoxy-7-methyl-1H-indol-4-yl)(hydroxy)methyl)-1H-benzo[d]imidazole-5-carbonitrile;

(+)-2-(hydroxy(5-isopropoxy-7-methyl-1H-indol-4-yl)methyl)-1H-benzo[d]imidazole-5-carbonitrile;

(−)-2-(hydroxy(5-isopropoxy-7-methyl-1H-indol-4-yl)methyl)-1H-benzo[d]imidazole-5-carbonitrile;

(±)-2-((7-chloro-5-($^2H_3$)methoxy-1H-indol-4-yl)(hydroxy)methyl)benzo[d]imidazole-5-carbonitrile;

2-(5-methoxy-7-methyl-1H-indole-4-carbonyl)-1H-benzo[d]imidazole-5-carbonitrile;

(+)-2-(1-hydroxy-1-(5-methoxy-7-methyl-1H-indol-4-yl)ethyl)-1H-benzo[d]imidazole-5-carbonitrile;

(−)-2-(1-hydroxy-1-(5-methoxy-7-methyl-1H-indol-4-yl)ethyl)-1H-benzo[d]imidazole-5-carbonitrile;

(+)-2-(1-(5-ethoxy-7-methyl-1H-indol-4-yl)-1-hydroxyethyl)-1H-benzo[d]imidazole-5-carbonitrile;

(−)-2-(1-(5-ethoxy-7-methyl-1H-indol-4-yl)-1-hydroxyethyl)-1H-benzo[d]imidazole-5-carbonitrile;

(+)-2-(1-hydroxy-1-(5-isopropoxy-7-methyl-1H-indol-4-yl)ethyl)-1H-benzo[d]imidazole-5-carbonitrile;

(−)-2-(1-hydroxy-1-(5-isopropoxy-7-methyl-1H-indol-4-yl)ethyl)-1H-benzo[d]imidazole-5-carbonitrile;

(+)-2-(1-hydroxy-1-(5-isopropoxy-7-methyl-1H-indol-4-yl)propyl)-1H-benzo[d]imidazole-5-carbonitrile;

(−)-2-(1-hydroxy-1-(5-isopropoxy-7-methyl-1H-indol-4-yl)propyl)-1H-benzo[d]imidazole-5-carbonitrile;

(+)-2-(1-(5-(cyclopropylmethoxy)-7-methyl-1H-indol-4-yl)-1-hydroxyethyl)-1H-benzo[d]imidazole-5-carbonitrile;

(−)-2-(1-(5-(cyclopropylmethoxy)-7-methyl-1H-indol-4-yl)-1-hydroxyethyl)-1H-benzo[d]imidazole-5-carbonitrile;

(+)-2-(1-methoxy-1-(5-methoxy-7-methyl-1H-indol-4-yl)ethyl)-1H-benzo[d]imidazole-5-carbonitrile;

(−)-2-(1-methoxy-1-(5-methoxy-7-methyl-1H-indol-4-yl)ethyl)-1H-benzo[d]imidazole-5-carbonitrile;

(±)-2-(1-(5-isopropoxy-7-methyl-1H-indol-4-yl)-1-methoxyethyl)-1H-benzo[d]imidazole-5-carbonitrile;

(+)-2-(cyclopropyl(methoxy)(5-methoxy-7-methyl-1H-indol-4-yl)methyl)-1H-benzo[d]imidazole-5-carbonitrile;

(−)-2-(cyclopropyl(methoxy)(5-methoxy-7-methyl-1H-indol-4-yl)methyl)-1H-benzo[d]imidazole-5-carbonitrile;

(+)-2-(($^2H_3$)methyl(methoxy)(5-methoxy-7-methyl-1H-indol-4-yl)methyl)-1H-benzo[d]imidazole-5-carbonitrile;

(−)-2-(($^2H_3$)methyl(methoxy)(5-methoxy-7-methyl-1H-indol-4-yl)methyl)-1H-benzo[d]imidazole-5-carbonitrile;

(+)-2-(1-($^2H_3$)methoxy-1-(5-methoxy-7-methyl-1H-indol-4-yl)ethyl)-1H-benzo[d]imidazole-5-carbonitrile;

(−)-2-(1-($^2H_3$)methoxy-1-(5-methoxy-7-methyl-1H-indol-4-yl)ethyl)-1H-benzo[d]imidazole-5-carbonitrile;

(+)-2-((3-chloro-5-methoxy-7-methyl-1H-indol-4-yl)(hydroxy)methyl)-1H-benzo[d]imidazole-6-carbonitrile;

(−)-2-((3-chloro-5-methoxy-7-methyl-1H-indol-4-yl)(hydroxy)methyl)-1H-benzo[d]imidazole-6-carbonitrile;

(−)-2-(1-(3-Chloro-5-methoxy-7-methyl-1H-indol-4-yl)-1-hydroxyethyl)-1H-benzo[d]imidazole-5-carbonitrile;

(+)-2-(1-(3-chloro-5-methoxy-7-methyl-1H-indol-4-yl)-1-hydroxyethyl)-1H-benzo[d]imidazole-5-carbonitrile;

(+)-2-(methoxy(5-methoxy-7-methyl-1H-indol-4-yl)methyl)-1H-benzo[d]imidazole-5-carbonitrile;

(−)-2-(methoxy(5-methoxy-7-methyl-1H-indol-4-yl)methyl)-1H-benzo[d]imidazole-5-carbonitrile;

(±)-2-((4-(1-(5-cyano-1H-benzo[d]imidazol-2-yl)-1-hydroxyethyl)-7-methyl-1H-indol-5-yl)oxy)acetamide;

(±)-2-((4-(1-(5-cyano-1H-benzo[d]imidazol-2-yl)-1-hydroxyethyl)-7-methyl-1H-indol-5-yl)oxy)acetic acid;

(+)-2-(2,2,2-trifluoro-1-hydroxy-1-(5-methoxy-7-methyl-1H-indol-4-yl)ethyl)-1H-benzo[d]imidazole-5-carbonitrile;

(−)-2-(2,2,2-trifluoro-1-hydroxy-1-(5-methoxy-7-methyl-1H-indol-4-yl)ethyl)-1H-benzo[d]imidazole-5-carbonitrile;

(+)-2-(1-(5-ethoxy-7-methyl-1H-indol-4-yl)-2,2,2-trifluoro-1-hydroxyethyl)-1H-benzo[d]imidazole-5-carbonitrile;

(−)-2-(1-(5-ethoxy-7-methyl-1H-indol-4-yl)-2,2,2-trifluoro-1-hydroxyethyl)-1H-benzo[d]imidazole-5-carbonitrile;

(±)-2-(2,2,2-trifluoro-1-hydroxy-1-(5-isopropoxy-7-methyl-1H-indol-4-yl)ethyl)-benzo[d]imidazole-5-carbonitrile;

(+)-2-(2,2,2-trifluoro-1-methoxy-1-(5-methoxy-7-methyl-1H-indol-4-yl)ethyl)-1H-benzo[d]imidazole-5-carbonitrile;

(−)-2-(2,2,2-trifluoro-1-methoxy-1-(5-methoxy-7-methyl-1H-indol-4-yl)ethyl)-1H-benzo[d]imidazole-5-carbonitrile;

(±)-Methyl 2-(1-(5-cyano-1H-benzo[d]imidazol-2-yl)-2,2,2-trifluoro-1-(5-methoxy-7-methyl-1H-indol-4-yl)ethoxy)acetate;
(+)-2-(1-(5-cyano-1H-benzo[d]imidazol-2-yl)-2,2,2-trifluoro-1-(5-methoxy-7-methyl-1H-indol-4-yl)ethoxy)acetic acid;
(−)-2-(1-(5-cyano-1H-benzo[d]imidazol-2-yl)-2,2,2-trifluoro-1-(5-methoxy-7-methyl-1H-indol-4-yl)ethoxy)acetic acid;
(+)-2-(1-amino-2,2,2-trifluoro-1-(5-methoxy-7-methyl-1H-indol-4-yl)ethyl)-1H-benzo[d]imidazole-5-carbonitrile;
(−)-2-(1-amino-2,2,2-trifluoro-1-(5-methoxy-7-methyl-1H-indol-4-yl)ethyl)-1H-benzo[d]imidazole-5-carbonitrile;
(±)-2-(1-amino-2,2,2-trifluoro-1-(5-isopropoxy-7-methyl-1H-indol-4-yl)ethyl)-1H-benzo[d]imidazole-5-carbonitrile;
(+)-2-(2,2,2-trifluoro-1-(5-methoxy-7-methyl-1H-indol-4-yl)-1-(methylamino)ethyl)-1H-benzo[d]imidazole-5-carbonitrile;
(−)-2-(2,2,2-trifluoro-1-(5-methoxy-7-methyl-1H-indol-4-yl)-1-(methylamino)ethyl)-1H-benzo[d]imidazole-5-carbonitrile;
(±)-2-(1-(dimethylamino)-2,2,2-trifluoro-1-(5-methoxy-7-methyl-1H-indol-4-yl)ethyl)-1H-benzo[d]imidazole-5-carbonitrile;
(+)-2-(amino(5-methoxy-7-methyl-1H-indol-4-yl)methyl)-1H-benzo[d]imidazole-5-carbonitrile;
(−)-2-(amino(5-methoxy-7-methyl-1H-indol-4-yl)methyl)-1H-benzo[d]imidazole-5-carbonitrile;
(±)-2-(amino(5-isopropoxy-7-methyl-1H-indol-4-yl)methyl)-1H-benzo[d]imidazole-5-carbonitrile;
(−)-2-(1-amino-1-(5-methoxy-7-methyl-1H-indol-4-yl)ethyl)-1H-benzo[d]imidazole-5-carbonitrile;
(+)-2-(1-amino-1-(5-methoxy-7-methyl-1H-indol-4-yl)ethyl)-1H-benzo[d]imidazole-5-carbonitrile;
(+)-2-(1-(5-methoxy-7-methyl-1H-indol-4-yl)-1-(methylamino)ethyl)-1H-benzo[d]imidazole-5-carbonitrile;
(−)-2-(1-(5-methoxy-7-methyl-1H-indol-4-yl)-1-(methylamino)ethyl)-1H-benzo[d]imidazole-5-carbonitrile;
(±)-2-((dimethylamino)(5-methoxy-7-methyl-1H-indol-4-yl)methyl)-1H-benzo[d]imidazole-5-carbonitrile;
(±)-2-(2-amino-1-(5-ethoxy-7-methyl-1H-indol-4-yl)ethyl)-1H-benzo[d]imidazole-5-carbonitrile;
(±)-2-(1-(5-ethoxy-7-methyl-1H-indol-4-yl)-2-(methylamino)ethyl)-1H-benzo[d]imidazole-5-carbonitrile
2-((5,7-dimethyl-1H-indol-4-yl)methyl)-1H-benzo[d]imidazole-5-carbonitrile;
2-((5-(hydroxymethyl)-7-methyl-1H-indol-4-yl)methyl)-1H-benzo[d]imidazole-5-carbonitrile;
2-((5-(aminomethyl)-7-methyl-1H-indol-4-yl)methyl)-1H-benzo[d]imidazole-5-carbonitrile;
N-((4-((5-cyano-1H-benzo[d]imidazol-2-yl)methyl)-7-methyl-1H-indol-5-yl)methyl)acetamide;
2-((5,7-dimethyl-1H-indol-4-yl)methyl)-7-fluoro-1H-benzo[d]imidazole-5-carbonitrile;
2-((5-ethyl-7-methyl-1H-indol-4-yl)methyl)-1H-benzo[d]imidazole-5-carbonitrile;
2-((5-chloro-7-methyl-1H-indol-4-yl)methyl)-1H-benzo[d]imidazole-5-carbonitrile;
2-((5-vinyl-7-methyl-1H-indol-4-yl)methyl)-1H-benzo[d]imidazole-5-carbonitrile;
2-((5-methoxymethyl-7-methyl-1H-indol-4-yl)methyl)-1H-benzo[d]imidazole-5-carbonitrile;
2-((5,7-dimethyl-1H-indol-4-yl)methyl)-4-methyl-1H-benzo[d]imidazole-5-carbonitrile;
2-((5,7-dimethyl-1H-indol-4-yl)methyl)-6-fluoro-1H-benzo[d]imidazole-5-carbonitrile;
2-((5-ethyl-7-methyl-1H-indol-4-yl)methyl)-6-fluoro-1H-benzo[d]imidazole-5-carbonitrile;
6-chloro-2-((5,7-dimethyl-1H-indol-4-yl)methyl)-1H-benzo[d]imidazole-5-carbonitrile;
2-((5,7-dimethyl-1H-indol-4-yl)methyl)-6-methoxy-1H-benzo[d]imidazole-5-carbonitrile;
(+)-2-((5,7-dimethyl-1H-indol-4-yl)(hydroxy)methyl)benzo[d]imidazole-5-carbonitrile;
(−)-2-((5,7-dimethyl-1H-indol-4-yl)(hydroxy)methyl)benzo[d]imidazole-5-carbonitrile;
(+)-2-(hydroxy(5-(hydroxymethyl)-7-methyl-1H-indol-4-yl)methyl)-1H-benzo[d]imidazole-5-carbonitrile;
(−)-2-(hydroxy(5-(hydroxymethyl)-7-methyl-1H-indol-4-yl)methyl)-1H-benzo[d]imidazole-5-carbonitrile;
(+)-2-((5-(ethoxymethyl)-7-methyl-1H-indol-4-yl)(hydroxy)methyl)-1H-benzo[d]imidazole-5-carbonitrile;
(−)-2-((5-(ethoxymethyl)-7-methyl-1H-indol-4-yl)(hydroxy)methyl)-1H-benzo[d]imidazole-5-carbonitrile;
(+)-2-((5-ethyl-7-methyl-1H-indol-4-yl)(hydroxy)methyl)-1H-benzo[d]imidazole-5-carbonitrile;
(−)-2-((5-ethyl-7-methyl-1H-indol-4-yl)(hydroxy)methyl)-1H-benzo[d]imidazole-5-carbonitrile;
(±)-2-((5-cyclopropyl-7-methyl-1H-indol-4-yl)(hydroxy)methyl)-1H-benzo[d]imidazole-5-carbonitrile;
(+)-2-(hydroxy(5-(isobutyl)-7-methyl-1H-indol-4-yl)methyl)-1H-benzo[d]imidazole-5-carbonitrile;
(−)-2-(hydroxy(5-(isobutyl)-7-methyl-1H-indol-4-yl)methyl)-1H-benzo[d]imidazole-5-carbonitrile;
(+)-2-(hydroxy(5-isopropyl-7-methyl-1H-indol-4-yl)methyl)-1H-benzo[d]imidazole-5-carbonitrile;
(−)-2-(hydroxy(5-isopropyl-7-methyl-1H-indol-4-yl)methyl)-1H-benzo[d]imidazole-5-carbonitrile;
(+)-2-((5-chloro-7-methyl-1H-indol-4-yl)(hydroxy)methyl)-1H-benzo[d]imidazole-5-carbonitrile;
(−)-2-((5-chloro-7-methyl-1H-indol-4-yl)(hydroxy)methyl)-1H-benzo[d]imidazole-5-carbonitrile;
(±)-2-((5-bromo-7-methyl-1H-indol-4-yl)(hydroxy)methyl)-1H-benzo[d]imidazole-5-carbonitrile;
(+)-2-((5,7-dimethyl-1H-indol-4-yl)(hydroxy)methyl)-4-methyl-1H-benzo[d]imidazole-5-carbonitrile;
(−)-2-((5,7-dimethyl-1H-indol-4-yl)(hydroxy)methyl)-4-methyl-1H-benzo[d]imidazole-5-carbonitrile;
(±)-2-((5-cyclopropyl-7-methyl-1H-indol-4-yl)(hydroxy)methyl)-6-fluoro-1H-benzo[d]imidazole-5-carbonitrile;
(±)-2-((5,7-dimethyl-1H-indol-4-yl)(methoxy)methyl)-1H-benzo[d]imidazole-5-carbonitrile;
(±)-2-((5-cyano-1H-benzo[d]imidazol-2-yl)(5,7-dimethyl-1H-indol-4-yl)methoxy)acetic acid;
(+)-2-((5-ethyl-7-methyl-1H-indol-4-yl)(methoxy)methyl)-1H-benzo[d]imidazole-5-carbonitrile;
(−)-2-((5-ethyl-7-methyl-1H-indol-4-yl)(methoxy)methyl)-1H-benzo[d]imidazole-5-carbonitrile;
(+)-2-((5-isobutyl-7-methyl-1H-indol-4-yl)(methoxy)methyl)-1H-benzo[d]imidazole-5-carbonitrile;
(−)-2-((5-isobutyl-7-methyl-1H-indol-4-yl)(methoxy)methyl)-1H-benzo[d]imidazole-5-carbonitrile;
(±)-2-((5,7-dimethyl-1H-indol-4-yl)(ethoxy)methyl)-1H-benzo[d]imidazole-5-carbonitrile;
(±)-2-((5,7-dimethyl-1H-indol-4-yl)(2-methoxyethoxy)methyl)benzo[d]imidazole-5-carbonitrile;
(±)-2-(1-(5,7-dimethyl-1H-indol-4-yl)ethyl)-1H-benzo[d]imidazole-5-carbonitrile;
(+)-2-(1-(5,7-dimethyl-1H-indol-4-yl)-1-hydroxyethyl)-1H-benzo[d]imidazole-5-carbonitrile;

(−)-2-(1-(5,7-dimethyl-1H-indol-4-yl)-1-hydroxyethyl)-1H-benzo[d]imidazole-5-carbonitrile;
(+)-2-(1-(5-ethyl-7-methyl-1H-indol-4-yl)-1-hydroxyethyl)-1H-benzo[d]imidazole-5-carbonitrile;
(−)-2-(1-(5-ethyl-7-methyl-1H-indol-4-yl)-1-hydroxyethyl)-1H-benzo[d]imidazole-5-carbonitrile;
2-(5-ethyl-7-methyl-1H-indole-4-carbonyl)-1H-benzo[d]imidazole-5-carbonitrile;
(±)-2-(1-hydroxy-1-(7-methyl-5-propyl-1H-indol-4-yl)ethyl)-1H-benzo[d]imidazole-5-carbonitrile;
(+)-2-(1-hydroxy-1-(5-isopropyl-7-methyl-1H-indol-4-yl)ethyl)-1H-benzo[d]imidazole-5-carbonitrile;
(−)-2-(1-hydroxy-1-(5-isopropyl-7-methyl-1H-indol-4-yl)ethyl)-1H-benzo[d]imidazole-5-carbonitrile;
(+)-2-(1-(5-cyclopropyl-7-methyl-1H-indol-4-yl)-1-hydroxyethyl)-1H-benzo[d]imidazole-5-carbonitrile;
(−)-2-(1-(5-cyclopropyl-7-methyl-1H-indol-4-yl)-1-hydroxyethyl)-1H-benzo[d]imidazole-5-carbonitrile;
(+)-2-(1-hydroxy-1-(5-isobutyl-7-methyl-1H-indol-4-yl)ethyl)-1H-benzo[d]imidazole-5-carbonitrile;
(−)-2-(1-hydroxy-1-(5-isobutyl-7-methyl-1H-indol-4-yl)ethyl)-1H-benzo[d]imidazole-5-carbonitrile;
(+)-2-(1-(5-chloro-7-methyl-1H-indol-4-yl)-1-hydroxyethyl)-1H-benzo[d]imidazole-5-carbonitrile;
(−)-2-(1-(5-chloro-7-methyl-1H-indol-4-yl)-1-hydroxyethyl)-1H-benzo[d]imidazole-5-carbonitrile;
(+)-2-(1-(5-bromo-7-methyl-1H-indol-4-yl)-1-hydroxyethyl)-1H-benzo[d]imidazole-5-carbonitrile;
(−)-2-(1-(5-bromo-7-methyl-1H-indol-4-yl)-1-hydroxyethyl)-1H-benzo[d]imidazole-5-carbonitrile;
(±)-2-(1-(5,7-dimethyl-1H-indol-4-yl)-1-hydroxypropyl)-1H-benzo[d]imidazole-5-carbonitrile;
(±)-2-(cyclopropyl(5,7-dimethyl-1H-indol-4-yl)(hydroxy)methyl)-1H-benzo[d]imidazole-5-carbonitrile;
(±)-2-((5,7-dimethyl-1H-indol-4-yl)(hydroxy)(phenyl)methyl)-1H-benzo[d]imidazole-5-carbonitrile;
(+)-2-(1-(5-ethyl-7-methyl-1H-indol-4-yl)-2,2,2-trifluoro-1-hydroxyethyl)-1H-benzo[d]imidazole-5-carbonitrile;
(−)-2-(1-(5-ethyl-7-methyl-1H-indol-4-yl)-2,2,2-trifluoro-1-hydroxyethyl)-1H-benzo[d]imidazole-5-carbonitrile;
(+)-2-(1-(5-ethyl-7-methyl-1H-indol-4-yl)-1-methoxyethyl)-1H-benzo[d]imidazole-5-carbonitrile;
(−)-2-(1-(5-ethyl-7-methyl-1H-indol-4-yl)-1-methoxyethyl)-1H-benzo[d]imidazole-5-carbonitrile;
(+)-2-(1-(5-cyclopropyl-7-methyl-1H-indol-4-yl)-2,2,2-trifluoro-1-hydroxyethyl)-1H-benzo[d]imidazole-5-carbonitrile;
(−)-2-(1-(5-cyclopropyl-7-methyl-1H-indol-4-yl)-2,2,2-trifluoro-1-hydroxyethyl)-1H-benzo[d]imidazole-5-carbonitrile;
(+)-2-(2,2,2-trifluoro-1-hydroxy-1-(5-isopropyl-7-methyl-1H-indol-4-yl)ethyl)-1H-benzo[d]imidazole-5-carbonitrile;
(−)-2-(2,2,2-trifluoro-1-hydroxy-1-(5-isopropyl-7-methyl-1H-indol-4-yl)ethyl)-1H-benzo[d]imidazole-5-carbonitrile;
(±)-2-(2,2,2-trifluoro-1-hydroxy-1-(5-(hydroxymethyl)-7-methyl-1H-indol-4-yl)ethyl)-1H-benzo[d]imidazole-5-carbonitrile;
(±)-4-(1-(5-cyano-1H-benzo[d]imidazol-2-yl)-2,2,2-trifluoro-1-hydroxyethyl)-N,7-dimethyl-1H-indole-5-carboxamide;
(±)-2-(1-hydroxy-1-(7-methyl-5-(trifluoromethyl)-1H-indol-4-yl)ethyl)-1H-benzo[d]imidazole-5-carbonitrile;
(+)-2-(1-(5,7-dimethyl-1H-indol-4-yl)-1-methoxyethyl)-1H-benzo[d]imidazole-5-carbonitrile;
(−)-2-(1-(5,7-dimethyl-1H-indol-4-yl)-1-methoxyethyl)-1H-benzo[d]imidazole-5-carbonitrile;
(+)-2-(1-(5-ethyl-7-methyl-1H-indol-4-yl)-1-methoxyethyl)-1H-benzo[d]imidazole-5-carbonitrile;
(−)-2-(1-(5-ethyl-7-methyl-1H-indol-4-yl)-1-methoxyethyl)-1H-benzo[d]imidazole-5-carbonitrile;
(+)-2-(1-(5-ethyl-7-methyl-1H-indol-4-yl)-2,2,2-trifluoro-1-methoxyethyl)-1H-benzo[d]imidazole-5-carbonitrile;
(−)-2-(1-(5-ethyl-7-methyl-1H-indol-4-yl)-2,2,2-trifluoro-1-methoxyethyl)-1H-benzo[d]imidazole-5-carbonitrile;
(+)-2-(1-(5-isobutyl-7-methyl-1H-indol-4-yl)-1-methoxyethyl)-1H-benzo[d]imidazole-5-carbonitrile;
(−)-2-(1-(5-isobutyl-7-methyl-1H-indol-4-yl)-1-methoxyethyl)-1H-benzo[d]imidazole-5-carbonitrile;
2-((3-bromo-5,7-dimethyl-1H-indol-4-yl)methyl)-1H-benzo[d]imidazole-5-carbonitrile;
2-((3-chloro-5,7-dimethyl-1H-indol-4-yl)methyl)-1H-benzo[d]imidazole-5-carbonitrile;
(±)-2-((3-chloro-5-ethyl-7-methyl-1H-indol-4-yl)(hydroxy)methyl)-1H-benzo[d]imidazole-5-carbonitrile;
(+)-2-(1-(5-ethyl-7-methyl-3-(trifluoromethyl)-1H-indol-4-yl)-1-hydroxyethyl)-1H-benzo[d]imidazole-5-carbonitrile;
(±)-2-(hydroxy(3,5,7-trimethyl-1H-indol-4-yl)methyl)-1H-benzo[d]imidazole-5-carbonitrile;
2-((3-cyano-5-ethyl-7-methyl-1H-indol-4-yl)methyl)-1H-benzo[d]imidazole-5-carbonitrile;
(−)-2-((3-cyano-5-ethyl-7-methyl-1H-indol-4-yl)(methoxy)methyl)-1H-benzo[d]imidazole-5-carbonitrile;
(±)-2-((5-ethyl-7-methyl-3-(2,2,2-trifluoro-1-hydroxyethyl)-1H-indol-4-yl)methyl)-1H-benzo[d]imidazole-5-carbonitrile;
(+)-2-(5-hydroxy-6,8-dimethyl-1,3,4,5-tetrahydrobenzo[cd]indol-5-yl)-1H-benzo[d]imidazole-5-carbonitrile;
(−)-2-(5-hydroxy-6,8-dimethyl-1,3,4,5-tetrahydrobenzo[cd]indol-5-yl)-1H-benzo[d]imidazole-5-carbonitrile;
(+)-2-(6-ethyl-5-hydroxy-8-methyl-1,3,4,5-tetrahydrobenzo[cd]indol-5-yl)-1H-benzo[d]imidazole-5-carbonitrile;
(−)-2-(6-ethyl-5-hydroxy-8-methyl-1,3,4,5-tetrahydrobenzo[cd]indol-5-yl)-1H-benzo[d]imidazole-5-carbonitrile;
(+)-2-(amino(5,7-dimethyl-1H-indol-4-yl)methyl)-1H-benzo[d]imidazole-5-carbonitrile;
(−)-2-(amino(5,7-dimethyl-1H-indol-4-yl)methyl)-1H-benzo[d]imidazole-5-carbonitrile;
(+)-2-(amino(5-ethyl-7-methyl-1H-indol-4-yl)methyl)-1H-benzo[d]imidazole-5-carbonitrile;
(−)-2-(amino(5-ethyl-7-methyl-1H-indol-4-yl)methyl)-1H-benzo[d]imidazole-5-carbonitrile;
(+)-2-(amino(5-isopropyl-7-methyl-1H-indol-4-yl)methyl)-1H-benzo[d]imidazole-5-carbonitrile;
(−)-2-(amino(5-isopropyl-7-methyl-1H-indol-4-yl)methyl)-1H-benzo[d]imidazole-5-carbonitrile;
(±)-2-((5,7-dimethyl-1H-indol-4-yl)(methylamino)methyl)-1H-benzo[d]imidazole-5-carbonitrile;
(±)-N-((5-cyano-1H-benzo[d]imidazol-2-yl)(5,7-dimethyl-1H-indol-4-yl)methyl)methanesulfonamide;
(±)-N-((5-cyano-1H-benzo[d]imidazol-2-yl)(5,7-dimethyl-1H-indol-4-yl)methyl)acetamide;
(+)-2-(1-amino-1-(5,7-dimethyl-1H-indol-4-yl)ethyl)-1H-benzo[d]imidazole-5-carbonitrile;

(−)-2-(1-amino-1-(5,7-dimethyl-1H-indol-4-yl)ethyl)-1H-benzo[d]imidazole-5-carbonitrile;
(+)-2-(1-amino-1-(5-ethyl-7-methyl-1H-indol-4-yl)ethyl)-1H-benzo[d]imidazole-5-carbonitrile;
(−)-2-(1-amino-1-(5-ethyl-7-methyl-1H-indol-4-yl)ethyl)-1H-benzo[d]imidazole-5-carbonitrile;
(+)-2-(1-amino-1-(5-cyclopropyl-7-methyl-1H-indol-4-yl)ethyl)-1H-benzo[d]imidazole-5-carbonitrile;
(−)-2-(1-amino-1-(5-cyclopropyl-7-methyl-1H-indol-4-yl)ethyl)-1H-benzo[d]imidazole-5-carbonitrile;
(+)-2-(1-amino-1-(5-isopropyl-7-methyl-1H-indol-4-yl)ethyl)-1H-benzo[d]imidazole-5-carbonitrile;
(−)-2-(1-amino-1-(5-isopropyl-7-methyl-1H-indol-4-yl)ethyl)-1H-benzo[d]imidazole-5-carbonitrile;
(±)-2-(1-(5,7-dimethyl-1H-indol-4-yl)-1-(methylamino)ethyl)-1H-benzo[d]imidazole-6-carbonitrile;
(±)-2-(1-(5,7-dimethyl-1H-indol-4-yl)-1-(dimethylamino)ethyl)-1H-benzo[d]imidazole-5-carbonitrile;
(+)-2-(1-amino-1-(5-bromo-7-methyl-1H-indol-4-yl)-2,2,2-trifluoroethyl)-1H-benzo[d]imidazole-5-carbonitrile;
(−)-2-(1-amino-1-(5-bromo-7-methyl-1H-indol-4-yl)-2,2,2-trifluoroethyl)-1H-benzo[d]imidazole-5-carbonitrile;
(+)-2-(1-(5-bromo-7-methyl-1H-indol-4-yl)-2,2,2-trifluoro-1-(methylamino)ethyl)-1H-benzo[d]imidazole-5-carbonitrile;
(−)-2-(1-(5-bromo-7-methyl-1H-indol-4-yl)-2,2,2-trifluoro-1-(methylamino)ethyl)-1H-benzo[d]imidazole-5-carbonitrile;
(+)-2-(1-(5-ethyl-7-methyl-1H-indol-4-yl)-2,2,2-trifluoro-1-(methylamino)ethyl)-1H-benzo[d]imidazole-5-carbonitrile;
(−)-2-(1-(5-ethyl-7-methyl-1H-indol-4-yl)-2,2,2-trifluoro-1-(methylamino)ethyl)-1H-benzo[d]imidazole-5-carbonitrile;
(+)-2-(1-amino-1-(5-ethyl-7-methyl-1H-indol-4-yl)-2,2,2-trifluoroethyl)-1H-benzo[d]imidazole-5-carbonitrile;
(−)-2-(1-amino-1-(5-ethyl-7-methyl-1H-indol-4-yl)-2,2,2-trifluoroethyl)-1H-benzo[d]imidazole-5-carbonitrile;
(+)-2-(1-amino-1-(5-cyclopropyl-7-methyl-1H-indol-4-yl)-2,2,2-trifluoroethyl)-1H-benzo[d]imidazole-5-carbonitrile;
(−)-2-(1-amino-1-(5-cyclopropyl-7-methyl-1H-indol-4-yl)-2,2,2-trifluoroethyl)-1H-benzo[d]imidazole-5-carbonitrile;
(+)-2-(1-(5-cyclopropyl-7-methyl-1H-indol-4-yl)-2,2,2-trifluoro-1-(methylamino)ethyl)-1H-benzo[d]imidazole-5-carbonitrile;
(−)-2-(1-(5-cyclopropyl-7-methyl-1H-indol-4-yl)-2,2,2-trifluoro-1-(methylamino)ethyl)-1H-benzo[d]imidazole-5-carbonitrile;
(±)-2-(1-(5,7-dimethyl-1H-indol-4-yl)-2-hydroxyethyl)-1H-benzo[d]imidazole-5-carbonitrile;
(±)-2-(1-(5-cyano-1H-benzo[d]imidazol-2-yl)-1-(5-ethyl-7-methyl-1H-indol-4-yl)-2,2,2-trifluoroethoxy)acetic acid;
2-((7-chloro-5-methyl-1H-indol-4-yl)methyl)-1H-benzo[d]imidazole-5-carbonitrile;
2-((7-ethyl-5-methyl-1H-indol-4-yl)methyl)-1H-benzo[d]imidazole-5-carbonitrile;
2-((7-bromo-5-methyl-1H-indol-4-yl)methyl)-1H-benzo[d]imidazole-5-carbonitrile;
2-((7-(hydroxymethyl)-5-methyl-1H-indol-4-yl)methyl)-1H-benzo[d]imidazole-5-carbonitrile;
2-(1-(5-ethyl-7-methyl-1H-indol-4-yl)vinyl)-1H-benzo[d]imidazole-5-carbonitrile;
2-(1-(5-methoxy-7-methyl-1H-indol-4-yl)vinyl)-1H-benzo[d]imidazole-5-carbonitrile;

2-((5-ethyl-7-methyl-3-(1H-pyrazol-5-yl)-1H-indol-4-yl)methyl)-1H-benzo[d]imidazole-5-carbonitrile;
(±)-2-((5-ethyl-7-methyl-3-phenyl-1H-indol-4-yl)(hydroxy)methyl)-1H-benzo[d]imidazole-5-carbonitrile;
(+)-2-((5,7-dimethyl-3-phenyl-1H-indol-4-yl)(hydroxy)methyl)-1H-benzo[d]imidazole-5-carbonitrile;
(−)-2-((5,7-dimethyl-3-phenyl-1H-indol-4-yl)(hydroxy)methyl)-1H-benzo[d]imidazole-5-carbonitrile;
(+)-2-((5,7-dimethyl-3-(1-methyl-1H-pyrazol-4-yl)-1H-indol-4-yl)(hydroxy)methyl)-1H-benzo[d]imidazole-5-carbonitrile;
(−)-2-((5,7-dimethyl-3-(1-methyl-1H-pyrazol-4-yl)-1H-indol-4-yl)(hydroxy)methyl)-1H-benzo[d]imidazole-5-carbonitrile;
(+)-2-((5,7-dimethyl-3-(pyridin-3-yl)-1H-indol-4-yl)(hydroxy)methyl)-1H-benzo[d]imidazole-5-carbonitrile;
(−)-2-((5,7-dimethyl-3-(pyridin-3-yl)-1H-indol-4-yl)(hydroxy)methyl)-1H-benzo[d]imidazole-5-carbonitrile;
(±)-2-((5,7-dimethyl-3-(1H-pyrazol-5-yl)-1H-indol-4-yl)(hydroxy)methyl)-1H-benzo[d]imidazole-5-carbonitrile;
2-(2-(5-methoxy-7-methyl-1H-indol-4-yl)propan-2-yl)-1H-benzo[d]imidazole-5-carbonitrile;
2-((5,7-dimethylindolin-4-yl)methyl)-1H-benzo[d]imidazole-5-carbonitrile;
(+)-2-(1-methoxy-1-(5-methoxy-7-methylindolin-4-yl)ethyl)-1H-benzo[d]imidazole-5-carbonitrile;
(−)-2-(1-methoxy-1-(5-methoxy-7-methylindolin-4-yl)ethyl)-1H-benzo[d]imidazole-5-carbonitrile;
(+)-ethyl 2-(1-(5-cyano-1H-benzo[d]imidazol-2-yl)-2,2,2-trifluoro-1-(5-methoxy-7-methyl-1H-indol-4-yl)ethoxy)acetate;
(−)-ethyl 2-(1-(5-cyano-1H-benzo[d]imidazol-2-yl)-2,2,2-trifluoro-1-(5-methoxy-7-methyl-1H-indol-4-yl)ethoxy)acetate;
(±)-2-(1-(5-cyano-1H-benzo[d]imidazol-2-yl)-2,2,2-trifluoro-1-(5-methoxy-7-methyl-1H-indol-4-yl)ethoxy)-2-fluoroacetic acid;
(±)-2-(2,2,2-trifluoro-1-(5-methoxy-7-methyl-1H-indol-4-yl)-1-((5-methyl-1,3,4-oxadiazol-2-yl)methoxy)ethyl)-1H-benzo[d]imidazole-5-carbonitrile;
(+)-2-(6-methoxy-8-methyl-5-(trifluoromethyl)-1,3,4,5-tetrahydropyrrolo[4,3,2-de]isoquinolin-5-yl)-1H-benzo[d]imidazole-5-carbonitrile;
(−)-2-(1-((2-aminoethyl)amino)-2,2,2-trifluoro-1-(5-methoxy-7-methyl-1H-indol-4-yl)ethyl)-1H-benzo[d]imidazole-5-carbonitrile;
(+)-2-(1-((2-aminoethyl)amino)-2,2,2-trifluoro-1-(5-methoxy-7-methyl-1H-indol-4-yl)ethyl)-1H-benzo[d]imidazole-5-carbonitrile;
(±)-2-(1-(5-cyano-1H-benzo[d]imidazol-2-yl)-1-(5-cyclopropyl-7-methyl-1H-indol-4-yl)-2,2,2-trifluoroethoxy)acetic acid;
(+)-2-(1-amino-1-(5-bromo-7-methyl-1H-indol-4-yl)ethyl)-1H-benzo[d]imidazole-5-carbonitrile;
(−)-2-(1-amino-1-(5-bromo-7-methyl-1H-indol-4-yl)ethyl)-1H-benzo[d]imidazole-5-carbonitrile;
(±)-2-(1-amino-1-(6-fluoro-5-methoxy-7-methyl-1H-indol-4-yl)ethyl)-1H-benzo[d]imidazole-5-carbonitrile;
(±)-2-(1-(6-fluoro-5-methoxy-7-methyl-1H-indol-4-yl)-1-methoxyethyl)-1H-benzo[d]imidazole-6-carbonitrile;
(−)-2-(1-($^{2}H_3$)methoxy-1-(5-methoxy-7-methyl-1H-indol-4-yl)ethyl)-1H-benzo[d]imidazole-5-carbonitrile;
(+)-2-(1-($^{2}H_3$)methoxy-1-(5-methoxy-7-methyl-1H-indol-4-yl)ethyl)-1H-benzo[d]imidazole-5-carbonitrile;

(±)-2-(2,2,2-trifluoro-1-((2-hydroxyethyl)amino)-1-(5-methoxy-7-methyl-1H-indol-4-yl)ethyl)-1H-benzo[d]imidazole-5-carbonitrile;

(±)-2-((1-(5-cyano-1H-benzo[d]imidazol-2-yl)-2,2,2-trifluoro-1-(5-methoxy-7-methyl-1H-indol-4-yl)ethyl)amino)acetic acid;

(+) or (−)-2-(1-amino-2,2,2-trifluoro-1-(5-hydroxy-7-methyl-1H-indol-4-yl)ethyl)-1H-benzo[d]imidazole-6-carbonitrile;

(±)-2-(5-cyano-1H-benzo[d]imidazol-2-yl)-2-(5-methoxy-7-methyl-1H-indol-4-yl)cyclopropanecarboxylic acid;

(±)-3-(5-cyano-1H-benzo[d]imidazol-2-yl)-3-(5-methoxy-7-methyl-1H-indol-4-yl)propanoic acid;

(±)-2-(3-hydroxy-1-(5-methoxy-7-methyl-1H-indol-4-yl)propyl)-1H-benzo[d]imidazole-5-carbonitrile;

(±)-4-(5-cyano-1H-benzo[d]imidazol-2-yl)-4-(5-methoxy-7-methyl-1H-indol-4-yl)butanoic acid;

(±)-3-(5-cyano-1H-benzo[d]imidazol-2-yl)-3-(5-methoxy-7-methyl-1H-indol-4-yl)-2-methylpropanoic acid;

(±)-2-(3-hydroxy-1-(5-methoxy-7-methyl-1H-indol-4-yl)-2-methylpropyl)-1H-benzo[d]imidazole-5-carbonitrile;

(±)-2-(4-hydroxy-1-(5-methoxy-7-methyl-1H-indol-4-yl)-3-methylbutyl)-1H-benzo[d]imidazole-5-carbonitrile;

(±)-2-(1-(5-methoxy-7-methyl-1H-indol-4-yl)-2-(2H-tetrazol-5-yl)ethyl)-1H-benzo[d]imidazole-5-carbonitrile;

(±)-4-(5-cyano-1H-benzo[d]imidazol-2-yl)-4-(5-methoxy-7-methyl-1H-indol-4-yl)pentanoic acid;

(±)-3-(5-cyano-1H-benzo[d]imidazol-2-yl)-3-(5-methoxy-7-methyl-1H-indol-4-yl)butanoic acid;

(±)-5-(5-cyano-1H-benzo[d]imidazol-2-yl)-5-(5-methoxy-7-methyl-1H-indol-4-yl)pentanoic acid; and (±)-2-(1-(6-fluoro-5-methoxy-7-methyl-1H-indol-4-yl)-1-methoxyethyl)-1H-benzo[d]imidazole-5-carbonitrile;

and salts, stereoisomers, racemates and tautomers thereof.

17. A pharmaceutical composition comprising one or more pharmaceutically acceptable carriers and a therapeutically effective amount of a compound of claim 1.

18. A pharmaceutical combination, comprising a therapeutically effective amount of the compound according to claim 1 and a second therapeutically active agent.

19. The compound of claim 2, or salt or tautomer thereof, according to Formula (Ia):

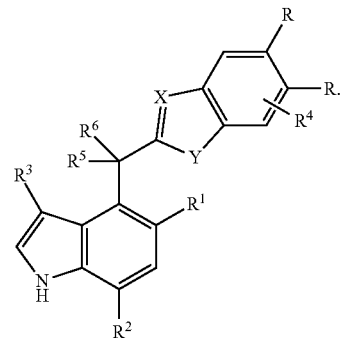

20. The compound of claim 2, or salt or tautomer thereof, wherein $R^4$ is absent.

21. The compound of claim 2, or salt or tautomer thereof, wherein $R^3$ is hydrogen, chloro or phenyl.

22. The compound of claim 2, or salt or tautomer thereof, wherein $R^3$ is hydrogen.

23. The compound of claim 2, or a salt or tautomer thereof, wherein $R^2$ is methyl.

24. The compound of claim 2, or a salt or tautomer thereof, wherein $R^1$ is halogen, $C_1$-$C_4$alkyl, vinyl, cyclopropyl, $C_1$-$C_4$alkoxy, hydroxy$C_1$-$C_4$alkyl, $C_1$-$C_4$alkoxy$C_1$-$C_4$alkyl, $C_1$-$C_4$alkoxy$C_1$-$C_4$alkoxy, cyclopropyl$C_1$-$C_4$alkoxy, halo$C_1$-$C_4$alkoxy or $S(O)_2C_1$-$C_4$alkyl.

25. The compound of claim 2, or a salt or tautomer thereof, wherein $R^1$ is $C_1$-$C_4$alkyl, $C_1$-$C_4$alkoxy, cyclopropyl, bromo or difluoromethoxy.

26. The compound of claim 2, or a salt or tautomer thereof, wherein $R^5$ is hydrogen, methyl, ethyl cyclopropyl or trifluoromethyl.

27. The compound of claim 2, or a salt or tautomer thereof, wherein $R^6$ is hydrogen, hydroxy, methoxy, amino, mono- and di-methylamino or $CH_2R^7$; and $R^7$ is hydroxy, amino, $N(H)CH_3$ or $N(CH_3)_2$.

28. The compound of claim 2, or a salt or tautomer thereof, wherein $R^5$ is methyl or trifluoromethyl;
$R^6$ is hydroxy, methoxy, amino, methylamino or $CH_2R^7$; and
$R^7$ is hydroxy, amino, $N(H)CH_3$ or $N(CH_3)_2$.

29. The compound of claim 1, or a salt or tautomer thereof, which is (−)-2-(1-amino-2,2,2-trifluoro-1-(5-methoxy-7-methyl-1H-indol-4-yl)ethyl)-1H-benzo[d]imidazole-5-carbonitrile.

* * * * *